US011649500B2

(12) United States Patent
Koumbaris et al.

(10) Patent No.: US 11,649,500 B2
(45) Date of Patent: May 16, 2023

(54) TARGET-ENRICHED MULTIPLEXED PARALLEL ANALYSIS FOR ASSESSMENT OF FETAL DNA SAMPLES

(71) Applicant: NIPD GENETICS PUBLIC COMPANY LIMITED, Nicosia (CY)

(72) Inventors: George Koumbaris, Lithrodontas (CY); Marios Ioannides, Nicosia (CY); Elena Kypri, Nicosia (CY); Acilleas Achilleos, Limassol (CY); Petros Mina, Nicosia (CY); Kyriakos Tsangaras, Limassol (CY); Philippos Patsalis, Nicosia (CY)

(73) Assignee: NIPD GENETICS PUBLIC COMPANY LIMITED, Nicosia (CY)

( * ) Notice: Subject to any disclaimer, the term of this patent is extended or adjusted under 35 U.S.C. 154(b) by 249 days.

(21) Appl. No.: 16/625,437

(22) PCT Filed: Jul. 6, 2018

(86) PCT No.: PCT/EP2018/068414
§ 371 (c)(1),
(2) Date: Dec. 20, 2019

(87) PCT Pub. No.: WO2019/008153
PCT Pub. Date: Jan. 10, 2019

(65) Prior Publication Data
US 2021/0147936 A1 May 20, 2021

Related U.S. Application Data

(60) Provisional application No. 62/529,790, filed on Jul. 7, 2017.

(51) Int. Cl.
*C12Q 1/6883* (2018.01)
*C12Q 1/6806* (2018.01)

(52) U.S. Cl.
CPC ......... *C12Q 1/6883* (2013.01); *C12Q 1/6806* (2013.01); *C12Q 2600/156* (2013.01)

(58) Field of Classification Search
CPC ................................................ C12Q 2535/122
See application file for complete search history.

(56) References Cited

U.S. PATENT DOCUMENTS

| | | |
|---|---|---|
| 7,888,017 B2 | 2/2011 | Quake et al. |
| 8,008,018 B2 | 8/2011 | Quake et al. |
| 8,195,415 B2 | 6/2012 | Fan et al. |
| 8,296,076 B2 | 10/2012 | Fan et al. |
| 8,682,594 B2 | 3/2014 | Fan et al. |
| 2008/0194414 A1* | 8/2008 | Albert ............ C12Q 1/6834 506/1 |
| 2011/0039304 A1 | 2/2011 | Church et al. |
| 2011/0201507 A1 | 8/2011 | Rava et al. |
| 2012/0270212 A1* | 10/2012 | Rabinowitz .......... C12Q 1/6806 435/6.12 |
| 2012/0270739 A1 | 10/2012 | Rava et al. |
| 2015/0203907 A1 | 7/2015 | Gilbert et al. |
| 2016/0068889 A1 | 3/2016 | Gole et al. |
| 2016/0340733 A1 | 11/2016 | Koumbaris et al. |
| 2017/0051355 A1 | 2/2017 | Zimmermann et al. |

FOREIGN PATENT DOCUMENTS

| | | |
|---|---|---|
| EP | 2902500 A1 | 8/2015 |
| EP | 3298166 B1 | 2/2020 |
| WO | WO-2016/024134 A2 | 2/2016 |
| WO | WO-2016/189388 A1 | 12/2016 |
| WO | WO-2019/008148 A1 | 1/2019 |
| WO | WO-2019/008153 A1 | 1/2019 |

OTHER PUBLICATIONS

Koumbaris, G. et al., Cell-Free DNA Analysis of Targeted Genomic Regions in Maternal Plasma for Non-Invasive Prenatal TestingClin. Chem., vol. 62, supplemental material pp. 1-33 (Year: 2016).*
Romiguier, J. et al., Contrasting GC-content dynamics across 33 mammalian genomes: Relationship with life-history traits and chromosome sizes, Genome Res., vol. 20, pp. 1001-1009 (Year: 2010).*
Dunham, A. et al., The DNA sequence and analysis of human chromosome 13, Nature, vol. 428, pp. 522-528 (Year: 2004).*
Weiner, M.P. et al., Kits and their unique role in molecular biology: a brief retrospective, Biotechniques, vol. 44, pp. 701-704 (Year: 2008).*
Maricic T et al., Multiplexed DNA Sequence Capture of Mitochondrial Genomes Using PCR ProductsPLOS One, vol. 5(11), e14004, pp. 1-5 (Year: 2010).*
Maricic T et al., Multiplexed DNA Sequence Capture of Mitochondrial Genomes Using PCR ProductsPLOS One, vol. 5(11), e14004, supplemental material, pp. 1-8 (Year: 2010).*
Qi, Q. et al., Copy number variation sequencing-based prenatal diagnosis using cell-free fetal DNA in amniotic fluid, Prenatal Diagn., vol. 36, pp. 576-583 (Year: 2016).*
Bianchi, D.W. et al. (2012) "Genome-wide Fetal Aneuploidy Detection by Maternal Plasma DNA Sequencing ", Obstet. Gynecol. 119:890-901.
Chan, K.C. (2004) "Size Distributions of Maternal and Fetal DNA in Maternal Plasma", Clin. Chem. 50:88-92.
Chen, E.Z. et al. (2011) "Noninvasive Prenatal Diagnosis of Fetal Trisomy 18 and Trisomy 13 by Maternal Plasma DNA Sequencing", PLoS One 6:e21791.
Chiu, R. W. et al.(2008) "Noninvasive Prenatal Diagnosis of Fetal Chromosomal Aneuploidy by Massively Parallel Genomic Sequencing of DNA in Maternal Plasma", Proc. Natl. Acad. Sci. USA 105:20458-20463.

(Continued)

*Primary Examiner* — Teresa E Strzelecka
(74) *Attorney, Agent, or Firm* — Ballard Spahr LLP

(57) ABSTRACT

The invention provides methods for assessment of fetal DNA samples using target-enriched multiplexed parallel analysis. The methods of the invention utilize Target Capture Sequences (TACS) to thereby enrich for target sequences of interest, followed by massive parallel sequencing and statistical analysis of the enriched population. The methods can be used with fetal or embryonic DNA samples, for example for the detection of the presence of genetic abnormalities, e.g., for purposes of IVF Pre-implantation Genetic Screening (PGS) and Diagnosis (PGD). Kits for carrying out the methods of the invention are also provided.

12 Claims, 91 Drawing Sheets
Specification includes a Sequence Listing.

(56) References Cited

OTHER PUBLICATIONS

Duncavage et al: "Targeted next generation sequencing of clinically significant gene mutations and translocations in leukemia", Modern Pathology, vol. 25, No. 6, (2012), pp. 795-804.
Ehrich, M. et al. (2011) "Noninvasive detection of fetal Trisomy 21 by sequencing of DNA in maternal blood: a study in a clinical setting", Am. J. Obstet. Gynecol. 204:205e1-11.
Forbes, S.A. et al. (2017) "COSMIC: somatic cancer genetics at high-resolution", Nucl. Acids Res. 45:D777-D783.
Jiang et al., (2015), "Lengthening and shortening of plasma DNA in hepatocellular carcinoma patients", Proceedings of the National Academy of Sciences, 112(11), pp. E1317-E1325.
Koumbaris, G. et al. (2015) "Cell-Free DNA Analysis of Targeted Genomic Regions in Maternal Plasma for Non-Invasive Prenatal Testing of Trisomy 21, Trisomy 18, Trisomy 13, and Fetal Sex", Clinical chemistry, 62(6):848-855.
Li, H. and Durbin, R. (2009) "Fast and Accurate Short Read Alignment With Burrows-Wheeler Transform", Bioinformatics 25:1754-1760.
Li, H. et al. (2009) "The Sequence Alignment/Map Format and SAMtools ", Bioinformatics 25:2078-2079.
Liang, L. et al. (2013) "Identification of Chromosomal Errors in Human Preimplantation Embryos with Oligonucleotide DNA Microarray",PLoS One 8(4):e61838.
Liao, G.J. et al. (2012) "Noninvasive Prenatal Diagnosis of Fetal Trisomy 21 by Allelic Ratio Analysis Using Targeted Massively Parallel Sequencing of Maternal Plasma DNA", PLoS One 7:e38154.
Lin et al: "Applications of targeted gene capture and next-generation sequencing technologies in studies of human deafness and other genetic disabilities", Hearing Research, vol. 288, No. 1, (2012), pp. 67-76.
Maricic, T. et al. (2010) "Multiplexed DNA Sequence Capture of Mitochondrial Genomes Using PCR Products ", PLoS One 5:e14004.
Nicolaides, K.H. et al. (2013) "Validation of Targeted Sequencing of Single-Nucleotide Polymorphisms for Non-Invasive Prenatal Detection of Aneuploidy of Chromosomes 13, 18, 21, X, and Y", Prenat. Diagn. 33:575-579.
Palomaki, G.E. et al. (2011) "DNA Sequencing of Maternal Plasma to Detect Down Syndrome: An International Clinical Validation Study", Genet. Med. 13:913-920.
Palomaki, G.E. et al. (2012); "DNA Sequencing of Maternal Plasma Reliably Identifies Trisomy 18 and Trisomy 13 as Well as Down Syndrome: An International Collaborative Study", Genet. Med. 14:296-305.
Prior et al. (2012) "A Comprehensive Survey of Ras Mutations in Cancer", Cancer Res. 72:2457-2467.
Sehnert, A.J. et al. (2011) "Optimal Detection of Fetal Chromosomal Abnormalities by Massively Parallel DNA Sequencing of Cell-Free Fetal DNA From Maternal Blood", Clin. Chem. 57:1042-1049.
Shar, N.A. et al. (2016) "Cancer somatic mutations cluster in a subset of regulatory sites predicted from the ENCODE data", Mol. Canc. 15:76.
Sparks, A.B. et al. (2012) "Selective Analysis of Cell-Free DNA in Maternal Blood for Evaluation of Fetal Trisomy", Prenat. Diagn. 32:3-9.
Tarasov, Artem, et al. "Sambamba: fast processing of NGS alignment formats." Bioinformatics 31.12 (2015): 2032-2034.
Tewhey, R. et al.(2009) "Enrichment of sequencing targets from the human genome by solution hybridization", Genome Biol. 10:R116.
Treangen et al. (2012) "Repetitive DNA and Next-Generation Sequencing: Computational Challenges and Solutions", Nature Reviews Genet. 13:36-46.
Tsangaras, K. et al. (2014) "Hybridization Capture Using Short PCR Products Enriches Small Genomes by Capturing Flanking Sequences (CapFlank)", PLoS One 9:e109101.
Zimmerman, B. et al. (2012) "Noninvasive Prenatal Aneuploidy Testing of Chromosomes 13, 18, 21, X, and Y, Using Targeted Sequencing of Polymorphic Loci", Prenat. Diag. 32:1233-1241.
International Search Report and Written Opinion were dated Oct. 23, 2018 by the International Searching Authority for International Application No. PCT/EP2018/068402, filed on Jul. 6, 2018 and published as WO 2019/008148 on Jan. 10, 2019 (Applicant—NIPD Genetics Public Company Limited) (12 Pages).
International Preliminary Report on Patentability was dated Jan. 7, 2020 by the International Searching Authority for International Application No. PCT/EP2018/068402, filed on Jul. 6, 2018 and published as WO 2019/008148 on Jan. 10, 2019 (Applicant—NIPD Genetics Public Company Limited) (8 Pages).
International Search Report and Written Opinion were dated Oct. 11, 2018 by the International Searching Authority for International Application No. PCT/EP2018/068414, filed on Jul. 6, 2018 and published as WO 2019/008153 on Jan. 10, 2019 (Applicant—NIPD Genetics Public Company Limited) (13 Pages).
International Preliminary Report on Patentability was dated Jan. 7, 2020 by the International Searching Authority for International Application No. PCT/EP2018/068414, filed on Jul. 6, 2018 and published as WO 2019/008153 on Jan. 10, 2019 (Applicant—NIPD Genetics Public Company Limited) (9 Pages).
International Search Report and Written Opinion were dated Oct. 18, 2018 by the International Searching Authority for International Application No. PCT/EP2018/068431, filed on Jul. 6, 2018 and published as WO/2019/008167 on Jan. 10, 2019 (Applicant—NIPD Genetics Public Company Limited) (13 Pages).
International Preliminary Report on Patentability was dated Jan. 7, 2020 by the International Searching Authority for International Application No. PCT/EP2018/068431, filed on Jul. 6, 2018 and published as WO/2019/008167 on Jan. 10, 2019 (Applicant—NIPD Genetics Public Company Limited) (9 Pages).

* cited by examiner

| chromosome | start | stop | forward primer | reverse primer | SEQ ID NOs: |
| --- | --- | --- | --- | --- | --- |
| chr13 | 91049752 | 91050001 | TCT TCT CGT TCA AGA TGC CG | AAG GGT GGA AGC ACA TTG AC | 1, 2 |
| chr13 | 92177139 | 92177388 | AAA TTA CAT GCA AGG CTA CCA C | ATA GAG GAA CAA GCT GCA CA | 3, 4 |
| chr13 | 93071049 | 93071298 | ACA GGA AGA AAG GGG AGT TAC | CTC GTC CCT TGC ACA TCT TA | 5, 6 |
| chr13 | 94326973 | 94327222 | TTC AGG TTG TGT GAT GTG TC | AGG TGG GGA AGA ACA AAA CA | 7, 8 |
| chr13 | 94415507 | 94415756 | TAA GCA GAG GTT TTG TTG CC | GAG AGT AGG TGC AGG GAA AC | 9, 10 |
| chr13 | 95600034 | 95600283 | GTG AAG TAT TTG CTG CCA CC | ATC CCG CAT TCT TAA CCA CA | 11, 12 |
| chr13 | 112910529 | 112910778 | ATG GTC ATC TCA ACA GCA CA | GAC TAA GCA AAA GCA TCT CCC | 13, 14 |
| chr13 | 53328405 | 53328654 | TCC ACT GAC GTT GAG ATT CG | TTC TTA CAG GCT CAG GGT AT | 15, 16 |
| chr13 | 20533985 | 20534234 | CGA ACC TCC TTG ACC TCT TA | CCC ATA GCT TAA CCC CTA CAA | 17, 18 |
| chr13 | 20535728 | 20535977 | GTT ATG TTG ATA GGG GAA GCT T | TCT TCA TCT TAC TGT CTA GCA C | 19, 20 |
| chr13 | 20544227 | 20544476 | AAG CCC TCT ACT CCA TCT GT | TCA TAC CCT ATC CCT GTG ATC | 21, 22 |
| chr13 | 20567359 | 20567607 | TCA GAA CTC GTC AGT GGA AG | TCT TGC CCT TGA TTT GTT TCC | 23, 24 |
| chr13 | 20577159 | 20577407 | GAA GGG CCA GAC AGC TTA T | GCC TTT TAT CCA TAT GCC ACC | 25, 26 |
| chr13 | 20598772 | 20599021 | ATT TGC TTT GTT TTT GTC CCT | GCC CTC AAC TTT GCT TTT CA | 27, 28 |
| chr13 | 20600556 | 20600804 | GAT CAT TGC TTT GTT TGG ACC | AAA AAC CTG CAC TGT GTT CG | 29, 30 |
| chr13 | 20610779 | 20611027 | AGG AGA GGA AAA ATC TTG ACC | TTT TTA CAG CAA TCT TCA CTG C | 31, 32 |

FIG. 2

| chromosome | start | stop | forward primer | reverse primer | SEQ ID NOs: |
|---|---|---|---|---|---|
| chr13 | 20621336 | 20621585 | CTG CCT GCA GCC ATT ATT GT | TAA GCC GGA ATG ATT TGT AAG G | 33, 34 |
| chr13 | 20624392 | 20624641 | CCT TGG GGT ATG TTT GTT ATG T | TAC CCT TTG GCT TAA CAG CT | 35, 36 |
| chr13 | 20625461 | 20625710 | ACT TTT TCT GTA TCA GTC ACG G | AGT TGT CAT GTT GGG CTC AT | 37, 38 |
| chr13 | 20632609 | 20632857 | CTG CTT TTG TGT GTT CCC TT | TGT CCT AAG TTA CCT GTC TGA C | 39, 40 |
| chr13 | 20635196 | 20635444 | CCA GTT CCT GTT TTT CTG CC | GCC CTG GAA AGT ACT GTA ACA | 41, 42 |
| chr13 | 21127405 | 21127653 | GCC TTC ACT GAT CCT ACT TTC | TGT TAC AGC CAG GCT TTC AT | 43, 44 |
| chr13 | 21163998 | 21164247 | GGA TAT GGG GTA GGT TTT TGT | CAA CGA ACA CAG GGT TTA CA | 45, 46 |
| chr13 | 21170950 | 21171199 | ACT CAT AGA ACT GGG GCT TT | CCA GGA CTC TCT CTT TTC TTC | 47, 48 |
| chr13 | 21172515 | 21172764 | CTT TGT AGG TCC TCC AGA GA | GAC ACA TAA GAC CAC TTT AGG C | 49, 50 |
| chr13 | 21173774 | 21174022 | CCT GTT TTC AGT GGG TTG AA | GAT ATG TTC TGG AGG ACT GCT | 51, 52 |
| chr13 | 21182580 | 21182828 | CCA CGT TGT ACC TTT CCA TG | TGA TTC TCA CAG GCT CCT TG | 53, 54 |
| chr13 | 21203385 | 21203634 | GAG ATT CAA AAC AGT GGT GGC | TGA TGG AAG TTT CTA GGT CAG T | 55, 56 |
| chr13 | 21217173 | 21217422 | ACA ACA CTG TCC TTG GGT T | AAC ACT CTT GCT CCC TAT GT | 57, 58 |
| chr13 | 21228403 | 21228652 | TAA ATG TCC TGT GTG CTC GG | TTT CTC TCC CAG CTT GAT CTT | 59, 60 |
| chr13 | 21237418 | 21237656 | GAC AGG ACA CAT GGA GAG AG | CTG TGC AGA GAC GAA CTA AG | 61, 62 |
| chr13 | 21239719 | 21239968 | AAC TGA TGG TGA TTT GCA TGT | CTC TCG GAG CAA AGA CCT T | 63, 64 |

FIG. 2 CONTINUED

| chromosome | start | stop | forward primer | reverse primer | SEQ ID NOs: |
|---|---|---|---|---|---|
| chr13 | 21245232 | 21245481 | GGC TTC TGG AAA CAT CTT GC | ACC TCA TAA GTA CGC CCA TC | 65, 66 |
| chr13 | 21251423 | 21251672 | CAA TAG AAG TAG GGG GTG AGG | TGA TCT TCC TTT GCT CCT GT | 67, 68 |
| chr13 | 21276601 | 21276850 | AGC TGG GAT GGG TTG TTT AT | ATG ACG ACG ATG TTG GAG AG | 69, 70 |
| chr13 | 21296989 | 21297237 | GCC AGT TGT CAG AAG AAT CC | TCC TTC AGC AAG CCT CTT TT | 71, 72 |
| chr13 | 21321012 | 21321261 | CAA CTG CAT TCC AAA ACA GC | TGA GGG TGA TAA CCT GTG AG | 73, 74 |
| chr13 | 21330138 | 21330386 | GAA GGG AAA CAG TGA GAA AGA | GGC TTG AAG TTT GTC TGT GA | 75, 76 |
| chr13 | 21348854 | 21349102 | TCA AGC GCC GTA AGT ATG TA | GGA TTT TCA CAT TGC TCA GC | 77, 78 |
| chr13 | 21351692 | 21351941 | TAA CCA TAA CAT CCA GGG CA | TAG CAT GAG AGT GAA CTG AGG | 79, 80 |
| chr13 | 21356527 | 21356775 | TTG TAA GCT GGC ACA CTG AA | CAG CCA CAT AGC CCA TAT CT | 81, 82 |
| chr13 | 21361621 | 21361869 | TTA AGA AAG TGC CGT GTT GC | TGC CCA TGA GTC TAC TTG TG | 83, 84 |
| chr13 | 21396343 | 21396591 | ATG GGT CCA TGA AGA GAA GC | AAG TGG ACT GAG GGA CAA TT | 85, 86 |
| chr13 | 21399744 | 21399992 | AGT TGT TTC CAG TAC TGC CA | TCA GAC TGA GCA TTA AAT CAC C | 87, 88 |
| chr13 | 21417352 | 21417601 | GTA TGC TTT CAA GTG ACG CC | TAG GTC TGG AAG AAT GCC AG | 89, 90 |
| chr13 | 21422981 | 21423229 | GAA GAC AAT GCA ATG AGG TGT | AGT ATC TTG GGC TTG TGA CA | 91, 92 |
| chr13 | 21607075 | 21607324 | AGA CCC AAT GAG AAC AGG AA | GCT CCA CTT CCA GTC TTT CT | 93, 94 |
| chr13 | 21631007 | 21631256 | TGA TGG AGG AAG TGT GAA GC | TTG GAA TAG TGA GCC TCC CT | 95, 96 |

FIG. 2 CONTINUED

| chromosome | start | stop | forward primer | reverse primer | SEQ ID NOs: |
|---|---|---|---|---|---|
| chr13 | 22114538 | 22114907 | TGG CTT TTC TGT AGT TTG GG | TCT GGG GCT CTT TGT CTT TG | 97, 98 |
| chr13 | 22130955 | 22131205 | AGC AGC AAG AGT TGA GAA GA | ATT TTT CCT CCC CTG TAG CT | 99, 100 |
| chr13 | 22189915 | 22190164 | GGC TTT GAA AAA TCA CCA TGG | CTG GGC ACA CTG TAT TAC CA | 101, 102 |
| chr13 | 22270443 | 22270692 | AGA GGT TTC CAT CGT TGC TA | CAC CAC GTT TCT AAT GCA GA | 103, 104 |
| chr13 | 22396225 | 22396474 | AAC AGC CCC AAA CTT CCT AC | GAG TTG AAA AAG GTC CAC GC | 105, 106 |
| chr13 | 22609278 | 22609527 | ATC ACT GCC AAC AAG CCA TT | CAG AGG AAA GAC ACA GTG CT | 107, 108 |
| chr13 | 22691882 | 22692131 | TGA GTT GTG GGG GAT AAA GG | TCT TGG TTT TGA GGC TGT CA | 109, 110 |
| chr13 | 22765144 | 22765393 | TCT GGG CAC TTT CCT TAT GA | ATC AGC CTA ATT CTC CCC AC | 111, 112 |
| chr13 | 27175379 | 27175628 | GCA GTT TTG AGG GGA GAA GA | ATC CCC CAT CAT CCA TAC TC | 113, 114 |
| chr13 | 27405837 | 27406086 | TTC ATG ATG CCA CCT CCT C | CAT AGC TAG GCC TGT GAG TG | 115, 116 |
| chr13 | 27646720 | 27646969 | GCC CAA ATA CCC CTT CAG TA | TCA GCT TGC TGC TCC TTC TCT G | 117, 118 |
| chr13 | 27674747 | 27674996 | GCA CCT CAA TCC CGT ACA AT | CTA GGT CCT CAG CAG TGT TT | 119, 120 |
| chr13 | 27959360 | 27959609 | GCG TTT TAA GCA GCT GTG TA | TCC CAG AGT TAA CAA TAC CCC | 121, 122 |
| chr13 | 27978231 | 27978480 | TCT CCA GAT CGA AAC AGC AT | CCA TTT GCA CTG CCG ATT TC | 123, 124 |
| chr13 | 28003481 | 28003730 | TCA TTC AAA GCC AAG ATG CC | ACT AGT CCC AAA AGC CTA CAC | 125, 126 |
| chr13 | 28073180 | 28073429 | ACA CGC TAC ATA GAC ACT GG | AAC AGC AGC GTC AGA ATA AC | 127, 128 |

FIG. 2 CONTINUED

| chromosome | start | stop | forward primer | reverse primer | SEQ ID NOs: |
|---|---|---|---|---|---|
| chr13 | 28077809 | 28078058 | CAA TCG AGG TCA CAT TCA CC | AGG TCT TTA CGG GAA GGA AA | 129, 130 |
| chr13 | 28217786 | 28218035 | TGA CAC GCT GAA GAA AAT AGC | TGA GGG AGA AGT TTG GTA GG | 131, 132 |
| chr13 | 28302961 | 28303210 | GGA GGG AAT GGC AGA AGT AA | CCC TGT CTA AAG AGC CAT GT | 133, 134 |
| chr13 | 28325874 | 28326123 | GGA TTT TCA GAG CAG AGG TTG | GTT TGG AGT TTC GAT GCC TT | 135, 136 |
| chr13 | 28395893 | 28396142 | AAG AGT TGC CTG TAC CCT TC | ATG TTT TGG TCC TGG GAG AA | 137, 138 |
| chr13 | 28545591 | 28545840 | GTC TCT TTA CTG GGA GCG T | GGA AGT GGT TAG GGC AGA TT | 139, 140 |
| chr13 | 28592602 | 28592851 | ACA TTG CCC CTG ACA ACA TA | AGC CCA GTA AAG ATA AGA GGC | 141, 142 |
| chr13 | 28608293 | 28608542 | TCA TTA TCT GAG GAG CCG G | CCC TTC CCT TTC ATC CAA GA | 143, 144 |
| chr13 | 28617043 | 28617292 | GGC TCC ATA ATC TTC TGC AAT | CTG AAA CCT TCT CCT TAG CC | 145, 146 |
| chr13 | 28622471 | 28622720 | CGT ACA TCT GAT TTG TGG GT | ATT ATC CAA CCT GAC CTG CA | 147, 148 |
| chr13 | 28623594 | 28623843 | TGC CAC TGA TGA TAC AAA AGC | AGG TGC AAA GCT GTT CAT G | 149, 150 |
| chr13 | 28941450 | 28941699 | GAA ACG TGT GGT GTC CTC TA | AAT GCC AAG ATT GTC CTT CA | 151, 152 |
| chr13 | 28958898 | 28959147 | AGT GTT TGG GGC TCT ATC AG | TGC GAA ACC TCA GTG ATC A | 153, 154 |
| chr13 | 28960375 | 28960624 | CTT TCC CTT TTG AGT CCT GC | CAC TTC CTT CAG CAC ACT TT | 155, 156 |
| chr13 | 29003985 | 29004234 | TCT CGC TTA CCT TGC TAC AT | CCG GCT CTC TAT GAA AGT GA | 157, 158 |
| chr13 | 29052686 | 29052935 | AAA GCG GGA ATT GGA ACT TT | ACT TGT CTG TCT GCC TGT TT | 159, 160 |

FIG. 2 CONTINUED

| chromosome | start | stop | forward primer | reverse primer | SEQ ID NOs: |
|---|---|---|---|---|---|
| chr13 | 52293092 | 52293341 | GGG GAA CAT TGG GAA GAG AT | CTG ATG CGC TGA AAA CCA A | 161, 162 |
| chr13 | 52302656 | 52302905 | TCT ACC AGC TAC AAA CCC AT | TTC CAT GTG TTC TTC CTC CC | 163, 164 |
| chr13 | 53286404 | 53286653 | TCA GCC AAT ACC CAT AGC AG | AGC AGT AGG GTT AAC AGG AG | 165, 166 |
| chr13 | 53306303 | 53306552 | AAT CAG AGG AAG ATG GGT CG | GCA GCA ATG TTT CGG TGT A | 167, 168 |
| chr13 | 53497224 | 53497473 | GAG AAC TCC ACC CTG TCT TT | TAC TAA TGG CTG GGG GTA AC | 169, 170 |
| chr13 | 53548644 | 53548893 | GGG AGT GTG TGA ATG TGT CT | CTG ATG AGG CTA AAG GAC CA | 171, 172 |
| chr13 | 53652715 | 53652964 | AAG CTT TAC ATC ATG GCA CTG | CAG AGT TCT CCA TCC CAG AC | 173, 174 |
| chr13 | 53861872 | 53862121 | AAA GGT CCA TAG GCT CAC AT | CTG AGT TCC TCC TTT TGC CT | 175, 176 |
| chr13 | 53897429 | 53897678 | TTG ACC AAT GCC ATT AAG CC | GCA AAA GGT GGT GTT AGC TG | 177, 178 |
| chr13 | 53938205 | 53938454 | ACC AGG GAA ATG TTA GCT TCT | ATC CAC ATC CCA TGC CTA AG | 179, 180 |
| chr13 | 54626806 | 54627055 | TGC TCT GTT ATG GTT GGA GTT | TCT ATT CCT TTG GCA CCT CC | 181, 182 |
| chr13 | 54740174 | 54740423 | GAA GCG GCA GTA ATT CAG GA | AGG AAA GGA GAG CTT TGT CC | 183, 184 |
| chr13 | 54753834 | 54754083 | AAC TGT GTC CTA AGC AGT GA | CCT TTC AGC TTC CAA GTC CT | 185, 186 |
| chr13 | 54768238 | 54768487 | GTC ACC TCC AGA GCT TTC AT | GCT CTC TTC CTC CCA CTA AAA | 187, 188 |
| chr13 | 54773333 | 54773582 | GAA CAA TGC AAC CTG AGA ACT | ACT GCC TGT GTT TTC TTC CT | 189, 190 |
| chr13 | 54910969 | 54911218 | TGA TTG TCC TCT ACC ATG CAT | AAA GCA ATT TCT TCC CCA GC | 191, 192 |

FIG. 2 CONTINUED

| chromosome | start | stop | forward primer | reverse primer | SEQ ID NOs: |
|---|---|---|---|---|---|
| chr13 | 54917347 | 54917596 | AGG CTT GAA ACA CCA CCT TTA | TGT CTG TTG CCA TTC CTT CT | 193, 194 |
| chr13 | 54926251 | 54926500 | TTG ATT TGT TGG GTG GTT GG | TGA CTG TGA CTT GTG CTT TC | 195, 196 |
| chr13 | 55309732 | 55309981 | TGC CAA TCT GAG GTT TTT CC | GAA TTA CAT TTC CCT GGG CG | 197, 198 |
| chr13 | 59785342 | 59785591 | ACT CTG CTT TAG GGC TTC TG | TGA AAC CGT CTT CCT TGT CT | 199, 200 |
| chr13 | 60086302 | 60086551 | GCA GAA AAG CTC CCA AAC AA | TTT AAA GCA GAG CAG GAC CT | 201, 202 |
| chr13 | 60668020 | 60668269 | GAA AAG AGG TGG AGA GGG AG | TTT ATG ACA CAC AGA GCA GC | 203, 204 |
| chr13 | 60707747 | 60707996 | AGG ACC CTT TTG CTG ATT TC | ATG TGT TTG ACC CTT TCC CT | 205, 206 |
| chr13 | 60975949 | 60976198 | CTG GCC CAA GTG CAT ACA TA | ATC CTG AAG TTG TTC CAC ATC | 207, 208 |
| chr13 | 61177164 | 61177413 | AAC CAG AGA GAC ACC TTG AC | GAC CCT GCT TTG TTA CTA GGA | 209, 210 |
| chr13 | 61493655 | 61493904 | TCC TCC CTA TCT CCT GTG AC | TGG ACA TGG ACA TTT CAA CG | 211, 212 |
| chr13 | 67720914 | 67721163 | ACT CTG CCA GAA AAG CCT AC | AAA AAT GCT TCC ACT TGC CT | 213, 214 |
| chr13 | 67799557 | 67799806 | CCT TTG TCT TGA AGC CTC CT | GCA CCT CCA ACA ACA TTC AA | 215, 216 |
| chr13 | 70101783 | 70102032 | TTG ACT GAG CAG AGT AGA GC | TTG GAA ATG GGG CTG GAG | 217, 218 |
| chr13 | 71512697 | 71512946 | TTC TAC CTA CAA GCA AAG AGA G | ACT GGT CTA TTG GGG GAA AAT | 219, 220 |
| chr13 | 71821654 | 71821903 | TCA CCA ACA GAG GAT CAA ACT | AGT GTT AGG AAA GCA GAG TG | 221, 222 |
| chr13 | 72405844 | 72406093 | CCG AGG GAT AAC ATA CAG CT | TGG ACA GGG TTT CAC AAG AT | 223, 224 |

FIG. 2 CONTINUED

| chromosome | start | stop | forward primer | reverse primer | SEQ ID NOs: |
|---|---|---|---|---|---|
| chr13 | 74087455 | 74087704 | CAC TAG TCA CAG AAG CAG GT | CTC CTC TCC ATC TTT CCA GG | 225, 226 |
| chr13 | 74192477 | 74192726 | GTA GAA ACC CCG AGA CAA CT | ATA GGC TGA CTT CCA CAT CTC | 227, 228 |
| chr13 | 74260893 | 74261142 | CAA TTT GCT GTT CAG AGG CT | TGT GGG GGT CAA TTC TAA CG | 229, 230 |
| chr13 | 78218364 | 78218613 | TCA TGA TGT GGC TTA GTG GG | CCA ACG GGT AGT GGT AGA TT | 231, 232 |
| chr13 | 88033439 | 88033688 | TAC ACC CAC ATG CAT ACA CA | CTT ACC CCA CTT CTT CCT GA | 233, 234 |
| chr13 | 90954378 | 90954627 | GAA GTG TGC ATG GGA GAG T | CCT GTC ACA ACT GCC TTT G | 235, 236 |
| chr13 | 91240109 | 91240358 | TTT GGG TGG CTC TAT GTT AGG | TTT GCC ATT TTG TGA TGC CA | 237, 238 |
| chr13 | 91874767 | 91875016 | CTC CTT GAC TCA TTT CCC GT | GGA GTT TCA GGT TGG CAG AA | 239, 240 |
| chr13 | 92125914 | 92126163 | AGA GTA CCA CTG CCA AGA AA | ACA GCT TGC TTC AAA CTA CA | 241, 242 |
| chr13 | 92308079 | 92308328 | CTG CTA GTC TGT CAG GAG AG | TTG AAG GGG CAA AAT ACA GC | 243, 244 |
| chr13 | 92971372 | 92971621 | GGG CAG CAG TAT AAA CAT CC | GCC CCA AAT TGT AAC AAA GC | 245, 246 |
| chr13 | 94063232 | 94063481 | GAC ATT CCC TTC CAT TGA GC | TGA CGA AGA CTC CAA CAC AA | 247, 248 |
| chr13 | 94453836 | 94454085 | TTC CTG GTA AAT GTG CTG GT | AAG TCA GGG AAA TGA AGC TG | 249, 250 |
| chr13 | 94713643 | 94713892 | GGC CAG ATT TGC AGT GAT TT | GTA ACA CAG TGC TCC TTC TC | 251, 252 |
| chr13 | 95766126 | 95766375 | AGA ATC AAC AAC AAT GGC AGG | GGC CCC AAT TAG CTG ATT TC | 253, 254 |
| chr13 | 95814599 | 95814848 | CTC TGA GGA AAG CTT GTA GGA | CTG AGC AGG GAA AAA TCC AG | 255, 256 |

FIG. 2 CONTINUED

| chromosome | start | stop | forward primer | reverse primer | SEQ ID NOs: |
|---|---|---|---|---|---|
| chr13 | 111956688 | 111956937 | AGG TTT TCG TTC TGC TTC AG | ACA AAG GAT TCA GGT GCA GT | 257, 258 |
| chr13 | 112517966 | 112518215 | CGG GTC AGT GAT TCT AGC T | ACA GGT TTT GCT CTT CAG GA | 259, 260 |
| chr13 | 112531519 | 112531768 | GTC ACT ATG GAA TGG GGG TT | GGC AAG TTT GTC TGG TTC ATT | 261, 262 |
| chr13 | 112986709 | 112986958 | GCT TCT TCC CCG CAA TAT GA | CCA TCT GCA TCT GTC TCC TT | 263, 264 |
| chr13 | 113000054 | 113000303 | CGG TTC AGA GTC AAT GCC TA | GCT CCT CTC CTT CTC CCT T | 265, 266 |
| chr13 | 21391429 | 21391678 | TAC CCA ACA AGC CAG AGA AAT | TGT ATA AGG GCA ATC GTG GT | 267, 268 |
| chr13 | 21394616 | 21394865 | AGA GGG AAA GTG CAA GGA AT | AAG GAA CCA GGT CAG ACA AG | 269, 270 |
| chr13 | 21404268 | 21404516 | GTT TTT CAG CAC ACT GTC CC | GTT AGA AGG CAA ACA TCA TGC | 271, 272 |
| chr13 | 21618233 | 21618482 | ACC ACA TTA CTC ACA ACC CT | TGC AGT CAT AGG AAA AGG CT | 273, 274 |
| chr13 | 21619521 | 21619769 | AAG CCC TTT TCA TCT CCA CA | GCA GTC AGA ATG GTT TGG C | 275, 276 |
| chr13 | 21629602 | 21629851 | CCA GAG CTG AGA CAA CTA CT | AGA CAT TGG TTT GGT TGG TTC | 277, 278 |
| chr13 | 21654127 | 21654376 | GAA GCA ATT CCT CAC ACC AC | ACA CAA ATG AAA GCC CGT AC | 279, 280 |
| chr13 | 22215795 | 22216044 | TTC AGT CAG AAT GAG GAG CC | GGT CTG CTG TTT CTC TTT GC | 281, 282 |
| chr13 | 22227261 | 22227510 | CTC CTC TCC CCT CTG ATT TT | AGA GCC TTA CCA AGC TGA AG | 283, 284 |
| chr13 | 22243011 | 22243260 | TTT TAA AGC GAC AGT CAC ACG | GGG ATG GTT ACT TAG TGG GG | 285, 286 |
| chr13 | 22255153 | 22255402 | TCC TCT GCC TTC TAC CCT TT | TTA CAC TCG CCT TCC AAA CA | 287, 288 |

FIG. 2 CONTINUED

| chromosome | start | stop | forward primer | reverse primer | SEQ ID NOs: |
|---|---|---|---|---|---|
| chr13 | 22639387 | 22639636 | TGT TGT GCC TTT TGT TCT GG | GAG AGA GGA GGA GTT GGA AG | 289, 290 |
| chr13 | 27183101 | 27183350 | TTA GGA GGT AAG GCT GGA AAA A | ATC CAC GAC ATC CAA AAT CA | 291, 292 |
| chr13 | 27387690 | 27387939 | CTG TCA GCA ATT TCA GGT CAG | TTG TGC AAG AAG AAA CCT GC | 293, 294 |
| chr13 | 30456189 | 30456438 | AGA CAA AGG CTT CAC GGA AC | GGC CTT GCA TAA ACC ACA TT | 295, 296 |
| chr13 | 30977198 | 30977447 | TTC CTC TGT GTC TTG AAG GT | TTT GTA ATT GGT CCT CGC CT | 297, 298 |
| chr13 | 31061235 | 31061484 | ATC AAT GCA GGT GAG TGT GA | CAA GTA TTT CAT GGC GCT CC | 299, 300 |
| chr13 | 31205037 | 31205286 | CAC TCC ACA TAA GCC TCA GA | GTC AAC AGT ATC AGC TTC CAA | 301, 302 |
| chr13 | 32625308 | 32625557 | AGG ATG TAG TTG GGT GAG GA | TGG GCT TCT TTT TCA TTC CG | 303, 304 |
| chr13 | 34428102 | 34428351 | CAG TCA TCA CGG GGA GAT AC | TCA ACA AGC TCT CTG TTC AC | 305, 306 |
| chr13 | 36054899 | 36055148 | GAC AGA TAT TTG TGC AGG GT | GTG CAA ACA GTG ACC TCA AT | 307, 308 |
| chr13 | 36105686 | 36105935 | TCC TAG CCC TTA CCT TTC CT | GCT GGG CTG CTT TAA TTT CT | 309, 310 |
| chr13 | 40675702 | 40675951 | AGC CTG AAT GTC ACT GAT CA | GGA ATT GTG GGG TCA AAT GG | 311, 312 |
| chr13 | 40745383 | 40745632 | ACT CAT CAC TTC TGG CTG C | CTA GTG CTT CTA CCT CCA GAC | 313, 314 |
| chr13 | 49281723 | 49281972 | TCT TGT GTT TCC TGC CCT AT | AAC CAC ACA CTA ACA GGG AA | 315, 316 |
| chr13 | 53624527 | 53624776 | TTG CTG TGG ATG AGA ATG GA | TCT AGT TTG CCC TCT TTC CC | 317, 318 |
| chr13 | 60069277 | 60069526 | TGA GGG CAG AAA GAA ACA GA | CGA ATT GCT TCC TTG CTC TG | 319, 320 |

FIG. 2 CONTINUED

| chromosome | start | stop | forward primer | reverse primer | SEQ ID NOs: |
|---|---|---|---|---|---|
| chr13 | 60654975 | 60655224 | GGG GTC ACA CAT CAC TTT TC | TCT ATC ACA GCA GGA AAT CAC T | 321, 322 |
| chr13 | 61151386 | 61151635 | ATA GGG TCA CAA TCC ACT GC | TCT TCG TGT TTC TCT AGC CC | 323, 324 |
| chr13 | 62064603 | 62064852 | ATA TTG AGC CCC GCA TGT TA | TTG AAG AGC TAA AGG GGG AG | 325, 326 |
| chr13 | 71479359 | 71479608 | GGT TGC AGG AGA AAG AAC AT | TGT CAC CGT ACT ACC TAA GC | 327, 328 |
| chr13 | 39233534 | 39233783 | TGC CAT GTA ATT GCC AAG AT | AGT ACG CTC CTT TGC AGA G | 329, 330 |
| chr13 | 39281667 | 39281916 | CCT GTT CTC CAT CCC TCT G | TTA CGG GGA CAC AAA ATG GT | 331, 332 |
| chr13 | 39343524 | 39343773 | TCA CAA ACT ACC CAA CAC CTA | CTG TGC TTT GCC CTT GAA G | 333, 334 |
| chr13 | 39444897 | 39445146 | CAG AAT TAG TTG GGG AGC TGT | AAG TCA ACC CAT ATG CCA CT | 335, 336 |
| chr13 | 39469458 | 39469707 | GCC ATC TCC TGA AAT AGT GC | ACA TTC AGG CTG TCA CAC AT | 337, 338 |
| chr13 | 39486237 | 39486486 | GCA AGT GTT CCC ATC TAG AA | TC ATG TCA CTA GTT TTA TAA GGC | 339, 340 |
| chr13 | 39541262 | 39541511 | ATT GAT ACC CCT CTC CCC AG | AGT AGT GAG GCT CCA AAG TG | 341, 342 |
| chr13 | 39597307 | 39597556 | AAG TAA GCT GTC TCC TGG C | TGG GAG GAG TTT GCT GTT TA | 343, 344 |
| chr13 | 39662550 | 39662799 | AGG TTG GTT GGC ATG AAG AA | TTC TAA GCC TGT GAC TGA CA | 345, 346 |
| chr13 | 39681445 | 39681694 | AGC AGA GTT TCA AGA CAA GC | TGA ACC TGA CTT TCC TTG GG | 347, 348 |
| chr13 | 39707053 | 39707302 | TTT TAC ACA GGC CTC TT | GCC ATT CTA TCA TCT CGG GA | 349, 350 |
| chr13 | 39791099 | 39791348 | GCA ACT CCA AAT TAT CAG GGC | AGT CTC TCC CTG AAA CCC A | 351, 352 |

FIG. 2 CONTINUED

| chromosome | start | stop | forward primer | reverse primer | SEQ ID NOs: |
|---|---|---|---|---|---|
| chr13 | 39882804 | 39883053 | CAG CAC CTT CCC TTA GCA AA | AAG AGT TGG CTT GGA GTT GA | 353, 354 |
| chr13 | 39887397 | 39887646 | CTT GTT GTC TTG TAG CCC TG | CCC ACA ATT ATG AAA GGA GGT | 355, 356 |
| chr13 | 40023378 | 40023527 | CAC AGA TAC AGA CGT CCA CA | TTG ACC AGG ACA AAT GAG GA | 357, 358 |
| chr13 | 40038277 | 40038526 | AGC TCA GCA ATT AAA CAG TCC | CAC TTT GTT GGT CTG GGT CA | 359, 360 |
| chr13 | 40071926 | 40072175 | TGT TGA GAG TGC CAG AGA TG | GGG ACT CTA GGT GGG GTT AA | 361, 362 |
| chr13 | 40138914 | 40139163 | CTT CCA CCT TCT GCC AAT GA | GTT TAT GCC TTG GGA TTG CC | 363, 364 |
| chr13 | 40171414 | 40171663 | TTC TGA CAT TTG CAA GCA CC | GTG TGG TAA GGA TGC TAG GA | 365, 366 |
| chr13 | 40405751 | 40406000 | CTG TTG CTA GTT TCT TGG GC | GAA AGT GAC TCC TCC CTG AC | 367, 368 |
| chr13 | 40483291 | 40483540 | TTT TCC AGT CCC AGC ACA T | CCA GGT TCT GTT CTC TGT CA | 369, 370 |
| chr13 | 40562330 | 40562579 | TCT CTC TCT TCC TGA AAC AGC | GTG AGA CAT GGT TGC TGT TC | 371, 372 |
| chr13 | 40590631 | 40590880 | AAC CTC TGC TTT GTG TAG TGA | CTT TCT CCT GCT CCA CCT AT | 373, 374 |
| chr13 | 40639444 | 40639693 | GAG AGA ATG CAA GGT TCA GC | CTA TGT GTG TTC CAA CCC GA | 375, 376 |
| chr13 | 40644042 | 40644291 | TAC AGC ATC AAA GAG GAA GC | GGG ACC TTC TAA CCA TGT GT | 377, 378 |
| chr13 | 40661582 | 40661831 | GAG GGG ATG AGG GGA AAA AG | CGG GAT TTT GAA AAG GCA GA | 379, 380 |
| chr13 | 40667939 | 40668188 | CAT GAC CTC TGA CGG ATC TG | GTG TTG TCT CTC AGC TCC TC | 381, 382 |
| chr13 | 40684306 | 40684555 | AGG CAA TGA GGT CAA GGA C | GTT CTC TGG TTA AGG CCC TT | 383, 384 |

FIG. 2 CONTINUED

| chromosome | start | stop | forward primer | reverse primer | SEQ ID NOs: |
|---|---|---|---|---|---|
| chr13 | 40747946 | 40748195 | ATG ATG GCC CCA ACT TCT TC | CCT CTT CAC CTA TAA GCC CC | 385, 386 |
| chr13 | 40767281 | 40767530 | TTC TAG ACA CTG AGG GAG CA | TAG GGG ACA GTA AGC CAG AT | 387, 388 |
| chr13 | 41165017 | 41165266 | AAC GCT ACA CTT TAC GAG CT | ACG ATG GAC CTC TGT TGA AC | 389, 390 |
| chr13 | 41176869 | 41177118 | TCA ACA CTA CCT GCC AAT CA | ATT CCC ATC CAT CCA TCA CTC | 391, 392 |
| chr13 | 41573543 | 41573792 | TGC CGA CAC AAA AGA ATG C | TCG TTT TTG GAT GGT GGT TG | 393, 394 |
| chr13 | 41581284 | 41581533 | AAA GTG TTC CTC CCT GCT G | GAA GTT CCT CCA GTA GAC TCA | 395, 396 |
| chr13 | 41588844 | 41589093 | AGG AGC AAA ATA GTC TGG CT | TTG TTT GAG TCT GGG AGG AA | 397, 398 |
| chr13 | 41628316 | 41628565 | ACC ACT CTT GAA TCA TTG CAG | AAT ACT GTG AGA CTG CCA CC | 399, 400 |
| chr13 | 41633944 | 41634193 | CCA GCC AAT TTT CTC TTT CCC | CAG TCA CCG AAA GTA CCC TC | 401, 402 |
| chr13 | 41827812 | 41828061 | ACT GTC CCT ACT GCC AAT TT | ACC ATG TTT CCC TCT GTC AC | 403, 404 |
| chr13 | 42280338 | 42280587 | ATC TGG TTT GAA CTT GCC AAC | TTA CCA AGG GAC AGG ATG GA | 405, 406 |
| chr13 | 42349979 | 42350228 | CAC TCT GAA TAG CTC TCC CC | CCC TAG AGG TCA AGG TAT GG | 407, 408 |
| chr13 | 42589616 | 42589865 | TTA TCC GGG ACA GTT TCA GG | ATA GGC CCT GTG TGT TAG TT | 409, 410 |
| chr13 | 42773088 | 42773337 | GAA TCT TTT GGC CCA CAC TG | AGA AAG TCC CCT CCA TTT CT | 411, 412 |
| chr13 | 42811933 | 42812182 | GTC AGA CAC ACT TAG CTG GT | GCC AAT GCC AAA GTC AGT TA | 413, 414 |
| chr13 | 44211957 | 44212206 | ACA CAT TTC ACC TTC ACC CT | GAG GAC GAG TTG AAC AAA GC | 415, 416 |

FIG. 2 CONTINUED

| chromosome | start | stop | forward primer | reverse primer | SEQ ID NOs: |
|---|---|---|---|---|---|
| chr13 | 44239246 | 44239495 | GCA CTA ATC CAG GGG CTT AA | ATA CTG GTC TCA AGG TAG CAC | 417, 418 |
| chr13 | 44247433 | 44247682 | CCC CTT ACC ACC ACT TCT AC | ACC AAG TGA AGC TGA GTT AAT G | 419, 420 |
| chr13 | 44359516 | 44359765 | TTC AGA TCC CTT AAG CAC GC | CCC AGA TAC ACT CCT GCT TC | 421, 422 |
| chr13 | 44388992 | 44389241 | ACC TAA GGC CTC AAA TTC CA | CAA ACA TGA GAG GGG GAG AA | 423, 424 |
| chr13 | 44493443 | 44493692 | CAG ACC ACG GGC ATA AGA AA | AAA CAC AGC AAT GAG GAA GG | 425, 426 |
| chr13 | 44557886 | 44558135 | TGG ATG TGT GGA TTT GGA GA | GAT ACT CCC CTG TGT TGC TT | 427, 428 |
| chr13 | 44959162 | 44959411 | CTG GCT GTC TTC TGG GAA A | GCT CTT ACT AGG ATG GCA GG | 429, 430 |
| chr13 | 45043950 | 45044199 | CAA GCA GAA CTG AGA AGA GTC | GTT TCC AGC AGC AAT CCT TT | 431, 432 |
| chr13 | 45115235 | 45115484 | AGT GGA ACG AGG ATT GTG TT | CTG TGC AGA AGG GTT AGC T | 433, 434 |
| chr13 | 45147386 | 45147635 | CTC CCA TCT GAA ACT GCT GA | AAA CCC CTG CTA CCC AAA AT | 435, 436 |
| chr13 | 47067063 | 47067312 | ACA TCA CAA CCA CCC TGA C | AAT GCC CAG ATG CTG TTT TC | 437, 438 |
| chr13 | 47120595 | 47120844 | GTG TTG ACC TGA TTT GCC AA | GAG TGG TTG TTC TCT CCA GAT | 439, 440 |
| chr13 | 47154937 | 47155186 | GAA CAA AGA GGA ACA GAG CC | CAG TCT AGA AGC TCA CCC AG | 441, 442 |
| chr13 | 47258834 | 47259083 | TTC ATG ATT CCA GGG TCC TC | TCT CCT CTA CCC CTA CAC TG | 443, 444 |
| chr13 | 47261849 | 47262098 | GGA CGG ATT TAG TGT ACA TTG G | GGT GTA AAT GTG GCC TCT CC | 445, 446 |
| chr13 | 47286641 | 47286890 | TTT CCT TCC AAC ACC ACA GA | ACA AAG CTA CAA ACT CTG GC | 447, 448 |

FIG. 2 CONTINUED

| chromosome | start | stop | forward primer | reverse primer | SEQ ID NOs: |
|---|---|---|---|---|---|
| chr13 | 47314093 | 47314342 | TCC TTA GGG TTC TGC GAA AT | TTT CAC TGG GAG ACT GAT GC | 449, 450 |
| chr13 | 47623498 | 47623747 | GGA AAC TCC CTG CCT TCT AC | CTG TTC TGT TCC TGA GGC TA | 451, 452 |
| chr13 | 48562058 | 48562307 | TCT TCC AAA CAC CAG GTC TA | TGT GTA TCC ATT GCC TCA TCT | 453, 454 |
| chr13 | 48698166 | 48698415 | ACT CAA TGG AAG GAA GGG C | GAA GAG GGT GTG TGT AGG AC | 455, 456 |
| chr13 | 48762184 | 48762433 | AAG GAC TTG TGC TGT ATT GC | TGG TTG CTC TTC CTA GTT CC | 457, 458 |
| chr13 | 48805515 | 48805764 | GAC GGG AGC CAG TAT TCT AC | CAA TGT GGA GGA AGC TCT TG | 459, 460 |
| chr13 | 48811339 | 48811588 | GGG ATT GAG AGC TTG GTT CT | TTG CAC ACC CAA TAT GCT AC | 461, 462 |
| chr13 | 49119202 | 49119451 | CTC CCC ACC AAG ATG TTC AA | TCC AAG GTT TCT CTA GCG AC | 463, 464 |
| chr13 | 49479756 | 49480005 | GTT TTG GGT CAT GCA GTG TT | TCG CTA TTC TCC TTG CCA TA | 465, 466 |
| chr13 | 49503070 | 49503319 | GAC AAA AAC ACT TGC CAG AC | AAC AGC CTC TTT CCT TAG CA | 467, 468 |
| chr13 | 49530727 | 49530976 | AAC CAT GGC TTT GCA AGT AC | TTT TTG GCT CAG TGG GAT GT | 469, 470 |
| chr13 | 50387096 | 50387317 | GGA ACC CTC TGC TAT TTT GC | CTG TTC ATT CTT CTT CAG GGC | 471, 472 |
| chr13 | 50860526 | 50860775 | TAC TCC TTG TGT GAA CCC CT | TTC CCG AGC CCA TAA ACT AC | 473, 474 |
| chr13 | 51783208 | 51783457 | ACC TTT ACC CCA TAC CAT CC | TGC TCA GAT TTC AGC TTC CT | 475, 476 |
| chr13 | 51816719 | 51816968 | CAT TCC TTT GGT TGG TGT CC | GTC AGC GAT GTG GAT GTC TA | 477, 478 |
| chr13 | 51822241 | 51822490 | CTA ATG GGC CTG TTG TTC CT | AAC TGA CTC CAT GAC CTG TG | 479, 480 |

FIG. 2 CONTINUED

| chromosome | start | stop | forward primer | reverse primer | SEQ ID NOs: |
|---|---|---|---|---|---|
| chr13 | 52025153 | 52025402 | CAA CCT ACC TGC CCA TAG TT | GAA GCT GCT ACT TGG TGA AC | 481, 482 |
| chr13 | 52249504 | 52249753 | CGT AGC AAA TTA TGG CGA GG | TTT TCC TCC TGT TCT GTT GC | 483, 484 |
| chr13 | 29111011 | 29111260 | GGT CAG AAG GGA AAG GGT TC | TTC TCA AAT GCA AGC ACT CC | 485, 486 |
| chr13 | 29192994 | 29193243 | CCA GAT TAA AAC GTG GTG CC | CTG GCC CTT CAA TTT CAT GC | 487, 488 |
| chr13 | 29233772 | 29234021 | CCC ACA ACT ATA GGT CGC AT | CCA GCA GTA CCG ATA TCA GAG | 489, 490 |
| chr13 | 29310139 | 29310388 | AGT TGT TCC ATT TGT ACC AGC | CAG AAG GCA GGA GAT GGA TT | 491, 492 |
| chr13 | 29563140 | 29563389 | TTG GCT GCA CTT TGA GTC A | AAG CAA CCA TTT TCC TGA GC | 493, 494 |
| chr13 | 29580073 | 29580322 | CAG ATG GCC CAT TGT AAC AA | TCA CCC TTC ATC TAC CCA CT | 495, 496 |
| chr13 | 29929175 | 29929424 | TAT TGA GGT TCC CGT GCT G | AAG CTG GTG ACC TTC TAC AG | 497, 498 |
| chr13 | 29934475 | 29934724 | AGA ATG TGA AGT GGC TCC AT | AAA ATT CTG GTT GGG GAG GA | 499, 500 |
| chr13 | 29939640 | 29939889 | TTT GGG TTT GTG TGT GTG TG | CCA TAC CTC ATC ATC TGC TCT GT | 501, 502 |
| chr13 | 29957853 | 29958102 | AGG AAT CTC TCT CTG CCA AG | GGC TGT CCC TGA ACT ACT TT | 503, 504 |
| chr13 | 29995732 | 29995981 | TCT TCA AGG CAG GTC ATA GG | CTT GGC TTA AAC TCT GCT CC | 505, 506 |
| chr13 | 30003375 | 30003624 | GAA ACC TAA GAC GTT CCA CTG | GAC TTG AAC ACA CCC TCA GA | 507, 508 |
| chr13 | 30014954 | 30015203 | GAG TGA AGG GAT TGG AGC AA | AGG AGA AGA GAC CAT TGC AG | 509, 510 |
| chr13 | 30114022 | 30114271 | ATG TCT CAG GCT AGG TGT TC | TTA GCT AAG TCT GTG CGG AG | 511, 512 |

FIG. 2 CONTINUED

| chromosome | start | stop | forward primer | reverse primer | SEQ ID NOs: |
|---|---|---|---|---|---|
| chr13 | 30145894 | 30146143 | ACA CTC ACA AAG CCC AGT TA | GAA GCA ACA CTG TAC ACG C | 513, 514 |
| chr13 | 30187253 | 30187502 | GTG CAG ACT CAT GTT ATG GC | TCT GAT AAA GGC TGG CTC AT | 515, 516 |
| chr13 | 30421518 | 30421767 | AGG ATC TCA AAG CAC CAC AG | TAA AAC AGT GCC GCT ACT TC | 517, 518 |
| chr13 | 30531947 | 30532196 | AAC GGG AAG AGG GAA ACT TT | AGT GCT ATG AGT CTT GGT CC | 519, 520 |
| chr13 | 30778718 | 30778967 | ATG TTC AAC AGA GTC AGG CT | GGA AAA CAT GCG GTG GTC TA | 521, 522 |
| chr13 | 30805760 | 30806009 | CAG TAA CAG TCC AGG GTC TT | GCA GAG AAA TGG GTT AAG GG | 523, 524 |
| chr13 | 31011560 | 31011809 | AGT CTG GGA GCC TAG AAT CA | GGT AGA GGT GGG TTA TCT GT | 525, 526 |
| chr13 | 31089936 | 31090185 | CAT TGT AGT TTC AGG ACA CCA A | CTG TAA ATC TCC GGG GGT G | 527, 528 |
| chr13 | 31227324 | 31227573 | ACC ACA GAA TGA CTT GCA GC | GGC GAG AAT GGA GAG AGA AA | 529, 530 |
| chr13 | 31430437 | 31430686 | TTT CAC GTG TAA CAG GAG CA | TCC CAA GCC AGG ATT CTT TT | 531, 532 |
| chr13 | 31575060 | 31575309 | TGC TAC AGG GAA AAT GGT CT | GAA CAA GTA CAA CCG TGC AG | 533, 534 |
| chr13 | 31641685 | 31641934 | TCC ACT GCT TAG TTT GCC TT | ACA AAT GCC CCA TAT CAA CC | 535, 536 |
| chr13 | 31718167 | 31718416 | ACA GGT GGG GAG AAA AGG TA | GGA AAG AGG CCT GGA GTA AT | 537, 538 |
| chr13 | 31723797 | 31724044 | CTG CCA CTA CTA CAC AGC TA | TTT CCA CTG GAT GTC GTC AT | 539, 540 |
| chr13 | 32249897 | 32250146 | ATG GGT CTC TGG AAT GCA TG | AGG ACA AAG TTT CAG CCT CT | 541, 542 |
| chr13 | 32296888 | 32297137 | AGT TCT CCA CAG CAC ATC AT | ACT CAG GAC ACG ACT TCA TAC | 543, 544 |

FIG. 2 CONTINUED

| chromosome | start | stop | forward primer | reverse primer | SEQ ID NOs: |
|---|---|---|---|---|---|
| chr13 | 32311823 | 32312072 | TCT TTC ATC TCA GCT CTG CA | ACA TCT TTG GCT CAC TGG TT | 545, 546 |
| chr13 | 32316395 | 32316644 | CCG AAC AGT ATT TTG AGG GG | TCA CAG TGG GCT TCA TTC AG | 547, 548 |
| chr13 | 32321163 | 32321412 | TTT GGC TGT TTC CTG TTT CC | AGC TGG AAT CTA TGT AGG ATG G | 549, 550 |
| chr13 | 32348262 | 32348511 | ACC TAA CTT GCC TTG TCC TT | CTG CGG AAG GAT CTA GTC TT | 551, 552 |
| chr13 | 32565108 | 32565357 | ACA GGA GAA CAA GCA GCA TA | TGA GAA GTA TTC AGC ATT TCC C | 553, 554 |
| chr13 | 32578964 | 32579213 | CAG CCT AGT ATA TGG GAA CGT | CAC TCA CGG ACT TTT AGG C | 555, 556 |
| chr13 | 32584041 | 32584290 | ACC CAT ATG TAG TAT CGC TCT TG | CCT CCA ACT TCC ACT CCA ATG | 557, 558 |
| chr13 | 32596887 | 32597136 | TAT GGG TTT TTC TGC TCC ACT | TCA CAC GCC AGG TTA TTA CA | 559, 560 |
| chr13 | 32651705 | 32651954 | AAA TGT GAG GGA GAG TCG TC | AAG TGG GTT TGC AGT TTG GA | 561, 562 |
| chr13 | 32760468 | 32760717 | GCA GGA CCC TTC AGC ATT A | ATG TAC GTG TGT GTC CAT GT | 563, 564 |
| chr13 | 32829312 | 32829561 | GAC TGG ATG ATG CAA AGG TG | AGG CGG GTT GGT CAA TAA TA | 565, 566 |
| chr13 | 32852622 | 32852871 | AAC ATT TGC AGG GGG ATC AA | CCA CAA ATC CCA TCA ACA CA | 567, 568 |
| chr13 | 32872003 | 32872252 | AAA GAT GCC TCC TTG TGT CT | TTT CAC AGT AAC ATC GGC AC | 569, 570 |
| chr13 | 33535420 | 33535669 | AAG TTA TCT GCC CAG GGA AA | CTG ACA GCC TGC ATT TGA TT | 571, 572 |
| chr13 | 33634729 | 33634978 | TCC TGG CTA GTT TTG CTG AA | TTT CCT GGA GTA AAG CGA TCT | 573, 574 |
| chr13 | 33660356 | 33660615 | CTC CTT GCT TGC CTT TAC AC | CCC ACA ATC ACC CAT CTC TA | 575, 576 |

FIG. 2 CONTINUED

| chromosome | start | stop | forward primer | reverse primer | SEQ ID NOs: |
|---|---|---|---|---|---|
| chr13 | 33742309 | 33742558 | AGC CTT AAT TCC CCA TGC AT | TAT CTC ACT CCA CAG CTT CC | 577, 578 |
| chr13 | 33760763 | 33761012 | TTT TTC TGT GGA GTG TGG CT | ACA GGT AGT TTG GTG GTG TC | 579, 580 |
| chr13 | 33787480 | 33787729 | AAA GAG TCA ACC ATG CAC TG | GCT GTT GAA TGC CAG AAC TT | 581, 582 |
| chr13 | 33803219 | 33803468 | GGT GAA GCA GCC TGA ATA AA | ATA GGG TCG GTT TTG GTC TG | 583, 584 |
| chr13 | 33925858 | 33926107 | TCT TTG TAC CAA GCT GCC A | CAT CAT CCC TGT CAT TCC CA | 585, 586 |
| chr13 | 34286418 | 34286667 | GCT TCT ACT TTC CCC TCC AG | GTG GGC TAA GAA AAC ACC TC | 587, 588 |
| chr13 | 34301780 | 34302029 | AGA AAA GCC AAC CTC CTC TT | ATT GTG GTT TGT GGC ATG TG | 589, 590 |
| chr13 | 34380783 | 34381032 | CCA GGG TAC TAA AAG GGG AC | CCA GAT TCA GCC TGT ATT CC | 591, 592 |
| chr13 | 34504924 | 34505173 | TTG TGG GTC AAT GTC AAC AC | GCC CAT GGA AGT AAA CAG TC | 593, 594 |
| chr13 | 35532835 | 35533084 | AGA AAA GGT GGA GGA AGG GA | AGG TTT GAC ATA ATA GTG CTG C | 595, 596 |
| chr13 | 35538772 | 35539021 | GGA GTT GTT TAC AGG TGG ACT | AAT CCT TTC CCC ACT CAC TG | 597, 598 |
| chr13 | 36233165 | 36233414 | TAG CTT CCA ATT CAC AGG TCA | CAC AAA GCA GTT CCA TGT CC | 599, 600 |
| chr13 | 36343466 | 36343715 | TTA AAT GCG CCA AGT CCC TA | GGA CAA TTT CTC ACT TGC CA | 601, 602 |
| chr13 | 36348003 | 36348252 | ATT TCC TGG GTC AAG CTC TT | AAG GGG TGT TGT TAG ATG CT | 603, 604 |
| chr13 | 36380590 | 36380839 | CTT GGA CCA GGA ATG CTC TA | GCA TCA CAC ACA GCA GAT AC | 605, 606 |
| chr13 | 36386774 | 36387023 | AGG CAG TCA GAT CCA CCT AT | AAA ATG TCC GTC CCA GAT GA | 607, 608 |

FIG. 2 CONTINUED

| chromosome | start | stop | forward primer | reverse primer | SEQ ID NOs: |
|---|---|---|---|---|---|
| chr13 | 36410707 | 36410956 | AAA ATT GCC TGC TGT TTG GA | GGG GGA AAA TGT GTT GTG TT | 609, 610 |
| chr13 | 36427833 | 36428082 | GCA CCA TCA TGA AAC CTC CT | AAC TGT TAG CTT CTC CAC CC | 611, 612 |
| chr13 | 36445018 | 36445267 | ATA GGC CAG TCT CAG GTA GA | CGA GTG TAG GTT CCG GTT TA | 613, 614 |
| chr13 | 36451093 | 36451342 | AGA TTG CAG CCT ACC CAA AG | AGA ATG CCC ATT TCA GGA GT | 615, 616 |
| chr13 | 36568336 | 36568585 | TTG ACT GAA GTG TTC CAG GT | ATA TGT GGT TTG AGG TCA GCT | 617, 618 |
| chr13 | 36578882 | 36577131 | GCT TCT TTC AAC CAT CCA CC | GGC TTT GGT CAC ATG GAG A | 619, 620 |
| chr13 | 36663599 | 36663848 | GCA GCA CTC AAC TAT TCC AC | TGA GGC AAG ATT CAG TGA CT | 621, 622 |
| chr13 | 37595672 | 37595921 | CAG GAG TTA TGG CAC CAG TG | ACT TCA TCT TGA CAG CAG CT | 623, 624 |
| chr13 | 38283224 | 38283473 | GAG AGT GTG GAG GCA GAA AA | CAC TTC CTC ATG ATG TTT TGG A | 625, 626 |
| chr13 | 38320894 | 38321143 | GCC CAA CTT ATT TTC CAG CT | GGC CAG CCC ACT TAT TTT TG | 627, 628 |
| chr13 | 38361974 | 38362223 | TCA AGC CCC TTA GAT TGA ACA | CTC AGG GTG GAG TTT CAA AC | 629, 630 |
| chr13 | 38380696 | 38380945 | GCT GGG CAT GTA GAA CTC AA | GAT CTT TCT TCC CCT CCT CC | 631, 632 |
| chr13 | 38789453 | 38789702 | GGG AAA TTG TCA AGG GCT TT | TGT ACA TCC ACC ACT TGT TTG | 633, 634 |
| chr13 | 39009512 | 39009761 | CTT AGT TGC TGT TGT GCT TCT | AGC GGT AGT AAG AAG GCA AA | 635, 636 |
| chr13 | 39096011 | 39096260 | AGT TGT AGC TGT ATC TGG GT | AGA CAG GTG ACC ATT TTC CC | 637, 638 |
| chr13 | 39202882 | 39203131 | AGC TGA GTC ATG TTT AAG GC | TGT GGA ACT TTT GAG CCA GA | 639, 640 |

FIG. 2 CONTINUED

| chromosome | start | stop | forward primer | reverse primer | SEQ ID NOs: |
|---|---|---|---|---|---|
| chrX | 44044660 | 44044908 | CAA TTC AGA CTT TGC CCA AAC | CAT AAC GAA ATA GGG CCT TCC | 641, 642 |
| chrX | 44805572 | 44805821 | CAA TCA TTC CCA CAG TTC CAA | ATT TCT GCC TCT TCT CTT CCC | 643, 644 |
| chrX | 80622102 | 80622351 | CTG TGA TGG TCC ATT CAA GG | TCA TCA AGT CAC CTC TCC AC | 645, 646 |
| chrX | 81576088 | 81576337 | TAG CTG GAA ATT GCA AGG AG | TGG AAA ACT AGA CAG CAG CC | 647, 648 |
| chrX | 83458870 | 83459119 | TCT GTT CAC CTG AGC CTT T | GGA AAG GGG AAA AGG TGA CA | 649, 650 |
| chrX | 83461989 | 83462238 | TAA CTT GGA CTG TGA ACC CA | CTG TCC TCT GTC CCA CAT AA | 651, 652 |
| chrX | 83972195 | 83972444 | CGC AAC AGG ATG AAG GAA AT | TTT CTG AGT CCA TTC CCC AT | 653, 654 |
| chrX | 83973091 | 83973340 | GAC TCA CAC TCT GAA AGC CT | GGC CAT CCT GAT ATC TTC CA | 655, 656 |
| chrX | 84308155 | 84308404 | AAT TTA GGT AGC ACT GAC CCC | CAG AGA GAT GCA GAG GTT CA | 657, 658 |
| chrX | 84412933 | 84413182 | CTG GGG AAT TAG GAA GCA GA | TGT GTG TGA GCT AGC TGA AT | 659, 660 |
| chrX | 84530826 | 84531075 | ATG ACA AGG CTG GCT CAT C | GGT TTC CCA TCC TAC CAC AT | 661, 662 |
| chrX | 84531356 | 84531605 | TTA GTT TTG GCA TGT GGT GG | GGT GCT TTT GTT GCC TTA CT | 663, 664 |
| chrX | 84561384 | 84561633 | TGG TGA GGG AGT GTT CTT TT | ACT AGA AAG CAG GGT ACA GT | 665, 666 |
| chrX | 85583338 | 85583587 | TCA TTG GGG GAG TCA TTC AC | GCT TTT TCC AAC TTC TGC TG | 667, 668 |
| chrX | 85584098 | 85584347 | GAA GTG GTG TGA TGA GGG TG | CAA CAG ACA AGT CAC CTC CT | 669, 670 |
| chrX | 85643367 | 85643616 | AAG TTA GGC CCT GTT AAG CA | GGT TCT TCC TGG ACT TCA AA | 671, 672 |

FIG. 2 CONTINUED

| chromosome | start | stop | forward primer | reverse primer | SEQ ID NOs: |
|---|---|---|---|---|---|
| chrX | 85643847 | 85644096 | TGT TGG TCG GAG TCA GAA AT | GAA AGC AGT AGT TTC AGG TGT | 673, 674 |
| chrX | 85644765 | 85645014 | GTA AAA GAG GTT GGG ATG CC | TGA AAG ACT CTG TTG CCA TG | 675, 676 |
| chrX | 85682212 | 85682461 | CGT TGG ACA TGG ATC ATA CC | CAC TAC ACG CTC AGA ACA AA | 677, 678 |
| chrX | 85715710 | 85715959 | TCA CAA CAA GGG AAA TAG CCT A | AAG GCA AGC AAT AAT GAG GC | 679, 680 |
| chrX | 85764768 | 85765017 | TAG TCA GGT AAA CAA CGC CT | GGA CAG TCT GTG AAA ATT GCT | 681, 682 |
| chrX | 85988749 | 85988998 | TCT GTT TCT TGT TTG GCT GAG | ACA AAC AAC CCT TAA TGC CC | 683, 684 |
| chrX | 85989214 | 85989463 | ACA TAG GTC ACA CAA AGG GT | TGA AAC AGT GAA TCC GCA AT | 685, 686 |
| chrX | 85997574 | 85997823 | GTG TGA CAC TTT TCT GCC TT | AAG GGA AAT GTG GAT GCA GTA | 687, 688 |
| chrX | 87223841 | 87226090 | CTG GAA ATA GAA GGC CTT TGC | TTG AAG GGA AGC GGA AAG T | 689, 690 |
| chrX | 91517109 | 91517358 | TCT TGG TCT GGG AAT AAG CC | ATT TCC AGC TAA TGA TGC TCC | 691, 692 |
| chrX | 91517578 | 91517827 | TGC CCC TAT GAA CAA CAG AA | GCT CAC TTA CGC ATT AAC CA | 693, 694 |
| chrX | 94601042 | 94601291 | TGA ACG TCT TGC TTA CCC AC | ACA GGC AAA ATT CAG TTG GA | 695, 696 |
| chrX | 95282210 | 95282459 | GAA GGA AGG CAG AGG TCA A | AGG CTG AAT CAC GTC AAA AC | 697, 698 |
| chrX | 95700693 | 95700942 | CTT CCA CAA AGT CCT GCA AC | CCT CGT TCA CAT TTG ACG C | 699, 700 |
| chrX | 96016317 | 96016566 | ATG TGA ACC ATT GAG AGG CA | TGT CTG GGT TCA ACT GTT TG | 701, 702 |
| chrX | 96474722 | 96474971 | AAG AGA AAC TAC CCT GGC AA | ATT TTG CAT GCC TGT TGA GA | 703, 704 |

FIG. 2 CONTINUED

| chromosome | start | stop | forward primer | reverse primer | SEQ ID NOs: |
|---|---|---|---|---|---|
| chrX | 96475190 | 96475439 | GCA TGT AGT TCA GTT CAG GC | GCT CTC CTC AAA ACC CAA GT | 705, 706 |
| chrX | 96522258 | 96522507 | ATG AAA TGT AAT GGG GTG CG | CTT AAT GAG GGG GCA CAA AG | 707, 708 |
| chrX | 96685785 | 96686034 | TTT TGG CAG TGA TGA CCT TG | TTT TCG TCC AGT CTT CCA CC | 709, 710 |
| chrX | 98226881 | 98227130 | TTC TTG GCT TTT CTG ACC CT | TAC AGG ACC GTC AGT GAG AG | 711, 712 |
| chrX | 98227467 | 98227716 | TTG AGA AAG ACC CCA ACA GAA | TTA GCT ACT GAC GCT TCA CC | 713, 714 |
| chrX | 98314697 | 98314946 | GAA AAT AAC ACA GTA GGG ATG C | GCA CAG ACA ACA TGC TAG TT | 715, 716 |
| chrX | 98331718 | 98331967 | GAA TGG AGA GGC AGT TTT CA | TTA GTC TGT TCA CTG GCA CA | 717, 718 |
| chrX | 102986351 | 102986600 | CAC CCT TTT CCT GTT TTG CA | CTT ATC AGC AGG GCA CAG T | 719, 720 |
| chrX | 112117885 | 112118134 | AGA AGA AAC TTG CAG TGT TGG | TTG CAT CAA ACA AAG CCA CA | 721, 722 |
| chrX | 116461543 | 116461792 | TGC AGC ATT ATT CTT TCT GGG | GAG AGA CAA GTC ACC CCT TC | 723, 724 |
| chrX | 116746667 | 116746916 | ACA CAC ATA TTA GGG AAC AGC | AGT CAA CTA CAA ATG GGG GA | 725, 726 |
| chrX | 117121287 | 117121536 | GAG TGT AGG TGC TTG GGT AT | GTG CCA AAA TCA ACG AAA GC | 727, 728 |
| chrX | 117494627 | 117494876 | CCT TAG AAT CCT AGC GCC TT | AAG GAG GGA GTA CAA AGT GAG | 729, 730 |
| chrX | 118400460 | 118400709 | TCA TGA GGT TGC CAG TGT TT | ATC ACA TTT TCA GCA CGA GG | 731, 732 |
| chrX | 119760145 | 119760394 | CCC CAT ACA TCA TCA CAT GC | CAG GGA GGG ATG ATT TGG AA | 733, 734 |
| chrX | 120436725 | 120436974 | GGG TAA TGC TTT CTT GGG GA | AGA ACT GAG AGG GGA GCA TA | 735, 736 |

| chromosome | start | stop | forward primer | reverse primer | SEQ ID NOs: |
|---|---|---|---|---|---|
| chrX | 120437307 | 120437556 | AGT TGA GAA GGG AAG GCA AG | CAG TCA CCA ACA AAG GCT TT | 737, 738 |
| chrX | 121854317 | 121854566 | CTC CTG GTG GCT TAT TTT TGA | TCC CCA TCT CCC TAA CTC AT | 739, 740 |
| chrX | 121855104 | 121855353 | TCT GGA TTT TGG CTA CTC ATG A | TTT TTC TGC TGC ATC CAA GG | 741, 742 |
| chrX | 122863038 | 122863287 | GTA GTC CTC CTT TGC CCT TC | ACT GTA CGC CAT GAA AAA CA | 743, 744 |
| chrX | 123203756 | 123204005 | GAC ATG CAC AGA TCG AAA CC | GGC AAA TCA AGT GAG CTG AC | 745, 746 |
| chrX | 123989030 | 123989279 | CGC ATT TGA CAA CAG GGA TC | CGT GGG TGG AGA ATT TCA CA | 747, 748 |
| chrX | 124394967 | 124395216 | AAG CCA CCT GTT CTC TCT CA | ACT TAG GTC AGT TGC TTG GT | 749, 750 |
| chrX | 125455385 | 125455634 | ATT CCA ACC ATT CCG ACA CC | GAC TTC ATC AGC ACG TAC TT | 751, 752 |
| chrX | 125500101 | 125500350 | AAA GAA AAT GGT GAA CGT GC | TGC AGG CAA AAT TAG CAT GG | 753, 754 |
| chrX | 125500582 | 125500831 | TGA TCA GGG CTT TAG AGG TC | GAC TTA TCT GCT TTC ACC CC | 755, 756 |
| chrX | 127973758 | 127974007 | ACT CCC TAT TGT TCT CCC CT | CCC CAT GAA CCT AAG ACC AT | 757, 758 |
| chrX | 128274367 | 128274616 | CTC CTT GAC AGA TGT GAC CC | TCT GGA CAT GTC TTT GCG TA | 759, 760 |
| chrX | 128274689 | 128274938 | TTT TGG AGT CTG AGC CAC AA | CTC CAG GAC ATC TCA GCA AT | 761, 762 |
| chrX | 128275238 | 128275487 | TTG AAG TCC CGT TGC TGA T | CCT CTC GTG TGG GAA ATG TA | 763, 764 |
| chrX | 128694864 | 128695113 | TTG GGG TCA GTT CTA ACA GT | TAT CTC TGG CTA CCT CCT GT | 765, 766 |
| chrX | 131201343 | 131201592 | TTT TCA CCA CCT CTT CCC TC | CCC CAT CCC TGT ACC AAA G | 767, 768 |

FIG. 2 CONTINUED

| chromosome | start | stop | forward primer | reverse primer | SEQ ID NOs: |
|---|---|---|---|---|---|
| chrX | 132160888 | 132161137 | ACC TGA CCA CAA GCT TTA CA | CTG CAG AGA TAT TCC ATG GC | 769, 770 |
| chrX | 133560531 | 133560780 | CAC ATA TTG GCG CAC AGT AC | AAA GCT GGG TTC TTA GGC TT | 771, 772 |
| chrX | 133847304 | 133847553 | GCC ATG CAC CGA TGA AAA AT | GCT GTT TTA GGG GCA CAT TT | 773, 774 |
| chrX | 133886077 | 133886326 | TTG TGA GGA GAT TTC TGG GC | AAG AGG CAA TGT GGA GGT TA | 775, 776 |
| chrX | 133886778 | 133887027 | CAC ACT AAG AGC ACT GGG AA | GCC CAA ACA ATC TGC CTT TTA | 777, 778 |
| chrX | 135279738 | 135279987 | ATG ACC TAG CAC ATC TTC CC | TGG CTT CAA ATA ACT GGG CT | 779, 780 |
| chrX | 135581031 | 135581280 | ACA TTT TCC CCA TTC CAT GC | AGA GCA CAC AGA ACA GAA CT | 781, 782 |
| chrX | 136941543 | 136941792 | GTC TGT CAA CCA CAC TTT GC | CTG GTG GAT TTC TCG TCA GA | 783, 784 |
| chrX | 138913313 | 138913562 | CTG TCT CTC CTC TTT TTG CCA AA | TAG GTG TTT GTG TGA GGC TT | 785, 786 |
| chrX | 138913920 | 138914169 | AGT AAC CTG CGA CTC TCA GT | GCC TCA CTG CTC CTA TCT TT | 787, 788 |
| chrX | 139857034 | 139857283 | TAG CAT TTA AGG AGT GGG CT | CTC TAG CAG CTG TTC CTC C | 789, 790 |
| chrX | 139857318 | 139857567 | GGC CTC CTC AGT GAT TTG AA | CGT CGT ATC TCT GGC TTT GT | 791, 792 |
| chrX | 141400062 | 141400311 | CTT TCT TTG CCT CCC CTG TA | GTC CCC AAC CTC ATC TTT CA | 793, 794 |
| chrX | 141408144 | 141408393 | ACT TCC ATT TGT GTC AAC GG | TCT TCA AAG ATG GCT GCA AA | 795, 796 |
| chrX | 141408548 | 141408797 | TCT TGC TTT GGG TTA GAG GG | AGT ATA ACC AGA TAG CCG TGC | 797, 798 |
| chrX | 142517923 | 142518172 | AAC CAC ACC TCC ACA AGA AA | TGT CCT CAG GGC AAT AAA GT | 799, 800 |

FIG. 2 CONTINUED

| chromosome | start | stop | forward primer | reverse primer | SEQ ID NOs: |
|---|---|---|---|---|---|
| chrX | 143466384 | 143466633 | CAA GAT ATG AGG GAG GGG AA | TTT GCT GCT TGA AGT GGA AC | 801, 802 |
| chrX | 147765073 | 147765322 | TCT AAC CTG GGC CCT TTC TT | GCT GCA ATG ACC TGA TTT CT | 803, 804 |
| chrX | 147869477 | 147869726 | TGC CCT TCC AGA ACT GTA AA | TCC CTC TCT CCT CCA AAT GA | 805, 806 |
| chrX | 147880766 | 147881015 | GCC AGG TCA CTT AAC AAA GC | TGC CAC AGT AGG TAT AGG TTG | 807, 808 |
| chrX | 147881811 | 147882060 | CAA TAA GGC GCC AAG TTC G | CCC TCG CCC TAA AGA AAC TA | 809, 810 |
| chrX | 151796091 | 151796340 | GTC ATC AGG GGA GCA AAT GT | CCC CTG AAT CCC TAC CTC AT | 811, 812 |
| chrX | 104102171 | 104102420 | AAC ATG CAA TCC CTG GAA TTC | TGT TGT ACA AGT GTC GAG CCA TTC | 813, 814 |
| chrX | 104124449 | 104124698 | AGT TGT TTC AGG ACA GGA TCT | ACC AAG CAA TCA ACT CAC TCT | 815, 816 |
| chrX | 104234605 | 104234854 | TCC TCC TGC CTT TAA TAA GCT | GCC CAA TTT GTC TAG CCA ATA | 817, 818 |
| chrX | 104235195 | 104235444 | TTA CAA GGC ATC TGA CAG GAA | CTA CTG ATC CCA AAG AAG GCA | 819, 820 |
| chrX | 104291380 | 104291629 | TTA CTG GTA GGT TTG AGC ACA | GTG AAA GGT TCT ATC TGC CAA | 821, 822 |
| chrX | 104291786 | 104292035 | GAG CTA CGT TCT TTC TCA TCA C | GGC ATA CCG AGC ATA CAT AGA | 823, 824 |
| chrX | 104647680 | 104647929 | CAC CAA TTA AAG TGT GCT GCA | CAC CTG TTT CAC CAA ATC ACT | 825, 826 |
| chrX | 104648691 | 104648940 | TCC CTT CCA AAG TGC CTT ATA | TCT CAT GCT CTG ACA GAC AAG | 827, 828 |
| chrX | 106886942 | 106887191 | TGG TTG GTT TGG GAT ACT TGA | TTG TCC TGT TTC TCT TGT GAC | 829, 830 |
| chrX | 3343487 | 3343736 | GAA CCC AAA TCG ATC ATG CAT | CAC AGG ACT GCA TGC CTA TTA | 831, 832 |

FIG. 2 CONTINUED

| chromosome | start | stop | forward primer | reverse primer | SEQ ID NOs: |
|---|---|---|---|---|---|
| chrX | 4013011 | 4013260 | AGA GTT AAA CGT GCA ATG TGG | GAC TCT CTC AGC ATC GAG TTT | 833, 834 |
| chrX | 5008870 | 5009119 | GTT CGT TGG TCA TAG TTG TTG T | CTG ATG GAA GGG CAT TAT CCA | 835, 836 |
| chrX | 5687782 | 5688031 | AGT TTA GCC AAA GGA TTC AGC | TTC TGG TTC CAT AAA TCC ATG C | 837, 838 |
| chrX | 5717003 | 5717252 | TCA ACC ATT TAG AAC CAC CTT G | GGG ATT ATT GTT GGC TAC TGA G | 839, 840 |
| chrX | 5808998 | 5809247 | AAT GTC CAC TTT AGC GGA GAG | AAT TGG TGA CCT AGG GAT CAG | 841, 842 |
| chrX | 5814187 | 5814436 | GGA GTA TTC TGT TCA TGT TGG G | GGG TTT GGT AAG GGA GAA TGA | 843, 844 |
| chrX | 5836574 | 5836823 | TTT CTA GAA TTG AGG AAG GGC A | AA GAC ATC CCA GTT ATG CAT TGT | 845, 846 |
| chrX | 5849776 | 5850025 | AGG ATA AGA CGA GGC ATC AAT | AGA TGG GAG GGA GAT TAG ACA | 847, 848 |
| chrX | 6895474 | 6895723 | TTC TGT GTT GAC ATG TAC CTC T | GAG TAG CAA CAA CAC ATG GAG | 849, 850 |
| chrX | 6965226 | 6965475 | TCC AAC ATT TCT CTC TGT CCC | TTC TCC TTC ATT AGC CAC ACA | 851, 852 |
| chrX | 6965573 | 6965822 | ATA ACG TGT ACT CCT CAG CC | AGT CTG CAC TGT ACT CTT CTG | 853, 854 |
| chrX | 7152743 | 7152992 | GCA CTT GGA GGA TGT AAA GAC | ACA AAT GGT TCA TGA TGG TGG | 855, 856 |
| chrX | 9529739 | 9529988 | TGT ATG CTT TAG GAC CCA GTT | GGT ACT CAC GTT TCA GTT TCC | 857, 858 |
| chrX | 9605323 | 9605572 | AAC TCC ACA GGA ATC TTT CTG A | GTT CAT TTC TAC AGT CCA GGC | 859, 860 |
| chrX | 9615158 | 9615407 | CAT TTC TCC TGG GAC CGA AT | CTC TCA CTG TGC TTA AAG | 861, 862 |
| chrX | 9766329 | 9766578 | TTC TGA AGC TGA CGA AAT TCC | CAA AGA ATT CCA CAG AGA TGG G | 863, 864 |

FIG. 2 CONTINUED

| chromosome | start | stop | forward primer | reverse primer | SEQ ID NOs: |
|---|---|---|---|---|---|
| chrX | 9793372 | 9793621 | GTT GCT TAG TCC TTG CTT CAC | TGA GCT ACA GAC AAG ATT GCA | 865, 866 |
| chrX | 9849298 | 9849547 | AGG TCA TTG GTC TGC AGT TAT | TCA CAT GGG ATC GAC ATA TGC | 867, 868 |
| chrX | 9850182 | 9850431 | AGC ATT TAG AGA ACA GCA GTC | CCA CAC AAT TTC CTG GCT ATG | 869, 870 |
| chrX | 10002581 | 10002830 | GTG TAA GAA GTG GTT GGG TTT | TCT TGC TTC TGG AGA GTT CTT | 871, 872 |
| chrX | 10301512 | 10301761 | AAA GGC AGA GCA GTG TAT TTA G | AGG TTA TGC AGA CTT CAG GAA | 873, 874 |
| chrX | 10354762 | 10355011 | AGA CAA GAG AAC AAT CAG GTG A | AAG CCA ATT CTG CCT CTC TAG | 875, 876 |
| chrX | 10375361 | 10375610 | CAA AGA AGC TCT AGG ACA GGA | TCC CTT CCT TAT TCT GGC AAC | 877, 878 |
| chrX | 10384260 | 10384509 | TGG TGG AGG AAA TCA ATG TTG | GCT TCA AAC ACT CTA AAG GGC | 879, 880 |
| chrX | 10398645 | 10398894 | CAC AAG GGA GGA AAC GTT CT | TGC CAT TAA TGA GAA GTG CTG | 881, 882 |
| chrX | 10572719 | 10572968 | TGA GAT TTA GTG CCA GCT AGA | TGG CAA TCC TGT TAA ACA ACT C | 883, 884 |
| chrX | 10579800 | 10580049 | AGG ATT AGT TTG GCT CCT CAG | CCC GAA CAT TGA TAA CAG AAG A | 885, 886 |
| chrX | 10580482 | 10580731 | CCT GCA CTA TTT CCT CAA AGC | GCA ACT CAG GAA AGA CTA CAT C | 887, 888 |
| chrX | 10627502 | 10627751 | CAA TTT CCT TCT CAC TGA GCC | TTA AGA AAG TAC CCA TCC TCC C | 889, 890 |
| chrX | 10645064 | 10645313 | ACG CTT CCC AAA TCT ATC TGG | GTC ATG CCT TAC AAC TTA GCA | 891, 892 |
| chrX | 10669664 | 10669913 | CTT ATT TGT GTG CCC AAT ACC A | AAT CTT TGC CAA GGT ATG AGC | 893, 894 |
| chrX | 10709674 | 10709923 | TTG CAG CAG GAA CAC CAT AAA | GCC ACT TAT ACC TCC AGA CAT | 895, 896 |

FIG. 2 CONTINUED

| chromosome | start | stop | forward primer | reverse primer | SEQ ID NOs: |
|---|---|---|---|---|---|
| chrX | 10710087 | 10710336 | CTG TTC ATG TTG CTA CCA CAG | CCA CAA TCC TGA ATG CCA TG | 897, 898 |
| chrX | 11139863 | 11140112 | CTG CCT TAG ATT CAC TTT CGG | CTG CAA GGT ACA ACA CAA GTC | 899, 900 |
| chrX | 11658912 | 11659161 | CCA TCT GTG AGG TCT TCT TTG | ATC TCT GTG CCA GCA AGT ATT | 901, 902 |
| chrX | 11681358 | 11681607 | TCC TTG GTT GTG TCG TAT TTA GCC | ATT GGG AAA CTG TCA CTG ATG | 903, 904 |
| chrX | 11686196 | 11686445 | AGA CTC AAC TCA CAT TGG CC | GCC CTA ATA GAG AAG CAA AGC | 905, 906 |
| chrX | 11686913 | 11687162 | GGT CTG ACT CTG TGG TTT GG | GGG AGC CAA TCA GAT AGA AGT | 907, 908 |
| chrX | 11687182 | 11687431 | TTT CAT TTC ATC CTG CCC ATG | GGG AAG TTG GGC TAT TTA ATG C | 909, 910 |
| chrX | 11917847 | 11918096 | TTC TGT TAT TCG CCA TCA GTC | AAC TGT GTA GAG CGA CCA AAT | 911, 912 |
| chrX | 12016424 | 12016723 | GAA TTG GGA ACT TGG GAA GC | CAG TAA GGC CAT GGT CTA GAT | 913, 914 |
| chrX | 12158815 | 12159064 | GAA CTT TGG AGA GGA CAG TGT | CTC AGA ACA TTT GCA CCT TCT | 915, 916 |
| chrX | 12485152 | 12485401 | AAC TGT CAT GTG TGT CTG CTA | ACC TGA TAC AAT GGA GCA TGT | 917, 918 |
| chrX | 12608017 | 12608266 | TGA TTC CTT CCA CCT ACC AAA | GGG ACC TAA ACT CCT TTG GAA | 919, 920 |
| chrX | 12724960 | 12725209 | GCC AAG GTC CAT TAT CTC AAG | TCT GCA GTG GTG TTA TCT AGT | 921, 922 |
| chrX | 12841791 | 12842040 | GAA CCT GCA TTG TCA TTC TCT | CAC TTA AGT TTC CAC GCC AG | 923, 924 |
| chrX | 12904558 | 12904807 | AAG AAC ATC AAC AAA CTC CAG G | GTA ATG GCG AGA GGT TAA AGC | 925, 926 |
| chrX | 12937788 | 12938037 | TCA ATT CTC TTT CAC ACG TGC | TTT AGG TAT CGA AGT TGG GTC A | 927, 928 |

FIG. 2 CONTINUED

| chromosome | start | stop | forward primer | reverse primer | SEQ ID NOs: |
|---|---|---|---|---|---|
| chrX | 12938100 | 12938349 | AGG TGC TGG ATC TTG AAT TCA | GAT AAG TTT GGA AGC TGC ATC A | 929, 930 |
| chrX | 12992266 | 12992515 | TCC CTC TAC CCG AAT CTC TTA | AAG CTC TGC CAT TGA CTT TAC | 931, 932 |
| chrX | 12995926 | 12996175 | TGG GTT TAA AGG ACA CTA GCA | CCC TAC AGA ACC GAG GAA TC | 933, 934 |
| chrX | 12997273 | 12997522 | CGA AGG TCA CAC AGT TTA GTC | TCA ATC TTT GCA TAC ACA GCC | 935, 936 |
| chrX | 13293562 | 13293811 | ATG TGC CTT GTT GAT TGA TGG | GTA GGT TTA CAT GGA CAG ATG C | 937, 938 |
| chrX | 13338207 | 13338456 | AGA TGG TAT GTC ACA AAG CAC | TCT TCT GTT TAG TGC TGT GGT | 939, 940 |
| chrX | 13340422 | 13340671 | ACA CTT TGG AGA GCT TCA GAT | CAA GTT CAT TTC TTC CCT GCA | 941, 942 |
| chrX | 13351532 | 13351781 | GTG CCC AGA ATT ATT TGT GTC T | TGC AGG AAT ACA TGG TAG ACA | 943, 944 |
| chrX | 13624857 | 13625106 | GCT CTC TTG TGG AAA CGA TTA | CAT AGG CCT TCA TGT CTC TCA | 945, 946 |
| chrX | 15525635 | 15525884 | AGT TTG TTT CTC TGG CCT ACT | TAT GAG GGT GCA CTA ACA GAT | 947, 948 |
| chrX | 15543469 | 15543718 | ACC ACC TCA AAG ATT TCA TGG | GGT GCT ACT ACT GGT GTA TGT | 949, 950 |
| chrX | 15543853 | 15544102 | GTC TTC ATC TAT TTC GTG AGC C | GCC ATG CAA TAT CAA ATC CCA | 951, 952 |
| chrX | 15848810 | 15849059 | TCA TCC CAG ATT CAG AAT GCC | GAA ACC AAA GAC TAG TGC AGC | 953, 954 |
| chrX | 16860721 | 16860970 | CGT TCA ATG AAG TCC CTT GTC | ATG ACT AAC ACT CTG CCA AGT | 955, 956 |
| chrX | 16851729 | 16861978 | TTC ACA AGA ACT CTG CTG GAT | AAC AAA TGC ATC CCA GAC AGA | 957, 958 |
| chrX | 18307677 | 18307926 | GAA GCC TTC TAG TGG GAC TAA | GCA GAG AGG AGT ATG TGG TAT | 959, 960 |

FIG. 2 CONTINUED

| chromosome | start | stop | forward primer | reverse primer | SEQ ID NOs: |
|---|---|---|---|---|---|
| chrX | 18608682 | 18608931 | GTT AGG GTC ATG GGT CAC TTT | ATG GGT CAT TCT ACG AAG CAA | 961, 962 |
| chrX | 19376384 | 19376633 | GCC TTT GTA GAG TGG ACT TCT | TGG TGT GTG TGG TGA TAA TTA G | 963, 964 |
| chrX | 20026004 | 20026253 | GGC TTC TTG ATA CTG CTT TCC | AGT GAC CCT CTG AAT AAC CTG | 965, 966 |
| chrX | 20627108 | 20627357 | AGG TGT GCA ATA CTC AAG GAA | TCA GCA AGT AAA CCT GAG ACC | 967, 968 |
| chrX | 21537202 | 21537451 | AAG GTC TTA GGA GTG AGG ACA | GTA CCT TCA CCC TCC AGA TC | 969, 970 |
| chrX | 21629967 | 21630216 | TCG TGC TAT TTC AGT CAG ATC T | TCA TCA AAT TGC CCA CTC CTA | 971, 972 |
| chrX | 21887062 | 21887311 | TGT CCA GCC GTA ACA TTT CAT | CAT CAG ACT GTC TTG CCT TTC | 973, 974 |
| chrX | 22202443 | 22202692 | AAT GGA CAT CTT TCA GGT CTG | CAT TCT TGC TGA CAT TTC CCA | 975, 976 |
| chrX | 23018625 | 23018874 | TCA AAT TGG GAT CGC ATT AGG | GAA GAT CAG GGT ATT GCT GAA A | 977, 978 |
| chrX | 23019006 | 23019255 | ATG CCT GGG TTT ATT CAT CTT G | TTT GTA GGT CAT TCA GCC TCC | 979, 980 |
| chrX | 24521525 | 24521774 | GGA GAA GTT TGG GTT TGA TCC | TGG CTA GGA TTC ACT TAG GAA A | 981, 982 |
| chrX | 24522047 | 24522296 | TGA TAG GAG CCA TCA GTT CTT | GCA AAC AGG GTG AAT TAT GCT | 983, 984 |
| chrX | 25401534 | 25401783 | AGC AGA TGT TGT TAG CTT TCC | AGA AGT CTG GGA AAC GAA GAG | 985, 986 |
| chrX | 25403300 | 25403549 | TTC TCT GTC ACT TCC ATG AGG | CAG ATG CTC CAT TAC TAG GTG | 987, 988 |
| chrX | 28689766 | 28690015 | CCA GTA ACT TAT TCT GCC AGA G | CAC ATG GAG AAA GGT GAA TCA | 989, 990 |
| chrX | 28693600 | 28693849 | TGA GAG ACA AGC TGC ATT ACA | TCC CAT CCA ATA CTG CCT TC | 991, 992 |

FIG. 2 CONTINUED

| chromosome | start | stop | forward primer | reverse primer | SEQ ID NOs: |
|---|---|---|---|---|---|
| chrX | 28717026 | 28717275 | GCA CAG AAA TTA CAG TTC ATG G | TCT GGC TCA AAG GAT CAC ATG | 993, 994 |
| chrX | 28720131 | 28720380 | GCT CTC GTA TCT GAC AGT GAA | AAG ATC CCA TTG ACC CTG AAT | 995, 996 |
| chrX | 28808128 | 28808377 | CAG GCA TCT TGG TTT GTA GTG | CCA CAG GCT CTC TAG AAC TAA | 997, 998 |
| chrX | 28824813 | 28825062 | CGT GAT GAA CAG TGA TGA CTT | TTG AGA GGG TTT ACA AGG TCC | 999, 1000 |
| chrX | 28825844 | 28826093 | CGC CAT TTG TTC TCC TAT TCA | CTT CTC CTA CTC TGC ATT CTC A | 1001, 1002 |
| chrX | 29487025 | 29487274 | TTC GTT AGC TAC TGG GTA CTC | GAC ATT AGT GGA TTC AGG CCA | 1003, 1004 |
| chrX | 30847194 | 30847443 | CCA CCC TTT ACA CCT ATC CAA | GCT GAA GTG GAG GCA ATT AAC | 1005, 1006 |
| chrX | 32660941 | 32661190 | AGA GTG CAC AAA GGA GAA GAC | TAT AAC TGT TGA GTC TGC CCA | 1007, 1008 |
| chrX | 32949975 | 32950224 | TCT ACT GTG TCA AAG CAG ATT G | ACT GAG CTT ACA TTC ATG CAC | 1009, 1010 |
| chrX | 35971182 | 35971431 | TTC TTC CTA GCC TTC CTT TCC | GCC ACT TCT TCT GCA AAG AAT | 1011, 1012 |
| chrX | 35971544 | 35971793 | TCT CTG GCT GTG CAG TAA ATT | ACT TCC TAC GGA CTC AAA TCT | 1013, 1014 |
| chrX | 43599991 | 43600240 | AAA CTC CCA GCT TTA ATC CCT | GGC TCT CAT TAC AAT TGG CTG | 1015, 1016 |
| chrX | 43600262 | 43600511 | AAG AAT GGG TGA ATT GCC AAG TCT | ATT GCT TTC AGT GGT GGA TTG | 1017, 1018 |
| chrX | 43807492 | 43807741 | GGA AAC TGA ATT GCC AAG TCT | GGA ATG AAA CAG AGG AGT CCC | 1019, 1020 |
| chrX | 63137429 | 63137678 | CTC CCA ACT TTT ATG CAG CC | AAG ATG CTA GAA ACC CAC AAG | 1021, 1022 |
| chrX | 63137928 | 63138177 | GCT CAG GGA ATA TCT TGG GAA | AAT GGG TGG GTT ACA GAG AG | 1023, 1024 |

FIG. 2 CONTINUED

| chromosome | start | stop | forward primer | reverse primer | SEQ ID NOs: |
|---|---|---|---|---|---|
| chrX | 74269728 | 74269977 | ACA TTC AGC AAG TAG GAA GGA | GCA TTT GGA CAT GAA CAA GC | 1025, 1026 |
| chrX | 74270926 | 74271175 | CCC AGA AGA GCA GTA ACA AC | CAT TGG TGG GTG GAT AGC TG | 1027, 1028 |
| chrX | 74282022 | 74282271 | GAA AAA GGG GGA TAG GCA TT | ACC AGG AGG AGA AAA GCA AA | 1029, 1030 |
| chrX | 74329664 | 74329913 | CCC AAC AAC TGC AAT AAA AGG | CGG AAA ACA AAC CCT GAA GT | 1031, 1032 |
| chrX | 74344769 | 74345018 | ACC GAA ATT GCT TGC TCT TA | ACC TGC ATA TTG AGC CAT AC | 1033, 1034 |
| chrX | 74741441 | 74741690 | CCT TAG TGT GAC AGG ACA GG | TGT TCT TTC ACT TTT AGC CCC | 1035, 1036 |
| chrX | 76192017 | 76192266 | CCA AGA CAA CTA GGC CAA TG | TTT CTA GAA CCC TCA GCA ACT | 1037, 1038 |
| chrX | 76194203 | 76194452 | GAA GAG ATG ATG CAA AAG AGC | CCC CCA ACA GTT TTT AGT GGT | 1039, 1040 |
| chrX | 76221949 | 76222198 | TCC AAG CAA GGG ATC TCT TC | AAG GCA AAA CAC TCC CTT TT | 1041, 1042 |
| chrX | 76226569 | 76226818 | GAA TGG TCA GGG AAG GGT TT | CAG TGA TTG CCT CTA GAA AAG G | 1043, 1044 |
| chrX | 76234682 | 76234931 | AGT CTT CAG CCA TCT TCC TG | CTA AGC AGA TTG AAG CAG CT | 1045, 1046 |
| chrX | 76308591 | 76308840 | GCA TTT CCA GGC TTT ACA AGT | TGT CCC CAG GCT TAA GAA TC | 1047, 1048 |
| chrX | 76647025 | 76647274 | CTC TCT CTC CCT GGT CAG AT | AGC CAG AAT AAG CAA CTG TC | 1049, 1050 |
| chrX | 76711476 | 76711725 | CAG CAA TTC TCA GGC TCA GA | TTT CTC CTA TCC CAG CTT GC | 1051, 1052 |
| chrX | 76759387 | 76759636 | TCT GAA ACA AAG CCT CCT TAG | AGT ACA GAG GAT AAC AAG GGT | 1053, 1054 |
| chrX | 76778190 | 76778439 | AGG ATA AGG TTT CCC ATG CTC | CTC CCA TCA CCC TCT CT | 1055, 1056 |

FIG. 2 CONTINUED

| chromosome | start | stop | forward primer | reverse primer | SEQ ID NOs: |
|---|---|---|---|---|---|
| chrX | 76778847 | 76779096 | ATG TAT CTG AAG GAG CTC TGC | GGA ATG CCT AAA CCA TAC TGT | 1057, 1058 |
| chrX | 76875971 | 76876220 | GGC CTT CAT CAC AAA CAA CA | AGT GGT ATT TCA ATG CTC TAC C | 1059, 1060 |
| chrX | 76923678 | 76923927 | TGT GTC CCA TCT ACA AAG CC | GCA GTA CAT CGT CCT GGA A | 1061, 1062 |
| chrX | 76937441 | 76937690 | TCC TTG AAC TCT TTC CAA GC | CCT GAG CGA GAA GAA ATT TGT | 1063, 1064 |
| chrX | 76938848 | 76939097 | TGT TTT CCT GTC CAA GTC CA | GGA ACT GAA CAA GAA GTG GAG | 1065, 1066 |
| chrX | 76939481 | 76939730 | CAG CAT CCA TCG CTC GAA A | ACC TAC TCT TAT TCC GCA CT | 1067, 1068 |
| chrX | 76949897 | 76950146 | GGT ATT GGT GGG GGA AAT GA | TGA CAG CCT CTC TCT TCA AT | 1069, 1070 |
| chrX | 76951314 | 76951563 | GCA CTG CTG TAA AAG ATC TAT GAG | TGT CAC ATA CCT CTC AAC TGT TG | 1071, 1072 |
| chrX | 77040328 | 77040577 | ACT CAA AGG CAC ATT TCG C | GCT GTT TTT CTG TGT GCT TC | 1073, 1074 |
| chrX | 77168344 | 77168593 | ATT CTA TTC CGA TCA CAG CCT T | ATG TAT TTC CTT TAG CGC CC | 1075, 1076 |
| chrX | 77634270 | 77634519 | CTA CCT GAC AAA TGG AGC TT | AAT TTT GCA AGA CTT CCG GT | 1077, 1078 |
| chrX | 78176076 | 78176325 | GAA ATG GCC ATG TGT ACT GAG | TCC CAG TTG TGA ACA TTT GC | 1079, 1080 |
| chrX | 78176555 | 78176804 | GAA GCC TCT CAA GCT ACA AG | ATG GGT TTT TGC ACA GAT GAC | 1081, 1082 |
| chrX | 78178901 | 78179150 | GAA TGA GAT TAG GGA GCA AAG T | GGG AGT CAG AAG GAG GTC A | 1083, 1084 |
| chrX | 78208245 | 78208494 | GGA AGT AAG AAG AGT GCT GC | CCT CTT TTT GCA TGA ACC TGA | 1085, 1086 |
| chrX | 78290291 | 78290540 | GCT CCT GAT TGA AGA AGT GT | CCT TAC CCT TTC CAC TCA GA | 1087, 1088 |

FIG. 2 CONTINUED

| chromosome | start | stop | forward primer | reverse primer | SEQ ID NOs: |
|---|---|---|---|---|---|
| chrX | 78401753 | 78402002 | CTG CTC CTT TGT CTC CTG T | GAC TGG TAT AAT CTT GCC GTG | 1089, 1090 |
| chrX | 78403248 | 78403497 | TAA GGT GAG AGT GTG AGG AAG | TGT CTG CAT CTT GAT CTC TGG | 1091, 1092 |
| chrX | 78405536 | 78405785 | CCA GGG GAA CAT TTA CTC AGA | GGT TCC ACA GCA TTT GAG C | 1093, 1094 |
| chrX | 78411791 | 78412040 | AGG GTA CAT GTA AGG CAG CT | AGG AGC CCT TAA CTA TGG TG | 1095, 1096 |
| chrX | 78427326 | 78427575 | TTC TGT GGC ATT GTG TCT TG | TGG CTT GGG TAT TGC AGA TA | 1097, 1098 |
| chrX | 78430991 | 78431240 | CCC CAA ATT TAC CCC ACT CT | GGG GAC AGT AGA AGA TGA GT | 1099, 1100 |
| chrX | 78431372 | 78431621 | ATC CCT AGC ACT TTC AGG AC | AGT TGT TTC TGG ACG GAC TT | 1101, 1102 |
| chrX | 78437851 | 78438100 | TTA CCA ATC CAT CCA GCC TG | AGA ATT TCC CTG TCC ATA CCA | 1103, 1104 |
| chrX | 78526539 | 78526788 | AGA AGC TAA ACA GGT TGC CC | AGT GAG TGA ACT TGC CAT CA | 1105, 1106 |
| chrX | 78531686 | 78531935 | CAT AAG AGC ACA GCC AAG AT | GGC TTT TCT CTG CAC TGA TT | 1107, 1108 |
| chrX | 78996675 | 78996824 | TGT CCT GCC ACT TTT ACA TC | GCA AAG GAA ACA GGC TAA CTA | 1109, 1110 |
| chrX | 107682036 | 107682285 | GAG CTA AGC AGA ACC TAA GGA | ATG GCA GCT GAA TCG ATA TCT | 1111, 1112 |
| chrX | 107683930 | 107684179 | TTA AGC AAC AGG AAC CTA CCC | TAG GTG ATG GGC AAA TTC TCA | 1113, 1114 |
| chrX | 110366745 | 110366994 | GCC AAG GGT AAT CAT AGC AAC | GAA ATG CCT TCC CAC TTA CAA T | 1115, 1116 |
| chrX | 110367927 | 110368175 | TCA TAA TGA AAC CCT TGC TGC | ATT GGC AAA TGT ACC TGA AGC | 1117, 1118 |
| chrX | 110368330 | 110368579 | AAT CCT AGT GCA TGA GAC TCC | CAA TGA TTG CTC TTG TGC CAA | 1119, 1120 |

FIG. 2 CONTINUED

| chromosome | start | stop | forward primer | reverse primer | SEQ ID NOs: |
|---|---|---|---|---|---|
| chrX | 110443307 | 110443556 | TAC TGC CTG CAT CAT TAC CAC | AGC TGT CCT CCT CTC CAT ATA | 1121, 1122 |
| chrX | 110466084 | 110466333 | ATT AAC AAT GAG GAG CCA GGT | GGC GTT CAA GTT ACT CGA TTG | 1123, 1124 |
| chrX | 110537791 | 110538040 | GAG AGA TGG TTG AGA AAT GCC | TAG TGA CTA GCT TTG GAG AGT | 1125, 1126 |
| chrX | 110538060 | 110538309 | ACT ACA ACC ACC AAT TAC AGC | AGC CAA TGA TCC CTT ATG ACT T | 1127, 1128 |
| chrX | 110538444 | 110538693 | AGT GAC ATT TCC AAG GGC TTT | AAC TAA ACT GGT AGG CAA TCG | 1129, 1130 |
| chrX | 110575740 | 110575989 | GGA GAT GGG AAG ACG ATT AGA | CAA TCA GAC CAC AGG AAG GAA | 1131, 1132 |
| chrX | 110576099 | 110576348 | AGT CTT TCA GTC TTA CAT GGG T | GAT GTG TTT ATT GCC TGT GGT | 1133, 1134 |
| chrX | 110950649 | 110950898 | TAG TTT CTG TGA TCC TGG CAG | GCT CCT TTC ATA GTT TCA GGG | 1135, 1136 |
| chrX | 110971144 | 110971393 | TTT CTC CCA GCT GTT CCT AG | ACA CAC TGC AGT TCT CAC TAT A | 1137, 1138 |
| chrX | 121597454 | 121597703 | TAC GGA ACT TCG AAT CAA CTC | TGA ATC AAG TGA CAT GAC AGC | 1139, 1140 |
| chrX | 135558463 | 135558712 | TCA AGT CAC CCT CAT TGT AGG | TTC TTA CAG TCC TCA GCA CTT | 1141, 1142 |
| chrX | 135570815 | 135571064 | TGT AAC GTG GAT GTG AGA TTG | CCA CTA GGC TGC ACT AAT GTA | 1143, 1144 |
| chrX | 135760826 | 135761075 | TTG AGC TAA GTC TGC ATC ACT | CAC TAG CTT CTG TAA CTG TGT G | 1145, 1146 |
| chrX | 135831981 | 135832230 | CTA GAG AAA GCA ACG CCT AAG | GTC TCA CAC TGC TCA TTT CCA | 1147, 1148 |
| chrX | 136044394 | 136044643 | AGC ACC TTC CAT AGC TTC TTT | CAC TAG GGT TCA TCA GCT GTT | 1149, 1150 |
| chrX | 136318161 | 136318410 | GTG TCT TCT GAT GGC CAA ATG | CAA CCA ACA TTA GAG TGA CCC | 1151, 1152 |

FIG. 2 CONTINUED

| chromosome | start | stop | forward primer | reverse primer | SEQ ID NOs: |
|---|---|---|---|---|---|
| chrX | 136320360 | 136320609 | AAT CAG GTG AAA GGT ACC TCC | GCT GGT TGA GAG AGA GAG AGA | 1153, 1154 |
| chrX | 139380500 | 139380749 | CCT TCA CAA TTC AGG GAA CAA | ACA CCA GCC GAA TAC AGA TTT | 1155, 1156 |
| chrX | 139381074 | 139381323 | TGG ACC CAG TTC TAT GCA ATT | TGC TTC ATA CCT TTC TGC TTC | 1157, 1158 |
| chrX | 144897923 | 144898172 | AAT GAC CCT TAC AAC TCC GAA | ATT TCC CAT GCC TTT CAA CTC | 1159, 1160 |
| chrX | 144908837 | 144909086 | TTT GGG AAG TGA TTG TTG TGA AGG | TCT CTC AGT AGG CGT CTT TAA | 1161, 1162 |
| chrX | 144958353 | 144958602 | TCA GCT GCA TAG ACC TTG TTT | TGA CTG CTA CGC TAG ACT TG | 1163, 1164 |
| chrX | 144959377 | 144959626 | TCA TTT GTT CTC ATT ACG GGC | GGA TAG AGG AAA CCC AGG TG | 1165, 1166 |
| chrX | 145799354 | 145799603 | TTC TAC CTG GGT TCT CTT GG | GGC TCT TTC AAA GTA TCC AGG | 1167, 1168 |
| chrX | 145922717 | 145922966 | TAA CTT CCT GAG CAC ACA TCA | AGA CTT TCT TTG TTG CCT TCA G | 1169, 1170 |
| chrX | 146994477 | 146994726 | GGG TAA ATT CAG GAA TGC ACA | GCC TCA ACA ATT CAG TCC AC | 1171, 1172 |
| chrX | 146995311 | 146995560 | ATT TCT TCT GGT GAG TTT GCG | CAT AAG TTG CTG GAA GAG AAC A | 1173, 1174 |
| chrX | 147540977 | 147541226 | CCT CTT CCT GAC ATG TTG TTG | TCG ACT GCT TTA AGT GAA GGA | 1175, 1176 |
| chrX | 149764787 | 149765036 | GTT GGT GCC AGA TTG TAA CTT | ACC AGT GCT TAG TGT TTC TCC T | 1177, 1178 |
| chrX | 150808513 | 150808762 | GCC TGG CTC AAT AAT AGT CCT | CAA GAC ACA CAC AAA CAC ACA | 1179, 1180 |
| chrX | 150809248 | 150809497 | ATG TTG CCT TCT CTA CGT TTG | GGT AAG AGT TGC CCT AAT GTC | 1181, 1182 |
| chrX | 150942801 | 150943050 | GAG TGG AGC GCT ACC TTT AT | GCT TGG CTT CTC ACA AAT GT | 1183, 1184 |

FIG. 2 CONTINUED

| chromosome | start | stop | forward primer | reverse primer | SEQ ID NOs: |
|---|---|---|---|---|---|
| chrX | 79712826 | 79713075 | AGA ATG GGA AAT GGG AAG GA | GTT TGC CAG TAG AAA TGG GA | 1185, 1186 |
| chrX | 80374192 | 80374441 | CAC AAT ACA TGG GCT GCT TT | GTA AAG TGT TCA GAG GAC GG | 1187, 1188 |
| chrX | 80491243 | 80491492 | CCA CTC CAA CTC TGC TTT TAC | ACT AGG GAG AAG AAT TGG CAG | 1189, 1190 |
| chrX | 80514786 | 80515035 | GAT GTG GAT TGT CTT TGT TGC | CCA GTT CAT TCC AGC TTC CA | 1191, 1192 |
| chrX | 80553311 | 80553560 | AGC CTT TCA TTG CAC ATT TCA G | GAT CGC CAA CCT GTT TTA TAA G | 1193, 1194 |
| chrX | 104028154 | 104028403 | TCC CAC CAC AAG ACC AAT TT | GCT GTC AAA GTG GAG ATA ACC | 1195, 1196 |
| chrX | 104039199 | 104039448 | GAA GAT AGG TGG TGG AGT TCA | AAC GCT TCC ATC CAC CTA ATT | 1197, 1198 |
| chrX | 104101675 | 104101924 | CTG TTT GAA TGA AGT TGG CTG | ACC TGC CTG TCT TAC CAT TAA | 1199, 1200 |
| chr21 | 17021878 | 17022127 | TAT ACA TGG GTG GGA TTT GTC | GAT ACT TTC CTT TCT CCA GAT CT | 1201, 1202 |
| chr21 | 17046718 | 17046967 | TTT GTG ATG GAC CAT CTA ACC | GGC CGC AGT TTT TGA TTT AG | 1203, 1204 |
| chr21 | 17088576 | 17088825 | GAA GAT CTG GTG TCC CAC TA | TGG GAA GGA CGG TTT GTT A | 1205, 1206 |
| chr21 | 17134784 | 17135033 | ATC TGA AGA TCT CCG TGG TA | TGA ATC ATG CTG TGG AGA AC | 1207, 1208 |
| chr21 | 17161709 | 17161958 | ATG TAT GAA CCA TTT CCT GCT | ATA GAA GAG GTA CCC AGC AA | 1209, 1210 |
| chr21 | 17183683 | 17183932 | AGC ACA GAA TTG AAT GAA GGA A | CCC TGA CTA TGC TAA GTT GC | 1211, 1212 |
| chr21 | 17301983 | 17302232 | GCA TGA GTA AGG CTG AAG TG | TGC AAG CAA AAT GAA ACC AG | 1213, 1214 |
| chr21 | 17302814 | 17303063 | AAA GGC TTA TAT TGC TTT TGA ATC A | AAC TTA AAG TTT GAT GGG CAC T | 1215, 1216 |

FIG. 2 CONTINUED

| chromosome | start | stop | forward primer | reverse primer | SEQ ID NOs: |
|---|---|---|---|---|---|
| chr21 | 17336649 | 17336898 | TTG CTG TTG TTG GGA TCA AG | CAG CTG CTC CTT CTT TAG C | 1217, 1218 |
| chr21 | 17346228 | 17346477 | GCT TCT GCA TCC ACC TAT CT | TAT ACT GCC AAA GGT GAC CT | 1219, 1220 |
| chr21 | 17348050 | 17348299 | AAA AGC TGC CTA AAA TGC CA | GAA GCA TAA TGA GAA CCT CCA | 1221, 1222 |
| chr21 | 17351309 | 17351558 | AGT CAG GCA AGT TAG CAG AGA AA | AAC CCA ACT TGC AGA CAA TC | 1223, 1224 |
| chr21 | 17362239 | 17362488 | CCC ACA TTT ATC CCT TGT CC | ATC TGT TTG CTG TGT CAG AA | 1225, 1226 |
| chr21 | 17367713 | 17367962 | TGT CTG ATT CCA TCT TTC CC | TCC AGA TAT ATT CAA AAG GGA GA | 1227, 1228 |
| chr21 | 17506670 | 17506919 | CAG CCA CCA AAA CAC AAT G | AGG TTT TTA TCA AAG CCC CA | 1229, 1230 |
| chr21 | 17548792 | 17549041 | AAG GCC TGT TTT GTG TGT AG | GGG ACT TGA TGT TCT AAG CAA | 1231, 1232 |
| chr21 | 17591325 | 17591574 | ACA GCT CAC AGA TCT TTA AGC | CCT ACA TGA TAC GCA CAG TC | 1233, 1234 |
| chr21 | 17695933 | 17696182 | GGC ATT ATA AAG AGA TAG CTC CA | ACT GAA GCT GCC CAA ATC CA | 1235, 1236 |
| chr21 | 19087043 | 19087292 | TGT TTT TCC TTG CCC TGT AA | GTT TTT CTC TAC CCA GCA CA | 1237, 1238 |
| chr21 | 19178365 | 19178614 | TAA CCA GAT GAA TGA GGG CA | CTC TAA TTT GCC ACC CTC TTT | 1239, 1240 |
| chr21 | 22579319 | 22579568 | CAA CAA GCC AAA ACC ACA TC | GAA CGC TAA AGC TTT TCC CA | 1241, 1242 |
| chr21 | 22605212 | 22605461 | GTT GGT TCT TGA AGA CCT GA | TCT TTC TCC TGC CAA GTA GA | 1243, 1244 |
| chr21 | 22954667 | 22954916 | TGT GGT AAG TAG TCT CTA AAG A | ATA ACA CTG TCC TTC TGG GC | 1245, 1246 |
| chr21 | 22984832 | 22985081 | ACC AAA TTT CCA GAT CAC GG | GAG CCT ACT CTC TGA TAC GA | 1247, 1248 |

FIG. 2 CONTINUED

| chromosome | start | stop | forward primer | reverse primer | SEQ ID NOs: |
|---|---|---|---|---|---|
| chr21 | 22985386 | 22985635 | AAT GAA TGG TCA TGG CTC AC | CCA GTT GTT CAC TTC TCT GAT | 1249, 1250 |
| chr21 | 36076596 | 36076845 | GCC CTG AAG CAC ATT AAA GT | GCC TTA AAA CCA AAC TGT GT | 1251, 1252 |
| chr21 | 36169368 | 36169617 | GCC TCC AGG TTT ATG ACA AC | CTG GAC TTC AAT CAC CCA AG | 1253, 1254 |
| chr21 | 36789088 | 36789337 | CAG CTC TAT TCC CCT TCT GA | TGA ACA AAT TGC TGT GCT GA | 1255, 1256 |
| chr21 | 37939587 | 37939836 | CCT TGG AAG GGA AAG TTG AT | CCC CCT AAA TGA AAG TGG TC | 1257, 1258 |
| chr21 | 37959766 | 37960015 | GTC CCA CCC TGC TCT TAG | CAG AGA AGA TGC TGG AAT CCA C | 1259, 1260 |
| chr21 | 37983316 | 37983565 | CAG AGT AAG ACA GTG GGA CA | TGA GTG CTT GGA ATT TTG CA | 1261, 1262 |
| chr21 | 38559539 | 38559788 | AAG TGT GGT GCA TAA AGG AT | GGT TGG CTA CTT CAT GGT AC | 1263, 1264 |
| chr21 | 38751525 | 38751774 | CTG TAA GAA GGA GGG TTT GG | TCA CTG CAT TCC TAG AAC CT | 1265, 1266 |
| chr21 | 39173262 | 39173511 | GAG GTT GAT GAG AGG TAG GG | ATA ACT CAG GCA AAA TGG GG | 1267, 1268 |
| chr21 | 39285267 | 39285516 | AGC CAG GGA TAT TGT TGA AG | CCT TCT GCT CTC ACT TTA CG | 1269, 1270 |
| chr21 | 39330340 | 39330589 | CAG GTA AGT GTG TGT TCC AG | GGA TAC TAG CAG AGG TGG AG | 1271, 1272 |
| chr21 | 39442392 | 39442641 | TTG ATT TCC ATG CAG AAG GG | TGT ACA CAA TAT GCC AGG AAC | 1273, 1274 |
| chr21 | 39499219 | 39499468 | TAA TTT GGC CTT AGG GGT TG | GCA CTT GAG TTA TGG GAC T | 1275, 1276 |
| chr21 | 39541298 | 39541547 | TCC ATA AAA GGT GCT TAA AGC | TGT GAT ATG TAG TGT GTA TCA GT | 1277, 1278 |
| chr21 | 39563720 | 39563969 | TTG TAT CAC ACC ATC GTG GA | GAA TGT GTT CAA AGG AGG GT | 1279, 1280 |

FIG. 2 CONTINUED

| chromosome | start | stop | forward primer | reverse primer | SEQ ID NOs: |
|---|---|---|---|---|---|
| chr21 | 39584873 | 39585122 | ACT GCT GAG AAC AAT CAT GC | GAT GAA GGG GAT TAC GGG AA | 1281, 1282 |
| chr21 | 46530377 | 46530731 | GGT GTG GAG AAT TTG TTT GC | TTT AGG AAG CAG CAC AAG AA | 1283, 1284 |
| chr21 | 46534043 | 46534292 | TGA TAT TAG GCG GTG GCT TA | GAG GGT GCT GGG GTT ATC | 1285, 1286 |
| chr21 | 46535763 | 46536012 | TCT CAC CTA AAA TCT GGG GC | CCC GAA AGC ACT TAC CTT TT | 1287, 1288 |
| chr21 | 46537454 | 46537703 | AGG ACT GTG ACA CTT TAT CTT T | TTC ATG AGC TGC AAT GTG TT | 1289, 1290 |
| chr21 | 46542089 | 46542338 | ATG CGA GGT AGA AAA TGA GAG | TGC TAT GAA AAG AGG GAC CA | 1291, 1292 |
| chr21 | 46556856 | 46557105 | TGT GGC TTT AAG GTT CTG AAG | GTC CTG GAT CTA CAC GTG AA | 1293, 1294 |
| chr21 | 46564465 | 46564714 | TCG TTG CTA TTC TGC TTT GA | GTA AAT CTG TGT GCC AGC AA | 1295, 1296 |
| chr21 | 46567255 | 46567504 | TCC CTT TTG TGG TTT CTT GG | TAA AAG AGG CGT GTG GAA AA | 1297, 1298 |
| chr21 | 46572969 | 46573218 | TTG CCG CAC TCT TCA TTA AT | CCA GTA GCT TGT GAT GTG TA | 1299, 1300 |
| chr21 | 46605329 | 46605578 | ACT GGC TTC TCC TCA TTA GT | TAC AGG CCT CTG AAA GAT GA | 1301, 1302 |
| chr21 | 32134809 | 32135058 | ACT GAT TTG CCA TGT AGA GC | AGA GCA TGC TAG ACG TCT TT | 1303, 1304 |
| chr21 | 32148136 | 32148385 | GAA TGT CAT ATT GCC TGC CA | CTG GGC TGT AAT TAA GGC TC | 1305, 1306 |
| chr21 | 32165994 | 32166243 | TCA CTC GCT TAG AAT GTT GC | AAC ACC TGC ACA CTT TGA AA | 1307, 1308 |
| chr21 | 32174173 | 32174422 | ACC ATT AAC TTC CTG CAA ACT | AAT GAA CTT TGT GGG CTG AA | 1309, 1310 |
| chr21 | 32179882 | 32180131 | TAA AGC CCC ATA CCA GGA TT | CCA CAC TCT CAC TGG TTC TA | 1311, 1312 |

FIG. 2 CONTINUED

| chromosome | start | stop | forward primer | reverse primer | SEQ ID NOs: |
|---|---|---|---|---|---|
| chr21 | 32181384 | 32181633 | CCA AAA ATC ACC CAT ATG CG | CAC AGT GGA TAC CTC AGG AA | 1313, 1314 |
| chr21 | 32184463 | 32184712 | ATA ACC CAG GTG CTT CAA AG | CCA ACA CAG GAG GAA CTT TT | 1315, 1316 |
| chr21 | 32201994 | 32202243 | TCC ACA GCA GAA GTA ACG A | GAG AAA AGC CAA CAA AAA TGT G | 1317, 1318 |
| chr21 | 32208609 | 32208858 | AGG AAA GCT ATG AAG AAA GGG | TGT CAT TAC TAG AAG CAC CTT T | 1319, 1320 |
| chr21 | 32319600 | 32319849 | AGC TCC AGA GTG TCA GTA TT | TGG TGT GAG TTC AGG AGG GTT TA | 1321, 1322 |
| chr21 | 35034581 | 35034830 | TTG ATT TCC AGC ACT GAA CTT T | ACC ATT TCT GAC AGA ACA GA | 1323, 1324 |
| chr21 | 35060177 | 35060426 | TGT TTG ATT TTT CAG GCT GA | TGA TGC TTA AAC ACA TGC CT | 1325, 1326 |
| chr21 | 35070605 | 35070854 | CTG GTC ATT CCT GAG TGT CT | AAG GGA TAT GCA GCT TGT TC | 1327, 1328 |
| chr21 | 35093305 | 35093554 | TCC TGT TTT ACA CTT TTC TAA CTT T | GCT TTA AAC TAT GGA ACT GCT GA | 1329, 1330 |
| chr21 | 35094930 | 35095179 | ACC TCA ACC TGT TTT AGC AC | GTT GTC ATT CAA ATG TCA CCA C | 1331, 1332 |
| chr21 | 35099418 | 35099667 | CAG TGT GTG TCA TGC CAA AT | CTC AGA TTC CAG AGC CCT C | 1333, 1334 |
| chr21 | 35138457 | 35138706 | GGT CTA TGT TAA TCT TGG GCC | ACA TTG CTA GCA GCT TTT GT | 1335, 1336 |
| chr21 | 35152877 | 35153126 | AGC CAG TCT GTA TCT AAA GGT | ACT TGC CAA GAA CAG TAT CTG | 1337, 1338 |
| chr21 | 35157173 | 35157422 | ACT CTT GGG GTT TCT TCA GT | TTC CTT CTT CCA GGT GAA CA | 1339, 1340 |
| chr21 | 35161795 | 35162044 | CGA ACC AAA AGC AAA ATC CTT | TGT TTC TCC TTC ATC TGG TC | 1341, 1342 |
| chr21 | 35296082 | 35296331 | AAT CTA TGG AGG TCA CTG GG | TGT CAC CTT GCA GAT ACA GG | 1343, 1344 |

FIG. 2 CONTINUED

| chromosome | start | stop | forward primer | reverse primer | SEQ ID NOs: |
|---|---|---|---|---|---|
| chr21 | 35460331 | 35460580 | AGG TCC TTG TAG TTT GCT TG | ATT GTT CAC AGG GTC AAG TC | 1345, 1346 |
| chr21 | 35473022 | 35473271 | GTG AGA GCC AAT AGA GTG TG | ATG AGC CAG GAG AAT CAT CA | 1347, 1348 |
| chr21 | 35473971 | 35474220 | GCA TGG TGT GTG AAA GTG AT | CAT CAT TTC AAA GGG GCT CA | 1349, 1350 |
| chr21 | 35498164 | 35498413 | ATG CTG CTT TTG ACT GAT GT | TCT TCT CTA ACA CCC ACT CC | 1351, 1352 |
| chr21 | 35540943 | 35541192 | CGA AGC TGT ATT CCT GTC TC | ACC CTT ACC AAA GTA GCA TC | 1353, 1354 |
| chr21 | 35702965 | 35703214 | ATG GAC TAA CTG GAG AGC G | ATC ACG ACG CCT TGT TTA TT | 1355, 1356 |
| chr21 | 28574819 | 28575068 | ATG TCC TGC CAG TAA ACA CA | ACT TTC CTG CCA ACA ATC TC | 1357, 1358 |
| chr21 | 28586377 | 28586626 | TGC CAC TAA ACA CCT AAG GA | TTG ATA GTT GCA TCT GGG GA | 1359, 1360 |
| chr21 | 28597009 | 28597258 | TTG GAA ATT TTG GGG TCA GG | TTT GTT AAC TAA CGT GAT TCC A | 1361, 1362 |
| chr21 | 28616121 | 28616370 | TTC TGA CCT CCC TTA CTG AG | CCC ACT CTC CAT GTG TTC TT | 1363, 1364 |
| chr21 | 28631408 | 28631657 | TAT GTG CTT GCG ATG TGT T | TCC TGC TTC AAC TCA ATA CG | 1365, 1366 |
| chr21 | 28891355 | 28891604 | GAA CCT TAG GGC CAG TCT AT | ACC CCT CAT TTT CGT ATG TC | 1367, 1368 |
| chr21 | 28892223 | 28892472 | AGA ACC TGA TGT GTT TTC CTC | ACA GTT ATG GAG GAA TTG CG | 1369, 1370 |
| chr21 | 28919446 | 28919695 | ATG TGA GAG AAG CAA AAC CC | TCA AAC CTC TTT TAT CTG TCC C | 1371, 1372 |
| chr21 | 29012106 | 29012355 | GTA GTT GTC TTG AGG GCT TT | ATT TCA CGT AAC ACT CTG GT | 1373, 1374 |
| chr21 | 29021007 | 29021256 | CCT GGT CAA CAA CAT ATG GG | CTC TGG CAA AAC TTT CTG GAT | 1375, 1376 |

FIG. 2 CONTINUED

| chromosome | start | stop | forward primer | reverse primer | SEQ ID NOs: |
|---|---|---|---|---|---|
| chr21 | 29753618 | 29753867 | AGA ATA TTG CAT TTG GCC AGA | GCT TCT CAT GCT CAC ACT G | 1377, 1378 |
| chr21 | 29796479 | 29796728 | AAA GCT ATG CAA ATA GTG GCA | AAT ATG ACT TGC CCT TTT GAA | 1379, 1380 |
| chr21 | 29812165 | 29812414 | AGT TCC CAA CAG AGG CTA AT | TCA CAG CCA GTT ACA CAG A | 1381, 1382 |
| chr21 | 29813966 | 29814215 | AGT TAT AGG TGA GGA AGG GC | CTA CAG TGC AGA AGA AGA GTC CC | 1383, 1384 |
| chr21 | 29814951 | 29815200 | CAC TGC AAA AGA AGG AGG TT | TTG GTT TCA TGT GGC TTT GA | 1385, 1386 |
| chr21 | 29820028 | 29820277 | TCT CAA CAT CGC TGA TCT AGT | TCC TTC TCC CCA ACT TTC TT | 1387, 1388 |
| chr21 | 29825992 | 29826241 | AGG TAG CTG GAA AAG GAG AA | CTT TAG ATT CCA GGG CTC TTG | 1389, 1390 |
| chr21 | 29827616 | 29827865 | TGA AAT TGC CCA GAA TTG AGT | TGA AAG CGT GAA AAT CAG CT | 1391, 1392 |
| chr21 | 29841662 | 29841911 | ATT TTC CTG GAC TTC TGA CA | ACT CGA TCC CTA GGT AAT GT | 1393, 1394 |
| chr21 | 29884231 | 29884480 | TGT TAT TCC TCT TCC TGT CCA | ACA AGT GGG TAG GGA TGT TC | 1395, 1396 |
| chr21 | 29898255 | 29898504 | TAA CCA CAC AAC TAC AGC TT | GCA CAA GTT TTC AGG GAA TG | 1397, 1398 |
| chr21 | 30368230 | 30368479 | ATT CAA AAT GGG GAC GAG AG | GTG GAA AGT CTC GTC AGA AT | 1399, 1400 |
| chr21 | 30413906 | 30414155 | TCC CAG TTT GCT ACT CTG G | TCC ACC TCT GAG CAT AAC AT | 1401, 1402 |
| chr21 | 30415555 | 30415804 | TCT CAT TAT GTG AAG ATT GCT TTC | TTG ATC TTC ATC CTC CAC TGT CT | 1403, 1404 |
| chr21 | 30428953 | 30429202 | TTA AGA TTA AGC AGT CTT CTT GG | CCA AAC TGA CCG ACT TAC ACC | 1405, 1406 |
| chr21 | 30477650 | 30477899 | CAA CAG ATC TGA TTC TGC CC | CCA TCC CAC TTC TCC AGA TA | 1407, 1408 |

FIG. 2 CONTINUED

| chromosome | start | stop | forward primer | reverse primer | SEQ ID NOs: |
|---|---|---|---|---|---|
| chr21 | 30528161 | 30528410 | CAT GTG TTT CAA AGT TGG CT | CCA CCT TCC TGC TTA AAG AA | 1409, 1410 |
| chr21 | 30550132 | 30550381 | ACT ATA GCA TTA GGG TGA GGG | CTC CTT ACT TGC ACT GAG TT | 1411, 1412 |
| chr21 | 30580738 | 30580987 | GAG ATT TGG ACA TGC TTT CA | GGG AAA ACT TAC GGG AAC TT | 1413, 1414 |
| chr21 | 30600446 | 30600695 | CCC ACC ACC AGT TGT CAT C | TAG AAA TGT TTA GGG TGC ATG A | 1415, 1416 |
| chr21 | 30628668 | 30628917 | GCC ACT CAC TTC CTA GAT AAT | TAC CCC TCT TTT CCA TCT GC | 1417, 1418 |
| chr21 | 30660609 | 30660858 | ACA GTA TCT CAG GGC CTT AT | GCA TTT TGA CAG GAA AGT GG | 1419, 1420 |
| chr21 | 30680391 | 30680640 | TCA GTA GTT CCT CAG ATG CTA | TAG GGC CAC AGT TTC TCA AT | 1421, 1422 |
| chr21 | 30720214 | 30720463 | AAT GCA TGA AAG TCC AGG AA | GAA TGA GAA ATC TGG CAG GA | 1423, 1424 |
| chr21 | 30782462 | 30782711 | ACA TGC ACT CTT GTC TTA TGC | TCA GAT GCC TGA TGA CCA TA | 1425, 1426 |
| chr21 | 30810199 | 30810448 | CAC ATA TAC TGG CTT TCT GGT C | AAT ATG CAG TGG GTA GGA GC | 1427, 1428 |
| chr21 | 30849402 | 30849651 | GCA CAT GTC ATT AGC AGG G | GAC AAC AGC TGA CTT CCA TT | 1429, 1430 |
| chr21 | 30868525 | 30868774 | ACA TGC TCA ATT ATG GAG CC | CAC TCT CTG GAA CAA ACA CA | 1431, 1432 |
| chr21 | 30988776 | 30989025 | ACA AAG ACA GGA ATA GGG CT | GTT TTG AGG CGG TTT CAT GA | 1433, 1434 |
| chr21 | 31012406 | 31012655 | CAA TCT GCT GAC TTG CTT CTT TTC A | GGC ACT GAG GAA ATT CTG AGA C | 1435, 1436 |
| chr21 | 31032720 | 31032969 | CTT TGG CTC AGA ATC TTC CAA | GAA CAC CTC AAA GTT GCT CA | 1437, 1438 |
| chr21 | 31085356 | 31085605 | TGT ATG AGG ACC AGC AGT AAA | AAG AAG CAA GGA CAA GGA TG | 1439, 1440 |

FIG. 2 CONTINUED

| chromosome | start | stop | forward primer | reverse primer | SEQ ID NOs: |
|---|---|---|---|---|---|
| chr21 | 31494755 | 31495004 | TCT TTT CCC CTT GTG CAT AG | GAA ACA ACC ACC ACA ACA AA | 1441, 1442 |
| chr21 | 31560367 | 31560916 | GCT TAG TGT GTG TGA TCC GT | CCA CCA TGT TTA CAC CGT TT | 1443, 1444 |
| chr21 | 31605973 | 31606222 | ACT CAC CTT TCC CAA GAA GA | TTT ACC CAT GAA TTG CTG CA | 1445, 1446 |
| chr21 | 31621826 | 31622075 | TGG TAG TGG GAA GAG GTT GA | AGT TTG CAT TTG TTC AGG GA | 1447, 1448 |
| chr21 | 31653822 | 31654071 | GCA TGG AGA ACA AAA GCT GA | TTC GGA TGG CTT TGA TTG TC | 1449, 1450 |
| chr21 | 31670830 | 31671079 | TGT GAG CAA GAA ACT GAA GG | CAT TGT AAA TTA AAC GGC CTC | 1451, 1452 |
| chr21 | 31691347 | 31691596 | AGT ATC ACT TGT CCA GCT CA | CTA ATG CAA GCT GCT TCT CT | 1453, 1454 |
| chr21 | 31708936 | 31709185 | CAC AGG ACT AGG TAG GCT TT | TGT CTA GTG GTA ATC TGG GG | 1455, 1456 |
| chr21 | 31733443 | 31733692 | GTG TTA ACA GCT TTC CCT TCA | TCT GGA CAG TGG AGT TGA AA | 1457, 1458 |
| chr21 | 31768996 | 31769245 | TCA TGT ACA GAA AGA ATT AGC CT | ACC ACC ACA AAC ATA GCT GA | 1459, 1460 |
| chr21 | 31886189 | 31886438 | AGA GGC CAA GTG ACC AAA TA | AGG AGA GAC ATA ACT GGT CT | 1461, 1462 |
| chr21 | 31888808 | 31887057 | AAG CCA GTA ATT CAT CTT CCC | ATT GCA ATG TCT GTG GAT GT | 1463, 1464 |
| chr21 | 32119833 | 32120082 | CCA TGA CAT AAC ACA TCA CCA | AAG AAG TTG AGG TAG CAC G | 1465, 1466 |
| chr21 | 32125263 | 32125512 | ATA GAT TTC CTC CTG GGC TG | AGT GTC CTT TCC TCC AGT TC | 1467, 1468 |
| chr21 | 25795207 | 25795456 | CCA CCT CTG TAC CCA CTA TC | TTG AAC CTG AAA GGA ACT GTG | 1469, 1470 |
| chr21 | 25802273 | 25802522 | TTC CCT GGA AGA TAG CCA AT | GCT CAA TCA CCT GTT CCC TT | 1471, 1472 |

FIG. 2 CONTINUED

| chromosome | start | stop | forward primer | reverse primer | SEQ ID NOs: |
|---|---|---|---|---|---|
| chr21 | 26355452 | 26355702 | TGG ACA CGT AAA AGA AGG TG | CAT TGA AGC TCA CTC TAA GGG | 1473, 1474 |
| chr21 | 26365770 | 26366019 | CTG AGA ACC TTG TCC AAC TG | CTA AAG TTT GGG TTA GGG GT | 1475, 1476 |
| chr21 | 26373440 | 26373689 | TTT CGC TAG TCT TTG CAC TT | TGC CTT ACA TTT TCT GTG GG | 1477, 1478 |
| chr21 | 26374774 | 26375023 | GCG GCA ATA ATT GTC ACA AA | GCC ATA AGA TTT CCC CAC TC | 1479, 1480 |
| chr21 | 26390279 | 26390528 | CAG AAA TGT GTC AGG CTA CA | ACA AAG CAA GAG GAT GAA ACA | 1481, 1482 |
| chr21 | 26390951 | 26391200 | AAC TCT TCA TTT TGA CGG GG | CAA AGC ACC ATC AAC ACT TA | 1483, 1484 |
| chr21 | 26402802 | 26403051 | TGT GTT GTG CTG TTG TTT AG | CAC TGC AAC TCT TAG AAT GA | 1485, 1486 |
| chr21 | 26496769 | 26497018 | GCT CAG CTC CTT TCA TCT G | TGT GGG GAA ATT GCT GTT TA | 1487, 1488 |
| chr21 | 26515400 | 26515649 | AGG ACA TTC AGC CTA TTT GC | GTA TGG GCA GCT GTA ACT TG | 1489, 1490 |
| chr21 | 26571662 | 26571911 | ACA CAG TAT CAA GGT CAA CA | TCA CAA GCC ACT GAA AAT GT | 1491, 1492 |
| chr21 | 26589786 | 26590035 | GCA GAA CCA CAG TCT ATG AG | TGT ATG TTA AGC TAG CCA ACA | 1493, 1494 |
| chr21 | 26604824 | 26605073 | AAT GCT CCA AGT TAT TCC AGA | TGT GTT ATT GAA CTT TGC CA | 1495, 1496 |
| chr21 | 26933670 | 26933919 | AAG AGA GAA GCG ACA AAA CC | TTC ATC CCT ACC TCA TCA CC | 1497, 1498 |
| chr21 | 26950703 | 26950952 | AAT GAG AAG GAA TTG GGT GC | AGA TCA CTT TTG GCT GTA ACC | 1499, 1500 |
| chr21 | 27045134 | 27045383 | AAT GAA GTG TTA GGG CCA TC | CAA GTG ACA ATC TCA GCC AA | 1501, 1502 |
| chr21 | 27398390 | 27398639 | GCT CAT CAC AGT TTA AGG AGT | GCA TTT TCA GAT GGT TCC CT | 1503, 1504 |

FIG. 2 CONTINUED

| chromosome | start | stop | forward primer | reverse primer | SEQ ID NOs: |
|---|---|---|---|---|---|
| chr21 | 27441346 | 27441595 | ATG TGG AAG CAA GAG AAA GG | ATG GAG AGT TTG AGT GGA GT | 1505, 1506 |
| chr21 | 27465490 | 27465739 | TGA AAG GTG AAG TGG CTT TT | CTG CCA CTG GGT TTA TAG AAA A | 1507, 1508 |
| chr21 | 27485182 | 27485431 | GTA AGT AAG GGG TCC TAG CT | ACA CCT TTA CTC CTG TGG AT | 1509, 1510 |
| chr21 | 27486006 | 27486255 | TGT GAC TTC CAT GAA ACT GG | GAT GTA GGG CCT TAT CCA CA | 1511, 1512 |
| chr21 | 27502429 | 27502678 | GCT GAC AAA CTA ACC TTC CA | AGC TTG GTG ATC TTC AAA CA | 1513, 1514 |
| chr21 | 27520192 | 27520441 | AAA ACC TCC CAA AAC AGA CT | TGA AAT GGT GGG TAA TGC TC | 1515, 1516 |
| chr21 | 27539803 | 27540052 | AGT TTA GTG GCC ACG TGA AA | CAT GCA AGT TCA CGA GGT TA | 1517, 1518 |
| chr21 | 27623130 | 27623379 | GGC AGA AGT TTC AAT TCC CT | AGT CTG AGG AAG AAG CAA CT | 1519, 1520 |
| chr21 | 27623692 | 27623941 | AAA GCC TCT GTT TGC ACT TT | GAG TCC AAT CTT TTC CCA CA | 1521, 1522 |
| chr21 | 27763679 | 27763928 | TCA GTC AGC TTC TTG AGT CA | TCC ACT GCG TTC TTA TCC TT | 1523, 1524 |
| chr21 | 27894000 | 27894249 | TGT TTC ATT TGG GTC ATG GA | GGA CAG AAC AGC TAC AAA GG | 1525, 1526 |
| chr21 | 27926498 | 27926747 | TAC AGC ACT AGG ATC ACT CTG | CTG GCT TGT GAA TTA GAG GG | 1527, 1528 |
| chr21 | 28077177 | 28077426 | ATG CAT GTT TCT TGC AAA GG | GTA AGA TGG TGG GCA GGA T | 1529, 1530 |
| chr21 | 28122462 | 28122711 | GTA GGA TTC AGG GCA TTT CA | AGA AGG GCT CAA AAC ACA TC | 1531, 1532 |
| chr21 | 28151337 | 28151586 | AAC TGG AAC TGA GCG TGA G | TCA TGT TAG GCT TCT GAT TTT | 1533, 1534 |
| chr21 | 28180925 | 28181174 | TGT ATG CAG TTA CCT CCA GA | TGT AGC TCT TGA CCT AGC AA | 1535, 1536 |

FIG. 2 CONTINUED

| chromosome | start | stop | forward primer | reverse primer | SEQ ID NOs: |
|---|---|---|---|---|---|
| chr21 | 28275754 | 28276003 | GGA TGT ATA CCA GAC CCC TT | TAA GTT CAC GGT GAA GTC AAC | 1537, 1538 |
| chr21 | 28291449 | 28291698 | CGA AAG ATG TTA GCA CCT CA | GTG GCT TCA ACT AAC TGG AC | 1539, 1540 |
| chr21 | 28294820 | 28295069 | AAT TGG CTT TGC AGT GTT TC | ACC CGT AAG TGT TTG AGT GA | 1541, 1542 |
| chr21 | 28295351 | 28295600 | GCT TGC TGG TAG GAG GTA TA | TGT AGA AGT AGG GTT TGC GT | 1543, 1544 |
| chr21 | 28295857 | 28296106 | CTG GAA ACG GAA GGA AGT TG | CAG GGG ACA TTT GAA GAT GG | 1545, 1546 |
| chr21 | 28311866 | 28312115 | CTG TGT TCA GTA AGT GGC TG | GAA ATT GTG CAG TGA AAG CA | 1547, 1548 |
| chr21 | 28334784 | 28335033 | GAC AGT GAA GTG TGA TCG TT | ATG TAA GAA GTG CGT TGC TTA | 1549, 1550 |
| chr21 | 28354814 | 28355063 | TGG TGA TGC TGT TTT GGA AA | AGA TCT GGA ATC TGA GAC TCC | 1551, 1552 |
| chr21 | 28415341 | 28415590 | TTC TTT CAG GCA GAA GAA ATG A | TAT AGG ATA AGG TCA AGC AGG T | 1553, 1554 |
| chr21 | 28433186 | 28433435 | AAG TTC CAT TAC TGT ATT GAA AAT T | TCC AAA ACA ATT CTA GGC CCC | 1555, 1556 |
| chr21 | 28450226 | 28450475 | GGA CGT ACG TGC TTA TTT CA | TCA GTG AAT GAG GAA TCA TGC | 1557, 1558 |
| chr21 | 28474083 | 28474332 | CAG CCT GAT ATT CCC ATT GAG | TTC TCA GGA GTA CCA CAA GC | 1559, 1560 |
| chr21 | 28491062 | 28491311 | TCA TGA GGC TGA GTG AGT AT | GGA TGA AAC ACA GAA CCA TG | 1561, 1562 |
| chr21 | 28509439 | 28509688 | AAA GCT CTC CTA TCT CCA GT | CAG ATC CCT TTC ATT TTG CA | 1563, 1564 |
| chr21 | 28534176 | 28534425 | ACA AAG AGT CTG GAC TAT CCT | GGA AAA GTG CTC AAT TAG GC | 1565, 1566 |
| chr21 | 40042441 | 40042690 | TGC CTA AAA ATA CCC AAA GCT | CTG GCA GTT ATA GTC ACC AA | 1567, 1568 |

FIG. 2 CONTINUED

| chromosome | start | stop | forward primer | reverse primer | SEQ ID NOs: |
|---|---|---|---|---|---|
| chr21 | 40427338 | 40427587 | CCA AGA CAC TCA CTC CAA AG | AGG AAG TCC TTA TGA TGC CA | 1569, 1570 |
| chr21 | 40509976 | 40510225 | CCA GGA AAA GGA GCA GTT TT | GCT GGT GAA GTT GGA GTT TT | 1571, 1572 |
| chr21 | 40531291 | 40531540 | GTT CAA CTC TTT CTG CGA AC | GCT GGG TTT AAG CCA CAT AT | 1573, 1574 |
| chr21 | 40578323 | 40578572 | CCA CTT CTT CTG TTT CCA AC | TGT AGC CTA AAT AGC AGC CT | 1575, 1576 |
| chr21 | 40601158 | 40601407 | GGG AAG GGC ATG CTA ATC A | AGG AAT TGC TTT TAT TTT AAC CA | 1577, 1578 |
| chr21 | 40630577 | 40630826 | TGT TCA ATC ACC TCT CCA TC | GCT GCT TTC AGG TTT TTG TG | 1579, 1580 |
| chr21 | 41280723 | 41280972 | AGA GGA GAG GCT AAG CTT TG | ATG GTG CAG AAA AGA GCA AT | 1581, 1582 |
| chr21 | 41607273 | 41607522 | ACA AGA GAG GAA GCT GTC AG | GTG TGG TGC CAT TTT CTT TC | 1583, 1584 |
| chr21 | 41629820 | 41630069 | AGC CCC TTT CTC CTT ATT CT | GAA CAA TAC TTT CTC CCC GG | 1585, 1586 |
| chr21 | 41703462 | 41703711 | AGG GAA GCA GGA TTT TAA CG | GAA ATG GCC ATG CTA GGA AT | 1587, 1588 |
| chr21 | 41728089 | 41729338 | AAG TTT CAC AAT ACC CAG GT | ACT TCC AGT AAC ATG GAT GC | 1589, 1590 |
| chr21 | 41761636 | 41761885 | TCG CAG AAT GGA CAA GTA CT | GAA ACA CCC AGA CTT GTA GC | 1591, 1592 |
| chr21 | 41838021 | 41839270 | GGC TCC CAG ATT TTG ATC AT | TTA AAT CTT TGT GTG CGT GT | 1593, 1594 |
| chr21 | 41908902 | 41909151 | CCT AGA ACT GCA AAA CAC CT | CCT CCA GGA ACT TTG TTC AG | 1595, 1596 |
| chr21 | 41933321 | 41933570 | TTC CAT TAT TTT CTC ACC GGC | AAA AAC CTT CAC AAA CCC CA | 1597, 1598 |
| chr21 | 41981868 | 41982117 | CAG TCC AAC AAA GAG GTC AC | GAG TGG ATA TTG TCT CGC TG | 1599, 1600 |

FIG. 2 CONTINUED

| chromosome | start | stop | forward primer | reverse primer | SEQ ID NOs: |
| --- | --- | --- | --- | --- | --- |
| chr21 | 42029142 | 42029391 | TTG TGT GTG TTG AAG CCT AG | ACT AGC CCA CTA ATG TTG CT | 1601, 1602 |
| chr21 | 42030642 | 42030891 | AGT GGG GGT AGG AAG AAA AA | CGA TTA TCA GAA CAG ATG AGG T | 1603, 1604 |
| chr21 | 42080190 | 42080439 | GTT CCA ACA ATG TAA GGC AC | ATT GCA CAG CTG AAA ATC CT | 1605, 1606 |
| chr21 | 42251219 | 42251468 | GGA ACC CTC TAT GGT CAA AG | GGC ACA CTG ACC GTA TTT AT | 1607, 1608 |
| chr21 | 42593559 | 42593808 | ATT GCT GTG TAG TTC CTT GA | TGG TAG TGG GTC AGG AAT TT | 1609, 1610 |
| chr21 | 42601828 | 42602077 | TTT CTT GCC ACC ATT CTG AC | TCT CTT GAA AAG AAA GGC GG | 1611, 1612 |
| chr21 | 42851340 | 42851589 | CAC ACG TTC TAA CCA AGT GC | TGA ATT ACA CAG CAA AGC CC | 1613, 1614 |
| chr21 | 42872713 | 42872962 | TAG CCA CAT CTT AAC AGA CCT | CTG CCA ATG GGA TCG AAT TT | 1615, 1616 |
| chr21 | 43032728 | 43032977 | ATT CCT GAG GGT GAC ATG AA | GAG TGA CGC TGT TCA TTC TT | 1617, 1618 |
| chr21 | 43406661 | 43406910 | CCT GCC CCA TCA ACT TAA AA | GAT AGT AAC CGG GTG TAG CA | 1619, 1620 |
| chr21 | 46521300 | 46521549 | CTG GGT GCA GAG GAT CTC | TCC AAA AGC AAA AGG ATC ACT GA | 1621, 1622 |
| chr21 | 16323548 | 16323797 | TTG AGT TGA ACT TTG CTT TAG A | TCT AAT AAG GGA TTG ATG GAG TT | 1623, 1624 |
| chr21 | 16330249 | 16330498 | GAA CTA GGA GAC ACT GGG TT | GGG AGA TTT CCT GCT TGT AG | 1625, 1626 |
| chr21 | 16332622 | 16332871 | CAA GAA TAG CTA ACT GGT GCT | AAT CCA TGC AGC TTC TCT CT | 1627, 1628 |
| chr21 | 16333315 | 16333564 | AGT TAC ACA CTG AAT CAT GGG | TGC ATT GTC TCT GGT TTG AA | 1629, 1630 |
| chr21 | 16335355 | 16335604 | CCC ATG TGG CTT CAC TAA TA | TCC TGA ATG CAT CCT TAA CC | 1631, 1632 |

FIG. 2 CONTINUED

| chromosome | start | stop | forward primer | reverse primer | SEQ ID NOs: |
|---|---|---|---|---|---|
| chr21 | 16344361 | 16344610 | GAT TGT GGT CAC GTG GAG AG | TGG GAA AGG TGA GAA GGA TT | 1633, 1634 |
| chr21 | 16349606 | 16349855 | CAG ATC CAG GTA TTC GGA GA | TTC GGG ACC CAT ACC TAA AA | 1635, 1636 |
| chr21 | 16358650 | 16358899 | ACA ACA ACA ACC ATT ACC CA | TCT TTT CTG GAC CCA CAT GA | 1637, 1638 |
| chr21 | 15713251 | 15713500 | TGG CCA TAG TAC TGC TTG TA | GAC CTC TAC ATC TGT ATC TTC C | 1639, 1640 |
| chr21 | 15714357 | 15714606 | TGT CTC ACT GTT GGG AAC TT | CCC TTC ATT TTC TGT CCC AT | 1641, 1642 |
| chr21 | 15725977 | 15726226 | TTT GTC TGT ATC CTA TGC CC | TCA GCC TTG AGT ATT AGC CTA | 1643, 1644 |
| chr21 | 15731366 | 15731615 | GCT GAC AAA ATT GGA TCC CA | AAG TTT GCC ATG AAG GTC AT | 1645, 1646 |
| chr21 | 15816232 | 15816481 | AAA ATC CTC CTG AGT CCT CT | GAC TTC TGG TTG TTT CCT CA | 1647, 1648 |
| chr21 | 15843963 | 15844212 | TTC ACT GGG CTC TTC AGC TA | ATG TGT CTA TTG CCC TAC CT | 1649, 1650 |
| chr21 | 15858450 | 15858699 | AAA GGG CAG GAG TTA GGT AA | GTG AAC TTC AGG CTG CTT A | 1651, 1652 |
| chr21 | 15859015 | 15859264 | AGG CAT AAG AAA CCA GGT TG | TGG TTT CGT CCC GTA AAT AG | 1653, 1654 |
| chr21 | 16003625 | 16003874 | GTA GTT CGG TCC AAT GTC AG | AAT TCC TTT CAA TGC TGG CT | 1655, 1656 |
| chr21 | 16030414 | 16030663 | GAT GGT CAC AAT GCT AGG TT | AGA AAG ACA CAT ATG CCA TGG | 1657, 1658 |
| chr21 | 16063119 | 16063368 | GCC AAA GAT CTC AAT TGC CA | TTG TTG GTG TCA GTT CTG AA | 1659, 1660 |
| chr21 | 16068358 | 16068607 | GAC CAA GAC TGT CTC TCC TT | TGT AGG AAC AGA TTA GGG CA | 1661, 1662 |
| chr21 | 16071495 | 16071744 | TAA TGG TCA AAT CCC TCT CAA A | | 1663, 1664 |

FIG. 2 CONTINUED

| chromosome | start | stop | forward primer | reverse primer | SEQ ID NOs: |
|---|---|---|---|---|---|
| chr21 | 16081282 | 16081531 | CAT GTA GGC TGA AGA CTC CT | CTG CAA GCT GAT ATG CCA TC | 1665, 1666 |
| chr21 | 16115078 | 16115327 | TTT CTC TCC AAA CTG GTT GC | CCA CCC CTC ATT TCT TCC TT | 1667, 1668 |
| chr21 | 16122085 | 16122334 | TAC AGG CAA GAA ATA GTG TCT | GGG TCC TTC GTT TTC TGT TT | 1669, 1670 |
| chr21 | 16130688 | 16130937 | TTC AGC AAG AAT GGG GAT TC | TAG GAA ACA GGC TAA AAG GGA | 1671, 1672 |
| chr21 | 16133865 | 16134114 | CAA AGA GAG AGC CAT CAC AG | TAC TGT GTA GAA GGC AGT GT | 1673, 1674 |
| chr21 | 16139969 | 16140218 | TGA GAA CAC TGC TAT TTC TGC | GCT AAG GAC AAA GAA CCA CT | 1675, 1676 |
| chr21 | 16141592 | 16141841 | GCA TGG TCA GGA CAT TGG | AAA GAC AAG GGA AAA GGT GAC A | 1677, 1678 |
| chr21 | 16160517 | 16160766 | GAT TGA ATC AGG AGG GAA GC | TGG CTA AGA CCA GGA TTG TT | 1679, 1680 |
| chr21 | 16165861 | 16166110 | AGC TTA AAT GAT GAA GTG CTT TC | TCT TAT GTT TGG TGA TTT GGA CTT T | 1681, 1682 |
| chr21 | 16189746 | 16189995 | TTC TCC TAC GTA TCT TGG CA | TGA TAG GCA GAT CAT TCC CC | 1683, 1684 |
| chr21 | 16190806 | 16191055 | ACC TGG GAC ATA ACC TTG AT | GCA AAT GGC AAA GGG AAA AC | 1685, 1686 |
| chr21 | 16192618 | 16192867 | CCA TTT TCC TAC TGC GTG TC | CAC GGC TAG TGC TCA TTT T | 1687, 1688 |
| chr21 | 16195809 | 16196058 | GAA CAT ACC AAA CCC ACT GG | CCG TAA TAC CCA AGT CAT CTG | 1689, 1690 |
| chr21 | 16198337 | 16198586 | ACC CAA TGA TGT ACA GTT CC | AGC AAA CTA AAA CAG CAA CTT C | 1691, 1692 |
| chr21 | 16203731 | 16203980 | ACC TAT TCG ACT TGA AAC TCA G | AGC CTG CTA TCT TCA CTG G | 1693, 1694 |
| chr21 | 16207035 | 16207284 | ATT TCT GCA CAA CTG TTC CA | ACC ACA TAT ATA GAG ACT TTG AAG | 1695, 1696 |

FIG. 2 CONTINUED

| chromosome | start | stop | forward primer | reverse primer | SEQ ID NOs: |
|---|---|---|---|---|---|
| chr21 | 16209341 | 16209590 | GCT GTA ATG TGA CTA ACC CT | CTC CAG ACT CTG CAA GGA T | 1697, 1698 |
| chr21 | 16211270 | 16211519 | TTT CCC GAG GTT CAC AGA TA | TTT CCT GTT GCT CTT GAT CA | 1699, 1700 |
| chr21 | 16219907 | 16220156 | GAA CTT GTG TGA CCC AAA AC | CCA CAA AGA TGA AGG CCA AG | 1701, 1702 |
| chr21 | 16230785 | 16231034 | CAT TGC ACT GTG ATG TCA TG | CCA TAC CTT AGT TCT CAG GGT | 1703, 1704 |
| chr21 | 16236026 | 16236275 | GCA CTG GAA ATT GAC ATC AC | GTA AGA GAG AGC TGG GAC AA | 1705, 1706 |
| chr21 | 16241139 | 16241388 | GGG AGA GGC TGA AAG AAG AA | TGT GAC CAT CCT ATC CAC AA | 1707, 1708 |
| chr21 | 16242812 | 16243061 | TGT ATC ACT TCC TCA TGC CA | AGA ACC AGT AGT TGT ACG AGT TC | 1709, 1710 |
| chr21 | 16246944 | 16247193 | CCA AGA GTT TCC TGT TTC CA | AGT CTT CTC CCT TCC TTG TC | 1711, 1712 |
| chr21 | 16265484 | 16265733 | ATG ACA CAT ACA TCC ATT TAC A | GCC CTT TTC TCT CTT TGA CC | 1713, 1714 |
| chr21 | 16273734 | 16273983 | CTC AAA CTG CCC AGT GAT TT | TCT TGT TCC AAG TAT TCC TGG | 1715, 1716 |
| chr21 | 16275865 | 16276114 | TCC TAG CTT GCC AAA GAA AT | ACC ACT TTA GCC CAT CTC TT | 1717, 1718 |
| chr21 | 16290234 | 16290483 | CCT CCT CTC CAG GCA TTT TA | GTG GTG GAT TAT TGA GCT GG | 1719, 1720 |
| chr21 | 16293877 | 16294126 | AAC AGA GTA GCA CAG AGA GT | TGC TTA ATG GGA TCA TTG ACC | 1721, 1722 |
| chr21 | 16296687 | 16296936 | TTC AGA GAG ACA GAC AGC AT | CCC ACA TAG TGC AAA AGA CA | 1723, 1724 |
| chr21 | 16298842 | 16299091 | AGA GGA AAA TCA CAA GCA GT | GTA TGT GTG AAG TAG CCG AG | 1725, 1726 |
| chr21 | 16316213 | 16316462 | TTT GAA AAC CCA ACA GAC CT | TGG TCC TAA CTC AGA CCT TT | 1727, 1728 |

FIG. 2 CONTINUED

| chromosome | start | stop | forward primer | reverse primer | SEQ ID NOs: |
|---|---|---|---|---|---|
| chr21 | 16319836 | 16320085 | AAT CCA CAC ACC AAC AGA GG | AAC ATG AAG GGA AGG TTG TG | 1729, 1730 |
| chr18 | 64634331 | 64634580 | TGT TCA CAT CTG TTG GTT TGC | TAT ACT TCA ACT TGC AGG CAG | 1731, 1732 |
| chr18 | 64645925 | 64646174 | GTT ACT CGG TGG GTG ATA TTT | GCC AAA GAC AAT GAG AGA GTC | 1733, 1734 |
| chr18 | 64975938 | 64976187 | AAG AAA CAC CAG CAT CAG TTC | ATT TAG CAG CCA TGA CCA GTA | 1735, 1736 |
| chr18 | 64996573 | 64996822 | AGG TTT AGA GGT GAG TGA ACA | TGG GCC AAT TCC TAA TCC ATT | 1737, 1738 |
| chr18 | 65066425 | 65066674 | AGA AAC TTC ACT GTC TTC CAC T | CGA TCT CAT GAA TAA GTC TGA CC | 1739, 1740 |
| chr18 | 65073729 | 65073978 | TGT GAT GGA CAT TGG TAC CTG | TGG AAA GCA GAC TAA CAG TGA | 1741, 1742 |
| chr18 | 65074170 | 65074419 | ATA TCA TCT GCC TGT CCC AAC | GGG ACC CTA TGT AGA GAT TGT | 1743, 1744 |
| chr18 | 66343957 | 66344206 | GAG TGC TCT GTG TTT GTT TCA | GGA GCC CAA GGA TGT ATT AGA | 1745, 1746 |
| chr18 | 66344406 | 66344655 | TCA GTG GTG AGC TCT TGA ATA T | CTA ATA GCT GGT TCT GCA CAC | 1747, 1748 |
| chr18 | 66585247 | 66585496 | ACT CTC TCT TCA CAC ATG CAA | GAT GAA ATG AAT GCT GAC TCT C | 1749, 1750 |
| chr18 | 66596489 | 66596738 | GTG TTG AAG TCA GTA AAG CCT | AAA CTG AAG CTT CGA GAA CCC | 1751, 1752 |
| chr18 | 66601231 | 66601480 | TGC TTT CAC ATG GCA CTA GAT | TGC CGA CAA CTA CTT TAG GTA | 1753, 1754 |
| chr18 | 69966208 | 69966457 | GGA GAG AGA AAT CCC AAC TGA | TGT ATC CAA TCA CCT GTC AGA | 1755, 1756 |
| chr18 | 70088939 | 70089188 | GGG AGA TGT CAA CAC TAG GTC | CAG CAC CTT AAG CAG AAA TCA | 1757, 1758 |
| chr18 | 70093354 | 70093613 | ATA TGA CAT GGT GGC TCT CC | AAG CCC TTC ATC ATC TTC TCT | 1759, 1760 |

FIG. 2 CONTINUED

| chromosome | start | stop | forward primer | reverse primer | SEQ ID NOs: |
|---|---|---|---|---|---|
| chr18 | 70107935 | 70108184 | AAC ATA GAG CCA TGG GAG GTA | ATC TTG GTG CCA TCT TAA GGT | 1761, 1762 |
| chr18 | 70198868 | 70199117 | GAT AGC CTT CAA ATC ATG CCT | AGC AAA CCA ATC GCA AAC TAG | 1763, 1764 |
| chr18 | 70200128 | 70200377 | GAA AGC GGG TGA ACA ACA ATA | AAT CAT CAT CTT CAT CAG CTC G | 1765, 1766 |
| chr18 | 70200907 | 70201156 | GAT AGA GAG CAC AAA GAG CAT | CCT TTC GCC TTG CTT ATA TGG | 1767, 1768 |
| chr18 | 70674976 | 70675225 | AAC AAG AGG AAT AGG AGC CAG | ACT ACT CAA CAG CCT ACC AAA | 1769, 1770 |
| chr18 | 70682967 | 70683216 | TGG GTG CTG ATA GTA ACA AAG | TGG AGC TGG GAA CTT TAA TGT | 1771, 1772 |
| chr18 | 73541191 | 73541440 | ACT ATT GAA CTG TTG GCT TCG | GAA GAG AGA GAG AAT GCG TGT | 1773, 1774 |
| chr18 | 73548315 | 73548564 | TCC ACT AAA GAG CAA CCA AAC | GAC ATG GAT ATT CTG GTG CCA | 1775, 1776 |
| chr18 | 73605288 | 73605537 | TGA AGT GGT CAG TAA CAA TGG | CTG TTG CAA GAT GAC CCA AAT | 1777, 1778 |
| chr18 | 73704485 | 73704734 | ATT TCA GAG CTC CTT TGT CCT | AGA TAC ACA CAC GTT CAC AAA C | 1779, 1780 |
| chr18 | 73752546 | 73752795 | GGC AAA GAA ATC TGG TGT TCA | GAT GGC AAT GCT TGA TAA CGA | 1781, 1782 |
| chr18 | 73764755 | 73765004 | TTG CTG GTT GAT AGG CAT TTG | TTC CAT GAA GTT CCT CAA GAC T | 1783, 1784 |
| chr18 | 73768420 | 73768669 | ATT CCC GCA ATT GTG AGA TTC | CCA CCC ACA TAC CCT GAA ATT | 1785, 1786 |
| chr18 | 73775027 | 73775276 | AAA GAG GTA CAG AAC TCA GAC C | GTA ACA CAC GGA TGC TGA AG | 1787, 1788 |
| chr18 | 73788751 | 73789000 | GTC TTC ATG AAC GTT GCC AAT | TGG ACA CGA GGC TAT TTG TAG | 1789, 1790 |
| chr18 | 73851108 | 73851357 | CTT CTC AGG GCT CTT TGT GTA | GGC TTA AGA AGG AGA GTG GTT | 1791, 1792 |

FIG. 2 CONTINUED

| chromosome | start | stop | forward primer | reverse primer | SEQ ID NOs: |
|---|---|---|---|---|---|
| chr18 | 73854713 | 73854962 | GCA ACA GAA ACC AAG ATT CCT | TAG TTT CCT TTG GCC TTC TCC | 1793, 1794 |
| chr18 | 73871422 | 73871671 | TCA TTG TCT ACC TCA AAG AGC A | CTA GGG TTC CCA GTT CAC AAA | 1795, 1796 |
| chr18 | 73876103 | 73876352 | CTC TGA AGG AAC AAA GGA TGG | GAA ACA ACA TTG AGG GCA TTG | 1797, 1798 |
| chr18 | 73879805 | 73880054 | CAT TAG AAT GCG GTG GTT TCA | GAG CTC TTT GAA GTA GAA GCA | 1799, 1800 |
| chr18 | 73884248 | 73884497 | GAT GTC TGG GCT GAG GTT TAA | CCA TTC CAA CAA AGC TTC CG | 1801, 1802 |
| chr18 | 73931865 | 73932114 | TTC CTC TTG AAG ATG CAC TGG | CTA CTT GCC CTA TTG TGT CGA | 1803, 1804 |
| chr18 | 73938014 | 73938263 | CCA GCA TGT GAG GAA TTG AAC | CCA GGG TGT TTG AAG GTA GAA | 1805, 1806 |
| chr18 | 73943212 | 73943461 | CCC ACT TAG TCA TCC ACA CAT | CTG GAG GTA AGA AGG AAT GCA | 1807, 1808 |
| chr18 | 73947628 | 73947877 | GTT TCA CAC ACC AGA AGA GAG | ATG TGG GAC TCT TTG CTC TC | 1809, 1810 |
| chr18 | 73964168 | 73964417 | CCA TAC ACC TGC TCT GAC ATT | ATG AAT ACA GCT TTG CAT GGC | 1811, 1812 |
| chr18 | 73966321 | 73966570 | ATC AGT AAC AGT CCC ATT GCT | GTT AAA GCA TTC ACA GCC CTC | 1813, 1824 |
| chr18 | 73974071 | 73974320 | CAT GAG GCA TTT GAT CCA TGG | CTG GGA CTT GTC TAT CCT CCT | 1815, 1816 |
| chr18 | 73983549 | 73983798 | ACC CTG TTT CAC TGA ACA ACT | ATG TCT GTC CAA GTG AAC AGT | 1817, 1818 |
| chr18 | 73987174 | 73987423 | CCC TGT AAT GAG AGC GTT ATT | AAA GTA TCC AGA CCC AGA ACC | 1819, 1820 |
| chr18 | 48466085 | 48466335 | GAG AGA ATG GGT TAA ATC TGC C | ATA GGC CAG CAC TCC AAA TAA | 1821, 1822 |
| chr18 | 48928528 | 48928777 | CTG CCT GAC TTA GCC TTA AAT | CAA ATC AAG TCC CAT GGT AGG | 1823, 1824 |

FIG. 2 CONTINUED

| chromosome | start | stop | forward primer | reverse primer | SEQ ID NOs: |
|---|---|---|---|---|---|
| chr18 | 48929878 | 48929327 | AAC CAG AAT GTT ACT AGC CCA | CTT TCC GTC TTT ATA GGC AGC | 1825, 1826 |
| chr18 | 48951524 | 48951773 | CAA TCC TGT GTG TTT AGT GGA | AGA AAT CGT GTT CAC AGC CTA | 1827, 1828 |
| chr18 | 48951856 | 48952105 | TGT GGG AAG CAT TGA CTC TT | CCG TAA ATG AAG TGG CTT GAA | 1829, 1830 |
| chr18 | 48959882 | 48960131 | TCC TGT GAG AAA TGG AGC TTT | CCT TTC TTG CAA CCT TGA GAT | 1831, 1832 |
| chr18 | 48960304 | 48960553 | GTT GCC AAG CTT AAA TAC CTG T | CTC TAG ATG CTC AAC CTC AGG | 1833, 1834 |
| chr18 | 49004516 | 49004765 | CCA CAA CAA CAT AAA CAC TGC | AAT AAC AGT CCA CCA GAA CCA | 1835, 1836 |
| chr18 | 49006425 | 49006674 | TCT TCC AGG CAT ATT CAT TGC | TCC AAG GAC CTG CAA ATG TTA | 1837, 1838 |
| chr18 | 49017695 | 49017944 | ATC CAT TCT CTC TAC TTG GGA | AGG TTA CAT CAT TCA CCC ACA | 1839, 1840 |
| chr18 | 49148010 | 49148259 | GGC TAG AGG GTG ATT ATA AGC T | ATG AAG ACA ATG ACA TCT GCG | 1841, 1842 |
| chr18 | 49149627 | 49149876 | TAC TCA TCC CGA TTT CTT CCC | CAC TTG TCA TGG TTT AGG GAC | 1843, 1844 |
| chr18 | 49149933 | 49150182 | TTC TCT TTC TCT TCT GGG CAG | ACC TCC ACC TTA TTG CTT CAA | 1845, 1846 |
| chr18 | 49150459 | 49150708 | TTG TGA GAC TCA AGG CCA TTT | GAA TTG CAA AGG ATG GGT AGG | 1847, 1848 |
| chr18 | 50239403 | 50239652 | TTG GTA GAG AGA GGC CAT TTG | CTG CAT TGT GAG TCC ATG TAA | 1849, 1850 |
| chr18 | 50242789 | 50243038 | GGA GGA AGC TCT TGA AGA CAT | TCC TAT CTT CAT CCC TCT TCC | 1851, 1852 |
| chr18 | 50243069 | 50243318 | AGC ATC TTC CGT TTA ACT CCA | TTC CAT TTA GCC TCC CAT CTG | 1853, 1854 |
| chr18 | 50243357 | 50243616 | CTG CCT GCC AAG TAT GTT CT | TAG CTT TAT GGG CCT TGT TCT | 1855, 1856 |

FIG. 2 CONTINUED

| chromosome | start | stop | forward primer | reverse primer | SEQ ID NOs: |
|---|---|---|---|---|---|
| chr18 | 50247229 | 50247478 | CTA CTC CTT GTG TCA TTG GCT | CCA CCT CTC AAA CCC AGA TTT | 1857, 1858 |
| chr18 | 50308727 | 50308976 | TGA TTC TGA GAC ACG TGC TTA | GTC AGC GTA TTT GGG ATT GAA T | 1859, 1860 |
| chr18 | 50309031 | 50309280 | CTT GAG GAC CTT TCA TGC TTG | AAA TCT GCC ACC CAT TTC TTC | 1861, 1862 |
| chr18 | 50338747 | 50338996 | TTG TGA TTT CAG GTA GGA GGG | TAT TCT GAG TTC TAC CCA GGT | 1863, 1864 |
| chr18 | 50423284 | 50423533 | TTC CCT CAG AGA CAG TAT CCT | TAC ATG AGA CCC AGA AAC AGA | 1865, 1866 |
| chr18 | 50424422 | 50424671 | AAA GGA GGT CTG GCT TTG AA | CTT CTT GGC AGA CTA TCA GGA | 1867, 1868 |
| chr18 | 50424789 | 50425038 | GCA TAA ACC TGG ACT GTG AAA | AAG CTG CTA AAT CTG TAG GGA | 1869, 1870 |
| chr18 | 50448837 | 50449086 | CAC TCA GCG ATT CTC CTC AC | CTG ACC AGA CCT GTT GAC TAA | 1871, 1872 |
| chr18 | 50449492 | 50449741 | AAA GCC AGA CAC AGA CTA GTT | TGA TAT GTT CAG TTT GCC TAC C | 1873, 1874 |
| chr18 | 50514079 | 50514328 | ATT CCT GGG ACC ACA AGC AT | AGC TTG AGT TTC TTG CTG GG | 1875, 1876 |
| chr18 | 50519889 | 50520138 | TAT TGC CTC ATG TGG TTG TG | TTC CCG CAA AGT AGA AGC TAT | 1877, 1878 |
| chr18 | 56064244 | 56064493 | GTG TTG ACT TGA AAG GAA TCA C | AAA CGC ATA CAA ACA GGA GAC | 1879, 1880 |
| chr18 | 56148666 | 56148915 | CAG GTT AGG AAT GAC AGT GGG | CTT CTA AAC CCA TCA CCT GCT | 1881, 1882 |
| chr18 | 56149037 | 56149286 | TTA GGT TAC CCA GGG ACG TTA | CAC CCA AAC TCA CAG GTA CAA | 1883, 1884 |
| chr18 | 56244171 | 56244420 | CGG TTT GCT TTC TGA ACA ACA | TGA ATT CTG AGA TCG AGA GCC | 1885, 1886 |
| chr18 | 56245242 | 56245491 | CAT TTG GGA CCC TTT GAA ACT | AGA TTA ACT GTT GCC TCA CTG | 1887, 1888 |

FIG. 2 CONTINUED

| chromosome | start | stop | forward primer | reverse primer | SEQ ID NOs: |
|---|---|---|---|---|---|
| chr18 | 56247063 | 56247312 | GGT TAT CTC TGG GCA AAG TTC | CAA GAC AGT GCA TTC CAT GG | 1889, 1890 |
| chr18 | 56527049 | 56527298 | TAG AGA GCA GAG AAC AAA CCC | CCA AGG AAA GAG TTG AGA AGG | 1891, 1892 |
| chr18 | 56528011 | 56528260 | ATA AGG GCA TTT GGA GGG AAA | TGA GTG CAG TCG ATA AGG AAG | 1893, 1894 |
| chr18 | 56532190 | 56532439 | AAT GCA CAC TTA GAC ACC ACA | AAC ACC GAG AAA GAG AGA GAG | 1895, 1896 |
| chr18 | 56532882 | 56533131 | GGA TTG CTA CCC AGG AGA TAA | TGT ACT GCT TTC GTC TTA TGC | 1897, 1898 |
| chr18 | 56534208 | 56534457 | AGA GGT TCT GTG TAT GAG TGT | CAT ATT CGC ACT GTA TAG CCG | 1899, 1900 |
| chr18 | 56601487 | 56601736 | TAG AGA ATT GTA CGC TGG ACA | CTG ATG GAT TCT CTG GTG TGA | 1901, 1902 |
| chr18 | 56633131 | 56633380 | TCT GGA GAA ATG CAC AAG AGA | TCA AGG AGA AGA GAG AGG GTA | 1903, 1904 |
| chr18 | 56635259 | 56635508 | TGG GTT AGA ACA TGG TGC TTA | TCT CCC AAA GCA GAC AAA GAC | 1905, 1906 |
| chr18 | 56719296 | 56719545 | ATC GCA TCA CAC CCT TAC TAT | AGT CAG TTG TTA CGT GCA AAG | 1907, 1908 |
| chr18 | 58037828 | 58038077 | GGA AAT TTA GCT TGA CAT GGC | AAA GGT TTG TTC ATC CTC CCT | 1909, 1920 |
| chr18 | 58038328 | 58038577 | TTT GTA AAT CCA CAG TGC CTA C | ACA GAG CAC GCA ATA TAG GAA | 1911, 1912 |
| chr18 | 58039111 | 58039360 | GGT ACT GGA GAG CAT AGA AGA | CTG CAT TCA CCC ATG TAC TTT | 1913, 1914 |
| chr18 | 58040290 | 58040539 | AAA CAA GCT ATC TTC AGG CAG | TCC AGC CAT ACC ATG TCT ATC | 1915, 1916 |
| chr18 | 59424085 | 59424334 | CGA ACA ATC AGA GAC TCG ACT | CTC ACT AGG GAA GAA CAG CAG | 1917, 1928 |
| chr18 | 59424763 | 59425014 | CTG GTT GAC AAT CTG CAA GTT | TGC TGG GTC TGA GTG TTA TAA A | 1919, 1920 |

FIG. 2 CONTINUED

| chromosome | start | stop | forward primer | reverse primer | SEQ ID NOs: |
|---|---|---|---|---|---|
| chr18 | 59441324 | 59441573 | ACC ATC CAA GTC GTC TTC ATA | GTT GTG TGA ATG GTG CTG TTA | 1921, 1922 |
| chr18 | 59499718 | 59499967 | ATA GCT ACG CAT ACC CTG TAG | GGC CCA GAA GAC TCT TGT AAT | 1923, 1924 |
| chr18 | 59500226 | 59500475 | AGC AGA AGA AAC AGT AAG GCA | CGA CCT ACA TCA GCT AAT GGT | 1925, 1926 |
| chr18 | 59507920 | 59508169 | ACC CAG GGA CCT ATT TGT TC | AAG GGA AGA ATA ACA ATG GTG C | 1927, 1928 |
| chr18 | 59543044 | 59543293 | CAA GGG CTC AGG TCT TCA TTA | ATG GGA GTA TGG GAG TAG GAA | 1929, 1930 |
| chr18 | 59556453 | 59556702 | TCA CTG TGA CTT GGA GAC TAA | TTG GTG GCT TGC AGA GAT TT | 1931, 1932 |
| chr18 | 59614976 | 59615225 | TGC TCT GCT TCA CTG TGA TTA | TCA CAC GAT CAT CAT ACT CAC A | 1933, 1934 |
| chr18 | 59623553 | 59623802 | GAT GAA TGA CTA ATA GCC CAC G | GGT AGC AGA TGA CTA GAC GAT | 1935, 1936 |
| chr18 | 59631090 | 59631339 | CCA TGT TTA GTT TGG TGC TGT | ACG CCT CTG TCA TTT CCT AAC | 1937, 1938 |
| chr18 | 59631779 | 59632028 | AGC CAA GTG AGG TGC TAA AT | CAG TTG ACT CAA TGG TGC AAT | 1939, 1940 |
| chr18 | 59632388 | 59632637 | TCA GGG AGA AAT GAT GTC ACC | ATA GGT TAC AGA TTG CCA CGT | 1941, 1942 |
| chr18 | 59695718 | 59695967 | CAG TAG CTG GCA AGA ATC ATC | GAT GCT GCT ATC AAA GGA ACA | 1943, 1944 |
| chr18 | 59696087 | 59696336 | CAA CAC TGC TAG AAT TCC CAA | AAG ACA AAG AGA TGG AAG GCA | 1945, 1946 |
| chr18 | 59696563 | 59696812 | CCT GAG AAG CAC CTG ATT GTA | AAT ACC CTC TTC CCT TCC TCA | 1947, 1948 |
| chr18 | 59712419 | 59712668 | TGT TGT CAG AAA TCC CAG GAA | CCA CCG TCA ATA TTT ATC AGC T | 1949, 1950 |
| chr18 | 59756979 | 59757228 | AAC TGG AGC CAT ATA ACG ATG | GCC TCA GTC CAA ATC TTA GAT | 1951, 1952 |

FIG. 2 CONTINUED

| chromosome | start | stop | forward primer | reverse primer | SEQ ID NOs: |
|---|---|---|---|---|---|
| chr18 | 59770789 | 59771038 | GAA ATG GTG CCC TAT TGT TGA | CCT TAG GAT TCT CAA AGA GTG T | 1953, 1954 |
| chr18 | 59805993 | 59806242 | TCT TAC ATG CAG TCA TAC TCC T | GCA GTA CAG ATT CTT GAA CAG T | 1955, 1956 |
| chr18 | 59813876 | 59814125 | GTC CCT CAG TAA CAC CAT CTT A | AGA GGA TTA GAT GTC TTG CTG T | 1957, 1958 |
| chr18 | 59855411 | 59855660 | GAA GCA AGA GGA TCA GGC AAT | TAC TGC AGG CAA TTC AGG TAA | 1959, 1960 |
| chr18 | 59909054 | 59909303 | AGT GTT TCA GAG GCT TGA AAG | GAA GAG GTC CAG TAA GTG AGG | 1961, 1962 |
| chr18 | 59909336 | 59909585 | ATC CGG CAT CCT TTA AAC TCT | TTG TGA GTC CTT GTC TCC TTG | 1963, 1964 |
| chr18 | 59910140 | 59910389 | AGG CTA GGA AGA AAT GGG AAA | GAC GAC TAA GAC ATT GCA TCA | 1965, 1966 |
| chr18 | 59910602 | 59910851 | ACA CAT ATG CTC TGT CTC TCA | AGA AGT CTC TCT CCG TTG TTT | 1967, 1968 |
| chr18 | 59973803 | 59974052 | AGT TAG TTA TCA CCT CGT CCC | CTT ATG TGC ATC AAC TGT GCT | 1969, 1970 |
| chr18 | 59996728 | 59996977 | TGT GTA TTT CCC TCT AGT TGC A | AGT GTC TCT CAG AAT CAG GAC | 1971, 1972 |
| chr18 | 60010541 | 60010790 | AGC CTC TTT CTA CAT CGT TCG | TTT ATT TCC CTA CGC AAA GCC | 1973, 1974 |
| chr18 | 60011381 | 60011630 | TTA CCT GTG CAG AAG AGT GAC | AGC CTT TGA TGA CTG AGT TGA | 1975, 1976 |
| chr18 | 60246694 | 60246943 | TCT TGT GTT CTA GCG TGT TTG | TTG GTT TCT ATT CTG CAC TGC | 1977, 1978 |
| chr18 | 60378353 | 60378602 | TGT GGT TAG TCA GAA ATG TGG | TTA GAG CTT GCT AGT ATC GGG | 1979, 1980 |
| chr18 | 60384593 | 60384842 | GGG TCC TGA TGA GTC TTT GTC | GAA ATC CCA AAC TGC CTG AAA | 1981, 1982 |
| chr18 | 60384979 | 60385228 | TGG TGC CTT TGT TTA TTC AGC | ATC CTT CTT GTG AAC CTT CCT | 1983, 1984 |

FIG. 2 CONTINUED

| chromosome | start | stop | forward primer | reverse primer | SEQ ID NOs: |
|---|---|---|---|---|---|
| chr18 | 60389544 | 60389793 | TGT TAT GTG CCA GGG TTT AAC | ACC AGA TGC ATG TGA TTA AAG G | 1985, 1986 |
| chr18 | 60401084 | 60401333 | ATT GGT TCC AGA TAC AGT CGA | GTG TAC TCT AGG CTA CTG TCA | 1987, 1988 |
| chr18 | 60412199 | 60412448 | GGA AGG AAG TAC AGC ATG GAT | GTC AGC AGC AAG TAA AGG TTC | 1989, 1990 |
| chr18 | 60420053 | 60420302 | CCT TAT TGA AGC TGA CCA TGC | CAT CTA GTC AAG GGT TCC ACA | 1991, 1992 |
| chr18 | 60434561 | 60434810 | CAG TGG GAA ATG TGC TTA CAT | CAA GTC ATG CTC CAA ACT GTT | 1993, 1994 |
| chr18 | 60449047 | 60449296 | AAA GGG CCT ATA TTC ACC AGA | AGG ACT TAG GAC AAC AGA GAA | 1995, 1996 |
| chr18 | 60452471 | 60452720 | AGA GCC ATT TAA GAC TCT CTG T | TGC CCA ACA CCA TCT CTA ATA | 1997, 1998 |
| chr18 | 60456757 | 60457006 | TAC CTT GTT CTC TGC CTC AAT | GCC TTC ATC ACT CAG AAC TTC | 1999, 2000 |
| chr18 | 60467147 | 60467396 | TTT AGA AGG ATG TGG ACA GGG | AGG GTA TCT ATT CTC CGG ACA | 2001, 2002 |
| chr18 | 60469757 | 60470006 | AGC AGG ACA TGG ACT TCA AA | ATT TGC CCA AGT AAG TTC CAC | 2003, 2004 |
| chr18 | 60524168 | 60524417 | GCG GCT CTT GTT CTT GAA ATC | TGG AAG TAC ATG GGA TGC ATT | 2005, 2006 |
| chr18 | 60537888 | 60538137 | ACA GGT AGG AGT TCA GAG ACA | CTT GAA GAG TTC CAA TGC CAA | 2007, 2008 |
| chr18 | 60544380 | 60544629 | TTT CCT ATT CTG CTC TTC TGC T | CGC TGC TGT TTA AAT CGA TCA | 2009, 2010 |
| chr18 | 60544742 | 60544991 | AAA TGC TGC TCA GGG TTA GAG | GCT CTG CTT TGC TCA AAT TCT | 2011, 2012 |
| chr18 | 60545407 | 60545656 | CAA CTT TAC TCT GCA CAG CTC | TGA GCT CCA GAA TTA GAT GTG T | 2013, 2014 |
| chr18 | 60611934 | 60612183 | CAG TGC CAC TAC AAA GAA ATC A | AAC ACC TCC TTT CTC ACT ACA G | 2015, 2016 |

FIG. 2 CONTINUED

| chromosome | start | stop | forward primer | reverse primer | SEQ ID NOs: |
|---|---|---|---|---|---|
| chr18 | 60617081 | 60617330 | AGA AGC AGA GGT TGG ATA TGG | ACA AAC TTC ATT CAC CGC AG | 2017, 2018 |
| chr18 | 60617641 | 60617890 | CCA CAA TCC CAT AGT CAC CAT | AAC TAC GCC ACC CAA CTA AA | 2019, 2020 |
| chr18 | 60630438 | 60630687 | GCT GGT TCT TGT TGC TGA TAA | GCT TCA GTG TAA CCA TGA CTC | 2021, 2022 |
| chr18 | 60630849 | 60631098 | TCC CTC ACG ACT TAT GTT TGA | TGC ACA ATT AAG CTA CTT CTC C | 2023, 2024 |
| chr18 | 60633840 | 60640089 | CTA CCT TCT CCA GTG CAC TAT | CAA CAC CAA ACT TGC CTG AAT | 2025, 2026 |
| chr18 | 60640300 | 60640549 | GGA CCT CTC TTT GAA ATG GAC | TCC ACA ATT TCT ACA GCA ACC | 2027, 2028 |
| chr18 | 60776944 | 60777193 | TGG GTG TTG TTT CTC TGA CTT | GTG TCA TTT GAT TGG TGC TCT | 2029, 2030 |
| chr18 | 60813738 | 60813987 | TAC AAG CCT TCT TTA ACC CTT | GGG TGT TTC AGT AGG TTA GGA T | 2031, 2032 |
| chr18 | 60814585 | 60814834 | AAA GGG TTT GAT ACA GTT GGG | TGG GAT TCT AAT GTC TGG TGC | 2033, 2034 |
| chr18 | 60938666 | 60938915 | AGG TAT TGG AGA GCA AGA AAG A | AGA GGT GGT TGG TTG GTT | 2035, 2036 |
| chr18 | 60939202 | 60939451 | GCA AAC TGG AGC TAA AGT CAT | GGG CAT CCT GTC TGA AAT ATG | 2037, 2038 |
| chr18 | 60950541 | 60950790 | TTG GTT GCT AGC TCT CAA ATG | AAG AAG CGC AGA TAC AGT ACA | 2039, 2040 |
| chr18 | 60953225 | 60953474 | TTC AAT GCC CTT ACT TCT CCT | CAC AGC AAG TTT GAA CCT AGT | 2041, 2042 |
| chr18 | 60958474 | 60958723 | GCT TGA GGC GCA TAT GAT TG | AGT GCA AAT GAT GAC CTG TTG | 2043, 2044 |
| chr18 | 60960879 | 60961128 | CAT ATG GTG CTT GTT CTG GG | GAA CTG TTG CAT GAG AGG TAC | 2045, 2046 |
| chr18 | 60965583 | 60965832 | CAA ACT CAC CAC CCT TCA TTC | CTT TGT CCT TCT CTG TTG TGT | 2047, 2048 |

FIG. 2 CONTINUED

| chromosome | start | stop | forward primer | reverse primer | SEQ ID NOs: |
|---|---|---|---|---|---|
| chr18 | 60970251 | 60970300 | CCT TAG CCC TGC AAA TAA CAC | TTT CTT CTA GAG TCC AGA GGT G | 2049, 2050 |
| chr18 | 60974839 | 60975088 | TCA CAG ATA CGG ACA AGC TC | ATT CTC TTC TCT CTT CCA GCC | 2051, 2052 |
| chr18 | 60984378 | 60984627 | GCC ACA GGT ATC AAT CAC TTC | TAT GGC TTT GCT ACC TTG TCA | 2053, 2054 |
| chr18 | 61055997 | 61056246 | GCT TCT GTG GCA CTA ATC AAG | CTA TTT CTC TGG CTC TTG ACC | 2055, 2056 |
| chr18 | 61086669 | 61086918 | GCC TTA TTG ACT TAC TGG ACT G | TTC TTA AAC CTC TGT GTG GCT | 2057, 2058 |
| chr18 | 61090462 | 61090711 | GTC AGG GAT TAG AGG CAG AAC | TGG ACA AAC AAG AAC TGG GTA | 2059, 2060 |
| chr18 | 61100325 | 61100574 | CAA TCA CTT GGT CAG ATA GTG T | CCA TGA TCA CTG AAA CCA ACA | 2061, 2062 |
| chr18 | 61154459 | 61154708 | AGT GGA GAG GTT GAG TAT AGT G | CCA TAT GCC CTG CTC TTT AAG | 2063, 2064 |
| chr18 | 61162901 | 61163150 | TGA GAA GGG AGG AAG AAT GTG | GGG TGG ACA AAG CAA TTC AAA | 2065, 2066 |
| chr18 | 61170629 | 61170878 | AAG GTC AAA CTC TCC ATT CCA | CAG CAT TCA ATT CAT CCT TGT G | 2067, 2068 |
| chr18 | 61197492 | 61197741 | GGA GAT GTC TTT GCC CTG ATT | AAG TAG AAG CAA GCC CTG AAT | 2069, 2070 |
| chr18 | 61213452 | 61213701 | GGT CCT CGT TTG TCC TTA AGA | GTG TGG TAG GGA TGA GAA TTA T | 2071, 2072 |
| chr18 | 61213800 | 61214149 | AGT ATT GCT TTG AGG GCT CTA | TCA GGT AAG CTT CCC TCC AC | 2073, 2074 |
| chr18 | 61216749 | 61216998 | AGC TAT CAT GTA AGT CAC TCC C | ACT GGT TGT AGA AAG GAC CTC | 2075, 2076 |
| chr18 | 61232928 | 61233177 | AGG AAA TTC AGT ACC TCA GCT | AGT AAG AGG CCA GAA GTC AGA | 2077, 2078 |
| chr18 | 61236079 | 61236328 | CAA CCT TCT CAT TGT TGA AGC T | GCA GTG CAG GCC TAT ATA TAG | 2079, 2080 |

FIG. 2 CONTINUED

| chromosome | start | stop | forward primer | reverse primer | SEQ ID NOs: |
|---|---|---|---|---|---|
| chr18 | 61253277 | 61253526 | GGT GAC TTT GCT TTC CCA AG | AAA TCT GTG AGT CGG CCA TAA | 2081, 2082 |
| chr18 | 61259478 | 61259727 | GCT GAC AAA CGG AGG GAG AG | AGG CAT GGC AAA CTT ACT TG | 2083, 2084 |
| chr18 | 61264533 | 61264782 | TGT TCT TCA TCA GGC ACA ATG | CAT TTC ACT TTC GAG GAT GGT | 2085, 2086 |
| chr18 | 61289440 | 61289689 | ACC ATT TGT GTG ATC CAG AAC | GTC AGA CTA AAG TGA GGA CCA | 2087, 2088 |
| chr18 | 61368889 | 61369138 | CTT GTC TTG AGT GCG GTA CA | CCA GCC CTA CCT AAA GTG AAT | 2089, 2090 |
| chr18 | 61370663 | 61370912 | GCC TCT CAG TTT CCT CTT ATA G | CCC TTT CAC AAG ACT CTT CTC | 2091, 2092 |
| chr18 | 63685629 | 63685878 | CCT AGA TCA GTG CAG AGA ATT TAG T | TGC TGT ATA AAC ACC TTC TGA AGA | 2093, 2094 |
| chr18 | 63711583 | 63711832 | CTT TAG TTT GGA GGC CTC ATT C | CCA AAT GTA GAA CAG GAT CAG C | 2095, 2096 |
| chr18 | 63721183 | 63721432 | CTG ACA TCG ATG GAA TTC GGC | TAG CAG TAG GTG TGG CTT TC | 2097, 2098 |
| chr18 | 64379625 | 64379874 | ACA AAC TTG GTG CTC AGT GGT | TTG GAT TCT CTT GGT TGT GAG | 2099, 2100 |
| chr18 | 64398368 | 64398617 | ATA AAC TTG GTG CTC AGT GGT | CAA CGC TTT GGT ATA GTT TGT G | 2101, 2102 |
| chr18 | 64410092 | 64410341 | ACA AGC ATT ACA GAA TTC GGC | CCA GGT GCC ATC GTT AAA GAA | 2103, 2104 |
| chr18 | 64412606 | 64412855 | ACT GAC AGA TTC TCA CCT ATA TCA G | ACA ATC CAA ACT CTT CAT GCA GT | 2105, 2106 |
| chr18 | 64417267 | 64417516 | GGA TCA AAG CCA CTC TAG ACT | GGA TAA GTC AAC TAC CAT GGT T | 2107, 2108 |
| chr18 | 64421562 | 64421811 | TTG AGA TGG CAT CAA GTT CAA G | AAT GGA ATT ACT CAG CTG TGG | 2109, 2110 |
| chr18 | 64426871 | 64427120 | ACT GGA TTC ATG CGT TAT CAA G | GGC AGA AAC TGA TAG AGA CTG | 2111, 2112 |

FIG. 2 CONTINUED

| chromosome | start | stop | forward primer | reverse primer | SEQ ID NOs: |
|---|---|---|---|---|---|
| chr18 | 64436287 | 64436536 | TAT TCT TGT GTG GAC CCT GTG | ACC ATG TTC TGA GTA CCT CTT | 2113, 2114 |
| chr18 | 64593727 | 64593976 | TGA TAT TGC ATG AAA GTC CCT G | AG TCC TGA ATC AAT GTC TAA CAC | 2115, 2116 |
| chr18 | 24962594 | 24962843 | TCA CAC ATG AGG AGT AGA CA | TGG TCC CTG TGC TTT GAT AT | 2117, 2118 |
| chr18 | 24964748 | 24964997 | CAC AGC AGG AGA CAT GAG AA | TGG CTT TTC TTT CCT CGG TA | 2119, 2120 |
| chr18 | 25003553 | 25003802 | TTT CCT CCT GGC TTG ATC AC | CCA AGG CTG CTT TAA TTC CA | 2121, 2122 |
| chr18 | 25033345 | 25033594 | CAA AGG AGA GAA GTG ACC CA | CAA ACT ATC GCT GAG GAC CT | 2123, 2124 |
| chr18 | 25037434 | 25037683 | CTA CGA GTG AAA CAG AGT GC | GTC TGC TGC CAT TGA GTT AT | 2125, 2126 |
| chr18 | 25052992 | 25053241 | AGA CTA AAA GCC TCC AAG CC | GGT CAC CCT CTC TTC TCT CT | 2127, 2128 |
| chr18 | 25080042 | 25080291 | TAG AAT ATG TCA CCC AGC CC | ACC TGT TTC TCC CAG TTA CA | 2129, 2130 |
| chr18 | 25124915 | 25125164 | ACA GAA TCA TCC CAT AGC CA | GCC CAT GAA AGA GAA ACC AG | 2131, 2132 |
| chr18 | 25128057 | 25128306 | CGC CAT TCT GTG CTT AAT TTG | CTC CAT CAG TGC AGA AGT CC | 2133, 2134 |
| chr18 | 25140257 | 25140506 | GTG AAG CAA GAG AAA GCA AGA | ACA GTC AGC AGC CCT AAA AT | 2135, 2136 |
| chr18 | 25140722 | 25140971 | TGA TTC GGC TGC AGG TTA TT | GCC TCC TTC ACA TAA TGC AG | 2137, 2138 |
| chr18 | 25147759 | 25148008 | CTG GCT TCA AAT GCA TCT GA | TTG TCA ACA GAG AGT CAG CT | 2139, 2140 |
| chr18 | 25157828 | 25158077 | ACT GGG AAA TTG GAA TTC GC | CTG AAA TGG TCT GGG AGT CT | 2141, 2142 |
| chr18 | 25160244 | 25160493 | GGT AAA ACT GCC TGG AAA CT | TCA AAG ACA GAG TGA GTG GA | 2143, 2144 |

FIG. 2 CONTINUED

| chromosome | start | stop | forward primer | reverse primer | SEQ ID NOs: |
|---|---|---|---|---|---|
| chr18 | 25166254 | 25166603 | AGA CCA CGG GCT CTA TCT AT | TTT GGG GGT TAC ACT TCA TAG | 2145, 2146 |
| chr18 | 25172986 | 25173235 | CAT CTT GCT TAT TGG CTT ACG A | AGC CAG CAG AAT AAT ACC AGG | 2147, 2148 |
| chr18 | 25174972 | 25175221 | GAG GTA GAG GCA GTG TCT TG | ACC TCA TCT TTT GTC AGC CT | 2149, 2150 |
| chr18 | 25175640 | 25175889 | TAG TCC TTG AAC TCC CTG GT | ACA GTT CCA TAG GCA GGT TT | 2151, 2152 |
| chr18 | 25182855 | 25183104 | CCA GCT TAG CGT CTG TTT TT | GCA GTT CCA GAT CCA ATA TGC | 2153, 2154 |
| chr18 | 25198531 | 25198780 | GAC CAC AAC TAT CAA GAG CAC | TTT GGG AAA GAT GGG AGA GC | 2155, 2156 |
| chr18 | 25201886 | 25202135 | CCA AAG AAA GGT TGA AGC CC | TTG CAG GTA AGG TAC AGA AGA | 2157, 2158 |
| chr18 | 25209395 | 25209644 | AAT AAT GTG CAC TGT GAT GGC | CTT CAG CTG CAT CTT GAG C | 2159, 2160 |
| chr18 | 25213880 | 25214129 | TTT AAG GGT CTG ATG GTT GC | GGC ACT TCA AAA ACA AAC CC | 2161, 2162 |
| chr18 | 25216888 | 25217137 | GAA AAT GCC CAT CGT CTC AA | AGG GTT TTA TGG TCT CCT GG | 2163, 2164 |
| chr18 | 25228617 | 25228866 | ATT CCT TGT CTT TCC CCC TC | TCA ACA CGG AGA ACT GAA AAC | 2165, 2166 |
| chr18 | 25231535 | 25231784 | TCA TTT CTC TAG CCC AAA GAT G | TCC GTG TAA ATG AAC AAA GCA C | 2167, 2168 |
| chr18 | 25245662 | 25245911 | TTG GTT TGT TGA CTT CAG CC | TTC AGG GAA TGG TTT GCA TT | 2169, 2170 |
| chr18 | 25246300 | 25246549 | GCT CAG TGA CAG TTG GGA TT | GAG ATG CCA TTC CCA AAA GG | 2171, 2172 |
| chr18 | 25254843 | 25255092 | GTC TTG TCT CTC TTC TTC CAC T | CCC TAC CAT AGT GCC AGA TG | 2173, 2174 |
| chr18 | 25265476 | 25265725 | TTT AGA GCA GGT GGA AAC GA | CAG CTT TCA GTG ACA GAG GA | 2175, 2176 |

FIG. 2 CONTINUED

| chromosome | start | stop | forward primer | reverse primer | SEQ ID NOs: |
|---|---|---|---|---|---|
| chr18 | 25278532 | 25278781 | CTT GGG TTT TTA TCG GTT GCT | CCA AAG GCA GAT GAG TGT TT | 2177, 2178 |
| chr18 | 25279010 | 25279259 | GTT GCC TGG ATT GCT CTA AA | GCC TGG GAT AGA AAT GGG AA | 2179, 2180 |
| chr18 | 25283817 | 25284066 | AAA TCA CGA CGT AGG AAA CC | GGA AAG GAA AGG AAG CTG TG | 2181, 2182 |
| chr18 | 25292042 | 25292291 | TCA CCT TGG AGC AGG TCA TA | TCA GAG AGG TCT TGC TGA AG | 2183, 2184 |
| chr18 | 25295429 | 25295678 | CGA AGA AGG TCT GGG AGA TG | TCT CTC TGT TGC TTG TTT CCT | 2185, 2186 |
| chr18 | 25330345 | 25330594 | CAC CAT TGT TTC ATC AGG ACT | CGC ATG TGG TAG ATC ATC AG | 2187, 2188 |
| chr18 | 25332963 | 25333212 | TTG CAT CAT CAG CTC ACA TAC | TAT AAC ACC CTC ACC TCC CA | 2189, 2190 |
| chr18 | 25333284 | 25333533 | AGA CCT GGA AAA TGA TGG GT | CAC CCA AAT CAC CTT GCT ATG | 2191, 2192 |
| chr18 | 25345252 | 25345501 | CCT GGA AGT GTG TAA CAA GC | CAA CTA CCG TGG ATT CCG TT | 2193, 2194 |
| chr18 | 25384702 | 25384951 | CTC CCT AGC AAA AAC TTC TCA | TCT ATC ATG AGT CGC TTC CA | 2195, 2196 |
| chr18 | 25510767 | 25511016 | TGC CTT ATT CAC TGT GCA AC | TTT CTG TCA CTT TCT GGG CT | 2197, 2198 |
| chr18 | 25519108 | 25519357 | TGA TGG CCT AGT GAG TTT CC | CGT GTG TTT CTA GTG CAT TGT | 2199, 2200 |
| chr18 | 25531724 | 25531973 | TGC AAT GTA ACA AAA GCG TG | GGG CTC AGA GGG AAT ATC AG | 2201, 2202 |
| chr18 | 25543168 | 25543417 | GCC ACA TTT GCT TTC ACA CA | CCG ACG AAT GGA TGA AAG AC | 2203, 2204 |
| chr18 | 25547425 | 25547674 | ACG TCA TTG GGT TCA TGG C | ACC CAA ATT CCA TGC CTA CT | 2205, 2206 |
| chr18 | 25557343 | 25557592 | ATT TTA CCC CCT TAG GCA CC | TGT ACA GCA GTC TCC AGA AA | 2207, 2208 |

FIG. 2 CONTINUED

| chromosome | start | stop | forward primer | reverse primer | SEQ ID NOs: |
|---|---|---|---|---|---|
| chr18 | 25564483 | 25564732 | TCT TCT ACA CAG CCC TTC AG | GCC CTC TTA CCC TTT CTC AT | 2209, 2210 |
| chr18 | 25583087 | 25583336 | ATT GGG ATC GTC AGC ATC AA | CAT TCA AAG ATC CAG ACC AGG | 2211, 2212 |
| chr18 | 25585083 | 25585332 | TGA TTG TCT TGT CCA CTG GT | ATC TGT GAT TGC TGC CCT C | 2213, 2214 |
| chr18 | 25589902 | 25590151 | ACA TCA CAC TTC ATG CCC TT | CTA GAA ACT CCC AGG ACA GA | 2215, 2216 |
| chr18 | 25601966 | 25602215 | ATG AAG GCA TTA GGA GGG AG | CAT GTG TGG AAA GGA TTG GT | 2217, 2218 |
| chr18 | 25611986 | 25612235 | AAA GTG GAG AAG TGG CAG AT | TAT GAA TGA ACC GTG GCT CA | 2219, 2220 |
| chr18 | 25617498 | 25617747 | CCT TAG GAT TCT GAG AGG TGA G | AAG TTG AGT CGT TTG TCC CA | 2221, 2222 |
| chr18 | 25629105 | 25629354 | AGG GCT TCT GAT TGA TTT GC | TAG TGT TTC AGG AGC GTG TT | 2223, 2224 |
| chr18 | 25631180 | 25631429 | CAG GGT AGT CGG GAT TTC TC | CCA GGA CAA GCA GAC ATT TT | 2225, 2226 |
| chr18 | 25643639 | 25643888 | CCC GGT AAT GAT CTA CAG CA | GCT GCT GGT GAT TTT TGA AGA | 2227, 2228 |
| chr18 | 25645371 | 25645620 | AAC GGC ACT TGG TTC ACT A | CTC TGG GCA AAC AAG AAA CC | 2229, 2230 |
| chr18 | 25665025 | 25665274 | ACT CTG AAC TCC TCC TCC TG | GTG TGT GTT TGT GGA AGT GT | 2231, 2232 |
| chr18 | 25666614 | 25666863 | TTT GCT CAC ACA CAA GAC AC | AAA GCC CAA TCT CTC TGG TTA | 2233, 2234 |
| chr18 | 25667057 | 25667306 | ACG ACT GCA TCC TTT TCA TG | TAG GCG GGC TTA TTG TGT TT | 2235, 2236 |
| chr18 | 25670741 | 25670990 | CCA TCA TAG CCT ACA AAT ACC C | TCA ATG TAA ACT GCC CGG AG | 2237, 2238 |
| chr18 | 25673208 | 25673457 | AGA GAG TTG AAA ATA TCC CCC A | ATG GGA GTC GAA TGG TGT AAA | 2239, 2240 |

FIG. 2 CONTINUED

| chromosome | start | stop | forward primer | reverse primer | SEQ ID NOs: |
|---|---|---|---|---|---|
| chr18 | 25681018 | 25681267 | ACT TTC TTG AAC ACC CCA GT | TAA CAT TTG AGG GCA TGG GA | 2241, 2242 |
| chr18 | 25682079 | 25682328 | TGC CTG TGT CCT ACT TTT CC | CAG AAT ACC CTC ACT GTG CT | 2243, 2244 |
| chr18 | 25689906 | 25690155 | TGA CTG CCC AAG AAT GTA CA | GGA GAT AAC AGC AGA GGT CC | 2245, 2246 |
| chr18 | 25700540 | 25700789 | CCG AAC ACG CTG TAT GTA TT | TGT GGG TGA TAT CTG TGT CT | 2247, 2248 |
| chr18 | 25703648 | 25703897 | GGA AGG GAA TTG AAG CAC AG | GCC ATC CTG TAA CTG AAT GC | 2249, 2250 |
| chr18 | 25707188 | 25707437 | TCA TCC TAT CCA CCA ACC TG | GTA TTT TCC CTT TGC CGC AG | 2251, 2252 |
| chr18 | 25716100 | 25716349 | AAT GAA CTG GCC CTG ACT TA | ATT ACA GCA AAG AAC GTG GC | 2253, 2254 |
| chr18 | 25722951 | 25723200 | TAA GAT ACC ATA CCG CAG CT | TCT GTG TGT TTT GCA TTG GT | 2255, 2256 |
| chr18 | 25725055 | 25725304 | TCA GCG TTC ATG GTA CCA ATA | GTG ACA GTT TTC CAA GGC AT | 2257, 2258 |
| chr18 | 25748105 | 25748354 | GTT TCC CAA CCA ACA AAC AAG | GCA TTA CTT TTT CGC ACA CT | 2259, 2260 |
| chr18 | 26214441 | 26214690 | TCT ATC GGG ATG GAG AGT GA | GGG GAT TGT TTT AAG CAG GC | 2261, 2262 |
| chr18 | 26236788 | 26237037 | GTT CAG ACA GGT GGA CTA GG | CCA TTG TTC TCA CCA ACT CT | 2263, 2264 |
| chr18 | 26261336 | 26261585 | AAG CAA CCT GGG AAA TTG TG | CCT GAA ACA CAA GCA GCA G | 2265, 2266 |
| chr18 | 26265937 | 26266186 | GGG TTA AGG TTG CTG GGT TA | AGC TGC CTA TTT GAT TGG TG | 2267, 2268 |
| chr18 | 26285286 | 26285535 | GTG AAA TGT GGT TGT AGT GCA | CAG TAC AGT CAG CCT TCC TT | 2269, 2270 |
| chr18 | 26289006 | 26289255 | GTG ACT GCC TTG CTT CAT TT | TGC ATT CAA ACT ACC CCA AG | 2271, 2272 |

FIG. 2 CONTINUED

| chromosome | start | stop | forward primer | reverse primer | SEQ ID NOs: |
|---|---|---|---|---|---|
| chr18 | 26308405 | 26308654 | CAG TTC TGG AGC CTT CTA CT | CCG AAA AGA GGC AAG CAA TT | 2273, 2274 |
| chr18 | 26308962 | 26309211 | TTA GGG CAG GAT GTA CAG AA | GTC ACC TCA ACC TAA CTC CA | 2275, 2276 |
| chr18 | 26312054 | 26312303 | GCT GGT GAC CTT CAT TCA AG | GCA ACA GTC TAC CCG TCT AG | 2277, 2278 |
| chr18 | 26316149 | 26316398 | TAA AAC CAT GTT CGG GGC A | ATC AAT GCT CTG ACC TCC TG | 2279, 2280 |
| chr18 | 47100905 | 47101154 | CTA CCT GTC CGT TTC CCT TAC | ATA CAT CAG GCC TCC AGA ATT | 2281, 2282 |
| chr18 | 47130278 | 47130527 | GAC AAA GAT GAC TGG AGG TGA | CAC ATC TTT AGA GCT CAG GTG A | 2283, 2284 |
| chr18 | 47366936 | 47367185 | GGG TGG ATG GTG AGA TAT GTG | CCA TCA CTT CAC AAT CCA CAC | 2285, 2286 |
| chr18 | 47371131 | 47371380 | CTT CAA ACC TGA TCC ATG TGC | AAT CCT GCA GTC ATC TTC CC | 2287, 2288 |
| chr18 | 47680868 | 47680117 | GCA GAA ACA GCA TGA ATC TCC | CAA GTC TGG TTT GTG AGA AGC | 2289, 2290 |
| chr18 | 47690267 | 47690516 | TGA CTT CAA ACA TCC CAT CCA | GGG AGC TTC TGT AGT CTT TGA | 2291, 2292 |
| chr18 | 47703689 | 47703938 | GTG GGA TGA GTT CTA GAG GAA | TAA GGA GAG CAG GAC TTA CAG | 2293, 2294 |
| chr18 | 47708139 | 47708388 | AGT CAC ACA CAT ACA CAC AGT | CCA ACG GTT CAT TTG TCG TAT | 2295, 2296 |
| chr18 | 47717445 | 47717694 | ACG ACT TCC CTG TGT AAC TTA | CCT TGC TCT GTT AAT GGG TTT | 2297, 2298 |
| chr18 | 47738531 | 47738780 | CCT TCT CTT GTC TCT AGT GCC | AAC AAT GCT TAA CGG GAA TCC | 2299, 2300 |
| chr18 | 47777438 | 47777687 | CTG GAA ATA CAC ACA CAC CTG | GCA GAG TTC ATA GAA GGG TCA | 2301, 2302 |
| chr18 | 47794212 | 47794461 | ATT TGT AAA CCA CCC ACT TCG | AAA CCG AGA CGA CCA CCT AAT | 2303, 2304 |

FIG. 2 CONTINUED

| chromosome | start | stop | forward primer | reverse primer | SEQ ID NOs: |
|---|---|---|---|---|---|
| chr18 | 47799400 | 47799649 | TCA CTG TGC TGA CAA ATC CTA | GAG TGA TGA TGA GCC ATG ATG | 2305, 2306 |
| chr18 | 47802662 | 47802911 | CCC ATC ATC CCT TCA GAC | GGA TAT TGG AGA TAG CAG GCA | 2307, 2308 |
| chr18 | 39874986 | 39875235 | TCA TCA CTT TAT CCT CCC AGT | GTT TGG CAC TGC AAC TAG ATA | 2309, 2310 |
| chr18 | 39891490 | 39891739 | ATG GGC ACA GGT AAA GAG TTT | TGA AAT AAG GGA AGC CAC ACA | 2311, 2312 |
| chr18 | 42202240 | 42202489 | TTT GTA AGC TGA GTG TGA GGT | TCC TTA GTG TGC CAA TTA GCC | 2313, 2314 |
| chr18 | 42313146 | 42313395 | TTA CTG TTT GAA TGC CAG CTC | TTA ATG TGG AGA GAC AGG CC | 2315, 2316 |
| chr18 | 42313939 | 42314188 | TCC CTT CTC CCA TCA CAA TTC | CAA TGC ATC TTA CTC ACC CTT | 2317, 2318 |
| chr18 | 42314302 | 42314551 | GAA GAC TGC ATG TGT GTC CTA | AGT ATG GAA GTG GGA ATT GGA | 2319, 2320 |
| chr18 | 42349923 | 42350172 | TTC TCA CTC TCA ACT GAA CCA | TTG CTT CCA CAG AAA CTC TTC | 2321, 2322 |
| chr18 | 42407165 | 42407414 | TCA GGG AGC TTC TAA TTA AGG A | AAC CGA CCT ATT CCA AAG TCT | 2323, 2324 |
| chr18 | 42418033 | 42418282 | AAG ATG ATC CCA GGC TTA AGG | TGT GAA GCG AAT ACA GCT CAA | 2325, 2326 |
| chr18 | 42449702 | 42449951 | GTT GAG GTT TGC TGA TCT TGG | GTT CTA ACT ACA CCA GGC TCT | 2327, 2328 |
| chr18 | 42450400 | 42450649 | CAA AGA TAG ATT CGC ACA CCA | GTA TGA GTG TAG GTG TGG AGG | 2329, 2330 |
| chr18 | 42461427 | 42461676 | GAG CTG GAC AAA TTA AAT GGC | AAT CTG GAT CTA GCG AAG GAC | 2331, 2332 |
| chr18 | 42462834 | 42463083 | CCA GTG CAT TTG GTT TGA CA | TAA TGA GAA GGC AGG ATG AGG | 2333, 2334 |
| chr18 | 42468595 | 42468844 | TAT GTG AAT CCT CTG TGT GGC | AAG ACA ACT CTC TAG GCC TCA | 2335, 2336 |

FIG. 2 CONTINUED

| chromosome | start | stop | forward primer | reverse primer | SEQ ID NOs: |
|---|---|---|---|---|---|
| chr18 | 42468938 | 42469187 | AGC TTC TCT CTC ATT CTG CTT | GTT TAT GGT TGT CCC TGG AGA | 2337, 2338 |
| chr18 | 42644003 | 42644252 | GAC TCC CGA TTT CAT TTG CTG | TCC ACC TTC TGA TCA CAC AAT | 2339, 2340 |
| chr18 | 42644494 | 42644743 | TCC CAA TCG TTG TGA AAC ATA C | AAG ATC AGG TAC CAA GGC ATT | 2341, 2342 |
| chr18 | 42645387 | 42645636 | TCT TTA CAG GAA GTT GGG ACC | ATG ATG TGA AGT CCA TGG TGA | 2343, 2344 |
| chr18 | 42741059 | 42741308 | TAA GTT CAG ATC AGG GAG CAG | TCC AAA TTG ACT TCC ATG AGC | 2345, 2346 |
| chr18 | 42745733 | 42745982 | GTT GAA AGT CTT ACA GAA CGC T | GTG GTT TCA GGA ATT TGG AGG | 2347, 2348 |
| chr18 | 42746460 | 42746709 | CAA CAT AGG CAC ATT GTC CTC | TAT TTG CTG CTT CAT TCT TCC C | 2349, 2350 |
| chr18 | 42746911 | 42747160 | GTC AGG CCT CAT AAC TCT CTT | AAG TCA TTA CGT CCC ACA CTG | 2351, 2352 |
| chr18 | 42747473 | 42747722 | GTT GTG TGG CTT TCC TTA TCA | AAA GTC ATC AGA AGG GTA GCA | 2353, 2354 |
| chr18 | 43796659 | 43796908 | CCT GCA GCT CTG TGT AAA TTT | AAT GAT GCC GAA CAG TGA GTA | 2355, 2356 |
| chr18 | 43820471 | 43820720 | CTT TGG CCA GTT CTT TCT CTC | AAT GTA AGA CAG GGA CAG AGA | 2357, 2358 |
| chr18 | 43841913 | 43842162 | GTG GCC CAG CAT TAT TTG TT | TGA ATT CCA CAG TCC AGT CAA | 2359, 2360 |
| chr18 | 43842202 | 43842451 | TCT TGG TGT GAC TTG CTA ACA | AAT GCC TTC AAA GAC AGT GAC | 2361, 2362 |
| chr18 | 43842647 | 43842896 | TTT CTG GCT GAG ATA AGA CCC | CAC ACC TGC AAT TGA GAT GAA | 2363, 2364 |
| chr18 | 43845701 | 43845950 | ACA ATT CCG TGG TAT ACA GCT | GTC ATG ATG ATG CAA CAG CTA | 2365, 2366 |
| chr18 | 43846353 | 43846602 | TGA TTG TGC CCT AAC CAA ACT | TTT CAC GGT AAG AGG AGC AAA | 2367, 2368 |

FIG. 2 CONTINUED

| chromosome | start | stop | forward primer | reverse primer | SEQ ID NOs: |
|---|---|---|---|---|---|
| chr18 | 43917652 | 43917901 | TGT CGT ATC CTG CTG TTT AGA | TTC TCT CTA GGC AGG TGA ACT | 2369, 2370 |
| chr18 | 43918519 | 43918768 | TCA GGA GTA AAG TCA GGA CCT | ACC CTT TGA AAG AAC CAG GAA | 2371, 2372 |
| chr18 | 43918998 | 43919247 | TGA GCT GAT TTA CTG TGA CAC | AAT GAG CCA CTG TTC TCT AGG | 2373, 2374 |
| chr18 | 43919244 | 43919793 | TAG CAC CTT GAC TTC AGG ATT | ATT TGC ACA TTA GGG CCT CAA | 2375, 2376 |
| chr18 | 44086123 | 44086372 | TGA GGT TGG AAA GGG TCA ATT | GAA CTT CCC TGC TTC CTT CT | 2377, 2378 |
| chr18 | 44094299 | 44094548 | CAG CTT TCC TTC CTC TTC TCT | AAA TAC TTG GCT GTG ACC ATG | 2379, 2380 |
| chr18 | 44167214 | 44167463 | ACA GTG AGA GGA AAG AAC AGC | AAG ACC CTT GAG AAC TTC CAA | 2381, 2382 |
| chr18 | 44167791 | 44168040 | GGA AAT AAA TTG TGA GCT GGC | ATG TGT AAA GAC GTC CTG GAA | 2383, 2384 |
| chr18 | 44168296 | 44168545 | AGA CAG CCC TTC AAT CCA TAC | TCT ATG TGG AGG GAT TTG ACA | 2385, 2386 |
| chr18 | 44173512 | 44173761 | CCT ACA TCC CTT CCT CCT TTC | TTC CTG AAG TTT ATG GTG CAA C | 2387, 2388 |
| chr18 | 44174626 | 44174875 | TCA CCC ATC TTC CAA TTA GCT | AAG GTT GAA TGA GGA TCA AGC | 2389, 2390 |
| chr18 | 44857765 | 44858014 | TTT CTA AGC ACA AAC TGA CAC C | GAG GGA AGA ACA CAA CAC ATG | 2391, 2392 |
| chr18 | 45110525 | 45110774 | GAT GTT TGC ACT GGA GGG ATA | CAG ACT AGC CTA CAA TCC TCC | 2393, 2394 |
| chr18 | 45197621 | 45197870 | GAA GAC TAA ATG TTG GCC GAA | CAT TCA GGT TCT TAA GGG CTG | 2395, 2396 |
| chr18 | 45197871 | 45198120 | GTA GAG AGA GGG AGG ATC ACA | GAA AGG CAG ACG ATG AAA GAG | 2397, 2398 |
| chr18 | 45198760 | 45199009 | CTT GCC ATG AAG TTT GAC CAG | ATC TCC ATC AGC ACA GGA ATT | 2399, 2400 |

FIG. 2 CONTINUED

| chromosome | start | stop | forward primer | reverse primer | SEQ ID NOs: |
|---|---|---|---|---|---|
| chr18 | 45234886 | 45235135 | AGG ATG AGC ATT TGT AAC CTG | GCA GTG TGA CAT CTG TGA ATG | 2401, 2402 |
| chr18 | 45235523 | 45235772 | TGT CGC TTT CAA ATT ACC CAC | AGA CTT TCC TGT TCC TCT TCA | 2403, 2404 |
| chr18 | 45238370 | 45238619 | CAT ACA AGT GCT CTG TTA GGC | TTT ACA ATG AAC TAG CCA GGC | 2405, 2406 |
| chr18 | 45335896 | 45336145 | AGG ACT TGG AAC CAG AAA GAC | TAA CAT CTG CCT GAA AGC TTC | 2407, 2408 |
| chr18 | 45336353 | 45336602 | AAA GAG GGC TGA TAT CGT CTG | CTC GTG TGT GCA ATT TGG AAT | 2409, 2410 |
| chr18 | 45357461 | 45357710 | CTC ACT GCA AAC TAT GGA ACC | GGA GAG ATG GAG AAG ACC TTT | 2411, 2412 |
| chr18 | 45357745 | 45357994 | TAT TCT GCC CAT CTT CTT CCT | AAT GTA TTA CTG TGC TCC CGT | 2413, 2414 |
| chr18 | 45358502 | 45358751 | GGA GAC AGC CCA AAC ATA GA | ACC ACC TGC CAC TGT ATA AAT | 2415, 2416 |
| chr18 | 45362379 | 45362628 | AGC AAT GGT GAA GTT CTG GAT | AAT TCT TCT GGT GCA AGG | 2417, 2418 |
| chr18 | 45397588 | 45397837 | CTG GTC AGT GAG AGA AGG GAA | TTG CCC TTT GAA CTG TTG ATC | 2419, 2420 |
| chr18 | 45864183 | 45864432 | TTT CTC CAC TGG CAT GAA CT | AAG CAC ACT AAG GCC TGA TAA | 2421, 2422 |
| chr18 | 46464382 | 46464631 | CAT GAT CAC AAT TCC AAG CCA | TCA GTA TCC ATT CAG CAT CCA | 2423, 2424 |
| chr18 | 46473428 | 46473677 | ACC CAG TCA AGT TAC AGT CTT | TAA CCG AAG CCC ATA CTC TG | 2425, 2426 |
| chr18 | 46474545 | 46474794 | TGT AAA GCA TAT CAA GGG AAC G | TCC TTA CTC CAG ATA CCC GAT | 2427, 2428 |
| chr18 | 46481797 | 46482046 | TGC AGA GAT ATG TTC CCG TAT | TCT GGC TTC TTT CTT GGA GAG | 2429, 2430 |
| chr18 | 46483016 | 46483265 | AGA AGA CAG TAC AAG GAA GGC | GCA ACA TTC ATT TCA TCC TGC | 2431, 2432 |

FIG. 2 CONTINUED

| chromosome | start | stop | forward primer | reverse primer | SEQ ID NOs: |
|---|---|---|---|---|---|
| chr18 | 46589014 | 46589263 | TGT TTG CCA TTT GTT CTC CTC | CAT CAC GAC ATC CAT TTC CAC | 2433, 2434 |
| chr18 | 46599847 | 46600096 | TTG AAG GCA AGA GAA GTT TGG | GTG GTT ATT ATC GGT GGG TGA | 2435, 2436 |
| chr18 | 46601866 | 46602115 | GCC AAG GAA ATG TAG GGA AAG | CTG CCA TTC CTT GTT TCC AA | 2437, 2438 |
| chr18 | 46983278 | 46983527 | AAC CTT CAC ACC TAG AGA CAG | ATT TGG ACT TGA AGC AGC CT | 2439, 2440 |
| chr18 | 47013103 | 47013352 | GCA TAA CAG GGA AAG TCA CCT | CTG TAT TCT TTG TCC ACC ACC | 2441, 2442 |
| chr18 | 47016802 | 47017051 | AGG ATG TTA GTG GTT TGG GTA | GAC AGG ACA CCT TGG ATT GAT | 2443, 2444 |
| chr18 | 286722 | 286971 | TCT GAC ACT GAC CTT CAA CT | GAG TAA TTC CCC CGA TGC AG | 2445, 2446 |
| chr18 | 298393 | 298642 | GAA ACA TTG CTT TCC CTC CA | TGA GAA TCA TTG AGC CAA ACC | 2447, 2448 |
| chr18 | 338127 | 338376 | TTC CAC ACA TCT CTT CTC CG | AAT TGT GAG CGT TAG AGT GC | 2449, 2450 |
| chr18 | 340427 | 340676 | GGG AGC CTT GAA AAC CTG AA | CCA GTG GGT CTT AAC ATT GAG | 2451, 2452 |
| chr18 | 387135 | 387384 | ATT GGT AGC GTT GTC AGC A | AAA AGG CTA GTA GAG GGT GC | 2453, 2454 |
| chr18 | 391175 | 391424 | TTC CTG CAT CTT GTA GAC CC | TCG CTG AAG AAC TGA GAC AC | 2455, 2456 |
| chr18 | 434440 | 434689 | GGG CTA ATG TTT TGC TTC CA | GGG AAG TGA TTG GAG AGA GG | 2457, 2458 |
| chr18 | 457527 | 457776 | TGT TGA TTA GAG CTT CCC CC | CCG CTT GGT ATA GAG TGC TG | 2459, 2460 |
| chr18 | 460384 | 460633 | AGA GGT TTT CTT CCC CGT G | TTG AGG TTG TCA GGA AAG CT | 2461, 2462 |
| chr18 | 469281 | 469530 | TAG TGC CCT CTA TTG TGC CT | TCT TGG GAA AGG GTC ATT CT | 2463, 2464 |

FIG. 2 CONTINUED

| chromosome | start | stop | forward primer | reverse primer | SEQ ID NOs: |
|---|---|---|---|---|---|
| chr18 | 572716 | 572965 | ACT GCT GGA CTT TGA AAT GC | TCT CTT CCA TGC ACT CCA C | 2465, 2466 |
| chr18 | 598352 | 598601 | CAA ACA GTG AGA TGT GGC TG | GAT CTG ACC CTC TGC TCA C | 2467, 2468 |
| chr18 | 615413 | 615662 | TTG CTT CCT GAA AAC TGG TTC | CCT GAA AGA TGC ATG GTT GG | 2469, 2470 |
| chr18 | 618280 | 618529 | ATT CCA ATC ACG TCT CTG CA | GCC ACA GAA CAA CCA GAT TC | 2471, 2472 |
| chr18 | 901111 | 901360 | ACA ATC TCA CAG CCT GGA AA | TGG GGT TAA GAG CTC AAG AG | 2473, 2474 |
| chr18 | 939383 | 939632 | TCA GAT GGG TGA GGT TCT TG | AGT GTG GAT GAC TTC TGC AA | 2475, 2476 |
| chr18 | 26321283 | 26321532 | CTG CTC CTT CCC TCC AAT TA | GCC CCA TTA TCC TCC TTT GT | 2477, 2478 |
| chr18 | 26337865 | 26338114 | AAA TGC CAG TCC TGT AAA GG | CAA ATC AGA CCC ACT AAG CAC | 2479, 2480 |
| chr18 | 26345717 | 26345966 | TGT CCC ATT GCT TAG GAA GT | TGT TTT GGA CTG CTT CAC TC | 2481, 2482 |
| chr18 | 26365387 | 26365636 | TGT GTG ATC CAG AGA CCC TA | ATT ATC ATG CTC ACT CCT CCA | 2483, 2484 |
| chr18 | 26367518 | 26367767 | ACC AAT GTA GAC TTA GCG GG | GAC ATA GCA CGG GAG GAG TA | 2485, 2486 |
| chr18 | 26392500 | 26392749 | ACT CTC ATA TTG CCC CAC TT | GCT AGT GGC GTT TTA GGA AA | 2487, 2488 |
| chr18 | 26406499 | 26406748 | CCA GGG ATT GAT GTA TCT GT | TCG CTT GGA AGT CAT AGC C | 2489, 2490 |
| chr18 | 26711590 | 26711839 | AAT TCT GGT CTA TCT GGC GT | CAG AGC TGC TTT GAA GAT AAT CC | 2491, 2492 |
| chr18 | 26729342 | 26729591 | GCC AGC CCT TTT CAC ATA TT | GAA GCC TGA TAG ATG TGC CT | 2493, 2494 |
| chr18 | 26733981 | 26734230 | AAC TAC ACC ATC CCC TGT TT | TAC CTC TGC CTC CAA TTG TC | 2495, 2496 |

FIG. 2 CONTINUED

| chromosome | start | stop | forward primer | reverse primer | SEQ ID NOs: |
|---|---|---|---|---|---|
| chr18 | 26739336 | 26739585 | CCA TTT CAA ACA TGC TGG TC | CCC ATG TAG ACA AAG TGC TT | 2497, 2498 |
| chr18 | 26750685 | 26750934 | AGA TTA TAA GAA GGC AGG GAA C | GGC AGG TTT GTC TTA CAG TT | 2499, 2500 |
| chr18 | 26752487 | 26752736 | GTA GAG GGC TTA AAA CAT GTC C | TGT GAG ATT GCA TTC CCC TT | 2501, 2502 |
| chr18 | 26757573 | 26757822 | ACA AGA ACA CAG TCG TTA AGC | CGG GTC AGA GAA AGA TCA GG | 2503, 2504 |
| chr18 | 27244230 | 27244479 | TCT CTC CTT CAC TCC CTT CA | AAA CAT TTG TAA CCA CTC CCT G | 2505, 2506 |
| chr18 | 35076347 | 35076596 | TGT CCA CCC CTC TTT GAT TG | CCT GTA ATA TGG GAC TCC TGG | 2507, 2508 |
| chr18 | 35147912 | 35148161 | TTT AGC TTC TCC TGC CTT TG | CCA AAC CAC ACA CAC AAA CT | 2509, 2510 |
| chr18 | 35282655 | 35282904 | AGA AGC AAT TCA CCA GGT CA | AGG AGA AGG ACA TTT CAC AGG | 2511, 2512 |
| chr18 | 35292141 | 35292390 | TGG AGT CAG AAG TGT GTG TT | AGG CCG ATA ATA AGA CAA GGT TC | 2513, 2514 |
| chr18 | 35304227 | 35304496 | TCT GGT GTC AAA GCT TAG GG | GTT TCC CAT AGA GCC CTG G | 2515, 2516 |
| chr18 | 35311302 | 35311551 | TGC CGA TGA TGT GTG TTT TG | CTC CAC TCT CTC CAA CCA AC | 2517, 2518 |
| chr18 | 36463709 | 36463958 | TGT CCC TTC CTA ATC CCA AA | AAA CTG TGA AAG GAC GAG GA | 2519, 2520 |
| chr18 | 36473033 | 36473282 | AGG ATG TTT AAG TTG CAG CA | TCC CTT GCT TTT GTA CCA GG | 2521, 2522 |
| chr18 | 36475403 | 36475652 | TAT GCA GTT TTA CCC CCT CC | CAT GTG TGT ACT GTG CCT CA | 2523, 2524 |
| chr18 | 36479145 | 36479394 | TTC TGT GTG GTC TCC TCT TG | TCT TTC ACT GTC ACT ATG GGG | 2525, 2526 |
| chr18 | 36482038 | 36482287 | ATG GAG GGA CAA GTG AGA CA | AAA TGC AGC TTC CCA ACA TC | 2527, 2528 |

FIG. 2 CONTINUED

| chromosome | start | stop | forward primer | reverse primer | SEQ ID NOs: |
|---|---|---|---|---|---|
| chr18 | 36483959 | 36484208 | GGG GAA CAT GGA GCT GTA AA | GAG ACT TTC TGG AGG ACG AA | 2529, 2530 |
| chr18 | 36485761 | 36486010 | GGA CCC CCT ACC ACA TTT AC | GAA ACG TAA TTT AGT GAC TGG C | 2531, 2532 |
| chr18 | 36487627 | 36487876 | AGA TGG AGA AAT GTG CAG AGA | ATG TGT CTA TTG CTA CCT GTG A | 2533, 2534 |
| chr18 | 36489135 | 36489384 | ATG ACT GCA TCC AAG AGC A | CTC CTT CAT TTT GCT GGT GG | 2535, 2536 |
| chr18 | 36531244 | 36531493 | CAG AAT TTC CAG GCA GTT GT | GGT GAT CAT TTG TCT GCA CA | 2537, 2538 |
| chr18 | 36554006 | 36554255 | GAA TCC AGA AGC TCA GTC CTT | TGA AGG GAT GAA GGC AGA AG | 2539, 2540 |
| chr18 | 36558050 | 36558299 | AGC CCT GGA ATC TTG ACA TT | ATT GTG TTG TCC TTC CGT TT | 2541, 2542 |
| chr18 | 36569619 | 36569868 | GTG CAT TAT ACG GAT GGC C | CTG AAG CAT CAC TGG CAT TG | 2543, 2544 |
| chr18 | 1017928 | 1018177 | GGT AGA GGG TCC TGT GAT TC | AAG CTT GTA GTC TGG GTA GC | 2545, 2546 |
| chr18 | 241538 | 241787 | GTA ACT GCT AGC CAC TGA GT | TCC CTC TGT ACT ATG TAG CAT G | 2547, 2548 |
| chr18 | 242831 | 243080 | GCC TTT TTG GGA ATC CTA GT | TTC ATT TCC CTT TGT TGC CC | 2549, 2550 |

FIG. 2 CONTINUED

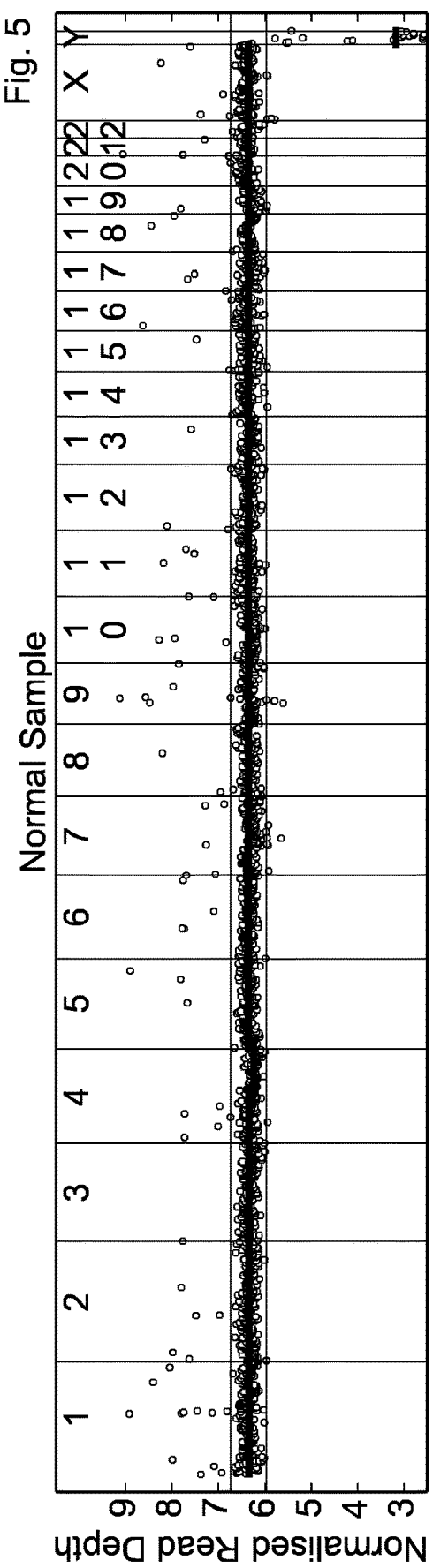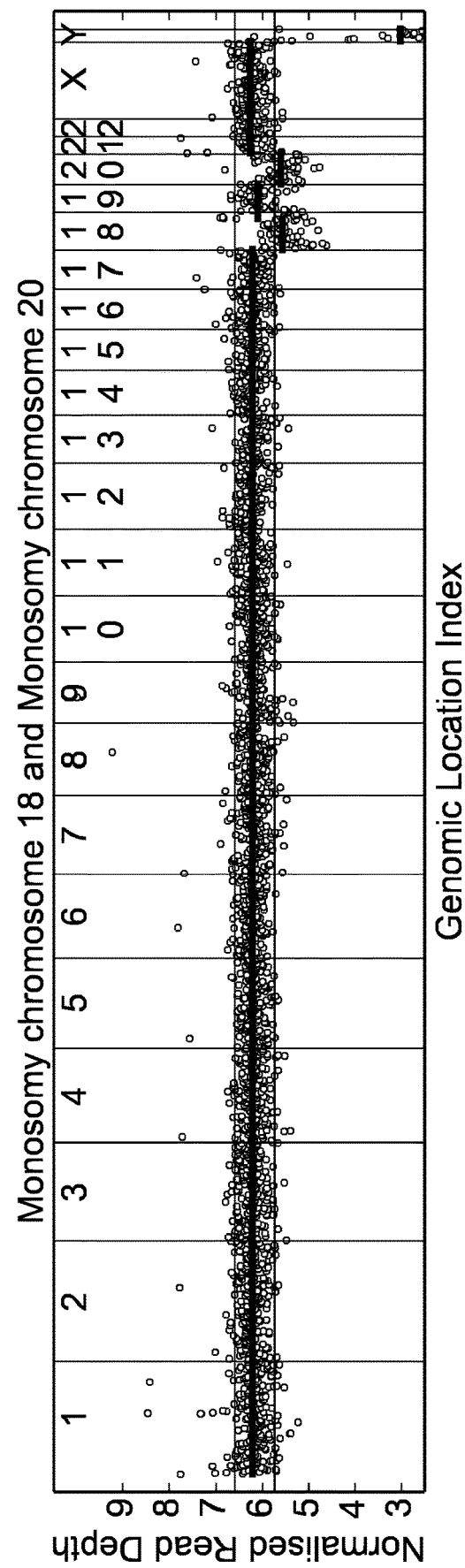
Fig. 5

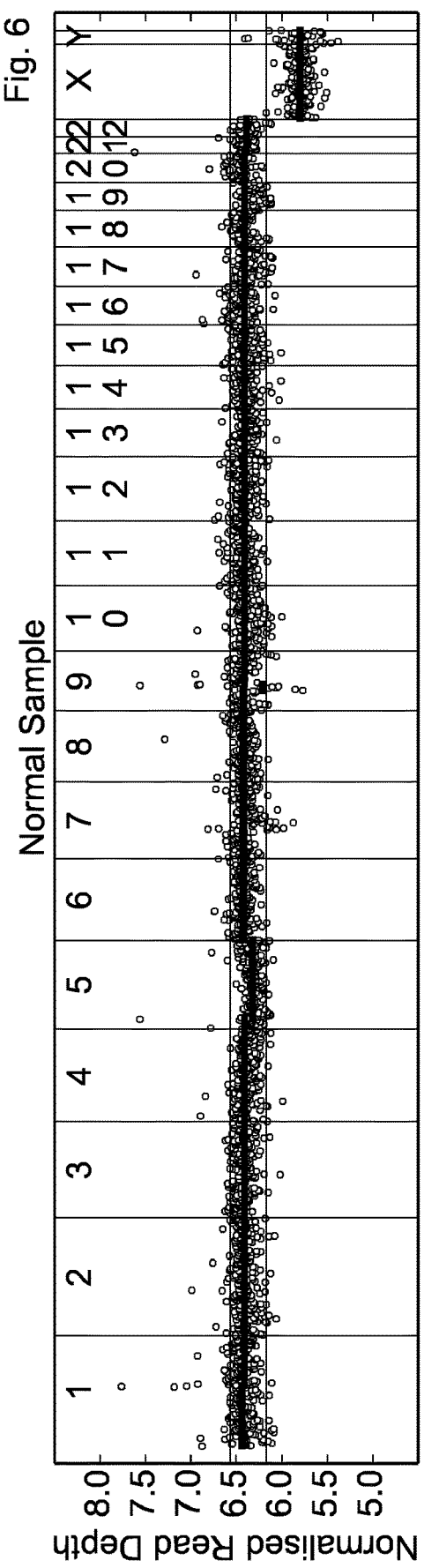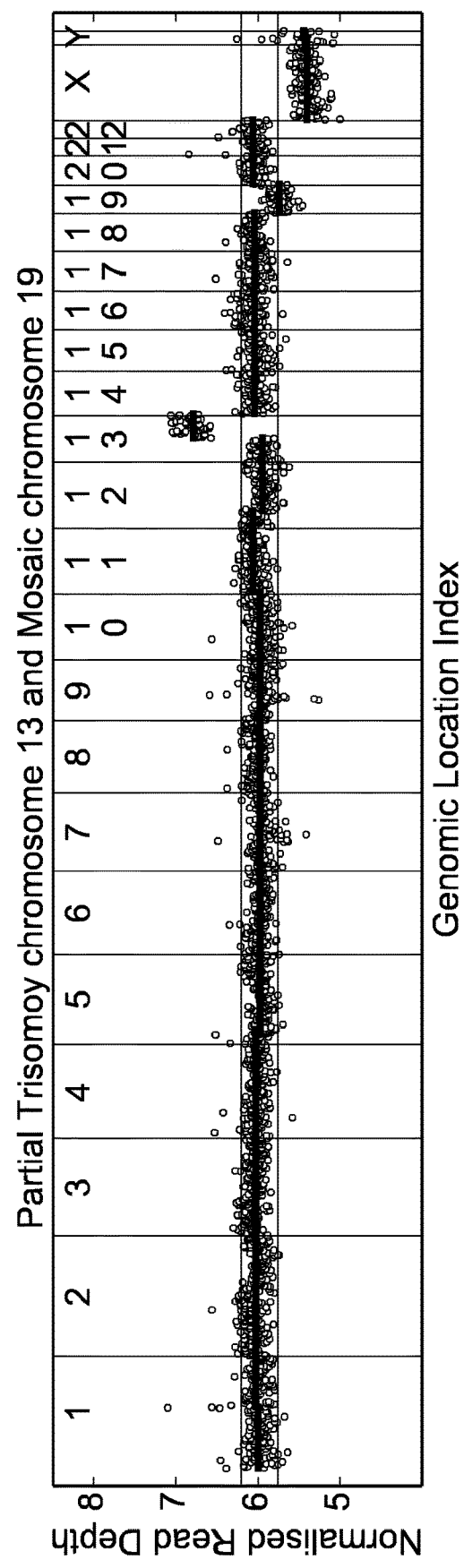
Fig. 6

TARGET-ENRICHED MULTIPLEXED PARALLEL ANALYSIS FOR ASSESSMENT OF FETAL DNA SAMPLES

CROSS REFERENCE TO RELATED PATENT APPLICATIONS

This application is a U.S. national phase application of International Application No. PCT/EP2018/068414, which was filed on Jul. 6, 2018, and claims priority to U.S. Provisional Application No. 62/529,790, which was filed on Jul. 7, 2017. The content of these earlier filed applications is hereby incorporated by reference herein in its entirety.

INCORPORATION OF THE SEQUENCE LISTING

The present application contains a sequence listing that was submitted herewith in ASCII format via EFS-Web, containing the file name "37578_0071U1_Revised_Sequence Listing.txt," which is 389,120 bytes in size, created on Jun. 23, 2022, and is herein incorporated by reference in its entirety pursuant to 37 C.F.R. § 1.52(e)(5).

FIELD OF THE INVENTION

The invention is in the field of biology, medicine and chemistry, more in particular in the field of molecular biology and more in particular in the field of molecular diagnostics.

BACKGROUND OF THE INVENTION

The discovery of free fetal DNA (ffDNA) in maternal circulation (Lo, Y. M. et al. (1997) Lancet 350:485-487) was a landmark towards the development of non-invasive prenatal testing for chromosomal abnormalities and has opened up new possibilities in the clinical setting. However, direct analysis of the limited amount of ffDNA in the presence of an excess of maternal DNA is a great challenge for Non-Invasive Prenatal Testing (NIPT) of chromosomal abnormalities. The implementation of next generation sequencing (NGS) technologies in the development of NIPT has revolutionized the field. In 2008, two independent groups demonstrated that NIPT of trisomy 21 could be achieved using next generation massively parallel shotgun sequencing (MPSS) (Chiu, R. W. et al. (2008) Proc. Natl. Acad. Sci. USA 105:20458-20463; Fan, H. C. et al. (2008) Proc. Natl. Acad. Sci. USA 105:16266-162710). The new era of NIPT for chromosomal abnormalities has opened new possibilities for the implementation of these technologies into clinical practice. Biotechnology companies that are partly or wholly dedicated to the development of NIPT tests have initiated large-scale clinical studies towards their implementation (Palomaki, G. E. et al. (2011) Genet. Med. 13:913-920; Ehrich, M. et al. (2011) Am. J. Obstet. Gynecol. 204:205e1-11; Chen, E. Z. et al. (2011) PLoS One 6:e21791; Sehnert, A. J. et al. (2011) Clin. Chem. 57:1042-1049; Palomaki, G. E. et al. (2012); Genet. Med. 14:296-305; Bianchi, D. W. et al. (2012) Obstet. Gynecol. 119:890-901; Zimmerman, B. et al. (2012) Prenat. Diag. 32:1233-1241; Nicolaides, K. H. et al. (2013) Prenat. Diagn. 33:575-579; Sparks, A. B. et al. (2012) Prenat. Diagn. 32:3-9)

Initial NIPT approaches used massively parallel shotgun sequencing (MPSS) NGS methodologies (see e.g., U.S. Pat. Nos. 7,888,017; 8,008,018; 8,195,415; 8,296,076; 8,682,594; US Patent Publication 20110201507; US Patent Publication 20120270739). Thus, these approaches are whole genome-based, in which the entire maternal sample containing both maternal DNA and free fetal DNA is subjected to amplification, sequencing and analysis.

More recently, targeted-based NGS approaches for NIPT, in which only specific sequences of interest are sequenced, have been developed. For example, a targeted NIPT approach using TArget Capture Sequences (TACS) for identifying fetal chromosomal abnormalities using a maternal blood sample has been described (PCT Publication WO 2016/189388; US Patent Publication 2016/0340733; Koumbaris, G. et al. (2015) Clinical chemistry, 62(6), pp. 848-855).

Such targeted approaches require significantly less sequencing than the MPSS approaches, since sequencing is only performed on specific loci on the target sequence of interest rather than across the whole genome. Additional methodologies for NGS-based approaches are still needed, in particular approaches that can target specific sequences of interest, thereby greatly reducing the amount of sequencing needed as compared to whole genome-based approaches, as well as increasing the read-depth of regions of interest, thus enabling detection of low signal to noise ratio regions. In particular, additional methodologies are still needed that allow for genetic aberrations present in diminutive amounts in a sample can be reliably detected. For example, additional methodologies are still needed that allow for analysis of DNA samples that contain predominantly fetal or embryonic DNA, since such samples contain only diminutive amounts of fetal or embryonic DNA.

SUMMARY OF THE INVENTION

This invention provides improved methods for enriching targeted genomic regions of interest to be analyzed by multiplexed parallel sequencing, wherein the DNA sample used in the method contains predominantly or only fetal/embryonic DNA. Accordingly, the methods allow for analysis of very small starting amounts of fetal or embryonic DNA. The methods of the disclosure can be used in the analysis of fetal or embryonic DNA samples, e.g., for the presence of genetic abnormalities, for example for purposes of IVF Pre-implantation Genetic Screening (PGS) and Diagnosis (PGD). The methods of the invention utilize a pool of TArget Capture Sequences (TACS) designed such that the sequences within the pool have features that optimize the efficiency, specificity and accuracy of genetic assessment. In one embodiment, the pool of TACS comprises member sequences whose binding encompasses all chromosomes within the human genome (chromosomes 1-22, X and Y), thereby allowing for evaluation of the entire human genome in a single fetal/embryonic DNA sample.

Accordingly, in one aspect, the invention pertains to a method of testing for risk of a genetic abnormality in a DNA sample comprising predominantly fetal or embryonic DNA and comprising genomic sequences of interest, the method comprising:

(a) preparing a sequencing library from the DNA sample comprising predominantly fetal or embryonic DNA;

(b) hybridizing the sequencing library to a pool of double-stranded TArget Capture Sequences (TACS) wherein the pool of TACS comprises sequences that bind to one or more genomic sequences of interest comprising a genetic abnormality;

(c) isolating members of the sequencing library that bind to the pool of TACS to obtain an enriched library;

(d) amplifying and sequencing the enriched library; and
(e) performing statistical analysis on the enriched library sequences to thereby determine risk of a genetic abnormality in the DNA sample.

In one embodiment:
(i) each member sequence within the pool of TACS is between 100-500 base pairs in length, each member sequence having a 5' end and a 3' end;
(ii) each member sequence binds to the same genomic sequence of interest at least 50 base pairs away, on both the 5' end and the 3' end, from regions harboring Copy Number Variations (CNVs), Segmental duplications or repetitive DNA elements; and
(iii) the GC content of the pool of TACS is between 19% and 80%, as determined by calculating the GC content of each member within the pool of TACS.

In various embodiments, the DNA sample is from, for example, a pre-implantation embryo, intact trophoblasts collected from a maternal Papanicolaou smear or a fetal cell found in maternal plasma. In one embodiment, the DNA sample is obtained directly from fetal or embryonic tissue. In certain embodiments, the DNA sample is obtained directly from fetal tissue, or amniotic fluid, or chorionic villi, or medium where products of conception were grown.

In one embodiment, the pool of TACS comprises members that bind to chromosomes 1-22, X and Y of the human genome. In one embodiment, each member sequence within the pool of TACS is at least 160 base pairs in length. In certain embodiments, the GC content of the pool of TACS is between 19% and 80% or is between 19% and 46%. Alternative % ranges for the GC content of the pool of TACS are described herein.

In one embodiment, the pool of TACS comprises a plurality of TACS families, wherein each member of a TACS family binds to the same target sequence of interest but with different start and/or stop positions on the sequence with respect to a reference coordinate system (i.e., binding of TACS family members to the target sequence is staggered) to thereby enrich for target sequences of interest, followed by massive parallel sequencing and statistical analysis of the enriched population. The use of families of TACS with the TACS pool that bind to each target sequence of interest, as compared to use of a single TACS within the TACS pool that binds to each target sequence of interest, significantly increases enrichment for the target sequences of interest, as evidenced by a greater than 50% average increase in read-depth for the family of TACS versus a single TACS.

Accordingly, in one embodiment, the pool of TACS comprises a plurality of TACS families directed to different genomic sequences of interest, wherein each TACS family comprises a plurality of member sequences, wherein each member sequence binds to the same genomic sequence of interest but has different start and/or stop positions with respect to a reference coordinate system for the genomic sequence of interest.

In certain embodiments, each TACS family comprises at least 3 member sequences or at least 5 member sequences. Alternative numbers of member sequences in each TACS family are described herein. In one embodiment, the pool of TACS comprises at least 50 different TACS families. Alternative numbers of different TACS families within the pool of TACS are described herein. In certain embodiments, the start and/or stop positions for the member sequences within a TACS family, with respect to a reference coordinate system for the genomic sequence of interest, are staggered by at least 3 base pairs or by at least 10 base pairs.

Alternative lengths (sizes) for the number of base pairs within the stagger are described herein.

In one embodiment, the genomic abnormality is a chromosomal aneuploidy. In other embodiments, the genomic abnormality is a structural abnormality, including but not limited to copy number changes including microdeletions and microduplications, insertions, deletions, translocations, inversions and small-size mutations including point mutations and mutational signatures.

In one embodiment, the pool of TACS is fixed to a solid support. For example, in one embodiment, the TACS are biotinylated and are bound to streptavidin-coated magnetic beads.

In one embodiment, amplification of the enriched library is performed in the presence of blocking sequences that inhibit amplification of wild-type sequences.

In one embodiment, members of the sequencing library that bind to the pool of TACS are partially complementary to the TACS.

In one embodiment, the statistical analysis comprises a segmentation algorithm, for example, likelihood-based segmentation, segmentation using small overlapping windows, segmentation using parallel pairwise testing, and combinations thereof. In one embodiment, the statistical analysis comprises a score-based classification system. In on embodiment, sequencing of the enriched library provides a read-depth for the genomic sequences of interest and read-depths for reference loci and the statistical analysis comprises applying an algorithm that tests sequentially the read-depth of the loci of from the genomic sequences of interest against the read-depth of the reference loci, the algorithm comprising steps for: (a) removal of inadequately sequenced loci; (b) GC-content bias alleviation; and (c) ploidy status determination. In one embodiment, GC-content bias is alleviated by grouping together loci of matching GC content. In one embodiment, sequencing of the enriched library provides the number and size of sequenced fragments for TACS-specific coordinates and the statistical analysis comprises applying an algorithm that tests sequentially the fragment-size proportion for the genomic sequence of interest against the fragment-size proportion of the reference loci, the algorithm comprising steps for: (a) removal of fragment-size outliers; (b) fragment-size proportion calculation; and (c) ploidy status determination.

In another aspect, the invention pertains to a method of testing for risk of a genetic abnormality in a DNA sample comprising predominantly fetal or embryonic DNA and comprising genomic sequences of interest, the method comprising:
(a) preparing a sequencing library from the DNA sample comprising predominantly fetal or embryonic DNA;
(b) hybridizing the sequencing library to a pool of double-stranded TArget Capture Sequences (TACS), wherein the pool of TACS comprises a plurality of TACS families directed to different genomic sequences of interest, wherein each TACS family comprises a plurality of member sequences, wherein each member sequence binds to the same genomic sequence of interest but has different start and/or stop positions with respect to a reference coordinate system for the genomic sequence of interest, and further wherein:
(i) each member sequence within each TACS family is between 100-500 base pairs in length, each member sequence having a 5' end and a 3' end;
(ii) each member sequence binds to the same genomic sequence of interest at least 50 base pairs away, on both the 5' end and the 3' end, from regions harboring Copy Number Variations (CNVs), Segmental duplications or repetitive DNA elements; and
(iii) the GC content of the pool of TACS is between 19% and 80%, as determined by calculating the GC content of each member within each family of TACS;
(c) isolating members of the sequencing library that bind to the pool of TACS to obtain an enriched library;
(d) amplifying and sequencing the enriched library; and
(e) performing statistical analysis on the enriched library sequences to thereby determine risk of a genetic abnormality in the DNA sample.

In another aspect, kits for performing the methods of the invention are also encompassed.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 2 is a listing of exemplary chromosomal regions for amplifying TACS that bind to for example chromosomes 13, 18, 21 or X. A more extensive list is shown in Table 1 below. The TACS in Table 1 are those preferred herein.

FIG. 4A shows loci enriched using a family of TACS (square symbol) as compared to loci enriched using a single TACS (X symbol), with different target sequences shown on the X-axis and the fold change in read-depth shown on the Y-axis. FIG. 4B is a bar graph illustrating the average fold-increase in read-depth (54.7%) using a family of TACS (right) versus a single TACS (left).

FIG. 5 is a graph of results from fetal DNA samples that underwent ploidy status determination using likelihood-based segmentation analysis and whole-genome sequencing data. The horizontal blue line indicates the average read-depth of each chromosome. The red lines indicate threshold intervals of expected diploids. Data above the top red line is classified as more than diploid and data below the red line is classified as less than diploid. The top panel illustrates the results of a euploid female sample (i.e., a female fetus with diploid X chromosome, no Y chromosome, and without any ploidy abnormalities present). The bottom panel illustrates the results of a female aneuploid sample (i.e., a female fetus with diploid X chromosome and no Y chromosome) with monosomy 18 and monosomy 20. Values on the y-axis are log of read-depth.

FIG. 6 is a graph of results from fetal DNA samples that underwent ploidy status determination by whole genome sequencing, followed by segmentation analysis using small overlapping windows analysis. The horizontal blue line indicates the average read-depth of each chromosome. The red lines indicate threshold intervals of expected diploids. The top panel illustrates the results of a euploid male sample (i.e., a male fetus with a single copy of X and Y chromosomes and without any ploidy abnormalities present). The bottom panel illustrates the results of an aneuploid male sample (i.e., a male fetus with a single copy of X and Y chromosomes) and with aneuploidies on chromosomes 13 and 19 (trisomy 13 and mosaicism on chromosome 19). Values are log of read-depth.

Figure 1:
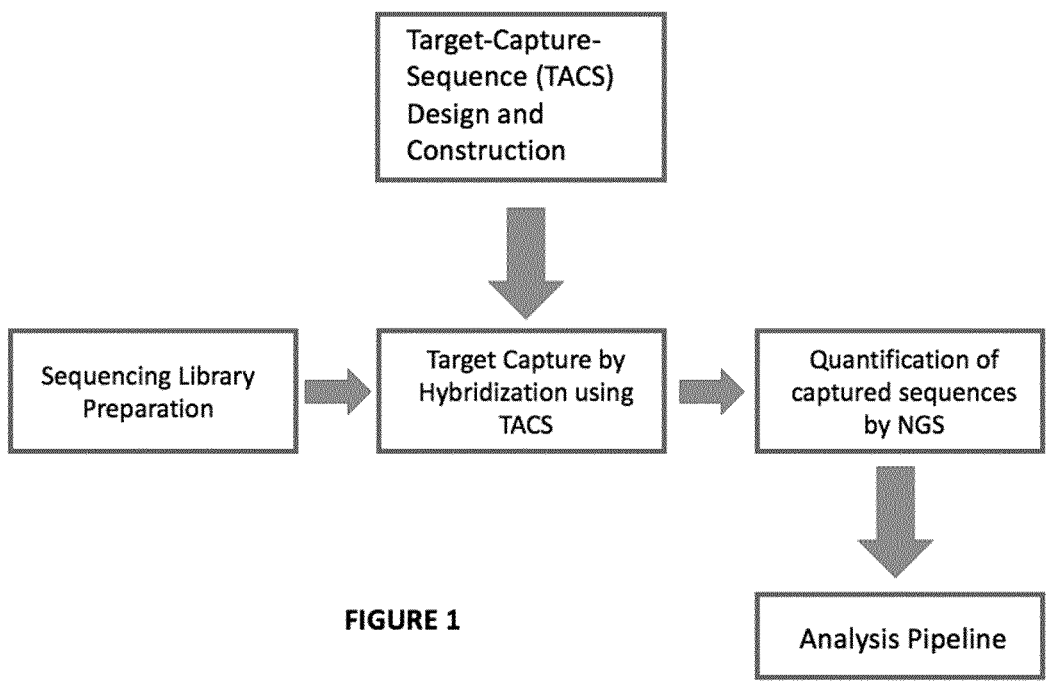
FIG. 1 is a schematic diagram of multiplexed parallel analysis of targeted genomic regions for non-invasive pre-natal testing using TArget Capture Sequences (TACS).

Table 1 shows exemplary and preferred TACS positions. The corresponding sequences are depicted in the sequence protocol.

| Ch. | Start | Stop | GC content |
|---|---|---|---|
| chr1 | 1321966 | 1322216 | 0.348 |
| chr1 | 2223227 | 2223477 | 0.348 |
| chr1 | 3047692 | 3047942 | 0.348 |
| chr1 | 4134402 | 4134652 | 0.348 |

| Ch. | Start | Stop | GC content |
| --- | --- | --- | --- |
| chr1 | 5007713 | 5007963 | 0.348 |
| chr1 | 5865510 | 5865760 | 0.348 |
| chr1 | 6714342 | 6714592 | 0.348 |
| chr1 | 7651255 | 7651505 | 0.348 |
| chr1 | 8470924 | 8471174 | 0.348 |
| chr1 | 9407377 | 9407627 | 0.324 |
| chr1 | 10209181 | 10209431 | 0.296 |
| chr1 | 11076652 | 11076902 | 0.348 |
| chr1 | 12295996 | 12296246 | 0.348 |
| chr1 | 13923467 | 13923717 | 0.348 |
| chr1 | 14770392 | 14770642 | 0.348 |
| chr1 | 15578046 | 15578296 | 0.348 |
| chr1 | 16593363 | 16593613 | 0.348 |
| chr1 | 17424880 | 17425130 | 0.348 |
| chr1 | 18298306 | 18298556 | 0.348 |
| chr1 | 19423315 | 19423565 | 0.348 |
| chr1 | 20230997 | 20231247 | 0.348 |
| chr1 | 21064982 | 21065232 | 0.348 |
| chr1 | 22007055 | 22007305 | 0.348 |
| chr1 | 22807861 | 22808111 | 0.344 |
| chr1 | 23611830 | 23612080 | 0.348 |
| chr1 | 24692851 | 24693101 | 0.348 |
| chr1 | 25500621 | 25500871 | 0.348 |
| chr1 | 26321343 | 26321593 | 0.348 |
| chr1 | 27450716 | 27450966 | 0.348 |
| chr1 | 28296472 | 28296722 | 0.296 |
| chr1 | 29098007 | 29098257 | 0.348 |
| chr1 | 30034947 | 30035197 | 0.348 |
| chr1 | 30884476 | 30884726 | 0.348 |
| chr1 | 31759697 | 31759947 | 0.348 |
| chr1 | 32646478 | 32646728 | 0.348 |
| chr1 | 33479257 | 33479507 | 0.348 |
| chr1 | 34305150 | 34305400 | 0.348 |
| chr1 | 35132601 | 35132851 | 0.348 |
| chr1 | 35939215 | 35939465 | 0.348 |
| chr1 | 36744730 | 36744980 | 0.336 |
| chr1 | 37623596 | 37623846 | 0.348 |
| chr1 | 38444825 | 38445075 | 0.348 |
| chr1 | 39248090 | 39248340 | 0.348 |
| chr1 | 40135959 | 40136209 | 0.348 |
| chr1 | 41158448 | 41158698 | 0.348 |
| chr1 | 42642199 | 42642449 | 0.348 |
| chr1 | 43546530 | 43546780 | 0.308 |
| chr1 | 44429847 | 44430097 | 0.348 |
| chr1 | 45307055 | 45307305 | 0.348 |
| chr1 | 46108116 | 46108366 | 0.348 |
| chr1 | 47100462 | 47100712 | 0.324 |
| chr1 | 48012499 | 48012749 | 0.348 |
| chr1 | 48821604 | 48821854 | 0.268 |
| chr1 | 49632073 | 49632323 | 0.336 |
| chr1 | 50440111 | 50440361 | 0.332 |
| chr1 | 51241903 | 51242153 | 0.312 |
| chr1 | 52076744 | 52076994 | 0.348 |
| chr1 | 53710264 | 53710514 | 0.348 |
| chr1 | 54512550 | 54512800 | 0.344 |
| chr1 | 55394792 | 55395042 | 0.348 |
| chr1 | 56384481 | 56384731 | 0.348 |
| chr1 | 57349269 | 57349519 | 0.348 |
| chr1 | 58229509 | 58229759 | 0.348 |
| chr1 | 59040876 | 59041126 | 0.348 |
| chr1 | 59858357 | 59858607 | 0.304 |
| chr1 | 60930291 | 60930541 | 0.348 |
| chr1 | 62103549 | 62103799 | 0.304 |
| chr1 | 62916429 | 62916679 | 0.348 |
| chr1 | 64067557 | 64067807 | 0.348 |
| chr1 | 64969248 | 64969498 | 0.348 |
| chr1 | 65878461 | 65878711 | 0.348 |
| chr1 | 67063532 | 67063782 | 0.336 |
| chr1 | 67873342 | 67873592 | 0.348 |
| chr1 | 70446150 | 70446400 | 0.272 |
| chr1 | 71372533 | 71372783 | 0.348 |
| chr1 | 72327150 | 72327400 | 0.348 |
| chr1 | 73213150 | 73213400 | 0.332 |
| chr1 | 74040085 | 74040335 | 0.344 |
| chr1 | 74845564 | 74845814 | 0.348 |
| chr1 | 75862550 | 75862800 | 0.316 |
| chr1 | 76678210 | 76678460 | 0.348 |
| chr1 | 77512868 | 77513118 | 0.348 |
| chr1 | 78324741 | 78324991 | 0.284 |
| chr1 | 79622150 | 79622400 | 0.324 |
| chr1 | 79622150 | 79622400 | 0.324 |
| chr1 | 81028150 | 81028400 | 0.28 |
| chr1 | 81829490 | 81829740 | 0.3 |
| chr1 | 82631657 | 82631907 | 0.344 |
| chr1 | 83432297 | 83432547 | 0.348 |
| chr1 | 84232408 | 84232658 | 0.348 |
| chr1 | 85186300 | 85186550 | 0.348 |
| chr1 | 85987798 | 85988048 | 0.312 |
| chr1 | 86792219 | 86792469 | 0.3 |
| chr1 | 88716354 | 88716604 | 0.348 |
| chr1 | 89574150 | 89574400 | 0.344 |
| chr1 | 90818292 | 90818542 | 0.348 |
| chr1 | 91937586 | 91937836 | 0.332 |
| chr1 | 92757305 | 92757555 | 0.32 |
| chr1 | 93564210 | 93564460 | 0.328 |
| chr1 | 94366822 | 94367072 | 0.348 |
| chr1 | 94473766 | 94474015 | 0.53012 |
| chr1 | 94476259 | 94476508 | 0.566265 |
| chr1 | 94496446 | 94496695 | 0.546185 |
| chr1 | 94508204 | 94508453 | 0.554217 |
| chr1 | 94508724 | 94508973 | 0.570281 |
| chr1 | 94517145 | 94517394 | 0.369478 |
| chr1 | 94525991 | 94526240 | 0.477912 |
| chr1 | 95460410 | 95460660 | 0.336 |
| chr1 | 96550309 | 96550559 | 0.348 |
| chr1 | 97375580 | 97375830 | 0.348 |
| chr1 | 98175941 | 98176191 | 0.256 |
| chr1 | 99069150 | 99069400 | 0.3 |
| chr1 | 99919444 | 99919694 | 0.34 |
| chr1 | 100316484 | 100316734 | 0.34 |
| chr1 | 100316495 | 100316745 | 0.348 |
| chr1 | 100340820 | 100341070 | 0.344 |
| chr1 | 100346760 | 100347010 | 0.38 |
| chr1 | 100381830 | 100382080 | 0.28 |
| chr1 | 100381939 | 100382189 | 0.292 |
| chr1 | 100382143 | 100382393 | 0.356 |
| chr1 | 100881150 | 100881400 | 0.272 |
| chr1 | 101683272 | 101683522 | 0.348 |
| chr1 | 102490150 | 102490400 | 0.292 |
| chr1 | 103317424 | 103317674 | 0.348 |
| chr1 | 104122384 | 104122634 | 0.344 |
| chr1 | 104943912 | 104944162 | 0.328 |
| chr1 | 105852554 | 105852804 | 0.328 |
| chr1 | 107171238 | 107171488 | 0.32 |
| chr1 | 108028411 | 108028661 | 0.348 |
| chr1 | 108856564 | 108856814 | 0.288 |
| chr1 | 109676087 | 109676337 | 0.348 |
| chr1 | 110522602 | 110522852 | 0.348 |
| chr1 | 111340253 | 111340503 | 0.34 |
| chr1 | 112949435 | 112949685 | 0.332 |
| chr1 | 113770383 | 113770633 | 0.332 |
| chr1 | 114637753 | 114638003 | 0.348 |
| chr1 | 115437771 | 115438021 | 0.3 |
| chr1 | 116573150 | 116573400 | 0.32 |
| chr1 | 117560545 | 117560795 | 0.348 |
| chr1 | 118572363 | 118572613 | 0.308 |
| chr1 | 119423232 | 119423482 | 0.332 |
| chr1 | 119957941 | 119958191 | 0.512 |
| chr1 | 119964669 | 119964919 | 0.508 |
| chr1 | 120230467 | 120230717 | 0.348 |
| chr1 | 120269395 | 120269645 | 0.58 |
| chr1 | 120277828 | 120278078 | 0.612 |
| chr1 | 120277930 | 120278180 | 0.604 |
| chr1 | 120284326 | 120284576 | 0.58 |
| chr1 | 120285389 | 120285639 | 0.636 |
| chr1 | 120286404 | 120286654 | 0.556 |
| chr1 | 144917078 | 144917328 | 0.312 |
| chr1 | 145416495 | 145416745 | 0.54 |
| chr1 | 145732849 | 145733099 | 0.348 |
| chr1 | 147385212 | 147385462 | 0.344 |
| chr1 | 149912055 | 149912305 | 0.348 |
| chr1 | 150722611 | 150722861 | 0.348 |
| chr1 | 151586322 | 151586572 | 0.348 |
| chr1 | 152399440 | 152399690 | 0.344 |

| Ch. | Start | Stop | GC content |
|---|---|---|---|
| chr1 | 153275352 | 153275602 | 0.348 |
| chr1 | 154245900 | 154246150 | 0.536 |
| chr1 | 154247516 | 154247766 | 0.464 |
| chr1 | 154812453 | 154812703 | 0.348 |
| chr1 | 155204665 | 155204914 | 0.562249 |
| chr1 | 155204957 | 155205206 | 0.574297 |
| chr1 | 155205406 | 155205655 | 0.521212 |
| chr1 | 155205538 | 155205717 | 0.564246 |
| chr1 | 155210424 | 155210673 | 0.562249 |
| chr1 | 155691410 | 155691660 | 0.348 |
| chr1 | 156691635 | 156691885 | 0.304 |
| chr1 | 157494327 | 157494577 | 0.348 |
| chr1 | 158381408 | 158381658 | 0.348 |
| chr1 | 159416150 | 159416400 | 0.348 |
| chr1 | 161320957 | 161321207 | 0.348 |
| chr1 | 162192273 | 162192523 | 0.348 |
| chr1 | 162995450 | 162995700 | 0.324 |
| chr1 | 163811190 | 163811440 | 0.348 |
| chr1 | 164673253 | 164673503 | 0.348 |
| chr1 | 165475943 | 165476193 | 0.348 |
| chr1 | 166300688 | 166300938 | 0.336 |
| chr1 | 167123296 | 167123546 | 0.336 |
| chr1 | 169063150 | 169063400 | 0.324 |
| chr1 | 170055150 | 170055400 | 0.328 |
| chr1 | 170920233 | 170920483 | 0.328 |
| chr1 | 171773161 | 171773411 | 0.348 |
| chr1 | 172673411 | 172673661 | 0.348 |
| chr1 | 173542401 | 173542651 | 0.288 |
| chr1 | 174517204 | 174517454 | 0.348 |
| chr1 | 175778380 | 175778630 | 0.332 |
| chr1 | 176580310 | 176580560 | 0.348 |
| chr1 | 177395900 | 177396150 | 0.348 |
| chr1 | 178513548 | 178513798 | 0.324 |
| chr1 | 179452150 | 179452400 | 0.344 |
| chr1 | 179521616 | 179521866 | 0.532 |
| chr1 | 179521631 | 179521881 | 0.52 |
| chr1 | 179526237 | 179526487 | 0.42 |
| chr1 | 179530337 | 179530587 | 0.376 |
| chr1 | 179544561 | 179544811 | 0.596 |
| chr1 | 180255735 | 180255985 | 0.316 |
| chr1 | 181056840 | 181057090 | 0.348 |
| chr1 | 182634465 | 182634715 | 0.348 |
| chr1 | 183811332 | 183811582 | 0.348 |
| chr1 | 184719150 | 184719400 | 0.308 |
| chr1 | 185737400 | 185737400 | 0.344 |
| chr1 | 186544294 | 186544544 | 0.336 |
| chr1 | 187345956 | 187346206 | 0.348 |
| chr1 | 188148703 | 188148953 | 0.328 |
| chr1 | 188964150 | 188964400 | 0.3 |
| chr1 | 189860180 | 189860430 | 0.312 |
| chr1 | 191057168 | 191057418 | 0.348 |
| chr1 | 191860751 | 191861001 | 0.344 |
| chr1 | 192733150 | 192733400 | 0.348 |
| chr1 | 193629150 | 193629400 | 0.268 |
| chr1 | 194870567 | 194870817 | 0.272 |
| chr1 | 195678176 | 195678426 | 0.348 |
| chr1 | 196491241 | 196491491 | 0.308 |
| chr1 | 197292396 | 197292646 | 0.312 |
| chr1 | 198093741 | 198093991 | 0.288 |
| chr1 | 199102394 | 199102644 | 0.32 |
| chr1 | 199910959 | 199911209 | 0.348 |
| chr1 | 200726178 | 200726428 | 0.336 |
| chr1 | 201594767 | 201595017 | 0.348 |
| chr1 | 202763399 | 202763649 | 0.348 |
| chr1 | 203583274 | 203583524 | 0.344 |
| chr1 | 204505599 | 204505849 | 0.348 |
| chr1 | 205323323 | 205323573 | 0.348 |
| chr1 | 206199203 | 206199453 | 0.348 |
| chr1 | 207040001 | 207040251 | 0.348 |
| chr1 | 208628219 | 208628469 | 0.348 |
| chr1 | 209429745 | 209429995 | 0.348 |
| chr1 | 211050331 | 211050581 | 0.348 |
| chr1 | 211854312 | 211854562 | 0.308 |
| chr1 | 212715103 | 212715353 | 0.332 |
| chr1 | 213681370 | 213681620 | 0.348 |
| chr1 | 214976150 | 214976400 | 0.32 |
| chr1 | 215844302 | 215844552 | 0.416 |
| chr1 | 215853595 | 215853845 | 0.416 |
| chr1 | 215992471 | 215992721 | 0.328 |
| chr1 | 216420312 | 216420562 | 0.46 |
| chr1 | 216420402 | 216420652 | 0.4 |
| chr1 | 216497437 | 216497687 | 0.328 |
| chr1 | 216792844 | 216793094 | 0.348 |
| chr1 | 217599535 | 217599785 | 0.276 |
| chr1 | 219297150 | 219297400 | 0.32 |
| chr1 | 220100279 | 220100529 | 0.348 |
| chr1 | 220903327 | 220903577 | 0.348 |
| chr1 | 222029233 | 222029483 | 0.348 |
| chr1 | 222831067 | 222831317 | 0.304 |
| chr1 | 223637903 | 223638153 | 0.348 |
| chr1 | 224462520 | 224462770 | 0.324 |
| chr1 | 225395150 | 225395400 | 0.328 |
| chr1 | 226223152 | 226223402 | 0.348 |
| chr1 | 227178529 | 227178779 | 0.348 |
| chr1 | 228644123 | 228644373 | 0.348 |
| chr1 | 229446849 | 229447099 | 0.348 |
| chr1 | 230259328 | 230259578 | 0.328 |
| chr1 | 231872599 | 231872849 | 0.332 |
| chr1 | 232812441 | 232812691 | 0.328 |
| chr1 | 233881150 | 233881400 | 0.296 |
| chr1 | 234687934 | 234688184 | 0.312 |
| chr1 | 235489202 | 235489452 | 0.324 |
| chr1 | 236335526 | 236335776 | 0.348 |
| chr1 | 237165928 | 237166178 | 0.348 |
| chr1 | 238564150 | 238564400 | 0.308 |
| chr1 | 239364391 | 239364641 | 0.3 |
| chr1 | 240522579 | 240522829 | 0.344 |
| chr1 | 242534150 | 242534400 | 0.328 |
| chr1 | 243386411 | 243386661 | 0.332 |
| chr1 | 244192638 | 244192888 | 0.348 |
| chr1 | 245000355 | 245000605 | 0.348 |
| chr1 | 245854798 | 245855048 | 0.348 |
| chr1 | 246660293 | 246660543 | 0.316 |
| chr1 | 247618340 | 247618590 | 0.348 |
| chr1 | 248428706 | 248428956 | 0.308 |
| chr2 | 65470 | 65720 | 0.348 |
| chr2 | 887693 | 887943 | 0.32 |
| chr2 | 1696872 | 1697122 | 0.348 |
| chr2 | 2498456 | 2498706 | 0.304 |
| chr2 | 3336432 | 3336682 | 0.348 |
| chr2 | 4140186 | 4140436 | 0.348 |
| chr2 | 4957104 | 4957354 | 0.348 |
| chr2 | 6772150 | 6772400 | 0.34 |
| chr2 | 7580936 | 7581186 | 0.348 |
| chr2 | 8382165 | 8382415 | 0.348 |
| chr2 | 9193965 | 9194215 | 0.348 |
| chr2 | 10008838 | 10009088 | 0.304 |
| chr2 | 10811702 | 10811952 | 0.34 |
| chr2 | 11639024 | 11639274 | 0.348 |
| chr2 | 12448608 | 12448858 | 0.336 |
| chr2 | 13475150 | 13475400 | 0.34 |
| chr2 | 14298194 | 14298444 | 0.348 |
| chr2 | 15098693 | 15098943 | 0.348 |
| chr2 | 15948834 | 15949084 | 0.344 |
| chr2 | 16749787 | 16750037 | 0.348 |
| chr2 | 17563803 | 17564053 | 0.288 |
| chr2 | 18584239 | 18584489 | 0.348 |
| chr2 | 19417426 | 19417676 | 0.348 |
| chr2 | 20234783 | 20235033 | 0.348 |
| chr2 | 21034816 | 21035066 | 0.348 |
| chr2 | 21841601 | 21841851 | 0.328 |
| chr2 | 22644838 | 22645088 | 0.348 |
| chr2 | 23466443 | 23466693 | 0.348 |
| chr2 | 24289207 | 24289457 | 0.332 |
| chr2 | 25100859 | 25101109 | 0.348 |
| chr2 | 25957531 | 25957781 | 0.348 |
| chr2 | 26782767 | 26783017 | 0.348 |
| chr2 | 27595658 | 27595908 | 0.348 |
| chr2 | 28407842 | 28408092 | 0.316 |
| chr2 | 29274893 | 29275143 | 0.348 |
| chr2 | 30090065 | 30090315 | 0.348 |
| chr2 | 30952180 | 30952430 | 0.348 |
| chr2 | 31755042 | 31755292 | 0.348 |
| chr2 | 32583549 | 32583799 | 0.348 |

-continued

| Ch. | Start | Stop | GC content |
|---|---|---|---|
| chr2 | 33391150 | 33391400 | 0.276 |
| chr2 | 34383150 | 34383400 | 0.348 |
| chr2 | 35195332 | 35195582 | 0.344 |
| chr2 | 36137213 | 36137463 | 0.348 |
| chr2 | 36943435 | 36943685 | 0.348 |
| chr2 | 37916535 | 37916785 | 0.348 |
| chr2 | 38718989 | 38719239 | 0.348 |
| chr2 | 39520447 | 39520697 | 0.252 |
| chr2 | 40715152 | 40715402 | 0.348 |
| chr2 | 41775150 | 41775400 | 0.336 |
| chr2 | 42935152 | 42935402 | 0.348 |
| chr2 | 43736701 | 43736951 | 0.288 |
| chr2 | 44201259 | 44201509 | 0.356 |
| chr2 | 45388418 | 45388668 | 0.34 |
| chr2 | 46218740 | 46218990 | 0.348 |
| chr2 | 47124807 | 47125057 | 0.328 |
| chr2 | 48209532 | 48209782 | 0.348 |
| chr2 | 49436565 | 49436815 | 0.348 |
| chr2 | 50262150 | 50262400 | 0.312 |
| chr2 | 51067246 | 51067496 | 0.304 |
| chr2 | 51923177 | 51923427 | 0.348 |
| chr2 | 52934234 | 52934484 | 0.348 |
| chr2 | 53762231 | 53762481 | 0.348 |
| chr2 | 54564438 | 54564688 | 0.348 |
| chr2 | 55380451 | 55380701 | 0.348 |
| chr2 | 56181574 | 56181824 | 0.348 |
| chr2 | 57163150 | 57163400 | 0.316 |
| chr2 | 58358268 | 58358518 | 0.34 |
| chr2 | 59360150 | 59360400 | 0.328 |
| chr2 | 60236150 | 60236400 | 0.34 |
| chr2 | 61078467 | 61078717 | 0.348 |
| chr2 | 61898047 | 61898297 | 0.348 |
| chr2 | 63027252 | 63027502 | 0.348 |
| chr2 | 64476343 | 64476593 | 0.348 |
| chr2 | 65539531 | 65539781 | 0.348 |
| chr2 | 66468258 | 66468508 | 0.348 |
| chr2 | 67310247 | 67310497 | 0.348 |
| chr2 | 68121736 | 68121986 | 0.348 |
| chr2 | 68937150 | 68937400 | 0.324 |
| chr2 | 69754384 | 69754634 | 0.348 |
| chr2 | 70609376 | 70609626 | 0.348 |
| chr2 | 71418299 | 71418549 | 0.348 |
| chr2 | 72388795 | 72389045 | 0.348 |
| chr2 | 73673243 | 73673493 | 0.348 |
| chr2 | 74477048 | 74477298 | 0.348 |
| chr2 | 75293899 | 75294149 | 0.348 |
| chr2 | 76188150 | 76188400 | 0.348 |
| chr2 | 77065379 | 77065629 | 0.288 |
| chr2 | 77963477 | 77963727 | 0.292 |
| chr2 | 79082465 | 79082715 | 0.316 |
| chr2 | 79883120 | 79883370 | 0.324 |
| chr2 | 80684819 | 80685069 | 0.348 |
| chr2 | 81668320 | 81668570 | 0.348 |
| chr2 | 82672150 | 82672400 | 0.316 |
| chr2 | 83483150 | 83483400 | 0.344 |
| chr2 | 84462272 | 84462522 | 0.348 |
| chr2 | 85281169 | 85281419 | 0.348 |
| chr2 | 86625495 | 86625745 | 0.32 |
| chr2 | 88326662 | 88326912 | 0.28 |
| chr2 | 89132432 | 89132682 | 0.348 |
| chr2 | 90105696 | 90105946 | 0.328 |
| chr2 | 95627799 | 95628049 | 0.284 |
| chr2 | 96845176 | 96845426 | 0.348 |
| chr2 | 97651219 | 97651469 | 0.348 |
| chr2 | 98452233 | 98452483 | 0.348 |
| chr2 | 99255916 | 99256166 | 0.332 |
| chr2 | 100057041 | 100057291 | 0.348 |
| chr2 | 100890150 | 100890400 | 0.3 |
| chr2 | 102415179 | 102415429 | 0.316 |
| chr2 | 103622548 | 103622798 | 0.348 |
| chr2 | 104670507 | 104670757 | 0.348 |
| chr2 | 105567150 | 105567400 | 0.332 |
| chr2 | 106412373 | 106412623 | 0.336 |
| chr2 | 107768153 | 107768403 | 0.348 |
| chr2 | 108612236 | 108612486 | 0.284 |
| chr2 | 109664556 | 109664806 | 0.316 |
| chr2 | 110464569 | 110464819 | 0.348 |

-continued

| Ch. | Start | Stop | GC content |
|---|---|---|---|
| chr2 | 111395348 | 111395598 | 0.3 |
| chr2 | 112278329 | 112278579 | 0.348 |
| chr2 | 113583150 | 113583400 | 0.304 |
| chr2 | 114468912 | 114469162 | 0.264 |
| chr2 | 115268995 | 115269245 | 0.348 |
| chr2 | 116107157 | 116107407 | 0.328 |
| chr2 | 117369331 | 117369581 | 0.344 |
| chr2 | 118244266 | 118244516 | 0.316 |
| chr2 | 119059803 | 119060053 | 0.348 |
| chr2 | 119900354 | 119900604 | 0.348 |
| chr2 | 121044398 | 121044648 | 0.304 |
| chr2 | 122113389 | 122113639 | 0.348 |
| chr2 | 122919222 | 122919472 | 0.348 |
| chr2 | 123777443 | 123777693 | 0.348 |
| chr2 | 124919150 | 124919400 | 0.332 |
| chr2 | 126026342 | 126026592 | 0.292 |
| chr2 | 126917504 | 126917754 | 0.344 |
| chr2 | 128045375 | 128045625 | 0.336 |
| chr2 | 129682980 | 129683230 | 0.252 |
| chr2 | 130487549 | 130487799 | 0.348 |
| chr2 | 131534801 | 131535051 | 0.34 |
| chr2 | 133127584 | 133127834 | 0.348 |
| chr2 | 134661154 | 134661404 | 0.348 |
| chr2 | 135922383 | 135922633 | 0.348 |
| chr2 | 136723496 | 136723746 | 0.348 |
| chr2 | 137528425 | 137528675 | 0.344 |
| chr2 | 138373550 | 138373800 | 0.34 |
| chr2 | 139318150 | 139318400 | 0.288 |
| chr2 | 140527261 | 140527511 | 0.348 |
| chr2 | 141332198 | 141332448 | 0.312 |
| chr2 | 142149579 | 142149829 | 0.348 |
| chr2 | 142949600 | 142949850 | 0.268 |
| chr2 | 144077240 | 144077490 | 0.328 |
| chr2 | 144964208 | 144964458 | 0.348 |
| chr2 | 145817150 | 145817400 | 0.332 |
| chr2 | 146618150 | 146618400 | 0.312 |
| chr2 | 147969538 | 147969788 | 0.348 |
| chr2 | 149217150 | 149217400 | 0.304 |
| chr2 | 150017703 | 150017953 | 0.348 |
| chr2 | 150828995 | 150829245 | 0.336 |
| chr2 | 151767165 | 151767415 | 0.348 |
| chr2 | 152568463 | 152568713 | 0.348 |
| chr2 | 153683234 | 153683484 | 0.3 |
| chr2 | 154938150 | 154938400 | 0.348 |
| chr2 | 156008150 | 156008400 | 0.32 |
| chr2 | 156870242 | 156870492 | 0.348 |
| chr2 | 158163167 | 158163417 | 0.348 |
| chr2 | 159077150 | 159077400 | 0.288 |
| chr2 | 159891571 | 159891821 | 0.348 |
| chr2 | 161025175 | 161025425 | 0.348 |
| chr2 | 161831540 | 161831790 | 0.348 |
| chr2 | 162632193 | 162632443 | 0.316 |
| chr2 | 163715424 | 163715674 | 0.3 |
| chr2 | 165052569 | 165052819 | 0.348 |
| chr2 | 166288165 | 166288415 | 0.348 |
| chr2 | 167465150 | 167465400 | 0.296 |
| chr2 | 168517553 | 168517803 | 0.348 |
| chr2 | 169362170 | 169362420 | 0.348 |
| chr2 | 169780201 | 169780451 | 0.5 |
| chr2 | 169826516 | 169826766 | 0.484 |
| chr2 | 169832981 | 169833231 | 0.404 |
| chr2 | 169847204 | 169847454 | 0.444 |
| chr2 | 170163218 | 170163468 | 0.288 |
| chr2 | 171000920 | 171001170 | 0.348 |
| chr2 | 171805339 | 171805589 | 0.308 |
| chr2 | 172606368 | 172606618 | 0.3 |
| chr2 | 173421849 | 173422099 | 0.348 |
| chr2 | 174223616 | 174223866 | 0.348 |
| chr2 | 175024289 | 175024539 | 0.252 |
| chr2 | 176231150 | 176231400 | 0.328 |
| chr2 | 177265150 | 177265400 | 0.304 |
| chr2 | 178168408 | 178168658 | 0.348 |
| chr2 | 178969134 | 178969384 | 0.348 |
| chr2 | 179769150 | 179769400 | 0.344 |
| chr2 | 181084474 | 181084724 | 0.348 |
| chr2 | 181981239 | 181981489 | 0.348 |
| chr2 | 182819465 | 182819715 | 0.348 |

| Ch. | Start | Stop | GC content |
|---|---|---|---|
| chr2 | 183718150 | 183718400 | 0.3 |
| chr2 | 184593423 | 184593673 | 0.292 |
| chr2 | 185397270 | 185397520 | 0.316 |
| chr2 | 186197382 | 186197632 | 0.28 |
| chr2 | 187064150 | 187064400 | 0.284 |
| chr2 | 187967150 | 187967400 | 0.348 |
| chr2 | 188804233 | 188804483 | 0.32 |
| chr2 | 189831150 | 189831400 | 0.348 |
| chr2 | 190812502 | 190812752 | 0.328 |
| chr2 | 191629581 | 191629831 | 0.348 |
| chr2 | 192431709 | 192431959 | 0.348 |
| chr2 | 193235999 | 193236249 | 0.348 |
| chr2 | 194633277 | 194633527 | 0.3 |
| chr2 | 195731550 | 195731800 | 0.344 |
| chr2 | 196720594 | 196720844 | 0.348 |
| chr2 | 198035335 | 198035585 | 0.344 |
| chr2 | 198852416 | 198852666 | 0.308 |
| chr2 | 199715449 | 199715699 | 0.348 |
| chr2 | 200878150 | 200878400 | 0.272 |
| chr2 | 202016150 | 202016400 | 0.34 |
| chr2 | 202966480 | 202966730 | 0.348 |
| chr2 | 203783437 | 203783687 | 0.284 |
| chr2 | 204585253 | 204585503 | 0.348 |
| chr2 | 205421450 | 205421700 | 0.332 |
| chr2 | 206266431 | 206266681 | 0.348 |
| chr2 | 207571598 | 207571848 | 0.348 |
| chr2 | 208734150 | 208734400 | 0.34 |
| chr2 | 209711150 | 209711400 | 0.32 |
| chr2 | 210732509 | 210732759 | 0.328 |
| chr2 | 211568334 | 211568584 | 0.348 |
| chr2 | 212713453 | 212713703 | 0.348 |
| chr2 | 213773225 | 213773475 | 0.332 |
| chr2 | 214848150 | 214848400 | 0.296 |
| chr2 | 216079487 | 216079737 | 0.348 |
| chr2 | 216891573 | 216891823 | 0.304 |
| chr2 | 217729569 | 217729819 | 0.348 |
| chr2 | 218601613 | 218601863 | 0.344 |
| chr2 | 219412476 | 219412726 | 0.348 |
| chr2 | 219525688 | 219525938 | 0.576 |
| chr2 | 219525751 | 219526001 | 0.58 |
| chr2 | 219525833 | 219526083 | 0.532 |
| chr2 | 219525881 | 219526131 | 0.504 |
| chr2 | 219526345 | 219526595 | 0.548 |
| chr2 | 219526444 | 219526694 | 0.536 |
| chr2 | 219526446 | 219526696 | 0.536 |
| chr2 | 219527213 | 219527463 | 0.588 |
| chr2 | 219527776 | 219528026 | 0.572 |
| chr2 | 219676946 | 219677196 | 0.568 |
| chr2 | 219677019 | 219677269 | 0.552 |
| chr2 | 219677317 | 219677567 | 0.572 |
| chr2 | 219677348 | 219677598 | 0.564 |
| chr2 | 219677704 | 219677954 | 0.592 |
| chr2 | 219679007 | 219679257 | 0.54 |
| chr2 | 219679057 | 219679307 | 0.536 |
| chr2 | 219679259 | 219679509 | 0.604 |
| chr2 | 219679350 | 219679600 | 0.628 |
| chr2 | 220712330 | 220712580 | 0.348 |
| chr2 | 221621220 | 221621470 | 0.348 |
| chr2 | 222580464 | 222580714 | 0.348 |
| chr2 | 223398818 | 223399068 | 0.348 |
| chr2 | 224206872 | 224207122 | 0.32 |
| chr2 | 225175548 | 225175798 | 0.348 |
| chr2 | 226463150 | 226463400 | 0.3 |
| chr2 | 227271729 | 227271979 | 0.316 |
| chr2 | 227872066 | 227872316 | 0.536 |
| chr2 | 227872698 | 227872948 | 0.632 |
| chr2 | 227896640 | 227896890 | 0.508 |
| chr2 | 227896844 | 227897094 | 0.516 |
| chr2 | 228173604 | 228173854 | 0.42 |
| chr2 | 228720266 | 228720516 | 0.348 |
| chr2 | 229615501 | 229615751 | 0.324 |
| chr2 | 230420658 | 230420908 | 0.288 |
| chr2 | 232026193 | 232026443 | 0.348 |
| chr2 | 232832077 | 232832327 | 0.348 |
| chr2 | 233404678 | 233404928 | 0.64 |
| chr2 | 233405261 | 233405511 | 0.632 |
| chr2 | 233407577 | 233407827 | 0.612 |
| chr2 | 233722288 | 233722538 | 0.348 |
| chr2 | 234669321 | 234669571 | 0.552 |
| chr2 | 234669649 | 234669899 | 0.44 |
| chr2 | 234675613 | 234675863 | 0.372 |
| chr2 | 234676780 | 234677030 | 0.484 |
| chr2 | 235489755 | 235490005 | 0.348 |
| chr2 | 236310414 | 236310664 | 0.348 |
| chr2 | 237286150 | 237286400 | 0.312 |
| chr2 | 238626336 | 238626586 | 0.348 |
| chr2 | 239657398 | 239657648 | 0.328 |
| chr2 | 240490228 | 240490478 | 0.348 |
| chr2 | 241499243 | 241499493 | 0.348 |
| chr2 | 241808489 | 241808739 | 0.62 |
| chr2 | 241808572 | 241808822 | 0.62 |
| chr2 | 242312643 | 242312893 | 0.348 |
| chr3 | 106582 | 106832 | 0.348 |
| chr3 | 908384 | 908634 | 0.312 |
| chr3 | 1765150 | 1765400 | 0.312 |
| chr3 | 2567150 | 2567400 | 0.304 |
| chr3 | 3462150 | 3462400 | 0.316 |
| chr3 | 4337222 | 4337472 | 0.348 |
| chr3 | 5258275 | 5258525 | 0.348 |
| chr3 | 6270433 | 6270683 | 0.348 |
| chr3 | 7086564 | 7086814 | 0.348 |
| chr3 | 8132516 | 8132766 | 0.336 |
| chr3 | 8945155 | 8945405 | 0.348 |
| chr3 | 10011145 | 10011395 | 0.344 |
| chr3 | 10874086 | 10874336 | 0.348 |
| chr3 | 11859185 | 11859435 | 0.348 |
| chr3 | 12659562 | 12659812 | 0.308 |
| chr3 | 13508599 | 13508849 | 0.348 |
| chr3 | 14357844 | 14358094 | 0.348 |
| chr3 | 15686845 | 15687095 | 0.544 |
| chr3 | 15718550 | 15718800 | 0.34 |
| chr3 | 16857172 | 16857422 | 0.348 |
| chr3 | 18013150 | 18013400 | 0.328 |
| chr3 | 18993185 | 18993435 | 0.348 |
| chr3 | 19802245 | 19802495 | 0.336 |
| chr3 | 20604117 | 20604367 | 0.348 |
| chr3 | 21451150 | 21451400 | 0.324 |
| chr3 | 22286462 | 22286712 | 0.348 |
| chr3 | 23158341 | 23158591 | 0.348 |
| chr3 | 24158297 | 24158547 | 0.348 |
| chr3 | 25277173 | 25277423 | 0.348 |
| chr3 | 26446293 | 26446543 | 0.328 |
| chr3 | 27249004 | 27249254 | 0.324 |
| chr3 | 28051902 | 28052152 | 0.348 |
| chr3 | 28868402 | 28868652 | 0.348 |
| chr3 | 29670992 | 29671242 | 0.32 |
| chr3 | 30519197 | 30519447 | 0.348 |
| chr3 | 31364183 | 31364433 | 0.348 |
| chr3 | 32524425 | 32524675 | 0.348 |
| chr3 | 33428371 | 33428621 | 0.348 |
| chr3 | 34284461 | 34284711 | 0.348 |
| chr3 | 35362150 | 35362400 | 0.34 |
| chr3 | 36162197 | 36162447 | 0.348 |
| chr3 | 36969914 | 36970164 | 0.348 |
| chr3 | 37806754 | 37807004 | 0.348 |
| chr3 | 38725451 | 38725701 | 0.348 |
| chr3 | 39545431 | 39545681 | 0.348 |
| chr3 | 40346322 | 40346572 | 0.32 |
| chr3 | 41182781 | 41183031 | 0.348 |
| chr3 | 42062642 | 42062892 | 0.348 |
| chr3 | 42870181 | 42870431 | 0.348 |
| chr3 | 43679165 | 43679415 | 0.348 |
| chr3 | 44511929 | 44512179 | 0.332 |
| chr3 | 45335638 | 45335888 | 0.336 |
| chr3 | 46151421 | 46151671 | 0.348 |
| chr3 | 47066811 | 47067061 | 0.348 |
| chr3 | 47901166 | 47901416 | 0.348 |
| chr3 | 48730727 | 48730977 | 0.348 |
| chr3 | 49570998 | 49571248 | 0.348 |
| chr3 | 50643833 | 50644083 | 0.348 |
| chr3 | 51451458 | 51451708 | 0.348 |
| chr3 | 52301455 | 52301705 | 0.348 |
| chr3 | 53125457 | 53125707 | 0.332 |
| chr3 | 53930140 | 53930390 | 0.308 |

| Ch. | Start | Stop | GC content | Ch. | Start | Stop | GC content |
|---|---|---|---|---|---|---|---|
| chr3 | 54731843 | 54732093 | 0.348 | chr3 | 127455014 | 127455264 | 0.348 |
| chr3 | 55552366 | 55552616 | 0.348 | chr3 | 129170444 | 129170694 | 0.348 |
| chr3 | 56374796 | 56375046 | 0.344 | chr3 | 131092150 | 131092400 | 0.336 |
| chr3 | 57175379 | 57175629 | 0.268 | chr3 | 132208201 | 132208451 | 0.328 |
| chr3 | 58002540 | 58002790 | 0.32 | chr3 | 133852268 | 133852518 | 0.348 |
| chr3 | 58914444 | 58914694 | 0.316 | chr3 | 135245150 | 135245400 | 0.336 |
| chr3 | 60826550 | 60826800 | 0.28 | chr3 | 135975298 | 135975548 | 0.396 |
| chr3 | 62217159 | 62217409 | 0.348 | chr3 | 135980686 | 135980936 | 0.432 |
| chr3 | 63145150 | 63145400 | 0.344 | chr3 | 135980741 | 135980991 | 0.456 |
| chr3 | 64458150 | 64458400 | 0.348 | chr3 | 136009682 | 136009932 | 0.332 |
| chr3 | 65372154 | 65372404 | 0.348 | chr3 | 136045901 | 136046151 | 0.536 |
| chr3 | 66316150 | 66316400 | 0.348 | chr3 | 136045956 | 136046206 | 0.536 |
| chr3 | 67172150 | 67172400 | 0.324 | chr3 | 136046361 | 136046611 | 0.504 |
| chr3 | 67972470 | 67972720 | 0.304 | chr3 | 136048668 | 136048918 | 0.476 |
| chr3 | 68775683 | 68775933 | 0.348 | chr3 | 136048719 | 136048969 | 0.444 |
| chr3 | 69819562 | 69819812 | 0.348 | chr3 | 136271150 | 136271400 | 0.272 |
| chr3 | 70622150 | 70622400 | 0.256 | chr3 | 137101096 | 137101346 | 0.348 |
| chr3 | 71422272 | 71422522 | 0.348 | chr3 | 138709161 | 138709411 | 0.348 |
| chr3 | 72235107 | 72235357 | 0.336 | chr3 | 139558134 | 139558384 | 0.348 |
| chr3 | 73035206 | 73035456 | 0.348 | chr3 | 140396238 | 140396488 | 0.348 |
| chr3 | 73959481 | 73959731 | 0.348 | chr3 | 141198475 | 141198725 | 0.296 |
| chr3 | 74759920 | 74760170 | 0.252 | chr3 | 142016082 | 142016332 | 0.348 |
| chr3 | 75954621 | 75954871 | 0.284 | chr3 | 143067286 | 143067536 | 0.316 |
| chr3 | 76763596 | 76763846 | 0.348 | chr3 | 143869968 | 143870218 | 0.348 |
| chr3 | 77570832 | 77571082 | 0.344 | chr3 | 144671028 | 144671278 | 0.308 |
| chr3 | 78386873 | 78387123 | 0.348 | chr3 | 145486925 | 145487175 | 0.3 |
| chr3 | 79188557 | 79188807 | 0.348 | chr3 | 146287344 | 146287594 | 0.348 |
| chr3 | 80261571 | 80261821 | 0.348 | chr3 | 147094525 | 147094775 | 0.348 |
| chr3 | 81419171 | 81419421 | 0.348 | chr3 | 147896273 | 147896523 | 0.336 |
| chr3 | 81697870 | 81698120 | 0.304 | chr3 | 148857589 | 148857839 | 0.336 |
| chr3 | 82375279 | 82375529 | 0.348 | chr3 | 148881618 | 148881868 | 0.312 |
| chr3 | 83179213 | 83179463 | 0.316 | chr3 | 149900583 | 149900833 | 0.348 |
| chr3 | 83997183 | 83997433 | 0.292 | chr3 | 150645769 | 150646019 | 0.38 |
| chr3 | 84798234 | 84798484 | 0.312 | chr3 | 150645848 | 150646098 | 0.404 |
| chr3 | 85600581 | 85600831 | 0.328 | chr3 | 150690222 | 150690472 | 0.532 |
| chr3 | 86406853 | 86407103 | 0.296 | chr3 | 150859582 | 150859832 | 0.348 |
| chr3 | 87309262 | 87309512 | 0.348 | chr3 | 151668293 | 151668543 | 0.304 |
| chr3 | 88400150 | 88400400 | 0.3 | chr3 | 152474698 | 152474948 | 0.344 |
| chr3 | 89682150 | 89682400 | 0.3 | chr3 | 153432150 | 153432400 | 0.316 |
| chr3 | 93653233 | 93653483 | 0.336 | chr3 | 154235025 | 154235275 | 0.344 |
| chr3 | 94486575 | 94486825 | 0.344 | chr3 | 155041150 | 155041400 | 0.328 |
| chr3 | 95493267 | 95493517 | 0.312 | chr3 | 155924313 | 155924563 | 0.348 |
| chr3 | 96311242 | 96311492 | 0.276 | chr3 | 157018150 | 157018400 | 0.32 |
| chr3 | 97326150 | 97326400 | 0.276 | chr3 | 158109466 | 158109716 | 0.348 |
| chr3 | 98164597 | 98164847 | 0.288 | chr3 | 159249551 | 159249801 | 0.332 |
| chr3 | 98967593 | 98967843 | 0.348 | chr3 | 160003430 | 160003680 | 0.296 |
| chr3 | 99767959 | 99768209 | 0.34 | chr3 | 160316406 | 160316656 | 0.348 |
| chr3 | 100568517 | 100568767 | 0.332 | chr3 | 161438158 | 161438408 | 0.348 |
| chr3 | 102171151 | 102171401 | 0.332 | chr3 | 162238201 | 162238451 | 0.26 |
| chr3 | 104463150 | 104463400 | 0.344 | chr3 | 163049817 | 163050067 | 0.276 |
| chr3 | 105267545 | 105267795 | 0.348 | chr3 | 163869741 | 163869991 | 0.34 |
| chr3 | 106008363 | 106008613 | 0.276 | chr3 | 164670585 | 164670835 | 0.3 |
| chr3 | 106219344 | 106219594 | 0.332 | chr3 | 165478954 | 165479204 | 0.348 |
| chr3 | 107172470 | 107172720 | 0.348 | chr3 | 165491155 | 165491404 | 0.313253 |
| chr3 | 108216183 | 108216433 | 0.304 | chr3 | 165548392 | 165548641 | 0.401606 |
| chr3 | 109044868 | 109045118 | 0.348 | chr3 | 166281735 | 166281985 | 0.328 |
| chr3 | 110072469 | 110072719 | 0.348 | chr3 | 167085940 | 167086190 | 0.308 |
| chr3 | 110913541 | 110913791 | 0.348 | chr3 | 168459468 | 168459718 | 0.308 |
| chr3 | 111996421 | 111996671 | 0.348 | chr3 | 169309551 | 169309801 | 0.344 |
| chr3 | 113052335 | 113052585 | 0.348 | chr3 | 170492150 | 170492400 | 0.324 |
| chr3 | 113880193 | 113880443 | 0.348 | chr3 | 171325476 | 171325726 | 0.312 |
| chr3 | 115100591 | 115100841 | 0.348 | chr3 | 172228471 | 172228721 | 0.348 |
| chr3 | 116316282 | 116316532 | 0.348 | chr3 | 173228258 | 173228508 | 0.348 |
| chr3 | 117419150 | 117419400 | 0.34 | chr3 | 174030196 | 174030446 | 0.348 |
| chr3 | 118228268 | 118228518 | 0.348 | chr3 | 174909327 | 174909577 | 0.348 |
| chr3 | 119031004 | 119031254 | 0.348 | chr3 | 176159550 | 176159800 | 0.272 |
| chr3 | 119848682 | 119848932 | 0.348 | chr3 | 177050167 | 177050417 | 0.296 |
| chr3 | 120369570 | 120369820 | 0.508 | chr3 | 178235166 | 178235416 | 0.34 |
| chr3 | 120393624 | 120393874 | 0.488 | chr3 | 179511583 | 179511833 | 0.348 |
| chr3 | 120394586 | 120394836 | 0.408 | chr3 | 180752251 | 180752501 | 0.344 |
| chr3 | 121124509 | 121124759 | 0.288 | chr3 | 181861577 | 181861827 | 0.348 |
| chr3 | 121967180 | 121967430 | 0.348 | chr3 | 182665063 | 182665313 | 0.268 |
| chr3 | 123211159 | 123211409 | 0.348 | chr3 | 183472150 | 183472400 | 0.348 |
| chr3 | 124011977 | 124012227 | 0.316 | chr3 | 184526150 | 184526400 | 0.312 |
| chr3 | 124820334 | 124820584 | 0.284 | chr3 | 185410377 | 185410627 | 0.348 |
| chr3 | 125753018 | 125753268 | 0.336 | chr3 | 186420548 | 186420798 | 0.324 |
| chr3 | 126599445 | 126599695 | 0.348 | chr3 | 187267150 | 187267400 | 0.348 |

| Ch. | Start | Stop | GC content |
|---|---|---|---|
| chr3 | 188173164 | 188173414 | 0.348 |
| chr3 | 189008153 | 189008403 | 0.348 |
| chr3 | 189809150 | 189809400 | 0.28 |
| chr3 | 190627116 | 190627366 | 0.348 |
| chr3 | 191447581 | 191447831 | 0.348 |
| chr3 | 192375286 | 192375536 | 0.348 |
| chr3 | 193179318 | 193179568 | 0.288 |
| chr3 | 194874250 | 194874500 | 0.348 |
| chr3 | 195777466 | 195777716 | 0.348 |
| chr3 | 196621577 | 196621827 | 0.312 |
| chr3 | 197424150 | 197424400 | 0.308 |
| chr4 | 524439 | 524689 | 0.348 |
| chr4 | 1694543 | 1694793 | 0.296 |
| chr4 | 1806047 | 1806226 | 0.653631 |
| chr4 | 2590392 | 2590642 | 0.348 |
| chr4 | 3408543 | 3408793 | 0.348 |
| chr4 | 4248009 | 4248259 | 0.34 |
| chr4 | 5073125 | 5073375 | 0.32 |
| chr4 | 5911997 | 5912247 | 0.292 |
| chr4 | 6786181 | 6786431 | 0.348 |
| chr4 | 7889150 | 7889400 | 0.284 |
| chr4 | 8768669 | 8768919 | 0.348 |
| chr4 | 11023186 | 11023436 | 0.348 |
| chr4 | 11924150 | 11924400 | 0.332 |
| chr4 | 12802731 | 12802981 | 0.348 |
| chr4 | 13608443 | 13608693 | 0.3 |
| chr4 | 14700204 | 14700454 | 0.348 |
| chr4 | 15516150 | 15516400 | 0.316 |
| chr4 | 16593239 | 16593489 | 0.348 |
| chr4 | 17959355 | 17959605 | 0.34 |
| chr4 | 19122551 | 19122801 | 0.348 |
| chr4 | 20409254 | 20409504 | 0.348 |
| chr4 | 21274269 | 21274519 | 0.32 |
| chr4 | 22246426 | 22246676 | 0.34 |
| chr4 | 23364150 | 23364400 | 0.348 |
| chr4 | 24165166 | 24165416 | 0.348 |
| chr4 | 25408550 | 25408800 | 0.268 |
| chr4 | 26570550 | 26570800 | 0.292 |
| chr4 | 27713150 | 27713400 | 0.3 |
| chr4 | 28518303 | 28518553 | 0.348 |
| chr4 | 29328570 | 29328820 | 0.348 |
| chr4 | 30272440 | 30272690 | 0.32 |
| chr4 | 31367442 | 31367692 | 0.348 |
| chr4 | 32172526 | 32172776 | 0.34 |
| chr4 | 32976113 | 32976363 | 0.268 |
| chr4 | 33782576 | 33782826 | 0.34 |
| chr4 | 35566150 | 35566400 | 0.268 |
| chr4 | 36384406 | 36384656 | 0.328 |
| chr4 | 37187183 | 37187433 | 0.348 |
| chr4 | 38037150 | 38037400 | 0.34 |
| chr4 | 38857304 | 38857554 | 0.348 |
| chr4 | 39657375 | 39657625 | 0.3 |
| chr4 | 40457994 | 40458244 | 0.332 |
| chr4 | 41262121 | 41262371 | 0.348 |
| chr4 | 42799150 | 42799400 | 0.324 |
| chr4 | 43607150 | 43607400 | 0.308 |
| chr4 | 44408802 | 44409052 | 0.276 |
| chr4 | 45217030 | 45217280 | 0.32 |
| chr4 | 46213423 | 46213673 | 0.348 |
| chr4 | 47159179 | 47159429 | 0.348 |
| chr4 | 48947216 | 48947466 | 0.348 |
| chr4 | 52703125 | 52703375 | 0.348 |
| chr4 | 53519881 | 53520131 | 0.348 |
| chr4 | 54575550 | 54575800 | 0.308 |
| chr4 | 55541150 | 55541400 | 0.332 |
| chr4 | 56681150 | 56681400 | 0.268 |
| chr4 | 57640467 | 57640717 | 0.348 |
| chr4 | 58471328 | 58471578 | 0.344 |
| chr4 | 59809215 | 59809465 | 0.348 |
| chr4 | 60849558 | 60849808 | 0.32 |
| chr4 | 61651913 | 61652163 | 0.3 |
| chr4 | 62453032 | 62453282 | 0.348 |
| chr4 | 63256751 | 63257001 | 0.304 |
| chr4 | 64088143 | 64088393 | 0.256 |
| chr4 | 64899871 | 64900121 | 0.304 |
| chr4 | 65701600 | 65701850 | 0.296 |
| chr4 | 66514018 | 66514268 | 0.348 |
| chr4 | 67894302 | 67894552 | 0.348 |
| chr4 | 68776550 | 68776800 | 0.34 |
| chr4 | 69576924 | 69577174 | 0.348 |
| chr4 | 70382938 | 70383188 | 0.288 |
| chr4 | 71237341 | 71237591 | 0.348 |
| chr4 | 72411150 | 72411400 | 0.336 |
| chr4 | 73710150 | 73710400 | 0.344 |
| chr4 | 75071150 | 75071400 | 0.328 |
| chr4 | 76179362 | 76179612 | 0.348 |
| chr4 | 77033574 | 77033824 | 0.348 |
| chr4 | 77846718 | 77846968 | 0.288 |
| chr4 | 78648984 | 78649234 | 0.272 |
| chr4 | 79457938 | 79458188 | 0.344 |
| chr4 | 80278331 | 80278581 | 0.34 |
| chr4 | 81378288 | 81378538 | 0.324 |
| chr4 | 82584150 | 82584400 | 0.348 |
| chr4 | 83424150 | 83424400 | 0.284 |
| chr4 | 84768150 | 84768400 | 0.34 |
| chr4 | 86164348 | 86164598 | 0.32 |
| chr4 | 87420154 | 87420404 | 0.348 |
| chr4 | 88759560 | 88759810 | 0.348 |
| chr4 | 89613224 | 89613474 | 0.348 |
| chr4 | 90622593 | 90622843 | 0.348 |
| chr4 | 91908223 | 91908473 | 0.344 |
| chr4 | 92715215 | 92715465 | 0.348 |
| chr4 | 94023452 | 94023702 | 0.308 |
| chr4 | 95644839 | 95645089 | 0.288 |
| chr4 | 96736322 | 96736572 | 0.348 |
| chr4 | 98008150 | 98008400 | 0.316 |
| chr4 | 99308150 | 99308400 | 0.284 |
| chr4 | 100232150 | 100232400 | 0.332 |
| chr4 | 100543788 | 100544038 | 0.42 |
| chr4 | 101068550 | 101068800 | 0.344 |
| chr4 | 101875150 | 101875400 | 0.348 |
| chr4 | 102676263 | 102676513 | 0.348 |
| chr4 | 103487276 | 103487526 | 0.308 |
| chr4 | 104289731 | 104289981 | 0.296 |
| chr4 | 105095425 | 105095675 | 0.284 |
| chr4 | 105907870 | 105908120 | 0.332 |
| chr4 | 107094224 | 107094474 | 0.332 |
| chr4 | 108325550 | 108325800 | 0.332 |
| chr4 | 109267150 | 109267400 | 0.344 |
| chr4 | 110081150 | 110081400 | 0.296 |
| chr4 | 110970150 | 110970400 | 0.348 |
| chr4 | 111958216 | 111958466 | 0.348 |
| chr4 | 112823591 | 112823841 | 0.348 |
| chr4 | 113629945 | 113630195 | 0.264 |
| chr4 | 115384150 | 115384400 | 0.328 |
| chr4 | 116190298 | 116190548 | 0.348 |
| chr4 | 117009231 | 117009481 | 0.3 |
| chr4 | 117809721 | 117809971 | 0.336 |
| chr4 | 118609887 | 118610137 | 0.324 |
| chr4 | 119597337 | 119597587 | 0.348 |
| chr4 | 120411943 | 120412193 | 0.268 |
| chr4 | 121214719 | 121214969 | 0.348 |
| chr4 | 122018543 | 122018793 | 0.348 |
| chr4 | 122820118 | 122820368 | 0.332 |
| chr4 | 123622182 | 123622432 | 0.284 |
| chr4 | 123663257 | 123663507 | 0.36 |
| chr4 | 123663787 | 123664037 | 0.392 |
| chr4 | 123663985 | 123664235 | 0.408 |
| chr4 | 123664405 | 123664655 | 0.436 |
| chr4 | 124422894 | 124423144 | 0.324 |
| chr4 | 125512382 | 125512632 | 0.264 |
| chr4 | 126813261 | 126813511 | 0.348 |
| chr4 | 127615051 | 127615301 | 0.3 |
| chr4 | 128419953 | 128420203 | 0.348 |
| chr4 | 129523487 | 129523737 | 0.348 |
| chr4 | 130323522 | 130323772 | 0.348 |
| chr4 | 131125980 | 131126230 | 0.256 |
| chr4 | 131938368 | 131938618 | 0.304 |
| chr4 | 132925295 | 132925545 | 0.332 |
| chr4 | 133727028 | 133727278 | 0.292 |
| chr4 | 134535097 | 134535347 | 0.336 |
| chr4 | 135337052 | 135337302 | 0.284 |
| chr4 | 136137384 | 136137634 | 0.276 |
| chr4 | 136938690 | 136938940 | 0.328 |

| Ch. | Start | Stop | GC content |
|---|---|---|---|
| chr4 | 137875318 | 137875568 | 0.348 |
| chr4 | 138925335 | 138925585 | 0.348 |
| chr4 | 139726418 | 139726668 | 0.348 |
| chr4 | 140766433 | 140766683 | 0.348 |
| chr4 | 142917150 | 142917400 | 0.284 |
| chr4 | 143721319 | 143721569 | 0.344 |
| chr4 | 144616150 | 144616400 | 0.272 |
| chr4 | 145420015 | 145420265 | 0.332 |
| chr4 | 146237783 | 146238033 | 0.3 |
| chr4 | 146560230 | 146560480 | 0.436 |
| chr4 | 146560327 | 146560577 | 0.396 |
| chr4 | 146560432 | 146560682 | 0.404 |
| chr4 | 146560450 | 146560700 | 0.396 |
| chr4 | 146560519 | 146560769 | 0.372 |
| chr4 | 146560579 | 146560829 | 0.356 |
| chr4 | 146563453 | 146563703 | 0.4 |
| chr4 | 146563507 | 146563757 | 0.436 |
| chr4 | 146567088 | 146567338 | 0.38 |
| chr4 | 146567195 | 146567445 | 0.352 |
| chr4 | 146576280 | 146576530 | 0.476 |
| chr4 | 147039150 | 147039400 | 0.348 |
| chr4 | 147861172 | 147861422 | 0.348 |
| chr4 | 148947515 | 148947765 | 0.348 |
| chr4 | 149763150 | 149763400 | 0.336 |
| chr4 | 151024279 | 151024529 | 0.3 |
| chr4 | 151837404 | 151837654 | 0.308 |
| chr4 | 152647195 | 152647445 | 0.324 |
| chr4 | 154417224 | 154417474 | 0.348 |
| chr4 | 155217502 | 155217752 | 0.348 |
| chr4 | 156024046 | 156024296 | 0.348 |
| chr4 | 156824354 | 156824604 | 0.316 |
| chr4 | 157626326 | 157626576 | 0.332 |
| chr4 | 158431044 | 158431294 | 0.296 |
| chr4 | 159237626 | 159237876 | 0.348 |
| chr4 | 160045854 | 160046104 | 0.28 |
| chr4 | 160857413 | 160857663 | 0.312 |
| chr4 | 161657414 | 161657664 | 0.344 |
| chr4 | 162457547 | 162457797 | 0.304 |
| chr4 | 163258332 | 163258582 | 0.348 |
| chr4 | 164775219 | 164775469 | 0.348 |
| chr4 | 165581368 | 165581618 | 0.332 |
| chr4 | 166385754 | 166386004 | 0.348 |
| chr4 | 167194635 | 167194885 | 0.332 |
| chr4 | 167998589 | 167998839 | 0.296 |
| chr4 | 168813970 | 168814220 | 0.324 |
| chr4 | 169620754 | 169621004 | 0.32 |
| chr4 | 170428650 | 170428900 | 0.292 |
| chr4 | 172239593 | 172239843 | 0.308 |
| chr4 | 173054299 | 173054549 | 0.348 |
| chr4 | 173854598 | 173854848 | 0.268 |
| chr4 | 174658150 | 174658400 | 0.348 |
| chr4 | 175674466 | 175674716 | 0.348 |
| chr4 | 176773440 | 176773690 | 0.324 |
| chr4 | 177574380 | 177574630 | 0.288 |
| chr4 | 178354254 | 178354504 | 0.344 |
| chr4 | 178376420 | 178376670 | 0.348 |
| chr4 | 179177025 | 179177275 | 0.324 |
| chr4 | 179990413 | 179990663 | 0.324 |
| chr4 | 180955150 | 180955400 | 0.332 |
| chr4 | 181758151 | 181758401 | 0.348 |
| chr4 | 182559169 | 182559419 | 0.348 |
| chr4 | 183364952 | 183365202 | 0.348 |
| chr4 | 184169569 | 184169819 | 0.308 |
| chr4 | 184975478 | 184975728 | 0.328 |
| chr4 | 185777424 | 185777674 | 0.348 |
| chr4 | 186586136 | 186586386 | 0.272 |
| chr4 | 187195222 | 187195472 | 0.476 |
| chr4 | 187201287 | 187201537 | 0.512 |
| chr4 | 187833378 | 187833628 | 0.348 |
| chr4 | 188635326 | 188635576 | 0.348 |
| chr4 | 189455666 | 189455916 | 0.348 |
| chr5 | 925341 | 925591 | 0.348 |
| chr5 | 1760577 | 1760827 | 0.348 |
| chr5 | 2571762 | 2572012 | 0.348 |
| chr5 | 3908300 | 3908550 | 0.328 |
| chr5 | 5808362 | 5808612 | 0.348 |
| chr5 | 7066150 | 7066400 | 0.332 |
| chr5 | 7929390 | 7929640 | 0.348 |
| chr5 | 8884167 | 8884417 | 0.348 |
| chr5 | 9694150 | 9694400 | 0.312 |
| chr5 | 11072336 | 11072586 | 0.348 |
| chr5 | 11925598 | 11925848 | 0.348 |
| chr5 | 12734408 | 12734658 | 0.348 |
| chr5 | 14411235 | 14411485 | 0.348 |
| chr5 | 16434161 | 16434411 | 0.348 |
| chr5 | 16434161 | 16434411 | 0.348 |
| chr5 | 17378337 | 17378587 | 0.348 |
| chr5 | 18379157 | 18379407 | 0.348 |
| chr5 | 19179651 | 19179901 | 0.32 |
| chr5 | 19982105 | 19982355 | 0.272 |
| chr5 | 21021592 | 21021842 | 0.332 |
| chr5 | 22260550 | 22260800 | 0.308 |
| chr5 | 23427408 | 23427658 | 0.316 |
| chr5 | 24333150 | 24333400 | 0.252 |
| chr5 | 25638150 | 25638400 | 0.32 |
| chr5 | 26472150 | 26472400 | 0.344 |
| chr5 | 27277073 | 27277323 | 0.348 |
| chr5 | 28441164 | 28441414 | 0.328 |
| chr5 | 29277434 | 29277684 | 0.348 |
| chr5 | 30147460 | 30147710 | 0.28 |
| chr5 | 30965150 | 30965400 | 0.304 |
| chr5 | 32276489 | 32276739 | 0.348 |
| chr5 | 33120530 | 33120780 | 0.336 |
| chr5 | 33963570 | 33963820 | 0.348 |
| chr5 | 34808150 | 34808400 | 0.276 |
| chr5 | 35611221 | 35611471 | 0.34 |
| chr5 | 36450561 | 36450811 | 0.348 |
| chr5 | 38217206 | 38217456 | 0.348 |
| chr5 | 39308293 | 39308543 | 0.344 |
| chr5 | 40243400 | 40243650 | 0.348 |
| chr5 | 41069505 | 41069755 | 0.308 |
| chr5 | 42023181 | 42023431 | 0.348 |
| chr5 | 42907557 | 42907807 | 0.264 |
| chr5 | 43869212 | 43869462 | 0.348 |
| chr5 | 44811198 | 44811448 | 0.348 |
| chr5 | 45614193 | 45614443 | 0.348 |
| chr5 | 49559754 | 49560004 | 0.288 |
| chr5 | 51558414 | 51558664 | 0.328 |
| chr5 | 52572333 | 52572583 | 0.348 |
| chr5 | 53692364 | 53692614 | 0.348 |
| chr5 | 54615371 | 54615621 | 0.344 |
| chr5 | 55613299 | 55613549 | 0.316 |
| chr5 | 56865222 | 56865472 | 0.348 |
| chr5 | 57694196 | 57694446 | 0.276 |
| chr5 | 58497233 | 58497483 | 0.252 |
| chr5 | 59329150 | 59329400 | 0.312 |
| chr5 | 60144254 | 60144504 | 0.32 |
| chr5 | 60953095 | 60953345 | 0.348 |
| chr5 | 62167485 | 62167735 | 0.348 |
| chr5 | 63311150 | 63311400 | 0.328 |
| chr5 | 64114150 | 64114400 | 0.312 |
| chr5 | 64921258 | 64921508 | 0.348 |
| chr5 | 65772331 | 65772581 | 0.348 |
| chr5 | 66826161 | 66826411 | 0.348 |
| chr5 | 67641208 | 67641458 | 0.348 |
| chr5 | 68472969 | 68473219 | 0.348 |
| chr5 | 70238181 | 70238430 | 0.37751 |
| chr5 | 70241800 | 70241994 | 0.35567 |
| chr5 | 70247767 | 70247866 | 0.343434 |
| chr5 | 70752734 | 70752984 | 0.348 |
| chr5 | 71556027 | 71556277 | 0.332 |
| chr5 | 72610157 | 72610407 | 0.348 |
| chr5 | 73516578 | 73516828 | 0.316 |
| chr5 | 74016348 | 74016598 | 0.428 |
| chr5 | 74321150 | 74321400 | 0.3 |
| chr5 | 75142529 | 75142779 | 0.324 |
| chr5 | 75949606 | 75949856 | 0.34 |
| chr5 | 76753702 | 76753952 | 0.308 |
| chr5 | 77564503 | 77564753 | 0.348 |
| chr5 | 78373076 | 78373326 | 0.348 |
| chr5 | 79271575 | 79271825 | 0.348 |
| chr5 | 80322374 | 80322624 | 0.348 |
| chr5 | 81143414 | 81143664 | 0.348 |
| chr5 | 82115520 | 82115770 | 0.328 |

| Ch. | Start | Stop | GC content | Ch. | Start | Stop | GC content |
|---|---|---|---|---|---|---|---|
| chr5 | 83161167 | 83161417 | 0.252 | chr5 | 149357622 | 149357872 | 0.416 |
| chr5 | 83962946 | 83963196 | 0.34 | chr5 | 149360046 | 149360296 | 0.396 |
| chr5 | 84798100 | 84798350 | 0.292 | chr5 | 149360988 | 149361238 | 0.448 |
| chr5 | 85607624 | 85607874 | 0.28 | chr5 | 150168418 | 150168668 | 0.348 |
| chr5 | 86610487 | 86610737 | 0.348 | chr5 | 151153336 | 151153586 | 0.312 |
| chr5 | 87453348 | 87453598 | 0.348 | chr5 | 151974339 | 151974589 | 0.252 |
| chr5 | 88723150 | 88723400 | 0.268 | chr5 | 153079172 | 153079422 | 0.348 |
| chr5 | 90119327 | 90119577 | 0.348 | chr5 | 154769590 | 154769840 | 0.348 |
| chr5 | 91072151 | 91072401 | 0.348 | chr5 | 155629221 | 155629471 | 0.348 |
| chr5 | 91927392 | 91927642 | 0.316 | chr5 | 155771459 | 155771709 | 0.46 |
| chr5 | 93066150 | 93066400 | 0.272 | chr5 | 156569984 | 156570234 | 0.348 |
| chr5 | 94084150 | 94084400 | 0.336 | chr5 | 157381960 | 157382210 | 0.336 |
| chr5 | 94884324 | 94884574 | 0.308 | chr5 | 158468169 | 158468419 | 0.348 |
| chr5 | 95817279 | 95817529 | 0.348 | chr5 | 159465150 | 159465400 | 0.304 |
| chr5 | 96673550 | 96673800 | 0.3 | chr5 | 160279480 | 160279730 | 0.348 |
| chr5 | 97504150 | 97504400 | 0.308 | chr5 | 161080261 | 161080511 | 0.348 |
| chr5 | 98705396 | 98705646 | 0.348 | chr5 | 161901345 | 161901595 | 0.344 |
| chr5 | 99560435 | 99560685 | 0.32 | chr5 | 162917271 | 162917521 | 0.32 |
| chr5 | 100365824 | 100366074 | 0.34 | chr5 | 163717664 | 163717914 | 0.348 |
| chr5 | 101174653 | 101174903 | 0.292 | chr5 | 164517680 | 164517930 | 0.304 |
| chr5 | 102365150 | 102365400 | 0.308 | chr5 | 165319177 | 165319427 | 0.348 |
| chr5 | 103728150 | 103728400 | 0.332 | chr5 | 167015237 | 167015487 | 0.348 |
| chr5 | 104531179 | 104531429 | 0.252 | chr5 | 167919124 | 167919374 | 0.328 |
| chr5 | 105350391 | 105350641 | 0.284 | chr5 | 168721160 | 168721410 | 0.348 |
| chr5 | 106531361 | 106531611 | 0.348 | chr5 | 169550080 | 169550330 | 0.336 |
| chr5 | 107570373 | 107570623 | 0.348 | chr5 | 170379303 | 170379553 | 0.316 |
| chr5 | 108926232 | 108926482 | 0.348 | chr5 | 171180930 | 171181180 | 0.348 |
| chr5 | 110027150 | 110027400 | 0.328 | chr5 | 172017300 | 172017550 | 0.296 |
| chr5 | 111196451 | 111196701 | 0.332 | chr5 | 172827926 | 172828176 | 0.348 |
| chr5 | 112021809 | 112022059 | 0.348 | chr5 | 173664137 | 173664387 | 0.348 |
| chr5 | 113013150 | 113013400 | 0.328 | chr5 | 174480831 | 174481081 | 0.328 |
| chr5 | 114065262 | 114065512 | 0.348 | chr5 | 175574930 | 175575180 | 0.348 |
| chr5 | 114872251 | 114872501 | 0.348 | chr5 | 176381946 | 176382196 | 0.348 |
| chr5 | 115988311 | 115988561 | 0.348 | chr5 | 177419684 | 177419934 | 0.62 |
| chr5 | 117001555 | 117001805 | 0.348 | chr5 | 177419909 | 177420159 | 0.572 |
| chr5 | 117930159 | 117930409 | 0.348 | chr5 | 177421022 | 177421272 | 0.588 |
| chr5 | 118788222 | 118788472 | 0.656 | chr5 | 178424528 | 178424778 | 0.348 |
| chr5 | 119230150 | 119230400 | 0.328 | chr5 | 179368971 | 179369221 | 0.348 |
| chr5 | 120473241 | 120473491 | 0.348 | chr5 | 180175488 | 180175738 | 0.34 |
| chr5 | 121394548 | 121394798 | 0.348 | chr6 | 722215 | 722465 | 0.348 |
| chr5 | 122571402 | 122571652 | 0.348 | chr6 | 1809311 | 1809561 | 0.332 |
| chr5 | 123678502 | 123678752 | 0.348 | chr6 | 2680150 | 2680400 | 0.288 |
| chr5 | 124774217 | 124774467 | 0.348 | chr6 | 3484150 | 3484400 | 0.336 |
| chr5 | 125616247 | 125616497 | 0.348 | chr6 | 4620332 | 4620582 | 0.344 |
| chr5 | 126426335 | 126426585 | 0.348 | chr6 | 5431006 | 5431256 | 0.348 |
| chr5 | 127322174 | 127322424 | 0.336 | chr6 | 6236906 | 6237156 | 0.348 |
| chr5 | 128479275 | 128479525 | 0.324 | chr6 | 7045378 | 7045628 | 0.348 |
| chr5 | 129376150 | 129376400 | 0.34 | chr6 | 7964447 | 7964697 | 0.348 |
| chr5 | 130223163 | 130223413 | 0.348 | chr6 | 9467470 | 9467720 | 0.348 |
| chr5 | 131031617 | 131031867 | 0.28 | chr6 | 10269525 | 10269775 | 0.348 |
| chr5 | 131713947 | 131714197 | 0.496 | chr6 | 11927322 | 11927572 | 0.348 |
| chr5 | 131719848 | 131720098 | 0.488 | chr6 | 12773150 | 12773400 | 0.316 |
| chr5 | 131722606 | 131722856 | 0.544 | chr6 | 13976150 | 13976400 | 0.34 |
| chr5 | 131726399 | 131726649 | 0.524 | chr6 | 14834528 | 14834778 | 0.348 |
| chr5 | 131726406 | 131726656 | 0.536 | chr6 | 16162150 | 16162400 | 0.348 |
| chr5 | 131728056 | 131728306 | 0.52 | chr6 | 18388156 | 18388406 | 0.348 |
| chr5 | 131728165 | 131728415 | 0.52 | chr6 | 19660443 | 19660693 | 0.348 |
| chr5 | 131877011 | 131877261 | 0.348 | chr6 | 20718512 | 20718762 | 0.348 |
| chr5 | 132746346 | 132746596 | 0.348 | chr6 | 21534150 | 21534400 | 0.336 |
| chr5 | 133549999 | 133550249 | 0.268 | chr6 | 22919570 | 22919820 | 0.348 |
| chr5 | 134367800 | 134368157 | 0.348 | chr6 | 23724897 | 23725147 | 0.344 |
| chr5 | 135271150 | 135271400 | 0.328 | chr6 | 24533878 | 24534128 | 0.348 |
| chr5 | 136109975 | 136110225 | 0.348 | chr6 | 25335487 | 25335737 | 0.284 |
| chr5 | 136919859 | 136920109 | 0.348 | chr6 | 26142116 | 26142366 | 0.348 |
| chr5 | 137721384 | 137721634 | 0.348 | chr6 | 26999810 | 27000060 | 0.328 |
| chr5 | 138617755 | 138618005 | 0.348 | chr6 | 27984245 | 27984495 | 0.348 |
| chr5 | 139437032 | 139437282 | 0.32 | chr6 | 29227316 | 29227566 | 0.348 |
| chr5 | 140243745 | 140243995 | 0.284 | chr6 | 30035500 | 30035750 | 0.348 |
| chr5 | 141342082 | 141342332 | 0.348 | chr6 | 32257190 | 32257440 | 0.276 |
| chr5 | 142430497 | 142430747 | 0.348 | chr6 | 33061928 | 33062178 | 0.348 |
| chr5 | 143263150 | 143263400 | 0.312 | chr6 | 34249129 | 34249379 | 0.348 |
| chr5 | 144100481 | 144100731 | 0.348 | chr6 | 35564395 | 35564645 | 0.348 |
| chr5 | 144924251 | 144924501 | 0.332 | chr6 | 36402380 | 36402630 | 0.292 |
| chr5 | 145821033 | 145821283 | 0.348 | chr6 | 37220892 | 37221142 | 0.344 |
| chr5 | 146723352 | 146723602 | 0.284 | chr6 | 38024507 | 38024757 | 0.348 |
| chr5 | 148103150 | 148103400 | 0.348 | chr6 | 38825212 | 38825462 | 0.348 |
| chr5 | 149357488 | 149357738 | 0.448 | chr6 | 39628292 | 39628542 | 0.348 |

| Ch. | Start | Stop | GC content |
| --- | --- | --- | --- |
| chr6 | 40473041 | 40473291 | 0.348 |
| chr6 | 41760316 | 41760566 | 0.348 |
| chr6 | 42561087 | 42561337 | 0.312 |
| chr6 | 43513955 | 43514205 | 0.348 |
| chr6 | 45170150 | 45170400 | 0.272 |
| chr6 | 46210189 | 46210439 | 0.348 |
| chr6 | 47012116 | 47012366 | 0.348 |
| chr6 | 47816800 | 47817050 | 0.336 |
| chr6 | 49160150 | 49160400 | 0.296 |
| chr6 | 50331150 | 50331400 | 0.348 |
| chr6 | 51133231 | 51133481 | 0.348 |
| chr6 | 51524100 | 51524284 | 0.429348 |
| chr6 | 51524387 | 51524577 | 0.452632 |
| chr6 | 51524477 | 51524726 | 0.417671 |
| chr6 | 51612557 | 51612806 | 0.453815 |
| chr6 | 51612759 | 51613008 | 0.413655 |
| chr6 | 51613242 | 51613431 | 0.47619 |
| chr6 | 51617943 | 51618148 | 0.463415 |
| chr6 | 51637377 | 51637626 | 0.35743 |
| chr6 | 51712574 | 51712767 | 0.492228 |
| chr6 | 51747804 | 51748053 | 0.381526 |
| chr6 | 51824498 | 51824736 | 0.390756 |
| chr6 | 51882240 | 51882489 | 0.522088 |
| chr6 | 51889261 | 51889460 | 0.432161 |
| chr6 | 51889530 | 51889709 | 0.430168 |
| chr6 | 51889613 | 51889863 | 0.488 |
| chr6 | 51890671 | 51890920 | 0.566265 |
| chr6 | 51892991 | 51893208 | 0.562212 |
| chr6 | 51907748 | 51907997 | 0.37751 |
| chr6 | 51910894 | 51911114 | 0.413636 |
| chr6 | 51914920 | 51915167 | 0.538462 |
| chr6 | 51923055 | 51923235 | 0.522222 |
| chr6 | 51927226 | 51927475 | 0.473896 |
| chr6 | 51934785 | 51935035 | 0.348 |
| chr6 | 51935792 | 51936041 | 0.409639 |
| chr6 | 51944632 | 51944881 | 0.465863 |
| chr6 | 51947894 | 51948003 | 0.40367 |
| chr6 | 52866150 | 52866400 | 0.316 |
| chr6 | 53861150 | 53861400 | 0.336 |
| chr6 | 54968397 | 54968647 | 0.344 |
| chr6 | 56323494 | 56323744 | 0.348 |
| chr6 | 57132985 | 57133235 | 0.348 |
| chr6 | 58613218 | 58613468 | 0.348 |
| chr6 | 61967821 | 61968071 | 0.348 |
| chr6 | 62792394 | 62792644 | 0.344 |
| chr6 | 63594685 | 63594935 | 0.304 |
| chr6 | 64396571 | 64396821 | 0.332 |
| chr6 | 65487243 | 65487493 | 0.336 |
| chr6 | 66471331 | 66471581 | 0.348 |
| chr6 | 67540150 | 67540400 | 0.344 |
| chr6 | 68869150 | 68869400 | 0.32 |
| chr6 | 69669354 | 69669604 | 0.268 |
| chr6 | 70496481 | 70496731 | 0.332 |
| chr6 | 71310224 | 71310474 | 0.348 |
| chr6 | 72112966 | 72113216 | 0.304 |
| chr6 | 73660449 | 73660699 | 0.348 |
| chr6 | 74960150 | 74960400 | 0.324 |
| chr6 | 76010150 | 76010400 | 0.332 |
| chr6 | 76814286 | 76814536 | 0.348 |
| chr6 | 78002389 | 78002639 | 0.348 |
| chr6 | 78924155 | 78924405 | 0.348 |
| chr6 | 79983150 | 79983400 | 0.312 |
| chr6 | 81262398 | 81262648 | 0.328 |
| chr6 | 82072150 | 82072400 | 0.336 |
| chr6 | 83412551 | 83412801 | 0.348 |
| chr6 | 84224150 | 84224400 | 0.336 |
| chr6 | 85024384 | 85024634 | 0.348 |
| chr6 | 85824865 | 85825115 | 0.328 |
| chr6 | 86646607 | 86646857 | 0.348 |
| chr6 | 87730150 | 87730400 | 0.328 |
| chr6 | 89879586 | 89879836 | 0.3 |
| chr6 | 90941239 | 90941489 | 0.348 |
| chr6 | 91745267 | 91745517 | 0.348 |
| chr6 | 92548166 | 92548416 | 0.348 |
| chr6 | 93371163 | 93371413 | 0.276 |
| chr6 | 94317550 | 94317800 | 0.316 |
| chr6 | 95153242 | 95153492 | 0.348 |
| chr6 | 96076584 | 96076834 | 0.304 |
| chr6 | 96895352 | 96895602 | 0.34 |
| chr6 | 97836178 | 97836428 | 0.336 |
| chr6 | 99178177 | 99178427 | 0.348 |
| chr6 | 100312150 | 100312400 | 0.304 |
| chr6 | 101668268 | 101668518 | 0.348 |
| chr6 | 102469310 | 102469560 | 0.252 |
| chr6 | 103270888 | 103271138 | 0.348 |
| chr6 | 104071706 | 104071956 | 0.348 |
| chr6 | 104881263 | 104881513 | 0.348 |
| chr6 | 105881364 | 105881614 | 0.328 |
| chr6 | 106961211 | 106961461 | 0.348 |
| chr6 | 107880456 | 107880706 | 0.348 |
| chr6 | 108681536 | 108681786 | 0.348 |
| chr6 | 109481761 | 109482011 | 0.344 |
| chr6 | 110618500 | 110618750 | 0.348 |
| chr6 | 111427143 | 111427393 | 0.348 |
| chr6 | 112231415 | 112231665 | 0.348 |
| chr6 | 113042291 | 113042541 | 0.336 |
| chr6 | 113895590 | 113895840 | 0.348 |
| chr6 | 115006168 | 115006418 | 0.348 |
| chr6 | 115806345 | 115806595 | 0.348 |
| chr6 | 116616751 | 116617001 | 0.312 |
| chr6 | 117765567 | 117765817 | 0.348 |
| chr6 | 119110166 | 119110416 | 0.348 |
| chr6 | 119969535 | 119969785 | 0.344 |
| chr6 | 121313474 | 121313724 | 0.324 |
| chr6 | 122234150 | 122234400 | 0.316 |
| chr6 | 123082150 | 123082400 | 0.348 |
| chr6 | 123883938 | 123884188 | 0.336 |
| chr6 | 124688304 | 124688554 | 0.324 |
| chr6 | 125488626 | 125488876 | 0.34 |
| chr6 | 126295238 | 126295488 | 0.312 |
| chr6 | 127319150 | 127319400 | 0.348 |
| chr6 | 128124694 | 128124944 | 0.344 |
| chr6 | 128939956 | 128940206 | 0.32 |
| chr6 | 129747756 | 129748006 | 0.284 |
| chr6 | 130556422 | 130556672 | 0.288 |
| chr6 | 131359186 | 131359436 | 0.252 |
| chr6 | 133276306 | 133276556 | 0.348 |
| chr6 | 134312325 | 134312575 | 0.348 |
| chr6 | 135908218 | 135908468 | 0.348 |
| chr6 | 136827150 | 136827400 | 0.276 |
| chr6 | 137166633 | 137166883 | 0.356 |
| chr6 | 137219252 | 137219502 | 0.396 |
| chr6 | 137219252 | 137219502 | 0.396 |
| chr6 | 137899299 | 137899549 | 0.304 |
| chr6 | 138928325 | 138928575 | 0.348 |
| chr6 | 139961518 | 139961768 | 0.288 |
| chr6 | 141196497 | 141196747 | 0.312 |
| chr6 | 142305254 | 142305504 | 0.348 |
| chr6 | 143107636 | 143107886 | 0.336 |
| chr6 | 144133389 | 144133639 | 0.348 |
| chr6 | 145572150 | 145572400 | 0.336 |
| chr6 | 146529266 | 146529516 | 0.348 |
| chr6 | 147476386 | 147476636 | 0.348 |
| chr6 | 148521155 | 148521405 | 0.316 |
| chr6 | 149329190 | 149329440 | 0.348 |
| chr6 | 150131788 | 150132038 | 0.332 |
| chr6 | 151419594 | 151419844 | 0.348 |
| chr6 | 153113150 | 153113400 | 0.304 |
| chr6 | 153913332 | 153913582 | 0.348 |
| chr6 | 154720810 | 154721060 | 0.34 |
| chr6 | 155536244 | 155536494 | 0.348 |
| chr6 | 156340604 | 156340854 | 0.332 |
| chr6 | 157146448 | 157146698 | 0.316 |
| chr6 | 157956774 | 157957024 | 0.348 |
| chr6 | 159061159 | 159061409 | 0.348 |
| chr6 | 159870327 | 159870577 | 0.264 |
| chr6 | 160671116 | 160671366 | 0.328 |
| chr6 | 161473227 | 161473477 | 0.348 |
| chr6 | 162969538 | 162969788 | 0.336 |
| chr6 | 163775420 | 163775670 | 0.348 |
| chr6 | 164598389 | 164598639 | 0.272 |
| chr6 | 165405401 | 165405651 | 0.348 |
| chr6 | 166950248 | 166950498 | 0.348 |
| chr6 | 167769909 | 167770159 | 0.348 |

| Ch. | Start | Stop | GC content |
|---|---|---|---|
| chr6 | 168608835 | 168609085 | 0.348 |
| chr6 | 170242603 | 170242853 | 0.348 |
| chr7 | 55429 | 55679 | 0.348 |
| chr7 | 877046 | 877296 | 0.348 |
| chr7 | 2149206 | 2149456 | 0.348 |
| chr7 | 3107789 | 3108039 | 0.348 |
| chr7 | 3909387 | 3909637 | 0.348 |
| chr7 | 4730421 | 4730671 | 0.336 |
| chr7 | 5703807 | 5704057 | 0.332 |
| chr7 | 6513490 | 6513740 | 0.276 |
| chr7 | 7313867 | 7314117 | 0.348 |
| chr7 | 8124150 | 8124400 | 0.336 |
| chr7 | 8927574 | 8927824 | 0.348 |
| chr7 | 9852228 | 9852478 | 0.348 |
| chr7 | 10714290 | 10714540 | 0.344 |
| chr7 | 11521626 | 11521876 | 0.348 |
| chr7 | 12357745 | 12357995 | 0.332 |
| chr7 | 13758296 | 13758546 | 0.3 |
| chr7 | 14961489 | 14961739 | 0.336 |
| chr7 | 15766151 | 15766401 | 0.348 |
| chr7 | 16571000 | 16571250 | 0.348 |
| chr7 | 18364511 | 18364761 | 0.348 |
| chr7 | 19288150 | 19288400 | 0.296 |
| chr7 | 20093589 | 20093839 | 0.304 |
| chr7 | 20903165 | 20903415 | 0.348 |
| chr7 | 21813150 | 21813400 | 0.308 |
| chr7 | 22626926 | 22627176 | 0.34 |
| chr7 | 24588150 | 24588400 | 0.32 |
| chr7 | 25393154 | 25393404 | 0.348 |
| chr7 | 26207116 | 26207366 | 0.348 |
| chr7 | 27014593 | 27014843 | 0.296 |
| chr7 | 28180480 | 28180730 | 0.336 |
| chr7 | 29609491 | 29609741 | 0.348 |
| chr7 | 30505246 | 30505496 | 0.348 |
| chr7 | 31323318 | 31323568 | 0.288 |
| chr7 | 32129428 | 32129678 | 0.348 |
| chr7 | 32929838 | 32930088 | 0.348 |
| chr7 | 34109582 | 34109832 | 0.348 |
| chr7 | 35308294 | 35308544 | 0.348 |
| chr7 | 36109511 | 36109761 | 0.348 |
| chr7 | 37108150 | 37108400 | 0.348 |
| chr7 | 37908361 | 37908611 | 0.348 |
| chr7 | 38864325 | 38864575 | 0.308 |
| chr7 | 39665162 | 39665412 | 0.348 |
| chr7 | 40477320 | 40477570 | 0.348 |
| chr7 | 41459497 | 41459747 | 0.348 |
| chr7 | 43302476 | 43302726 | 0.348 |
| chr7 | 44330188 | 44330438 | 0.348 |
| chr7 | 45260099 | 45260349 | 0.348 |
| chr7 | 46071390 | 46071640 | 0.288 |
| chr7 | 47421295 | 47421545 | 0.348 |
| chr7 | 48228113 | 48228363 | 0.348 |
| chr7 | 49030589 | 49030839 | 0.348 |
| chr7 | 50227150 | 50227400 | 0.336 |
| chr7 | 52176118 | 52176368 | 0.296 |
| chr7 | 53041150 | 53041400 | 0.32 |
| chr7 | 54163159 | 54163409 | 0.348 |
| chr7 | 54971120 | 54971370 | 0.324 |
| chr7 | 55800266 | 55800516 | 0.348 |
| chr7 | 62624136 | 62624386 | 0.34 |
| chr7 | 63426305 | 63426555 | 0.308 |
| chr7 | 64230137 | 64230387 | 0.292 |
| chr7 | 65372594 | 65372844 | 0.344 |
| chr7 | 67064459 | 67064709 | 0.348 |
| chr7 | 67898887 | 67899137 | 0.348 |
| chr7 | 69412264 | 69412514 | 0.348 |
| chr7 | 70213263 | 70213513 | 0.328 |
| chr7 | 71054944 | 71055194 | 0.28 |
| chr7 | 71874807 | 71875057 | 0.348 |
| chr7 | 72864826 | 72865076 | 0.348 |
| chr7 | 75956713 | 75956963 | 0.348 |
| chr7 | 76814033 | 76814283 | 0.32 |
| chr7 | 77713150 | 77713400 | 0.348 |
| chr7 | 78530571 | 78530821 | 0.276 |
| chr7 | 79336977 | 79337227 | 0.348 |
| chr7 | 80660150 | 80660400 | 0.332 |
| chr7 | 81471944 | 81472194 | 0.34 |
| chr7 | 82293809 | 82294059 | 0.348 |
| chr7 | 83095588 | 83095838 | 0.348 |
| chr7 | 83895809 | 83896059 | 0.344 |
| chr7 | 84696541 | 84696791 | 0.336 |
| chr7 | 85502525 | 85502775 | 0.344 |
| chr7 | 86361434 | 86361684 | 0.324 |
| chr7 | 87162681 | 87162931 | 0.348 |
| chr7 | 87968369 | 87968619 | 0.316 |
| chr7 | 89087150 | 89087400 | 0.328 |
| chr7 | 90162150 | 90162400 | 0.312 |
| chr7 | 91015164 | 91015414 | 0.348 |
| chr7 | 91942336 | 91942586 | 0.348 |
| chr7 | 92132375 | 92132625 | 0.336 |
| chr7 | 92745515 | 92745765 | 0.348 |
| chr7 | 94032150 | 94032400 | 0.312 |
| chr7 | 94879455 | 94879705 | 0.348 |
| chr7 | 95728150 | 95728400 | 0.312 |
| chr7 | 96535542 | 96535792 | 0.348 |
| chr7 | 97356883 | 97357133 | 0.328 |
| chr7 | 98237766 | 98238016 | 0.324 |
| chr7 | 99150089 | 99150339 | 0.348 |
| chr7 | 100141414 | 100141664 | 0.348 |
| chr7 | 101399346 | 101399596 | 0.348 |
| chr7 | 102451481 | 102451731 | 0.324 |
| chr7 | 103335561 | 103335811 | 0.296 |
| chr7 | 104416150 | 104416400 | 0.32 |
| chr7 | 105400093 | 105400343 | 0.348 |
| chr7 | 106232404 | 106232654 | 0.252 |
| chr7 | 107034859 | 107035109 | 0.348 |
| chr7 | 107323858 | 107324108 | 0.336 |
| chr7 | 107330445 | 107330695 | 0.468 |
| chr7 | 107330540 | 107330790 | 0.492 |
| chr7 | 107420025 | 107420275 | 0.356 |
| chr7 | 107542660 | 107542910 | 0.356 |
| chr7 | 107557622 | 107557872 | 0.408 |
| chr7 | 107557669 | 107557919 | 0.432 |
| chr7 | 107557724 | 107557974 | 0.46 |
| chr7 | 107847587 | 107847837 | 0.348 |
| chr7 | 108648804 | 108649054 | 0.348 |
| chr7 | 109458628 | 109458878 | 0.328 |
| chr7 | 110524210 | 110524460 | 0.312 |
| chr7 | 111335538 | 111335788 | 0.332 |
| chr7 | 112398549 | 112398799 | 0.348 |
| chr7 | 113200896 | 113201146 | 0.324 |
| chr7 | 114001693 | 114001943 | 0.328 |
| chr7 | 114966262 | 114966512 | 0.348 |
| chr7 | 115771663 | 115771913 | 0.316 |
| chr7 | 116585570 | 116585820 | 0.296 |
| chr7 | 117149047 | 117149297 | 0.324 |
| chr7 | 117170889 | 117171139 | 0.412 |
| chr7 | 117171034 | 117171284 | 0.38 |
| chr7 | 117199521 | 117199770 | 0.369478 |
| chr7 | 117199607 | 117199796 | 0.354497 |
| chr7 | 117227720 | 117227969 | 0.349398 |
| chr7 | 117227791 | 117227987 | 0.357143 |
| chr7 | 117232148 | 117232398 | 0.372 |
| chr7 | 117246704 | 117246954 | 0.292 |
| chr7 | 117267461 | 117267711 | 0.344 |
| chr7 | 117267636 | 117267886 | 0.428 |
| chr7 | 117279890 | 117280140 | 0.336 |
| chr7 | 117282492 | 117282741 | 0.393574 |
| chr7 | 117622151 | 117622401 | 0.348 |
| chr7 | 118923150 | 118923400 | 0.34 |
| chr7 | 119723802 | 119724052 | 0.348 |
| chr7 | 120536847 | 120537097 | 0.296 |
| chr7 | 121388365 | 121388615 | 0.34 |
| chr7 | 122225191 | 122225441 | 0.288 |
| chr7 | 123119241 | 123119491 | 0.332 |
| chr7 | 124015307 | 124015557 | 0.348 |
| chr7 | 124862547 | 124862797 | 0.308 |
| chr7 | 125665148 | 125665398 | 0.348 |
| chr7 | 126472650 | 126472900 | 0.316 |
| chr7 | 127285399 | 127285649 | 0.348 |
| chr7 | 128300359 | 128300609 | 0.34 |
| chr7 | 129107063 | 129107313 | 0.348 |
| chr7 | 129978355 | 129978605 | 0.348 |
| chr7 | 130780700 | 130780950 | 0.308 |

| Ch. | Start | Stop | GC content |
|---|---|---|---|
| chr7 | 131649229 | 131649479 | 0.324 |
| chr7 | 132518150 | 132518400 | 0.34 |
| chr7 | 133418423 | 133418673 | 0.336 |
| chr7 | 134286655 | 134286905 | 0.332 |
| chr7 | 135090145 | 135090395 | 0.348 |
| chr7 | 135899265 | 135899515 | 0.332 |
| chr7 | 136699464 | 136699714 | 0.328 |
| chr7 | 137847153 | 137847403 | 0.348 |
| chr7 | 139280295 | 139280545 | 0.348 |
| chr7 | 140159009 | 140159259 | 0.348 |
| chr7 | 140970360 | 140970610 | 0.348 |
| chr7 | 141800731 | 141800981 | 0.348 |
| chr7 | 142632884 | 142633134 | 0.348 |
| chr7 | 143580134 | 143580384 | 0.348 |
| chr7 | 144381506 | 144381756 | 0.348 |
| chr7 | 145240150 | 145240400 | 0.324 |
| chr7 | 146040527 | 146040777 | 0.272 |
| chr7 | 146864156 | 146864406 | 0.348 |
| chr7 | 147665180 | 147665430 | 0.348 |
| chr7 | 148467130 | 148467380 | 0.348 |
| chr7 | 150033270 | 150033520 | 0.348 |
| chr7 | 150852375 | 150852625 | 0.348 |
| chr7 | 151664082 | 151664332 | 0.296 |
| chr7 | 152570612 | 152570862 | 0.348 |
| chr7 | 153378130 | 153378380 | 0.332 |
| chr7 | 154190449 | 154190699 | 0.348 |
| chr7 | 155072739 | 155072989 | 0.348 |
| chr7 | 155881209 | 155881459 | 0.328 |
| chr7 | 157364150 | 157364400 | 0.324 |
| chr7 | 158567174 | 158567424 | 0.348 |
| chr8 | 192250 | 192500 | 0.348 |
| chr8 | 1003693 | 1003943 | 0.348 |
| chr8 | 1968353 | 1968603 | 0.348 |
| chr8 | 2785184 | 2785434 | 0.348 |
| chr8 | 3594564 | 3594814 | 0.296 |
| chr8 | 4462150 | 4462400 | 0.32 |
| chr8 | 5272274 | 5272524 | 0.348 |
| chr8 | 6079383 | 6079633 | 0.348 |
| chr8 | 6896439 | 6896689 | 0.348 |
| chr8 | 8120898 | 8121148 | 0.284 |
| chr8 | 9159532 | 9159782 | 0.344 |
| chr8 | 9964948 | 9965198 | 0.348 |
| chr8 | 10849178 | 10849428 | 0.348 |
| chr8 | 11664231 | 11664481 | 0.348 |
| chr8 | 12579602 | 12579852 | 0.308 |
| chr8 | 13417150 | 13417400 | 0.328 |
| chr8 | 14462150 | 14462400 | 0.336 |
| chr8 | 15294599 | 15294849 | 0.316 |
| chr8 | 16098431 | 16098681 | 0.348 |
| chr8 | 16901802 | 16902052 | 0.348 |
| chr8 | 17701806 | 17702056 | 0.348 |
| chr8 | 18503290 | 18503540 | 0.328 |
| chr8 | 19316094 | 19316344 | 0.348 |
| chr8 | 20358596 | 20358846 | 0.336 |
| chr8 | 21164416 | 21164666 | 0.316 |
| chr8 | 22141422 | 22141672 | 0.348 |
| chr8 | 22961278 | 22961528 | 0.348 |
| chr8 | 23765128 | 23765378 | 0.348 |
| chr8 | 24589150 | 24589400 | 0.344 |
| chr8 | 25395976 | 25396226 | 0.348 |
| chr8 | 26196689 | 26196939 | 0.344 |
| chr8 | 27061150 | 27061400 | 0.348 |
| chr8 | 27954533 | 27954783 | 0.324 |
| chr8 | 28755361 | 28755611 | 0.332 |
| chr8 | 29557790 | 29558040 | 0.348 |
| chr8 | 30361271 | 30361521 | 0.348 |
| chr8 | 31611150 | 31611400 | 0.304 |
| chr8 | 32611550 | 32611800 | 0.272 |
| chr8 | 33482560 | 33482810 | 0.348 |
| chr8 | 34286695 | 34286945 | 0.292 |
| chr8 | 35095509 | 35095759 | 0.348 |
| chr8 | 35898952 | 35899202 | 0.336 |
| chr8 | 36702296 | 36702546 | 0.348 |
| chr8 | 37538504 | 37538754 | 0.348 |
| chr8 | 39232335 | 39232585 | 0.34 |
| chr8 | 40057492 | 40057742 | 0.348 |
| chr8 | 40861155 | 40861405 | 0.348 |
| chr8 | 41687779 | 41688029 | 0.348 |
| chr8 | 42488236 | 42488486 | 0.348 |
| chr8 | 43296893 | 43297143 | 0.344 |
| chr8 | 47456494 | 47456744 | 0.276 |
| chr8 | 49739152 | 49739402 | 0.348 |
| chr8 | 50539626 | 50539876 | 0.348 |
| chr8 | 51348600 | 51348850 | 0.348 |
| chr8 | 52687557 | 52687807 | 0.284 |
| chr8 | 53732150 | 53732400 | 0.328 |
| chr8 | 54556748 | 54556998 | 0.348 |
| chr8 | 55362843 | 55363093 | 0.348 |
| chr8 | 56218408 | 56218658 | 0.3 |
| chr8 | 57024628 | 57024878 | 0.348 |
| chr8 | 57939209 | 57939459 | 0.348 |
| chr8 | 59069598 | 59069848 | 0.348 |
| chr8 | 62008281 | 62008531 | 0.348 |
| chr8 | 63859170 | 63859420 | 0.348 |
| chr8 | 64808260 | 64808510 | 0.308 |
| chr8 | 67203150 | 67203400 | 0.328 |
| chr8 | 68461150 | 68461400 | 0.348 |
| chr8 | 69596150 | 69596400 | 0.34 |
| chr8 | 70457150 | 70457400 | 0.308 |
| chr8 | 71266150 | 71266400 | 0.348 |
| chr8 | 72260292 | 72260542 | 0.34 |
| chr8 | 73118183 | 73118433 | 0.316 |
| chr8 | 74441212 | 74441462 | 0.348 |
| chr8 | 75565150 | 75565400 | 0.336 |
| chr8 | 76518550 | 76518800 | 0.292 |
| chr8 | 77509332 | 77509582 | 0.348 |
| chr8 | 77895920 | 77896170 | 0.36 |
| chr8 | 78423319 | 78423569 | 0.324 |
| chr8 | 79227653 | 79227903 | 0.328 |
| chr8 | 80038233 | 80038483 | 0.296 |
| chr8 | 80846150 | 80846400 | 0.336 |
| chr8 | 81657150 | 81657400 | 0.292 |
| chr8 | 82795491 | 82795741 | 0.348 |
| chr8 | 83607557 | 83607807 | 0.312 |
| chr8 | 84412845 | 84413095 | 0.288 |
| chr8 | 85516336 | 85516586 | 0.336 |
| chr8 | 86873337 | 86873587 | 0.32 |
| chr8 | 87681621 | 87681871 | 0.332 |
| chr8 | 88481908 | 88482158 | 0.348 |
| chr8 | 90093162 | 90093412 | 0.348 |
| chr8 | 90983285 | 90983535 | 0.288 |
| chr8 | 91158369 | 91158619 | 0.348 |
| chr8 | 92065468 | 92065718 | 0.348 |
| chr8 | 92901150 | 92901400 | 0.328 |
| chr8 | 94611550 | 94611800 | 0.296 |
| chr8 | 95411550 | 95411800 | 0.348 |
| chr8 | 96629348 | 96629598 | 0.272 |
| chr8 | 97873150 | 97873400 | 0.292 |
| chr8 | 99476228 | 99476478 | 0.344 |
| chr8 | 100281617 | 100281867 | 0.348 |
| chr8 | 100454657 | 100454907 | 0.412 |
| chr8 | 100523378 | 100523628 | 0.348 |
| chr8 | 100733076 | 100733326 | 0.392 |
| chr8 | 100830576 | 100830826 | 0.356 |
| chr8 | 100835931 | 100836181 | 0.3 |
| chr8 | 101099280 | 101099530 | 0.344 |
| chr8 | 102559150 | 102559400 | 0.332 |
| chr8 | 104722173 | 104722423 | 0.304 |
| chr8 | 105808550 | 105808800 | 0.348 |
| chr8 | 106610467 | 106610717 | 0.348 |
| chr8 | 107422394 | 107422644 | 0.308 |
| chr8 | 108285311 | 108285561 | 0.348 |
| chr8 | 109090412 | 109090662 | 0.348 |
| chr8 | 109972262 | 109972512 | 0.344 |
| chr8 | 110795150 | 110795400 | 0.316 |
| chr8 | 111908174 | 111908424 | 0.264 |
| chr8 | 112711020 | 112711270 | 0.252 |
| chr8 | 113514731 | 113514981 | 0.348 |
| chr8 | 114740243 | 114740493 | 0.348 |
| chr8 | 115568249 | 115568499 | 0.324 |
| chr8 | 116514193 | 116514443 | 0.348 |
| chr8 | 117360167 | 117360417 | 0.348 |
| chr8 | 118611150 | 118611400 | 0.348 |
| chr8 | 119426175 | 119426425 | 0.348 |

| Ch. | Start | Stop | GC content |
|---|---|---|---|
| chr8 | 120338150 | 120338400 | 0.328 |
| chr8 | 121474337 | 121474587 | 0.348 |
| chr8 | 122274620 | 122274870 | 0.336 |
| chr8 | 123089214 | 123089464 | 0.348 |
| chr8 | 124026007 | 124026257 | 0.348 |
| chr8 | 124844530 | 124844780 | 0.348 |
| chr8 | 125653991 | 125654241 | 0.348 |
| chr8 | 126510926 | 126511176 | 0.348 |
| chr8 | 127312793 | 127313043 | 0.34 |
| chr8 | 128133591 | 128133841 | 0.34 |
| chr8 | 129022031 | 129022281 | 0.348 |
| chr8 | 129839921 | 129840171 | 0.328 |
| chr8 | 130654835 | 130655085 | 0.348 |
| chr8 | 131476472 | 131476722 | 0.292 |
| chr8 | 133133387 | 133133637 | 0.348 |
| chr8 | 134746852 | 134747102 | 0.348 |
| chr8 | 135547920 | 135548170 | 0.312 |
| chr8 | 136372136 | 136372386 | 0.348 |
| chr8 | 137311150 | 137311400 | 0.328 |
| chr8 | 138113279 | 138113529 | 0.348 |
| chr8 | 138930098 | 138930348 | 0.348 |
| chr8 | 139733141 | 139733391 | 0.348 |
| chr8 | 140552082 | 140552332 | 0.304 |
| chr8 | 143927698 | 143927948 | 0.348 |
| chr8 | 145640016 | 145640266 | 0.648 |
| chr8 | 145640554 | 145640804 | 0.688 |
| chr8 | 145946790 | 145947040 | 0.348 |
| chr9 | 441472 | 441722 | 0.348 |
| chr9 | 1249421 | 1249671 | 0.344 |
| chr9 | 2865702 | 2865952 | 0.308 |
| chr9 | 3684579 | 3684829 | 0.348 |
| chr9 | 4499494 | 4499744 | 0.3 |
| chr9 | 5611467 | 5611717 | 0.348 |
| chr9 | 6417235 | 6417485 | 0.348 |
| chr9 | 7244553 | 7244803 | 0.348 |
| chr9 | 8056430 | 8056680 | 0.344 |
| chr9 | 8856701 | 8856951 | 0.348 |
| chr9 | 9660879 | 9661129 | 0.348 |
| chr9 | 10463146 | 10463396 | 0.296 |
| chr9 | 11263700 | 11263950 | 0.332 |
| chr9 | 12065601 | 12065851 | 0.344 |
| chr9 | 12872277 | 12872527 | 0.348 |
| chr9 | 13678510 | 13678760 | 0.348 |
| chr9 | 14494878 | 14495128 | 0.348 |
| chr9 | 15310150 | 15310400 | 0.332 |
| chr9 | 16415150 | 16415400 | 0.332 |
| chr9 | 17466150 | 17466400 | 0.3 |
| chr9 | 21059391 | 21059641 | 0.348 |
| chr9 | 22073150 | 22073400 | 0.34 |
| chr9 | 22959266 | 22959516 | 0.348 |
| chr9 | 24120550 | 24120800 | 0.292 |
| chr9 | 25117165 | 25117415 | 0.348 |
| chr9 | 26013411 | 26013661 | 0.348 |
| chr9 | 26820970 | 26821220 | 0.348 |
| chr9 | 27623659 | 27623909 | 0.308 |
| chr9 | 28464150 | 28464400 | 0.272 |
| chr9 | 29277441 | 29277691 | 0.348 |
| chr9 | 30170150 | 30170400 | 0.32 |
| chr9 | 31049150 | 31049400 | 0.316 |
| chr9 | 33112448 | 33112698 | 0.348 |
| chr9 | 33917453 | 33917703 | 0.348 |
| chr9 | 34744366 | 34744616 | 0.348 |
| chr9 | 36071273 | 36071523 | 0.34 |
| chr9 | 38018399 | 38018649 | 0.348 |
| chr9 | 71032343 | 71032593 | 0.348 |
| chr9 | 71833417 | 71833667 | 0.348 |
| chr9 | 72920150 | 72920400 | 0.316 |
| chr9 | 73915530 | 73915780 | 0.32 |
| chr9 | 75167488 | 75167738 | 0.348 |
| chr9 | 76531468 | 76531718 | 0.348 |
| chr9 | 77413560 | 77413810 | 0.348 |
| chr9 | 78522150 | 78522400 | 0.332 |
| chr9 | 79507397 | 79507647 | 0.3 |
| chr9 | 80739535 | 80739785 | 0.348 |
| chr9 | 81567279 | 81567529 | 0.348 |
| chr9 | 82372319 | 82372569 | 0.348 |
| chr9 | 83221150 | 83221400 | 0.348 |
| chr9 | 84202150 | 84202400 | 0.348 |
| chr9 | 85081150 | 85081400 | 0.332 |
| chr9 | 85987217 | 85987467 | 0.348 |
| chr9 | 86799808 | 86800058 | 0.32 |
| chr9 | 87600430 | 87600680 | 0.34 |
| chr9 | 88575150 | 88575400 | 0.328 |
| chr9 | 89393921 | 89394171 | 0.348 |
| chr9 | 90196155 | 90196405 | 0.348 |
| chr9 | 91389150 | 91389400 | 0.316 |
| chr9 | 92224150 | 92224400 | 0.34 |
| chr9 | 93027865 | 93028115 | 0.348 |
| chr9 | 93881161 | 93881411 | 0.348 |
| chr9 | 94685863 | 94686113 | 0.332 |
| chr9 | 95551224 | 95551474 | 0.324 |
| chr9 | 96382913 | 96383163 | 0.348 |
| chr9 | 97206756 | 97207006 | 0.348 |
| chr9 | 98010068 | 98010318 | 0.3 |
| chr9 | 98910804 | 98911054 | 0.348 |
| chr9 | 100612919 | 100613169 | 0.348 |
| chr9 | 102040150 | 102040400 | 0.348 |
| chr9 | 103037412 | 103037662 | 0.348 |
| chr9 | 104113326 | 104113576 | 0.348 |
| chr9 | 104184056 | 104184306 | 0.512 |
| chr9 | 104187132 | 104187382 | 0.516 |
| chr9 | 104187690 | 104187940 | 0.52 |
| chr9 | 104189655 | 104189905 | 0.512 |
| chr9 | 104192058 | 104192308 | 0.544 |
| chr9 | 104193030 | 104193280 | 0.524 |
| chr9 | 104920172 | 104920422 | 0.336 |
| chr9 | 105721671 | 105721921 | 0.304 |
| chr9 | 106523521 | 106523771 | 0.264 |
| chr9 | 107485162 | 107485412 | 0.348 |
| chr9 | 108536234 | 108536484 | 0.348 |
| chr9 | 109563573 | 109563823 | 0.348 |
| chr9 | 110626420 | 110626670 | 0.348 |
| chr9 | 111662458 | 111662708 | 0.444 |
| chr9 | 111732400 | 111732650 | 0.348 |
| chr9 | 113340650 | 113340900 | 0.332 |
| chr9 | 114144997 | 114145247 | 0.308 |
| chr9 | 114957028 | 114957278 | 0.348 |
| chr9 | 115762575 | 115762825 | 0.308 |
| chr9 | 116577087 | 116577337 | 0.348 |
| chr9 | 117441289 | 117441539 | 0.328 |
| chr9 | 118963361 | 118963611 | 0.348 |
| chr9 | 119460264 | 119460514 | 0.6 |
| chr9 | 119888150 | 119888400 | 0.288 |
| chr9 | 121125150 | 121125400 | 0.336 |
| chr9 | 122426151 | 122426401 | 0.348 |
| chr9 | 123520150 | 123520400 | 0.332 |
| chr9 | 124683228 | 124683478 | 0.348 |
| chr9 | 125485603 | 125485853 | 0.34 |
| chr9 | 127505527 | 127505777 | 0.348 |
| chr9 | 128307968 | 128308218 | 0.348 |
| chr9 | 129109844 | 129110094 | 0.348 |
| chr9 | 129916775 | 129917025 | 0.348 |
| chr9 | 131244670 | 131244920 | 0.348 |
| chr9 | 132573290 | 132573540 | 0.348 |
| chr9 | 133333811 | 133334061 | 0.64 |
| chr9 | 133413285 | 133413535 | 0.348 |
| chr9 | 134486613 | 134486863 | 0.348 |
| chr9 | 135288372 | 135288622 | 0.348 |
| chr9 | 136280107 | 136280357 | 0.348 |
| chr9 | 137460915 | 137461165 | 0.32 |
| chr9 | 138342214 | 138342464 | 0.348 |
| chr9 | 139306976 | 139307226 | 0.268 |
| chr9 | 140524526 | 140524776 | 0.348 |
| chr10 | 871150 | 871400 | 0.348 |
| chr10 | 2124524 | 2124774 | 0.252 |
| chr10 | 2929327 | 2929577 | 0.348 |
| chr10 | 4220150 | 4220400 | 0.336 |
| chr10 | 5176559 | 5176809 | 0.336 |
| chr10 | 6343194 | 6343444 | 0.344 |
| chr10 | 7390225 | 7390475 | 0.348 |
| chr10 | 8257298 | 8257548 | 0.348 |
| chr10 | 9058150 | 9058400 | 0.3 |
| chr10 | 9876196 | 9876446 | 0.348 |
| chr10 | 10677282 | 10677532 | 0.348 |

| Ch. | Start | Stop | GC content |
|---|---|---|---|
| chr10 | 11492282 | 11492532 | 0.348 |
| chr10 | 12401604 | 12401854 | 0.348 |
| chr10 | 13224650 | 13224900 | 0.348 |
| chr10 | 14043964 | 14044214 | 0.348 |
| chr10 | 14853423 | 14853673 | 0.348 |
| chr10 | 15658199 | 15658449 | 0.316 |
| chr10 | 16622416 | 16622666 | 0.344 |
| chr10 | 17516150 | 17516400 | 0.276 |
| chr10 | 18901507 | 18901757 | 0.336 |
| chr10 | 19710316 | 19710566 | 0.344 |
| chr10 | 20513351 | 20513601 | 0.348 |
| chr10 | 21313889 | 21314139 | 0.348 |
| chr10 | 22142078 | 22142328 | 0.348 |
| chr10 | 22944374 | 22944624 | 0.348 |
| chr10 | 25115150 | 25115400 | 0.34 |
| chr10 | 25924260 | 25924510 | 0.348 |
| chr10 | 26730024 | 26730274 | 0.3 |
| chr10 | 27655856 | 27656106 | 0.348 |
| chr10 | 28491351 | 28491601 | 0.348 |
| chr10 | 29660163 | 29660413 | 0.348 |
| chr10 | 30460737 | 30460987 | 0.332 |
| chr10 | 31312134 | 31312384 | 0.312 |
| chr10 | 32164168 | 32164418 | 0.348 |
| chr10 | 33112517 | 33112767 | 0.308 |
| chr10 | 34810150 | 34810400 | 0.296 |
| chr10 | 35813150 | 35813400 | 0.34 |
| chr10 | 37514244 | 37514494 | 0.288 |
| chr10 | 38417233 | 38417483 | 0.348 |
| chr10 | 42889111 | 42889361 | 0.34 |
| chr10 | 43849286 | 43849536 | 0.348 |
| chr10 | 44650414 | 44650664 | 0.348 |
| chr10 | 45497370 | 45497620 | 0.32 |
| chr10 | 49404717 | 49404967 | 0.348 |
| chr10 | 50210193 | 50210443 | 0.348 |
| chr10 | 51026129 | 51026379 | 0.348 |
| chr10 | 52010556 | 52010806 | 0.348 |
| chr10 | 53059445 | 53059695 | 0.348 |
| chr10 | 54008212 | 54008462 | 0.304 |
| chr10 | 55079406 | 55079656 | 0.328 |
| chr10 | 55884413 | 55884663 | 0.348 |
| chr10 | 57175168 | 57175418 | 0.304 |
| chr10 | 58259360 | 58259610 | 0.32 |
| chr10 | 59429265 | 59429515 | 0.348 |
| chr10 | 60330265 | 60330515 | 0.348 |
| chr10 | 61209233 | 61209483 | 0.348 |
| chr10 | 62192170 | 62192420 | 0.348 |
| chr10 | 63359159 | 63359409 | 0.348 |
| chr10 | 64382591 | 64382841 | 0.332 |
| chr10 | 65188150 | 65188400 | 0.336 |
| chr10 | 65996966 | 65997216 | 0.348 |
| chr10 | 66856797 | 66857047 | 0.34 |
| chr10 | 67661286 | 67661536 | 0.348 |
| chr10 | 68465570 | 68465820 | 0.348 |
| chr10 | 69265603 | 69265853 | 0.284 |
| chr10 | 70087603 | 70087853 | 0.284 |
| chr10 | 70891648 | 70891898 | 0.312 |
| chr10 | 71718353 | 71718603 | 0.348 |
| chr10 | 72578751 | 72579001 | 0.344 |
| chr10 | 73736422 | 73736672 | 0.348 |
| chr10 | 74541034 | 74541284 | 0.348 |
| chr10 | 75344307 | 75344557 | 0.296 |
| chr10 | 76146051 | 76146301 | 0.288 |
| chr10 | 76988866 | 76989116 | 0.348 |
| chr10 | 78429430 | 78429680 | 0.348 |
| chr10 | 79322018 | 79322268 | 0.348 |
| chr10 | 80218152 | 80218402 | 0.348 |
| chr10 | 81110884 | 81111134 | 0.348 |
| chr10 | 82759514 | 82759764 | 0.348 |
| chr10 | 83909150 | 83909400 | 0.324 |
| chr10 | 84718905 | 84719155 | 0.348 |
| chr10 | 85528253 | 85528503 | 0.348 |
| chr10 | 86363170 | 86363420 | 0.348 |
| chr10 | 87163913 | 87164163 | 0.348 |
| chr10 | 87972367 | 87972617 | 0.348 |
| chr10 | 89475150 | 89475400 | 0.348 |
| chr10 | 90512150 | 90512400 | 0.328 |
| chr10 | 91327550 | 91327800 | 0.336 |
| chr10 | 92191303 | 92191553 | 0.348 |
| chr10 | 92993341 | 92993591 | 0.312 |
| chr10 | 93806630 | 93806880 | 0.304 |
| chr10 | 95371273 | 95371523 | 0.32 |
| chr10 | 96172179 | 96172429 | 0.324 |
| chr10 | 96973624 | 96973874 | 0.3 |
| chr10 | 97793018 | 97793268 | 0.34 |
| chr10 | 98599885 | 98600135 | 0.308 |
| chr10 | 99371221 | 99371471 | 0.608 |
| chr10 | 99444709 | 99444959 | 0.348 |
| chr10 | 100283039 | 100283289 | 0.336 |
| chr10 | 101099626 | 101099876 | 0.264 |
| chr10 | 101913511 | 101913761 | 0.348 |
| chr10 | 102718384 | 102718634 | 0.34 |
| chr10 | 103725234 | 103725484 | 0.348 |
| chr10 | 104591173 | 104591423 | 0.576 |
| chr10 | 104594996 | 104595246 | 0.568 |
| chr10 | 104595007 | 104595257 | 0.568 |
| chr10 | 104596713 | 104596963 | 0.532 |
| chr10 | 104596835 | 104597085 | 0.536 |
| chr10 | 104596913 | 104597163 | 0.552 |
| chr10 | 104816277 | 104816527 | 0.348 |
| chr10 | 105676155 | 105676405 | 0.348 |
| chr10 | 106811336 | 106811586 | 0.348 |
| chr10 | 107659600 | 107659850 | 0.304 |
| chr10 | 108512082 | 108512332 | 0.348 |
| chr10 | 109373152 | 109373402 | 0.348 |
| chr10 | 110180327 | 110180577 | 0.348 |
| chr10 | 110981331 | 110981581 | 0.348 |
| chr10 | 112590150 | 112590400 | 0.324 |
| chr10 | 113580385 | 113580635 | 0.348 |
| chr10 | 115419322 | 115419572 | 0.348 |
| chr10 | 116388354 | 116388604 | 0.276 |
| chr10 | 117195710 | 117195960 | 0.264 |
| chr10 | 118001417 | 118001667 | 0.348 |
| chr10 | 118804036 | 118804286 | 0.312 |
| chr10 | 119604589 | 119604839 | 0.348 |
| chr10 | 121415468 | 121415718 | 0.348 |
| chr10 | 122562221 | 122562471 | 0.344 |
| chr10 | 123467150 | 123467400 | 0.324 |
| chr10 | 124501500 | 124501750 | 0.348 |
| chr10 | 125600180 | 125600430 | 0.348 |
| chr10 | 126768584 | 126768834 | 0.348 |
| chr10 | 127706472 | 127706722 | 0.348 |
| chr10 | 128534329 | 128534579 | 0.348 |
| chr10 | 129334357 | 129334607 | 0.348 |
| chr10 | 130135711 | 130135961 | 0.348 |
| chr10 | 131363498 | 131363748 | 0.348 |
| chr10 | 132216150 | 132216400 | 0.316 |
| chr10 | 133163299 | 133163549 | 0.348 |
| chr10 | 133998082 | 133998332 | 0.348 |
| chr11 | 244145 | 244395 | 0.348 |
| chr11 | 1320632 | 1320882 | 0.348 |
| chr11 | 2819685 | 2819935 | 0.348 |
| chr11 | 3630780 | 3631030 | 0.312 |
| chr11 | 4437568 | 4437818 | 0.312 |
| chr11 | 5246865 | 5247108 | 0.465021 |
| chr11 | 5247849 | 5248045 | 0.540816 |
| chr11 | 5247863 | 5248085 | 0.531532 |
| chr11 | 5247979 | 5248198 | 0.511416 |
| chr11 | 5248145 | 5248333 | 0.510638 |
| chr11 | 5261108 | 5261358 | 0.348 |
| chr11 | 6415310 | 6415560 | 0.576 |
| chr11 | 6415651 | 6415901 | 0.604 |
| chr11 | 6444321 | 6444571 | 0.348 |
| chr11 | 7612590 | 7612840 | 0.348 |
| chr11 | 8563550 | 8563800 | 0.292 |
| chr11 | 9416225 | 9416475 | 0.348 |
| chr11 | 10216982 | 10217232 | 0.324 |
| chr11 | 11061166 | 11061416 | 0.344 |
| chr11 | 12380273 | 12380523 | 0.348 |
| chr11 | 13235472 | 13235722 | 0.348 |
| chr11 | 14037966 | 14038216 | 0.268 |
| chr11 | 14864472 | 14864722 | 0.308 |
| chr11 | 15678839 | 15679089 | 0.344 |
| chr11 | 16481891 | 16482141 | 0.32 |
| chr11 | 17299219 | 17299469 | 0.312 |

-continued

| Ch. | Start | Stop | GC content |
|---|---|---|---|
| chr11 | 18110459 | 18110709 | 0.316 |
| chr11 | 18956824 | 18957074 | 0.348 |
| chr11 | 19766011 | 19766261 | 0.348 |
| chr11 | 20882553 | 20882803 | 0.348 |
| chr11 | 21696859 | 21697109 | 0.348 |
| chr11 | 22498768 | 22499018 | 0.348 |
| chr11 | 23301963 | 23302213 | 0.328 |
| chr11 | 24105150 | 24105400 | 0.304 |
| chr11 | 25703491 | 25703741 | 0.348 |
| chr11 | 26517322 | 26517572 | 0.348 |
| chr11 | 27334775 | 27335025 | 0.332 |
| chr11 | 28364408 | 28364658 | 0.32 |
| chr11 | 29209327 | 29209577 | 0.348 |
| chr11 | 30166480 | 30166730 | 0.324 |
| chr11 | 31761546 | 31761796 | 0.348 |
| chr11 | 32622160 | 32622410 | 0.348 |
| chr11 | 33583297 | 33583547 | 0.348 |
| chr11 | 34970150 | 34970400 | 0.284 |
| chr11 | 35911282 | 35911532 | 0.348 |
| chr11 | 37092305 | 37092555 | 0.268 |
| chr11 | 37909582 | 37909832 | 0.348 |
| chr11 | 38712541 | 38712791 | 0.3 |
| chr11 | 39522829 | 39523079 | 0.348 |
| chr11 | 40714150 | 40714400 | 0.324 |
| chr11 | 41532238 | 41532488 | 0.348 |
| chr11 | 42571467 | 42571717 | 0.348 |
| chr11 | 43660553 | 43660803 | 0.336 |
| chr11 | 44580611 | 44580861 | 0.348 |
| chr11 | 45451636 | 45451886 | 0.32 |
| chr11 | 46261790 | 46262040 | 0.348 |
| chr11 | 47072439 | 47072689 | 0.348 |
| chr11 | 47879220 | 47879470 | 0.348 |
| chr11 | 49919350 | 49919600 | 0.344 |
| chr11 | 55082493 | 55082743 | 0.348 |
| chr11 | 56022150 | 56022400 | 0.336 |
| chr11 | 56842806 | 56843056 | 0.34 |
| chr11 | 57725394 | 57725644 | 0.348 |
| chr11 | 58526329 | 58526579 | 0.288 |
| chr11 | 59347634 | 59347884 | 0.34 |
| chr11 | 60158561 | 60158811 | 0.348 |
| chr11 | 61095547 | 61095797 | 0.312 |
| chr11 | 61940132 | 61940382 | 0.348 |
| chr11 | 62810381 | 62810631 | 0.348 |
| chr11 | 63633992 | 63634242 | 0.348 |
| chr11 | 64538602 | 64538852 | 0.348 |
| chr11 | 65827667 | 65827917 | 0.348 |
| chr11 | 66889179 | 66889429 | 0.348 |
| chr11 | 67837487 | 67837737 | 0.348 |
| chr11 | 68763563 | 68763813 | 0.348 |
| chr11 | 69829791 | 69830041 | 0.348 |
| chr11 | 70707409 | 70707659 | 0.348 |
| chr11 | 71743478 | 71743728 | 0.332 |
| chr11 | 72548958 | 72549208 | 0.348 |
| chr11 | 73427854 | 73428104 | 0.324 |
| chr11 | 74260390 | 74260640 | 0.32 |
| chr11 | 75308356 | 75308606 | 0.348 |
| chr11 | 76140267 | 76140517 | 0.348 |
| chr11 | 76942624 | 76942874 | 0.312 |
| chr11 | 77810095 | 77810345 | 0.348 |
| chr11 | 78638250 | 78638500 | 0.324 |
| chr11 | 79439911 | 79440161 | 0.336 |
| chr11 | 80667558 | 80667808 | 0.308 |
| chr11 | 81817150 | 81817400 | 0.3 |
| chr11 | 82620784 | 82621034 | 0.3 |
| chr11 | 83424544 | 83424794 | 0.348 |
| chr11 | 84581358 | 84581608 | 0.336 |
| chr11 | 85477260 | 85477510 | 0.348 |
| chr11 | 86731237 | 86731487 | 0.348 |
| chr11 | 87860240 | 87860490 | 0.348 |
| chr11 | 88900460 | 88900710 | 0.316 |
| chr11 | 89859383 | 89859633 | 0.348 |
| chr11 | 90678351 | 90678601 | 0.316 |
| chr11 | 91493550 | 91493800 | 0.328 |
| chr11 | 92523358 | 92523608 | 0.348 |
| chr11 | 93330704 | 93330954 | 0.348 |
| chr11 | 94966331 | 94966581 | 0.348 |
| chr11 | 95920272 | 95920522 | 0.348 |

-continued

| Ch. | Start | Stop | GC content |
|---|---|---|---|
| chr11 | 96726378 | 96726628 | 0.288 |
| chr11 | 97527417 | 97527667 | 0.324 |
| chr11 | 98344481 | 98344731 | 0.324 |
| chr11 | 99148179 | 99148429 | 0.348 |
| chr11 | 100371430 | 100371680 | 0.336 |
| chr11 | 101194937 | 101195187 | 0.348 |
| chr11 | 102003016 | 102003266 | 0.348 |
| chr11 | 102809148 | 102809398 | 0.332 |
| chr11 | 103620204 | 103620454 | 0.348 |
| chr11 | 104509150 | 104509400 | 0.328 |
| chr11 | 106310150 | 106310400 | 0.336 |
| chr11 | 107416442 | 107416692 | 0.348 |
| chr11 | 108154976 | 108155226 | 0.38 |
| chr11 | 108203436 | 108203686 | 0.34 |
| chr11 | 108419336 | 108419586 | 0.348 |
| chr11 | 109219928 | 109220178 | 0.348 |
| chr11 | 110346453 | 110346703 | 0.348 |
| chr11 | 111248566 | 111248816 | 0.348 |
| chr11 | 112099263 | 112099513 | 0.356 |
| chr11 | 112103776 | 112104026 | 0.392 |
| chr11 | 112103798 | 112104048 | 0.384 |
| chr11 | 112361216 | 112361466 | 0.348 |
| chr11 | 113186794 | 113187044 | 0.348 |
| chr11 | 114018172 | 114018422 | 0.348 |
| chr11 | 115212550 | 115212800 | 0.3 |
| chr11 | 116431362 | 116431612 | 0.348 |
| chr11 | 117338011 | 117338261 | 0.348 |
| chr11 | 118182107 | 118182357 | 0.32 |
| chr11 | 118895800 | 118896050 | 0.544 |
| chr11 | 118895869 | 118896119 | 0.552 |
| chr11 | 118895879 | 118896129 | 0.552 |
| chr11 | 119078108 | 119078358 | 0.348 |
| chr11 | 120178614 | 120178864 | 0.348 |
| chr11 | 121065150 | 121065400 | 0.316 |
| chr11 | 122640481 | 122640731 | 0.348 |
| chr11 | 123618251 | 123618501 | 0.336 |
| chr11 | 124545250 | 124545500 | 0.348 |
| chr11 | 125353052 | 125353302 | 0.348 |
| chr11 | 126357309 | 126357559 | 0.348 |
| chr11 | 127164952 | 127165202 | 0.348 |
| chr11 | 127969605 | 127969855 | 0.348 |
| chr11 | 130098150 | 130098400 | 0.332 |
| chr11 | 131496162 | 131496412 | 0.34 |
| chr11 | 132296933 | 132297183 | 0.348 |
| chr11 | 133138077 | 133138327 | 0.348 |
| chr11 | 133944178 | 133944428 | 0.336 |
| chr12 | 1010150 | 1010400 | 0.316 |
| chr12 | 2078150 | 2078400 | 0.316 |
| chr12 | 2998433 | 2998683 | 0.348 |
| chr12 | 3852150 | 3852400 | 0.312 |
| chr12 | 4652702 | 4652952 | 0.252 |
| chr12 | 5476654 | 5476904 | 0.348 |
| chr12 | 7509182 | 7509432 | 0.348 |
| chr12 | 8602743 | 8602993 | 0.344 |
| chr12 | 10532150 | 10532400 | 0.32 |
| chr12 | 11669397 | 11669647 | 0.348 |
| chr12 | 12624150 | 12624400 | 0.348 |
| chr12 | 14017296 | 14017546 | 0.348 |
| chr12 | 14825153 | 14825403 | 0.348 |
| chr12 | 15864451 | 15864701 | 0.348 |
| chr12 | 17209511 | 17209801 | 0.348 |
| chr12 | 18564576 | 18564826 | 0.348 |
| chr12 | 19368406 | 19368656 | 0.312 |
| chr12 | 20169044 | 20169294 | 0.336 |
| chr12 | 21809388 | 21809638 | 0.348 |
| chr12 | 23194150 | 23194400 | 0.324 |
| chr12 | 24378150 | 24378400 | 0.336 |
| chr12 | 25261150 | 25261400 | 0.252 |
| chr12 | 26222263 | 26222513 | 0.348 |
| chr12 | 27032150 | 27032400 | 0.296 |
| chr12 | 28065150 | 28065400 | 0.312 |
| chr12 | 28867298 | 28867548 | 0.344 |
| chr12 | 29672600 | 29672850 | 0.348 |
| chr12 | 30484504 | 30484754 | 0.348 |
| chr12 | 31354128 | 31354378 | 0.28 |
| chr12 | 32233641 | 32233891 | 0.348 |
| chr12 | 33035048 | 33035298 | 0.348 |

| Ch. | Start | Stop | GC content |
|---|---|---|---|
| chr12 | 33852725 | 33852975 | 0.316 |
| chr12 | 38762712 | 38762962 | 0.312 |
| chr12 | 39568259 | 39568509 | 0.348 |
| chr12 | 41547550 | 41547800 | 0.304 |
| chr12 | 42374550 | 42374800 | 0.324 |
| chr12 | 43286446 | 43286696 | 0.324 |
| chr12 | 44125571 | 44125821 | 0.324 |
| chr12 | 44928251 | 44928501 | 0.348 |
| chr12 | 45741587 | 45741837 | 0.28 |
| chr12 | 47018150 | 47018400 | 0.32 |
| chr12 | 47954368 | 47954618 | 0.348 |
| chr12 | 48807366 | 48807616 | 0.348 |
| chr12 | 49653664 | 49653914 | 0.348 |
| chr12 | 50552411 | 50552661 | 0.348 |
| chr12 | 51355238 | 51355488 | 0.348 |
| chr12 | 52156338 | 52156588 | 0.348 |
| chr12 | 53047852 | 53048102 | 0.348 |
| chr12 | 53867986 | 53868236 | 0.348 |
| chr12 | 54849331 | 54849581 | 0.348 |
| chr12 | 55967213 | 55967463 | 0.328 |
| chr12 | 57136531 | 57136781 | 0.324 |
| chr12 | 58191150 | 58191400 | 0.276 |
| chr12 | 59121159 | 59121409 | 0.348 |
| chr12 | 59962108 | 59962358 | 0.324 |
| chr12 | 60789979 | 60790229 | 0.252 |
| chr12 | 62345357 | 62345607 | 0.348 |
| chr12 | 63226154 | 63226404 | 0.348 |
| chr12 | 64269210 | 64269460 | 0.256 |
| chr12 | 65278150 | 65278400 | 0.308 |
| chr12 | 66088150 | 66088400 | 0.348 |
| chr12 | 67025166 | 67025416 | 0.324 |
| chr12 | 68088206 | 68088456 | 0.348 |
| chr12 | 68891849 | 68892099 | 0.348 |
| chr12 | 70321174 | 70321424 | 0.332 |
| chr12 | 71418451 | 71418701 | 0.348 |
| chr12 | 72312150 | 72312400 | 0.296 |
| chr12 | 73121298 | 73121548 | 0.268 |
| chr12 | 74229436 | 74229686 | 0.308 |
| chr12 | 75137472 | 75137722 | 0.304 |
| chr12 | 75942150 | 75942400 | 0.32 |
| chr12 | 76747550 | 76747800 | 0.312 |
| chr12 | 77549810 | 77550060 | 0.26 |
| chr12 | 79018196 | 79018446 | 0.348 |
| chr12 | 79819302 | 79819552 | 0.288 |
| chr12 | 80623713 | 80623963 | 0.332 |
| chr12 | 81432262 | 81432512 | 0.324 |
| chr12 | 82234916 | 82235166 | 0.26 |
| chr12 | 83040197 | 83040447 | 0.348 |
| chr12 | 83842541 | 83842791 | 0.348 |
| chr12 | 84644338 | 84644588 | 0.272 |
| chr12 | 86518150 | 86518400 | 0.344 |
| chr12 | 87422150 | 87422400 | 0.288 |
| chr12 | 88420350 | 88420600 | 0.348 |
| chr12 | 89430494 | 89430744 | 0.348 |
| chr12 | 90270282 | 90270532 | 0.348 |
| chr12 | 91174165 | 91174415 | 0.264 |
| chr12 | 92085151 | 92085401 | 0.348 |
| chr12 | 92947510 | 92947760 | 0.348 |
| chr12 | 93971575 | 93971825 | 0.348 |
| chr12 | 95097150 | 95097400 | 0.34 |
| chr12 | 96292457 | 96292707 | 0.336 |
| chr12 | 97672267 | 97672517 | 0.348 |
| chr12 | 98631302 | 98631552 | 0.348 |
| chr12 | 99884150 | 99884400 | 0.276 |
| chr12 | 101143158 | 101143408 | 0.348 |
| chr12 | 102015150 | 102015400 | 0.324 |
| chr12 | 103234177 | 103234426 | 0.46988 |
| chr12 | 103234235 | 103234340 | 0.504762 |
| chr12 | 103237341 | 103237591 | 0.512 |
| chr12 | 103237398 | 103237647 | 0.477912 |
| chr12 | 103237926 | 103238175 | 0.405622 |
| chr12 | 103240539 | 103240788 | 0.477912 |
| chr12 | 103245348 | 103245598 | 0.5 |
| chr12 | 103245355 | 103245604 | 0.497992 |
| chr12 | 103245396 | 103245646 | 0.456 |
| chr12 | 103246529 | 103246778 | 0.538153 |
| chr12 | 103248878 | 103249127 | 0.453815 |
| chr12 | 103248915 | 103249165 | 0.464 |
| chr12 | 103260367 | 103260616 | 0.445783 |
| chr12 | 103260384 | 103260490 | 0.45283 |
| chr12 | 103262150 | 103262400 | 0.304 |
| chr12 | 103271293 | 103271492 | 0.492462 |
| chr12 | 103288527 | 103288776 | 0.441767 |
| chr12 | 103306591 | 103306840 | 0.345382 |
| chr12 | 104098004 | 104098254 | 0.348 |
| chr12 | 106181481 | 106181731 | 0.344 |
| chr12 | 107176462 | 107176712 | 0.348 |
| chr12 | 108008885 | 108009135 | 0.348 |
| chr12 | 108830808 | 108831058 | 0.332 |
| chr12 | 109748594 | 109748844 | 0.348 |
| chr12 | 109994761 | 109995011 | 0.504 |
| chr12 | 109994805 | 109995055 | 0.48 |
| chr12 | 110555517 | 110555767 | 0.328 |
| chr12 | 111363237 | 111363487 | 0.308 |
| chr12 | 112247405 | 112247655 | 0.348 |
| chr12 | 113673150 | 113673400 | 0.292 |
| chr12 | 114525604 | 114525854 | 0.348 |
| chr12 | 115358313 | 115358563 | 0.34 |
| chr12 | 116191119 | 116191369 | 0.348 |
| chr12 | 117911938 | 117912188 | 0.312 |
| chr12 | 118730793 | 118731043 | 0.348 |
| chr12 | 119551405 | 119551655 | 0.348 |
| chr12 | 120405381 | 120405631 | 0.348 |
| chr12 | 121175612 | 121175862 | 0.628 |
| chr12 | 121176887 | 121177137 | 0.648 |
| chr12 | 121176999 | 121177249 | 0.64 |
| chr12 | 121210585 | 121210835 | 0.348 |
| chr12 | 122377840 | 122378090 | 0.252 |
| chr12 | 123239426 | 123239676 | 0.336 |
| chr12 | 124104421 | 124104671 | 0.348 |
| chr12 | 125045274 | 125045524 | 0.348 |
| chr12 | 125856241 | 125856491 | 0.348 |
| chr12 | 126656299 | 126656549 | 0.348 |
| chr12 | 128000199 | 128000449 | 0.348 |
| chr12 | 128945526 | 128945776 | 0.348 |
| chr12 | 129761193 | 129761443 | 0.348 |
| chr12 | 130586431 | 130586681 | 0.348 |
| chr12 | 131407236 | 131407486 | 0.348 |
| chr12 | 132208361 | 132208611 | 0.348 |
| chr12 | 133160778 | 133161028 | 0.348 |
| chr13 | 19509424 | 19509674 | 0.348 |
| chr13 | 20346157 | 20346407 | 0.344 |
| chr13 | 21163780 | 21164030 | 0.288 |
| chr13 | 21966517 | 21966767 | 0.332 |
| chr13 | 22769312 | 22769562 | 0.344 |
| chr13 | 23577459 | 23577709 | 0.336 |
| chr13 | 23909041 | 23909291 | 0.352 |
| chr13 | 23910386 | 23910636 | 0.392 |
| chr13 | 24381225 | 24381475 | 0.348 |
| chr13 | 25685243 | 25685493 | 0.324 |
| chr13 | 26952583 | 26952833 | 0.344 |
| chr13 | 28009207 | 28009457 | 0.348 |
| chr13 | 29040155 | 29040405 | 0.348 |
| chr13 | 30258409 | 30258659 | 0.348 |
| chr13 | 31078371 | 31078621 | 0.348 |
| chr13 | 31990150 | 31990400 | 0.328 |
| chr13 | 32794049 | 32794299 | 0.348 |
| chr13 | 33596179 | 33596429 | 0.316 |
| chr13 | 34427302 | 34427552 | 0.348 |
| chr13 | 35241150 | 35241400 | 0.328 |
| chr13 | 36047181 | 36047431 | 0.296 |
| chr13 | 36965545 | 36965795 | 0.348 |
| chr13 | 37907550 | 37907800 | 0.328 |
| chr13 | 38920435 | 38920685 | 0.348 |
| chr13 | 39771325 | 39771575 | 0.336 |
| chr13 | 40882353 | 40882603 | 0.348 |
| chr13 | 41765150 | 41765400 | 0.32 |
| chr13 | 42575249 | 42575499 | 0.344 |
| chr13 | 43379109 | 43379359 | 0.348 |
| chr13 | 44311168 | 44311418 | 0.348 |
| chr13 | 45121408 | 45121658 | 0.312 |
| chr13 | 46109150 | 46109400 | 0.332 |
| chr13 | 47732544 | 47732794 | 0.328 |
| chr13 | 48942150 | 48942400 | 0.268 |

| Ch. | Start | Stop | GC content |
|---|---|---|---|
| chr13 | 49742819 | 49743069 | 0.348 |
| chr13 | 50549888 | 50550138 | 0.332 |
| chr13 | 51354438 | 51354688 | 0.348 |
| chr13 | 52162009 | 52162259 | 0.348 |
| chr13 | 52966531 | 52966781 | 0.348 |
| chr13 | 53770557 | 53770807 | 0.344 |
| chr13 | 54575830 | 54576080 | 0.348 |
| chr13 | 55376257 | 55376507 | 0.332 |
| chr13 | 57034150 | 57034400 | 0.34 |
| chr13 | 58422150 | 58422400 | 0.28 |
| chr13 | 59588150 | 59588400 | 0.332 |
| chr13 | 60397150 | 60397400 | 0.312 |
| chr13 | 61202290 | 61202540 | 0.324 |
| chr13 | 62004633 | 62004883 | 0.272 |
| chr13 | 63351150 | 63351400 | 0.328 |
| chr13 | 64158420 | 64158670 | 0.288 |
| chr13 | 64958934 | 64959184 | 0.252 |
| chr13 | 65964404 | 65964654 | 0.316 |
| chr13 | 66764993 | 66765243 | 0.32 |
| chr13 | 67565742 | 67565992 | 0.268 |
| chr13 | 68592150 | 68592400 | 0.32 |
| chr13 | 69974172 | 69974422 | 0.26 |
| chr13 | 70774901 | 70775151 | 0.292 |
| chr13 | 71711150 | 71711400 | 0.336 |
| chr13 | 72600186 | 72600436 | 0.348 |
| chr13 | 73459222 | 73459472 | 0.324 |
| chr13 | 74546150 | 74546400 | 0.308 |
| chr13 | 75459380 | 75459630 | 0.3 |
| chr13 | 76488150 | 76488400 | 0.312 |
| chr13 | 77291150 | 77291400 | 0.332 |
| chr13 | 77574876 | 77575126 | 0.3 |
| chr13 | 77574930 | 77575180 | 0.304 |
| chr13 | 78107382 | 78107632 | 0.348 |
| chr13 | 79007255 | 79007505 | 0.348 |
| chr13 | 79813627 | 79813877 | 0.348 |
| chr13 | 80621943 | 80622193 | 0.348 |
| chr13 | 81803150 | 81803400 | 0.288 |
| chr13 | 83285173 | 83285423 | 0.348 |
| chr13 | 84093150 | 84093400 | 0.344 |
| chr13 | 85142259 | 85142509 | 0.348 |
| chr13 | 86482550 | 86482800 | 0.292 |
| chr13 | 87283355 | 87283605 | 0.252 |
| chr13 | 88107306 | 88107556 | 0.32 |
| chr13 | 88911884 | 88912134 | 0.348 |
| chr13 | 89717798 | 89718048 | 0.3 |
| chr13 | 90777553 | 90777803 | 0.348 |
| chr13 | 91581084 | 91581334 | 0.348 |
| chr13 | 92381844 | 92382094 | 0.348 |
| chr13 | 93184022 | 93184272 | 0.348 |
| chr13 | 93988458 | 93988708 | 0.348 |
| chr13 | 94864550 | 94864800 | 0.344 |
| chr13 | 95767550 | 95767800 | 0.324 |
| chr13 | 96598197 | 96598447 | 0.256 |
| chr13 | 97398760 | 97399010 | 0.284 |
| chr13 | 98206114 | 98206364 | 0.328 |
| chr13 | 99147389 | 99147639 | 0.348 |
| chr13 | 99953575 | 99953825 | 0.348 |
| chr13 | 100764123 | 100764373 | 0.312 |
| chr13 | 100925353 | 100925603 | 0.368 |
| chr13 | 101572024 | 101572274 | 0.348 |
| chr13 | 102372104 | 102372354 | 0.34 |
| chr13 | 104448504 | 104448754 | 0.348 |
| chr13 | 105811166 | 105811416 | 0.348 |
| chr13 | 106646233 | 106646483 | 0.348 |
| chr13 | 107819307 | 107819557 | 0.288 |
| chr13 | 108621182 | 108621432 | 0.348 |
| chr13 | 109437750 | 109438000 | 0.348 |
| chr13 | 110244948 | 110245198 | 0.348 |
| chr13 | 111045509 | 111045759 | 0.304 |
| chr13 | 111854189 | 111854439 | 0.348 |
| chr13 | 112657452 | 112657702 | 0.348 |
| chr13 | 113458943 | 113459193 | 0.308 |
| chr13 | 114266718 | 114266968 | 0.348 |
| chr13 | 115077515 | 115077765 | 0.348 |
| chr14 | 20331746 | 20331996 | 0.332 |
| chr14 | 20731811 | 20732061 | 0.348 |
| chr14 | 21156990 | 21157240 | 0.348 |
| chr14 | 21963671 | 21963921 | 0.348 |
| chr14 | 23243450 | 23243700 | 0.48 |
| chr14 | 23945665 | 23945915 | 0.348 |
| chr14 | 24728884 | 24729134 | 0.62 |
| chr14 | 24903163 | 24903413 | 0.312 |
| chr14 | 25341210 | 25341460 | 0.348 |
| chr14 | 26002455 | 26002705 | 0.416 |
| chr14 | 26015264 | 26015514 | 0.348 |
| chr14 | 27132386 | 27132636 | 0.348 |
| chr14 | 27988150 | 27988400 | 0.312 |
| chr14 | 28789081 | 28789331 | 0.252 |
| chr14 | 29592176 | 29592426 | 0.348 |
| chr14 | 30393187 | 30393437 | 0.284 |
| chr14 | 31195558 | 31195808 | 0.324 |
| chr14 | 31600116 | 31600366 | 0.324 |
| chr14 | 32004544 | 32004794 | 0.32 |
| chr14 | 32806096 | 32806346 | 0.348 |
| chr14 | 33607614 | 33607864 | 0.336 |
| chr14 | 34411885 | 34412135 | 0.312 |
| chr14 | 35218148 | 35218398 | 0.348 |
| chr14 | 35615486 | 35615736 | 0.324 |
| chr14 | 37299150 | 37299400 | 0.34 |
| chr14 | 38183150 | 38183400 | 0.256 |
| chr14 | 38989082 | 38989332 | 0.28 |
| chr14 | 39789090 | 39789340 | 0.252 |
| chr14 | 40589667 | 40589917 | 0.348 |
| chr14 | 40993988 | 40994238 | 0.312 |
| chr14 | 41393524 | 41393774 | 0.348 |
| chr14 | 43262940 | 43263190 | 0.312 |
| chr14 | 44065317 | 44065567 | 0.348 |
| chr14 | 44870813 | 44871063 | 0.264 |
| chr14 | 45277796 | 45278046 | 0.344 |
| chr14 | 45673230 | 45673480 | 0.284 |
| chr14 | 46798150 | 46798400 | 0.284 |
| chr14 | 48248386 | 48248636 | 0.348 |
| chr14 | 49055150 | 49055400 | 0.336 |
| chr14 | 49869097 | 49869347 | 0.328 |
| chr14 | 50693325 | 50693575 | 0.348 |
| chr14 | 51202151 | 51202401 | 0.348 |
| chr14 | 51710426 | 51710676 | 0.32 |
| chr14 | 53399150 | 53399400 | 0.292 |
| chr14 | 54325152 | 54325402 | 0.348 |
| chr14 | 55133584 | 55133834 | 0.348 |
| chr14 | 55954997 | 55955247 | 0.348 |
| chr14 | 56356037 | 56356287 | 0.348 |
| chr14 | 56757300 | 56757550 | 0.348 |
| chr14 | 57562963 | 57563213 | 0.348 |
| chr14 | 58448295 | 58448545 | 0.344 |
| chr14 | 59330150 | 59330400 | 0.316 |
| chr14 | 60137150 | 60137400 | 0.324 |
| chr14 | 61029567 | 61029817 | 0.312 |
| chr14 | 61831817 | 61832067 | 0.348 |
| chr14 | 62234974 | 62235224 | 0.348 |
| chr14 | 62648150 | 62648400 | 0.32 |
| chr14 | 63451150 | 63451400 | 0.34 |
| chr14 | 64679200 | 64679450 | 0.348 |
| chr14 | 65479421 | 65479671 | 0.348 |
| chr14 | 66291609 | 66291859 | 0.348 |
| chr14 | 66707755 | 66708005 | 0.348 |
| chr14 | 67099658 | 67099908 | 0.336 |
| chr14 | 67900455 | 67900705 | 0.328 |
| chr14 | 68191809 | 68192059 | 0.532 |
| chr14 | 68193588 | 68193838 | 0.572 |
| chr14 | 68193689 | 68193939 | 0.552 |
| chr14 | 68195776 | 68196026 | 0.584 |
| chr14 | 68706399 | 68706649 | 0.348 |
| chr14 | 69519728 | 69519978 | 0.348 |
| chr14 | 70427169 | 70427419 | 0.348 |
| chr14 | 71955192 | 71955442 | 0.324 |
| chr14 | 72369138 | 72369388 | 0.348 |
| chr14 | 72780476 | 72780726 | 0.348 |
| chr14 | 73583334 | 73583584 | 0.348 |
| chr14 | 74419912 | 74420162 | 0.348 |
| chr14 | 74947285 | 74947535 | 0.412 |
| chr14 | 74950993 | 74951243 | 0.484 |
| chr14 | 74952902 | 74953152 | 0.444 |
| chr14 | 74952982 | 74953232 | 0.472 |

| Ch. | Start | Stop | GC content |
|---|---|---|---|
| chr14 | 75231341 | 75231591 | 0.348 |
| chr14 | 76128102 | 76128352 | 0.348 |
| chr14 | 76717009 | 76717259 | 0.348 |
| chr14 | 77352577 | 77352827 | 0.348 |
| chr14 | 78858150 | 78858400 | 0.348 |
| chr14 | 79899295 | 79899545 | 0.348 |
| chr14 | 81000150 | 81000400 | 0.34 |
| chr14 | 81938150 | 81938400 | 0.332 |
| chr14 | 82739526 | 82739776 | 0.308 |
| chr14 | 83277489 | 83277739 | 0.348 |
| chr14 | 83828150 | 83828400 | 0.312 |
| chr14 | 84903229 | 84903479 | 0.348 |
| chr14 | 85751567 | 85751817 | 0.34 |
| chr14 | 86625529 | 86625779 | 0.348 |
| chr14 | 87501333 | 87501583 | 0.348 |
| chr14 | 88407748 | 88407998 | 0.368 |
| chr14 | 88413964 | 88414214 | 0.452 |
| chr14 | 88650507 | 88650757 | 0.348 |
| chr14 | 89060856 | 89061106 | 0.328 |
| chr14 | 89464609 | 89464859 | 0.348 |
| chr14 | 90271098 | 90271348 | 0.336 |
| chr14 | 91072033 | 91072283 | 0.348 |
| chr14 | 91876716 | 91876966 | 0.348 |
| chr14 | 93250166 | 93250416 | 0.348 |
| chr14 | 94052683 | 94052933 | 0.348 |
| chr14 | 94626755 | 94627005 | 0.348 |
| chr14 | 94844782 | 94845032 | 0.504 |
| chr14 | 94844822 | 94845072 | 0.544 |
| chr14 | 94849223 | 94849473 | 0.54 |
| chr14 | 94888492 | 94888742 | 0.316 |
| chr14 | 96231311 | 96231561 | 0.348 |
| chr14 | 97299482 | 97299732 | 0.312 |
| chr14 | 98110316 | 98110566 | 0.348 |
| chr14 | 98925215 | 98925465 | 0.348 |
| chr14 | 99322526 | 99322776 | 0.348 |
| chr14 | 99726035 | 99726285 | 0.348 |
| chr14 | 100695219 | 100695469 | 0.348 |
| chr14 | 101528862 | 101529112 | 0.348 |
| chr14 | 102342620 | 102342870 | 0.316 |
| chr14 | 103166071 | 103166321 | 0.348 |
| chr14 | 104199459 | 104199709 | 0.348 |
| chr14 | 104799911 | 104800161 | 0.348 |
| chr14 | 106327752 | 106328002 | 0.348 |
| chr15 | 21937192 | 21937442 | 0.348 |
| chr15 | 22815525 | 22815775 | 0.336 |
| chr15 | 23062275 | 23062525 | 0.348 |
| chr15 | 23805462 | 23805712 | 0.328 |
| chr15 | 24856221 | 24856471 | 0.348 |
| chr15 | 25256023 | 25256273 | 0.3 |
| chr15 | 25656926 | 25657176 | 0.336 |
| chr15 | 27756150 | 27756400 | 0.344 |
| chr15 | 28437259 | 28437509 | 0.348 |
| chr15 | 29143960 | 29144210 | 0.316 |
| chr15 | 29946126 | 29946376 | 0.308 |
| chr15 | 31338150 | 31338400 | 0.308 |
| chr15 | 32115541 | 32115791 | 0.348 |
| chr15 | 32928697 | 32928947 | 0.348 |
| chr15 | 33816249 | 33816499 | 0.348 |
| chr15 | 34418150 | 34418400 | 0.34 |
| chr15 | 34532737 | 34532986 | 0.457831 |
| chr15 | 34536054 | 34536236 | 0.412088 |
| chr15 | 35006335 | 35006585 | 0.348 |
| chr15 | 36298291 | 36298541 | 0.348 |
| chr15 | 36751553 | 36751803 | 0.348 |
| chr15 | 37098509 | 37098759 | 0.348 |
| chr15 | 38023487 | 38023737 | 0.348 |
| chr15 | 39315508 | 39315758 | 0.348 |
| chr15 | 39870231 | 39870481 | 0.348 |
| chr15 | 40677150 | 40677400 | 0.336 |
| chr15 | 40707528 | 40707778 | 0.552 |
| chr15 | 42054189 | 42054439 | 0.348 |
| chr15 | 42693828 | 42694078 | 0.58 |
| chr15 | 42703005 | 42703255 | 0.548 |
| chr15 | 42955175 | 42955425 | 0.348 |
| chr15 | 44096462 | 44096712 | 0.348 |
| chr15 | 44492018 | 44492268 | 0.348 |
| chr15 | 44898296 | 44898546 | 0.312 |
| chr15 | 45699464 | 45699714 | 0.348 |
| chr15 | 46502884 | 46503134 | 0.348 |
| chr15 | 47004873 | 47005123 | 0.304 |
| chr15 | 47506569 | 47506819 | 0.348 |
| chr15 | 48748150 | 48748400 | 0.336 |
| chr15 | 49239150 | 49239400 | 0.34 |
| chr15 | 49912448 | 49912698 | 0.348 |
| chr15 | 50717615 | 50717865 | 0.348 |
| chr15 | 51503082 | 51503332 | 0.444 |
| chr15 | 51503089 | 51503339 | 0.444 |
| chr15 | 51510606 | 51510856 | 0.38 |
| chr15 | 51510730 | 51510980 | 0.4 |
| chr15 | 51514421 | 51514671 | 0.452 |
| chr15 | 51528775 | 51529025 | 0.34 |
| chr15 | 51749584 | 51749834 | 0.348 |
| chr15 | 52375584 | 52375834 | 0.32 |
| chr15 | 53488150 | 53488400 | 0.28 |
| chr15 | 54303419 | 54303669 | 0.348 |
| chr15 | 55400166 | 55400416 | 0.348 |
| chr15 | 55947150 | 55947400 | 0.324 |
| chr15 | 56611250 | 56611500 | 0.332 |
| chr15 | 57552150 | 57552400 | 0.32 |
| chr15 | 58755932 | 58756182 | 0.348 |
| chr15 | 59168782 | 59169132 | 0.348 |
| chr15 | 60057234 | 60057484 | 0.296 |
| chr15 | 61399384 | 61399634 | 0.348 |
| chr15 | 62048550 | 62048800 | 0.32 |
| chr15 | 62410361 | 62410611 | 0.348 |
| chr15 | 63213584 | 63213834 | 0.348 |
| chr15 | 63624114 | 63624364 | 0.348 |
| chr15 | 64025256 | 64025506 | 0.348 |
| chr15 | 64840241 | 64840491 | 0.332 |
| chr15 | 65674276 | 65674526 | 0.34 |
| chr15 | 66097124 | 66097374 | 0.348 |
| chr15 | 66541083 | 66541333 | 0.348 |
| chr15 | 67364323 | 67364573 | 0.268 |
| chr15 | 68461235 | 68461485 | 0.348 |
| chr15 | 68501858 | 68502108 | 0.58 |
| chr15 | 68503470 | 68503720 | 0.588 |
| chr15 | 68504006 | 68504256 | 0.592 |
| chr15 | 68504067 | 68504317 | 0.604 |
| chr15 | 69405375 | 69405625 | 0.348 |
| chr15 | 69906737 | 69906987 | 0.348 |
| chr15 | 70261781 | 70262031 | 0.348 |
| chr15 | 71298502 | 71298752 | 0.316 |
| chr15 | 72129534 | 72129784 | 0.336 |
| chr15 | 72638860 | 72639056 | 0.515306 |
| chr15 | 72640258 | 72640508 | 0.544 |
| chr15 | 73399350 | 73399600 | 0.332 |
| chr15 | 74451150 | 74451400 | 0.324 |
| chr15 | 75189266 | 75189516 | 0.532 |
| chr15 | 75465113 | 75465363 | 0.348 |
| chr15 | 75869324 | 75869574 | 0.316 |
| chr15 | 76301292 | 76301542 | 0.284 |
| chr15 | 77750576 | 77750826 | 0.344 |
| chr15 | 78309918 | 78310168 | 0.34 |
| chr15 | 78565345 | 78565595 | 0.348 |
| chr15 | 80450387 | 80450637 | 0.508 |
| chr15 | 80465310 | 80465560 | 0.576 |
| chr15 | 80472405 | 80472655 | 0.64 |
| chr15 | 80472447 | 80472697 | 0.624 |
| chr15 | 80473260 | 80473510 | 0.536 |
| chr15 | 80730551 | 80730801 | 0.348 |
| chr15 | 80938280 | 80938530 | 0.348 |
| chr15 | 81549150 | 81549400 | 0.328 |
| chr15 | 82355082 | 82355332 | 0.348 |
| chr15 | 83783444 | 83783694 | 0.348 |
| chr15 | 84178159 | 84178409 | 0.348 |
| chr15 | 85189700 | 85189950 | 0.348 |
| chr15 | 86017842 | 86018092 | 0.284 |
| chr15 | 86446885 | 86447135 | 0.312 |
| chr15 | 86821668 | 86821918 | 0.348 |
| chr15 | 87865458 | 87865708 | 0.348 |
| chr15 | 88320038 | 88320288 | 0.348 |
| chr15 | 88810009 | 88810259 | 0.348 |
| chr15 | 89644678 | 89644928 | 0.348 |
| chr15 | 89753895 | 89754145 | 0.564 |

| Ch. | Start | Stop | GC content |
|---|---|---|---|
| chr15 | 89860637 | 89860887 | 0.532 |
| chr15 | 89862087 | 89862337 | 0.596 |
| chr15 | 89862159 | 89862409 | 0.536 |
| chr15 | 89864054 | 89864304 | 0.536 |
| chr15 | 89866532 | 89866782 | 0.572 |
| chr15 | 89868746 | 89868996 | 0.612 |
| chr15 | 89870087 | 89870337 | 0.58 |
| chr15 | 89873301 | 89873551 | 0.588 |
| chr15 | 89873358 | 89873608 | 0.6 |
| chr15 | 90992339 | 90992589 | 0.348 |
| chr15 | 91879321 | 91879571 | 0.348 |
| chr15 | 92283729 | 92283979 | 0.348 |
| chr15 | 92694222 | 92694472 | 0.34 |
| chr15 | 93494887 | 93495137 | 0.348 |
| chr15 | 94516150 | 94516400 | 0.272 |
| chr15 | 94738150 | 94738400 | 0.336 |
| chr15 | 95430150 | 95430400 | 0.34 |
| chr15 | 96242150 | 96242400 | 0.34 |
| chr15 | 97236279 | 97236529 | 0.348 |
| chr15 | 97542332 | 97542582 | 0.292 |
| chr15 | 98054150 | 98054400 | 0.332 |
| chr15 | 99928187 | 99928437 | 0.348 |
| chr15 | 101013180 | 101013430 | 0.348 |
| chr15 | 101227226 | 101227476 | 0.348 |
| chr15 | 101907373 | 101907623 | 0.348 |
| chr16 | 258208 | 258458 | 0.348 |
| chr16 | 946720 | 946970 | 0.348 |
| chr16 | 1413133 | 1413383 | 0.348 |
| chr16 | 2320307 | 2320557 | 0.348 |
| chr16 | 3293218 | 3293428 | 0.52381 |
| chr16 | 3293284 | 3293534 | 0.536 |
| chr16 | 3293312 | 3293561 | 0.558233 |
| chr16 | 3293322 | 3293572 | 0.548 |
| chr16 | 3293404 | 3293654 | 0.516 |
| chr16 | 3297026 | 3297276 | 0.584 |
| chr16 | 3297026 | 3297276 | 0.584 |
| chr16 | 3304577 | 3304735 | 0.702532 |
| chr16 | 3699883 | 3700133 | 0.348 |
| chr16 | 4062366 | 4062616 | 0.348 |
| chr16 | 4883448 | 4883698 | 0.348 |
| chr16 | 6227319 | 6227569 | 0.348 |
| chr16 | 6622150 | 6622400 | 0.28 |
| chr16 | 7509405 | 7509655 | 0.348 |
| chr16 | 8312670 | 8312920 | 0.348 |
| chr16 | 8941497 | 8941747 | 0.6 |
| chr16 | 9148517 | 9148767 | 0.348 |
| chr16 | 9553912 | 9554162 | 0.348 |
| chr16 | 9952565 | 9952815 | 0.348 |
| chr16 | 10814797 | 10815047 | 0.348 |
| chr16 | 11641822 | 11642072 | 0.348 |
| chr16 | 12060400 | 12060650 | 0.348 |
| chr16 | 12521810 | 12522060 | 0.348 |
| chr16 | 13341606 | 13341856 | 0.32 |
| chr16 | 14167801 | 14168051 | 0.308 |
| chr16 | 14604714 | 14604964 | 0.348 |
| chr16 | 15052738 | 15052988 | 0.348 |
| chr16 | 15959882 | 15960132 | 0.32 |
| chr16 | 16859878 | 16860128 | 0.348 |
| chr16 | 17663171 | 17663421 | 0.336 |
| chr16 | 18119811 | 18120061 | 0.344 |
| chr16 | 18799227 | 18799477 | 0.348 |
| chr16 | 19621285 | 19621535 | 0.348 |
| chr16 | 20620997 | 20621247 | 0.288 |
| chr16 | 21600723 | 21600973 | 0.308 |
| chr16 | 21995758 | 21996008 | 0.348 |
| chr16 | 22413441 | 22413691 | 0.32 |
| chr16 | 23252457 | 23252707 | 0.348 |
| chr16 | 24097792 | 24098042 | 0.348 |
| chr16 | 24552683 | 24552933 | 0.34 |
| chr16 | 24939654 | 24939904 | 0.304 |
| chr16 | 25759791 | 25760041 | 0.348 |
| chr16 | 26644833 | 26645083 | 0.348 |
| chr16 | 26964539 | 26964789 | 0.348 |
| chr16 | 27504199 | 27504449 | 0.348 |
| chr16 | 29806827 | 29807077 | 0.348 |
| chr16 | 30764038 | 30764288 | 0.348 |
| chr16 | 31200605 | 31200855 | 0.328 |
| chr16 | 31656295 | 31656545 | 0.348 |
| chr16 | 32622254 | 32622504 | 0.348 |
| chr16 | 34199349 | 34199599 | 0.34 |
| chr16 | 35039854 | 35040104 | 0.348 |
| chr16 | 46501463 | 46501713 | 0.348 |
| chr16 | 46860612 | 46860862 | 0.324 |
| chr16 | 47307020 | 47307270 | 0.348 |
| chr16 | 48123485 | 48123735 | 0.348 |
| chr16 | 48979520 | 48979770 | 0.348 |
| chr16 | 49409741 | 49409991 | 0.34 |
| chr16 | 49854234 | 49854484 | 0.348 |
| chr16 | 50777251 | 50777501 | 0.348 |
| chr16 | 51611803 | 51612053 | 0.348 |
| chr16 | 52521397 | 52521647 | 0.344 |
| chr16 | 53001263 | 53001513 | 0.312 |
| chr16 | 53933270 | 53933520 | 0.348 |
| chr16 | 54744744 | 54744994 | 0.348 |
| chr16 | 55560218 | 55560468 | 0.336 |
| chr16 | 55979882 | 55980132 | 0.348 |
| chr16 | 56438259 | 56438509 | 0.344 |
| chr16 | 56548274 | 56548524 | 0.384 |
| chr16 | 56548356 | 56548606 | 0.44 |
| chr16 | 56903881 | 56904131 | 0.628 |
| chr16 | 57242761 | 57243011 | 0.336 |
| chr16 | 58047908 | 58048158 | 0.32 |
| chr16 | 58439726 | 58439976 | 0.348 |
| chr16 | 58854106 | 58854356 | 0.348 |
| chr16 | 59723150 | 59723400 | 0.32 |
| chr16 | 60845346 | 60845596 | 0.348 |
| chr16 | 61360230 | 61360480 | 0.252 |
| chr16 | 61758472 | 61758722 | 0.348 |
| chr16 | 62727578 | 62727828 | 0.348 |
| chr16 | 63914255 | 63914505 | 0.328 |
| chr16 | 64454577 | 64454827 | 0.268 |
| chr16 | 64980267 | 64980517 | 0.348 |
| chr16 | 65805485 | 65805735 | 0.336 |
| chr16 | 66650107 | 66650357 | 0.348 |
| chr16 | 67124434 | 67124684 | 0.348 |
| chr16 | 67597956 | 67598206 | 0.348 |
| chr16 | 68432415 | 68432665 | 0.348 |
| chr16 | 69235387 | 69235637 | 0.324 |
| chr16 | 70192752 | 70193002 | 0.348 |
| chr16 | 70597322 | 70597572 | 0.348 |
| chr16 | 71206932 | 71207182 | 0.348 |
| chr16 | 72033345 | 72033595 | 0.348 |
| chr16 | 72837496 | 72837746 | 0.348 |
| chr16 | 73239267 | 73239517 | 0.348 |
| chr16 | 73642603 | 73642853 | 0.336 |
| chr16 | 74481276 | 74481526 | 0.348 |
| chr16 | 75327074 | 75327324 | 0.328 |
| chr16 | 75766225 | 75766475 | 0.344 |
| chr16 | 76259454 | 76259704 | 0.348 |
| chr16 | 77308495 | 77308745 | 0.312 |
| chr16 | 78168150 | 78168400 | 0.348 |
| chr16 | 78721550 | 78721800 | 0.344 |
| chr16 | 78979256 | 78979506 | 0.336 |
| chr16 | 79786137 | 79786387 | 0.348 |
| chr16 | 80589959 | 80590209 | 0.348 |
| chr16 | 81009953 | 81010203 | 0.348 |
| chr16 | 81411556 | 81411806 | 0.348 |
| chr16 | 82958335 | 82958585 | 0.348 |
| chr16 | 83829502 | 83829752 | 0.348 |
| chr16 | 84166382 | 84166632 | 0.336 |
| chr16 | 85076447 | 85076697 | 0.348 |
| chr16 | 85907481 | 85907731 | 0.32 |
| chr16 | 86714059 | 86714309 | 0.324 |
| chr16 | 87736388 | 87736638 | 0.348 |
| chr16 | 88097355 | 88097605 | 0.348 |
| chr16 | 89161654 | 89161904 | 0.348 |
| chr16 | 89849148 | 89849398 | 0.484 |
| chr16 | 89849164 | 89849414 | 0.492 |
| chr16 | 89877010 | 89877260 | 0.384 |
| chr17 | 465619 | 465869 | 0.476 |
| chr17 | 559153 | 559403 | 0.348 |
| chr17 | 879453 | 879703 | 0.348 |
| chr17 | 1455714 | 1455964 | 0.348 |
| chr17 | 2287357 | 2287607 | 0.348 |

| Ch. | Start | Stop | GC content |
|---|---|---|---|
| chr17 | 2588173 | 2588423 | 0.348 |
| chr17 | 3088772 | 3089022 | 0.284 |
| chr17 | 3563424 | 3563674 | 0.576 |
| chr17 | 3916884 | 3917134 | 0.308 |
| chr17 | 5011281 | 5011531 | 0.348 |
| chr17 | 5431814 | 5432064 | 0.348 |
| chr17 | 6026560 | 6026810 | 0.348 |
| chr17 | 6830537 | 6830787 | 0.336 |
| chr17 | 7128160 | 7128410 | 0.628 |
| chr17 | 7651065 | 7651315 | 0.348 |
| chr17 | 7918695 | 7918945 | 0.604 |
| chr17 | 8263781 | 8264031 | 0.344 |
| chr17 | 8461018 | 8461268 | 0.348 |
| chr17 | 9328553 | 9328803 | 0.304 |
| chr17 | 9787971 | 9788221 | 0.348 |
| chr17 | 10223454 | 10223704 | 0.348 |
| chr17 | 11055587 | 11055837 | 0.32 |
| chr17 | 11886166 | 11886416 | 0.324 |
| chr17 | 12278449 | 12278699 | 0.308 |
| chr17 | 12691155 | 12691405 | 0.348 |
| chr17 | 14005537 | 14005787 | 0.348 |
| chr17 | 15093150 | 15093400 | 0.34 |
| chr17 | 15416497 | 15416747 | 0.336 |
| chr17 | 15901623 | 15901873 | 0.348 |
| chr17 | 16781645 | 16781895 | 0.348 |
| chr17 | 17377934 | 17378184 | 0.348 |
| chr17 | 17818108 | 17818358 | 0.348 |
| chr17 | 18764031 | 18764281 | 0.348 |
| chr17 | 19566518 | 19566768 | 0.352 |
| chr17 | 19999381 | 19999631 | 0.336 |
| chr17 | 20209152 | 20209402 | 0.336 |
| chr17 | 20829712 | 20829962 | 0.348 |
| chr17 | 22025919 | 22026169 | 0.348 |
| chr17 | 25630230 | 25630480 | 0.348 |
| chr17 | 27580360 | 27580610 | 0.276 |
| chr17 | 28417566 | 28417816 | 0.348 |
| chr17 | 28819459 | 28819709 | 0.32 |
| chr17 | 29219615 | 29219865 | 0.332 |
| chr17 | 30219281 | 30219531 | 0.348 |
| chr17 | 30657441 | 30657691 | 0.348 |
| chr17 | 31020026 | 31020276 | 0.312 |
| chr17 | 31982636 | 31982886 | 0.348 |
| chr17 | 33771316 | 33771566 | 0.348 |
| chr17 | 34382478 | 34382728 | 0.3 |
| chr17 | 34823051 | 34823301 | 0.348 |
| chr17 | 35632575 | 35632825 | 0.328 |
| chr17 | 36513607 | 36513857 | 0.348 |
| chr17 | 36957600 | 36957850 | 0.348 |
| chr17 | 37409895 | 37410145 | 0.348 |
| chr17 | 38280124 | 38280374 | 0.348 |
| chr17 | 38783515 | 38783765 | 0.348 |
| chr17 | 39080566 | 39080816 | 0.336 |
| chr17 | 40004497 | 40004747 | 0.348 |
| chr17 | 40695364 | 40695614 | 0.64 |
| chr17 | 40695461 | 40695711 | 0.66 |
| chr17 | 40695588 | 40695838 | 0.62 |
| chr17 | 40695755 | 40696005 | 0.632 |
| chr17 | 40695920 | 40696170 | 0.584 |
| chr17 | 40961983 | 40962233 | 0.332 |
| chr17 | 41052842 | 41053092 | 0.496 |
| chr17 | 41052881 | 41053131 | 0.484 |
| chr17 | 41062968 | 41063218 | 0.536 |
| chr17 | 41063053 | 41063303 | 0.588 |
| chr17 | 41362685 | 41362935 | 0.324 |
| chr17 | 41843202 | 41843452 | 0.348 |
| chr17 | 42736824 | 42737074 | 0.28 |
| chr17 | 43767203 | 43767453 | 0.348 |
| chr17 | 44271724 | 44271974 | 0.348 |
| chr17 | 44787702 | 44787952 | 0.324 |
| chr17 | 45676520 | 45676770 | 0.308 |
| chr17 | 46151588 | 46151838 | 0.348 |
| chr17 | 46492183 | 46492433 | 0.348 |
| chr17 | 47368119 | 47368369 | 0.348 |
| chr17 | 48244905 | 48245155 | 0.652 |
| chr17 | 48500926 | 48501176 | 0.332 |
| chr17 | 48925318 | 48925568 | 0.348 |
| chr17 | 49302069 | 49302319 | 0.348 |
| chr17 | 50153263 | 50153513 | 0.348 |
| chr17 | 51249262 | 51249512 | 0.308 |
| chr17 | 51650684 | 51650934 | 0.348 |
| chr17 | 52050727 | 52050977 | 0.304 |
| chr17 | 53502160 | 53502410 | 0.348 |
| chr17 | 54154294 | 54154544 | 0.348 |
| chr17 | 54514376 | 54514626 | 0.348 |
| chr17 | 55667460 | 55667710 | 0.348 |
| chr17 | 56296396 | 56296646 | 0.64 |
| chr17 | 56469489 | 56469739 | 0.348 |
| chr17 | 57271861 | 57272111 | 0.348 |
| chr17 | 58119107 | 58119357 | 0.348 |
| chr17 | 58529289 | 58529539 | 0.332 |
| chr17 | 58934643 | 58934893 | 0.348 |
| chr17 | 59737150 | 59737400 | 0.316 |
| chr17 | 60644768 | 60645018 | 0.332 |
| chr17 | 61051969 | 61052219 | 0.32 |
| chr17 | 61464852 | 61465102 | 0.348 |
| chr17 | 62271111 | 62271361 | 0.348 |
| chr17 | 62645048 | 62645298 | 0.304 |
| chr17 | 63117102 | 63117352 | 0.284 |
| chr17 | 63926144 | 63926394 | 0.348 |
| chr17 | 64736660 | 64736910 | 0.348 |
| chr17 | 65689242 | 65689492 | 0.348 |
| chr17 | 66804590 | 66804840 | 0.348 |
| chr17 | 67242150 | 67242400 | 0.34 |
| chr17 | 68050397 | 68050647 | 0.296 |
| chr17 | 69063221 | 69063471 | 0.332 |
| chr17 | 69978262 | 69978512 | 0.348 |
| chr17 | 70909150 | 70909400 | 0.336 |
| chr17 | 71861764 | 71862014 | 0.332 |
| chr17 | 72572363 | 72572613 | 0.308 |
| chr17 | 73007683 | 73007933 | 0.348 |
| chr17 | 73941279 | 73941529 | 0.348 |
| chr17 | 74441215 | 74441465 | 0.348 |
| chr17 | 75094873 | 75095123 | 0.348 |
| chr17 | 75957718 | 75957968 | 0.348 |
| chr17 | 76771456 | 76771706 | 0.348 |
| chr17 | 77357842 | 77358092 | 0.348 |
| chr17 | 77749872 | 77750122 | 0.348 |
| chr17 | 78078272 | 78078499 | 0.647577 |
| chr17 | 78078810 | 78079059 | 0.666667 |
| chr17 | 78086683 | 78086876 | 0.65285 |
| chr17 | 78090765 | 78090952 | 0.647059 |
| chr17 | 78091969 | 78092218 | 0.662651 |
| chr17 | 78184281 | 78184531 | 0.668 |
| chr17 | 78184353 | 78184603 | 0.624 |
| chr17 | 78187505 | 78187755 | 0.692 |
| chr17 | 78187877 | 78188127 | 0.644 |
| chr17 | 78188311 | 78188561 | 0.632 |
| chr17 | 78188412 | 78188662 | 0.604 |
| chr17 | 78559453 | 78559703 | 0.324 |
| chr17 | 79870994 | 79871244 | 0.348 |
| chr17 | 80358326 | 80358576 | 0.348 |
| chr18 | 352317 | 352567 | 0.348 |
| chr18 | 1376361 | 1376611 | 0.348 |
| chr18 | 1780339 | 1780589 | 0.348 |
| chr18 | 2178416 | 2178666 | 0.348 |
| chr18 | 2981417 | 2981667 | 0.348 |
| chr18 | 3133377 | 3133627 | 0.348 |
| chr18 | 4041313 | 4041563 | 0.344 |
| chr18 | 5367216 | 5367466 | 0.348 |
| chr18 | 6171554 | 6171804 | 0.328 |
| chr18 | 6578629 | 6578879 | 0.348 |
| chr18 | 6977250 | 6977500 | 0.348 |
| chr18 | 8023198 | 8023448 | 0.348 |
| chr18 | 8257365 | 8257615 | 0.348 |
| chr18 | 9211150 | 9211400 | 0.308 |
| chr18 | 10066349 | 10066599 | 0.348 |
| chr18 | 10924564 | 10924814 | 0.332 |
| chr18 | 11728526 | 11728776 | 0.34 |
| chr18 | 12529626 | 12529876 | 0.312 |
| chr18 | 12968418 | 12968668 | 0.348 |
| chr18 | 13399720 | 13399970 | 0.348 |
| chr18 | 14932813 | 14933063 | 0.348 |
| chr18 | 18540358 | 18540608 | 0.316 |
| chr18 | 19342552 | 19342802 | 0.288 |

| Ch. | Start | Stop | GC content |
|---|---|---|---|
| chr18 | 20143679 | 20143929 | 0.348 |
| chr18 | 20957400 | 20957650 | 0.3 |
| chr18 | 21115324 | 21115574 | 0.5 |
| chr18 | 21115522 | 21115772 | 0.536 |
| chr18 | 21116575 | 21116825 | 0.52 |
| chr18 | 21118438 | 21118688 | 0.512 |
| chr18 | 21118490 | 21118740 | 0.508 |
| chr18 | 21119268 | 21119518 | 0.456 |
| chr18 | 21119662 | 21119912 | 0.524 |
| chr18 | 21119781 | 21120031 | 0.504 |
| chr18 | 21121194 | 21121444 | 0.484 |
| chr18 | 21136270 | 21136520 | 0.552 |
| chr18 | 21148788 | 21149038 | 0.368 |
| chr18 | 21501150 | 21501400 | 0.312 |
| chr18 | 22195155 | 22195405 | 0.34 |
| chr18 | 23350150 | 23350400 | 0.32 |
| chr18 | 24154458 | 24154708 | 0.348 |
| chr18 | 25617594 | 25617844 | 0.348 |
| chr18 | 26133235 | 26133485 | 0.276 |
| chr18 | 26944340 | 26944590 | 0.32 |
| chr18 | 27750063 | 27750313 | 0.328 |
| chr18 | 28150278 | 28150528 | 0.296 |
| chr18 | 28550925 | 28551175 | 0.308 |
| chr18 | 29794550 | 29794800 | 0.34 |
| chr18 | 30206170 | 30206420 | 0.348 |
| chr18 | 30617559 | 30617809 | 0.328 |
| chr18 | 32104550 | 32104800 | 0.312 |
| chr18 | 33485167 | 33485417 | 0.348 |
| chr18 | 34661394 | 34661644 | 0.324 |
| chr18 | 35818572 | 35818822 | 0.348 |
| chr18 | 36409564 | 36409814 | 0.348 |
| chr18 | 36817547 | 36817797 | 0.284 |
| chr18 | 37631150 | 37631400 | 0.336 |
| chr18 | 37749565 | 37749815 | 0.344 |
| chr18 | 38710272 | 38710522 | 0.348 |
| chr18 | 39747382 | 39747632 | 0.34 |
| chr18 | 40637226 | 40637476 | 0.348 |
| chr18 | 41439110 | 41439360 | 0.276 |
| chr18 | 41829773 | 41830023 | 0.348 |
| chr18 | 42239853 | 42240103 | 0.336 |
| chr18 | 43040497 | 43040747 | 0.348 |
| chr18 | 43843110 | 43843360 | 0.348 |
| chr18 | 44175715 | 44175965 | 0.348 |
| chr18 | 44654383 | 44654633 | 0.348 |
| chr18 | 45454440 | 45454690 | 0.348 |
| chr18 | 45933306 | 45933556 | 0.348 |
| chr18 | 46473309 | 46473559 | 0.348 |
| chr18 | 47313188 | 47313438 | 0.32 |
| chr18 | 48143536 | 48143786 | 0.34 |
| chr18 | 48537991 | 48538241 | 0.348 |
| chr18 | 48948147 | 48948397 | 0.348 |
| chr18 | 49765022 | 49765272 | 0.348 |
| chr18 | 50569985 | 50570235 | 0.336 |
| chr18 | 50977389 | 50977639 | 0.348 |
| chr18 | 51386182 | 51386432 | 0.344 |
| chr18 | 52359206 | 52359456 | 0.252 |
| chr18 | 53778557 | 53778807 | 0.348 |
| chr18 | 54396170 | 54396420 | 0.348 |
| chr18 | 55361574 | 55361824 | 0.348 |
| chr18 | 56168157 | 56168407 | 0.344 |
| chr18 | 56575500 | 56575750 | 0.348 |
| chr18 | 56969651 | 56969901 | 0.348 |
| chr18 | 58270587 | 58270837 | 0.252 |
| chr18 | 58864470 | 58864720 | 0.348 |
| chr18 | 59829150 | 59829400 | 0.324 |
| chr18 | 60629990 | 60630240 | 0.348 |
| chr18 | 61030027 | 61030277 | 0.348 |
| chr18 | 61430302 | 61430552 | 0.348 |
| chr18 | 62397150 | 62397400 | 0.332 |
| chr18 | 63197866 | 63198116 | 0.312 |
| chr18 | 63594781 | 63595031 | 0.324 |
| chr18 | 63997888 | 63998138 | 0.26 |
| chr18 | 64798724 | 64798974 | 0.348 |
| chr18 | 65202000 | 65202250 | 0.336 |
| chr18 | 65599811 | 65600061 | 0.288 |
| chr18 | 66403127 | 66403377 | 0.348 |
| chr18 | 67205175 | 67205425 | 0.288 |
| chr18 | 67611261 | 67611511 | 0.316 |
| chr18 | 68016661 | 68016911 | 0.344 |
| chr18 | 68818492 | 68818742 | 0.332 |
| chr18 | 69633509 | 69633759 | 0.348 |
| chr18 | 70029267 | 70029517 | 0.32 |
| chr18 | 70436499 | 70436749 | 0.348 |
| chr18 | 71240897 | 71241147 | 0.316 |
| chr18 | 71643656 | 71643906 | 0.324 |
| chr18 | 72045281 | 72045531 | 0.348 |
| chr18 | 74383168 | 74383418 | 0.348 |
| chr18 | 74798379 | 74798629 | 0.348 |
| chr18 | 75604856 | 75605106 | 0.288 |
| chr18 | 76965150 | 76965400 | 0.332 |
| chr18 | 77566578 | 77566828 | 0.348 |
| chr19 | 1364412 | 1364662 | 0.348 |
| chr19 | 2857080 | 2857330 | 0.348 |
| chr19 | 4423005 | 4423255 | 0.348 |
| chr19 | 5389785 | 5390035 | 0.348 |
| chr19 | 5612398 | 5612648 | 0.348 |
| chr19 | 6103129 | 6103379 | 0.348 |
| chr19 | 7182731 | 7182981 | 0.304 |
| chr19 | 8516971 | 8517221 | 0.348 |
| chr19 | 8923201 | 8923451 | 0.348 |
| chr19 | 9341186 | 9341436 | 0.348 |
| chr19 | 9581544 | 9581794 | 0.348 |
| chr19 | 10244002 | 10244252 | 0.344 |
| chr19 | 10677063 | 10677313 | 0.348 |
| chr19 | 10781045 | 10781295 | 0.348 |
| chr19 | 11199420 | 11199670 | 0.348 |
| chr19 | 11216102 | 11216211 | 0.59633 |
| chr19 | 11711517 | 11711767 | 0.348 |
| chr19 | 12105696 | 12105946 | 0.32 |
| chr19 | 12360810 | 12361060 | 0.296 |
| chr19 | 12625145 | 12625395 | 0.348 |
| chr19 | 13006933 | 13007183 | 0.612 |
| chr19 | 13007001 | 13007251 | 0.612 |
| chr19 | 13007639 | 13007889 | 0.612 |
| chr19 | 14730075 | 14730325 | 0.348 |
| chr19 | 15394044 | 15394294 | 0.348 |
| chr19 | 15860722 | 15860972 | 0.348 |
| chr19 | 16508380 | 16508630 | 0.344 |
| chr19 | 16737060 | 16737310 | 0.348 |
| chr19 | 16960936 | 16961186 | 0.3 |
| chr19 | 19135821 | 19136071 | 0.348 |
| chr19 | 19510651 | 19510901 | 0.348 |
| chr19 | 19952103 | 19952353 | 0.308 |
| chr19 | 20230842 | 20231092 | 0.336 |
| chr19 | 20462509 | 20462759 | 0.348 |
| chr19 | 21130690 | 21130940 | 0.284 |
| chr19 | 21131150 | 21131400 | 0.336 |
| chr19 | 21575132 | 21575382 | 0.348 |
| chr19 | 21961594 | 21961844 | 0.348 |
| chr19 | 22306026 | 22306276 | 0.34 |
| chr19 | 22764711 | 22764961 | 0.34 |
| chr19 | 23219468 | 23219718 | 0.268 |
| chr19 | 23594704 | 23594954 | 0.344 |
| chr19 | 23778748 | 23778998 | 0.344 |
| chr19 | 23985429 | 23985679 | 0.348 |
| chr19 | 24324202 | 24324452 | 0.288 |
| chr19 | 28272923 | 28273173 | 0.312 |
| chr19 | 28780463 | 28780713 | 0.348 |
| chr19 | 29320557 | 29320807 | 0.348 |
| chr19 | 29588492 | 29588742 | 0.348 |
| chr19 | 30033997 | 30034247 | 0.348 |
| chr19 | 30458220 | 30458470 | 0.348 |
| chr19 | 30892388 | 30892638 | 0.348 |
| chr19 | 31361227 | 31361477 | 0.348 |
| chr19 | 31763334 | 31763584 | 0.348 |
| chr19 | 32165641 | 32165891 | 0.348 |
| chr19 | 32560119 | 32560369 | 0.348 |
| chr19 | 32976620 | 32976733 | 0.312 |
| chr19 | 33350683 | 33350933 | 0.624 |
| chr19 | 33350754 | 33351004 | 0.592 |
| chr19 | 33354962 | 33355212 | 0.592 |
| chr19 | 33355018 | 33355268 | 0.58 |
| chr19 | 33413996 | 33414246 | 0.348 |
| chr19 | 33823022 | 33823272 | 0.348 |

| Ch. | Start | Stop | GC content |
|---|---|---|---|
| chr19 | 34284602 | 34284852 | 0.348 |
| chr19 | 34669651 | 34669901 | 0.336 |
| chr19 | 34965785 | 34966035 | 0.336 |
| chr19 | 35249399 | 35249649 | 0.348 |
| chr19 | 35605042 | 35605292 | 0.348 |
| chr19 | 36122870 | 36123120 | 0.348 |
| chr19 | 36322130 | 36322380 | 0.596 |
| chr19 | 36342381 | 36342631 | 0.656 |
| chr19 | 36727027 | 36727277 | 0.348 |
| chr19 | 37128748 | 37128998 | 0.288 |
| chr19 | 37563389 | 37563639 | 0.348 |
| chr19 | 37829474 | 37829724 | 0.34 |
| chr19 | 38122751 | 38123001 | 0.34 |
| chr19 | 38312990 | 38313240 | 0.344 |
| chr19 | 38681154 | 38681404 | 0.348 |
| chr19 | 38782852 | 38783102 | 0.348 |
| chr19 | 40029441 | 40029691 | 0.32 |
| chr19 | 40503907 | 40504157 | 0.348 |
| chr19 | 40632336 | 40632586 | 0.348 |
| chr19 | 40871180 | 40871430 | 0.348 |
| chr19 | 41799074 | 41799324 | 0.296 |
| chr19 | 41928413 | 41928663 | 0.6 |
| chr19 | 42144707 | 42144957 | 0.348 |
| chr19 | 43138347 | 43138597 | 0.348 |
| chr19 | 44349101 | 44349351 | 0.312 |
| chr19 | 44682330 | 44682580 | 0.348 |
| chr19 | 45059901 | 45060151 | 0.312 |
| chr19 | 46056772 | 46057022 | 0.7 |
| chr19 | 46102932 | 46103182 | 0.348 |
| chr19 | 46560162 | 46560412 | 0.348 |
| chr19 | 46954415 | 46954665 | 0.328 |
| chr19 | 47389774 | 47390024 | 0.348 |
| chr19 | 47692993 | 47693243 | 0.344 |
| chr19 | 48475123 | 48475373 | 0.316 |
| chr19 | 48764479 | 48764729 | 0.348 |
| chr19 | 50146477 | 50146727 | 0.348 |
| chr19 | 51713109 | 51713359 | 0.34 |
| chr19 | 52513511 | 52513761 | 0.288 |
| chr19 | 52920188 | 52920438 | 0.348 |
| chr19 | 53343345 | 53343595 | 0.348 |
| chr19 | 53669499 | 53669749 | 0.348 |
| chr19 | 54586305 | 54586555 | 0.3 |
| chr19 | 55068461 | 55068711 | 0.348 |
| chr19 | 55199832 | 55200082 | 0.348 |
| chr19 | 56219609 | 56219859 | 0.28 |
| chr19 | 56884255 | 56884505 | 0.316 |
| chr19 | 57437830 | 57438080 | 0.328 |
| chr19 | 58054419 | 58054669 | 0.316 |
| chr20 | 77170 | 77420 | 0.348 |
| chr20 | 519040 | 519290 | 0.32 |
| chr20 | 1147375 | 1147625 | 0.348 |
| chr20 | 1571446 | 1571696 | 0.348 |
| chr20 | 1947536 | 1947786 | 0.348 |
| chr20 | 2814622 | 2814872 | 0.348 |
| chr20 | 3211047 | 3211297 | 0.56 |
| chr20 | 3274903 | 3275153 | 0.348 |
| chr20 | 3631249 | 3631499 | 0.348 |
| chr20 | 3975347 | 3975597 | 0.348 |
| chr20 | 4449545 | 4449795 | 0.348 |
| chr20 | 5279681 | 5279931 | 0.348 |
| chr20 | 5753870 | 5754120 | 0.348 |
| chr20 | 6094874 | 6095124 | 0.328 |
| chr20 | 6498522 | 6498772 | 0.348 |
| chr20 | 6901553 | 6901803 | 0.348 |
| chr20 | 7729464 | 7729714 | 0.348 |
| chr20 | 8536150 | 8536400 | 0.324 |
| chr20 | 8928565 | 8928815 | 0.348 |
| chr20 | 9340986 | 9341236 | 0.344 |
| chr20 | 9740652 | 9740902 | 0.348 |
| chr20 | 10146600 | 10146850 | 0.348 |
| chr20 | 11388150 | 11388400 | 0.308 |
| chr20 | 11803150 | 11803400 | 0.336 |
| chr20 | 12195420 | 12195670 | 0.348 |
| chr20 | 12767453 | 12767703 | 0.348 |
| chr20 | 13141217 | 13141467 | 0.348 |
| chr20 | 13949320 | 13949570 | 0.348 |
| chr20 | 14353712 | 14353962 | 0.348 |
| chr20 | 14755112 | 14755362 | 0.348 |
| chr20 | 15359150 | 15359400 | 0.276 |
| chr20 | 15913249 | 15913499 | 0.296 |
| chr20 | 17347289 | 17347539 | 0.32 |
| chr20 | 17763020 | 17763270 | 0.348 |
| chr20 | 18167149 | 18167399 | 0.348 |
| chr20 | 18596512 | 18596762 | 0.348 |
| chr20 | 19409652 | 19409902 | 0.348 |
| chr20 | 19818614 | 19818864 | 0.308 |
| chr20 | 20210274 | 20210524 | 0.348 |
| chr20 | 20532551 | 20532801 | 0.324 |
| chr20 | 21026150 | 21026400 | 0.324 |
| chr20 | 21832473 | 21832723 | 0.348 |
| chr20 | 22237542 | 22237792 | 0.312 |
| chr20 | 22640479 | 22640729 | 0.324 |
| chr20 | 23060135 | 23060385 | 0.348 |
| chr20 | 23474780 | 23475030 | 0.34 |
| chr20 | 24275650 | 24275900 | 0.348 |
| chr20 | 24685964 | 24686214 | 0.308 |
| chr20 | 25109531 | 25109781 | 0.32 |
| chr20 | 25714681 | 25714931 | 0.296 |
| chr20 | 29847069 | 29847319 | 0.312 |
| chr20 | 30657384 | 30657634 | 0.336 |
| chr20 | 31291810 | 31292060 | 0.348 |
| chr20 | 31692805 | 31693055 | 0.348 |
| chr20 | 32588884 | 32589134 | 0.296 |
| chr20 | 32990720 | 32990970 | 0.336 |
| chr20 | 33396858 | 33397108 | 0.324 |
| chr20 | 33930796 | 33931046 | 0.332 |
| chr20 | 34021766 | 34022016 | 0.596 |
| chr20 | 34021782 | 34022032 | 0.596 |
| chr20 | 34021955 | 34022205 | 0.584 |
| chr20 | 34227958 | 34228208 | 0.348 |
| chr20 | 35300398 | 35300648 | 0.348 |
| chr20 | 35695232 | 35695482 | 0.348 |
| chr20 | 36150135 | 36150385 | 0.348 |
| chr20 | 36623218 | 36623468 | 0.348 |
| chr20 | 37117167 | 37117417 | 0.348 |
| chr20 | 37921224 | 37921474 | 0.348 |
| chr20 | 38322240 | 38322490 | 0.348 |
| chr20 | 38729196 | 38729446 | 0.348 |
| chr20 | 39510398 | 39510648 | 0.348 |
| chr20 | 40534390 | 40534640 | 0.348 |
| chr20 | 41411185 | 41411435 | 0.348 |
| chr20 | 41830566 | 41830816 | 0.348 |
| chr20 | 42275434 | 42275684 | 0.348 |
| chr20 | 42643867 | 42644117 | 0.348 |
| chr20 | 43115223 | 43115473 | 0.348 |
| chr20 | 43254061 | 43254311 | 0.676 |
| chr20 | 43254984 | 43255234 | 0.58 |
| chr20 | 44152521 | 44152771 | 0.348 |
| chr20 | 44496561 | 44496811 | 0.348 |
| chr20 | 44996290 | 44996540 | 0.348 |
| chr20 | 45529150 | 45529400 | 0.344 |
| chr20 | 45871441 | 45871691 | 0.348 |
| chr20 | 46844718 | 46844968 | 0.348 |
| chr20 | 47174893 | 47175143 | 0.348 |
| chr20 | 47650289 | 47650539 | 0.3 |
| chr20 | 47904517 | 47904767 | 0.348 |
| chr20 | 48480440 | 48480690 | 0.348 |
| chr20 | 49334830 | 49335080 | 0.348 |
| chr20 | 50145781 | 50146031 | 0.348 |
| chr20 | 50550520 | 50550770 | 0.34 |
| chr20 | 50950756 | 50951006 | 0.348 |
| chr20 | 51753303 | 51753553 | 0.336 |
| chr20 | 52324562 | 52324812 | 0.348 |
| chr20 | 53054192 | 53054442 | 0.348 |
| chr20 | 53454757 | 53455007 | 0.336 |
| chr20 | 53859987 | 53860237 | 0.348 |
| chr20 | 55091227 | 55091477 | 0.348 |
| chr20 | 55951837 | 55952087 | 0.324 |
| chr20 | 56403014 | 56403264 | 0.348 |
| chr20 | 57228245 | 57228495 | 0.348 |
| chr20 | 57694540 | 57694790 | 0.348 |
| chr20 | 58161403 | 58161653 | 0.348 |
| chr20 | 58567922 | 58568172 | 0.348 |
| chr20 | 58978600 | 58978850 | 0.348 |

| Ch. | Start | Stop | GC content |
|---|---|---|---|
| chr20 | 59778987 | 59779237 | 0.348 |
| chr20 | 60196684 | 60196934 | 0.348 |
| chr20 | 62318999 | 62319249 | 0.672 |
| chr20 | 62321379 | 62321629 | 0.624 |
| chr20 | 62326842 | 62327092 | 0.668 |
| chr20 | 62375183 | 62375433 | 0.348 |
| chr21 | 15481051 | 15481301 | 0.252 |
| chr21 | 15950150 | 15950400 | 0.344 |
| chr21 | 16081282 | 16081531 | 0.353414 |
| chr21 | 16206810 | 16207060 | 0.28 |
| chr21 | 16333315 | 16333564 | 0.381526 |
| chr21 | 16793392 | 16793642 | 0.348 |
| chr21 | 17135293 | 17135543 | 0.348 |
| chr21 | 17301983 | 17302232 | 0.381526 |
| chr21 | 17489798 | 17490048 | 0.296 |
| chr21 | 17695933 | 17696182 | 0.325301 |
| chr21 | 17823960 | 17824210 | 0.34 |
| chr21 | 17827150 | 17827400 | 0.344 |
| chr21 | 18229813 | 18230063 | 0.348 |
| chr21 | 18629909 | 18630159 | 0.348 |
| chr21 | 19024530 | 19024780 | 0.312 |
| chr21 | 19434035 | 19434285 | 0.348 |
| chr21 | 19707300 | 19707550 | 0.348 |
| chr21 | 20093300 | 20093550 | 0.276 |
| chr21 | 20474486 | 20474736 | 0.292 |
| chr21 | 20487286 | 20487536 | 0.264 |
| chr21 | 20890626 | 20890876 | 0.348 |
| chr21 | 21288139 | 21288389 | 0.348 |
| chr21 | 21685666 | 21685916 | 0.28 |
| chr21 | 22088785 | 22089035 | 0.348 |
| chr21 | 22490319 | 22490569 | 0.328 |
| chr21 | 22888860 | 22889110 | 0.328 |
| chr21 | 23136575 | 23136825 | 0.332 |
| chr21 | 23398370 | 23398620 | 0.268 |
| chr21 | 23827150 | 23827400 | 0.336 |
| chr21 | 24353533 | 24353783 | 0.3 |
| chr21 | 24895230 | 24895480 | 0.324 |
| chr21 | 25370366 | 25370616 | 0.348 |
| chr21 | 25689068 | 25689318 | 0.348 |
| chr21 | 26010566 | 26010816 | 0.308 |
| chr21 | 26339803 | 26340053 | 0.328 |
| chr21 | 26507298 | 26507547 | 0.353414 |
| chr21 | 26676239 | 26676489 | 0.348 |
| chr21 | 26969283 | 26969533 | 0.348 |
| chr21 | 27268636 | 27268636 | 0.348 |
| chr21 | 27520192 | 27520441 | 0.373494 |
| chr21 | 27761493 | 27761743 | 0.34 |
| chr21 | 28111207 | 28111457 | 0.32 |
| chr21 | 28291449 | 28291698 | 0.373494 |
| chr21 | 28420042 | 28420292 | 0.348 |
| chr21 | 28574819 | 28575068 | 0.369478 |
| chr21 | 28732222 | 28732472 | 0.316 |
| chr21 | 28919446 | 28919695 | 0.385542 |
| chr21 | 29085150 | 29085400 | 0.348 |
| chr21 | 29481927 | 29482177 | 0.256 |
| chr21 | 29886036 | 29886286 | 0.344 |
| chr21 | 30154482 | 30154732 | 0.348 |
| chr21 | 30301073 | 30301322 | 0.341365 |
| chr21 | 30415695 | 30415945 | 0.324 |
| chr21 | 30550132 | 30550381 | 0.349398 |
| chr21 | 30686458 | 30686708 | 0.34 |
| chr21 | 30810199 | 30810448 | 0.325301 |
| chr21 | 30956196 | 30956446 | 0.348 |
| chr21 | 31120815 | 31121064 | 0.341365 |
| chr21 | 31295615 | 31295865 | 0.312 |
| chr21 | 31494755 | 31495004 | 0.301205 |
| chr21 | 31631465 | 31631715 | 0.344 |
| chr21 | 31768996 | 31769245 | 0.309237 |
| chr21 | 31963626 | 31963876 | 0.284 |
| chr21 | 32291970 | 32292220 | 0.348 |
| chr21 | 32297150 | 32297400 | 0.324 |
| chr21 | 32704164 | 32704414 | 0.348 |
| chr21 | 33101826 | 33102076 | 0.348 |
| chr21 | 33555477 | 33555727 | 0.348 |
| chr21 | 33853735 | 33853983 | 0.310484 |
| chr21 | 33975120 | 33975370 | 0.348 |
| chr21 | 34142020 | 34142268 | 0.310484 |
| chr21 | 34381366 | 34381616 | 0.348 |
| chr21 | 34787647 | 34787897 | 0.348 |
| chr21 | 35034581 | 35034830 | 0.341365 |
| chr21 | 35210083 | 35210333 | 0.348 |
| chr21 | 35450331 | 35450580 | 0.401606 |
| chr21 | 35628286 | 35628536 | 0.348 |
| chr21 | 36049058 | 36049308 | 0.336 |
| chr21 | 36447052 | 36447302 | 0.292 |
| chr21 | 36789088 | 36789337 | 0.409639 |
| chr21 | 36929380 | 36929630 | 0.348 |
| chr21 | 37306439 | 37306689 | 0.348 |
| chr21 | 37620268 | 37620518 | 0.348 |
| chr21 | 37998204 | 37998454 | 0.276 |
| chr21 | 38267857 | 38268107 | 0.348 |
| chr21 | 38308910 | 38309160 | 0.532 |
| chr21 | 38537188 | 38537438 | 0.348 |
| chr21 | 39149737 | 39149987 | 0.348 |
| chr21 | 39442392 | 39442641 | 0.325301 |
| chr21 | 39679043 | 39679293 | 0.348 |
| chr21 | 39977160 | 39977409 | 0.413655 |
| chr21 | 40125556 | 40125806 | 0.348 |
| chr21 | 40427338 | 40427587 | 0.389558 |
| chr21 | 40759240 | 40759493 | 0.363636 |
| chr21 | 40972106 | 40972356 | 0.348 |
| chr21 | 41160090 | 41160343 | 0.359684 |
| chr21 | 41344027 | 41344277 | 0.348 |
| chr21 | 41592339 | 41592583 | 0.311475 |
| chr21 | 41767335 | 41767585 | 0.296 |
| chr21 | 42029142 | 42029391 | 0.393574 |
| chr21 | 42263335 | 42263585 | 0.292 |
| chr21 | 42729150 | 42729400 | 0.34 |
| chr21 | 43306231 | 43306481 | 0.348 |
| chr21 | 43667110 | 43667358 | 0.310484 |
| chr21 | 43883150 | 43883400 | 0.316 |
| chr21 | 44196371 | 44196621 | 0.348 |
| chr21 | 44424545 | 44424795 | 0.348 |
| chr21 | 44482314 | 44482564 | 0.652 |
| chr21 | 44482356 | 44482606 | 0.648 |
| chr21 | 44482953 | 44483203 | 0.636 |
| chr21 | 44483059 | 44483309 | 0.584 |
| chr21 | 44483916 | 44484166 | 0.604 |
| chr21 | 44485497 | 44485747 | 0.648 |
| chr21 | 44625010 | 44625260 | 0.348 |
| chr21 | 44948824 | 44949074 | 0.336 |
| chr21 | 45178504 | 45178754 | 0.348 |
| chr21 | 45472144 | 45472394 | 0.348 |
| chr21 | 45706431 | 45706681 | 0.636 |
| chr21 | 46000694 | 46000944 | 0.336 |
| chr21 | 46270689 | 46270939 | 0.348 |
| chr21 | 46533710 | 46533960 | 0.348 |
| chr21 | 46760919 | 46761169 | 0.348 |
| chr21 | 47065442 | 47065692 | 0.348 |
| chr22 | 17280474 | 17280724 | 0.3 |
| chr22 | 17413925 | 17414175 | 0.348 |
| chr22 | 17781671 | 17781921 | 0.348 |
| chr22 | 17935494 | 17935744 | 0.284 |
| chr22 | 18094028 | 18094278 | 0.344 |
| chr22 | 18344493 | 18344743 | 0.348 |
| chr22 | 18595330 | 18595580 | 0.348 |
| chr22 | 19219301 | 19219551 | 0.324 |
| chr22 | 19565525 | 19565775 | 0.348 |
| chr22 | 19766919 | 19767169 | 0.348 |
| chr22 | 19947592 | 19947842 | 0.348 |
| chr22 | 20817080 | 20817330 | 0.34 |
| chr22 | 21139822 | 21140072 | 0.348 |
| chr22 | 21292445 | 21292695 | 0.316 |
| chr22 | 22024679 | 22024929 | 0.34 |
| chr22 | 22438898 | 22439148 | 0.348 |
| chr22 | 22839744 | 22839994 | 0.348 |
| chr22 | 23278902 | 23279152 | 0.348 |
| chr22 | 24248051 | 24248301 | 0.348 |
| chr22 | 24718846 | 24719096 | 0.348 |
| chr22 | 25113444 | 25113694 | 0.252 |
| chr22 | 25588970 | 25589220 | 0.348 |
| chr22 | 25966386 | 25966636 | 0.348 |
| chr22 | 26120347 | 26120597 | 0.348 |
| chr22 | 26362974 | 26363224 | 0.348 |

| Ch. | Start | Stop | GC content |
|---|---|---|---|
| chr22 | 26769343 | 26769593 | 0.304 |
| chr22 | 26922260 | 26922510 | 0.348 |
| chr22 | 27163955 | 27164205 | 0.348 |
| chr22 | 27601162 | 27601412 | 0.284 |
| chr22 | 27994362 | 27994612 | 0.312 |
| chr22 | 28270441 | 28270691 | 0.348 |
| chr22 | 28446625 | 28446875 | 0.348 |
| chr22 | 28640282 | 28640532 | 0.348 |
| chr22 | 28820811 | 28821061 | 0.348 |
| chr22 | 29045556 | 29045806 | 0.284 |
| chr22 | 29395916 | 29396166 | 0.348 |
| chr22 | 29412378 | 29412628 | 0.348 |
| chr22 | 29826594 | 29826844 | 0.308 |
| chr22 | 30000222 | 30000472 | 0.348 |
| chr22 | 30257427 | 30257677 | 0.348 |
| chr22 | 30425284 | 30425534 | 0.348 |
| chr22 | 30587479 | 30587729 | 0.348 |
| chr22 | 31117594 | 31117844 | 0.336 |
| chr22 | 31392528 | 31392778 | 0.348 |
| chr22 | 31691832 | 31692082 | 0.348 |
| chr22 | 32113185 | 32113435 | 0.348 |
| chr22 | 32353173 | 32353423 | 0.348 |
| chr22 | 32505557 | 32505807 | 0.348 |
| chr22 | 32969346 | 32969596 | 0.348 |
| chr22 | 33257698 | 33257948 | 0.348 |
| chr22 | 33562806 | 33563056 | 0.348 |
| chr22 | 33590196 | 33590446 | 0.348 |
| chr22 | 34018923 | 34019173 | 0.348 |
| chr22 | 34236108 | 34236358 | 0.328 |
| chr22 | 34418259 | 34418509 | 0.348 |
| chr22 | 34803406 | 34803656 | 0.328 |
| chr22 | 35219092 | 35219342 | 0.348 |
| chr22 | 35677229 | 35677479 | 0.348 |
| chr22 | 36136285 | 36136535 | 0.348 |
| chr22 | 36340176 | 36340426 | 0.348 |
| chr22 | 36559863 | 36560113 | 0.348 |
| chr22 | 36958950 | 36959200 | 0.288 |
| chr22 | 37366224 | 37366474 | 0.292 |
| chr22 | 38615284 | 38615534 | 0.348 |
| chr22 | 38882398 | 38882648 | 0.348 |
| chr22 | 39066577 | 39066827 | 0.268 |
| chr22 | 39483473 | 39483723 | 0.348 |
| chr22 | 39913116 | 39913366 | 0.348 |
| chr22 | 40285123 | 40285373 | 0.348 |
| chr22 | 40441816 | 40442066 | 0.348 |
| chr22 | 40724377 | 40724627 | 0.348 |
| chr22 | 40928202 | 40928452 | 0.348 |
| chr22 | 41164700 | 41164950 | 0.3 |
| chr22 | 41570976 | 41571226 | 0.34 |
| chr22 | 42031998 | 42032248 | 0.336 |
| chr22 | 42253945 | 42254195 | 0.348 |
| chr22 | 43414341 | 43414591 | 0.328 |
| chr22 | 43819506 | 43819756 | 0.348 |
| chr22 | 44083042 | 44083292 | 0.348 |
| chr22 | 44213665 | 44213915 | 0.348 |
| chr22 | 44359248 | 44359498 | 0.348 |
| chr22 | 44852852 | 44853102 | 0.348 |
| chr22 | 45225408 | 45225658 | 0.348 |
| chr22 | 45545508 | 45545758 | 0.312 |
| chr22 | 45714432 | 45714682 | 0.348 |
| chr22 | 46038547 | 46038797 | 0.348 |
| chr22 | 46231545 | 46231795 | 0.348 |
| chr22 | 46456342 | 46456592 | 0.344 |
| chr22 | 46757150 | 46757400 | 0.344 |
| chr22 | 46988693 | 46988943 | 0.348 |
| chr22 | 47288440 | 47288690 | 0.348 |
| chr22 | 47643065 | 47643315 | 0.348 |
| chr22 | 48053341 | 48053591 | 0.348 |
| chr22 | 48217987 | 48218237 | 0.348 |
| chr22 | 48451914 | 48452164 | 0.348 |
| chr22 | 48864259 | 48864509 | 0.316 |
| chr22 | 49252506 | 49252756 | 0.348 |
| chr22 | 49500880 | 49501130 | 0.348 |
| chr22 | 49668127 | 49668377 | 0.348 |
| chr22 | 50072698 | 50072948 | 0.348 |
| chr22 | 50281645 | 50281895 | 0.348 |
| chr22 | 50523016 | 50523266 | 0.62 |
| chr22 | 50523047 | 50523297 | 0.648 |
| chr22 | 50558794 | 50559044 | 0.348 |
| chr22 | 50979168 | 50979418 | 0.332 |
| chr22 | 51063685 | 51063935 | 0.632 |
| chr22 | 51063716 | 51063966 | 0.652 |
| chr22 | 51063856 | 51064106 | 0.636 |
| chr22 | 51064009 | 51064259 | 0.64 |
| chr22 | 51064554 | 51064804 | 0.636 |
| chr22 | 51064921 | 51065171 | 0.62 |
| chr22 | 51065196 | 51065446 | 0.644 |
| chr22 | 51065453 | 51065703 | 0.68 |
| chr22 | 51065622 | 51065872 | 0.692 |
| chr22 | 51065688 | 51065938 | 0.656 |
| chrX | 2653932 | 2654182 | 0.548 |
| chrX | 2770647 | 2770897 | 0.348 |
| chrX | 3968150 | 3968400 | 0.312 |
| chrX | 4779861 | 4780111 | 0.348 |
| chrX | 5885150 | 5885400 | 0.344 |
| chrX | 7690150 | 7690400 | 0.316 |
| chrX | 8539329 | 8539579 | 0.292 |
| chrX | 9558559 | 9558809 | 0.32 |
| chrX | 10440260 | 10440510 | 0.348 |
| chrX | 11270150 | 11270400 | 0.344 |
| chrX | 12084750 | 12084800 | 0.312 |
| chrX | 13139540 | 13139790 | 0.348 |
| chrX | 14033255 | 14033505 | 0.348 |
| chrX | 15180150 | 15180400 | 0.344 |
| chrX | 16478150 | 16478400 | 0.316 |
| chrX | 17543222 | 17543472 | 0.32 |
| chrX | 18343366 | 18343616 | 0.32 |
| chrX | 19620578 | 19620828 | 0.348 |
| chrX | 20660335 | 20660585 | 0.348 |
| chrX | 21600150 | 21600400 | 0.34 |
| chrX | 22488497 | 22488747 | 0.348 |
| chrX | 23421185 | 23421435 | 0.348 |
| chrX | 24286150 | 24286400 | 0.312 |
| chrX | 25225575 | 25225825 | 0.348 |
| chrX | 26415364 | 26415614 | 0.348 |
| chrX | 27442376 | 27442626 | 0.316 |
| chrX | 28358150 | 28358400 | 0.312 |
| chrX | 29322235 | 29322485 | 0.348 |
| chrX | 30143185 | 30143435 | 0.348 |
| chrX | 31244468 | 31244718 | 0.344 |
| chrX | 32330150 | 32330400 | 0.296 |
| chrX | 33207324 | 33207574 | 0.308 |
| chrX | 34080150 | 34080400 | 0.332 |
| chrX | 34915259 | 34915509 | 0.344 |
| chrX | 35745301 | 35745551 | 0.32 |
| chrX | 36960179 | 36960429 | 0.348 |
| chrX | 37778455 | 37778705 | 0.34 |
| chrX | 38654560 | 38654810 | 0.312 |
| chrX | 39492888 | 39493138 | 0.348 |
| chrX | 40403451 | 40403701 | 0.348 |
| chrX | 41413158 | 41413408 | 0.348 |
| chrX | 42505150 | 42505400 | 0.34 |
| chrX | 43341210 | 43341460 | 0.348 |
| chrX | 44349185 | 44349435 | 0.34 |
| chrX | 45184425 | 45184675 | 0.348 |
| chrX | 46580312 | 46580562 | 0.344 |
| chrX | 47466548 | 47466798 | 0.348 |
| chrX | 48435007 | 48435258 | 0.348 |
| chrX | 49458818 | 49459068 | 0.328 |
| chrX | 50267179 | 50267429 | 0.348 |
| chrX | 51169150 | 51169400 | 0.324 |
| chrX | 51984557 | 51984807 | 0.316 |
| chrX | 52850579 | 52850829 | 0.348 |
| chrX | 53651747 | 53651997 | 0.348 |
| chrX | 54703818 | 54704068 | 0.332 |
| chrX | 56115356 | 56115606 | 0.348 |
| chrX | 56993967 | 56994217 | 0.348 |
| chrX | 57799496 | 57799746 | 0.348 |
| chrX | 62058452 | 62058702 | 0.348 |
| chrX | 63165214 | 63165464 | 0.344 |
| chrX | 63970645 | 63970895 | 0.344 |
| chrX | 64917421 | 64917671 | 0.348 |
| chrX | 65735342 | 65735592 | 0.348 |
| chrX | 66564534 | 66564784 | 0.348 |

| Ch. | Start | Stop | GC content |
|---|---|---|---|
| chrX | 67367876 | 67368126 | 0.348 |
| chrX | 68232212 | 68232462 | 0.348 |
| chrX | 69033716 | 69033966 | 0.348 |
| chrX | 69844167 | 69844417 | 0.344 |
| chrX | 71427432 | 71427682 | 0.348 |
| chrX | 72458405 | 72458655 | 0.348 |
| chrX | 73325904 | 73326154 | 0.348 |
| chrX | 74137571 | 74137821 | 0.348 |
| chrX | 75450150 | 75450400 | 0.304 |
| chrX | 76759150 | 76759400 | 0.324 |
| chrX | 77931150 | 77931400 | 0.344 |
| chrX | 78819276 | 78819526 | 0.348 |
| chrX | 79927150 | 79927400 | 0.292 |
| chrX | 80748375 | 80748625 | 0.3 |
| chrX | 81551352 | 81551602 | 0.296 |
| chrX | 82359761 | 82360011 | 0.296 |
| chrX | 83477290 | 83477540 | 0.28 |
| chrX | 84366205 | 84366455 | 0.256 |
| chrX | 85465150 | 85465400 | 0.288 |
| chrX | 86318150 | 86318400 | 0.316 |
| chrX | 87144287 | 87144537 | 0.292 |
| chrX | 87968502 | 87968752 | 0.284 |
| chrX | 89282095 | 89282345 | 0.344 |
| chrX | 90302716 | 90302966 | 0.288 |
| chrX | 91429162 | 91429412 | 0.32 |
| chrX | 92438331 | 92438581 | 0.288 |
| chrX | 93246796 | 93247046 | 0.32 |
| chrX | 94085648 | 94085898 | 0.304 |
| chrX | 94891150 | 94891400 | 0.276 |
| chrX | 95711217 | 95711467 | 0.348 |
| chrX | 96648150 | 96648400 | 0.348 |
| chrX | 97471150 | 97471400 | 0.328 |
| chrX | 98557428 | 98557678 | 0.348 |
| chrX | 99863553 | 99863803 | 0.348 |
| chrX | 102182150 | 102182400 | 0.28 |
| chrX | 102990468 | 102990718 | 0.34 |
| chrX | 104258320 | 104258570 | 0.348 |
| chrX | 105096264 | 105096514 | 0.348 |
| chrX | 105974498 | 105974748 | 0.324 |
| chrX | 106776228 | 106776478 | 0.348 |
| chrX | 107581900 | 107582150 | 0.348 |
| chrX | 108432389 | 108432639 | 0.348 |
| chrX | 109447214 | 109447464 | 0.348 |
| chrX | 110387150 | 110387400 | 0.344 |
| chrX | 111297150 | 111297400 | 0.324 |
| chrX | 112213179 | 112213429 | 0.328 |
| chrX | 113024257 | 113024507 | 0.34 |
| chrX | 114142520 | 114142770 | 0.348 |
| chrX | 115476183 | 115476433 | 0.348 |
| chrX | 116479598 | 116479848 | 0.292 |
| chrX | 117493202 | 117493452 | 0.328 |
| chrX | 118384548 | 118384798 | 0.348 |
| chrX | 119427212 | 119427462 | 0.348 |
| chrX | 120380150 | 120380400 | 0.348 |
| chrX | 121219432 | 121219682 | 0.276 |
| chrX | 122166150 | 122166400 | 0.308 |
| chrX | 122994558 | 122994808 | 0.348 |
| chrX | 123971391 | 123971641 | 0.348 |
| chrX | 125186473 | 125186723 | 0.332 |
| chrX | 126046357 | 126046607 | 0.348 |
| chrX | 126855255 | 126855505 | 0.332 |
| chrX | 127687504 | 127687754 | 0.348 |
| chrX | 128495196 | 128495446 | 0.348 |
| chrX | 129596551 | 129596801 | 0.348 |
| chrX | 130429675 | 130429925 | 0.34 |
| chrX | 131260508 | 131260758 | 0.348 |
| chrX | 132208598 | 132208848 | 0.348 |
| chrX | 133010150 | 133010400 | 0.344 |
| chrX | 133923287 | 133923537 | 0.348 |
| chrX | 135091150 | 135091400 | 0.332 |
| chrX | 136037150 | 136037400 | 0.328 |
| chrX | 136863150 | 136863400 | 0.324 |
| chrX | 137744150 | 137744400 | 0.328 |
| chrX | 138579590 | 138579840 | 0.336 |
| chrX | 139824185 | 139824435 | 0.348 |
| chrX | 140904478 | 140904728 | 0.316 |
| chrX | 141983247 | 141983497 | 0.348 |

| Ch. | Start | Stop | GC content |
|---|---|---|---|
| chrX | 142791108 | 142791358 | 0.344 |
| chrX | 143621663 | 143621913 | 0.348 |
| chrX | 144958182 | 144958432 | 0.348 |
| chrX | 145759329 | 145759579 | 0.344 |
| chrX | 146589192 | 146589442 | 0.348 |
| chrX | 147591150 | 147591400 | 0.344 |
| chrX | 148452186 | 148452436 | 0.348 |
| chrX | 149357308 | 149357558 | 0.348 |
| chrX | 150240045 | 150240295 | 0.348 |
| chrX | 151043387 | 151043637 | 0.348 |
| chrX | 152016983 | 152017233 | 0.348 |
| chrX | 153113554 | 153113804 | 0.348 |
| chrX | 154180278 | 154180528 | 0.348 |
| chrY | 2660772 | 2661021 | 0.361446 |
| chrY | 2710538 | 2710787 | 0.445783 |
| chrY | 2818858 | 2819107 | 0.37751 |
| chrY | 2831578 | 2831827 | 0.349398 |
| chrY | 2846524 | 2846773 | 0.329317 |
| chrY | 2903702 | 2903952 | 0.3 |
| chrY | 3713664 | 3713914 | 0.312 |
| chrY | 6592835 | 6593085 | 0.348 |
| chrY | 6785795 | 6786044 | 0.433735 |
| chrY | 6991732 | 6991982 | 0.348 |
| chrY | 7619930 | 7620180 | 0.328 |
| chrY | 7628101 | 7628351 | 0.34 |
| chrY | 7645822 | 7646072 | 0.288 |
| chrY | 7655666 | 7655916 | 0.348 |
| chrY | 7859013 | 7859263 | 0.348 |
| chrY | 8234092 | 8234342 | 0.348 |
| chrY | 8843984 | 8844234 | 0.324 |
| chrY | 9004092 | 9004341 | 0.405622 |
| chrY | 9415984 | 9416234 | 0.332 |
| chrY | 9894154 | 9894404 | 0.328 |
| chrY | 14188444 | 14188694 | 0.336 |
| chrY | 14638059 | 14638309 | 0.348 |
| chrY | 15017843 | 15018092 | 0.445783 |
| chrY | 15021516 | 15021765 | 0.35743 |
| chrY | 15473334 | 15473583 | 0.353414 |
| chrY | 15819282 | 15819532 | 0.348 |
| chrY | 16228505 | 16228755 | 0.348 |
| chrY | 16629874 | 16630124 | 0.348 |
| chrY | 16837863 | 16838110 | 0.376518 |
| chrY | 17030033 | 17030283 | 0.296 |
| chrY | 17232877 | 17233127 | 0.308 |
| chrY | 17234803 | 17235053 | 0.308 |
| chrY | 17236192 | 17236442 | 0.288 |
| chrY | 17456632 | 17456882 | 0.348 |
| chrY | 17852621 | 17852871 | 0.304 |
| chrY | 18264936 | 18265186 | 0.308 |
| chrY | 18676622 | 18676872 | 0.304 |
| chrY | 18884770 | 18885020 | 0.3 |
| chrY | 19086733 | 19086983 | 0.348 |
| chrY | 19287757 | 19288007 | 0.348 |
| chrY | 19317270 | 19317520 | 0.348 |
| chrY | 19321140 | 19321390 | 0.28 |
| chrY | 19336515 | 19336765 | 0.348 |
| chrY | 19343744 | 19343994 | 0.308 |
| chrY | 19345482 | 19345732 | 0.348 |
| chrY | 19551092 | 19551342 | 0.34 |
| chrY | 20807527 | 20807777 | 0.34 |
| chrY | 21231948 | 21232198 | 0.328 |
| chrY | 21617999 | 21618249 | 0.304 |
| chrY | 21825259 | 21825509 | 0.34 |
| chrY | 21870303 | 21870553 | 0.348 |
| chrY | 21882430 | 21882680 | 0.348 |
| chrY | 21889152 | 21889402 | 0.312 |
| chrY | 21892914 | 21893164 | 0.336 |
| chrY | 21896890 | 21897140 | 0.308 |
| chrY | 22098161 | 22098411 | 0.252 |
| chrY | 22519572 | 22519822 | 0.28 |
| chrY | 22923958 | 22924208 | 0.348 |
| chrY | 23365875 | 23366125 | 0.344 |
| chrY | 23594574 | 23594824 | 0.348 |
| chrY | 23598786 | 23599036 | 0.32 |
| chrY | 23770609 | 23770859 | 0.348 |
| chrY | 23772351 | 23772601 | 0.344 |

DETAILED DESCRIPTION

The invention pertains to a method for analyzing genetic abnormalities that involves hybridization-based enrichment of selected target regions across the human genome in a multiplexed panel assay, followed by quantification, coupled with a novel bioinformatics and mathematical analysis pipeline. An overview of the method is shown schematically in FIG. 1.

In-solution hybridization enrichment has been used in the past to enrich specific regions of interest prior to sequencing (see e.g., Meyer, M and Kirchner, M. (2010) *Cold Spring Harb. Protoc.* 2010(6):pdbprot5448; Liao, G. J. et al. (2012) *PLoS One* 7:e38154; Maricic, T. et al. (2010) *PLoS One* 5:e14004; Tewhey, R. et al. (2009) *Genome Biol.* 10:R116; Tsangaras, K. et al. (2014) *PLoS One* 9:e109101; PCT Publication WO 2016/189388; US Patent Publication 2016/0340733; Koumbaris, G. et al. (2015) *Clinical chemistry*, 62(6), pp. 848-855). However, for the methods of the invention, the target sequences (referred to as TArget Capture Sequences, or TACS) used to enrich for specific regions of interest have been optimized for maximum efficiency, specificity and accuracy and, furthermore, allow for analysis of very small starting amounts of fetal or embryonic DNA in samples containing only or predominantly fetal or embryonic DNA.

Figure 3:
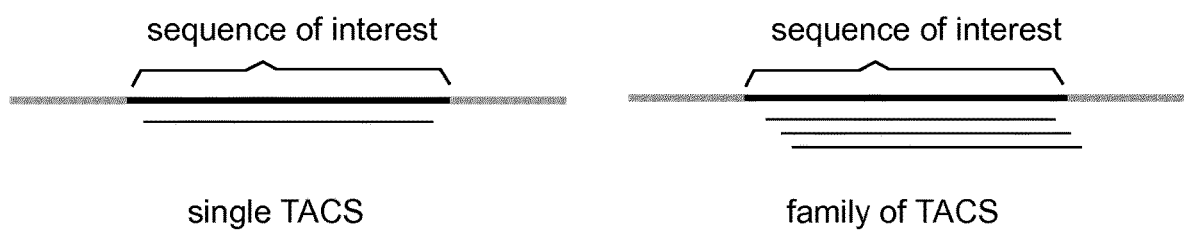
FIG. 3 is a schematic diagram of TACS-based enrichment of a sequence of interest (bold line) using a single TACS (left) versus TACS-based enrichment using a family of TACS (right).

Furthermore, in certain embodiments, the TACS used in the methods are families of TACS, comprising a plurality of members that bind to the same genomic sequence but with differing start and/or stop positions, such that enrichment of the genomic sequences of interest is significantly improved compared to use of a single TACS binding to the genomic sequence. The configuration of such families of TACS is illustrated schematically in FIG. 3, showing that the different start and/or stop positions of the members of the TACS family when bound to the genomic sequence of interest results in a staggered binding pattern for the family members.

The use of families of TACS with the TACS pool that bind to each target sequence of interest, as compared to use of a single TACS within the TACS pool that binds to each target sequence of interest, significantly increases enrichment for the target sequences of interest, as evidenced by a greater than 50% average increase in read-depth for the family of TACS versus a single TACS. Comparison of use of a family of TACS versus a single TACS, and the significantly improved read-depth that was observed, is described in detail in Example 5.

Analysis of Fetal/Embryonic DNA Samples

The methods and kits of the disclosure are used in the analysis of fetal or embryonic DNA samples, e.g., for the presence of genetic abnormalities, for example for purposes of IVF Pre-implantation Genetic Screening (PGS) and Diagnosis (PGD). Accordingly, in the methods of the invention, the DNA sample comprises predominantly or only fetal or embryonic DNA. The methods can be used with samples from a single or only a few fetal or embryonic cells. As used herein "a few" fetal or embryonic cells refers to 10 fetal or embryonic cells or less. Accordingly, the methods allow for analysis of very small amounts of fetal or embryonic DNA. The fetal or embryonic DNA sample contains predominantly or only fetal/embryonic DNA, described further below in the subsection on sample preparation. An exemplification of use of the method with samples from 3-day and 5-day biopsy embryos is described in Example 6.

Accordingly, in one aspect, the invention pertains to a method of testing for risk of a genetic abnormality in a DNA sample comprising predominantly fetal or embryonic DNA and comprising genomic sequences of interest, the method comprising:
  (a) preparing a sequencing library from the DNA sample comprising predominantly fetal or embryonic DNA;
  (b) hybridizing the sequencing library to a pool of double-stranded TArget Capture Sequences (TACS), wherein the pool of TACS comprises sequences that bind to one or more genomic sequences of interest comprising a genetic abnormality;
  (c) isolating members of the sequencing library that bind to the pool of TACS to obtain an enriched library;
  (d) amplifying and sequencing the enriched library; and
  (e) performing statistical analysis on the enriched library sequences to thereby determine risk of a genetic abnormality in the DNA sample.

In one embodiment:
  (i) each member sequence within the pool of TACS is between 100-500 base pairs in length, each member sequence having a 5' end and a 3' end;
  (ii) each member sequence binds to the same genomic sequence of interest at least 50 base pairs away, on both the 5' end and the 3' end, from regions harboring Copy Number Variations (CNVs), Segmental duplications or repetitive DNA elements; and
  (iii) the GC content of the pool of TACS is between 19% and 80%, as determined by calculating the GC content of each member within the pool of TACS.

In one embodiment, the pool of TACS comprises a plurality of TACS families, wherein each member of a TACS family binds to the same target sequence of interest but with different start and/or stop positions on the sequence with respect to a reference coordinate system (i.e., binding of TACS family members to the target sequence is staggered) to thereby enrich for target sequences of interest, followed by massive parallel sequencing and statistical analysis of the enriched population. The use of families of TACS with the TACS pool that bind to each target sequence of interest, as compared to use of a single TACS within the TACS pool that binds to each target sequence of interest, significantly increases enrichment for the target sequences of interest, as evidenced by a greater than 50% average increase in read-depth for the family of TACS versus a single TACS.

Accordingly, in one embodiment, the pool of TACS comprises a plurality of TACS families directed to different genomic sequences of interest, wherein each TACS family comprises a plurality of member sequences, wherein each member sequence binds to the same genomic sequence of interest but has different start and/or stop positions with respect to a reference coordinate system for the genomic sequence of interest.

Thus, in another aspect, the invention pertains to a method of testing for risk of a genetic abnormality in a DNA sample comprising predominantly fetal or embryonic DNA and comprising genomic sequences of interest, the method comprising:
  (a) preparing a sequencing library from the DNA sample comprising predominantly fetal or embryonic DNA;
  (b) hybridizing the sequencing library to a pool of double-stranded TArget Capture Sequences (TACS), wherein the pool of TACS comprises a plurality of TACS families directed to different genomic sequences of interest, wherein each TACS family comprises a plurality of member sequences, wherein each member sequence binds to the same genomic sequence of interest but has different start and/or stop positions with respect to a reference coordinate system for the genomic sequence of interest;
(c) isolating members of the sequencing library that bind to the pool of TACS to obtain an enriched library;
(d) amplifying and sequencing the enriched library; and
(e) performing statistical analysis on the enriched library sequences to thereby determine risk of a genetic abnormality in the DNA sample.

In one embodiment,
(i) each member sequence within each TACS family is between 100-500 base pairs in length, each member sequence having a 5' end and a 3' end;
(ii) each member sequence binds to the same genomic sequence of interest at least 50 base pairs away, on both the 5' end and the 3' end, from regions harboring Copy Number Variations (CNVs), Segmental duplications or repetitive DNA elements; and
(iii) the GC content of the pool of TACS is between 19% and 80%, as determined by calculating the GC content of each member within each family of TACS.

The TACS-enrichment based method of the disclosure can be used in the detection of a wide variety of genetic abnormalities. In one embodiment, the genetic abnormality is a chromosomal aneuploidy (such as a trisomy, a partial trisomy or a monosomy). In other embodiments, the genomic abnormality is a structural abnormality, including but not limited to copy number changes including microdeletions and microduplications, insertions, translocations, inversions and small-size mutations including point mutations and mutational signatures. In another embodiment, the genetic abnormality is a chromosomal mosaicism.

TArget Capture Sequence Design

As used herein, the term "TArget Capture Sequences" or "TACS" refers to short DNA sequences that are complementary to the region(s) of interest on a genomic sequence (s) of interest (e.g., chromosome(s) of interest) and which are used as "bait" to capture and enrich the region of interest from a large library of sequences, such as a whole genomic sequencing library prepared from a biological sample. A pool of TACS is used for enrichment wherein the sequences within the pool have been optimized with regard to: (i) the length of the sequences; (ii) the distribution of the TACS across the region(s) of interest; and (iii) the GC content of the TACS. The number of sequences within the TACS pool (pool size) has also been optimized.

It has been discovered that TACS having a length of 100-500 base pairs are optimal to maximize enrichment efficiency. In various other embodiments, each sequence within the pool of TACS is between 150-260 base pairs, 100-200 base pairs, 200-260 base pairs, 100-350 bp in length, or 100-500 bp in length. In preferred embodiments, the length of the TACS within the pool is at least 250 base pairs, or is 250 base pairs or is 260 base pairs or is 280 base pairs. It will be appreciated by the ordinarily skilled artisan that a slight variation in TACS size typically can be used without altering the results (e.g., the addition or deletion of a few base pairs on either end of the TACS); accordingly, the base pair lengths given herein are to be considered "about" or "approximate", allowing for some slight variation (e.g., 1-5%) in length. Thus, for example, a length of "250 base pairs" is intended to refer to "about 250 base pairs" or "approximately 250 base pairs", such that, for example, 248 or 252 base pairs is also encompassed.

The distribution of the TACS across each region or chromosome of interest has been optimized to avoid high copy repeats, low copy repeats and copy number variants, while at the same time also being able to target informative single nucleotide polymorphisms (SNPs) in order to enable both aneuploidy, or structural copy number change detection, and fetal fraction (ff) estimation. Accordingly, each sequence within the TACS pool is designed such that the 5' end and the 3' end are each at least 50 base pairs away from regions in the genome that are known to harbour one or more of the following genomic elements: Copy Number Variations (CNVs), Segmental duplications and/or repetitive DNA elements (such as transposable elements or tandem repeat areas). In various other embodiments, each sequence within the TACS pool is designed such that the 5' end and the 3' end are each at least 50, 100, 150, 200, 250, 300, 400 or 500 base pairs away from regions in the genome that are known to harbour one or more of the aforementioned elements.

The term "Copy Number Variations" is a term of art that refers to a form of structural variation in the human genome in which there can be alterations in the DNA of the genome in different individuals that can result in a fewer or greater than normal number of a section(s) of the genome in certain individuals. CNVs correspond to relatively large regions of the genome that may be deleted (e.g., a section that normally is A-B-C-D can be A-B-D) or may be duplicated (e.g., a section that normally is A-B-C-D can be A-B-C-C-D). CNVs account for roughly 13% of the human genome, with each variation ranging in size from about 1 kilobase to several megabases in size.

The term "Segmental duplications" (also known as "low-copy repeats") is also a term of art that refers to blocks of DNA that range from about 1 to 400 kilobases in length that occur at more than one site within the genome and typically share a high level (greater than 90%) of sequence identity. Segmental duplications are reviewed in, for example, Eichler. E. E. (2001) *Trends Genet.* 17:661-669.

The term "repetitive DNA elements" (also known as "repeat DNA" or "repeated DNA") is also a term of art that refers to patterns of DNA that occur in multiple copies throughout the genome. The term "repetitive DNA element" encompasses terminal repeats, tandem repeats and interspersed repeats, including transposable elements. Repetitive DNA elements in NGS is discussed further in, for example, Todd, J. et al. (2012) *Nature Reviews Genet.* 13:36-46.

The TACS are designed with specific GC content characteristics in order to minimize data GC bias and to allow a custom and innovative data analysis pipeline. It has been determined that TACS with a GC content of 19-80% achieve optimal enrichment and perform best with cell free fetal DNA. Within the pool of TACS, different sequences can have different % GC content, although to be selected for inclusion with the pool, the % GC content of each sequence is chosen as between 19-80%, as determined by calculating the GC content of each member within the pool of TACS or within each family of TACS. That is, every member within the pool or within each family of TACS in the pool has a % GC content within the given percentage range (e.g., between 19-80% GC content).

In some instances, the pool of TACS (e.g., each member within each family of TACS) may be chosen so as to define a different % GC content range, deemed to be more suitable for the assessment of specific genetic abnormalities. Non-limiting examples of various % GC content ranges, can be between 19% and 80%, or between 19% and 79%, or between 19% and 78%, or between 19% and 77%, or between 19% and 76%, or between 19% and 75%, or between 19% and 74%, or between 19% and 73%, or between 19% and 72%, or between 19% and 71%, or between 19% and 70%, or between 19% and 69%, or between 19% and 68%, or between 19% and 67%, or between 19% and 66%, or between 19% and 65%, or between 19% and 64%, or between 19% and 63%, or between 19% and 62%, or between 19% and 61%, or between 19% and 60%, or between 19% and 59%, or between 19% and 58%, or between 19% and 57%, or between 19% and 56%, or between 19% and 55%, or between 19% and 54%, or between 19% and 53%, or between 19% and 52%, or between 19% and 51%, or between 19% and 50%, or between 19% and 49%, or between 19% and 48%, or between 19% and 47%, or between 19% and 46%, or between 19% and 45%, or between 19% and 44%, or between 19% and 43%, or between 19% and 42%, or between 19% and 41%, or between 19% and 40%.

As described in further detail below with respect to one embodiment of the data analysis, following amplification and sequencing of the enriched sequences, the test loci and reference loci can then be "matched" or grouped together according to their % GC content (e.g., test loci with a % GC content of 40% is matched with reference loci with a % GC content of 40%). It is appreciated that the % GC content matching procedure may allow slight variation in the allowed matched % GC range. A non-limiting instance, and with reference to the previously described example in text, a test locus with % GC content of 40% could be matched with reference loci of % GC ranging from 39-41%, thereby encompassing the test locus % GC within a suitable range.

To prepare a pool of TACS having the optimized criteria set forth above with respect to size, placement within the human genome and % GC content, both manual and computerized analysis methods known in the art can be applied to the analysis of the human reference genome. In one embodiment, a semi-automatic method is implemented where regions are firstly manually designed based on the human reference genome build 19 (hg19) ensuring that the aforementioned repetitive regions are avoided and subsequently are curated for GC-content using software that computes the % GC-content of each region based on its coordinates on the human reference genome build 19 (hg19). In another embodiment, custom-built software is used to analyze the human reference genome in order to identify suitable TACS regions that fulfill certain criteria, such as but not limited to, % GC content, proximity to repetitive regions and/or proximity to other TACS.

The number of TACS in the pool has been carefully examined and adjusted to achieve the best balance between result robustness and assay cost/throughput. The pool typically contains at least 800 or more TACS, but can include more, such as 1500 or more TACS, 2000 or more TACS or 2500 or more TACS or 3500 or more TACS or 5000 or more TACS. It has been found that an optimal number of TACS in the pool is 5000. It will be appreciated by the ordinarily skilled artisan that a slight variation in pool size typically can be used without altering the results (e.g., the addition or removal of a small number of TACS); accordingly, the number sizes of the pool given herein are to be considered "about" or "approximate", allowing for some slight variation (e.g., 1-5%) in size. Thus, for example, a pool size of "1600 sequences" is intended to refer to "about 1600 sequences" or "approximately 1600 sequences", such that, for example, 1590 or 1610 sequences is also encompassed.

In view of the foregoing, in another aspect, the invention provides a method for preparing a pool of TACS for use in the method of the invention for detecting risk of a chromosomal and/or other genetic abnormality, wherein the method for preparing the pool of TACS comprises: selecting regions in one or more chromosomes of interest having the criteria set forth above (e.g., at least 50 base pairs away on either end from the aforementioned repetitive sequences and a GC content of between 19% and 80%, as determined by calculating the GC content of each member within each family of TACS), preparing primers that amplify sequences that hybridize to the selected regions, and amplifying the sequences, wherein each sequence is 100-500 base pairs in length.

For use in the methods of the disclosure, the pool of TACS typically is fixed to a solid support, such as beads (such as magnetic beads) or a column. In one embodiment, the pool of TACS are labeled with biotin and are bound to magnetic beads coated with a biotin-binding substance, such as streptavidin or avidin, to thereby fix the pool of TACS to a solid support. Other suitable binding systems for fixing the pool of TACS to a solid support (such as beads or column) are known to the skilled artisan and readily available in the art. When magnetic beads are used as the solid support, sequences that bind to the TACS affixed to the beads can be separated magnetically from those sequences that do not bind to the TACS.

Families of TACS

In one embodiment, the pool of TACS comprises a plurality of TACS families directed to different genomic sequences of interest. Each TACS family comprises a plurality of members that bind to the same genomic sequence of interest but having different start and/or stop positions with respect to a reference coordinate system for the genomic sequence of interest. Typically, the reference coordinate system that is used for analyzing human genomic DNA is the human reference genome built hg19, which is publically available in the art, but other coordinate systems may also be used. Alternatively, the reference coordinate system can be an artificially created genome based on built hg19 that contains only the genomic sequences of interest. Exemplary non-limiting examples of start/stop positions for TACS that bind to chromosome 13, 18, 21, X or Y are shown in FIG. 2.

Each TACS family comprises at least 2 members that bind to the same genomic sequence of interest. In various embodiments, each TACS family comprises at least 2 member sequences, or at least 3 member sequences, or at least 4 member sequences, or at least 5 member sequences, or at least 6 member sequences, or at least 7 member sequences, or at least 8 member sequence, or at least 9 member sequences, or at least 10 member sequences. In various embodiments, each TACS family comprises 2 member sequences, or 3 member sequences, or 4 member sequences, or 5 member sequences, or 6 member sequences, or 7 member sequences, or 8 member sequences, or 9 member sequences, or 10 member sequences. In various embodiments, the plurality of TACS families comprises different families having different numbers of member sequences. For example, a pool of TACS can comprise one TACS family that comprises 3 member sequences, another TACS family that comprises 4 member sequences, and yet another TACS family that comprises 5 member sequences, and the like. In one embodiment, a TACS family comprises 3-5 member sequences. In another embodiment, the TACS family comprises 4 member sequences.

The pool of TACS comprises a plurality of TACS families. Thus, a pool of TACS comprises at least 2 TACS families. In various embodiments, a pool of TACS comprises at least 3 different TACS families, or at least 5 different TACS families, or at least 10 different TACS families, or at least 50 different TACS families, or at least 100 different TACS families, or at least 500 different TACS families, or at least 1000 different TACS families, or at least 2000 TACS families, or at least 4000 TACS families, or at least 5000 TACS families.

Each member within a family of TACS binds to the same genomic region of interest but with different start and/or stop positions, with respect to a reference coordinate system for the genomic sequence of interest, such that the binding pattern of the members of the TACS family is staggered (see FIG. 3). In various embodiments, the start and/or stop positions are staggered by at least 3 base pairs, or at least 4 base pairs, or at least 5 base pairs, or at least 6 base pairs, or at least 7 base pairs, or at least 8 base pairs, or at least 9 base pairs, or at least 10 base pairs, or at least 15 base pairs, or at least 20 base pairs, or at least 25 base pairs. Typically, the start and/or stop positions are staggered by 5-10 base pairs. In one embodiment, the start and/or stop positions are staggered by 5 base pairs. In another embodiment, the start and/or stop positions are staggered by 10 base pairs.

Sample Collection and Preparation

The methods of the invention can be used with a variety of biological samples that contain only or predominantly fetal or embryonic DNA. As used herein, a sample containing "predominantly fetal or embryonic DNA" is one that contains more than 50% fetal or embryonic DNA, and typically contains more than 90%, or 95% or 99% fetal or embryonic DNA. In one embodiment, the source of the sample that contains predominantly fetal or embryonic DNA is fetal or embryonic cells obtained from embryo biopsy of in vitro fertilized (IVF) pre-implantation embryos. It has been demonstrated that intact cells can be obtained from IVF pre-implantation embryos for Pre-implantation Genetic Screening (PGS) and Pre-implantation Genetic Diagnosis (PGD) processes. An ovum is fertilized through IVF and resulting cells are collected during in vitro growth of the embryo. For example, cells can be collected from a day 3 embryo or a day 5 embryo. Typically, if cell harvesting is performed at day 3 a single fetal cell is obtained, also known as a blastomere, and if harvesting is performed at day 5 a few cells are obtained, also known as trophectoderm cells. Typically, the genetic integrity of the grown fetal cells is interrogated using array Comparative Genomic Hybridization (aCGH), a technology that can detect genetic abnormalities of a certain genomic size and above. The method of the disclosure provides an alternative means for detecting genomic abnormalities in fetal cells obtained from an embryo, which enables higher resolution of the interrogated genome.

In another embodiment, the source of the sample that contains predominantly fetal or embryonic DNA is fetal or embryonic cells obtained non-invasively from collecting intact cells (trophoblasts) from a maternal Papanicolaou smear (pap test). Recently it has been shown that this is a simple and safe approach for obtaining fetal or embryonic genetic material non-invasively and that the cells obtained from the pap test had an abundance (near 100%) of fetal or embryonic genetic material (Jain, C. V. et al. (2016) *Science Translational Medicine* 8(363):363re4-363re4).

In another embodiment, the source of the sample that contains predominantly fetal or embryonic DNA is one or a few fetal or embryonic cells found in maternal plasma. Thus, one or a few fetal or embryonic cells present in maternal plasma can be isolated and DNA from the one or a few cells can be used as the DNA sample in the methods of the invention.

In yet other embodiments, the sample containing predominantly fetal or embryonic DNA is a DNA sample that is obtained directly from fetal tissue, or from amniotic fluid, or from chorionic villi or from medium where products of conception were grown.

In another embodiment, the DNA sample that contains predominantly fetal or embryonic DNA is obtained directly from fetal or embryonic tissue.

For the biological sample preparation, typically cells are lysed and DNA is extracted using standard techniques known in the art, a non-limiting example of which is the QiAsymphony (Qiagen) protocol.

Following isolation, the cell free DNA of the sample is used for sequencing library construction to make the sample compatible with a downstream sequencing technology, such as Next Generation Sequencing. Typically this involves ligation of adapters onto the ends of the cell free DNA fragments, followed by amplification. Sequencing library preparation kits are commercially available. A non-limiting exemplary protocol for sequencing library preparation is described in detail in Example 1.

Enrichment by TACS Hybridization

The region(s) of interest on the chromosome(s) of interest is enriched by hybridizing the pool of TACS to the sequencing library, followed by isolation of those sequences within the sequencing library that bind to the TACS. To facilitate isolation of the desired, enriched sequences, typically the TACS sequences are modified in such a way that sequences that hybridize to the TACS can be separated from sequences that do not hybridize to the TACS. Typically, this is achieved by fixing the TACS to a solid support. This allows for physical separation of those sequences that bind the TACS from those sequences that do not bind the TACS. For example, each sequence within the pool of TACS can be labeled with biotin and the pool can then be bound to beads coated with a biotin-binding substance, such as streptavidin or avidin. In a preferred embodiment, the TACS are labeled with biotin and bound to streptavidin-coated magnetic beads. The ordinarily skilled artisan will appreciate, however, that other affinity binding systems are known in the art and can be used instead of biotin-streptavidin/avidin. For example, an antibody-based system can be used in which the TACS are labeled with an antigen and then bound to antibody-coated beads. Moreover, the TACS can incorporate on one end a sequence tag and can be bound to a solid support via a complementary sequence on the solid support that hybridizes to the sequence tag. Furthermore in addition to magnetic beads, other types of solid supports can be used, such as polymer beads and the like.

In certain embodiments, the members of the sequencing library that bind to the pool of TACS are fully complementary to the TACS. In other embodiments, the members of the sequencing library that bind to the pool of TACS are partially complementary to the TACS. For example, in certain circumstances it may be desirable to utilize and analyze data that are from DNA fragments that are products of the enrichment process but that do not necessarily belong to the genomic regions of interest (i.e., such DNA fragments could bind to the TACS because of part homologies (partial complementarity) with the TACS and when sequenced would produce very low coverage throughout the genome in non-TACS coordinates).

Following enrichment of the sequence(s) of interest using the TACS, thereby forming an enriched library, the members of the enriched library are eluted from the solid support and are amplified and sequenced using standard methods known in the art. Next Generation Sequencing is typically used, although other sequencing technologies can also be employed, which provides very accurate counting in addition to sequence information. To detect genetic abnormalities, such as but not limited to, aneuploidies or structural copy number changes requires very accurate counting and NGS is a type of technology that enables very accurate counting. Accordingly, for the detection of genetic abnormalities, such as but not limited to, aneuploidies or structural copy number changes, other accurate counting methods, such as digital PCR and microarrays can also be used instead of NGS. Non-limiting exemplary protocols for amplification and sequencing of the enriched library are described in detail in Example 3.

Data Analysis

The information obtained from the sequencing of the enriched library can be analyzed using an innovative biomathematical/biostatistical data analysis pipeline. Details of an exemplary analysis using this pipeline are described in depth in Example 4, and in further detail below. Alternative data analysis approaches for different purposes are also provided herein. For example, data analysis approaches for analyzing fetal and/or embryonic DNA samples for genetic abnormalities are described in detail in Example 6.

The analysis pipeline described in Example 4 exploits the characteristics of the TACS, and the high-efficiency of the target capture enables efficient detection of aneuploidies or structural copy number changes, as well as other types of genetic abnormalities. In the analysis, first the sample's sequenced DNA fragments are aligned to the human reference genome. QC metrics are used to inspect the aligned sample's properties and decide whether the sample is suitable to undergo classification. These QC metrics can include, but are not limited to, analysis of the enrichment patterns of the loci of interest, such as for example the overall sequencing depth of the sample, the on-target sequencing output of the sample, TACS performance, GC bias expectation, fraction of interest quantification. For determining the risk of a chromosomal abnormality in the fetal DNA of the sample, an innovative algorithm is applied. The steps of the algorithm include, but are not limited to, removal of inadequately sequenced loci, read-depth and fragment-size information extraction at TACS-specific coordinates, genetic (GC-content) bias alleviation and ploidy status classification.

Ploidy status determination is achieved using one or more statistical methods, non-limiting examples of which include a t-test method, a bootstrap method, a permutation test and/or a binomial test of proportions and/or segmentation-based methods and/or combinations thereof. It will be appreciated by the ordinarily skilled artisan that the selection and application of tests to be included in ploidy status determination is based on the number of data points available. As such, the suitability of each test is determined by various factors such as, but not limited to, the number of TACS utilized and the respective application for GC bias alleviation, if applicable. Thus, the aforementioned methods are to be taken as examples of the types of statistical analysis that may be employed and are not the only methods suitable for the determination of ploidy status. Typically, the statistical method results in a score value for the mixed sample and risk of the chromosomal abnormality in the fetal DNA is detected when the score value for the mixed sample is above a reference threshold value.

In particular, one aspect of the statistical analysis involves quantifying and alleviating GC-content bias. In addition to the challenge of detecting small signal changes in fetal DNA in the mixed sample, and/or other components of DNA of interest part of a mixed sample (for example, but not limited to, additional or less genetic material from certain chromosomal regions), the sequencing process itself introduces certain biases that can obscure signal detection. One such bias is the preferential sequencing/amplification of genetic regions based on their GC-content. As such, certain detection methods, such as but not limited to, read-depth based methods, need to account for such bias when examining sequencing data. Thus, the bias in the data needs to be quantified and, subsequently, suitable methods are applied to account for it such that genetic context dependencies cannot affect any statistical methods that may be used to quantify fetal genetic abnormality risk.

For example, one method of quantifying the GC-content bias is to use a locally weighted scatterplot smoothing (LOESS) technique on the sequencing data. Each targeted locus may be defined by its sequencing read-depth output and its' GC-content. A line of best fit through these two variables, for a large set of loci, provides an estimate of the expected sequencing read-depth given the GC-content. Once this GC-bias quantification step is completed, the next step is to use this information to account for possible biases in the data. One method is to normalize the read-depth of all loci by their expected read-depth (based on each locus' GC-content). In principle, this unlinks the read-depth data from their genetic context and makes all data comparable. As such, data that are retrieved from different GC-content regions, such as for example, but not limited, to different chromosomes, can now be used in subsequent statistical tests for detection of any abnormalities. Thus, using the LOESS procedure, the GC bias is unlinked from the data prior to statistical testing. In one embodiment, the statistical analysis of the enriched library sequences comprises alleviating GC bias using a LOESS procedure.

In an alternative embodiment, the GC-content bias is quantified and alleviated by grouping together loci of similar (matching) GC-content. Thus, conceptually this method for alleviating GC-content bias comprises of three steps, as follows:

1) identification and calculation of GC-content in the TACS;

2) alleviation/accounting of GC-content bias using various matching/grouping procedures of the TACS; and 3) calculation of risk of any genetic abnormalities that may be present in the fetus utilizing statistical and mathematical methods on datasets produced from step 2.

For the t-test method, the dataset is split into two groups; the test loci and the reference loci. For each group, subsets of groups are created where loci are categorized according to their GC-content as illustrated in a non-limiting example in the sample Table 1 below:

TABLE 1

| GC | Reference loci read-depth | Test loci read-depth |
|---|---|---|
| 40% | $x_1^{40}, x_2^{40}, \ldots, x_{nx40}^{40}$ | $y_1^{40}, y_2^{40}, \ldots, y_{ny40}^{40}$ |
| 41% | $x_1^{41}, x_2^{41}, \ldots, x_{nx41}^{41}$ | $y_1^{41}, y_2^{41}, \ldots, y_{ny41}^{41}$ |
| 42% | $x_1^{42}, x_2^{42}, \ldots, x_{nx42}^{42}$ | $y_1^{42}, y_2^{42}, \ldots, y_{ny42}^{42}$ |
| ... | ... | ... |

It is appreciated by the ordinarily skilled artisan that subgroup creation may involve encompassing a range of appropriate GC-content and/or a subset of loci that are defined by a given GC-content and/or GC-content range. Accordingly, the % GC content given in the non-limiting example of Table 1 are to be considered "about" or "approximate", allowing for some slight variation (e.g., 1-2%). Thus, for example, a % GC content of "40%" is intended to refer to "about 40%" or "approximately 40%", such that, for example, "39%-41%" GC-content loci may also be encompassed if deemed appropriate.

Hence, when referring to a particular GC-content it is understood that the reference and test loci subgroups may comprise of any number of loci related to a particular % GC content and/or range.

For statistical analysis using a permutation test, the dataset is sorted firstly into two groups, the test-loci and the reference loci. For each group, subsets of groups are created, where loci are categorized according to their GC-content similarity (see columns 2 and 3 of the non-limiting sample Table 2 below). The number of loci present in each test subgroup is also recorded. The loci of the test group are utilized to calculate an estimate of the test-group's read-depth, say Yobs. A representative number from each GC-content subgroup may be selected to do so. Any number of methods may be used to provide a read-depth estimate, such as but not limited to, the mean, median or mode of the chosen loci.

TABLE 2

| GC | Reference loci read- | Test loci read-depth | test loci | Merging of loci |
|---|---|---|---|---|
| 40% | $x_1^{40}, x_2^{40}, \ldots, x_{nx40}^{40}$ | $y_1^{40}, y_2^{40}, \ldots, y_{ny40}^{40}$ | ny40 | $x_1^{40}, \ldots, x_{nx40}^{40}, y_1^{40}, \ldots, y_{ny40}^{40}$ |
| 41% | $x_1^{41}, x_2^{41}, \ldots, x_{nx41}^{41}$ | $y_1^{41}, y_2^{41}, \ldots, y_{ny41}^{41}$ | ny41 | $x_1^{41}, \ldots, x_{nx41}^{41}, y_1^{41}, \ldots, y_{ny41}^{41}$ |
| 42% | $x_1^{42}, x_2^{42}, \ldots, x_{nx42}^{42}$ | $y_1^{42}, y_2^{42}, \ldots, y_{ny42}^{42}$ | ny42 | $x_1^{42}, \ldots, x_{nx42}^{42}, y_1^{42}, \ldots, y_{ny42}^{42}$ |
| ... | ... | ... | ... | ... |

Subsequently, for each GC-content subgroup, a representative read-depth is calculated. A number of methods may be utilized to choose this such as, but not limited to, the mean, median or mode of each set. Thus, two vectors of representative read-depth are created where one corresponds to the reference loci and the other to the test loci (e.g., Xm, Ym). In one embodiment, the two vectors may be tested against each other to identify significant differences in read-depth. In another embodiment, the difference of the two vectors may be used to assess if there are significant discrepancies between the test and reference loci. The sample is attributed the score of the test.

For statistical analysis using a bootstrap approach, the dataset is split into two groups, the test loci and the reference loci. The GC-content of each locus is then calculated. Then the following procedure is performed:

A random locus is selected from the reference loci; its read-depth and GC-content are recorded. Subsequently, a random locus from the test loci is selected, with the only condition being that its' GC-content is similar to that of the reference locus. Its read-depth is recorded. It is appreciated by the ordinarily skilled artisan that GC-content similarity may encompass a range of suitable GC-content. As such, referral to a specific % GC content may be considered as "approximate" or "proximal" or "within a suitable range" (e.g., 1%-2%) encompassing the specific % GC content under investigation. Thus, a reference-test locus pair of similar GC-content is created. The difference of the reference-test pair is recorded, say E1. The loci are then replaced to their respective groups. This process is repeated until a bootstrap sample of the same size as the number of test TACS present is created. A representative read-depth of the bootstrap sample is estimated, say E_mu, and recorded. A number of methods may be utilized to do so, such as but not limited to, the mean, mode or median value of the vector, and/or multiples thereof.

The process described above is repeated as many times as necessary and a distribution of E_mu is created. The sample is then attributed a score that corresponds to a percentile of this distribution.

A distribution to test Yobs is then built utilizing loci irrespective of their test or reference status as follows. The test and reference loci of each GC-content subgroup (see last column of sample Table 2) are combined to allow for calculation of a new read-depth estimate. From each merged subgroup a number of loci are chosen at random, where this number is upper-bounded by the number of test-loci utilized in the original calculation of Yobs (e.g., for GC content 40%, and in the context of the non-limiting sample Table 2, this number of loci may be in the range [1,ny40]). The new read-depth estimate is calculated from all the chosen loci. The procedure is iterated as many times as necessary in order to build a distribution of observed means. A sample is then attributed a score that corresponds to the position of Yobs in this distribution using a suitable transformation that accounts for the moments of the built distribution. As with the already described methods, it is appreciated that slight variation in % GC content is allowed (e.g., 1%-2%), if deemed appropriate. Hence, reference to a specific GC-content could be taken as "about" or "approximate", so that for example when referring to a 40% GC-content, loci that are "approximately" or "about" 40% (e.g., 39%-41%) may be utilized in the method.

For statistical analysis using a binomial test of proportions, fragment-sizes aligned to TACS-specific genomic coordinates are used. It has been shown that fragments of cell free genetic material originating from the placenta tend to be smaller in length when compared to other cell free genetic material (Chan, K. C. (2004) *Clin. Chem.* 50:88-92). Hence, the statistic of interest is whether the proportion of small-size fragments aligned to a TACS-specific test-region deviates significantly from what is expected when comparing it to the respective proportion of other TACS-specific reference-regions, as this would indicate fetal genetic abnormalities.

Thus, fragment-sizes are assigned into two groups. Sizes related to the test loci are assigned to one group and fragment-sizes related to the reference loci are assigned to the other group. Subsequently, in each group, fragment sizes are distributed into two subgroups, whereby small-size fragments are assigned into one subgroup and all remaining fragments are designated to the remaining subgroup. The last step computes the proportion of small-sized fragments in each group and uses these quantities in a binomial test of proportions. The score of the test is attributed to the sample under investigation.

The final result of a sample may be given by combining one or more scores derived from the different statistical methods, non-limiting examples of which are given in Example 4.

For statistical analysis using segmentation methods, the read-depth and sequence composition of non-overlapping genomic regions of interest of fixed-size is obtained. On the obtained dataset, GC-content read-depth bias alleviation may be performed, but is not limited to, using a local polynomial fitting method in order to estimate the expected read-depth of regions based on their GC content. The expected value, dependent on GC-content, is then used to normalize regions using suitable methods known to those skilled in the art. The normalized dataset is subsequently processed using one or more segmentation-based classification routines. To do so the algorithms process consecutive data points to detect the presence of read-depth deviations which manifest in the form of a "jump/drop" from their surrounding data points. Depending on the segmentation routine used, data points are given a score which is used towards assigning membership into segments of similar performing read-depths. For example, consecutive data points with score values within a suitable range may be classified as one segment, whereas consecutive data points with score values which exceed the set thresholds may be assigned to a different segment. Details of segmentation-based routines are given in Example 6.

Kits of the Invention

In another aspect, the invention provides kits for carrying out the methods of the disclosure. In one embodiment, the kit comprises a container consisting of the pool of TACS and instructions for performing the method. In one embodiment, the TACS are provided in a form that allows them to be bound to a solid support, such as biotinylated TACS. In another embodiment, the TACS are provided together with a solid support, such as biotinylated TACS provided together with streptavidin-coated magnetic beads.

In one embodiment, the kit comprises a container comprising the pool of TACS and instructions for performing the method, wherein the pool of TACS comprises a plurality of member sequences, wherein:
  (i) each member sequence within the TACS pool is between 100-500 base pairs in length, each member sequence having a 5' end and a 3' end;
  (ii) each member sequence binds to the same genomic sequence of interest at least 50 base pairs away, on both the 5' end and the 3' end, from regions harboring Copy Number Variations (CNVs), Segmental duplications or repetitive DNA elements; and
  (iii) the GC content of the pool of TACS is between 19% and 80%, as determined by calculating the GC content of each member within the pool of TACS.

In one embodiment, the pool of TACS comprises a plurality of TACS families, wherein each TACS family comprises a plurality of member sequences, wherein each member sequence binds to the same genomic sequence of interest but has different start and/or stop positions with respect to a reference coordinate system for the genomic sequence of interest, Furthermore, any of the various features described herein with respect to the design and structure of the TACS can be incorporated into the TACS that are included in the kit.

In various other embodiments, the kit can comprise additional components for carrying out other aspects of the method. For example, in addition to the pool of TACS, the kit can comprise one or more of the following (i) one or more components for isolating cell free DNA from a biological sample (e.g., as described in Example 1); (ii) one or more components for preparing the sequencing library (e.g., primers, adapters, buffers, linkers, restriction enzymes, ligation enzymes, polymerase enzymes and the like as described in detail in Example 1); (iii) one or more components for amplifying and/or sequencing the enriched library (e.g., as described in Example 3); and/or (iv) software for performing statistical analysis (e.g., as described in Example 4).

Fragment-Based Analysis

In another aspect, the invention pertains to fragment based analysis of samples, described further in Example 7. There is evidence from the literature that fetal cell free DNA can be found in the medium of IVF products of conception and it can be used for the assessment of chromosomal abnormalities (Liu, WeiQiang, et al. (2017)). Furthermore, specific types of genetic abnormalities can be characterized by and/or associated with fragments of a smaller size than the expected size of fragments originating from healthy tissues (Jiang et al, (2015), *Proceedings of the National Academy of Sciences*, 112(11), ppE1317-E1325).

Thus, fragments-based detection may be used to detect abnormalities. For example, a binomial test of proportions, as described Example 4, can be used for the detection of increased presence of nucleic acid material originating from abnormal cells based on fragment size. In particular, under the null hypothesis that the distribution of fragment sizes originating from both euploid and aneuploid cells is the same, a binomial test for proportions (as described in Example 4) using continuity correction can be utilized to quantify any evidence against it.

EXAMPLES

The present invention is further illustrated by the following examples, which should not be construed as further limiting. The contents of all references, appendices, Genbank entries, patents and published patent applications cited throughout this application are expressly incorporated herein by reference in their entirety.

Example 1: Sample Collection and Library Preparation

The general methodology for the TACS-based multiplexed parallel analysis approach for genetic assessment is shown schematically in FIG. 1. In this example, methods for collecting and processing a fetal or embryonic DNA sample, followed by sequencing library preparation for use in the methodology of FIG. 1 are described.

Sample Collection

Fetal cell samples were obtained from 3-day and 5-day biopsy embryos respectively were subjected to the TACS methodology shown in FIG. 1 to determine the status of genetic abnormalities. Protocols used for collecting samples for our study were approved by the Cyprus National Bioethics Committee, and informed consent was obtained from all participants.

Sequencing Library Preparation

Collected fetal cells were initially lysed and DNA extracted using the Rubicon Genomics PicoPLEX© WGA Kit (Liang, L. et al. (2013) PLoS One 8(4), p. e61838). Following a pre-amplification step, the lysed material was amplified using amplification enzyme and buffer supplied by the manufacturer. Subsequently, DNA was purified followed by fragmentation using sonication. Following fragmentation, standard library preparation methods were used with the following modifications. A negative control extraction library was prepared separately to monitor any contamination introduced during the experiment. During this step, 5' and 3' overhangs were filled-in, by adding 12 units of T4 polymerase (NEB) while 5' phosphates were attached using 40 units of T4 polynucleotide kinase (NEB) in a 100 µl reaction and subsequent incubation at 25° C. for 15 minutes and then 12° C. for 15 minutes. Reaction products were purified using the MinElute® kit (Qiagen). Subsequently, adaptors P5 and P7 (see adaptor preparation) were ligated at 1:10 dilution to both ends of the DNA using 5 units of T4 DNA ligase (NEB) in a 40 µl reaction for 20 minutes at room temperature, followed by purification using the MinElute® kit (Qiagen). Nicks were removed in a fill-in reaction with 16 units of Bst polymerase (NEB) in a 40 µl reaction with subsequent incubation at 65° C. for 25 minutes and then 12° C. for 20 minutes. Products were purified using the MinElute® kit (Qiagen). Library amplification was performed using a Fusion polymerase (Herculase® II Fusion DNA polymerase (Agilent Technologies) or Pfusion® High Fidelity Polymerase (NEB)) in 50 µl reactions and with the following cycling conditions, 95° C. for 3 minutes; followed by 10 cycles at 95° C. for 30 seconds, 60° C. for 30 seconds, 72° C. for 30 seconds and finally 72° C. for 3 minutes (Koumbaris, G. et al. (2015) *Clinical chemistry*, 62(6), pp. 848-855). The final library products were purified using the MinElute® Purification Kit (Qiagen) and measured by spectrophotometry.

Adaptor Preparation

Hybridization mixtures for adapter P5 and P7 were prepared separately and incubated for 10 seconds at 95° C. followed by a ramp from 95° C. to 12° C. at a rate of 0.1° C./second. P5 and P7 reactions were combined to obtain a ready-to-use adapter mix (100 µM of each adapter). Hybridization mixtures were prepared as follows: P5 reaction mixture contained adaptor P5_F (500 µM) at a final concentration of 200 µM, adaptor P5+P7_R (500 µM) at a final concentration of 200 µM with 1× oligo hybridization buffer. In addition, P7 reaction mixture contained adaptor P7_F (500 µM) at a final concentration of 200 IM, adapter P5+P7_R(500 µM) at a final concentration of 200 µM with 1× oligo hybridization buffer (Koumbaris, G. et al. (2015) *Clinical chemistry*, 62(6), pp. 848-855). Sequences were as follows, wherein *=a phosphorothioate bond (PTO) (Integrated DNA Technologies):

```
adaptor P5_F:
                                    (SEQ ID NO: XX)
A*C*A*C*TCTTTCCCTACACGACGCTCTTCCG*A*T*C*T adaptor P7_F:
                                    (SEQ ID NO: YY)
G*T*G*A*CTGGAGTTCAGACGTGTGCTCTTCCG*A*T*C*T, adaptor_P5 + P7_R:
                                    (SEQ ID NO: ZZ)
A*G*A*T*CGGAA*G*A*G*C
```

Example 2: TArget Capture Sequences (TACS) Design and Preparation

This example describes preparation of custom TACS for the detection of whole or partial chromosomal abnormalities for chromosomes 1-22, X and Y or any other chromosome, as well as other genetic abnormalities, such as but not limited to, chromosomal mosaicism, microdeletion/microduplication syndromes, translocations, inversions, insertions, and other point or small size mutations. The genomic target-loci used for TACS design were selected based on their GC content and their distance from repetitive elements (minimum 50 bp away). TACS size can be variable. In one embodiment of the method the TACS range from 100-500 bp in size and are generated through a PCR-based approach as described below. The TACS were prepared by simplex polymerase chain reaction using standard Taq polymerase, primers designed to amplify the target-loci, and normal DNA used as template.

All custom TACS were generated using the following cycling conditions: 95° C. for 3 minutes; 40 cycles at 95° C. for 15 seconds, 60° C. for 15 seconds, 72° C. for 12 seconds; and 72° C. for 12 seconds, followed by verification via agarose gel electrophoresis and purification using standard PCR clean up kits such as the QiAquick® PCR Purification Kit (Qiagen) or the NucleoSpin® 96 PCR clean-up (Mackerey Nagel) or the Agencourt® AMPure® XP Kit for PCR Purification (Beckman Coulter). Concentration was measured by Nanodrop (Thermo Scientific).

Example 3: TACS Hybridization and Amplification

This example describes the steps schematically illustrated in FIG. 1 of target capture by hybridization using TACS, followed by quantitation of captured sequences by Next Generation Sequencing (NGS).

TACS Biotinylation

TACS were prepared for hybridization, as previously described (Koumbaris, G. et al. (2015) *Clinical chemistry*, 62(6), pp. 848-855), starting with blunt ending with the Quick Blunting™ Kit (NEB) and incubation at room temperature for 30 minutes. Reaction products were subsequently purified using the MinElute® kit (Qiagen) and were ligated with a biotin adaptor using the Quick Ligation™ Kit (NEB) in a 40 µl reaction at RT for 15 minutes. The reaction products were purified with the MinElute® kit (Qiagen) and were denatured into single stranded DNA prior to immobilization on streptavidin coated magnetic beads (Invitrogen).

TACS Hybridization

Amplified libraries were mixed with blocking oligos (Koumbaris, G. et al. (2105) *Clinical chemistry*, 62(6), pp. 848-855) (200 µM), 5 µg of Cot-1 DNA (Invitrogen), 50 µg of Salmon Sperm DNA (Invitrogen), Agilent hybridization buffer 2×, Agilent blocking agent 10×, and were heated at 95° C. for 3 minutes to denature the DNA strands. Denaturation was followed by 30 minute incubation at 37° C. to block repetitive elements and adaptor sequences. The resulting mixture was then added to the biotinylated TACS. All samples were incubated in a rotating incubator for 12-48 hours at 66° C. After incubation, the beads were washed as described previously and DNA was eluted by heating (Koumbaris, G. et al. (2105) *Clinical chemistry*, 62(6), pp. 848-855). Eluted products were amplified using outer-bound adaptor primers. Enriched amplified products were pooled equimolarly and sequenced on a suitable platform.

Example 4: Bioinformatics Sample Analysis

This example describes representative statistical analysis approaches for use in the methodology illustrated in FIG. 1 ("analysis pipeline" in FIG. 1).

Human Genome Alignment

For each sample, the bioinformatic pipeline routine described below was applied in order to align the sample's sequenced DNA fragments to the human reference genome. Targeted paired-end read fragments obtained from NGS results were processed to remove adaptor sequences and poor quality reads (Q-score<25) using the cutadapt software (Martin, M. et al. (2011) *EMB.netJournal* 17.1). The quality of the raw and/or processed reads as well as any descriptive statistics which aid in the assessment of quality check of the sample's sequencing output were obtained using the FastQC software (Babraham Institute (2015) *FastQC*) and/or other custom-built software. Processed reads which were at least 25 bases long were aligned to the human reference genome built hg19 (UCSC Genome Bioinformatics) using the Burrows-Wheel Alignment algorithm (Li, H. and Durbin, R. (2009) *Bioinformatics* 25:1754-1760) but other algorithms known to those skilled in the art may be used as well. If relevant, duplicate reads were removed post-alignment. Where applicable, sequencing output pertaining to the same sample but processed on separate sequencing lanes, was merged to a single sequencing output file. The removal of duplicates and merging procedures were performed using the Picard tools software suite (Broad Institute (2015) *Picard*) and/or the Sambamba tools software suite (Tarasov, Artem, et al. "Sambamba: fast processing of NGS alignment formats." *Bioinformatics* 31.12 (2015): 2032-2034).

The above software analysis resulted in a final aligned version of a sequenced sample against the human reference genome and all subsequent steps were based on this aligned version. Information in terms of Short Nucleotide Polymorphisms (SNPs) at loci of interest was obtained using bcftools from the SAMtools software suite (Li, H. et al. (2009) *Bioinformatics* 25:2078-2079) and/or other software known to those skilled in the art. The read-depth per base, at loci of interest, was obtained using the mpileup option of the SAMtools software suite, from here on referred to as the mpileup file. Information pertaining to the size of the aligned fragments was obtained using the view option of the SAMtools software suite, from here on referred to as the fragment-sizes file and/or other software known to those skilled in the art.

The mpileup file and the fragment-sizes file were processed using custom-build application programming interfaces (APIs) written in the Python and R programming languages (Python Software Foundation (2015) *Python*; The R Foundation (2015) *The R Project for Statistical Computing*). The APIs were used to determine the ploidy state of chromosomes of interest, and/or other genetic abnormalities in regions of interest across the human genome, using a series of steps (collectively henceforth referred to as the "algorithm") and to also collect further descriptive statistics to be used as quality check metrics, such as but not limited to fetal fraction quantification (collectively henceforth referred to as the "QC metrics"). The APIs can also be used for the assessment of genetic abnormalities from data generated when applying the described method in cases of multiple gestation pregnancies, as well as other genetic abnormalities such as, but not limited to, microdeletions, microduplications, copy number variations, translocations, inversions, insertions, point mutations and other mutational signatures.

QC Metrics

QC metrics were used to inspect an aligned sample's properties and decide whether the sample was suitable to undergo classification. These metrics were, but are not limited to, the enrichment of a sample. The patterns of enrichment are indicative of whether a sample has had adequate enrichment across loci of interest in a particular sequencing experiment (herein referred to as a "run"). To assess this, various metrics are assessed, non-limiting examples of which are:

(i) overall sample on-target read depth,
(ii) sample on-target sequencing output with respect to total mapped reads,
(iii) individual TACS performance in terms of achieved read-depth,
(iv) kurtosis and skewness of individual TACS enrichment,
(v) kurtosis and skewness moments that arise from all TACS,
(vi) fragment size distribution,
(vii) percentage of duplication
(viii) percentage of paired reads and,
(ix) percentage of aligned reads, if applicable.

The above checks are also taken into consideration with regards to GC-bias enrichment. Samples that fail to meet one or more of the criteria given above are flagged for further inspection, prior to classification.

The Algorithm

The algorithm is a collection of data processing, mathematical and statistical model routines arranged as a series of steps. The algorithm's steps aim in deciding the relative ploidy state of a chromosome of interest with respect to all other chromosomes of the sequenced sample and is used for the detection of whole or partial chromosomal abnormalities for chromosomes 1-22, X and Y or any other chromosome, as well as other genetic abnormalities such as, but not limited to, chromosomal mosaicism, microdeletion/microduplication syndromes and other point or small size mutations. As such the algorithm can be used, but is not limited to, the detection of whole or partial chromosomal abnormalities for chromosomes 13, 18, 21, X, Y or any other chromosome, as well as other genetic abnormalities such as, but not limited to, microdeletions, microduplications, copy number variations, translocations, inversions, insertions, point mutations and other mutational signatures.

For read-depth associated tests, the algorithm compares sequentially the read-depth of loci from each chromosome of interest (herein referred to as the test chromosome) against the read-depth of all other loci (herein referred to as the reference loci) to classify its ploidy state. For each sample, these steps were, but are not limited to:

(a) Removal of inadequately sequenced loci. The read-depth of each locus was retrieved. Loci that have not achieved a minimum number of reads, were considered as inadequately enriched and were removed prior to subsequent steps.

(b) Genetic (GC-content) bias alleviation. The sequencing procedure may introduce discrepancies in read-depth across the loci of interest depending on their GC content. To account for such bias, a novel sequence-matching approach that increases both sensitivity and specificity to detect chromosomal aneuploidies was employed. The GC content of each locus on the test chromosome was identified and similar genetic loci were grouped together to form genetically matched groups. The procedure was repeated for the reference loci. Then, genetically matched groups from the test chromosome were conditionally paired with their genetically matched group counterparts on the reference chromosome(s). The groups may have any number of members. The conditionally matched groups were then used to assess the ploidy status of test chromosomes.

(c) Genetic abnormality determination. Ploidy status determination, or other genetic abnormalities of interest such as but not limited to microdeletions, microduplications, copy number variations, translocations, inversions, insertions, point mutations and other mutational signatures was achieved using a single statistical method and/or a weighted score approach on the result from the following, but not limited to, statistical methods:

Statistical Method 1: The differences in read-depth of the conditionally paired groups were tested for statistical significance using the t-test formula:

$$t = \frac{\hat{x} - \mu}{s / \sqrt{n}}$$

where t is the result of the t-test, tis the average of the differences of the conditionally paired groups, $\mu$ is the expected read-depth and is set to a value that represents insignificant read-depth differences between the two groups, s the standard deviation of the differences of the conditionally paired groups and n the length of the vector of the conditionally paired differences. The magnitude of the t-score was then used to identify evidence, if any, against the null hypothesis of same ploidy between reference and test chromosomes. Specifically, t>=c1 (where c1 is a predefined threshold belonging to the set of all positive numbers) shows evidence against the null hypothesis of no difference.

Statistical Method 2: Bivariate nonparametric bootstrap. The bootstrap method depends on the relationship between the random variables X (read-depth of reference loci) and Y (read-depth of test loci). Here, the read depth of baits on the reference group (random variable denoted by X) were treated as the independent covariate. The first step of the iterative procedure involved random sampling with replacement (bootstrapping) of the read-depths of loci on the reference chromosomes, i.e., (x1,g1), . . . , (xn,gn), where the parameter g is known and denotes the GC-content of the chosen bait. Then, for each randomly selected reference bait (xi,gi), a corresponding read depth was generated for a genetically matched locus i.e., (y1,g1), . . . , (yn,gn). Thus, the bivariate data (x1,y1), (x2,y2), . . . , (xn,yn) was arrived at, which was conditionally matched on their GC-content (parameter gi). The differences between the read depths of the genetically matched bootstrapped values xi and yi were used to compute the statistic of interest in each iteration. In one embodiment this statistical measure can be, but is not limited to, the mode, mean or median of the recorded differences, and/or multiples thereof. The procedure was repeated as necessary to build up the distribution of the statistic of interest from these differences. The sample was assigned a score that corresponds to a specific percentile of the built distribution (e.g. $5^{th}$ percentile). Under the null hypothesis the ploidy between chromosomes in the reference and test groups is not different. As such, samples whose score for a particular chromosome, was greater than a predefined threshold, say c2, were classified as statistically unlikely to have the same ploidy. Other statistical measures may be employed.

Statistical Method 3: Stratified permutation test. The statistic of interest is the read-depth estimate of the test chromosome, denoted by, $\hat{Y}_{obs}$ which is calculated using all loci of the test chromosome's genetically matched groups as follows:

$$\hat{Y}_{obs} = \frac{\sum_{j=1}^{j=T} \sum_{i=1}^{i=Nj} y_{ij}}{\sum_{j=1}^{j=T} Nj}$$

where $y_{ij}$ is the read-depth of locus i part of the genetically matched group j (i.e., loci belonging to a specific group based on their GC-content), Nj is the number of test loci part of the genetically matched group j and T is the number of genetically matched groups.

Subsequently, a null distribution to test $\hat{Y}_{obs}$ was built. To do so, for each group j, the test and reference loci were combined (exchangeability under the null hypothesis), and each group j was sampled randomly up to Nj times without replacement (stratified permutation). This created a vector of values, say yi, and from this the vector's average value, say, was calculated. The procedure was repeated as necessary to build the null distribution. Finally, $\hat{Y}_{obs}$ was studentised against the null distribution using the formula:

$$Z_{Yobs} = \frac{\hat{Y_{obs}} - \hat{Y}}{\sigma_Y}$$

where $\hat{Y}$ and $\sigma_Y$ are the first and square root of the second moment of all permuted $\hat{y}_i$ statistic values. Samples whose $Z_{Yobs}$ was greater than a predefined threshold, say c3, were statistically less likely to have the same ploidy in the reference and test groups.

In the case of fragment-size associated tests, the algorithm computes the proportion of small-size fragments found in test-loci and compares it with the respective proportion in reference-loci as described in Statistical Method 4 below.

Statistical Method 4: Fragment Size Proportions. For each sample the number and size of fragments aligned onto the human reference genome at the corresponding TACS coordinates, is extracted. The data is subsequently filtered so as to remove fragment-sizes considered statistical outliers using the median outlier detection method. Specifically, outliers are defined as those fragments whose size is above or below the thresholds, $F_{thr}$, set by equation:

$$F_{thr} = F_{median} \pm (X \times IQR)$$

where $F_{median}$ is the median fragment-size of all fragments of a sample, X is a variable that can take values from the set of R+, and IQR is the interquartile range of fragment sizes. Thereafter, a binomial test of proportions is carried out to test for supporting evidence against the null hypothesis, H0, where this is defined as:
H0: The proportion of small fragments of the test-region is not different from the proportion of small-fragments of the reference region.

In various embodiments of the invention, small fragments are defined as those fragments whose size is less than or equal to a subset of Z+ that is upper-bounded by 160 bp. If the set of all TACS are defined as T, then the test region can be any proper subset S which defines the region under investigation, and the reference region is the relative complement of S in T. For example, in one embodiment of the invention, the set S is defined by all TACS-captured sequences of chromosome 21 and thus the reference set is defined by all TACS-captured fragments on the reference chromosomes, and/or other reference loci The alternative hypothesis, H1, is defined as:
H1: The proportion of small fragments of the test-region is not equal to the proportion of test fragments of the reference region.

As such, and taking into account continuity correction, the following score is computed (Brown et. al, Harrel):

$$W_{test} = (\acute{p} - \acute{p}_{ref}) \Big/ \sqrt{\frac{\acute{p}(1-\acute{p})}{N_{test}}}$$

where $$\acute{p} = \frac{(\acute{F} + 0.5)}{(N_{test} + 1)}$$

$$\acute{p}_{ref} = \frac{(F_{ref} + 0.5)}{(N_{ref} + 1)}$$

$\acute{F}$ is the number of small-size fragments on the test-region, $F_{ref}$ the number of small size fragments on the reference region, $N_{test}$ the number of all fragments on the test region and $N_{ref}$ the number of all fragments on the reference region.

For each sample, the algorithm tests sequentially the proportion of fragment sizes of regions under investigation (for example, but not limited to, chromosome 21, chromosome 18, chromosome 13 or other (sub)chromosomal regions of interest) against reference regions; those not under investigation at the time of testing. For each sample a score is assigned for each test. Scores above a set-threshold, say c4, provide evidence against the null hypothesis.

Weighted Score method 1: In one embodiment of the method, a weighted score was attributed to each sample s, computed as a weighted sum of all statistical methods using the formula:

$$V_S(R,F) = z_1 \max\{R_S, F_S\} + (1-z_1) \min\{R_S, F_S\}$$

where $R_S$ is the run-specific corrected score arising from a weighted contribution of each read-depth related statistical method for sample s and is defined as:

$$R_s = \frac{\left(\sum_i w_i S_{is} - \acute{R}_r\right)}{\sigma_r}$$

and $\acute{R}_r$ is the run-specific median value calculated from the vector of all unadjusted read-depth related weighted scores that arise from a single sequencing run, and $\sigma_r$ is a multiple of the standard deviation of R scores calculated from a reference set of 100 euploid samples. The terms $\max\{R_S, F_S\}$ and $\min\{R_S, F_S\}$ denote the maximum and minimum values of the bracketed set, respectively.

$F_S$ is the run-specific corrected score arising from the fragment-size related statistical method and is defined as:

$$F_s = \frac{(W_{test} - \acute{R}_f)}{\sigma_f}$$

where $W_{test}$ is as defined earlier, $\acute{R}_f$ is the run specific median calculated from the vector of all unadjusted fragment-related statistical scores that arise from a single sequencing run, and $\sigma_f$ is a multiple of the standard deviation of F scores calculated from a reference set of 100 euploid samples.

A unique classification score of less than a predefined value indicates that there is no evidence from the observed data that a sample has a significant risk of aneuploidy.

Weighted Score method 2: In another embodiment of the method, the weighted score arising from the statistical methods described above was used to assign each sample a unique genetic abnormality risk score using the formula:

$$R(t,c) = \sum_{j=0}^{j=N} w_j \frac{t_j}{c_j}$$

where R is the weighted score result, $w_j$ the weight assigned to method j, $t_j$ the observed score resulting from method j, and $c_j$ the threshold of method j.

A unique classification score of less than a predefined value indicates that there is no evidence from the observed data that a sample has a significant risk of aneuploidy.

Since all read depths from baits in the reference group were assumed to be generated from the same population, and in order to have a universal threshold, run-specific adjustments were also employed to alleviate run-specific biases.

The aforementioned method(s), are also suitable for the detection of other genetic abnormalities, such as but not limited to, subchromosomal abnormalities. A non-limiting example is the contiguous partial loss of chromosomal material leading to a state of microdeletion, or the contiguous partial gain of chromosomal material leading to a state of microduplication. A known genetic locus subject to both such abnormalities is 7q11.23. In one embodiment of statistical method 1, synthetic plasma samples of 5%, 10% and 20% fetal material were tested for increased risk of microdeletion and/or microduplication states for the genetic locus 7q11.23.

For point mutations various binomial tests are carried out that take into consideration the fetal fraction estimate of the sample, f, the read-depth of the minor allele, r, and the total read-depth of the sequenced base, n. Two frequent, yet non-limiting examples involve assessment of the risk when the genetic abnormality is a recessive point mutation or a dominant point mutation.

In addition to the above, fetal sex determination methods were also developed, with non-limiting examples given below. In one embodiment of the invention, fetal sex was assigned to a sample using a Poisson test using the formula:

$$Pr(r_y \leq k) = e^{-\lambda} \sum_{i=0}^{i=k} \frac{\lambda^i}{i!}$$

where $$\lambda = \frac{fB\mu}{2}$$

and f is the fetal fraction estimate of the sample, B is the number of target sequences on chromosome Y, $\mu$ is the read-depth of the sample and k is the sum of reads obtained from all targets B. The null hypothesis of the Poisson test was that the sample is male. A value of $Pr(r_y)$ less than a threshold $c_y$ was considered as enough evidence to reject the null hypothesis, i.e. the sample is not male. If any of the terms for computing $Pr(r_y)$ were unavailable, then the sample's sex was classified as NA (not available).

In another embodiment of the invention, fetal sex was assigned using the average read-depth of target sequences on chromosome Y. If the average read-depth of the target-sequences was over a predefined threshold, where such threshold may be defined using other sample-specific characteristics such as read-depth and fetal-fraction estimate, the fetal sex was classified as male. If the average read-depth was below such threshold then the sample was classified as female.

Example 5: Target Enrichment Using Families of TACS

In this example, a family of TACS, containing a plurality of members that all bind to the same target sequence of interest, was used for enrichment, compared to use of a single TACS binding to a target sequence of interest. Each member of the family of TACS bound to the same target sequence of interest but had a different start and/or stop coordinates with respect to a reference coordinate system for that target sequence (e.g., the human reference genome built hg19). Thus, when aligned to the target sequence, the family of TACS exhibit a staggered binding pattern, as illustrated in FIG. 3. Typically, the members of a TACS family were staggered approximately 5-10 base pairs.

A family of TACS containing four members (i.e., four sequences that bound to the same target sequence but having different start/stop positions such that the binding of the members to the target sequence was staggered) was prepared. Single TACS hybridization was also prepared as a control. The TACS were fixed to a solid support by labelling with biotin and binding to magnetic beads coated with a biotin-binding substance (e.g., streptavidin or avidin) as described in Example 3. The family of TACS and single TACS were then hybridized to a sequence library, bound sequences were eluted and amplified, and these enriched amplified products were then pooled equimolarly and sequenced on a suitable sequencing platform, as described in Example 3.

Figure 4A:
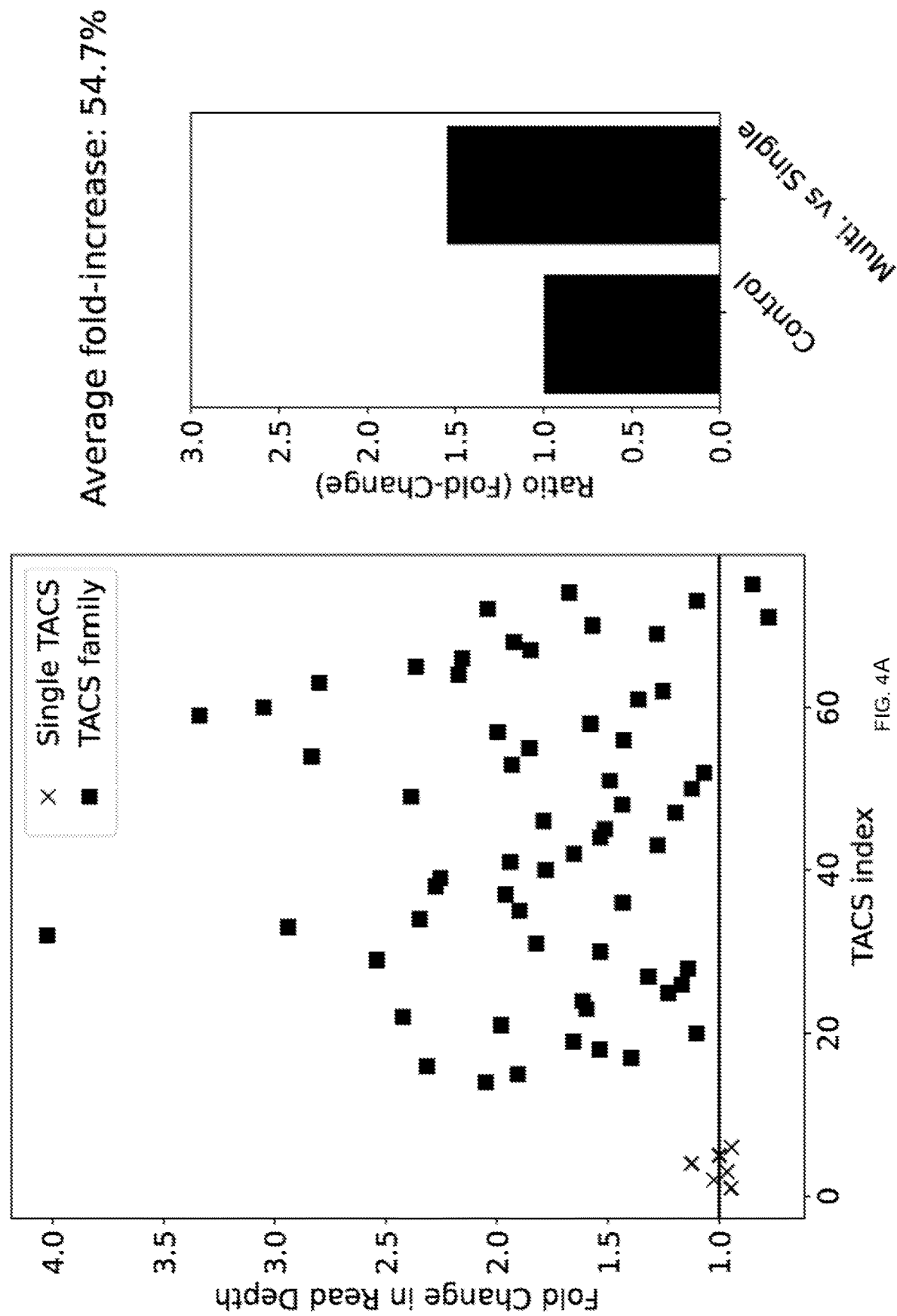
FIGS. 4A-4B are graphs showing enrichment using families of TACS versus a single TACS, as illustrated by increase in the average read-depth.
Figure 4B:
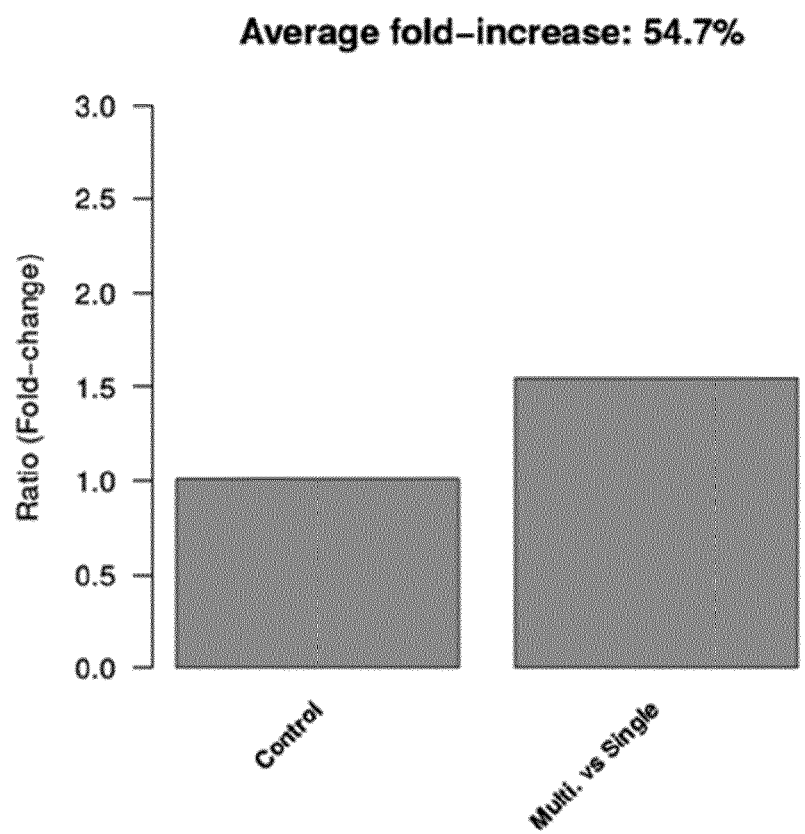

The enriched sequences from the family of TACS sample and the single TACS sample were analyzed for read-depth. The results are shown in FIGS. 4A and 4B. As shown in FIG. 4A, target sequences of interest enriched using the family of four TACS (square symbol) exhibited a fold-change in read-depth when compared to control sequences that were subjected to enrichment using only a single TACS (X symbol). Fold-change was assessed by normalizing the read-depth of each locus by the average read-depth of a sample, wherein the average read-depth was calculated from all loci enriched with a single TACS. As shown in FIG. 4B, an overall 54.7% average increase in read-depth was observed using the family of four TACS.

This example demonstrates that use of a family of TACS, as compared to a single TACS, results in significantly improved enrichment of a target sequence of interest resulting in significantly improved read-depth of that sequence.

Example 6: Analysis of Fetal DNA Samples from Embryo Biopsy

In this example, fetal DNA samples obtained from fetal cells from embryo biopsy were analyzed using the TACS-based methodology shown in FIG. 1 to detect chromosomal abnormalities in the fetal samples.

Fetal Sample Collection, Library Preparation and TACS Enrichment Fetal cell samples were obtained from 3-day and 5-day biopsy embryos respectively were subjected to the TACS methodology shown in FIG. 1 to determine the status of genetic abnormalities. All samples were previously referred for Pre-implantation Genetic Screening (PGS) and subjected to array Comparative Genomic Hybridization (aCGH) as part of the routine screening test. Results of aCGH were used as a reference standard for the results obtained.

Collected fetal cells were initially lysed and DNA extracted using the Rubicon Genomics PicoPLEX© WGA Kit (Liang, L. et al. (2013) PLoS One 8(4), p. e61838).

For certain samples in which whole-genome sequencing was to be performed, the lysed material was subjected to whole genome amplification using commercial whole genome amplification kits. Briefly, following a pre-amplification step, the lysed material was then amplified using amplification enzyme and buffer supplied by the manufacturer. Subsequently, DNA was purified followed by fragmentation using sonication. Fragmented DNA was then processed using standard sequencing library preparation methods such as described in Example 1, typically involving ligation of adapters onto the ends of the cell free DNA fragments, followed by amplification. In addition to the description provided in Example 1, sequencing library preparation kits are commercially available for this purpose.

For samples in which TACS-based enrichment was to be performed, then the sequencing library obtained from the above methods underwent TACS hybridization essentially as described in Example 3. The region(s) of interest on the chromosome(s) of interest were enriched by hybridizing the pool of TACS to the sequencing library, followed by isolation of those sequences within the sequencing library that bind to the TACS. To facilitate isolation of the desired, enriched sequences, typically the TACS sequences were modified such that sequences that hybridized to the TACS were separable from sequences that did not hybridize to the TACS. Typically this was achieved by fixing the TACS to a solid support such as described in Example 3, thereby allowing for physical separation of those sequences that bind the TACS from those sequences that do not bind the TACS. The pools of TACS used either can contain a plurality of single TACS that bind to different target sequences of interest or, alternatively, can contain a plurality of families of TACS containing a plurality of members that each bind to the same target sequence of interest but with different start and/or stop positions on the target sequence, as described in Example 5.

For analysis of fetal DNA samples by TACS-based enrichment, the pool of TACS can contain TACS that target a subset of chromosomes of interest (e.g., chromosomes 13, 18, 21, X and Y). More preferably, however, the pool of TACS contains various TACS that target every chromosome within the human genome (chromosomes 1-22, X and Y) such that the entire genome is encompassed, allowing for determination of chromosomal abnormalities in any chromosome within the human genome.

Next Generation Sequencing (NGS) typically was used to sequence the TACS-enriched sequences (or the whole genome for samples analyzed by whole genome sequencing), thereby providing very accurate counting as well as sequence information. Library products were pooled equimolarly and then subjected to sequencing.

Data Analysis

Sequencing data obtained from NGS were processed to remove adaptor sequences and poor quality reads. Reads whose length was at least 25 bases long post adaptor-removal were aligned to the human reference genome built hg19. If relevant, duplicate reads were removed post-alignment. Where applicable, sequencing output pertaining to the same sample but processed on separate sequencing lanes, was merged to a single sequencing output file. Software analysis provides a final aligned version of a sequenced sample against the human reference genome from which information was extracted in terms of Short Nucleotide Polymorphisms (SNPs) at loci of interest, read-depth per base and the size of aligned fragments.

For whole-genome sequencing and TACS-based whole-genome sequencing, the read-depth of non-overlapping genomic regions of fixed size (e.g. 50 kb or 1 Mb) was obtained by using the samtools bedcov tool, which provides the sum of all reads across a specified genomic region. The obtained value was divided by the length of the windows. For TACS targeted-based sequencing, the read-depth was obtained by using the samtools mpileup tool, which provides information on the read-depth per base, across specified contiguous sequences or the bedcov tool. The median value of the obtained information was assigned as the read-depth of a given locus. Removal of read-depth outliers was performed using either a median-based or mean-based outlier detection approach. Finally, GC-content read-depth bias alleviation was achieved using a local polynomial fitting method to estimate the expected read-depth of regions based on their GC content and then normalize regions using this expected value accordingly.

The normalized read-depth from all regions was used as input into
 (a) various segmentation-based classification algorithms (described further below), and/or
 (b) score-based classification algorithms (described further below),
which were then used to determine the ploidy status of the interrogated regions, as well as the size of any genetic aneuploidies. Score-based classification algorithms were used only with targeted enrichment sequencing data.

Ploidy Status Determination Using Segmentation Algorithms

Three different types of segmentation algorithms were developed and applied to fetal DNA sample analysis: (i) Likelihood-based segmentation; (ii) Segmentation using small overlapping windows; and (iii) Segmentation using parallel pairwise testing, each of which is described further below, along with the results for application of the algorithm.

Each algorithm is a collection of data processing and statistical modeling routines arranged as a series of steps with aim to decide if the observed sequencing data does not support the null hypothesis, H0 defined as:

H0=There are no ploidy deviations from the expected ploidy state.

For human genomes the expected ploidy state is the diploid state. The segmentation approach aims to discover breakpoints in consecutive data where there is a clear distinction between read-depths, which in turn indicates that there is a change in ploidy state. The algorithms are described below.

A. Likelihood-Based Segmentation

Given a set of ordered data points $\{x\_\{1\}, x\_\{2\}, x\_\{3\}, x\_\{4\}, \ldots, x\_\{N\}\}$, that describe read-depth, the aim was to infer at which point $x\_\{i\}$ the data changes distribution (i.e. there is a significant and consecutive change in read-depth). This was labeled as the break point $\vartheta\_\{1\}$. For example, if the data changes distribution after $x\_\{3\}$ then $\vartheta\{1\}=x\_\{3\}$. If more than one break point exists, then the algorithm will label the next discovered break point as $\vartheta\_\{2\}$. The algorithm steps were as follows:

(a) Given a sequence of data $(i, x\_\{i\})$, where $i=1 \ldots N$, the algorithm estimates the number of modes in the data. To this end, a process known as bivariate kernel density estimation was utilized. For example, if there was a single breakpoint, then the algorithm returned that there were 2 modes in our data distribution.

(b) Decide the position of the break point(s) in the data, if such point(s) exist(s). This was achieved with the following algorithm:

(1) Based on the number of breakpoints found in (a) define the probability density function (p.d.f) of the data, which depends on the unknown values of the breakpoints. This may be, but not limited to, a mixture of Normal distributions.

(2) Calculate the maximum likelihood estimate of the p.d.f in (1) for a fixed set of value(s) for the breakpoints.

(3) Repeat (2) for different sets of break point value(s).

(4) Select as estimated break point(s) the values that maximizes step (2).

It was noted that the algorithm does this by assigning membership in all combinations for all breakpoints estimated in part (a). As an example, if the probability is maximized when data points $x\_\{1\}$ to $x\_\{3\}$ come from the first distribution then $\vartheta\_\{1\}=x\_\{3\}$ and membership of $x\_\{1\}$ to $x\_\{3\}$ is assigned to the first distribution and $x\_\{4\}$ to $x\_\{N\}$ to the next identified distribution(s). If the likelihood is maximized with all data points $x\_\{i\}$ assigned to the same mode then no break-point is defined and all data points are assigned to the same distribution. Various distributions and computational methods known to those skilled in the art can be used to implement this.

Representative results of fetal DNA analysis using the likelihood-based segmentation algorithm are shown in FIG. 5. These results demonstrate that likelihood-based segmentation analysis can classify whole-chromosome aberrations in fetal DNA samples (e.g., from PGD/PGS products of conception). At the top panel of FIG. 5, a sample without any ploidy abnormalities subjected to whole-genome sequencing is presented. The expected read-depth of each chromosome (blue horizontal bars) lies within the red lines that indicate the range of values of normal ploidy, as decided from the data. Even if on occasion individual data points (grey dots) deviate from the confidence intervals this is not sufficient evidence of ploidy aberrations according to the probabilistic metric used. Conversely, if enough data points deviate from the confidence intervals then the probabilistic measure used can assign a different ploidy state. Such a case is presented at the bottom of FIG. 5, where the sample has been determined to have monosomy 18 and monosomy 20.

Figure 10:
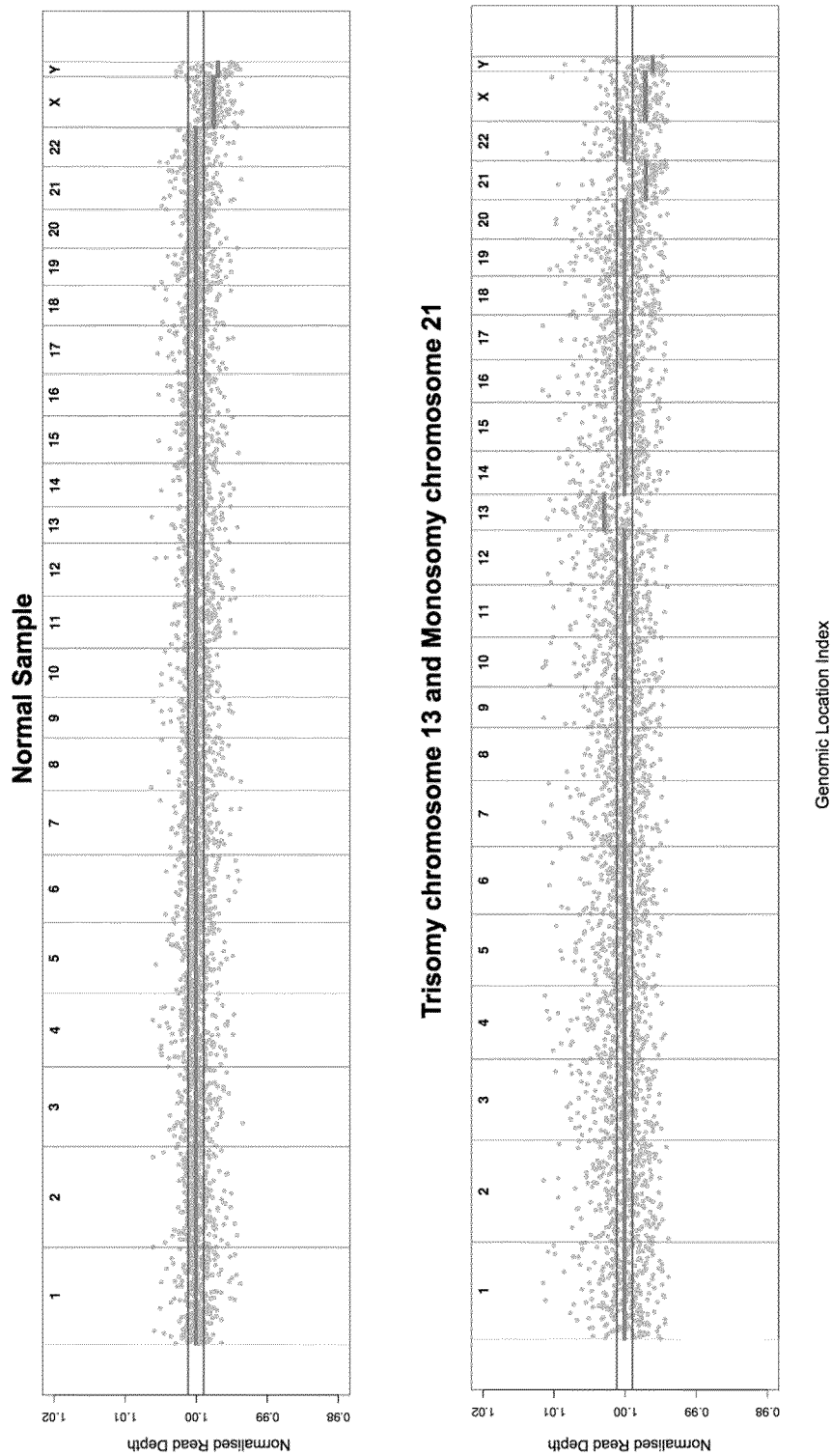
FIG. 10 is a graph of results from fetal DNA samples that underwent ploidy status determination using likelihood-based segmentation analysis and TACS-based enrichment whole genome sequencing data. The horizontal blue line indicates the average read-depth of each chromosome. The red lines indicate threshold intervals of expected diploids. Data above the top red line is classified as more than diploid and data below the red line is classified as less than diploid. The top panel illustrates the results of a euploid male sample (i.e., a male fetus with one copy of chromosome X chromosome and one copy of chromosome Y, and without any ploidy abnormalities present). The bottom panel illustrates the results of a male aneuploid sample with trisomy 13 and monosomy 21. Values on the y-axis are log-based transformations of read-depth.

In similar fashion, FIG. 10 presents results from the algorithm utilizing data derived from TACS specific coordinates combined with data from products of partial complementarity to the TACS that align to non-TACS coordinates thus producing low coverage throughout the genome. In the top panel of FIG. 10 a normal male sample is presented, whereas in the bottom panel the male sample is classified as having trisomy for chromosome 13 and monosomy for chromosome 21.

Figure 11:
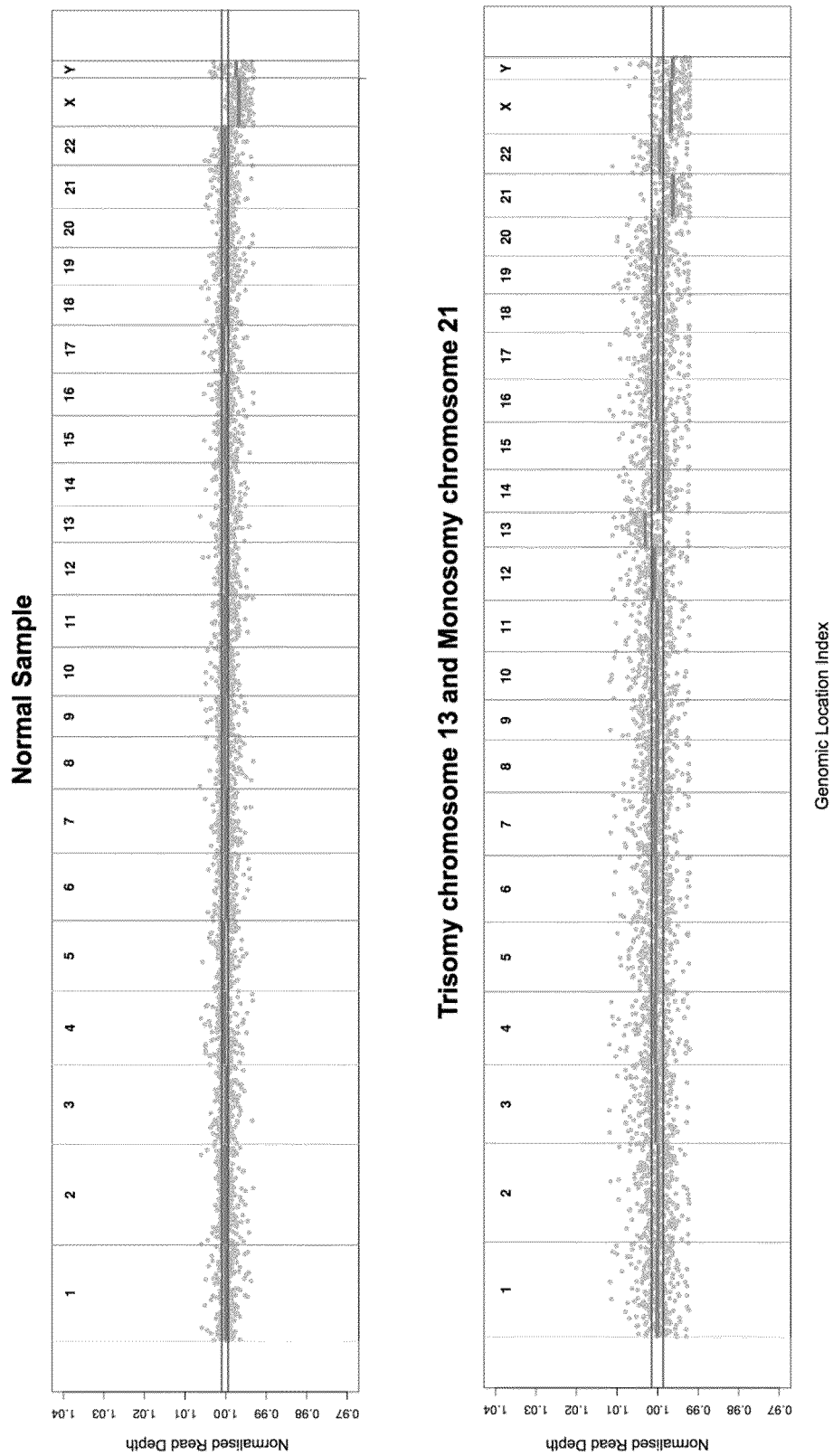
FIG. 11 is a graph of results from fetal DNA samples that underwent ploidy status determination using likelihood-based segmentation analysis and TACS-based enrichment data. The horizontal blue line indicates the average read-depth of each chromosome. The red lines indicate threshold intervals of expected diploids. Data above the top red line is classified as more than diploid and data below the red line is classified as less than diploid. The top panel illustrates the results of a euploid male sample (i.e., a male fetus with one copy of chromosome X chromosome and one copy of chromosome Y, and without any ploidy abnormalities present). The bottom panel illustrates the results of a male aneuploid sample with trisomy 13 and monosomy 21. Values on the y-axis are log-based transformations of read-depth.

FIG. 11 presents results from the algorithm utilizing data from TACS specific coordinates only. As with FIG. 10, in the top panel of FIG. 11 a normal male sample is presented, whereas in the bottom panel the male sample is classified as having trisomy for chromosome 13 and monosomy for chromosome 21.

Thus, it can be seen that the algorithm successfully classifies TACS-based enrichment and TACS-based whole genome sequencing data, allowing for correct classification of chromosomal abnormalities and at the same time requiring significantly less sequencing than massively parallel shotgun sequencing approaches.

B. Segmentation Using Small Overlapping Windows

Given a set of data points the aim was to decide membership of each data point into a set of clusters, based on a thresholding scheme. The algorithm does so as follows:

(a) Given a set of consecutive read-depth data $x\_\{i\}$ (i=1 to N) the data are divided into overlapping windows of fixed size. For example let $w\_\{1\}=\{x\_\{1\}, \ldots, x\{10\}\}$ denote the first window, then $w\_\{2\}=\{x\{2\}, \ldots, x\_\{11\}\}$, $w\_\{3\}=\{x\{3\}, \ldots, x\_\{12\}\}$ etc.

(b) For each window $w\_\{k\}$, a score $S(k)=(X\_\{k\}-m)/m$ is computed, where $X\_\{k\}$ is the median of $w\_\{k\}$ and m is the median from all $x\_\{i\}$ from all chromosomes.

(c) Assign cluster membership based on a thresholding value s, whereby:
if $S(k)<s$, assign to cluster1
if $s<=S(k)<C\_\{1\}s$ are assigned to cluster 2,
if $2s<=S(k)<C\_\{2\}s$ are assigned to cluster 3 etc.
where $C\_\{j\}$. are positive real numbers greater than one. For example, if s is a particular threshold value then all consecutive $w\_\{k\}$ where $S(k)<s$ are assigned to cluster 1. All consecutive $w\_\{k\}$ where $s<=S(k)<C\_\{1\}s$ are assigned to cluster 2. All consecutive $w\_\{k\}$ where $2s<=S(k)<C\_\{2\}s$ are assigned to cluster 3 etc. The threshold s can be either decided from the data or treated as a tuning parameter.

Representative results of ploidy determination for fetal DNA samples (e.g., PGS/PGD products of conception) using whole genome sequencing and small overlapping windows segmentation are shown in FIG. 6. The top panel illustrates a normal sample. As with FIG. 5, the expected read-depth of each chromosome (blue horizontal bars) lies within the red lines, which indicate the range of values of normal ploidy. The expected read-depth is calculated from the individual data points (grey dots). The average read-depth and data points of chromosomes X and Y lie below the bottom red-line, indicating that there is only a single copy of each chromosome, as expected for a male sample. An aneuploid sample is presented at the bottom of FIG. 6 where the sample is classified with trisomy 13 and mosaicism on chromosome 19.

C. Segmentation Using Parallel Pairwise Testing

This segmentation approach firstly performs full chromosome ploidy determination and then a sub-chromosomal ploidy determination as follows:

(a) Read-depth data from one candidate chromosome are compared with read-depth data from other chromosomes using non-parametric statistical tests. The process is repeated until all candidate chromosomes are tested.

(b) Perform a multiple comparisons adjustment on the results of the statistical tests to avoid false positive results.

(c) Depending on the statistical test result from the adjusted data, assign the relevant ploidy to candidate chromosomes that illustrate significant evidence against the null hypothesis (d) Once full-chromosomal ploidy is determined then sub-chromosomal ploidy is tested by randomly splitting regions of each chromosome into smaller sizes. Each sub-chromosomal region is then tested for significant deviations from its expected full-chromosomal read-depth using similar statistical tests as in steps (a)-(c).

Figure 7:
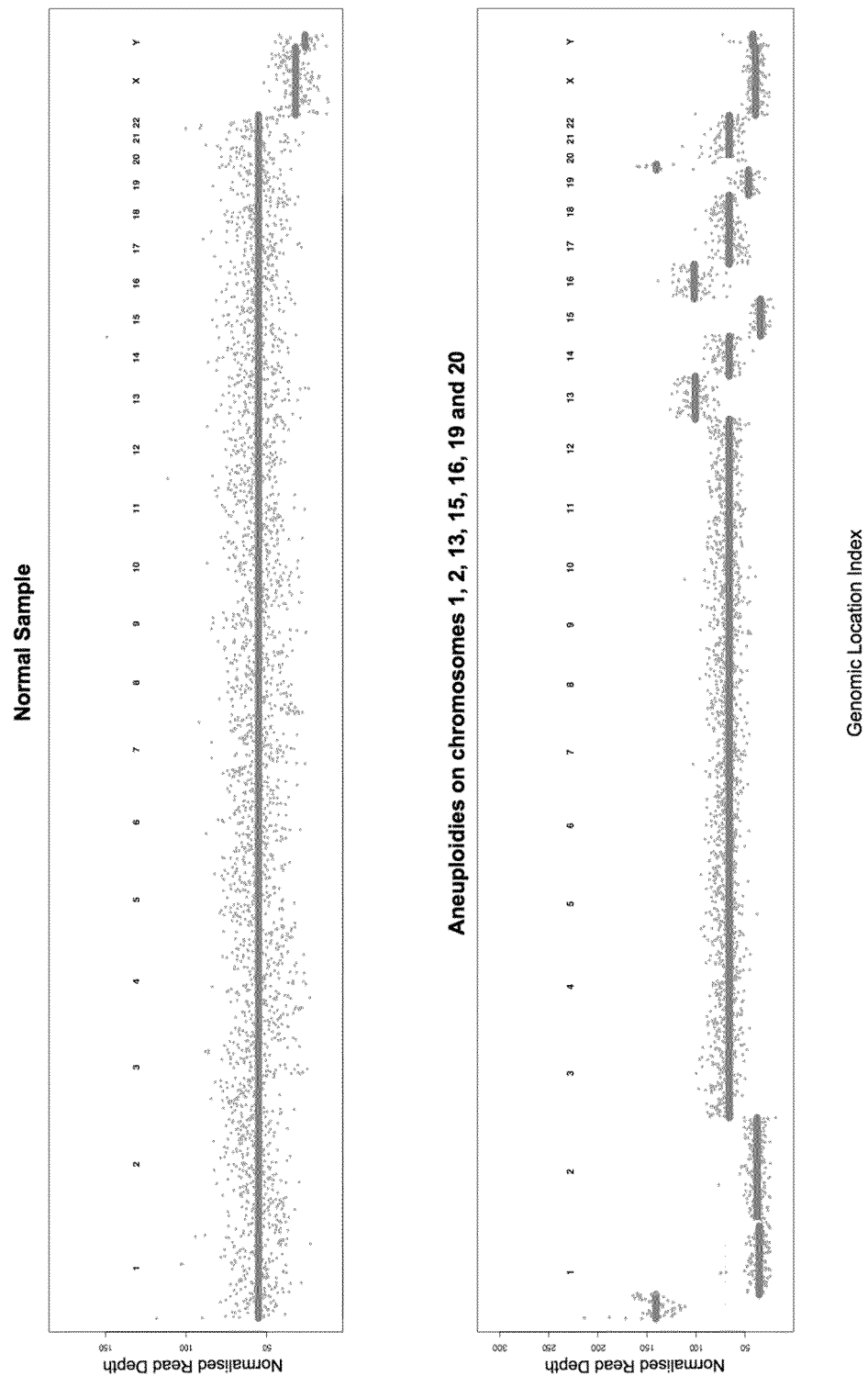
FIG. 7 is a graph of results from fetal DNA samples that underwent ploidy status determination by whole genome sequencing, followed by segmentation analysis using parallel pairwise testing. The top panel illustrates the results of a normal (euploid) sample and the bottom panel illustrates the results of an aneuploidy sample with aneuploidies on chromosomes 1, 2, 13, 15, 16, 19, and 20.

Representative results of ploidy determination for fetal DNA samples (e.g., PGS/PGD products of conception) using whole genome sequencing and small overlapping windows segmentation are presented in FIG. 7. The top panel illustrates a normal sample. As with FIGS. 5, 6, 10 and 11, the expected read-depth of each chromosome is illustrated using blue horizontal bars. In this instance, confidence interval bars have been omitted. A normal sample is presented at the top FIG. 7 whilst a sample presenting many abnormalities is presented at the bottom panel.

Ploidy Status Determination Using Score-Based Classification

Additionally or alternatively to the segmentation-based algorithms described above, fetal DNA samples can be analyzed using score-based classification. The read-depth data were firstly transformed using square root or logarithmic transformation in order to minimize variance biases. Then methods such as those described in Example 4 were performed to decide on the ploidy status of each tested region (chromosomal and sub-chromosomal regions may be tested).

Figure 8:
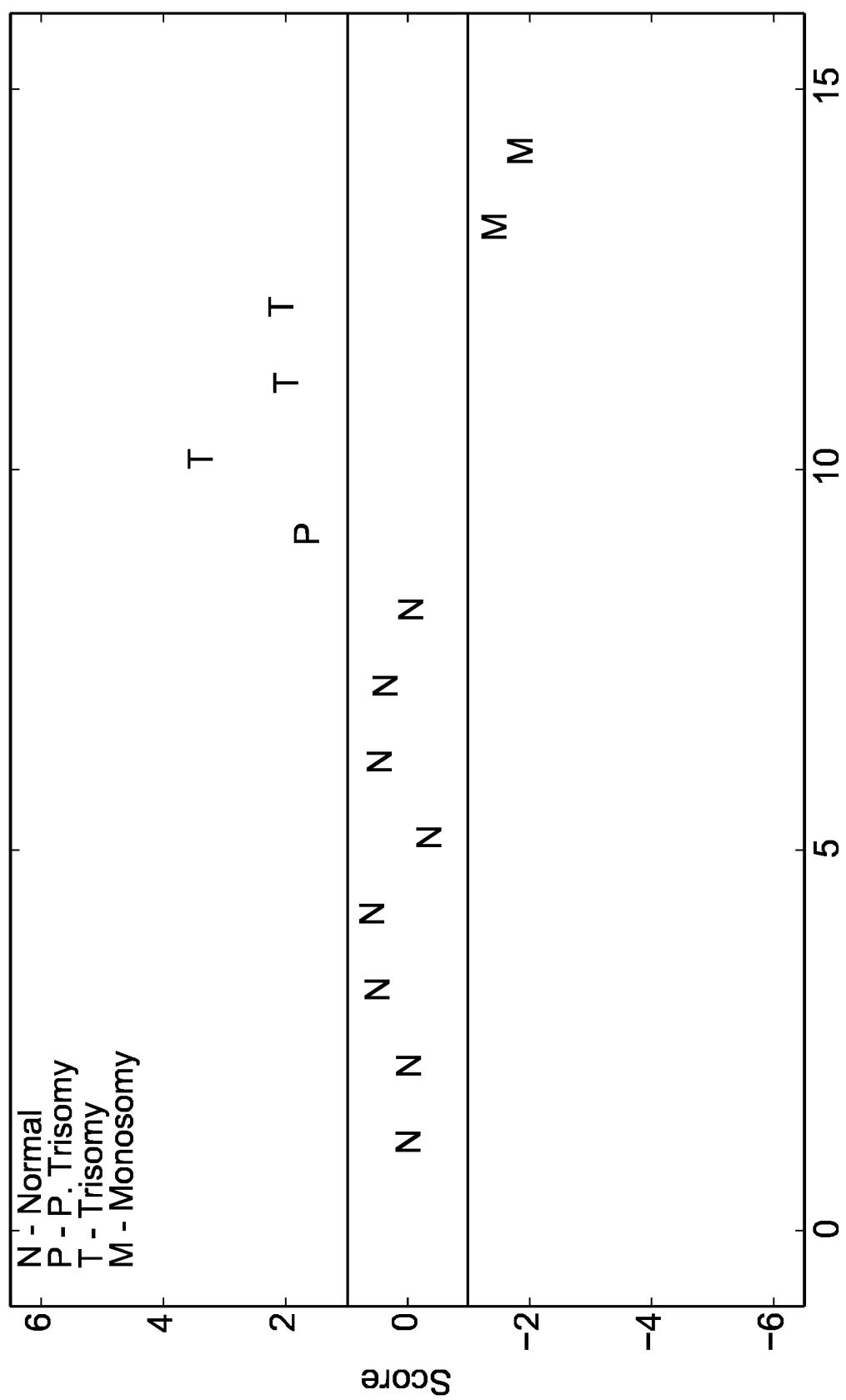
FIG. 8 is a graph depicting results from fetal DNA samples that underwent ploidy status determination using TACS-based enrichment, followed by a score-based classification. As per the key, samples plotted with N indicate normal ploidy status, the sample plotted with P illustrates partial trisomy, the samples plotted with T indicate trisomy and the samples plotted with M indicate monosomy.

Representative results using a score-based classification system on the fetal DNA samples (e.g., PGS/PGD products of conception) are shown in FIG. 8. Green dots illustrate normal ploidy samples whilst all others that lie above or below the normal ploidy thresholds illustrate some type of abnormality. Specifically, blue dots illustrate trisomy samples, cyan dots illustrate partial trisomy samples and red dots illustrate monosomy samples.

In summary, this example demonstrates the successful analysis of fetal DNA samples (e.g., PGS/PGD products of conception) for chromosomal abnormalities using either whole genome sequencing data, TACS-based whole genome sequencing data and TACS-based enrichment data, using a variety of statistical analysis approaches. Furthermore, the example illustrates that the methods used with whole genome sequencing data can be successfully applied to TACS-based whole genome sequencing data and TACS-based enrichment data.

Example 7: Fragment Size Based Tests

There is evidence from the literature that unhealthy tissue can be characterized by and/or associated with fragments in the plasma having a smaller size than the expected size of fragments originating from healthy tissues (Jiang et al, (2015), *Proceedings of the National Academy of Sciences,* 112(11), ppE1317-E1325). Furthermore, it has been shown that fetal cell free DNA can be found in the spent medium of embryo culture of PGS/PGD products of conception and that it can be used for the assessment of chromosomal abnormalities (Liu, WeiQiang, et al. (2017). Thus, a fragments-size based test can be utilized to detect the presence of somatic copy number variations. To this effect, a binomial test of proportions, as described Example 4, can be used for the detection of increased presence of nucleic acid material originating from non-healthy tissue based on fragment size. In particular, under the null hypothesis that the distribution of fragment sizes originating from both healthy and non-healthy cells is the same, a binomial test for proportions (as described in Example 4) using continuity correction can be utilized to quantify any evidence against it.

The same hypothesis holds true for fragments originating from the placenta/fetus (Chan, K. C. (2004) *Clin. Chem.* 50:88-92). Specifically, placenta derived fragments are generally of smaller size when compared to fragments originating from maternal tissues/cells. Accordingly, assessment of the fragment size-based test was performed using maternal plasma samples (i.e., mixed samples where cell free DNA is of maternal and fetal origin). The size of fragments that have aligned to TACS-enriched regions can be obtained from the aligned data. Subsequently, the proportion of fragments under a specific threshold from a test region is compared respective proportion of fragments from a reference region for evidence against the null hypothesis H0, H0: The proportion of small fragments of the test-region is not different from the proportion of small-fragments of the reference region.

Figure 9:
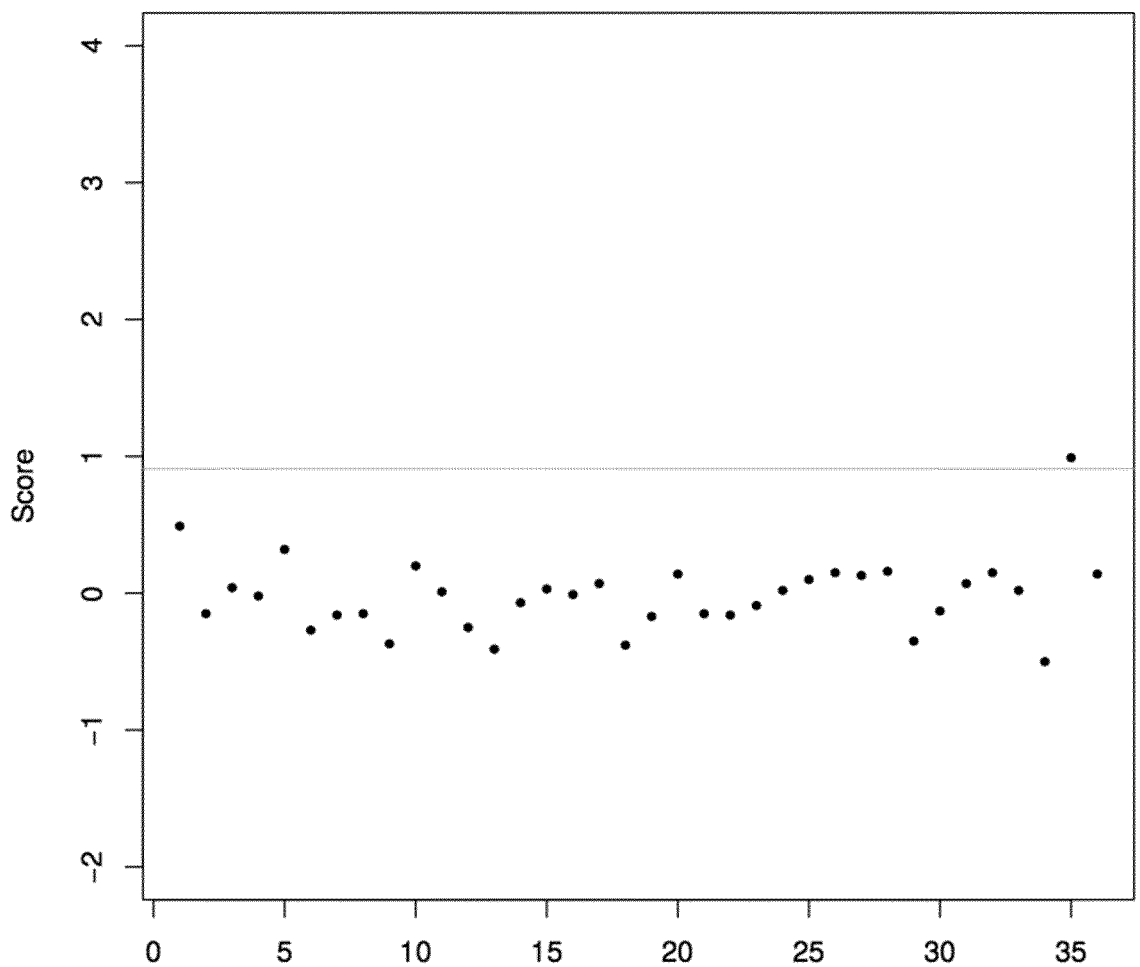
FIG. 9 is a dot plot graph showing results of a fragments-based test for detecting increased numbers of smaller-size fragments in a mixed sample. An abnormal, aneuploid sample, with an estimated fetal fraction of 2.8%, was correctly detected using this method. The black dots are individual samples. The x-axis shows the sample index. The y-axis shows the score result of the fragments-size based method. A score result greater than the threshold shown by the grey line indicates a deviation from the expected size of fragments illustrating the presence of aneuploidy.

FIG. 9 shows results when applying the fragment sizes method to the mixed sample containing maternal and fetal DNA. The black dots are individual samples. The x-axis shows the sample index. The y-axis shows the score result of the fragments-based method. A score result greater than the one indicated by the threshold, illustrated as a grey line, indicates a deviation from the expected size of fragments illustrating the presence of aneuploidy. The results demonstrate that an aneuploid sample, having an estimated fetal fraction equal to 2.8%, was correctly identified, illustrating that fragments-based detection may be used to detect abnormalities in samples with low signal-to-noise ratio (e.g., as is the case in detection of cancer).

Accordingly, this example demonstrates the successful ability of the fragments-based detection method in detecting genetic abnormalities present in diminutive amounts. In addition to this, since small-sized fragments are associated with fragments from non-healthy tissues (Jiang et al, (2015), *Proceedings of the National Academy of Sciences,* 112(11), ppE1317-E1325) they can also be leveraged for the detection of small-sized mutations, such as point mutations and mutational signatures.

The invention claimed is:

1. A method of testing for risk of a genetic abnormality in a DNA sample comprising predominantly fetal or embryonic DNA and comprising genomic sequences of interest, the method comprising:
   (a) preparing a sequencing library from the DNA sample comprising predominantly fetal or embryonic DNA;
   (b) hybridizing the sequencing library to a pool of single-stranded TArget Capture Sequences (TACS), wherein the pool of single-stranded TACS comprises a plurality of TACS families directed to different genomic sequences of interest comprising a genetic abnormality, wherein each TACS family comprises a plurality of member sequences, wherein each member sequence binds to the same genomic sequence of interest but has different start and/or stop positions with respect to a reference coordinate system for the genomic sequence of interest, wherein the start and/or stop positions for the member sequences within a TACS family, with respect to a reference coordinate system for the genomic sequence of interest are staggered by 5 to 10 base pairs, and wherein
      i. each member sequence within the pool of TACS is between 150-260 base pairs in length, each member sequence having a 5' end and a 3' end;
      ii. each member sequence within a TACS family binds to the same region on a genomic sequence of interest, wherein the 5' end and the 3' end of each member sequence are each at least 50 base pairs away from regions harboring Copy Number Variations (CNVs), Segmental duplications or repetitive DNA elements; and
      iii. the GC content of the pool of TACS is between 19% and 80% as determined by calculating the GC content of each member within the pool of TACS;
   (c) isolating members of the sequencing library that bind to the pool of TACS to obtain an enriched library;
   (d) amplifying and sequencing the enriched library;
   (e) aligning the enriched library to a reference genome, thereby obtaining read-depth information and allelic counts; and
   (f) performing statistical analysis on the enriched library sequences to thereby determine risk of a genetic abnormality in the DNA sample.

2. The method of claim 1, wherein the DNA sample is from a pre-implantation embryo, intact trophoblasts collected from a maternal Papanicolaou smear or a fetal cell found in maternal plasma.

3. The method of claim 1, wherein the DNA sample is obtained directly from fetal tissue, or amniotic fluid, or chorionic villi, or products of conception.

4. The method of claim 1, wherein the pool of TACS comprises members that bind to chromosomes 1-22, X and Y of the human genome.

5. The method of claim 1, wherein the pool of TACS comprises at least 5 different TACS families, or wherein each TACS family comprises at least 3 member sequences.

6. The method of claim 1, wherein the genetic abnormality is a chromosomal aneuploidy or wherein the genetic abnormality is a structural abnormality, including but not limited to copy number changes including microdeletions and microduplications, insertions, deletions, translocations, inversions and small-size mutations including point mutations and mutational signatures.

7. The method of claim 1, wherein the pool of TACS is fixed to a solid support, wherein the TACS are biotinylated and are bound to streptavidin-coated magnetic beads.

8. The method of claim 1, wherein amplification of the enriched library is performed in the presence of blocking sequences that inhibit amplification of wild-type sequences.

9. The method of claim 1, wherein members of the sequencing library that bind to the pool of TACS are partially complementary to the TACS.

10. The method of claim 1, wherein the statistical analysis comprises a segmentation algorithm.

11. The method of claim 1, further comprising the step of providing a read-depth for the genomic sequences of interest and read-depths for a plurality of reference loci and the statistical analysis comprises applying an algorithm that tests sequentially the read-depth of the loci of the genomic sequences of interest against the read-depth of the reference loci, the algorithm comprising steps for: (a) removal of inadequately sequenced loci; (b) GC-content bias alleviation; and (c) ploidy status determination.

12. The method of claim 1, further comprising the step of providing a number and size of sequenced fragments for TACS-specific coordinates and the statistical analysis comprises applying an algorithm that tests sequentially the fragment-size proportion of the genomic sequence of interest against the fragment-size proportion of a plurality of reference loci, the algorithm comprising steps for: (a) removal of fragment-size outliers; (b) fragment-size proportion calculation; and (c) ploidy status determination.

\* \* \* \* \*

```
SEQUENCE LISTING

<160> NUMBER OF SEQ ID NOS: 2553

<210> SEQ ID NO 1
<211> LENGTH: 20
<212> TYPE: DNA
<213> ORGANISM: Homo sapiens

<400> SEQUENCE: 1
tcttctcgtt caagatgccg                                                 20

<210> SEQ ID NO 2
<211> LENGTH: 20
<212> TYPE: DNA
<213> ORGANISM: Homo sapiens

<400> SEQUENCE: 2
aagggtggaa gcacattgac                                                 20

<210> SEQ ID NO 3
<211> LENGTH: 22
<212> TYPE: DNA
<213> ORGANISM: Homo sapiens

<400> SEQUENCE: 3
aaattacatg caaggctacc ac                                              22

<210> SEQ ID NO 4
<211> LENGTH: 20
<212> TYPE: DNA
<213> ORGANISM: Homo sapiens

<400> SEQUENCE: 4
atagaggaac aagctgcaca                                                 20

<210> SEQ ID NO 5
<211> LENGTH: 21
<212> TYPE: DNA
<213> ORGANISM: Homo sapiens

<400> SEQUENCE: 5
acaggaagaa agggagtta c                                                21

<210> SEQ ID NO 6
<211> LENGTH: 20
<212> TYPE: DNA
```

```
<213> ORGANISM: Homo sapiens

<400> SEQUENCE: 6
ctcgtccctt gcacatctta                                              20

<210> SEQ ID NO 7
<211> LENGTH: 20
<212> TYPE: DNA
<213> ORGANISM: Homo sapiens

<400> SEQUENCE: 7
ttcaggttgt gtgatgtgtc                                              20

<210> SEQ ID NO 8
<211> LENGTH: 20
<212> TYPE: DNA
<213> ORGANISM: Homo sapiens

<400> SEQUENCE: 8
aggtggggaa gaacaaaaca                                              20

<210> SEQ ID NO 9
<211> LENGTH: 20
<212> TYPE: DNA
<213> ORGANISM: Homo sapiens

<400> SEQUENCE: 9
taagcagagg ttttgttgcc                                              20

<210> SEQ ID NO 10
<211> LENGTH: 20
<212> TYPE: DNA
<213> ORGANISM: Homo sapiens

<400> SEQUENCE: 10
gagagtaggt gcagggaaac                                              20

<210> SEQ ID NO 11
<211> LENGTH: 20
<212> TYPE: DNA
<213> ORGANISM: Homo sapiens

<400> SEQUENCE: 11
gtgaagtatt tgctgccacc                                              20

<210> SEQ ID NO 12
<211> LENGTH: 20
<212> TYPE: DNA
<213> ORGANISM: Homo sapiens

<400> SEQUENCE: 12
atcccgcatt cttaaccaca                                              20

<210> SEQ ID NO 13
<211> LENGTH: 20
<212> TYPE: DNA
<213> ORGANISM: Homo sapiens

<400> SEQUENCE: 13
atggtcatct caacagcaca                                              20

<210> SEQ ID NO 14
<211> LENGTH: 21
```

```
<212> TYPE: DNA
<213> ORGANISM: Homo sapiens

<400> SEQUENCE: 14
gactaagcaa aagcatctcc c                                      21

<210> SEQ ID NO 15
<211> LENGTH: 20
<212> TYPE: DNA
<213> ORGANISM: Homo sapiens

<400> SEQUENCE: 15
tccactgacg ttgagattcg                                        20

<210> SEQ ID NO 16
<211> LENGTH: 20
<212> TYPE: DNA
<213> ORGANISM: Homo sapiens

<400> SEQUENCE: 16
ttcttacagg ctcagggtat                                        20

<210> SEQ ID NO 17
<211> LENGTH: 20
<212> TYPE: DNA
<213> ORGANISM: Homo sapiens

<400> SEQUENCE: 17
cgaacctcct tgacctctta                                        20

<210> SEQ ID NO 18
<211> LENGTH: 21
<212> TYPE: DNA
<213> ORGANISM: Homo sapiens

<400> SEQUENCE: 18
cccatagctt aaccccctaca a                                     21

<210> SEQ ID NO 19
<211> LENGTH: 22
<212> TYPE: DNA
<213> ORGANISM: Homo sapiens

<400> SEQUENCE: 19
gttatgttga tagggaagc tt                                      22

<210> SEQ ID NO 20
<211> LENGTH: 22
<212> TYPE: DNA
<213> ORGANISM: Homo sapiens

<400> SEQUENCE: 20
tcttcatctt actgtctagc ac                                     22

<210> SEQ ID NO 21
<211> LENGTH: 20
<212> TYPE: DNA
<213> ORGANISM: Homo sapiens

<400> SEQUENCE: 21
aagccctcta ctccatctgt                                        20

<210> SEQ ID NO 22
```

```
<211> LENGTH: 21
<212> TYPE: DNA
<213> ORGANISM: Homo sapiens

<400> SEQUENCE: 22
tcatacccta tccctgtgat c                                              21

<210> SEQ ID NO 23
<211> LENGTH: 20
<212> TYPE: DNA
<213> ORGANISM: Homo sapiens

<400> SEQUENCE: 23
tcagaactcg tcagtggaag                                                20

<210> SEQ ID NO 24
<211> LENGTH: 21
<212> TYPE: DNA
<213> ORGANISM: Homo sapiens

<400> SEQUENCE: 24 tcttgcccctt gatttgtttc c                                             21

<210> SEQ ID NO 25
<211> LENGTH: 19
<212> TYPE: DNA
<213> ORGANISM: Homo sapiens

<400> SEQUENCE: 25
gaagggccag acagcttat                                                 19

<210> SEQ ID NO 26
<211> LENGTH: 21
<212> TYPE: DNA
<213> ORGANISM: Homo sapiens

<400> SEQUENCE: 26
gccttttatc catatgccac c                                              21

<210> SEQ ID NO 27
<211> LENGTH: 21
<212> TYPE: DNA
<213> ORGANISM: Homo sapiens

<400> SEQUENCE: 27
atttgctttg tttttgtccc t                                              21

<210> SEQ ID NO 28
<211> LENGTH: 20
<212> TYPE: DNA
<213> ORGANISM: Homo sapiens

<400> SEQUENCE: 28
gccctcaact ttgcttttca                                                20

<210> SEQ ID NO 29
<211> LENGTH: 21
<212> TYPE: DNA
<213> ORGANISM: Homo sapiens

<400> SEQUENCE: 29
gatcattgct ttgtttggac c                                              21
```

```
<210> SEQ ID NO 30
<211> LENGTH: 20
<212> TYPE: DNA
<213> ORGANISM: Homo sapiens

<400> SEQUENCE: 30
aaaaacctgc actgtgttcg                                                20

<210> SEQ ID NO 31
<211> LENGTH: 21
<212> TYPE: DNA
<213> ORGANISM: Homo sapiens

<400> SEQUENCE: 31
aggagaggaa aaatcttgac c                                              21

<210> SEQ ID NO 32
<211> LENGTH: 22
<212> TYPE: DNA
<213> ORGANISM: Homo sapiens

<400> SEQUENCE: 32
tttttacagc aatcttcact gc                                             22

<210> SEQ ID NO 33
<211> LENGTH: 20
<212> TYPE: DNA
<213> ORGANISM: Homo sapiens

<400> SEQUENCE: 33
ctgcctgcag ccattattgt                                                20

<210> SEQ ID NO 34
<211> LENGTH: 22
<212> TYPE: DNA
<213> ORGANISM: Homo sapiens

<400> SEQUENCE: 34
taagccggaa tgatttgtaa gg                                             22

<210> SEQ ID NO 35
<211> LENGTH: 22
<212> TYPE: DNA
<213> ORGANISM: Homo sapiens

<400> SEQUENCE: 35
ccttggggta tgtttgttat gt                                             22

<210> SEQ ID NO 36
<211> LENGTH: 20
<212> TYPE: DNA
<213> ORGANISM: Homo sapiens

<400> SEQUENCE: 36
tacccttggg cttaacagct                                                20

<210> SEQ ID NO 37
<211> LENGTH: 22
<212> TYPE: DNA
<213> ORGANISM: Homo sapiens

<400> SEQUENCE: 37 acttttctg tatcagtcac gg                                              22
```

```
<210> SEQ ID NO 38
<211> LENGTH: 20
<212> TYPE: DNA
<213> ORGANISM: Homo sapiens

<400> SEQUENCE: 38
agttgtcatg ttgggctcat                                               20

<210> SEQ ID NO 39
<211> LENGTH: 20
<212> TYPE: DNA
<213> ORGANISM: Homo sapiens

<400> SEQUENCE: 39
ctgcttttgt gtgttcccctt                                              20

<210> SEQ ID NO 40
<211> LENGTH: 22
<212> TYPE: DNA
<213> ORGANISM: Homo sapiens

<400> SEQUENCE: 40
tgtcctaagt tacctgtctg ac                                            22

<210> SEQ ID NO 41
<211> LENGTH: 20
<212> TYPE: DNA
<213> ORGANISM: Homo sapiens

<400> SEQUENCE: 41
ccagttcctg tttttctgcc                                               20

<210> SEQ ID NO 42
<211> LENGTH: 21
<212> TYPE: DNA
<213> ORGANISM: Homo sapiens

<400> SEQUENCE: 42
gccctggaaa gtactgtaac a                                             21

<210> SEQ ID NO 43
<211> LENGTH: 21
<212> TYPE: DNA
<213> ORGANISM: Homo sapiens

<400> SEQUENCE: 43
gccttcactg atcctacttt c                                             21

<210> SEQ ID NO 44
<211> LENGTH: 20
<212> TYPE: DNA
<213> ORGANISM: Homo sapiens

<400> SEQUENCE: 44
tgttacagcc aggctttcat                                               20

<210> SEQ ID NO 45
<211> LENGTH: 21
<212> TYPE: DNA
<213> ORGANISM: Homo sapiens

<400> SEQUENCE: 45
ggatatgggg taggttttttg t                                            21
```

```
<210> SEQ ID NO 46
<211> LENGTH: 20
<212> TYPE: DNA
<213> ORGANISM: Homo sapiens

<400> SEQUENCE: 46
caacgaacac agggtttaca                                            20

<210> SEQ ID NO 47
<211> LENGTH: 20
<212> TYPE: DNA
<213> ORGANISM: Homo sapiens

<400> SEQUENCE: 47
actcatagaa ctggggcttt                                            20

<210> SEQ ID NO 48
<211> LENGTH: 21
<212> TYPE: DNA
<213> ORGANISM: Homo sapiens

<400> SEQUENCE: 48
ccaggactct ctcttttctt c                                          21

<210> SEQ ID NO 49
<211> LENGTH: 20
<212> TYPE: DNA
<213> ORGANISM: Homo sapiens

<400> SEQUENCE: 49
ctttgtaggt cctccagaga                                            20

<210> SEQ ID NO 50
<211> LENGTH: 22
<212> TYPE: DNA
<213> ORGANISM: Homo sapiens

<400> SEQUENCE: 50
gacacataag accactttag gc                                         22

<210> SEQ ID NO 51
<211> LENGTH: 20
<212> TYPE: DNA
<213> ORGANISM: Homo sapiens

<400> SEQUENCE: 51
cctgttttca gtgggttgaa                                            20

<210> SEQ ID NO 52
<211> LENGTH: 21
<212> TYPE: DNA
<213> ORGANISM: Homo sapiens

<400> SEQUENCE: 52
gatatgttct ggaggactgc t                                          21

<210> SEQ ID NO 53
<211> LENGTH: 20
<212> TYPE: DNA
<213> ORGANISM: Homo sapiens
```

```
<400> SEQUENCE: 53
ccacgttgta cctttccatg                                              20

<210> SEQ ID NO 54
<211> LENGTH: 20
<212> TYPE: DNA
<213> ORGANISM: Homo sapiens

<400> SEQUENCE: 54
tgattctcac aggctccttg                                              20

<210> SEQ ID NO 55
<211> LENGTH: 21
<212> TYPE: DNA
<213> ORGANISM: Homo sapiens

<400> SEQUENCE: 55
gagattcaaa acagtggtgg c                                            21

<210> SEQ ID NO 56
<211> LENGTH: 22
<212> TYPE: DNA
<213> ORGANISM: Homo sapiens

<400> SEQUENCE: 56
tgatggaagt ttctaggtca gt                                           22

<210> SEQ ID NO 57
<211> LENGTH: 19
<212> TYPE: DNA
<213> ORGANISM: Homo sapiens

<400> SEQUENCE: 57
acaacactgt ccttgggtt                                               19

<210> SEQ ID NO 58
<211> LENGTH: 20
<212> TYPE: DNA
<213> ORGANISM: Homo sapiens

<400> SEQUENCE: 58
aacactcttg ctccctatgt                                              20

<210> SEQ ID NO 59
<211> LENGTH: 20
<212> TYPE: DNA
<213> ORGANISM: Homo sapiens

<400> SEQUENCE: 59
taaatgtcct gtgtgctcgg                                              20

<210> SEQ ID NO 60
<211> LENGTH: 21
<212> TYPE: DNA
<213> ORGANISM: Homo sapiens

<400> SEQUENCE: 60
tttctctccc agcttgatct t                                            21

<210> SEQ ID NO 61
<211> LENGTH: 20
<212> TYPE: DNA
```

<213> ORGANISM: Homo sapiens

<400> SEQUENCE: 61
gacaggacac atggagagag                    20

<210> SEQ ID NO 62
<211> LENGTH: 20
<212> TYPE: DNA
<213> ORGANISM: Homo sapiens

<400> SEQUENCE: 62
ctgtgcagag acgaactaag                    20

<210> SEQ ID NO 63
<211> LENGTH: 21
<212> TYPE: DNA
<213> ORGANISM: Homo sapiens

<400> SEQUENCE: 63
aactgatggt gatttgcatg t                  21

<210> SEQ ID NO 64
<211> LENGTH: 19
<212> TYPE: DNA
<213> ORGANISM: Homo sapiens

<400> SEQUENCE: 64
ctctcggagc aaagacctt                     19

<210> SEQ ID NO 65
<211> LENGTH: 20
<212> TYPE: DNA
<213> ORGANISM: Homo sapiens

<400> SEQUENCE: 65
ggcttctgga aacatcttgc                    20

<210> SEQ ID NO 66
<211> LENGTH: 20
<212> TYPE: DNA
<213> ORGANISM: Homo sapiens

<400> SEQUENCE: 66
acctcataag tacgcccatc                    20

<210> SEQ ID NO 67
<211> LENGTH: 21
<212> TYPE: DNA
<213> ORGANISM: Homo sapiens

<400> SEQUENCE: 67
caatagaagt aggggggtgag g                 21

<210> SEQ ID NO 68
<211> LENGTH: 20
<212> TYPE: DNA
<213> ORGANISM: Homo sapiens

<400> SEQUENCE: 68
tgatcttcct ttgctcctgt                    20

<210> SEQ ID NO 69
<211> LENGTH: 20

<212> TYPE: DNA
<213> ORGANISM: Homo sapiens

<400> SEQUENCE: 69
agctgggatg ggttgtttat                                          20

<210> SEQ ID NO 70
<211> LENGTH: 20
<212> TYPE: DNA
<213> ORGANISM: Homo sapiens

<400> SEQUENCE: 70
atgacgacga tgttggagag                                          20

<210> SEQ ID NO 71
<211> LENGTH: 20
<212> TYPE: DNA
<213> ORGANISM: Homo sapiens

<400> SEQUENCE: 71
gccagttgtc agaagaatcc                                          20

<210> SEQ ID NO 72
<211> LENGTH: 20
<212> TYPE: DNA
<213> ORGANISM: Homo sapiens

<400> SEQUENCE: 72
tccttcagca agcctctttt                                          20

<210> SEQ ID NO 73
<211> LENGTH: 20
<212> TYPE: DNA
<213> ORGANISM: Homo sapiens

<400> SEQUENCE: 73
caactgcatt ccaaaacagc                                          20

<210> SEQ ID NO 74
<211> LENGTH: 20
<212> TYPE: DNA
<213> ORGANISM: Homo sapiens

<400> SEQUENCE: 74
tgagggtgat aacctgtgag                                          20

<210> SEQ ID NO 75
<211> LENGTH: 21
<212> TYPE: DNA
<213> ORGANISM: Homo sapiens

<400> SEQUENCE: 75
gaagggaaac agtgagaaag a                                        21

<210> SEQ ID NO 76
<211> LENGTH: 20
<212> TYPE: DNA
<213> ORGANISM: Homo sapiens

<400> SEQUENCE: 76
ggcttgaagt ttgtctgtga                                          20

<210> SEQ ID NO 77

```
<211> LENGTH: 20
<212> TYPE: DNA
<213> ORGANISM: Homo sapiens

<400> SEQUENCE: 77
tcaagcgccg taagtatgta                                                      20

<210> SEQ ID NO 78
<211> LENGTH: 20
<212> TYPE: DNA
<213> ORGANISM: Homo sapiens

<400> SEQUENCE: 78
ggattttcac attgctcagc                                                      20

<210> SEQ ID NO 79
<211> LENGTH: 20
<212> TYPE: DNA
<213> ORGANISM: Homo sapiens

<400> SEQUENCE: 79
taaccataac atccagggca                                                      20

<210> SEQ ID NO 80
<211> LENGTH: 21
<212> TYPE: DNA
<213> ORGANISM: Homo sapiens

<400> SEQUENCE: 80
tagcatgaga gtgaactgag g                                                    21

<210> SEQ ID NO 81
<211> LENGTH: 20
<212> TYPE: DNA
<213> ORGANISM: Homo sapiens

<400> SEQUENCE: 81
ttgtaagctg gcacactgaa                                                      20

<210> SEQ ID NO 82
<211> LENGTH: 20
<212> TYPE: DNA
<213> ORGANISM: Homo sapiens

<400> SEQUENCE: 82
cagccacata gcccatatct                                                      20

<210> SEQ ID NO 83
<211> LENGTH: 20
<212> TYPE: DNA
<213> ORGANISM: Homo sapiens

<400> SEQUENCE: 83
ttaagaaagt gccgtgttgc                                                      20

<210> SEQ ID NO 84
<211> LENGTH: 20
<212> TYPE: DNA
<213> ORGANISM: Homo sapiens

<400> SEQUENCE: 84
tgcccatgag tctacttgtg                                                      20
```

```
<210> SEQ ID NO 85
<211> LENGTH: 20
<212> TYPE: DNA
<213> ORGANISM: Homo sapiens

<400> SEQUENCE: 85
atgggtccat gaagagaagc                                              20

<210> SEQ ID NO 86
<211> LENGTH: 20
<212> TYPE: DNA
<213> ORGANISM: Homo sapiens

<400> SEQUENCE: 86
aagtggactg agggacaatt                                              20

<210> SEQ ID NO 87
<211> LENGTH: 20
<212> TYPE: DNA
<213> ORGANISM: Homo sapiens

<400> SEQUENCE: 87
agttgtttcc agtactgcca                                              20

<210> SEQ ID NO 88
<211> LENGTH: 22
<212> TYPE: DNA
<213> ORGANISM: Homo sapiens

<400> SEQUENCE: 88
tcagactgag cattaaatca cc                                           22

<210> SEQ ID NO 89
<211> LENGTH: 20
<212> TYPE: DNA
<213> ORGANISM: Homo sapiens

<400> SEQUENCE: 89
gtatgctttc aagtgacgcc                                              20

<210> SEQ ID NO 90
<211> LENGTH: 20
<212> TYPE: DNA
<213> ORGANISM: Homo sapiens

<400> SEQUENCE: 90
taggtctgga agaatgccag                                              20

<210> SEQ ID NO 91
<211> LENGTH: 21
<212> TYPE: DNA
<213> ORGANISM: Homo sapiens

<400> SEQUENCE: 91
gaagacaatg caatgaggtg t                                            21

<210> SEQ ID NO 92
<211> LENGTH: 20
<212> TYPE: DNA
<213> ORGANISM: Homo sapiens

<400> SEQUENCE: 92
agtatcttgg gcttgtgaca                                              20
```

```
<210> SEQ ID NO 93
<211> LENGTH: 20
<212> TYPE: DNA
<213> ORGANISM: Homo sapiens

<400> SEQUENCE: 93
agacccaatg agaacaggaa                                               20

<210> SEQ ID NO 94
<211> LENGTH: 20
<212> TYPE: DNA
<213> ORGANISM: Homo sapiens

<400> SEQUENCE: 94
gctccacttc cagtctttct                                               20

<210> SEQ ID NO 95
<211> LENGTH: 20
<212> TYPE: DNA
<213> ORGANISM: Homo sapiens

<400> SEQUENCE: 95
tgatggagga agtgtgaagc                                               20

<210> SEQ ID NO 96
<211> LENGTH: 20
<212> TYPE: DNA
<213> ORGANISM: Homo sapiens

<400> SEQUENCE: 96
ttggaatagt gagcctccct                                               20

<210> SEQ ID NO 97
<211> LENGTH: 20
<212> TYPE: DNA
<213> ORGANISM: Homo sapiens

<400> SEQUENCE: 97
tggcttttct gtagtttggg                                               20

<210> SEQ ID NO 98
<211> LENGTH: 20
<212> TYPE: DNA
<213> ORGANISM: Homo sapiens

<400> SEQUENCE: 98
tctggggctc tttgtctttg                                               20

<210> SEQ ID NO 99
<211> LENGTH: 20
<212> TYPE: DNA
<213> ORGANISM: Homo sapiens

<400> SEQUENCE: 99
agcagcaaga gttgagaaga                                               20

<210> SEQ ID NO 100
<211> LENGTH: 20
<212> TYPE: DNA
<213> ORGANISM: Homo sapiens

<400> SEQUENCE: 100
attttccctc ccctgtagct                                               20
```

<210> SEQ ID NO 101
<211> LENGTH: 21
<212> TYPE: DNA
<213> ORGANISM: Homo sapiens

<400> SEQUENCE: 101
ggctttgaaa aatcaccatg g                                    21

<210> SEQ ID NO 102
<211> LENGTH: 20
<212> TYPE: DNA
<213> ORGANISM: Homo sapiens

<400> SEQUENCE: 102
ctgggcacac tgtattacca                                      20

<210> SEQ ID NO 103
<211> LENGTH: 20
<212> TYPE: DNA
<213> ORGANISM: Homo sapiens

<400> SEQUENCE: 103
agaggtttcc atcgttgcta                                      20

<210> SEQ ID NO 104
<211> LENGTH: 20
<212> TYPE: DNA
<213> ORGANISM: Homo sapiens

<400> SEQUENCE: 104
caccacgttt ctaatgcaga                                      20

<210> SEQ ID NO 105
<211> LENGTH: 20
<212> TYPE: DNA
<213> ORGANISM: Homo sapiens

<400> SEQUENCE: 105
aacagcccca aacttcctac                                      20

<210> SEQ ID NO 106
<211> LENGTH: 20
<212> TYPE: DNA
<213> ORGANISM: Homo sapiens

<400> SEQUENCE: 106
gagttgaaaa aggtccacgc                                      20

<210> SEQ ID NO 107
<211> LENGTH: 20
<212> TYPE: DNA
<213> ORGANISM: Homo sapiens

<400> SEQUENCE: 107
atcactgcca acaagccatt                                      20

<210> SEQ ID NO 108
<211> LENGTH: 20
<212> TYPE: DNA
<213> ORGANISM: Homo sapiens

```
<400> SEQUENCE: 108
cagaggaaag acacagtgct                                              20

<210> SEQ ID NO 109
<211> LENGTH: 20
<212> TYPE: DNA
<213> ORGANISM: Homo sapiens

<400> SEQUENCE: 109
tgagttgtgg gggataaagg                                              20

<210> SEQ ID NO 110
<211> LENGTH: 20
<212> TYPE: DNA
<213> ORGANISM: Homo sapiens

<400> SEQUENCE: 110
tcttggtttt gaggctgtca                                              20

<210> SEQ ID NO 111
<211> LENGTH: 20
<212> TYPE: DNA
<213> ORGANISM: Homo sapiens

<400> SEQUENCE: 111
tctgggcact ttccttatga                                              20

<210> SEQ ID NO 112
<211> LENGTH: 20
<212> TYPE: DNA
<213> ORGANISM: Homo sapiens

<400> SEQUENCE: 112
atcagcctaa ttctccccac                                              20

<210> SEQ ID NO 113
<211> LENGTH: 20
<212> TYPE: DNA
<213> ORGANISM: Homo sapiens

<400> SEQUENCE: 113
gcagttttga ggggagaaga                                              20

<210> SEQ ID NO 114
<211> LENGTH: 20
<212> TYPE: DNA
<213> ORGANISM: Homo sapiens

<400> SEQUENCE: 114
atcccccatc atccatactc                                              20

<210> SEQ ID NO 115
<211> LENGTH: 19
<212> TYPE: DNA
<213> ORGANISM: Homo sapiens

<400> SEQUENCE: 115
ttcatgatgc cacctcctc                                               19

<210> SEQ ID NO 116
<211> LENGTH: 20
<212> TYPE: DNA
```

<213> ORGANISM: Homo sapiens

<400> SEQUENCE: 116
catagctagg cctgtgagtg                    20

<210> SEQ ID NO 117
<211> LENGTH: 20
<212> TYPE: DNA
<213> ORGANISM: Homo sapiens

<400> SEQUENCE: 117
gcccaaatac cccttcagta                    20

<210> SEQ ID NO 118
<211> LENGTH: 19
<212> TYPE: DNA
<213> ORGANISM: Homo sapiens

<400> SEQUENCE: 118
tcagcttgct ccttctctg                     19

<210> SEQ ID NO 119
<211> LENGTH: 20
<212> TYPE: DNA
<213> ORGANISM: Homo sapiens

<400> SEQUENCE: 119
gcacctcaat cccgtacaat                    20

<210> SEQ ID NO 120
<211> LENGTH: 20
<212> TYPE: DNA
<213> ORGANISM: Homo sapiens

<400> SEQUENCE: 120
ctaggtcctc agcagtgttt                    20

<210> SEQ ID NO 121
<211> LENGTH: 20
<212> TYPE: DNA
<213> ORGANISM: Homo sapiens

<400> SEQUENCE: 121
gcgttttaag cagctgtgta                    20

<210> SEQ ID NO 122
<211> LENGTH: 21
<212> TYPE: DNA
<213> ORGANISM: Homo sapiens

<400> SEQUENCE: 122
tcccagagtt aacaataccc c                  21

<210> SEQ ID NO 123
<211> LENGTH: 20
<212> TYPE: DNA
<213> ORGANISM: Homo sapiens

<400> SEQUENCE: 123
tctccagatc gaaacagcat                    20

<210> SEQ ID NO 124
<211> LENGTH: 20

```
<212> TYPE: DNA
<213> ORGANISM: Homo sapiens

<400> SEQUENCE: 124
ccatttgcac tgccgatttc                                              20

<210> SEQ ID NO 125
<211> LENGTH: 20
<212> TYPE: DNA
<213> ORGANISM: Homo sapiens

<400> SEQUENCE: 125
tcattcaaag ccaagatgcc                                              20

<210> SEQ ID NO 126
<211> LENGTH: 21
<212> TYPE: DNA
<213> ORGANISM: Homo sapiens

<400> SEQUENCE: 126
actagtccca aaagcctaca c                                            21

<210> SEQ ID NO 127
<211> LENGTH: 20
<212> TYPE: DNA
<213> ORGANISM: Homo sapiens

<400> SEQUENCE: 127
acacgctaca tagacactgg                                              20

<210> SEQ ID NO 128
<211> LENGTH: 20
<212> TYPE: DNA
<213> ORGANISM: Homo sapiens

<400> SEQUENCE: 128
aacagcagcg tcagaataac                                              20

<210> SEQ ID NO 129
<211> LENGTH: 20
<212> TYPE: DNA
<213> ORGANISM: Homo sapiens

<400> SEQUENCE: 129
caatcgaggt cacattcacc                                              20

<210> SEQ ID NO 130
<211> LENGTH: 20
<212> TYPE: DNA
<213> ORGANISM: Homo sapiens

<400> SEQUENCE: 130
aggtctttac gggaaggaaa                                              20

<210> SEQ ID NO 131
<211> LENGTH: 21
<212> TYPE: DNA
<213> ORGANISM: Homo sapiens

<400> SEQUENCE: 131
tgacacgctg aagaaaatag c                                            21

<210> SEQ ID NO 132
```

```
<211> LENGTH: 20
<212> TYPE: DNA
<213> ORGANISM: Homo sapiens

<400> SEQUENCE: 132
tgagggagaa gtttggtagg                                              20

<210> SEQ ID NO 133
<211> LENGTH: 20
<212> TYPE: DNA
<213> ORGANISM: Homo sapiens

<400> SEQUENCE: 133
ggagggaatg gcagaagtaa                                              20

<210> SEQ ID NO 134
<211> LENGTH: 20
<212> TYPE: DNA
<213> ORGANISM: Homo sapiens

<400> SEQUENCE: 134
ccctgtctaa agagccatgt                                              20

<210> SEQ ID NO 135
<211> LENGTH: 21
<212> TYPE: DNA
<213> ORGANISM: Homo sapiens

<400> SEQUENCE: 135
ggattttcag agcagaggtt g                                            21

<210> SEQ ID NO 136
<211> LENGTH: 20
<212> TYPE: DNA
<213> ORGANISM: Homo sapiens

<400> SEQUENCE: 136
gtttggagtt tcgatgcctt                                              20

<210> SEQ ID NO 137
<211> LENGTH: 20
<212> TYPE: DNA
<213> ORGANISM: Homo sapiens

<400> SEQUENCE: 137
aagagttgcc tgtacccttc                                              20

<210> SEQ ID NO 138
<211> LENGTH: 20
<212> TYPE: DNA
<213> ORGANISM: Homo sapiens

<400> SEQUENCE: 138
atgttttggt cctgggagaa                                              20

<210> SEQ ID NO 139
<211> LENGTH: 19
<212> TYPE: DNA
<213> ORGANISM: Homo sapiens

<400> SEQUENCE: 139
gtctctttac tgggagcgt                                               19
```

```
<210> SEQ ID NO 140
<211> LENGTH: 20
<212> TYPE: DNA
<213> ORGANISM: Homo sapiens

<400> SEQUENCE: 140
ggaagtggtt agggcagatt                                               20

<210> SEQ ID NO 141
<211> LENGTH: 20
<212> TYPE: DNA
<213> ORGANISM: Homo sapiens

<400> SEQUENCE: 141
acattgcccc tgacaacata                                               20

<210> SEQ ID NO 142
<211> LENGTH: 21
<212> TYPE: DNA
<213> ORGANISM: Homo sapiens

<400> SEQUENCE: 142
agcccagtaa agataagagg c                                             21

<210> SEQ ID NO 143
<211> LENGTH: 19
<212> TYPE: DNA
<213> ORGANISM: Homo sapiens

<400> SEQUENCE: 143
tcattatctg aggagccgg                                                19

<210> SEQ ID NO 144
<211> LENGTH: 20
<212> TYPE: DNA
<213> ORGANISM: Homo sapiens

<400> SEQUENCE: 144
cccttccctt tcatccaaga                                               20

<210> SEQ ID NO 145
<211> LENGTH: 21
<212> TYPE: DNA
<213> ORGANISM: Homo sapiens

<400> SEQUENCE: 145
ggctccataa tcttctgcaa t                                             21

<210> SEQ ID NO 146
<211> LENGTH: 20
<212> TYPE: DNA
<213> ORGANISM: Homo sapiens

<400> SEQUENCE: 146
ctgaaacctt ctccttagcc                                               20

<210> SEQ ID NO 147
<211> LENGTH: 20
<212> TYPE: DNA
<213> ORGANISM: Homo sapiens

<400> SEQUENCE: 147
cgtacatctg atttgtgggt                                               20
```

```
<210> SEQ ID NO 148
<211> LENGTH: 20
<212> TYPE: DNA
<213> ORGANISM: Homo sapiens

<400> SEQUENCE: 148
attatccaac ctgacctgca                                              20

<210> SEQ ID NO 149
<211> LENGTH: 21
<212> TYPE: DNA
<213> ORGANISM: Homo sapiens

<400> SEQUENCE: 149
tgccactgat gatacaaaag c                                            21

<210> SEQ ID NO 150
<211> LENGTH: 19
<212> TYPE: DNA
<213> ORGANISM: Homo sapiens

<400> SEQUENCE: 150
aggtgcaaag ctgttcatg                                               19

<210> SEQ ID NO 151
<211> LENGTH: 20
<212> TYPE: DNA
<213> ORGANISM: Homo sapiens

<400> SEQUENCE: 151
gaaacgtgtg gtgtcctcta                                              20

<210> SEQ ID NO 152
<211> LENGTH: 20
<212> TYPE: DNA
<213> ORGANISM: Homo sapiens

<400> SEQUENCE: 152
aatgccaaga ttgtccttca                                              20

<210> SEQ ID NO 153
<211> LENGTH: 20
<212> TYPE: DNA
<213> ORGANISM: Homo sapiens

<400> SEQUENCE: 153
agtgtttggg gctctatcag                                              20

<210> SEQ ID NO 154
<211> LENGTH: 19
<212> TYPE: DNA
<213> ORGANISM: Homo sapiens

<400> SEQUENCE: 154
tgcgaaacct cagtgatca                                               19

<210> SEQ ID NO 155
<211> LENGTH: 20
<212> TYPE: DNA
<213> ORGANISM: Homo sapiens

<400> SEQUENCE: 155
ctttcccttt tgagtcctgc                                              20
```

```
<210> SEQ ID NO 156
<211> LENGTH: 20
<212> TYPE: DNA
<213> ORGANISM: Homo sapiens

<400> SEQUENCE: 156
cacttccttc agcacactttt                                              20

<210> SEQ ID NO 157
<211> LENGTH: 20
<212> TYPE: DNA
<213> ORGANISM: Homo sapiens

<400> SEQUENCE: 157
tctcgcttac cttgctacat                                               20

<210> SEQ ID NO 158
<211> LENGTH: 20
<212> TYPE: DNA
<213> ORGANISM: Homo sapiens

<400> SEQUENCE: 158
ccggctctct atgaaagtga                                               20

<210> SEQ ID NO 159
<211> LENGTH: 20
<212> TYPE: DNA
<213> ORGANISM: Homo sapiens

<400> SEQUENCE: 159
aaagcgggaa ttggaacttt                                               20

<210> SEQ ID NO 160
<211> LENGTH: 20
<212> TYPE: DNA
<213> ORGANISM: Homo sapiens

<400> SEQUENCE: 160
acttgtctgt ctgcctgttt                                               20

<210> SEQ ID NO 161
<211> LENGTH: 20
<212> TYPE: DNA
<213> ORGANISM: Homo sapiens

<400> SEQUENCE: 161
ggggaacatt gggaagagat                                               20

<210> SEQ ID NO 162
<211> LENGTH: 19
<212> TYPE: DNA
<213> ORGANISM: Homo sapiens

<400> SEQUENCE: 162
ctgatgcgct gaaaaccaa                                                19

<210> SEQ ID NO 163
<211> LENGTH: 20
<212> TYPE: DNA
<213> ORGANISM: Homo sapiens
```

```
<400> SEQUENCE: 163
tctaccagct acaaacccat                                               20

<210> SEQ ID NO 164
<211> LENGTH: 20
<212> TYPE: DNA
<213> ORGANISM: Homo sapiens

<400> SEQUENCE: 164
ttccatgtgt tcttcctccc                                               20

<210> SEQ ID NO 165
<211> LENGTH: 20
<212> TYPE: DNA
<213> ORGANISM: Homo sapiens

<400> SEQUENCE: 165
tcagccaata cccatagcag                                               20

<210> SEQ ID NO 166
<211> LENGTH: 20
<212> TYPE: DNA
<213> ORGANISM: Homo sapiens

<400> SEQUENCE: 166
agcagtaggg ttaacaggag                                               20

<210> SEQ ID NO 167
<211> LENGTH: 20
<212> TYPE: DNA
<213> ORGANISM: Homo sapiens

<400> SEQUENCE: 167
aatcagagga agatgggtcg                                               20

<210> SEQ ID NO 168
<211> LENGTH: 19
<212> TYPE: DNA
<213> ORGANISM: Homo sapiens

<400> SEQUENCE: 168
gcagcaatgt ttcggtgta                                                19

<210> SEQ ID NO 169
<211> LENGTH: 20
<212> TYPE: DNA
<213> ORGANISM: Homo sapiens

<400> SEQUENCE: 169
gagaactcca ccctgtctttt                                              20

<210> SEQ ID NO 170
<211> LENGTH: 20
<212> TYPE: DNA
<213> ORGANISM: Homo sapiens

<400> SEQUENCE: 170
tactaatggc tgggggtaac                                               20

<210> SEQ ID NO 171
<211> LENGTH: 20
<212> TYPE: DNA
```

```
<213> ORGANISM: Homo sapiens

<400> SEQUENCE: 171
gggagtgtgt gaatgtgtct                                              20

<210> SEQ ID NO 172
<211> LENGTH: 20
<212> TYPE: DNA
<213> ORGANISM: Homo sapiens

<400> SEQUENCE: 172
ctgatgaggc taaaggacca                                              20

<210> SEQ ID NO 173
<211> LENGTH: 21
<212> TYPE: DNA
<213> ORGANISM: Homo sapiens

<400> SEQUENCE: 173
aagctttaca tcatggcact g                                            21

<210> SEQ ID NO 174
<211> LENGTH: 20
<212> TYPE: DNA
<213> ORGANISM: Homo sapiens

<400> SEQUENCE: 174
cagagttctc catcccagac                                              20

<210> SEQ ID NO 175
<211> LENGTH: 20
<212> TYPE: DNA
<213> ORGANISM: Homo sapiens

<400> SEQUENCE: 175
aaaggtccat aggctcacat                                              20

<210> SEQ ID NO 176
<211> LENGTH: 20
<212> TYPE: DNA
<213> ORGANISM: Homo sapiens

<400> SEQUENCE: 176
ctgagttcct cctttgcct                                               20

<210> SEQ ID NO 177
<211> LENGTH: 20
<212> TYPE: DNA
<213> ORGANISM: Homo sapiens

<400> SEQUENCE: 177
ttgaccaatg ccattaagcc                                              20

<210> SEQ ID NO 178
<211> LENGTH: 20
<212> TYPE: DNA
<213> ORGANISM: Homo sapiens

<400> SEQUENCE: 178
gcaaaaggtg gtgttagctg                                              20

<210> SEQ ID NO 179
<211> LENGTH: 21
```

```
<212> TYPE: DNA
<213> ORGANISM: Homo sapiens

<400> SEQUENCE: 179
accagggaaa tgttagcttc t                                         21

<210> SEQ ID NO 180
<211> LENGTH: 20
<212> TYPE: DNA
<213> ORGANISM: Homo sapiens

<400> SEQUENCE: 180
atccacatcc catgcctaag                                           20

<210> SEQ ID NO 181
<211> LENGTH: 21
<212> TYPE: DNA
<213> ORGANISM: Homo sapiens

<400> SEQUENCE: 181
tgctctgtta tggttggagt t                                         21

<210> SEQ ID NO 182
<211> LENGTH: 20
<212> TYPE: DNA
<213> ORGANISM: Homo sapiens

<400> SEQUENCE: 182
tctattcctt tggcacctcc                                           20

<210> SEQ ID NO 183
<211> LENGTH: 20
<212> TYPE: DNA
<213> ORGANISM: Homo sapiens

<400> SEQUENCE: 183
gaagcggcag taattcagga                                           20

<210> SEQ ID NO 184
<211> LENGTH: 20
<212> TYPE: DNA
<213> ORGANISM: Homo sapiens

<400> SEQUENCE: 184
aggaaaggag agctttgtcc                                           20

<210> SEQ ID NO 185
<211> LENGTH: 20
<212> TYPE: DNA
<213> ORGANISM: Homo sapiens

<400> SEQUENCE: 185
aactgtgtcc taagcagtga                                           20

<210> SEQ ID NO 186
<211> LENGTH: 20
<212> TYPE: DNA
<213> ORGANISM: Homo sapiens

<400> SEQUENCE: 186
cctttcagct tccaagtcct                                           20

<210> SEQ ID NO 187
```

```
<211> LENGTH: 20
<212> TYPE: DNA
<213> ORGANISM: Homo sapiens

<400> SEQUENCE: 187
gtcacctcca gagctttcat                                                  20

<210> SEQ ID NO 188
<211> LENGTH: 21
<212> TYPE: DNA
<213> ORGANISM: Homo sapiens

<400> SEQUENCE: 188
gctctcttcc tcccactaaa a                                                21

<210> SEQ ID NO 189
<211> LENGTH: 21
<212> TYPE: DNA
<213> ORGANISM: Homo sapiens

<400> SEQUENCE: 189
gaacaatgca acctgagaac t                                                21

<210> SEQ ID NO 190
<211> LENGTH: 20
<212> TYPE: DNA
<213> ORGANISM: Homo sapiens

<400> SEQUENCE: 190
actgcctgtg ttttcttcct                                                  20

<210> SEQ ID NO 191
<211> LENGTH: 21
<212> TYPE: DNA
<213> ORGANISM: Homo sapiens

<400> SEQUENCE: 191
tgattgtcct ctaccatgca t                                                21

<210> SEQ ID NO 192
<211> LENGTH: 20
<212> TYPE: DNA
<213> ORGANISM: Homo sapiens

<400> SEQUENCE: 192
aaagcaattt cttccccagc                                                  20

<210> SEQ ID NO 193
<211> LENGTH: 21
<212> TYPE: DNA
<213> ORGANISM: Homo sapiens

<400> SEQUENCE: 193
aggcttgaaa caccaccttt a                                                21

<210> SEQ ID NO 194
<211> LENGTH: 20
<212> TYPE: DNA
<213> ORGANISM: Homo sapiens

<400> SEQUENCE: 194
tgtctgttgc cattccttct                                                  20
```

```
<210> SEQ ID NO 195
<211> LENGTH: 20
<212> TYPE: DNA
<213> ORGANISM: Homo sapiens

<400> SEQUENCE: 195
ttgatttgtt gggtggttgg                                               20

<210> SEQ ID NO 196
<211> LENGTH: 20
<212> TYPE: DNA
<213> ORGANISM: Homo sapiens

<400> SEQUENCE: 196
tgactgtgac ttgtgctttc                                               20

<210> SEQ ID NO 197
<211> LENGTH: 20
<212> TYPE: DNA
<213> ORGANISM: Homo sapiens

<400> SEQUENCE: 197
tgccaatctg aggttttttcc                                              20

<210> SEQ ID NO 198
<211> LENGTH: 20
<212> TYPE: DNA
<213> ORGANISM: Homo sapiens

<400> SEQUENCE: 198
gaattacatt tccctgggcg                                               20

<210> SEQ ID NO 199
<211> LENGTH: 20
<212> TYPE: DNA
<213> ORGANISM: Homo sapiens

<400> SEQUENCE: 199
actctgcttt agggcttctg                                               20

<210> SEQ ID NO 200
<211> LENGTH: 20
<212> TYPE: DNA
<213> ORGANISM: Homo sapiens

<400> SEQUENCE: 200
tgaaaccgtc ttccttgtct                                               20

<210> SEQ ID NO 201
<211> LENGTH: 20
<212> TYPE: DNA
<213> ORGANISM: Homo sapiens

<400> SEQUENCE: 201
gcagaaaagc tcccaaacaa                                               20

<210> SEQ ID NO 202
<211> LENGTH: 20
<212> TYPE: DNA
<213> ORGANISM: Homo sapiens

<400> SEQUENCE: 202
tttaaagcag agcaggacct                                               20
```

```
<210> SEQ ID NO 203
<211> LENGTH: 20
<212> TYPE: DNA
<213> ORGANISM: Homo sapiens

<400> SEQUENCE: 203
gaaaagaggt ggagagggag                                               20

<210> SEQ ID NO 204
<211> LENGTH: 20
<212> TYPE: DNA
<213> ORGANISM: Homo sapiens

<400> SEQUENCE: 204
tttatgacac acagagcagc                                               20

<210> SEQ ID NO 205
<211> LENGTH: 20
<212> TYPE: DNA
<213> ORGANISM: Homo sapiens

<400> SEQUENCE: 205
aggacccttt tgctgatttc                                               20

<210> SEQ ID NO 206
<211> LENGTH: 20
<212> TYPE: DNA
<213> ORGANISM: Homo sapiens

<400> SEQUENCE: 206
atgtgtttga ccctttccct                                               20

<210> SEQ ID NO 207
<211> LENGTH: 20
<212> TYPE: DNA
<213> ORGANISM: Homo sapiens

<400> SEQUENCE: 207
ctggcccaag tgcatacata                                               20

<210> SEQ ID NO 208
<211> LENGTH: 21
<212> TYPE: DNA
<213> ORGANISM: Homo sapiens

<400> SEQUENCE: 208
atcctgaagt tgttccacat c                                             21

<210> SEQ ID NO 209
<211> LENGTH: 20
<212> TYPE: DNA
<213> ORGANISM: Homo sapiens

<400> SEQUENCE: 209
aaccagagag acaccttgac                                               20

<210> SEQ ID NO 210
<211> LENGTH: 21
<212> TYPE: DNA
<213> ORGANISM: Homo sapiens

<400> SEQUENCE: 210
gaccctgctt tgttactagg a                                             21
```

```
<210> SEQ ID NO 211
<211> LENGTH: 20
<212> TYPE: DNA
<213> ORGANISM: Homo sapiens

<400> SEQUENCE: 211
tcctccctat ctcctgtgac                                              20

<210> SEQ ID NO 212
<211> LENGTH: 20
<212> TYPE: DNA
<213> ORGANISM: Homo sapiens

<400> SEQUENCE: 212
tggacatgga catttcaacg                                              20

<210> SEQ ID NO 213
<211> LENGTH: 20
<212> TYPE: DNA
<213> ORGANISM: Homo sapiens

<400> SEQUENCE: 213
actctgccag aaaagcctac                                              20

<210> SEQ ID NO 214
<211> LENGTH: 20
<212> TYPE: DNA
<213> ORGANISM: Homo sapiens

<400> SEQUENCE: 214
aaaaatgctt ccacttgcct                                              20

<210> SEQ ID NO 215
<211> LENGTH: 20
<212> TYPE: DNA
<213> ORGANISM: Homo sapiens

<400> SEQUENCE: 215
cctttgtctt gaagcctcct                                              20

<210> SEQ ID NO 216
<211> LENGTH: 20
<212> TYPE: DNA
<213> ORGANISM: Homo sapiens

<400> SEQUENCE: 216
gcacctccaa caacattcaa                                              20

<210> SEQ ID NO 217
<211> LENGTH: 20
<212> TYPE: DNA
<213> ORGANISM: Homo sapiens

<400> SEQUENCE: 217
ttgactgagc agagtagagc                                              20

<210> SEQ ID NO 218
<211> LENGTH: 18
<212> TYPE: DNA
<213> ORGANISM: Homo sapiens
```

<400> SEQUENCE: 218
ttggaaatgg ggctggag                                          18

<210> SEQ ID NO 219
<211> LENGTH: 22
<212> TYPE: DNA
<213> ORGANISM: Homo sapiens

<400> SEQUENCE: 219
ttctacctac aagcaaagag ag                                     22

<210> SEQ ID NO 220
<211> LENGTH: 21
<212> TYPE: DNA
<213> ORGANISM: Homo sapiens

<400> SEQUENCE: 220
actggtctat tggggaaaa t                                       21

<210> SEQ ID NO 221
<211> LENGTH: 21
<212> TYPE: DNA
<213> ORGANISM: Homo sapiens

<400> SEQUENCE: 221
tcaccaacag aggatcaaac t                                      21

<210> SEQ ID NO 222
<211> LENGTH: 20
<212> TYPE: DNA
<213> ORGANISM: Homo sapiens

<400> SEQUENCE: 222
agtgttagga aagcagagtg                                        20

<210> SEQ ID NO 223
<211> LENGTH: 20
<212> TYPE: DNA
<213> ORGANISM: Homo sapiens

<400> SEQUENCE: 223
ccgagggata acatacagct                                        20

<210> SEQ ID NO 224
<211> LENGTH: 20
<212> TYPE: DNA
<213> ORGANISM: Homo sapiens

<400> SEQUENCE: 224
tggacagggt ttcacaagat                                        20

<210> SEQ ID NO 225
<211> LENGTH: 20
<212> TYPE: DNA
<213> ORGANISM: Homo sapiens

<400> SEQUENCE: 225
cactagtcac agaagcaggt                                        20

<210> SEQ ID NO 226
<211> LENGTH: 20
<212> TYPE: DNA

```
<213> ORGANISM: Homo sapiens

<400> SEQUENCE: 226
ctcctctcca tctttccagg                                            20

<210> SEQ ID NO 227
<211> LENGTH: 20
<212> TYPE: DNA
<213> ORGANISM: Homo sapiens

<400> SEQUENCE: 227
gtagaaaccc cgagacaact                                            20

<210> SEQ ID NO 228
<211> LENGTH: 21
<212> TYPE: DNA
<213> ORGANISM: Homo sapiens

<400> SEQUENCE: 228
ataggctgac ttccacatct c                                          21

<210> SEQ ID NO 229
<211> LENGTH: 20
<212> TYPE: DNA
<213> ORGANISM: Homo sapiens

<400> SEQUENCE: 229
caatttgctg ttcagaggct                                            20

<210> SEQ ID NO 230
<211> LENGTH: 20
<212> TYPE: DNA
<213> ORGANISM: Homo sapiens

<400> SEQUENCE: 230
tgtgggggtc aattctaacg                                            20

<210> SEQ ID NO 231
<211> LENGTH: 20
<212> TYPE: DNA
<213> ORGANISM: Homo sapiens

<400> SEQUENCE: 231
tcatgatgtg gcttagtggg                                            20

<210> SEQ ID NO 232
<211> LENGTH: 20
<212> TYPE: DNA
<213> ORGANISM: Homo sapiens

<400> SEQUENCE: 232
ccaacgggta gtggtagatt                                            20

<210> SEQ ID NO 233
<211> LENGTH: 20
<212> TYPE: DNA
<213> ORGANISM: Homo sapiens

<400> SEQUENCE: 233
tacacccaca tgcatacaca                                            20

<210> SEQ ID NO 234
<211> LENGTH: 20
```

<212> TYPE: DNA
<213> ORGANISM: Homo sapiens

<400> SEQUENCE: 234
cttaccccac ttcttcctga                                        20

<210> SEQ ID NO 235
<211> LENGTH: 19
<212> TYPE: DNA
<213> ORGANISM: Homo sapiens

<400> SEQUENCE: 235
gaagtgtgca tgggagagt                                         19

<210> SEQ ID NO 236
<211> LENGTH: 19
<212> TYPE: DNA
<213> ORGANISM: Homo sapiens

<400> SEQUENCE: 236
cctgtcacaa ctgcctttg                                         19

<210> SEQ ID NO 237
<211> LENGTH: 21
<212> TYPE: DNA
<213> ORGANISM: Homo sapiens

<400> SEQUENCE: 237
tttgggtggc tctatgttag g                                      21

<210> SEQ ID NO 238
<211> LENGTH: 20
<212> TYPE: DNA
<213> ORGANISM: Homo sapiens

<400> SEQUENCE: 238
tttgccattt tgtgatgcca                                        20

<210> SEQ ID NO 239
<211> LENGTH: 20
<212> TYPE: DNA
<213> ORGANISM: Homo sapiens

<400> SEQUENCE: 239
ctccttgact catttcccgt                                        20

<210> SEQ ID NO 240
<211> LENGTH: 20
<212> TYPE: DNA
<213> ORGANISM: Homo sapiens

<400> SEQUENCE: 240
ggagtttcag gttggcagaa                                        20

<210> SEQ ID NO 241
<211> LENGTH: 20
<212> TYPE: DNA
<213> ORGANISM: Homo sapiens

<400> SEQUENCE: 241
agagtaccac tgccaagaaa                                        20

<210> SEQ ID NO 242

```
<211> LENGTH: 20
<212> TYPE: DNA
<213> ORGANISM: Homo sapiens

<400> SEQUENCE: 242
acagcttgct tcaaactaca                                               20

<210> SEQ ID NO 243
<211> LENGTH: 20
<212> TYPE: DNA
<213> ORGANISM: Homo sapiens

<400> SEQUENCE: 243
ctgctagtct gtcaggagag                                               20

<210> SEQ ID NO 244
<211> LENGTH: 20
<212> TYPE: DNA
<213> ORGANISM: Homo sapiens

<400> SEQUENCE: 244
ttgaaggggc aaaatacagc                                               20

<210> SEQ ID NO 245
<211> LENGTH: 20
<212> TYPE: DNA
<213> ORGANISM: Homo sapiens

<400> SEQUENCE: 245
gggcagcagt ataaacatcc                                               20

<210> SEQ ID NO 246
<211> LENGTH: 20
<212> TYPE: DNA
<213> ORGANISM: Homo sapiens

<400> SEQUENCE: 246
gccccaaatt gtaacaaagc                                               20

<210> SEQ ID NO 247
<211> LENGTH: 20
<212> TYPE: DNA
<213> ORGANISM: Homo sapiens

<400> SEQUENCE: 247
gacattccct tccattgagc                                               20

<210> SEQ ID NO 248
<211> LENGTH: 20
<212> TYPE: DNA
<213> ORGANISM: Homo sapiens

<400> SEQUENCE: 248
tgacgaagac tccaacacaa                                               20

<210> SEQ ID NO 249
<211> LENGTH: 20
<212> TYPE: DNA
<213> ORGANISM: Homo sapiens

<400> SEQUENCE: 249
ttcctggtaa atgtgctggt                                               20
```

```
<210> SEQ ID NO 250
<211> LENGTH: 20
<212> TYPE: DNA
<213> ORGANISM: Homo sapiens

<400> SEQUENCE: 250
aagtcaggga aatgaagctg                                                   20

<210> SEQ ID NO 251
<211> LENGTH: 20
<212> TYPE: DNA
<213> ORGANISM: Homo sapiens

<400> SEQUENCE: 251
ggccagattt gcagtgattt                                                   20

<210> SEQ ID NO 252
<211> LENGTH: 20
<212> TYPE: DNA
<213> ORGANISM: Homo sapiens

<400> SEQUENCE: 252
gtaacacagt gctccttctc                                                   20

<210> SEQ ID NO 253
<211> LENGTH: 21
<212> TYPE: DNA
<213> ORGANISM: Homo sapiens

<400> SEQUENCE: 253
agaatcaaca acaatggcag g                                                 21

<210> SEQ ID NO 254
<211> LENGTH: 20
<212> TYPE: DNA
<213> ORGANISM: Homo sapiens

<400> SEQUENCE: 254
ggccccaatt agctgatttc                                                   20

<210> SEQ ID NO 255
<211> LENGTH: 21
<212> TYPE: DNA
<213> ORGANISM: Homo sapiens

<400> SEQUENCE: 255
ctctgaggaa agcttgtagg a                                                 21

<210> SEQ ID NO 256
<211> LENGTH: 20
<212> TYPE: DNA
<213> ORGANISM: Homo sapiens

<400> SEQUENCE: 256
ctgagcaggg aaaaatccag                                                   20

<210> SEQ ID NO 257
<211> LENGTH: 20
<212> TYPE: DNA
<213> ORGANISM: Homo sapiens

<400> SEQUENCE: 257
aggttttcgt tctgcttcag                                                   20
```

```
<210> SEQ ID NO 258
<211> LENGTH: 20
<212> TYPE: DNA
<213> ORGANISM: Homo sapiens

<400> SEQUENCE: 258
acaaaggatt caggtgcagt                                              20

<210> SEQ ID NO 259
<211> LENGTH: 19
<212> TYPE: DNA
<213> ORGANISM: Homo sapiens

<400> SEQUENCE: 259
cgggtcagtg attctagct                                               19

<210> SEQ ID NO 260
<211> LENGTH: 20
<212> TYPE: DNA
<213> ORGANISM: Homo sapiens

<400> SEQUENCE: 260
acaggttttg ctcttcagga                                              20

<210> SEQ ID NO 261
<211> LENGTH: 20
<212> TYPE: DNA
<213> ORGANISM: Homo sapiens

<400> SEQUENCE: 261
gtcactatgg aatgggggtt                                              20

<210> SEQ ID NO 262
<211> LENGTH: 21
<212> TYPE: DNA
<213> ORGANISM: Homo sapiens

<400> SEQUENCE: 262
ggcaagtttg tctggttcat t                                            21

<210> SEQ ID NO 263
<211> LENGTH: 20
<212> TYPE: DNA
<213> ORGANISM: Homo sapiens

<400> SEQUENCE: 263
gcttcttccc cgcaatatga                                              20

<210> SEQ ID NO 264
<211> LENGTH: 20
<212> TYPE: DNA
<213> ORGANISM: Homo sapiens

<400> SEQUENCE: 264
ccatctgcat ctgtctcctt                                              20

<210> SEQ ID NO 265
<211> LENGTH: 20
<212> TYPE: DNA
<213> ORGANISM: Homo sapiens

<400> SEQUENCE: 265
cggttcagag tcaatgccta                                              20
```

<210> SEQ ID NO 266
<211> LENGTH: 19
<212> TYPE: DNA
<213> ORGANISM: Homo sapiens

<400> SEQUENCE: 266
gctcctctcc ttctccctt                                                    19

<210> SEQ ID NO 267
<211> LENGTH: 21
<212> TYPE: DNA
<213> ORGANISM: Homo sapiens

<400> SEQUENCE: 267
tacccaacaa gccagagaaa t                                                 21

<210> SEQ ID NO 268
<211> LENGTH: 20
<212> TYPE: DNA
<213> ORGANISM: Homo sapiens

<400> SEQUENCE: 268
tgtataaggg caatcgtggt                                                   20

<210> SEQ ID NO 269
<211> LENGTH: 20
<212> TYPE: DNA
<213> ORGANISM: Homo sapiens

<400> SEQUENCE: 269
agagggaaag tgcaaggaat                                                   20

<210> SEQ ID NO 270
<211> LENGTH: 20
<212> TYPE: DNA
<213> ORGANISM: Homo sapiens

<400> SEQUENCE: 270
aaggaaccag gtcagacaag                                                   20

<210> SEQ ID NO 271
<211> LENGTH: 20
<212> TYPE: DNA
<213> ORGANISM: Homo sapiens

<400> SEQUENCE: 271 gttttttcagc acactgtccc                                                  20

<210> SEQ ID NO 272
<211> LENGTH: 21
<212> TYPE: DNA
<213> ORGANISM: Homo sapiens

<400> SEQUENCE: 272
gttagaaggc aaacatcatg c                                                 21

<210> SEQ ID NO 273
<211> LENGTH: 20
<212> TYPE: DNA
<213> ORGANISM: Homo sapiens

```
<400> SEQUENCE: 273
accacattac tcacaaccct                                               20

<210> SEQ ID NO 274
<211> LENGTH: 20
<212> TYPE: DNA
<213> ORGANISM: Homo sapiens

<400> SEQUENCE: 274
tgcagtcata ggaaaaggct                                               20

<210> SEQ ID NO 275
<211> LENGTH: 20
<212> TYPE: DNA
<213> ORGANISM: Homo sapiens

<400> SEQUENCE: 275
aagccctttt catctccaca                                               20

<210> SEQ ID NO 276
<211> LENGTH: 19
<212> TYPE: DNA
<213> ORGANISM: Homo sapiens

<400> SEQUENCE: 276
gcagtcagaa tggtttggc                                                19

<210> SEQ ID NO 277
<211> LENGTH: 20
<212> TYPE: DNA
<213> ORGANISM: Homo sapiens

<400> SEQUENCE: 277
ccagagctga gacaactact                                               20

<210> SEQ ID NO 278
<211> LENGTH: 21
<212> TYPE: DNA
<213> ORGANISM: Homo sapiens

<400> SEQUENCE: 278
agacattggt ttggttggtt c                                             21

<210> SEQ ID NO 279
<211> LENGTH: 20
<212> TYPE: DNA
<213> ORGANISM: Homo sapiens

<400> SEQUENCE: 279
gaagcaattc ctcacaccac                                               20

<210> SEQ ID NO 280
<211> LENGTH: 20
<212> TYPE: DNA
<213> ORGANISM: Homo sapiens

<400> SEQUENCE: 280
acacaaatga aagcccgtac                                               20

<210> SEQ ID NO 281
<211> LENGTH: 20
<212> TYPE: DNA
```

```
<213> ORGANISM: Homo sapiens

<400> SEQUENCE: 281
ttcagtcaga atgaggagcc                                               20

<210> SEQ ID NO 282
<211> LENGTH: 20
<212> TYPE: DNA
<213> ORGANISM: Homo sapiens

<400> SEQUENCE: 282
ggtctgctgt ttctctttgc                                               20

<210> SEQ ID NO 283
<211> LENGTH: 20
<212> TYPE: DNA
<213> ORGANISM: Homo sapiens

<400> SEQUENCE: 283
ctcctctccc ctctgatttt                                               20

<210> SEQ ID NO 284
<211> LENGTH: 20
<212> TYPE: DNA
<213> ORGANISM: Homo sapiens

<400> SEQUENCE: 284
agagccttac caagctgaag                                               20

<210> SEQ ID NO 285
<211> LENGTH: 21
<212> TYPE: DNA
<213> ORGANISM: Homo sapiens

<400> SEQUENCE: 285
ttttaaagcg acagtcacac g                                             21

<210> SEQ ID NO 286
<211> LENGTH: 20
<212> TYPE: DNA
<213> ORGANISM: Homo sapiens

<400> SEQUENCE: 286
gggatggtta cttagtgggg                                               20

<210> SEQ ID NO 287
<211> LENGTH: 20
<212> TYPE: DNA
<213> ORGANISM: Homo sapiens

<400> SEQUENCE: 287
tcctctgcct tctacccttt                                               20

<210> SEQ ID NO 288
<211> LENGTH: 20
<212> TYPE: DNA
<213> ORGANISM: Homo sapiens

<400> SEQUENCE: 288
ttacactcgc cttccaaaca                                               20

<210> SEQ ID NO 289
<211> LENGTH: 20
```

```
<212> TYPE: DNA
<213> ORGANISM: Homo sapiens

<400> SEQUENCE: 289
tgttgtgcct tttgttctgg                                                    20

<210> SEQ ID NO 290
<211> LENGTH: 20
<212> TYPE: DNA
<213> ORGANISM: Homo sapiens

<400> SEQUENCE: 290
gagagaggag gagttggaag                                                    20

<210> SEQ ID NO 291
<211> LENGTH: 22
<212> TYPE: DNA
<213> ORGANISM: Homo sapiens

<400> SEQUENCE: 291
ttaggaggta aggctggaaa aa                                                 22

<210> SEQ ID NO 292
<211> LENGTH: 20
<212> TYPE: DNA
<213> ORGANISM: Homo sapiens

<400> SEQUENCE: 292
atccacgaca tccaaaatca                                                    20

<210> SEQ ID NO 293
<211> LENGTH: 21
<212> TYPE: DNA
<213> ORGANISM: Homo sapiens

<400> SEQUENCE: 293
ctgtcagcaa tttcaggtca g                                                  21

<210> SEQ ID NO 294
<211> LENGTH: 20
<212> TYPE: DNA
<213> ORGANISM: Homo sapiens

<400> SEQUENCE: 294
ttgtgcaaga agaaacctgc                                                    20

<210> SEQ ID NO 295
<211> LENGTH: 20
<212> TYPE: DNA
<213> ORGANISM: Homo sapiens

<400> SEQUENCE: 295
agacaaaggc ttcacggaac                                                    20

<210> SEQ ID NO 296
<211> LENGTH: 20
<212> TYPE: DNA
<213> ORGANISM: Homo sapiens

<400> SEQUENCE: 296
ggccttgcat aaaccacatt                                                    20

<210> SEQ ID NO 297
```

```
<211> LENGTH: 20
<212> TYPE: DNA
<213> ORGANISM: Homo sapiens

<400> SEQUENCE: 297
ttcctctgtg tcttgaaggt                                               20

<210> SEQ ID NO 298
<211> LENGTH: 20
<212> TYPE: DNA
<213> ORGANISM: Homo sapiens

<400> SEQUENCE: 298
tttgtaattg gtcctcgcct                                               20

<210> SEQ ID NO 299
<211> LENGTH: 20
<212> TYPE: DNA
<213> ORGANISM: Homo sapiens

<400> SEQUENCE: 299
atcaatgcag gtgagtgtga                                               20

<210> SEQ ID NO 300
<211> LENGTH: 20
<212> TYPE: DNA
<213> ORGANISM: Homo sapiens

<400> SEQUENCE: 300
caagtatttc atggcgctcc                                               20

<210> SEQ ID NO 301
<211> LENGTH: 20
<212> TYPE: DNA
<213> ORGANISM: Homo sapiens

<400> SEQUENCE: 301
cactccacat aagcctcaga                                               20

<210> SEQ ID NO 302
<211> LENGTH: 21
<212> TYPE: DNA
<213> ORGANISM: Homo sapiens

<400> SEQUENCE: 302
gtcaacagta tcagcttcca a                                             21

<210> SEQ ID NO 303
<211> LENGTH: 20
<212> TYPE: DNA
<213> ORGANISM: Homo sapiens

<400> SEQUENCE: 303
aggatgtagt tgggtgagga                                               20

<210> SEQ ID NO 304
<211> LENGTH: 20
<212> TYPE: DNA
<213> ORGANISM: Homo sapiens

<400> SEQUENCE: 304
tgggcttctt tttcattccg                                               20
```

```
<210> SEQ ID NO 305
<211> LENGTH: 20
<212> TYPE: DNA
<213> ORGANISM: Homo sapiens

<400> SEQUENCE: 305
cagtcatcac ggggagatac                                              20

<210> SEQ ID NO 306
<211> LENGTH: 20
<212> TYPE: DNA
<213> ORGANISM: Homo sapiens

<400> SEQUENCE: 306
tcaacaagct ctctgttcac                                              20

<210> SEQ ID NO 307
<211> LENGTH: 20
<212> TYPE: DNA
<213> ORGANISM: Homo sapiens

<400> SEQUENCE: 307
gacagatatt tgtgcagggt                                              20

<210> SEQ ID NO 308
<211> LENGTH: 20
<212> TYPE: DNA
<213> ORGANISM: Homo sapiens

<400> SEQUENCE: 308
gtgcaaacag tgacctcaat                                              20

<210> SEQ ID NO 309
<211> LENGTH: 20
<212> TYPE: DNA
<213> ORGANISM: Homo sapiens

<400> SEQUENCE: 309
tcctagccct tacctttcct                                              20

<210> SEQ ID NO 310
<211> LENGTH: 20
<212> TYPE: DNA
<213> ORGANISM: Homo sapiens

<400> SEQUENCE: 310
gctgggctgc tttaatttct                                              20

<210> SEQ ID NO 311
<211> LENGTH: 20
<212> TYPE: DNA
<213> ORGANISM: Homo sapiens

<400> SEQUENCE: 311
agcctgaatg tcactgatca                                              20

<210> SEQ ID NO 312
<211> LENGTH: 20
<212> TYPE: DNA
<213> ORGANISM: Homo sapiens

<400> SEQUENCE: 312
ggaattgtgg ggtcaaatgg                                              20
```

```
<210> SEQ ID NO 313
<211> LENGTH: 19
<212> TYPE: DNA
<213> ORGANISM: Homo sapiens

<400> SEQUENCE: 313
actcatcact tctggctgc                                                  19

<210> SEQ ID NO 314
<211> LENGTH: 21
<212> TYPE: DNA
<213> ORGANISM: Homo sapiens

<400> SEQUENCE: 314
ctagtgcttc tacctccaga c                                               21

<210> SEQ ID NO 315
<211> LENGTH: 20
<212> TYPE: DNA
<213> ORGANISM: Homo sapiens

<400> SEQUENCE: 315
tcttgtgttt cctgccctat                                                 20

<210> SEQ ID NO 316
<211> LENGTH: 20
<212> TYPE: DNA
<213> ORGANISM: Homo sapiens

<400> SEQUENCE: 316
aaccacacac taacagggaa                                                 20

<210> SEQ ID NO 317
<211> LENGTH: 20
<212> TYPE: DNA
<213> ORGANISM: Homo sapiens

<400> SEQUENCE: 317
ttgctgtgga tgagaatgga                                                 20

<210> SEQ ID NO 318
<211> LENGTH: 20
<212> TYPE: DNA
<213> ORGANISM: Homo sapiens

<400> SEQUENCE: 318
tctagtttgc cctctttccc                                                 20

<210> SEQ ID NO 319
<211> LENGTH: 20
<212> TYPE: DNA
<213> ORGANISM: Homo sapiens

<400> SEQUENCE: 319
tgagggcaga aagaaacaga                                                 20

<210> SEQ ID NO 320
<211> LENGTH: 20
<212> TYPE: DNA
<213> ORGANISM: Homo sapiens

<400> SEQUENCE: 320
cgaattgctt ccttgctctg                                                 20
```

<210> SEQ ID NO 321
<211> LENGTH: 20
<212> TYPE: DNA
<213> ORGANISM: Homo sapiens

<400> SEQUENCE: 321
ggggtcacac atcacttttc                                                    20

<210> SEQ ID NO 322
<211> LENGTH: 22
<212> TYPE: DNA
<213> ORGANISM: Homo sapiens

<400> SEQUENCE: 322
tctatcacag caggaaatca ct                                                 22

<210> SEQ ID NO 323
<211> LENGTH: 20
<212> TYPE: DNA
<213> ORGANISM: Homo sapiens

<400> SEQUENCE: 323
atagggtcac aatccactgc                                                    20

<210> SEQ ID NO 324
<211> LENGTH: 20
<212> TYPE: DNA
<213> ORGANISM: Homo sapiens

<400> SEQUENCE: 324
tcttcgtgtt tctctagccc                                                    20

<210> SEQ ID NO 325
<211> LENGTH: 20
<212> TYPE: DNA
<213> ORGANISM: Homo sapiens

<400> SEQUENCE: 325
atattgagcc ccgcatgtta                                                    20

<210> SEQ ID NO 326
<211> LENGTH: 20
<212> TYPE: DNA
<213> ORGANISM: Homo sapiens

<400> SEQUENCE: 326
ttgaagagct aaaggggggag                                                   20

<210> SEQ ID NO 327
<211> LENGTH: 20
<212> TYPE: DNA
<213> ORGANISM: Homo sapiens

<400> SEQUENCE: 327
ggttgcagga gaaagaacat                                                    20

<210> SEQ ID NO 328
<211> LENGTH: 20
<212> TYPE: DNA
<213> ORGANISM: Homo sapiens -continued

<400> SEQUENCE: 328
tgtcaccgta ctacctaagc                                               20

<210> SEQ ID NO 329
<211> LENGTH: 20
<212> TYPE: DNA
<213> ORGANISM: Homo sapiens

<400> SEQUENCE: 329
tgccatgtaa ttgccaagat                                               20

<210> SEQ ID NO 330
<211> LENGTH: 19
<212> TYPE: DNA
<213> ORGANISM: Homo sapiens

<400> SEQUENCE: 330
agtacgctcc tttgcagag                                                19

<210> SEQ ID NO 331
<211> LENGTH: 19
<212> TYPE: DNA
<213> ORGANISM: Homo sapiens

<400> SEQUENCE: 331
cctgttctcc atccctctg                                                19

<210> SEQ ID NO 332
<211> LENGTH: 20
<212> TYPE: DNA
<213> ORGANISM: Homo sapiens

<400> SEQUENCE: 332
ttacggggac acaaaatggt                                               20

<210> SEQ ID NO 333
<211> LENGTH: 21
<212> TYPE: DNA
<213> ORGANISM: Homo sapiens

<400> SEQUENCE: 333
tcacaaacta cccaacacct a                                             21

<210> SEQ ID NO 334
<211> LENGTH: 19
<212> TYPE: DNA
<213> ORGANISM: Homo sapiens

<400> SEQUENCE: 334
ctgtgctttg cccttgaag                                                19

<210> SEQ ID NO 335
<211> LENGTH: 21
<212> TYPE: DNA
<213> ORGANISM: Homo sapiens

<400> SEQUENCE: 335
cagaattagt tggggagctg t                                             21

<210> SEQ ID NO 336
<211> LENGTH: 20
<212> TYPE: DNA

<213> ORGANISM: Homo sapiens

<400> SEQUENCE: 336
aagtcaaccc atatgccact                                               20

<210> SEQ ID NO 337
<211> LENGTH: 20
<212> TYPE: DNA
<213> ORGANISM: Homo sapiens

<400> SEQUENCE: 337
gccatctcct gaaatagtgc                                               20

<210> SEQ ID NO 338
<211> LENGTH: 20
<212> TYPE: DNA
<213> ORGANISM: Homo sapiens

<400> SEQUENCE: 338
acattcaggc tgtcacacat                                               20

<210> SEQ ID NO 339
<211> LENGTH: 20
<212> TYPE: DNA
<213> ORGANISM: Homo sapiens

<400> SEQUENCE: 339
gcaagtgttc ccatctagaa                                               20

<210> SEQ ID NO 340
<211> LENGTH: 23
<212> TYPE: DNA
<213> ORGANISM: Homo sapiens

<400> SEQUENCE: 340
tcatgtcact agttttataa ggc                                           23

<210> SEQ ID NO 341
<211> LENGTH: 20
<212> TYPE: DNA
<213> ORGANISM: Homo sapiens

<400> SEQUENCE: 341
attgataccc ctctccccag                                               20

<210> SEQ ID NO 342
<211> LENGTH: 20
<212> TYPE: DNA
<213> ORGANISM: Homo sapiens

<400> SEQUENCE: 342
agtagtgagg ctccaaagtg                                               20

<210> SEQ ID NO 343
<211> LENGTH: 19
<212> TYPE: DNA
<213> ORGANISM: Homo sapiens

<400> SEQUENCE: 343
aagtaagctg tctcctggc                                                19

<210> SEQ ID NO 344
<211> LENGTH: 20

<212> TYPE: DNA
<213> ORGANISM: Homo sapiens

<400> SEQUENCE: 344
tgggaggagt ttgctgttta                                          20

<210> SEQ ID NO 345
<211> LENGTH: 20
<212> TYPE: DNA
<213> ORGANISM: Homo sapiens

<400> SEQUENCE: 345
aggttggttg gcatgaagaa                                          20

<210> SEQ ID NO 346
<211> LENGTH: 20
<212> TYPE: DNA
<213> ORGANISM: Homo sapiens

<400> SEQUENCE: 346
ttctaagcct gtgactgaca                                          20

<210> SEQ ID NO 347
<211> LENGTH: 20
<212> TYPE: DNA
<213> ORGANISM: Homo sapiens

<400> SEQUENCE: 347
agcagagttt caagacaagc                                          20

<210> SEQ ID NO 348
<211> LENGTH: 20
<212> TYPE: DNA
<213> ORGANISM: Homo sapiens

<400> SEQUENCE: 348
tgaacctgac tttccttggg                                          20

<210> SEQ ID NO 349
<211> LENGTH: 20
<212> TYPE: DNA
<213> ORGANISM: Homo sapiens

<400> SEQUENCE: 349
ttttacacag caggcctctt                                          20

<210> SEQ ID NO 350
<211> LENGTH: 20
<212> TYPE: DNA
<213> ORGANISM: Homo sapiens

<400> SEQUENCE: 350
gccattctat catctcggga                                          20

<210> SEQ ID NO 351
<211> LENGTH: 21
<212> TYPE: DNA
<213> ORGANISM: Homo sapiens

<400> SEQUENCE: 351
gcaactccaa attatcaggg c                                        21

<210> SEQ ID NO 352

```
<211> LENGTH: 19
<212> TYPE: DNA
<213> ORGANISM: Homo sapiens

<400> SEQUENCE: 352
agtctctccc tgaaaccca                                                   19

<210> SEQ ID NO 353
<211> LENGTH: 20
<212> TYPE: DNA
<213> ORGANISM: Homo sapiens

<400> SEQUENCE: 353
cagcaccttc ccttagcaaa                                                  20

<210> SEQ ID NO 354
<211> LENGTH: 20
<212> TYPE: DNA
<213> ORGANISM: Homo sapiens

<400> SEQUENCE: 354
aagagttggc ttggagttga                                                  20

<210> SEQ ID NO 355
<211> LENGTH: 20
<212> TYPE: DNA
<213> ORGANISM: Homo sapiens

<400> SEQUENCE: 355
cttgttgtct tgtagccctg                                                  20

<210> SEQ ID NO 356
<211> LENGTH: 21
<212> TYPE: DNA
<213> ORGANISM: Homo sapiens

<400> SEQUENCE: 356
cccacaatta tgaaaggagg t                                                21

<210> SEQ ID NO 357
<211> LENGTH: 20
<212> TYPE: DNA
<213> ORGANISM: Homo sapiens

<400> SEQUENCE: 357
cacagataca gacgtccaca                                                  20

<210> SEQ ID NO 358
<211> LENGTH: 20
<212> TYPE: DNA
<213> ORGANISM: Homo sapiens

<400> SEQUENCE: 358
ttgaccagga caaatgagga                                                  20

<210> SEQ ID NO 359
<211> LENGTH: 21
<212> TYPE: DNA
<213> ORGANISM: Homo sapiens

<400> SEQUENCE: 359
agctcagcaa ttaaacagtc c                                                21
```

```
<210> SEQ ID NO 360
<211> LENGTH: 20
<212> TYPE: DNA
<213> ORGANISM: Homo sapiens

<400> SEQUENCE: 360
cactttgttg gtctgggtca                                               20

<210> SEQ ID NO 361
<211> LENGTH: 20
<212> TYPE: DNA
<213> ORGANISM: Homo sapiens

<400> SEQUENCE: 361
tgttgagagt gccagagatg                                               20

<210> SEQ ID NO 362
<211> LENGTH: 20
<212> TYPE: DNA
<213> ORGANISM: Homo sapiens

<400> SEQUENCE: 362
gggactctag gtggggttaa                                               20

<210> SEQ ID NO 363
<211> LENGTH: 20
<212> TYPE: DNA
<213> ORGANISM: Homo sapiens

<400> SEQUENCE: 363
cttccacctt ctgccaatga                                               20

<210> SEQ ID NO 364
<211> LENGTH: 20
<212> TYPE: DNA
<213> ORGANISM: Homo sapiens

<400> SEQUENCE: 364
gtttatgcct tgggattgcc                                               20

<210> SEQ ID NO 365
<211> LENGTH: 20
<212> TYPE: DNA
<213> ORGANISM: Homo sapiens

<400> SEQUENCE: 365
ttctgacatt tgcaagcacc                                               20

<210> SEQ ID NO 366
<211> LENGTH: 20
<212> TYPE: DNA
<213> ORGANISM: Homo sapiens

<400> SEQUENCE: 366
gtgtggtaag gatgctagga                                               20

<210> SEQ ID NO 367
<211> LENGTH: 20
<212> TYPE: DNA
<213> ORGANISM: Homo sapiens

<400> SEQUENCE: 367
ctgttgctag tttcttgggc                                               20
```

```
<210> SEQ ID NO 368
<211> LENGTH: 20
<212> TYPE: DNA
<213> ORGANISM: Homo sapiens

<400> SEQUENCE: 368
gaaagtgact cctccctgac                                              20

<210> SEQ ID NO 369
<211> LENGTH: 19
<212> TYPE: DNA
<213> ORGANISM: Homo sapiens

<400> SEQUENCE: 369
ttttccagtc ccagcacat                                               19

<210> SEQ ID NO 370
<211> LENGTH: 20
<212> TYPE: DNA
<213> ORGANISM: Homo sapiens

<400> SEQUENCE: 370
ccaggttctg ttctctgtca                                              20

<210> SEQ ID NO 371
<211> LENGTH: 21
<212> TYPE: DNA
<213> ORGANISM: Homo sapiens

<400> SEQUENCE: 371
tctctctctt cctgaaacag c                                            21

<210> SEQ ID NO 372
<211> LENGTH: 20
<212> TYPE: DNA
<213> ORGANISM: Homo sapiens

<400> SEQUENCE: 372
gtgagacatg gttgctgttc                                              20

<210> SEQ ID NO 373
<211> LENGTH: 21
<212> TYPE: DNA
<213> ORGANISM: Homo sapiens

<400> SEQUENCE: 373
aacctctgct ttgtgtagtg a                                            21

<210> SEQ ID NO 374
<211> LENGTH: 20
<212> TYPE: DNA
<213> ORGANISM: Homo sapiens

<400> SEQUENCE: 374
ctttctcctg ctccacctat                                              20

<210> SEQ ID NO 375
<211> LENGTH: 20
<212> TYPE: DNA
<213> ORGANISM: Homo sapiens

<400> SEQUENCE: 375
gagagaatgc aaggttcagc                                              20
```

<210> SEQ ID NO 376
<211> LENGTH: 20
<212> TYPE: DNA
<213> ORGANISM: Homo sapiens

<400> SEQUENCE: 376
ctatgtgtgt tccaacccga                                      20

<210> SEQ ID NO 377
<211> LENGTH: 20
<212> TYPE: DNA
<213> ORGANISM: Homo sapiens

<400> SEQUENCE: 377
tacagcatca aagaggaagc                                      20

<210> SEQ ID NO 378
<211> LENGTH: 20
<212> TYPE: DNA
<213> ORGANISM: Homo sapiens

<400> SEQUENCE: 378
gggaccttct aaccatgtgt                                      20

<210> SEQ ID NO 379
<211> LENGTH: 20
<212> TYPE: DNA
<213> ORGANISM: Homo sapiens

<400> SEQUENCE: 379
gaggggatga ggggaaaaag                                      20

<210> SEQ ID NO 380
<211> LENGTH: 20
<212> TYPE: DNA
<213> ORGANISM: Homo sapiens

<400> SEQUENCE: 380
cgggattttg aaaaggcaga                                      20

<210> SEQ ID NO 381
<211> LENGTH: 20
<212> TYPE: DNA
<213> ORGANISM: Homo sapiens

<400> SEQUENCE: 381
catgacctct gacggatctg                                      20

<210> SEQ ID NO 382
<211> LENGTH: 20
<212> TYPE: DNA
<213> ORGANISM: Homo sapiens

<400> SEQUENCE: 382
gtgttgtctc tcagctcctc                                      20

<210> SEQ ID NO 383
<211> LENGTH: 19
<212> TYPE: DNA
<213> ORGANISM: Homo sapiens

```
<400> SEQUENCE: 383
aggcaatgag gtcaaggac                                                19

<210> SEQ ID NO 384
<211> LENGTH: 20
<212> TYPE: DNA
<213> ORGANISM: Homo sapiens

<400> SEQUENCE: 384
gttctctggt taaggcccctt                                              20

<210> SEQ ID NO 385
<211> LENGTH: 20
<212> TYPE: DNA
<213> ORGANISM: Homo sapiens

<400> SEQUENCE: 385
atgatggccc caacttcttc                                               20

<210> SEQ ID NO 386
<211> LENGTH: 20
<212> TYPE: DNA
<213> ORGANISM: Homo sapiens

<400> SEQUENCE: 386
cctcttcacc tataagcccc                                               20

<210> SEQ ID NO 387
<211> LENGTH: 20
<212> TYPE: DNA
<213> ORGANISM: Homo sapiens

<400> SEQUENCE: 387
ttctagacac tgagggagca                                               20

<210> SEQ ID NO 388
<211> LENGTH: 20
<212> TYPE: DNA
<213> ORGANISM: Homo sapiens

<400> SEQUENCE: 388
taggggacag taagccagat                                               20

<210> SEQ ID NO 389
<211> LENGTH: 20
<212> TYPE: DNA
<213> ORGANISM: Homo sapiens

<400> SEQUENCE: 389
aacgctacac tttacgagct                                               20

<210> SEQ ID NO 390
<211> LENGTH: 20
<212> TYPE: DNA
<213> ORGANISM: Homo sapiens

<400> SEQUENCE: 390
acgatggacc tctgttgaac                                               20

<210> SEQ ID NO 391
<211> LENGTH: 20
<212> TYPE: DNA
```

<213> ORGANISM: Homo sapiens

<400> SEQUENCE: 391
tcaacactac ctgccaatca                    20

<210> SEQ ID NO 392
<211> LENGTH: 21
<212> TYPE: DNA
<213> ORGANISM: Homo sapiens

<400> SEQUENCE: 392
attcccatcc atccatcact c                  21

<210> SEQ ID NO 393
<211> LENGTH: 19
<212> TYPE: DNA
<213> ORGANISM: Homo sapiens

<400> SEQUENCE: 393
tgccgacaca aagaatgc                      19

<210> SEQ ID NO 394
<211> LENGTH: 20
<212> TYPE: DNA
<213> ORGANISM: Homo sapiens

<400> SEQUENCE: 394
tcgtttttgg atggtggttg                    20

<210> SEQ ID NO 395
<211> LENGTH: 19
<212> TYPE: DNA
<213> ORGANISM: Homo sapiens

<400> SEQUENCE: 395
aaagtgttcc tccctgctg                     19

<210> SEQ ID NO 396
<211> LENGTH: 21
<212> TYPE: DNA
<213> ORGANISM: Homo sapiens

<400> SEQUENCE: 396
gaagttcctc cagtagactc a                  21

<210> SEQ ID NO 397
<211> LENGTH: 20
<212> TYPE: DNA
<213> ORGANISM: Homo sapiens

<400> SEQUENCE: 397
aggagcaaaa tagtctggct                    20

<210> SEQ ID NO 398
<211> LENGTH: 20
<212> TYPE: DNA
<213> ORGANISM: Homo sapiens

<400> SEQUENCE: 398
ttgtttgagt ctgggaggaa                    20

<210> SEQ ID NO 399
<211> LENGTH: 21

```
<212> TYPE: DNA
<213> ORGANISM: Homo sapiens

<400> SEQUENCE: 399
accactcttg aatcattgca g                                          21

<210> SEQ ID NO 400
<211> LENGTH: 20
<212> TYPE: DNA
<213> ORGANISM: Homo sapiens

<400> SEQUENCE: 400
aatactgtga gactgccacc                                            20

<210> SEQ ID NO 401
<211> LENGTH: 21
<212> TYPE: DNA
<213> ORGANISM: Homo sapiens

<400> SEQUENCE: 401
ccagccaatt ttctctttcc c                                          21

<210> SEQ ID NO 402
<211> LENGTH: 20
<212> TYPE: DNA
<213> ORGANISM: Homo sapiens

<400> SEQUENCE: 402
cagtcacgga aagtaccctc                                            20

<210> SEQ ID NO 403
<211> LENGTH: 20
<212> TYPE: DNA
<213> ORGANISM: Homo sapiens

<400> SEQUENCE: 403
actgtcccta ctgccaattt                                            20

<210> SEQ ID NO 404
<211> LENGTH: 20
<212> TYPE: DNA
<213> ORGANISM: Homo sapiens

<400> SEQUENCE: 404
accatgtttc cctctgtcac                                            20

<210> SEQ ID NO 405
<211> LENGTH: 21
<212> TYPE: DNA
<213> ORGANISM: Homo sapiens

<400> SEQUENCE: 405
atctggtttg aacttgccaa c                                          21

<210> SEQ ID NO 406
<211> LENGTH: 20
<212> TYPE: DNA
<213> ORGANISM: Homo sapiens

<400> SEQUENCE: 406
ttaccaaggg acaggatgga                                            20

<210> SEQ ID NO 407
```

```
<211> LENGTH: 20
<212> TYPE: DNA
<213> ORGANISM: Homo sapiens

<400> SEQUENCE: 407
cactctgaat agctctcccc                                          20

<210> SEQ ID NO 408
<211> LENGTH: 20
<212> TYPE: DNA
<213> ORGANISM: Homo sapiens

<400> SEQUENCE: 408
ccctagaggt caaggtatgg                                          20

<210> SEQ ID NO 409
<211> LENGTH: 20
<212> TYPE: DNA
<213> ORGANISM: Homo sapiens

<400> SEQUENCE: 409
ttatccggga cagtttcagg                                          20

<210> SEQ ID NO 410
<211> LENGTH: 20
<212> TYPE: DNA
<213> ORGANISM: Homo sapiens

<400> SEQUENCE: 410
ataggccctg tgtgttagtt                                          20

<210> SEQ ID NO 411
<211> LENGTH: 20
<212> TYPE: DNA
<213> ORGANISM: Homo sapiens

<400> SEQUENCE: 411
gaatcttttg gcccacactg                                          20

<210> SEQ ID NO 412
<211> LENGTH: 20
<212> TYPE: DNA
<213> ORGANISM: Homo sapiens

<400> SEQUENCE: 412
agaaagtccc ctccatttct                                          20

<210> SEQ ID NO 413
<211> LENGTH: 20
<212> TYPE: DNA
<213> ORGANISM: Homo sapiens

<400> SEQUENCE: 413
gtcagacaca cttagctggt                                          20

<210> SEQ ID NO 414
<211> LENGTH: 20
<212> TYPE: DNA
<213> ORGANISM: Homo sapiens

<400> SEQUENCE: 414
gccaatgcca aagtcagtta                                          20
```

```
<210> SEQ ID NO 415
<211> LENGTH: 20
<212> TYPE: DNA
<213> ORGANISM: Homo sapiens

<400> SEQUENCE: 415
acacatttca ccttcaccct                                                 20

<210> SEQ ID NO 416
<211> LENGTH: 20
<212> TYPE: DNA
<213> ORGANISM: Homo sapiens

<400> SEQUENCE: 416
gaggacgagt tgaacaaagc                                                 20

<210> SEQ ID NO 417
<211> LENGTH: 20
<212> TYPE: DNA
<213> ORGANISM: Homo sapiens

<400> SEQUENCE: 417
gcactaatcc agggcttaa                                                  20

<210> SEQ ID NO 418
<211> LENGTH: 21
<212> TYPE: DNA
<213> ORGANISM: Homo sapiens

<400> SEQUENCE: 418
atactggtct caaggtagca c                                               21

<210> SEQ ID NO 419
<211> LENGTH: 20
<212> TYPE: DNA
<213> ORGANISM: Homo sapiens

<400> SEQUENCE: 419
ccccttacca ccacttctac                                                 20

<210> SEQ ID NO 420
<211> LENGTH: 22
<212> TYPE: DNA
<213> ORGANISM: Homo sapiens

<400> SEQUENCE: 420
accaagtgaa gctgagttaa tg                                              22

<210> SEQ ID NO 421
<211> LENGTH: 20
<212> TYPE: DNA
<213> ORGANISM: Homo sapiens

<400> SEQUENCE: 421
ttcagatccc ttaagcacgc                                                 20

<210> SEQ ID NO 422
<211> LENGTH: 20
<212> TYPE: DNA
<213> ORGANISM: Homo sapiens

<400> SEQUENCE: 422
cccagataca ctcctgcttc                                                 20
```

```
<210> SEQ ID NO 423
<211> LENGTH: 20
<212> TYPE: DNA
<213> ORGANISM: Homo sapiens

<400> SEQUENCE: 423
acctaaggcc tcaaattcca                                          20

<210> SEQ ID NO 424
<211> LENGTH: 20
<212> TYPE: DNA
<213> ORGANISM: Homo sapiens

<400> SEQUENCE: 424
caaacatgag aggggagaa                                           20

<210> SEQ ID NO 425
<211> LENGTH: 20
<212> TYPE: DNA
<213> ORGANISM: Homo sapiens

<400> SEQUENCE: 425
cagaccacgg gcataagaaa                                          20

<210> SEQ ID NO 426
<211> LENGTH: 20
<212> TYPE: DNA
<213> ORGANISM: Homo sapiens

<400> SEQUENCE: 426
aaacacagca atgaggaagg                                          20

<210> SEQ ID NO 427
<211> LENGTH: 20
<212> TYPE: DNA
<213> ORGANISM: Homo sapiens

<400> SEQUENCE: 427
tggatgtgtg gatttggaga                                          20

<210> SEQ ID NO 428
<211> LENGTH: 20
<212> TYPE: DNA
<213> ORGANISM: Homo sapiens

<400> SEQUENCE: 428
gatactcccc tgtgttgctt                                          20

<210> SEQ ID NO 429
<211> LENGTH: 19
<212> TYPE: DNA
<213> ORGANISM: Homo sapiens

<400> SEQUENCE: 429
ctggctgtct tctgggaaa                                           19

<210> SEQ ID NO 430
<211> LENGTH: 20
<212> TYPE: DNA
<213> ORGANISM: Homo sapiens

<400> SEQUENCE: 430
gctcttacta ggatggcagg                                          20
```

<210> SEQ ID NO 431
<211> LENGTH: 21
<212> TYPE: DNA
<213> ORGANISM: Homo sapiens

<400> SEQUENCE: 431
caagcagaac tgagaagagt c                                             21

<210> SEQ ID NO 432
<211> LENGTH: 20
<212> TYPE: DNA
<213> ORGANISM: Homo sapiens

<400> SEQUENCE: 432
gtttccagca gcaatccttt                                               20

<210> SEQ ID NO 433
<211> LENGTH: 20
<212> TYPE: DNA
<213> ORGANISM: Homo sapiens

<400> SEQUENCE: 433
agtggaacga ggattgtgtt                                               20

<210> SEQ ID NO 434
<211> LENGTH: 19
<212> TYPE: DNA
<213> ORGANISM: Homo sapiens

<400> SEQUENCE: 434
ctgtgcagaa gggttagct                                                19

<210> SEQ ID NO 435
<211> LENGTH: 20
<212> TYPE: DNA
<213> ORGANISM: Homo sapiens

<400> SEQUENCE: 435
ctcccatctg aaactgctga                                               20

<210> SEQ ID NO 436
<211> LENGTH: 20
<212> TYPE: DNA
<213> ORGANISM: Homo sapiens

<400> SEQUENCE: 436
aaacccctgc tacccaaaat                                               20

<210> SEQ ID NO 437
<211> LENGTH: 19
<212> TYPE: DNA
<213> ORGANISM: Homo sapiens

<400> SEQUENCE: 437
acatcacaac caccctgac                                                19

<210> SEQ ID NO 438
<211> LENGTH: 20
<212> TYPE: DNA
<213> ORGANISM: Homo sapiens

```
<400> SEQUENCE: 438
aatgcccaga tgctgttttc                                                 20

<210> SEQ ID NO 439
<211> LENGTH: 20
<212> TYPE: DNA
<213> ORGANISM: Homo sapiens

<400> SEQUENCE: 439
gtgttgacct gatttgccaa                                                 20

<210> SEQ ID NO 440
<211> LENGTH: 21
<212> TYPE: DNA
<213> ORGANISM: Homo sapiens

<400> SEQUENCE: 440
gagtggttgt tctctccaga t                                               21

<210> SEQ ID NO 441
<211> LENGTH: 20
<212> TYPE: DNA
<213> ORGANISM: Homo sapiens

<400> SEQUENCE: 441
gaacaaagag gaacagagcc                                                 20

<210> SEQ ID NO 442
<211> LENGTH: 20
<212> TYPE: DNA
<213> ORGANISM: Homo sapiens

<400> SEQUENCE: 442
cagtctagaa gctcacccag                                                 20

<210> SEQ ID NO 443
<211> LENGTH: 20
<212> TYPE: DNA
<213> ORGANISM: Homo sapiens

<400> SEQUENCE: 443
ttcatgattc cagggtcctc                                                 20

<210> SEQ ID NO 444
<211> LENGTH: 20
<212> TYPE: DNA
<213> ORGANISM: Homo sapiens

<400> SEQUENCE: 444
tctcctctac ccctacactg                                                 20

<210> SEQ ID NO 445
<211> LENGTH: 22
<212> TYPE: DNA
<213> ORGANISM: Homo sapiens

<400> SEQUENCE: 445
ggacggattt agtgtacatt gg                                              22

<210> SEQ ID NO 446
<211> LENGTH: 20
<212> TYPE: DNA
```

```
<213> ORGANISM: Homo sapiens

<400> SEQUENCE: 446
ggtgtaaatg tggcctctcc                                              20

<210> SEQ ID NO 447
<211> LENGTH: 20
<212> TYPE: DNA
<213> ORGANISM: Homo sapiens

<400> SEQUENCE: 447
tttccttcca acaccacaga                                              20

<210> SEQ ID NO 448
<211> LENGTH: 20
<212> TYPE: DNA
<213> ORGANISM: Homo sapiens

<400> SEQUENCE: 448
acaaagctac aaactctggc                                              20

<210> SEQ ID NO 449
<211> LENGTH: 20
<212> TYPE: DNA
<213> ORGANISM: Homo sapiens

<400> SEQUENCE: 449
tccttagggt tctgcgaaat                                              20

<210> SEQ ID NO 450
<211> LENGTH: 20
<212> TYPE: DNA
<213> ORGANISM: Homo sapiens

<400> SEQUENCE: 450
tttcactggg agactgatgc                                              20

<210> SEQ ID NO 451
<211> LENGTH: 20
<212> TYPE: DNA
<213> ORGANISM: Homo sapiens

<400> SEQUENCE: 451
ggaaactccc tgccttctac                                              20

<210> SEQ ID NO 452
<211> LENGTH: 20
<212> TYPE: DNA
<213> ORGANISM: Homo sapiens

<400> SEQUENCE: 452
ctgttctgtt cctgaggcta                                              20

<210> SEQ ID NO 453
<211> LENGTH: 20
<212> TYPE: DNA
<213> ORGANISM: Homo sapiens

<400> SEQUENCE: 453
tcttccaaac accaggtcta                                              20

<210> SEQ ID NO 454
<211> LENGTH: 21
```

<212> TYPE: DNA
<213> ORGANISM: Homo sapiens

<400> SEQUENCE: 454
tgtgtatcca ttgcctcatc t                                          21

<210> SEQ ID NO 455
<211> LENGTH: 19
<212> TYPE: DNA
<213> ORGANISM: Homo sapiens

<400> SEQUENCE: 455
actcaatgga aggaagggc                                             19

<210> SEQ ID NO 456
<211> LENGTH: 20
<212> TYPE: DNA
<213> ORGANISM: Homo sapiens

<400> SEQUENCE: 456
gaagagggtg tgtgtaggac                                            20

<210> SEQ ID NO 457
<211> LENGTH: 20
<212> TYPE: DNA
<213> ORGANISM: Homo sapiens

<400> SEQUENCE: 457
aaggacttgt gctgtattgc                                            20

<210> SEQ ID NO 458
<211> LENGTH: 20
<212> TYPE: DNA
<213> ORGANISM: Homo sapiens

<400> SEQUENCE: 458
tggttgctct tcctagttcc                                            20

<210> SEQ ID NO 459
<211> LENGTH: 20
<212> TYPE: DNA
<213> ORGANISM: Homo sapiens

<400> SEQUENCE: 459
gacgggagcc agtattctac                                            20

<210> SEQ ID NO 460
<211> LENGTH: 20
<212> TYPE: DNA
<213> ORGANISM: Homo sapiens

<400> SEQUENCE: 460
caatgtggag gaagctcttg                                            20

<210> SEQ ID NO 461
<211> LENGTH: 20
<212> TYPE: DNA
<213> ORGANISM: Homo sapiens

<400> SEQUENCE: 461
gggattgaga gcttggttct                                            20

<210> SEQ ID NO 462

```
<211> LENGTH: 20
<212> TYPE: DNA
<213> ORGANISM: Homo sapiens

<400> SEQUENCE: 462
ttgcacaccc aatatgctac                                              20

<210> SEQ ID NO 463
<211> LENGTH: 20
<212> TYPE: DNA
<213> ORGANISM: Homo sapiens

<400> SEQUENCE: 463
ctccccacca agatgttcaa                                              20

<210> SEQ ID NO 464
<211> LENGTH: 20
<212> TYPE: DNA
<213> ORGANISM: Homo sapiens

<400> SEQUENCE: 464
tccaaggttt ctctagcgac                                              20

<210> SEQ ID NO 465
<211> LENGTH: 20
<212> TYPE: DNA
<213> ORGANISM: Homo sapiens

<400> SEQUENCE: 465
gttttgggtc atgcagtgtt                                              20

<210> SEQ ID NO 466
<211> LENGTH: 20
<212> TYPE: DNA
<213> ORGANISM: Homo sapiens

<400> SEQUENCE: 466
tcgctattct ccttgccata                                              20

<210> SEQ ID NO 467
<211> LENGTH: 20
<212> TYPE: DNA
<213> ORGANISM: Homo sapiens

<400> SEQUENCE: 467
gacaaaaaca cttgccagac                                              20

<210> SEQ ID NO 468
<211> LENGTH: 20
<212> TYPE: DNA
<213> ORGANISM: Homo sapiens

<400> SEQUENCE: 468
aacagcctct ttccttagca                                              20

<210> SEQ ID NO 469
<211> LENGTH: 20
<212> TYPE: DNA
<213> ORGANISM: Homo sapiens

<400> SEQUENCE: 469
aaccatggct ttgcaagtac                                              20
```

```
<210> SEQ ID NO 470
<211> LENGTH: 20
<212> TYPE: DNA
<213> ORGANISM: Homo sapiens

<400> SEQUENCE: 470
tttttggctc agtgggatgt                                              20

<210> SEQ ID NO 471
<211> LENGTH: 20
<212> TYPE: DNA
<213> ORGANISM: Homo sapiens

<400> SEQUENCE: 471
ggaaccctct gctattttgc                                              20

<210> SEQ ID NO 472
<211> LENGTH: 21
<212> TYPE: DNA
<213> ORGANISM: Homo sapiens

<400> SEQUENCE: 472
ctgttcattc ttcttcaggg c                                            21

<210> SEQ ID NO 473
<211> LENGTH: 20
<212> TYPE: DNA
<213> ORGANISM: Homo sapiens

<400> SEQUENCE: 473
tactccttgt gtgaacccct                                              20

<210> SEQ ID NO 474
<211> LENGTH: 20
<212> TYPE: DNA
<213> ORGANISM: Homo sapiens

<400> SEQUENCE: 474
ttcccgagcc cataaactac                                              20

<210> SEQ ID NO 475
<211> LENGTH: 20
<212> TYPE: DNA
<213> ORGANISM: Homo sapiens

<400> SEQUENCE: 475
acctttaccc cataccatcc                                              20

<210> SEQ ID NO 476
<211> LENGTH: 20
<212> TYPE: DNA
<213> ORGANISM: Homo sapiens

<400> SEQUENCE: 476
tgctcagatt tcagcttcct                                              20

<210> SEQ ID NO 477
<211> LENGTH: 20
<212> TYPE: DNA
<213> ORGANISM: Homo sapiens

<400> SEQUENCE: 477
cattcctttg gttggtgtcc                                              20
```

<210> SEQ ID NO 478
<211> LENGTH: 20
<212> TYPE: DNA
<213> ORGANISM: Homo sapiens

<400> SEQUENCE: 478
gtcagcgatg tggatgtcta                                          20

<210> SEQ ID NO 479
<211> LENGTH: 20
<212> TYPE: DNA
<213> ORGANISM: Homo sapiens

<400> SEQUENCE: 479
ctaatgggcc tgttgttcct                                          20

<210> SEQ ID NO 480
<211> LENGTH: 20
<212> TYPE: DNA
<213> ORGANISM: Homo sapiens

<400> SEQUENCE: 480
aactgactcc atgacctgtg                                          20

<210> SEQ ID NO 481
<211> LENGTH: 20
<212> TYPE: DNA
<213> ORGANISM: Homo sapiens

<400> SEQUENCE: 481
caacctacct gcccatagtt                                          20

<210> SEQ ID NO 482
<211> LENGTH: 20
<212> TYPE: DNA
<213> ORGANISM: Homo sapiens

<400> SEQUENCE: 482
gaagctgcta cttggtgaac                                          20

<210> SEQ ID NO 483
<211> LENGTH: 20
<212> TYPE: DNA
<213> ORGANISM: Homo sapiens

<400> SEQUENCE: 483
cgtagcaaat tatggcgagg                                          20

<210> SEQ ID NO 484
<211> LENGTH: 20
<212> TYPE: DNA
<213> ORGANISM: Homo sapiens

<400> SEQUENCE: 484
ttttcctcct gttctgttgc                                          20

<210> SEQ ID NO 485
<211> LENGTH: 20
<212> TYPE: DNA
<213> ORGANISM: Homo sapiens

<400> SEQUENCE: 485
ggtcagaagg gaaagggttc                                          20

<210> SEQ ID NO 486
<211> LENGTH: 20
<212> TYPE: DNA
<213> ORGANISM: Homo sapiens

<400> SEQUENCE: 486
ttctcaaatg caaccactcc                                               20

<210> SEQ ID NO 487
<211> LENGTH: 20
<212> TYPE: DNA
<213> ORGANISM: Homo sapiens

<400> SEQUENCE: 487
ccagattaaa acgtggtgcc                                               20

<210> SEQ ID NO 488
<211> LENGTH: 20
<212> TYPE: DNA
<213> ORGANISM: Homo sapiens

<400> SEQUENCE: 488
ctggcccttc aatttcatgc                                               20

<210> SEQ ID NO 489
<211> LENGTH: 20
<212> TYPE: DNA
<213> ORGANISM: Homo sapiens

<400> SEQUENCE: 489
cccacaacta taggtcgcat                                               20

<210> SEQ ID NO 490
<211> LENGTH: 21
<212> TYPE: DNA
<213> ORGANISM: Homo sapiens

<400> SEQUENCE: 490
ccagcagtac cgatatcaga g                                             21

<210> SEQ ID NO 491
<211> LENGTH: 21
<212> TYPE: DNA
<213> ORGANISM: Homo sapiens

<400> SEQUENCE: 491
agttgttcca tttgtaccag c                                             21

<210> SEQ ID NO 492
<211> LENGTH: 20
<212> TYPE: DNA
<213> ORGANISM: Homo sapiens

<400> SEQUENCE: 492
cagaaggcag gagatggatt                                               20

<210> SEQ ID NO 493
<211> LENGTH: 19
<212> TYPE: DNA
<213> ORGANISM: Homo sapiens

<400> SEQUENCE: 493
ttggctgcac tttgagtca                                              19

<210> SEQ ID NO 494
<211> LENGTH: 20
<212> TYPE: DNA
<213> ORGANISM: Homo sapiens

<400> SEQUENCE: 494
aagcaaccat tttcctgagc                                             20

<210> SEQ ID NO 495
<211> LENGTH: 20
<212> TYPE: DNA
<213> ORGANISM: Homo sapiens

<400> SEQUENCE: 495
cagatggccc attgtaacaa                                             20

<210> SEQ ID NO 496
<211> LENGTH: 20
<212> TYPE: DNA
<213> ORGANISM: Homo sapiens

<400> SEQUENCE: 496
tcacccttca tctacccact                                             20

<210> SEQ ID NO 497
<211> LENGTH: 19
<212> TYPE: DNA
<213> ORGANISM: Homo sapiens

<400> SEQUENCE: 497
tattgaggtt cccgtgctg                                              19

<210> SEQ ID NO 498
<211> LENGTH: 20
<212> TYPE: DNA
<213> ORGANISM: Homo sapiens

<400> SEQUENCE: 498
aagctggtga ccttctacag                                             20

<210> SEQ ID NO 499
<211> LENGTH: 20
<212> TYPE: DNA
<213> ORGANISM: Homo sapiens

<400> SEQUENCE: 499
agaatgtgaa gtggctccat                                             20

<210> SEQ ID NO 500
<211> LENGTH: 20
<212> TYPE: DNA
<213> ORGANISM: Homo sapiens

<400> SEQUENCE: 500
aaaattctgg ttggggagga                                             20

<210> SEQ ID NO 501
<211> LENGTH: 20
<212> TYPE: DNA

<213> ORGANISM: Homo sapiens

<400> SEQUENCE: 501
tttgggtttg tgtgtgtgtg                                          20

<210> SEQ ID NO 502
<211> LENGTH: 20
<212> TYPE: DNA
<213> ORGANISM: Homo sapiens

<400> SEQUENCE: 502
ccatacctca tctgctctgt                                          20

<210> SEQ ID NO 503
<211> LENGTH: 20
<212> TYPE: DNA
<213> ORGANISM: Homo sapiens

<400> SEQUENCE: 503
aggaatctct ctctgccaag                                          20

<210> SEQ ID NO 504
<211> LENGTH: 20
<212> TYPE: DNA
<213> ORGANISM: Homo sapiens

<400> SEQUENCE: 504
ggctgtccct gaactacttt                                          20

<210> SEQ ID NO 505
<211> LENGTH: 20
<212> TYPE: DNA
<213> ORGANISM: Homo sapiens

<400> SEQUENCE: 505
tcttcaaggc aggtcatagg                                          20

<210> SEQ ID NO 506
<211> LENGTH: 20
<212> TYPE: DNA
<213> ORGANISM: Homo sapiens

<400> SEQUENCE: 506
cttggcttaa actctgctcc                                          20

<210> SEQ ID NO 507
<211> LENGTH: 21
<212> TYPE: DNA
<213> ORGANISM: Homo sapiens

<400> SEQUENCE: 507
gaaacctaag acgttccact g                                        21

<210> SEQ ID NO 508
<211> LENGTH: 20
<212> TYPE: DNA
<213> ORGANISM: Homo sapiens

<400> SEQUENCE: 508
gacttgaaca caccctcaga                                          20

<210> SEQ ID NO 509
<211> LENGTH: 20

```
<212> TYPE: DNA
<213> ORGANISM: Homo sapiens

<400> SEQUENCE: 509
gagtgaaggg attggagcaa                                              20

<210> SEQ ID NO 510
<211> LENGTH: 20
<212> TYPE: DNA
<213> ORGANISM: Homo sapiens

<400> SEQUENCE: 510
aggagaagag accattgcag                                              20

<210> SEQ ID NO 511
<211> LENGTH: 20
<212> TYPE: DNA
<213> ORGANISM: Homo sapiens

<400> SEQUENCE: 511
atgtctcagg ctaggtgttc                                              20

<210> SEQ ID NO 512
<211> LENGTH: 20
<212> TYPE: DNA
<213> ORGANISM: Homo sapiens

<400> SEQUENCE: 512
ttagctaagt ctgtgcggag                                              20

<210> SEQ ID NO 513
<211> LENGTH: 20
<212> TYPE: DNA
<213> ORGANISM: Homo sapiens

<400> SEQUENCE: 513
acactcacaa agcccagtta                                              20

<210> SEQ ID NO 514
<211> LENGTH: 19
<212> TYPE: DNA
<213> ORGANISM: Homo sapiens

<400> SEQUENCE: 514
gaagcaacac tgtacacgc                                               19

<210> SEQ ID NO 515
<211> LENGTH: 20
<212> TYPE: DNA
<213> ORGANISM: Homo sapiens

<400> SEQUENCE: 515
gtgcagactc atgttatggc                                              20

<210> SEQ ID NO 516
<211> LENGTH: 20
<212> TYPE: DNA
<213> ORGANISM: Homo sapiens

<400> SEQUENCE: 516
tctgataaag gctggctcat                                              20

<210> SEQ ID NO 517
```

```
<211> LENGTH: 20
<212> TYPE: DNA
<213> ORGANISM: Homo sapiens

<400> SEQUENCE: 517
aggatctcaa agcaccacag                                               20

<210> SEQ ID NO 518
<211> LENGTH: 20
<212> TYPE: DNA
<213> ORGANISM: Homo sapiens

<400> SEQUENCE: 518
taaaacagtg ccgctacttc                                               20

<210> SEQ ID NO 519
<211> LENGTH: 20
<212> TYPE: DNA
<213> ORGANISM: Homo sapiens

<400> SEQUENCE: 519
aacgggaaga gggaaacttt                                               20

<210> SEQ ID NO 520
<211> LENGTH: 20
<212> TYPE: DNA
<213> ORGANISM: Homo sapiens

<400> SEQUENCE: 520
agtgctatga gtcttggtcc                                               20

<210> SEQ ID NO 521
<211> LENGTH: 20
<212> TYPE: DNA
<213> ORGANISM: Homo sapiens

<400> SEQUENCE: 521
atgttcaaca gagtcaggct                                               20

<210> SEQ ID NO 522
<211> LENGTH: 20
<212> TYPE: DNA
<213> ORGANISM: Homo sapiens

<400> SEQUENCE: 522
ggaaaacatg cggtggtcta                                               20

<210> SEQ ID NO 523
<211> LENGTH: 20
<212> TYPE: DNA
<213> ORGANISM: Homo sapiens

<400> SEQUENCE: 523
cagtaacagt ccagggtctt                                               20

<210> SEQ ID NO 524
<211> LENGTH: 20
<212> TYPE: DNA
<213> ORGANISM: Homo sapiens

<400> SEQUENCE: 524
gcagagaaat gggttaaggg                                               20
```

```
<210> SEQ ID NO 525
<211> LENGTH: 20
<212> TYPE: DNA
<213> ORGANISM: Homo sapiens

<400> SEQUENCE: 525
agtctgggag cctagaatca                                                    20

<210> SEQ ID NO 526
<211> LENGTH: 20
<212> TYPE: DNA
<213> ORGANISM: Homo sapiens

<400> SEQUENCE: 526
ggtagaggtg ggttatctgt                                                    20

<210> SEQ ID NO 527
<211> LENGTH: 22
<212> TYPE: DNA
<213> ORGANISM: Homo sapiens

<400> SEQUENCE: 527
cattgtagtt tcaggacacc aa                                                 22

<210> SEQ ID NO 528
<211> LENGTH: 19
<212> TYPE: DNA
<213> ORGANISM: Homo sapiens

<400> SEQUENCE: 528
ctgtaaatct ccgggggtg                                                     19

<210> SEQ ID NO 529
<211> LENGTH: 20
<212> TYPE: DNA
<213> ORGANISM: Homo sapiens

<400> SEQUENCE: 529
accacagaat gacttgcagc                                                    20

<210> SEQ ID NO 530
<211> LENGTH: 20
<212> TYPE: DNA
<213> ORGANISM: Homo sapiens

<400> SEQUENCE: 530
ggcgagaatg gagagagaaa                                                    20

<210> SEQ ID NO 531
<211> LENGTH: 20
<212> TYPE: DNA
<213> ORGANISM: Homo sapiens

<400> SEQUENCE: 531
tttcacgtgt aacaggagca                                                    20

<210> SEQ ID NO 532
<211> LENGTH: 20
<212> TYPE: DNA
<213> ORGANISM: Homo sapiens

<400> SEQUENCE: 532
tcccaagcca ggattctttt                                                    20
```

```
<210> SEQ ID NO 533
<211> LENGTH: 20
<212> TYPE: DNA
<213> ORGANISM: Homo sapiens

<400> SEQUENCE: 533
tgctacaggg aaaatggtct                                                 20

<210> SEQ ID NO 534
<211> LENGTH: 20
<212> TYPE: DNA
<213> ORGANISM: Homo sapiens

<400> SEQUENCE: 534
gaacaagtac aaccgtgcag                                                 20

<210> SEQ ID NO 535
<211> LENGTH: 20
<212> TYPE: DNA
<213> ORGANISM: Homo sapiens

<400> SEQUENCE: 535
tccactgctt agtttgcctt                                                 20

<210> SEQ ID NO 536
<211> LENGTH: 20
<212> TYPE: DNA
<213> ORGANISM: Homo sapiens

<400> SEQUENCE: 536
acaaatgccc catatcaacc                                                 20

<210> SEQ ID NO 537
<211> LENGTH: 20
<212> TYPE: DNA
<213> ORGANISM: Homo sapiens

<400> SEQUENCE: 537
acaggtgggg agaaaaggta                                                 20

<210> SEQ ID NO 538
<211> LENGTH: 20
<212> TYPE: DNA
<213> ORGANISM: Homo sapiens

<400> SEQUENCE: 538
ggaaagaggc ctggagtaat                                                 20

<210> SEQ ID NO 539
<211> LENGTH: 20
<212> TYPE: DNA
<213> ORGANISM: Homo sapiens

<400> SEQUENCE: 539
ctgccactac tacacagcta                                                 20

<210> SEQ ID NO 540
<211> LENGTH: 20
<212> TYPE: DNA
<213> ORGANISM: Homo sapiens

<400> SEQUENCE: 540
tttccactgg atgtcgtcat                                                 20
```

```
<210> SEQ ID NO 541
<211> LENGTH: 20
<212> TYPE: DNA
<213> ORGANISM: Homo sapiens

<400> SEQUENCE: 541
atgggtctct ggaatgcatg                                              20

<210> SEQ ID NO 542
<211> LENGTH: 20
<212> TYPE: DNA
<213> ORGANISM: Homo sapiens

<400> SEQUENCE: 542
aggacaaagt ttcagcctct                                              20

<210> SEQ ID NO 543
<211> LENGTH: 20
<212> TYPE: DNA
<213> ORGANISM: Homo sapiens

<400> SEQUENCE: 543
agttctccac agcacatcat                                              20

<210> SEQ ID NO 544
<211> LENGTH: 21
<212> TYPE: DNA
<213> ORGANISM: Homo sapiens

<400> SEQUENCE: 544
actcaggaca cgacttcata c                                            21

<210> SEQ ID NO 545
<211> LENGTH: 20
<212> TYPE: DNA
<213> ORGANISM: Homo sapiens

<400> SEQUENCE: 545
tctttcatct cagctctgca                                              20

<210> SEQ ID NO 546
<211> LENGTH: 20
<212> TYPE: DNA
<213> ORGANISM: Homo sapiens

<400> SEQUENCE: 546
acatctttgg ctcactggtt                                              20

<210> SEQ ID NO 547
<211> LENGTH: 20
<212> TYPE: DNA
<213> ORGANISM: Homo sapiens

<400> SEQUENCE: 547
ccgaacagta ttttgagggg                                              20

<210> SEQ ID NO 548
<211> LENGTH: 20
<212> TYPE: DNA
<213> ORGANISM: Homo sapiens
```

```
<400> SEQUENCE: 548
tcacagtggg cttcattcag                                               20

<210> SEQ ID NO 549
<211> LENGTH: 20
<212> TYPE: DNA
<213> ORGANISM: Homo sapiens

<400> SEQUENCE: 549
tttggctgtt tcctgtttcc                                               20

<210> SEQ ID NO 550
<211> LENGTH: 22
<212> TYPE: DNA
<213> ORGANISM: Homo sapiens

<400> SEQUENCE: 550
agctggaatc tatgtaggat gg                                            22

<210> SEQ ID NO 551
<211> LENGTH: 20
<212> TYPE: DNA
<213> ORGANISM: Homo sapiens

<400> SEQUENCE: 551
acctaacttg ccttgtcctt                                               20

<210> SEQ ID NO 552
<211> LENGTH: 20
<212> TYPE: DNA
<213> ORGANISM: Homo sapiens

<400> SEQUENCE: 552
ctgcggaagg atctagtctt                                               20

<210> SEQ ID NO 553
<211> LENGTH: 20
<212> TYPE: DNA
<213> ORGANISM: Homo sapiens

<400> SEQUENCE: 553
acaggagaac aagcagcata                                               20

<210> SEQ ID NO 554
<211> LENGTH: 22
<212> TYPE: DNA
<213> ORGANISM: Homo sapiens

<400> SEQUENCE: 554
tgagaagtat tcagcatttc cc                                            22

<210> SEQ ID NO 555
<211> LENGTH: 21
<212> TYPE: DNA
<213> ORGANISM: Homo sapiens

<400> SEQUENCE: 555
cagcctagta tatgggaacg t                                             21

<210> SEQ ID NO 556
<211> LENGTH: 19
<212> TYPE: DNA
```

<213> ORGANISM: Homo sapiens

<400> SEQUENCE: 556
cactcacgga cttttaggc                                    19

<210> SEQ ID NO 557
<211> LENGTH: 23
<212> TYPE: DNA
<213> ORGANISM: Homo sapiens

<400> SEQUENCE: 557
acccatatgt agtatcgctc ttg                               23

<210> SEQ ID NO 558
<211> LENGTH: 21
<212> TYPE: DNA
<213> ORGANISM: Homo sapiens

<400> SEQUENCE: 558
cctccaactt ccactccaat g                                 21

<210> SEQ ID NO 559
<211> LENGTH: 21
<212> TYPE: DNA
<213> ORGANISM: Homo sapiens

<400> SEQUENCE: 559
tatgggtttt tctgctccac t                                 21

<210> SEQ ID NO 560
<211> LENGTH: 20
<212> TYPE: DNA
<213> ORGANISM: Homo sapiens

<400> SEQUENCE: 560
tcacacgcca ggttattaca                                   20

<210> SEQ ID NO 561
<211> LENGTH: 20
<212> TYPE: DNA
<213> ORGANISM: Homo sapiens

<400> SEQUENCE: 561
aaatgtgagg gagagtcgtc                                   20

<210> SEQ ID NO 562
<211> LENGTH: 20
<212> TYPE: DNA
<213> ORGANISM: Homo sapiens

<400> SEQUENCE: 562
aagtgggttt gcagtttgga                                   20

<210> SEQ ID NO 563
<211> LENGTH: 19
<212> TYPE: DNA
<213> ORGANISM: Homo sapiens

<400> SEQUENCE: 563
gcaggaccct tcagcatta                                    19

<210> SEQ ID NO 564
<211> LENGTH: 20

```
<212> TYPE: DNA
<213> ORGANISM: Homo sapiens

<400> SEQUENCE: 564
atgtacgtgt gtgtccatgt                                          20

<210> SEQ ID NO 565
<211> LENGTH: 20
<212> TYPE: DNA
<213> ORGANISM: Homo sapiens

<400> SEQUENCE: 565
gactggatga tgcaaaggtg                                          20

<210> SEQ ID NO 566
<211> LENGTH: 20
<212> TYPE: DNA
<213> ORGANISM: Homo sapiens

<400> SEQUENCE: 566
aggcgggttg gtcaataata                                          20

<210> SEQ ID NO 567
<211> LENGTH: 20
<212> TYPE: DNA
<213> ORGANISM: Homo sapiens

<400> SEQUENCE: 567
aacatttgca gggggatcaa                                          20

<210> SEQ ID NO 568
<211> LENGTH: 20
<212> TYPE: DNA
<213> ORGANISM: Homo sapiens

<400> SEQUENCE: 568
ccacaaatcc catcaacaca                                          20

<210> SEQ ID NO 569
<211> LENGTH: 20
<212> TYPE: DNA
<213> ORGANISM: Homo sapiens

<400> SEQUENCE: 569
aaagatgcct ccttgtgtct                                          20

<210> SEQ ID NO 570
<211> LENGTH: 20
<212> TYPE: DNA
<213> ORGANISM: Homo sapiens

<400> SEQUENCE: 570
tttcacagta acatcggcac                                          20

<210> SEQ ID NO 571
<211> LENGTH: 20
<212> TYPE: DNA
<213> ORGANISM: Homo sapiens

<400> SEQUENCE: 571
aagttatctg cccagggaaa                                          20

<210> SEQ ID NO 572
```

```
<211> LENGTH: 20
<212> TYPE: DNA
<213> ORGANISM: Homo sapiens

<400> SEQUENCE: 572
ctgacagcct gcatttgatt                                                20

<210> SEQ ID NO 573
<211> LENGTH: 20
<212> TYPE: DNA
<213> ORGANISM: Homo sapiens

<400> SEQUENCE: 573
tcctggctag ttttgctgaa                                                20

<210> SEQ ID NO 574
<211> LENGTH: 21
<212> TYPE: DNA
<213> ORGANISM: Homo sapiens

<400> SEQUENCE: 574
tttcctggag taaagcgatc t                                              21

<210> SEQ ID NO 575
<211> LENGTH: 20
<212> TYPE: DNA
<213> ORGANISM: Homo sapiens

<400> SEQUENCE: 575
ctccttgctt gcctttacac                                                20

<210> SEQ ID NO 576
<211> LENGTH: 20
<212> TYPE: DNA
<213> ORGANISM: Homo sapiens

<400> SEQUENCE: 576
cccacaatca cccatctcta                                                20

<210> SEQ ID NO 577
<211> LENGTH: 20
<212> TYPE: DNA
<213> ORGANISM: Homo sapiens

<400> SEQUENCE: 577
agccttaatt ccccatgcat                                                20

<210> SEQ ID NO 578
<211> LENGTH: 20
<212> TYPE: DNA
<213> ORGANISM: Homo sapiens

<400> SEQUENCE: 578
tatctcactc cacagcttcc                                                20

<210> SEQ ID NO 579
<211> LENGTH: 20
<212> TYPE: DNA
<213> ORGANISM: Homo sapiens

<400> SEQUENCE: 579
tttttctgtg gagtgtggct                                                20
```

```
<210> SEQ ID NO 580
<211> LENGTH: 20
<212> TYPE: DNA
<213> ORGANISM: Homo sapiens

<400> SEQUENCE: 580
acaggtagtt tggtggtgtc                                               20

<210> SEQ ID NO 581
<211> LENGTH: 20
<212> TYPE: DNA
<213> ORGANISM: Homo sapiens

<400> SEQUENCE: 581
aaagagtcaa ccatgcactg                                               20

<210> SEQ ID NO 582
<211> LENGTH: 20
<212> TYPE: DNA
<213> ORGANISM: Homo sapiens

<400> SEQUENCE: 582
gctgttgaat gccagaactt                                               20

<210> SEQ ID NO 583
<211> LENGTH: 20
<212> TYPE: DNA
<213> ORGANISM: Homo sapiens

<400> SEQUENCE: 583
ggtgaagcag cctgaataaa                                               20

<210> SEQ ID NO 584
<211> LENGTH: 20
<212> TYPE: DNA
<213> ORGANISM: Homo sapiens

<400> SEQUENCE: 584
atagggtcgg ttttggtctg                                               20

<210> SEQ ID NO 585
<211> LENGTH: 19
<212> TYPE: DNA
<213> ORGANISM: Homo sapiens

<400> SEQUENCE: 585
tctttgtacc aagctgcca                                                19

<210> SEQ ID NO 586
<211> LENGTH: 20
<212> TYPE: DNA
<213> ORGANISM: Homo sapiens

<400> SEQUENCE: 586
catcatccct gtcattccca                                               20

<210> SEQ ID NO 587
<211> LENGTH: 20
<212> TYPE: DNA
<213> ORGANISM: Homo sapiens

<400> SEQUENCE: 587
gcttctactt tcccctccag                                               20
```

```
<210> SEQ ID NO 588
<211> LENGTH: 20
<212> TYPE: DNA
<213> ORGANISM: Homo sapiens

<400> SEQUENCE: 588
gtgggctaag aaaacacctc                                                 20

<210> SEQ ID NO 589
<211> LENGTH: 20
<212> TYPE: DNA
<213> ORGANISM: Homo sapiens

<400> SEQUENCE: 589
agaaaagcca acctcctctt                                                 20

<210> SEQ ID NO 590
<211> LENGTH: 20
<212> TYPE: DNA
<213> ORGANISM: Homo sapiens

<400> SEQUENCE: 590
attgtggttt gtggcatgtg                                                 20

<210> SEQ ID NO 591
<211> LENGTH: 20
<212> TYPE: DNA
<213> ORGANISM: Homo sapiens

<400> SEQUENCE: 591
ccagggtact aaaaggggac                                                 20

<210> SEQ ID NO 592
<211> LENGTH: 20
<212> TYPE: DNA
<213> ORGANISM: Homo sapiens

<400> SEQUENCE: 592
ccagattcag cctgtattcc                                                 20

<210> SEQ ID NO 593
<211> LENGTH: 20
<212> TYPE: DNA
<213> ORGANISM: Homo sapiens

<400> SEQUENCE: 593
ttgtgggtca atgtcaacac                                                 20

<210> SEQ ID NO 594
<211> LENGTH: 20
<212> TYPE: DNA
<213> ORGANISM: Homo sapiens

<400> SEQUENCE: 594
gcccatggaa gtaaacagtc                                                 20

<210> SEQ ID NO 595
<211> LENGTH: 20
<212> TYPE: DNA
<213> ORGANISM: Homo sapiens

<400> SEQUENCE: 595
agaaaaggtg gaggaaggga                                                 20
```

```
<210> SEQ ID NO 596
<211> LENGTH: 22
<212> TYPE: DNA
<213> ORGANISM: Homo sapiens

<400> SEQUENCE: 596
aggtttgaca taatagtgct gc                                              22

<210> SEQ ID NO 597
<211> LENGTH: 21
<212> TYPE: DNA
<213> ORGANISM: Homo sapiens

<400> SEQUENCE: 597
ggagttgttt acaggtggac t                                               21

<210> SEQ ID NO 598
<211> LENGTH: 20
<212> TYPE: DNA
<213> ORGANISM: Homo sapiens

<400> SEQUENCE: 598
aatcctttcc ccactcactg                                                 20

<210> SEQ ID NO 599
<211> LENGTH: 21
<212> TYPE: DNA
<213> ORGANISM: Homo sapiens

<400> SEQUENCE: 599
tagcttccaa ttcacaggtc a                                               21

<210> SEQ ID NO 600
<211> LENGTH: 20
<212> TYPE: DNA
<213> ORGANISM: Homo sapiens

<400> SEQUENCE: 600
cacaaagcag ttccatgtcc                                                 20

<210> SEQ ID NO 601
<211> LENGTH: 20
<212> TYPE: DNA
<213> ORGANISM: Homo sapiens

<400> SEQUENCE: 601
ttaaatgcgc caagtcccta                                                 20

<210> SEQ ID NO 602
<211> LENGTH: 20
<212> TYPE: DNA
<213> ORGANISM: Homo sapiens

<400> SEQUENCE: 602
ggacaatttc tcacttgcca                                                 20

<210> SEQ ID NO 603
<211> LENGTH: 20
<212> TYPE: DNA
<213> ORGANISM: Homo sapiens
```

```
<400> SEQUENCE: 603
atttcctggg tcaagctctt                                               20

<210> SEQ ID NO 604
<211> LENGTH: 20
<212> TYPE: DNA
<213> ORGANISM: Homo sapiens

<400> SEQUENCE: 604 aagggggtgtt gttagatgct                                              20

<210> SEQ ID NO 605
<211> LENGTH: 20
<212> TYPE: DNA
<213> ORGANISM: Homo sapiens

<400> SEQUENCE: 605
cttggaccag gaatgctcta                                               20

<210> SEQ ID NO 606
<211> LENGTH: 20
<212> TYPE: DNA
<213> ORGANISM: Homo sapiens

<400> SEQUENCE: 606
gcatcacaca cagcagatac                                               20

<210> SEQ ID NO 607
<211> LENGTH: 20
<212> TYPE: DNA
<213> ORGANISM: Homo sapiens

<400> SEQUENCE: 607
aggcagtcag atccacctat                                               20

<210> SEQ ID NO 608
<211> LENGTH: 20
<212> TYPE: DNA
<213> ORGANISM: Homo sapiens

<400> SEQUENCE: 608
aaaatgtccg tcccagatga                                               20

<210> SEQ ID NO 609
<211> LENGTH: 20
<212> TYPE: DNA
<213> ORGANISM: Homo sapiens

<400> SEQUENCE: 609
aaaattgcct gctgtttgga                                               20

<210> SEQ ID NO 610
<211> LENGTH: 20
<212> TYPE: DNA
<213> ORGANISM: Homo sapiens

<400> SEQUENCE: 610
gggggaaaat gtgttgtgtt                                               20

<210> SEQ ID NO 611
<211> LENGTH: 20
<212> TYPE: DNA
```

<213> ORGANISM: Homo sapiens

<400> SEQUENCE: 611
gcaccatcat gaaacctcct                                              20

<210> SEQ ID NO 612
<211> LENGTH: 20
<212> TYPE: DNA
<213> ORGANISM: Homo sapiens

<400> SEQUENCE: 612
aactgttagc ttctccaccc                                              20

<210> SEQ ID NO 613
<211> LENGTH: 20
<212> TYPE: DNA
<213> ORGANISM: Homo sapiens

<400> SEQUENCE: 613
ataggccagt ctcaggtaga                                              20

<210> SEQ ID NO 614
<211> LENGTH: 20
<212> TYPE: DNA
<213> ORGANISM: Homo sapiens

<400> SEQUENCE: 614
cgagtgtagg ttccggttta                                              20

<210> SEQ ID NO 615
<211> LENGTH: 20
<212> TYPE: DNA
<213> ORGANISM: Homo sapiens

<400> SEQUENCE: 615
agattgcagc ctacccaaag                                              20

<210> SEQ ID NO 616
<211> LENGTH: 20
<212> TYPE: DNA
<213> ORGANISM: Homo sapiens

<400> SEQUENCE: 616
agaatgccca tttcaggagt                                              20

<210> SEQ ID NO 617
<211> LENGTH: 20
<212> TYPE: DNA
<213> ORGANISM: Homo sapiens

<400> SEQUENCE: 617
ttgactgaag tgttccaggt                                              20

<210> SEQ ID NO 618
<211> LENGTH: 21
<212> TYPE: DNA
<213> ORGANISM: Homo sapiens

<400> SEQUENCE: 618
atatgtggtt tgaggtcagc t                                            21

<210> SEQ ID NO 619
<211> LENGTH: 20

<212> TYPE: DNA
<213> ORGANISM: Homo sapiens

<400> SEQUENCE: 619
gcttctttca accatccacc                                               20

<210> SEQ ID NO 620
<211> LENGTH: 19
<212> TYPE: DNA
<213> ORGANISM: Homo sapiens

<400> SEQUENCE: 620
ggctttggtc acatggaga                                                19

<210> SEQ ID NO 621
<211> LENGTH: 20
<212> TYPE: DNA
<213> ORGANISM: Homo sapiens

<400> SEQUENCE: 621
gcagcactca actattccac                                               20

<210> SEQ ID NO 622
<211> LENGTH: 20
<212> TYPE: DNA
<213> ORGANISM: Homo sapiens

<400> SEQUENCE: 622
tgaggcaaga ttcagtgact                                               20

<210> SEQ ID NO 623
<211> LENGTH: 20
<212> TYPE: DNA
<213> ORGANISM: Homo sapiens

<400> SEQUENCE: 623
caggagttat ggcaccagtg                                               20

<210> SEQ ID NO 624
<211> LENGTH: 20
<212> TYPE: DNA
<213> ORGANISM: Homo sapiens

<400> SEQUENCE: 624
acttcatctt gacagcagct                                               20

<210> SEQ ID NO 625
<211> LENGTH: 20
<212> TYPE: DNA
<213> ORGANISM: Homo sapiens

<400> SEQUENCE: 625
gagagtgtgg aggcagaaaa                                               20

<210> SEQ ID NO 626
<211> LENGTH: 22
<212> TYPE: DNA
<213> ORGANISM: Homo sapiens

<400> SEQUENCE: 626
cacttcctca tgatgttttg ga                                            22

<210> SEQ ID NO 627

```
<211> LENGTH: 20
<212> TYPE: DNA
<213> ORGANISM: Homo sapiens

<400> SEQUENCE: 627
gcccaactta ttttccagct                                              20

<210> SEQ ID NO 628
<211> LENGTH: 20
<212> TYPE: DNA
<213> ORGANISM: Homo sapiens

<400> SEQUENCE: 628
ggccagccca cttatttttg                                              20

<210> SEQ ID NO 629
<211> LENGTH: 21
<212> TYPE: DNA
<213> ORGANISM: Homo sapiens

<400> SEQUENCE: 629
tcaagcccct tagattgaac a                                            21

<210> SEQ ID NO 630
<211> LENGTH: 20
<212> TYPE: DNA
<213> ORGANISM: Homo sapiens

<400> SEQUENCE: 630
ctcagggtgg agtttcaaac                                              20

<210> SEQ ID NO 631
<211> LENGTH: 20
<212> TYPE: DNA
<213> ORGANISM: Homo sapiens

<400> SEQUENCE: 631
gctgggcatg tagaactcaa                                              20

<210> SEQ ID NO 632
<211> LENGTH: 20
<212> TYPE: DNA
<213> ORGANISM: Homo sapiens

<400> SEQUENCE: 632
gatctttctt cccctcctcc                                              20

<210> SEQ ID NO 633
<211> LENGTH: 20
<212> TYPE: DNA
<213> ORGANISM: Homo sapiens

<400> SEQUENCE: 633
gggaaattgt caagggcttt                                              20

<210> SEQ ID NO 634
<211> LENGTH: 21
<212> TYPE: DNA
<213> ORGANISM: Homo sapiens

<400> SEQUENCE: 634
tgtacatcca ccacttgttt g                                            21
```

```
<210> SEQ ID NO 635
<211> LENGTH: 21
<212> TYPE: DNA
<213> ORGANISM: Homo sapiens

<400> SEQUENCE: 635
cttagttgct gttgtgcttc t                                              21

<210> SEQ ID NO 636
<211> LENGTH: 20
<212> TYPE: DNA
<213> ORGANISM: Homo sapiens

<400> SEQUENCE: 636
agcggtagta agaaggcaaa                                                20

<210> SEQ ID NO 637
<211> LENGTH: 20
<212> TYPE: DNA
<213> ORGANISM: Homo sapiens

<400> SEQUENCE: 637
agttgtagct gtatctgggt                                                20

<210> SEQ ID NO 638
<211> LENGTH: 20
<212> TYPE: DNA
<213> ORGANISM: Homo sapiens

<400> SEQUENCE: 638
agacaggtga ccattttccc                                                20

<210> SEQ ID NO 639
<211> LENGTH: 20
<212> TYPE: DNA
<213> ORGANISM: Homo sapiens

<400> SEQUENCE: 639
agctgagtca tgtttaaggc                                                20

<210> SEQ ID NO 640
<211> LENGTH: 20
<212> TYPE: DNA
<213> ORGANISM: Homo sapiens

<400> SEQUENCE: 640
tgtggaactt ttgagccaga                                                20

<210> SEQ ID NO 641
<211> LENGTH: 21
<212> TYPE: DNA
<213> ORGANISM: Homo sapiens

<400> SEQUENCE: 641
caattcagac tttgcccaaa c                                              21

<210> SEQ ID NO 642
<211> LENGTH: 21
<212> TYPE: DNA
<213> ORGANISM: Homo sapiens

<400> SEQUENCE: 642
cataacgaaa tagggccttc c                                              21
```

```
<210> SEQ ID NO 643
<211> LENGTH: 21
<212> TYPE: DNA
<213> ORGANISM: Homo sapiens

<400> SEQUENCE: 643
caatcattcc cacagttcca a                                            21

<210> SEQ ID NO 644
<211> LENGTH: 21
<212> TYPE: DNA
<213> ORGANISM: Homo sapiens

<400> SEQUENCE: 644
atttctgcct cttctcttcc c                                            21

<210> SEQ ID NO 645
<211> LENGTH: 20
<212> TYPE: DNA
<213> ORGANISM: Homo sapiens

<400> SEQUENCE: 645
ctgtgatggt ccattcaagg                                              20

<210> SEQ ID NO 646
<211> LENGTH: 20
<212> TYPE: DNA
<213> ORGANISM: Homo sapiens

<400> SEQUENCE: 646
tcatcaagtc acctctccac                                              20

<210> SEQ ID NO 647
<211> LENGTH: 20
<212> TYPE: DNA
<213> ORGANISM: Homo sapiens

<400> SEQUENCE: 647
tagctggaaa ttgcaaggag                                              20

<210> SEQ ID NO 648
<211> LENGTH: 20
<212> TYPE: DNA
<213> ORGANISM: Homo sapiens

<400> SEQUENCE: 648
tggaaaacta gacagcagcc                                              20

<210> SEQ ID NO 649
<211> LENGTH: 19
<212> TYPE: DNA
<213> ORGANISM: Homo sapiens

<400> SEQUENCE: 649
tctgttcacc tgagcctttt                                              19

<210> SEQ ID NO 650
<211> LENGTH: 20
<212> TYPE: DNA
<213> ORGANISM: Homo sapiens

<400> SEQUENCE: 650
ggaaagggga aaaggtgaca                                              20
```

<210> SEQ ID NO 651
<211> LENGTH: 20
<212> TYPE: DNA
<213> ORGANISM: Homo sapiens

<400> SEQUENCE: 651
taacttggac tgtgaaccca                                                    20

<210> SEQ ID NO 652
<211> LENGTH: 20
<212> TYPE: DNA
<213> ORGANISM: Homo sapiens

<400> SEQUENCE: 652
ctgtcctctg tcccacataa                                                    20

<210> SEQ ID NO 653
<211> LENGTH: 20
<212> TYPE: DNA
<213> ORGANISM: Homo sapiens

<400> SEQUENCE: 653
cgcaacagga tgaaggaaat                                                    20

<210> SEQ ID NO 654
<211> LENGTH: 20
<212> TYPE: DNA
<213> ORGANISM: Homo sapiens

<400> SEQUENCE: 654
tttctgagtc cattccccat                                                    20

<210> SEQ ID NO 655
<211> LENGTH: 20
<212> TYPE: DNA
<213> ORGANISM: Homo sapiens

<400> SEQUENCE: 655
gactcacact ctgaaagcct                                                    20

<210> SEQ ID NO 656
<211> LENGTH: 20
<212> TYPE: DNA
<213> ORGANISM: Homo sapiens

<400> SEQUENCE: 656
ggccatcctg atatcttcca                                                    20

<210> SEQ ID NO 657
<211> LENGTH: 21
<212> TYPE: DNA
<213> ORGANISM: Homo sapiens

<400> SEQUENCE: 657
aatttaggta gcactgaccc c                                                  21

<210> SEQ ID NO 658
<211> LENGTH: 20
<212> TYPE: DNA
<213> ORGANISM: Homo sapiens

```
<400> SEQUENCE: 658
cagagagatg cagaggttca                                               20

<210> SEQ ID NO 659
<211> LENGTH: 20
<212> TYPE: DNA
<213> ORGANISM: Homo sapiens

<400> SEQUENCE: 659
ctggggaatt aggaagcaga                                               20

<210> SEQ ID NO 660
<211> LENGTH: 20
<212> TYPE: DNA
<213> ORGANISM: Homo sapiens

<400> SEQUENCE: 660
tgtgtgtgag ctagctgaat                                               20

<210> SEQ ID NO 661
<211> LENGTH: 19
<212> TYPE: DNA
<213> ORGANISM: Homo sapiens

<400> SEQUENCE: 661
atgacaaggc tggctcatc                                                19

<210> SEQ ID NO 662
<211> LENGTH: 20
<212> TYPE: DNA
<213> ORGANISM: Homo sapiens

<400> SEQUENCE: 662
ggtttcccat cctaccacat                                               20

<210> SEQ ID NO 663
<211> LENGTH: 20
<212> TYPE: DNA
<213> ORGANISM: Homo sapiens

<400> SEQUENCE: 663
ttagttttgg catgtggtgg                                               20

<210> SEQ ID NO 664
<211> LENGTH: 20
<212> TYPE: DNA
<213> ORGANISM: Homo sapiens

<400> SEQUENCE: 664
ggtgcttttg ttgccttact                                               20

<210> SEQ ID NO 665
<211> LENGTH: 20
<212> TYPE: DNA
<213> ORGANISM: Homo sapiens

<400> SEQUENCE: 665
tggtgaggga gtgttctttt                                               20

<210> SEQ ID NO 666
<211> LENGTH: 20
<212> TYPE: DNA
```

<213> ORGANISM: Homo sapiens

<400> SEQUENCE: 666
actagaaagc agggtacagt                                          20

<210> SEQ ID NO 667
<211> LENGTH: 20
<212> TYPE: DNA
<213> ORGANISM: Homo sapiens

<400> SEQUENCE: 667
tcattggggg agtcattcac                                          20

<210> SEQ ID NO 668
<211> LENGTH: 20
<212> TYPE: DNA
<213> ORGANISM: Homo sapiens

<400> SEQUENCE: 668
gcttttccca acttctgctg                                          20

<210> SEQ ID NO 669
<211> LENGTH: 20
<212> TYPE: DNA
<213> ORGANISM: Homo sapiens

<400> SEQUENCE: 669
gaagtggtgt gatgagggtg                                          20

<210> SEQ ID NO 670
<211> LENGTH: 20
<212> TYPE: DNA
<213> ORGANISM: Homo sapiens

<400> SEQUENCE: 670
caacagacaa gtcacctcct                                          20

<210> SEQ ID NO 671
<211> LENGTH: 20
<212> TYPE: DNA
<213> ORGANISM: Homo sapiens

<400> SEQUENCE: 671
aagttaggcc ctgttaagca                                          20

<210> SEQ ID NO 672
<211> LENGTH: 20
<212> TYPE: DNA
<213> ORGANISM: Homo sapiens

<400> SEQUENCE: 672
ggttcttcct ggacttcaaa                                          20

<210> SEQ ID NO 673
<211> LENGTH: 20
<212> TYPE: DNA
<213> ORGANISM: Homo sapiens

<400> SEQUENCE: 673
tgttggtcgg agtcagaaat                                          20

<210> SEQ ID NO 674
<211> LENGTH: 21

```
<212> TYPE: DNA
<213> ORGANISM: Homo sapiens

<400> SEQUENCE: 674
gaaagcagta gtttcaggtg t                                        21

<210> SEQ ID NO 675
<211> LENGTH: 20
<212> TYPE: DNA
<213> ORGANISM: Homo sapiens

<400> SEQUENCE: 675
gtaaaagagg ttgggatgcc                                          20

<210> SEQ ID NO 676
<211> LENGTH: 20
<212> TYPE: DNA
<213> ORGANISM: Homo sapiens

<400> SEQUENCE: 676
tgaaagactc tgttgccatg                                          20

<210> SEQ ID NO 677
<211> LENGTH: 20
<212> TYPE: DNA
<213> ORGANISM: Homo sapiens

<400> SEQUENCE: 677
cgttggacat ggatcatacc                                          20

<210> SEQ ID NO 678
<211> LENGTH: 20
<212> TYPE: DNA
<213> ORGANISM: Homo sapiens

<400> SEQUENCE: 678
cactacacgc tcagaacaaa                                          20

<210> SEQ ID NO 679
<211> LENGTH: 22
<212> TYPE: DNA
<213> ORGANISM: Homo sapiens

<400> SEQUENCE: 679
tcacaacaag ggaaatagcc ta                                       22

<210> SEQ ID NO 680
<211> LENGTH: 20
<212> TYPE: DNA
<213> ORGANISM: Homo sapiens

<400> SEQUENCE: 680
aaggcaagca ataatgaggc                                          20

<210> SEQ ID NO 681
<211> LENGTH: 20
<212> TYPE: DNA
<213> ORGANISM: Homo sapiens

<400> SEQUENCE: 681
tagtcaggta aacaacgcct                                          20

<210> SEQ ID NO 682
```

```
<211> LENGTH: 21
<212> TYPE: DNA
<213> ORGANISM: Homo sapiens

<400> SEQUENCE: 682
ggacagtctg tgaaaattgc t                                              21

<210> SEQ ID NO 683
<211> LENGTH: 21
<212> TYPE: DNA
<213> ORGANISM: Homo sapiens

<400> SEQUENCE: 683
tctgtttctt gtttggctga g                                              21

<210> SEQ ID NO 684
<211> LENGTH: 20
<212> TYPE: DNA
<213> ORGANISM: Homo sapiens

<400> SEQUENCE: 684
acaaacaacc cttaatgccc                                                20

<210> SEQ ID NO 685
<211> LENGTH: 20
<212> TYPE: DNA
<213> ORGANISM: Homo sapiens

<400> SEQUENCE: 685
acataggtca cacaaagggt                                                20

<210> SEQ ID NO 686
<211> LENGTH: 20
<212> TYPE: DNA
<213> ORGANISM: Homo sapiens

<400> SEQUENCE: 686
tgaaacagtg aatccgcaat                                                20

<210> SEQ ID NO 687
<211> LENGTH: 20
<212> TYPE: DNA
<213> ORGANISM: Homo sapiens

<400> SEQUENCE: 687
gtgtgacact tttctgcctt                                                20

<210> SEQ ID NO 688
<211> LENGTH: 21
<212> TYPE: DNA
<213> ORGANISM: Homo sapiens

<400> SEQUENCE: 688
aagggaaatg tggatgcagt a                                              21

<210> SEQ ID NO 689
<211> LENGTH: 21
<212> TYPE: DNA
<213> ORGANISM: Homo sapiens

<400> SEQUENCE: 689
ctggaaatag aaggcctttg c                                              21
```

```
<210> SEQ ID NO 690
<211> LENGTH: 19
<212> TYPE: DNA
<213> ORGANISM: Homo sapiens

<400> SEQUENCE: 690
ttgaagggaa gcggaaagt                                            19

<210> SEQ ID NO 691
<211> LENGTH: 20
<212> TYPE: DNA
<213> ORGANISM: Homo sapiens

<400> SEQUENCE: 691
tcttggtctg ggaataagcc                                           20

<210> SEQ ID NO 692
<211> LENGTH: 21
<212> TYPE: DNA
<213> ORGANISM: Homo sapiens

<400> SEQUENCE: 692
atttccagct aatgatgctc c                                         21

<210> SEQ ID NO 693
<211> LENGTH: 20
<212> TYPE: DNA
<213> ORGANISM: Homo sapiens

<400> SEQUENCE: 693
tgcccctatg aacaacagaa                                           20

<210> SEQ ID NO 694
<211> LENGTH: 20
<212> TYPE: DNA
<213> ORGANISM: Homo sapiens

<400> SEQUENCE: 694
gctcacttac gcattaacca                                           20

<210> SEQ ID NO 695
<211> LENGTH: 20
<212> TYPE: DNA
<213> ORGANISM: Homo sapiens

<400> SEQUENCE: 695
tgaacgtctt gcttacccac                                           20

<210> SEQ ID NO 696
<211> LENGTH: 20
<212> TYPE: DNA
<213> ORGANISM: Homo sapiens

<400> SEQUENCE: 696
acaggcaaaa ttcagttgga                                           20

<210> SEQ ID NO 697
<211> LENGTH: 19
<212> TYPE: DNA
<213> ORGANISM: Homo sapiens

<400> SEQUENCE: 697
gaaggaaggc agaggtcaa                                            19
```

```
<210> SEQ ID NO 698
<211> LENGTH: 20
<212> TYPE: DNA
<213> ORGANISM: Homo sapiens

<400> SEQUENCE: 698
aggctgaatc acgtcaaaac                                               20

<210> SEQ ID NO 699
<211> LENGTH: 20
<212> TYPE: DNA
<213> ORGANISM: Homo sapiens

<400> SEQUENCE: 699
cttccacaaa gtcctgcaac                                               20

<210> SEQ ID NO 700
<211> LENGTH: 19
<212> TYPE: DNA
<213> ORGANISM: Homo sapiens

<400> SEQUENCE: 700
cctcgttcac atttgacgc                                                19

<210> SEQ ID NO 701
<211> LENGTH: 20
<212> TYPE: DNA
<213> ORGANISM: Homo sapiens

<400> SEQUENCE: 701
atgtgaacca ttgagaggca                                               20

<210> SEQ ID NO 702
<211> LENGTH: 20
<212> TYPE: DNA
<213> ORGANISM: Homo sapiens

<400> SEQUENCE: 702
tgtctgggtt caactgtttg                                               20

<210> SEQ ID NO 703
<211> LENGTH: 20
<212> TYPE: DNA
<213> ORGANISM: Homo sapiens

<400> SEQUENCE: 703
aagagaaact accctggcaa                                               20

<210> SEQ ID NO 704
<211> LENGTH: 20
<212> TYPE: DNA
<213> ORGANISM: Homo sapiens

<400> SEQUENCE: 704
attttgcatg cctgttgaga                                               20

<210> SEQ ID NO 705
<211> LENGTH: 20
<212> TYPE: DNA
<213> ORGANISM: Homo sapiens

<400> SEQUENCE: 705
gcatgtagtt cagttcaggc                                               20
```

<210> SEQ ID NO 706
<211> LENGTH: 20
<212> TYPE: DNA
<213> ORGANISM: Homo sapiens

<400> SEQUENCE: 706
gctctcctca aaacccaagt					20

<210> SEQ ID NO 707
<211> LENGTH: 20
<212> TYPE: DNA
<213> ORGANISM: Homo sapiens

<400> SEQUENCE: 707
atgaaatgta atggggtgcg					20

<210> SEQ ID NO 708
<211> LENGTH: 20
<212> TYPE: DNA
<213> ORGANISM: Homo sapiens

<400> SEQUENCE: 708
cttaatgagg gggcacaaag					20

<210> SEQ ID NO 709
<211> LENGTH: 20
<212> TYPE: DNA
<213> ORGANISM: Homo sapiens

<400> SEQUENCE: 709
ttttggcagt gatgaccttg					20

<210> SEQ ID NO 710
<211> LENGTH: 20
<212> TYPE: DNA
<213> ORGANISM: Homo sapiens

<400> SEQUENCE: 710
ttttcgtcca gtcttccacc					20

<210> SEQ ID NO 711
<211> LENGTH: 20
<212> TYPE: DNA
<213> ORGANISM: Homo sapiens

<400> SEQUENCE: 711
ttcttggctt ttctgaccct					20

<210> SEQ ID NO 712
<211> LENGTH: 20
<212> TYPE: DNA
<213> ORGANISM: Homo sapiens

<400> SEQUENCE: 712
tacaggaccg tcagtgagag					20

<210> SEQ ID NO 713
<211> LENGTH: 21
<212> TYPE: DNA
<213> ORGANISM: Homo sapiens

```
<400> SEQUENCE: 713
ttgagaaaga ccccaacaga a                                             21

<210> SEQ ID NO 714
<211> LENGTH: 20
<212> TYPE: DNA
<213> ORGANISM: Homo sapiens

<400> SEQUENCE: 714
ttagctactg acgcttcacc                                               20

<210> SEQ ID NO 715
<211> LENGTH: 22
<212> TYPE: DNA
<213> ORGANISM: Homo sapiens

<400> SEQUENCE: 715
gaaaataaca cagtagggat gc                                            22

<210> SEQ ID NO 716
<211> LENGTH: 20
<212> TYPE: DNA
<213> ORGANISM: Homo sapiens

<400> SEQUENCE: 716
gcacagacaa catgctagtt                                               20

<210> SEQ ID NO 717
<211> LENGTH: 20
<212> TYPE: DNA
<213> ORGANISM: Homo sapiens

<400> SEQUENCE: 717
gaatggagag gcagttttca                                               20

<210> SEQ ID NO 718
<211> LENGTH: 20
<212> TYPE: DNA
<213> ORGANISM: Homo sapiens

<400> SEQUENCE: 718
ttagtctgtt cactggcaca                                               20

<210> SEQ ID NO 719
<211> LENGTH: 20
<212> TYPE: DNA
<213> ORGANISM: Homo sapiens

<400> SEQUENCE: 719 caccctttc ctgttttgca                                                20

<210> SEQ ID NO 720
<211> LENGTH: 19
<212> TYPE: DNA
<213> ORGANISM: Homo sapiens

<400> SEQUENCE: 720
cttatcagca gggcacagt                                                19

<210> SEQ ID NO 721
<211> LENGTH: 21
<212> TYPE: DNA
```

<213> ORGANISM: Homo sapiens

<400> SEQUENCE: 721
agaagaaact tgcagtgttg g                    21

<210> SEQ ID NO 722
<211> LENGTH: 20
<212> TYPE: DNA
<213> ORGANISM: Homo sapiens

<400> SEQUENCE: 722
ttgcatcaaa caaagccaca                      20

<210> SEQ ID NO 723
<211> LENGTH: 21
<212> TYPE: DNA
<213> ORGANISM: Homo sapiens

<400> SEQUENCE: 723
tgcagcatta ttctttctgg g                    21

<210> SEQ ID NO 724
<211> LENGTH: 20
<212> TYPE: DNA
<213> ORGANISM: Homo sapiens

<400> SEQUENCE: 724
gagagacaag tcaccccttc                      20

<210> SEQ ID NO 725
<211> LENGTH: 21
<212> TYPE: DNA
<213> ORGANISM: Homo sapiens

<400> SEQUENCE: 725
acacacatat tagggaacag c                    21

<210> SEQ ID NO 726
<211> LENGTH: 20
<212> TYPE: DNA
<213> ORGANISM: Homo sapiens

<400> SEQUENCE: 726
agtcaactac aaatggggga                      20

<210> SEQ ID NO 727
<211> LENGTH: 20
<212> TYPE: DNA
<213> ORGANISM: Homo sapiens

<400> SEQUENCE: 727
gagtgtaggt gcttgggtat                      20

<210> SEQ ID NO 728
<211> LENGTH: 20
<212> TYPE: DNA
<213> ORGANISM: Homo sapiens

<400> SEQUENCE: 728
gtgccaaaat caacgaaagc                      20

<210> SEQ ID NO 729
<211> LENGTH: 20

```
<212> TYPE: DNA
<213> ORGANISM: Homo sapiens

<400> SEQUENCE: 729
ccttagaatc ctagcgcctt                                              20

<210> SEQ ID NO 730
<211> LENGTH: 21
<212> TYPE: DNA
<213> ORGANISM: Homo sapiens

<400> SEQUENCE: 730
aaggagggag tacaaagtga g                                            21

<210> SEQ ID NO 731
<211> LENGTH: 20
<212> TYPE: DNA
<213> ORGANISM: Homo sapiens

<400> SEQUENCE: 731
tcatgaggtt gccagtgttt                                              20

<210> SEQ ID NO 732
<211> LENGTH: 20
<212> TYPE: DNA
<213> ORGANISM: Homo sapiens

<400> SEQUENCE: 732
atcacatttt cagcacgagg                                              20

<210> SEQ ID NO 733
<211> LENGTH: 20
<212> TYPE: DNA
<213> ORGANISM: Homo sapiens

<400> SEQUENCE: 733
ccccatacat catcacatgc                                              20

<210> SEQ ID NO 734
<211> LENGTH: 20
<212> TYPE: DNA
<213> ORGANISM: Homo sapiens

<400> SEQUENCE: 734
cagggaggga tgatttggaa                                              20

<210> SEQ ID NO 735
<211> LENGTH: 20
<212> TYPE: DNA
<213> ORGANISM: Homo sapiens

<400> SEQUENCE: 735
gggtaatgct ttcttgggga                                              20

<210> SEQ ID NO 736
<211> LENGTH: 20
<212> TYPE: DNA
<213> ORGANISM: Homo sapiens

<400> SEQUENCE: 736
agaactgaga ggggagcata                                              20

<210> SEQ ID NO 737
```

```
<211> LENGTH: 20
<212> TYPE: DNA
<213> ORGANISM: Homo sapiens

<400> SEQUENCE: 737
agttgagaag ggaaggcaag                                                    20

<210> SEQ ID NO 738
<211> LENGTH: 20
<212> TYPE: DNA
<213> ORGANISM: Homo sapiens

<400> SEQUENCE: 738
cagtcaccaa caaaggcttt                                                    20

<210> SEQ ID NO 739
<211> LENGTH: 21
<212> TYPE: DNA
<213> ORGANISM: Homo sapiens

<400> SEQUENCE: 739
ctcctggtgg cttatttttg a                                                  21

<210> SEQ ID NO 740
<211> LENGTH: 20
<212> TYPE: DNA
<213> ORGANISM: Homo sapiens

<400> SEQUENCE: 740
tccccatctc cctaactcat                                                    20

<210> SEQ ID NO 741
<211> LENGTH: 22
<212> TYPE: DNA
<213> ORGANISM: Homo sapiens

<400> SEQUENCE: 741
tctggatttt ggctactcat ga                                                 22

<210> SEQ ID NO 742
<211> LENGTH: 20
<212> TYPE: DNA
<213> ORGANISM: Homo sapiens

<400> SEQUENCE: 742
tttttctgct gcatccaagg                                                    20

<210> SEQ ID NO 743
<211> LENGTH: 20
<212> TYPE: DNA
<213> ORGANISM: Homo sapiens

<400> SEQUENCE: 743
gtagtcctcc tttgcccttc                                                    20

<210> SEQ ID NO 744
<211> LENGTH: 20
<212> TYPE: DNA
<213> ORGANISM: Homo sapiens

<400> SEQUENCE: 744
actgtacgcc atgaaaaaca                                                    20
```

```
<210> SEQ ID NO 745
<211> LENGTH: 20
<212> TYPE: DNA
<213> ORGANISM: Homo sapiens

<400> SEQUENCE: 745
gacatgcaca gatcgaaacc                                             20

<210> SEQ ID NO 746
<211> LENGTH: 20
<212> TYPE: DNA
<213> ORGANISM: Homo sapiens

<400> SEQUENCE: 746
ggcaaatcaa gtgagctgac                                             20

<210> SEQ ID NO 747
<211> LENGTH: 20
<212> TYPE: DNA
<213> ORGANISM: Homo sapiens

<400> SEQUENCE: 747
cgcatttgac aacagggatc                                             20

<210> SEQ ID NO 748
<211> LENGTH: 20
<212> TYPE: DNA
<213> ORGANISM: Homo sapiens

<400> SEQUENCE: 748
cgtgggtgga gaatttcaca                                             20

<210> SEQ ID NO 749
<211> LENGTH: 20
<212> TYPE: DNA
<213> ORGANISM: Homo sapiens

<400> SEQUENCE: 749
aagccacctg ttctctctca                                             20

<210> SEQ ID NO 750
<211> LENGTH: 20
<212> TYPE: DNA
<213> ORGANISM: Homo sapiens

<400> SEQUENCE: 750
acttaggtca gttgcttggt                                             20

<210> SEQ ID NO 751
<211> LENGTH: 20
<212> TYPE: DNA
<213> ORGANISM: Homo sapiens

<400> SEQUENCE: 751
attccaacca ttccgacacc                                             20

<210> SEQ ID NO 752
<211> LENGTH: 20
<212> TYPE: DNA
<213> ORGANISM: Homo sapiens

<400> SEQUENCE: 752
gacttcatca gcacgtactt                                             20
```

```
<210> SEQ ID NO 753
<211> LENGTH: 20
<212> TYPE: DNA
<213> ORGANISM: Homo sapiens

<400> SEQUENCE: 753
aaagaaaatg gtgaacgtgc                                                20

<210> SEQ ID NO 754
<211> LENGTH: 20
<212> TYPE: DNA
<213> ORGANISM: Homo sapiens

<400> SEQUENCE: 754
tgcaggcaaa attagcatgg                                                20

<210> SEQ ID NO 755
<211> LENGTH: 20
<212> TYPE: DNA
<213> ORGANISM: Homo sapiens

<400> SEQUENCE: 755
tgatcagggc tttagaggtc                                                20

<210> SEQ ID NO 756
<211> LENGTH: 20
<212> TYPE: DNA
<213> ORGANISM: Homo sapiens

<400> SEQUENCE: 756
gacttatctg ctttcacccc                                                20

<210> SEQ ID NO 757
<211> LENGTH: 20
<212> TYPE: DNA
<213> ORGANISM: Homo sapiens

<400> SEQUENCE: 757
actccctatt gttctcccct                                                20

<210> SEQ ID NO 758
<211> LENGTH: 20
<212> TYPE: DNA
<213> ORGANISM: Homo sapiens

<400> SEQUENCE: 758
ccccatgaac ctaagaccat                                                20

<210> SEQ ID NO 759
<211> LENGTH: 20
<212> TYPE: DNA
<213> ORGANISM: Homo sapiens

<400> SEQUENCE: 759
ctccttgaca gatgtgaccc                                                20

<210> SEQ ID NO 760
<211> LENGTH: 20
<212> TYPE: DNA
<213> ORGANISM: Homo sapiens

<400> SEQUENCE: 760
tctggacatg tctttgcgta                                                20
```

<210> SEQ ID NO 761
<211> LENGTH: 20
<212> TYPE: DNA
<213> ORGANISM: Homo sapiens

<400> SEQUENCE: 761
ttttggagtc tgagccacaa					20

<210> SEQ ID NO 762
<211> LENGTH: 20
<212> TYPE: DNA
<213> ORGANISM: Homo sapiens

<400> SEQUENCE: 762
ctccaggaca tctcagcaat					20

<210> SEQ ID NO 763
<211> LENGTH: 19
<212> TYPE: DNA
<213> ORGANISM: Homo sapiens

<400> SEQUENCE: 763
ttgaagtccc gttgctgat					19

<210> SEQ ID NO 764
<211> LENGTH: 20
<212> TYPE: DNA
<213> ORGANISM: Homo sapiens

<400> SEQUENCE: 764
cctctcgtgt gggaaatgta					20

<210> SEQ ID NO 765
<211> LENGTH: 20
<212> TYPE: DNA
<213> ORGANISM: Homo sapiens

<400> SEQUENCE: 765
ttggggtcag ttctaacagt					20

<210> SEQ ID NO 766
<211> LENGTH: 20
<212> TYPE: DNA
<213> ORGANISM: Homo sapiens

<400> SEQUENCE: 766
tatctctggc tacctcctgt					20

<210> SEQ ID NO 767
<211> LENGTH: 20
<212> TYPE: DNA
<213> ORGANISM: Homo sapiens

<400> SEQUENCE: 767
ttttcaccac ctcttccctc					20

<210> SEQ ID NO 768
<211> LENGTH: 19
<212> TYPE: DNA
<213> ORGANISM: Homo sapiens

```
<400> SEQUENCE: 768
ccccatccct gtaccaaag                                            19

<210> SEQ ID NO 769
<211> LENGTH: 20
<212> TYPE: DNA
<213> ORGANISM: Homo sapiens

<400> SEQUENCE: 769
acctgaccac aagctttaca                                           20

<210> SEQ ID NO 770
<211> LENGTH: 20
<212> TYPE: DNA
<213> ORGANISM: Homo sapiens

<400> SEQUENCE: 770
ctgcagagat attccatggc                                           20

<210> SEQ ID NO 771
<211> LENGTH: 20
<212> TYPE: DNA
<213> ORGANISM: Homo sapiens

<400> SEQUENCE: 771
cacatattgg cgcacagtac                                           20

<210> SEQ ID NO 772
<211> LENGTH: 20
<212> TYPE: DNA
<213> ORGANISM: Homo sapiens

<400> SEQUENCE: 772
aaagctgggt tcttaggctt                                           20

<210> SEQ ID NO 773
<211> LENGTH: 20
<212> TYPE: DNA
<213> ORGANISM: Homo sapiens

<400> SEQUENCE: 773
gccatgcacc gatgaaaaat                                           20

<210> SEQ ID NO 774
<211> LENGTH: 20
<212> TYPE: DNA
<213> ORGANISM: Homo sapiens

<400> SEQUENCE: 774
gctgttttag gggcacattt                                           20

<210> SEQ ID NO 775
<211> LENGTH: 20
<212> TYPE: DNA
<213> ORGANISM: Homo sapiens

<400> SEQUENCE: 775
ttgtgaggag atttctgggc                                           20

<210> SEQ ID NO 776
<211> LENGTH: 20
<212> TYPE: DNA
```

<213> ORGANISM: Homo sapiens

<400> SEQUENCE: 776
aagaggcaat gtggaggtta                    20

<210> SEQ ID NO 777
<211> LENGTH: 20
<212> TYPE: DNA
<213> ORGANISM: Homo sapiens

<400> SEQUENCE: 777
cacactaaga gcactgggaa                    20

<210> SEQ ID NO 778
<211> LENGTH: 21
<212> TYPE: DNA
<213> ORGANISM: Homo sapiens

<400> SEQUENCE: 778
gcccaaacaa tctgcctttt a                  21

<210> SEQ ID NO 779
<211> LENGTH: 20
<212> TYPE: DNA
<213> ORGANISM: Homo sapiens

<400> SEQUENCE: 779
atgacctagc acatcttccc                    20

<210> SEQ ID NO 780
<211> LENGTH: 20
<212> TYPE: DNA
<213> ORGANISM: Homo sapiens

<400> SEQUENCE: 780
tggcttcaaa taactgggct                    20

<210> SEQ ID NO 781
<211> LENGTH: 20
<212> TYPE: DNA
<213> ORGANISM: Homo sapiens

<400> SEQUENCE: 781
acattttccc cattccatgc                    20

<210> SEQ ID NO 782
<211> LENGTH: 20
<212> TYPE: DNA
<213> ORGANISM: Homo sapiens

<400> SEQUENCE: 782
agagcacaca gaacagaact                    20

<210> SEQ ID NO 783
<211> LENGTH: 20
<212> TYPE: DNA
<213> ORGANISM: Homo sapiens

<400> SEQUENCE: 783
gtctgtcaac cacactttgc                    20

<210> SEQ ID NO 784
<211> LENGTH: 20

```
<212> TYPE: DNA
<213> ORGANISM: Homo sapiens

<400> SEQUENCE: 784
ctggtggatt tctcgtcaga                                              20

<210> SEQ ID NO 785
<211> LENGTH: 20
<212> TYPE: DNA
<213> ORGANISM: Homo sapiens

<400> SEQUENCE: 785
ctgtctctcc ttttgccaaa                                              20

<210> SEQ ID NO 786
<211> LENGTH: 20
<212> TYPE: DNA
<213> ORGANISM: Homo sapiens

<400> SEQUENCE: 786
taggtgtttg tgtgaggctt                                              20

<210> SEQ ID NO 787
<211> LENGTH: 20
<212> TYPE: DNA
<213> ORGANISM: Homo sapiens

<400> SEQUENCE: 787
agtaacctgc gactctcagt                                              20

<210> SEQ ID NO 788
<211> LENGTH: 20
<212> TYPE: DNA
<213> ORGANISM: Homo sapiens

<400> SEQUENCE: 788
gcctcactgc tcctatcttt                                              20

<210> SEQ ID NO 789
<211> LENGTH: 20
<212> TYPE: DNA
<213> ORGANISM: Homo sapiens

<400> SEQUENCE: 789
tagcatttaa ggagtgggct                                              20

<210> SEQ ID NO 790
<211> LENGTH: 19
<212> TYPE: DNA
<213> ORGANISM: Homo sapiens

<400> SEQUENCE: 790
ctctagcagc tgttcctcc                                               19

<210> SEQ ID NO 791
<211> LENGTH: 20
<212> TYPE: DNA
<213> ORGANISM: Homo sapiens

<400> SEQUENCE: 791
ggcctcctca gtgatttgaa                                              20

<210> SEQ ID NO 792
```

```
<211> LENGTH: 20
<212> TYPE: DNA
<213> ORGANISM: Homo sapiens

<400> SEQUENCE: 792
cgtcgtatct ctggctttgt                                               20

<210> SEQ ID NO 793
<211> LENGTH: 20
<212> TYPE: DNA
<213> ORGANISM: Homo sapiens

<400> SEQUENCE: 793
ctttctttgc ctcccctgta                                               20

<210> SEQ ID NO 794
<211> LENGTH: 20
<212> TYPE: DNA
<213> ORGANISM: Homo sapiens

<400> SEQUENCE: 794
gtccccaacc tcatctttca                                               20

<210> SEQ ID NO 795
<211> LENGTH: 20
<212> TYPE: DNA
<213> ORGANISM: Homo sapiens

<400> SEQUENCE: 795
acttccattt gtgtcaacgg                                               20

<210> SEQ ID NO 796
<211> LENGTH: 20
<212> TYPE: DNA
<213> ORGANISM: Homo sapiens

<400> SEQUENCE: 796
tcttcaaaga tggctgcaaa                                               20

<210> SEQ ID NO 797
<211> LENGTH: 20
<212> TYPE: DNA
<213> ORGANISM: Homo sapiens

<400> SEQUENCE: 797
tcttgctttg ggttagaggg                                               20

<210> SEQ ID NO 798
<211> LENGTH: 21
<212> TYPE: DNA
<213> ORGANISM: Homo sapiens

<400> SEQUENCE: 798
agtataacca gatagccgtg c                                             21

<210> SEQ ID NO 799
<211> LENGTH: 20
<212> TYPE: DNA
<213> ORGANISM: Homo sapiens

<400> SEQUENCE: 799
aaccacacct ccacaagaaa                                               20
```

```
<210> SEQ ID NO 800
<211> LENGTH: 20
<212> TYPE: DNA
<213> ORGANISM: Homo sapiens

<400> SEQUENCE: 800
tgtcctcagg gcaataaagt                                               20

<210> SEQ ID NO 801
<211> LENGTH: 20
<212> TYPE: DNA
<213> ORGANISM: Homo sapiens

<400> SEQUENCE: 801
caagatatga gggaggggaa                                               20

<210> SEQ ID NO 802
<211> LENGTH: 20
<212> TYPE: DNA
<213> ORGANISM: Homo sapiens

<400> SEQUENCE: 802
tttgctgctt gaagtggaac                                               20

<210> SEQ ID NO 803
<211> LENGTH: 20
<212> TYPE: DNA
<213> ORGANISM: Homo sapiens

<400> SEQUENCE: 803
tctaacctgg gcccttctt                                                20

<210> SEQ ID NO 804
<211> LENGTH: 20
<212> TYPE: DNA
<213> ORGANISM: Homo sapiens

<400> SEQUENCE: 804
gctgcaatga cctgatttct                                               20

<210> SEQ ID NO 805
<211> LENGTH: 20
<212> TYPE: DNA
<213> ORGANISM: Homo sapiens

<400> SEQUENCE: 805
tgcccttcca gaactgtaaa                                               20

<210> SEQ ID NO 806
<211> LENGTH: 20
<212> TYPE: DNA
<213> ORGANISM: Homo sapiens

<400> SEQUENCE: 806
tccctctctc ctccaaatga                                               20

<210> SEQ ID NO 807
<211> LENGTH: 20
<212> TYPE: DNA
<213> ORGANISM: Homo sapiens

<400> SEQUENCE: 807
gccaggtcac ttaacaaagc                                               20
```

```
<210> SEQ ID NO 808
<211> LENGTH: 21
<212> TYPE: DNA
<213> ORGANISM: Homo sapiens

<400> SEQUENCE: 808
tgccacagta ggtataggtt g                                               21

<210> SEQ ID NO 809
<211> LENGTH: 19
<212> TYPE: DNA
<213> ORGANISM: Homo sapiens

<400> SEQUENCE: 809
caataaggcg ccaagttcg                                                  19

<210> SEQ ID NO 810
<211> LENGTH: 20
<212> TYPE: DNA
<213> ORGANISM: Homo sapiens

<400> SEQUENCE: 810
ccctcgccct aaagaaacta                                                 20

<210> SEQ ID NO 811
<211> LENGTH: 20
<212> TYPE: DNA
<213> ORGANISM: Homo sapiens

<400> SEQUENCE: 811
gtcatcaggg gagcaaatgt                                                 20

<210> SEQ ID NO 812
<211> LENGTH: 20
<212> TYPE: DNA
<213> ORGANISM: Homo sapiens

<400> SEQUENCE: 812
cccctgaatc cctacctcat                                                 20

<210> SEQ ID NO 813
<211> LENGTH: 21
<212> TYPE: DNA
<213> ORGANISM: Homo sapiens

<400> SEQUENCE: 813
aacatgcaat ccctggaatt c                                               21

<210> SEQ ID NO 814
<211> LENGTH: 21
<212> TYPE: DNA
<213> ORGANISM: Homo sapiens

<400> SEQUENCE: 814
tgttgtacaa gtgagccatt c                                               21

<210> SEQ ID NO 815
<211> LENGTH: 21
<212> TYPE: DNA
<213> ORGANISM: Homo sapiens

<400> SEQUENCE: 815
agttgtttca ggacaggatc t                                               21
```

<210> SEQ ID NO 816
<211> LENGTH: 21
<212> TYPE: DNA
<213> ORGANISM: Homo sapiens

<400> SEQUENCE: 816
accaagcaat caactcactc t                                              21

<210> SEQ ID NO 817
<211> LENGTH: 21
<212> TYPE: DNA
<213> ORGANISM: Homo sapiens

<400> SEQUENCE: 817
tcctcctgcc tttaataagc t                                              21

<210> SEQ ID NO 818
<211> LENGTH: 21
<212> TYPE: DNA
<213> ORGANISM: Homo sapiens

<400> SEQUENCE: 818
gcccaatttg tctagccaat a                                              21

<210> SEQ ID NO 819
<211> LENGTH: 21
<212> TYPE: DNA
<213> ORGANISM: Homo sapiens

<400> SEQUENCE: 819
ttacaaggca tctgacagga a                                              21

<210> SEQ ID NO 820
<211> LENGTH: 21
<212> TYPE: DNA
<213> ORGANISM: Homo sapiens

<400> SEQUENCE: 820
ctactgatcc caaagaaggc a                                              21

<210> SEQ ID NO 821
<211> LENGTH: 21
<212> TYPE: DNA
<213> ORGANISM: Homo sapiens

<400> SEQUENCE: 821
ttactggtag gtttgagcac a                                              21

<210> SEQ ID NO 822
<211> LENGTH: 21
<212> TYPE: DNA
<213> ORGANISM: Homo sapiens

<400> SEQUENCE: 822
gtgaaaggtt ctatctgcca a                                              21

<210> SEQ ID NO 823
<211> LENGTH: 22
<212> TYPE: DNA
<213> ORGANISM: Homo sapiens

<400> SEQUENCE: 823
gagctacgtt ctttctcatc ac                                              22

<210> SEQ ID NO 824
<211> LENGTH: 21
<212> TYPE: DNA
<213> ORGANISM: Homo sapiens

<400> SEQUENCE: 824
ggcataccga gcatacatag a                                               21

<210> SEQ ID NO 825
<211> LENGTH: 21
<212> TYPE: DNA
<213> ORGANISM: Homo sapiens

<400> SEQUENCE: 825
caccaattaa agtgtgctgc a                                               21

<210> SEQ ID NO 826
<211> LENGTH: 21
<212> TYPE: DNA
<213> ORGANISM: Homo sapiens

<400> SEQUENCE: 826
cacctgtttc accaaatcac t                                               21

<210> SEQ ID NO 827
<211> LENGTH: 21
<212> TYPE: DNA
<213> ORGANISM: Homo sapiens

<400> SEQUENCE: 827
tcccttccaa agtgccttat a                                               21

<210> SEQ ID NO 828
<211> LENGTH: 21
<212> TYPE: DNA
<213> ORGANISM: Homo sapiens

<400> SEQUENCE: 828
tctcatgctc tgacagacaa g                                               21

<210> SEQ ID NO 829
<211> LENGTH: 21
<212> TYPE: DNA
<213> ORGANISM: Homo sapiens

<400> SEQUENCE: 829
tggttggttt gggatacttg a                                               21

<210> SEQ ID NO 830
<211> LENGTH: 21
<212> TYPE: DNA
<213> ORGANISM: Homo sapiens

<400> SEQUENCE: 830
ttgtcctgtt tctcttgtga c                                               21

<210> SEQ ID NO 831
<211> LENGTH: 21
<212> TYPE: DNA

-continued

<213> ORGANISM: Homo sapiens

<400> SEQUENCE: 831
gaacccaaat cgatcatgca t				21

<210> SEQ ID NO 832
<211> LENGTH: 21
<212> TYPE: DNA
<213> ORGANISM: Homo sapiens

<400> SEQUENCE: 832
cacaggactg catgcctatt a				21

<210> SEQ ID NO 833
<211> LENGTH: 21
<212> TYPE: DNA
<213> ORGANISM: Homo sapiens

<400> SEQUENCE: 833
agagttaaac gtgcaatgtg g				21

<210> SEQ ID NO 834
<211> LENGTH: 21
<212> TYPE: DNA
<213> ORGANISM: Homo sapiens

<400> SEQUENCE: 834
gactctctca gcatcgagtt t				21

<210> SEQ ID NO 835
<211> LENGTH: 22
<212> TYPE: DNA
<213> ORGANISM: Homo sapiens

<400> SEQUENCE: 835
gttcgttggt catagttgtt gt			22

<210> SEQ ID NO 836
<211> LENGTH: 21
<212> TYPE: DNA
<213> ORGANISM: Homo sapiens

<400> SEQUENCE: 836
ctgatggaag ggcattatcc a				21

<210> SEQ ID NO 837
<211> LENGTH: 21
<212> TYPE: DNA
<213> ORGANISM: Homo sapiens

<400> SEQUENCE: 837
agtttagcca aaggattcag c				21

<210> SEQ ID NO 838
<211> LENGTH: 22
<212> TYPE: DNA
<213> ORGANISM: Homo sapiens

<400> SEQUENCE: 838
ttctggttcc ataaatccat gc			22

<210> SEQ ID NO 839
<211> LENGTH: 22

<212> TYPE: DNA
<213> ORGANISM: Homo sapiens

<400> SEQUENCE: 839
tcaaccattt agaaccacct tg                                              22

<210> SEQ ID NO 840
<211> LENGTH: 22
<212> TYPE: DNA
<213> ORGANISM: Homo sapiens

<400> SEQUENCE: 840
gggattattg ttggctactg ag                                              22

<210> SEQ ID NO 841
<211> LENGTH: 21
<212> TYPE: DNA
<213> ORGANISM: Homo sapiens

<400> SEQUENCE: 841
aatgtccact ttagcggaga g                                               21

<210> SEQ ID NO 842
<211> LENGTH: 21
<212> TYPE: DNA
<213> ORGANISM: Homo sapiens

<400> SEQUENCE: 842
aattggtgac ctagggatca g                                               21

<210> SEQ ID NO 843
<211> LENGTH: 22
<212> TYPE: DNA
<213> ORGANISM: Homo sapiens

<400> SEQUENCE: 843
ggagtattct gttcatgttg gg                                              22

<210> SEQ ID NO 844
<211> LENGTH: 21
<212> TYPE: DNA
<213> ORGANISM: Homo sapiens

<400> SEQUENCE: 844
gggtttggta agggagaatg a                                               21

<210> SEQ ID NO 845
<211> LENGTH: 22
<212> TYPE: DNA
<213> ORGANISM: Homo sapiens

<400> SEQUENCE: 845
tttctagaat tgaggaaggg ca                                              22

<210> SEQ ID NO 846
<211> LENGTH: 23
<212> TYPE: DNA
<213> ORGANISM: Homo sapiens

<400> SEQUENCE: 846
aagacatccc agttatgcat tgt                                             23

<210> SEQ ID NO 847

```
<211> LENGTH: 21
<212> TYPE: DNA
<213> ORGANISM: Homo sapiens

<400> SEQUENCE: 847
aggataagac gaggcatcaa t                                              21

<210> SEQ ID NO 848
<211> LENGTH: 21
<212> TYPE: DNA
<213> ORGANISM: Homo sapiens

<400> SEQUENCE: 848
agatgggagg gagattagac a                                              21

<210> SEQ ID NO 849
<211> LENGTH: 22
<212> TYPE: DNA
<213> ORGANISM: Homo sapiens

<400> SEQUENCE: 849
ttctgtgttg acatgtacct ct                                             22

<210> SEQ ID NO 850
<211> LENGTH: 21
<212> TYPE: DNA
<213> ORGANISM: Homo sapiens

<400> SEQUENCE: 850
gagtagcaac aacacatgga g                                              21

<210> SEQ ID NO 851
<211> LENGTH: 21
<212> TYPE: DNA
<213> ORGANISM: Homo sapiens

<400> SEQUENCE: 851
tccaacattt ctctctgtcc c                                              21

<210> SEQ ID NO 852
<211> LENGTH: 21
<212> TYPE: DNA
<213> ORGANISM: Homo sapiens

<400> SEQUENCE: 852
ttctccttca ttagccacac a                                              21

<210> SEQ ID NO 853
<211> LENGTH: 20
<212> TYPE: DNA
<213> ORGANISM: Homo sapiens

<400> SEQUENCE: 853
ataacgtgta ctcctcagcc                                                20

<210> SEQ ID NO 854
<211> LENGTH: 21
<212> TYPE: DNA
<213> ORGANISM: Homo sapiens

<400> SEQUENCE: 854
agtctgcact gtactcttct g                                              21
```

```
<210> SEQ ID NO 855
<211> LENGTH: 21
<212> TYPE: DNA
<213> ORGANISM: Homo sapiens

<400> SEQUENCE: 855
gcacttggag gatgtaaaga c                                              21

<210> SEQ ID NO 856
<211> LENGTH: 21
<212> TYPE: DNA
<213> ORGANISM: Homo sapiens

<400> SEQUENCE: 856
acaaatggtt catgatggtg g                                              21

<210> SEQ ID NO 857
<211> LENGTH: 21
<212> TYPE: DNA
<213> ORGANISM: Homo sapiens

<400> SEQUENCE: 857
tgtatgcttt aggacccagt t                                              21

<210> SEQ ID NO 858
<211> LENGTH: 21
<212> TYPE: DNA
<213> ORGANISM: Homo sapiens

<400> SEQUENCE: 858
ggtactcacg tttcagtttc c                                              21

<210> SEQ ID NO 859
<211> LENGTH: 22
<212> TYPE: DNA
<213> ORGANISM: Homo sapiens

<400> SEQUENCE: 859
aactccacag gaatctttct ga                                             22

<210> SEQ ID NO 860
<211> LENGTH: 21
<212> TYPE: DNA
<213> ORGANISM: Homo sapiens

<400> SEQUENCE: 860
gttcatttct acagtccagg c                                              21

<210> SEQ ID NO 861
<211> LENGTH: 20
<212> TYPE: DNA
<213> ORGANISM: Homo sapiens

<400> SEQUENCE: 861
catttctcct gggaccgaat                                                20

<210> SEQ ID NO 862
<211> LENGTH: 21
<212> TYPE: DNA
<213> ORGANISM: Homo sapiens

<400> SEQUENCE: 862
ctctcactgt gctgcttaaa g                                              21
```

<210> SEQ ID NO 863
<211> LENGTH: 21
<212> TYPE: DNA
<213> ORGANISM: Homo sapiens

<400> SEQUENCE: 863
ttctgaagct gacgaaattc c                                             21

<210> SEQ ID NO 864
<211> LENGTH: 22
<212> TYPE: DNA
<213> ORGANISM: Homo sapiens

<400> SEQUENCE: 864
caaagaattc cacagagatg gg                                            22

<210> SEQ ID NO 865
<211> LENGTH: 21
<212> TYPE: DNA
<213> ORGANISM: Homo sapiens

<400> SEQUENCE: 865
gttgcttagt ccttgcttca c                                             21

<210> SEQ ID NO 866
<211> LENGTH: 21
<212> TYPE: DNA
<213> ORGANISM: Homo sapiens

<400> SEQUENCE: 866
tgagctacag acaagattgc a                                             21

<210> SEQ ID NO 867
<211> LENGTH: 21
<212> TYPE: DNA
<213> ORGANISM: Homo sapiens

<400> SEQUENCE: 867
aggtcattgg tctgcagtta t                                             21

<210> SEQ ID NO 868
<211> LENGTH: 21
<212> TYPE: DNA
<213> ORGANISM: Homo sapiens

<400> SEQUENCE: 868
tcacatggga tcgacatatg c                                             21

<210> SEQ ID NO 869
<211> LENGTH: 21
<212> TYPE: DNA
<213> ORGANISM: Homo sapiens

<400> SEQUENCE: 869
agcatttaga gaacagcagt c                                             21

<210> SEQ ID NO 870
<211> LENGTH: 21
<212> TYPE: DNA
<213> ORGANISM: Homo sapiens

<400> SEQUENCE: 870
ccacacaatt tcctggctat g                                             21

<210> SEQ ID NO 871
<211> LENGTH: 21
<212> TYPE: DNA
<213> ORGANISM: Homo sapiens

<400> SEQUENCE: 871
gtgtaagaag tggttgggtt t                                           21

<210> SEQ ID NO 872
<211> LENGTH: 21
<212> TYPE: DNA
<213> ORGANISM: Homo sapiens

<400> SEQUENCE: 872
tcttgcttct ggagagttct t                                           21

<210> SEQ ID NO 873
<211> LENGTH: 22
<212> TYPE: DNA
<213> ORGANISM: Homo sapiens

<400> SEQUENCE: 873
aaaggcagag cagtgtattt ag                                          22

<210> SEQ ID NO 874
<211> LENGTH: 21
<212> TYPE: DNA
<213> ORGANISM: Homo sapiens

<400> SEQUENCE: 874
aggttatgca gacttcagga a                                           21

<210> SEQ ID NO 875
<211> LENGTH: 22
<212> TYPE: DNA
<213> ORGANISM: Homo sapiens

<400> SEQUENCE: 875
agacaagaga acaatcaggt ga                                          22

<210> SEQ ID NO 876
<211> LENGTH: 21
<212> TYPE: DNA
<213> ORGANISM: Homo sapiens

<400> SEQUENCE: 876
aagccaattc tgcctctcta g                                           21

<210> SEQ ID NO 877
<211> LENGTH: 21
<212> TYPE: DNA
<213> ORGANISM: Homo sapiens

<400> SEQUENCE: 877
caaagaagct ctaggacagg a                                           21

<210> SEQ ID NO 878
<211> LENGTH: 21
<212> TYPE: DNA
<213> ORGANISM: Homo sapiens

```
<400> SEQUENCE: 878
tcccttcctt attctggcaa c                                              21

<210> SEQ ID NO 879
<211> LENGTH: 21
<212> TYPE: DNA
<213> ORGANISM: Homo sapiens

<400> SEQUENCE: 879
tggtggagga aatcaatgtt g                                              21

<210> SEQ ID NO 880
<211> LENGTH: 21
<212> TYPE: DNA
<213> ORGANISM: Homo sapiens

<400> SEQUENCE: 880
gcttcaaaca ctctaaaggg c                                              21

<210> SEQ ID NO 881
<211> LENGTH: 20
<212> TYPE: DNA
<213> ORGANISM: Homo sapiens

<400> SEQUENCE: 881
cacaagggag gaaacgttct                                                20

<210> SEQ ID NO 882
<211> LENGTH: 21
<212> TYPE: DNA
<213> ORGANISM: Homo sapiens

<400> SEQUENCE: 882
tgccattaat gagaagtgct g                                              21

<210> SEQ ID NO 883
<211> LENGTH: 21
<212> TYPE: DNA
<213> ORGANISM: Homo sapiens

<400> SEQUENCE: 883
tgagatttag tgccagctag a                                              21

<210> SEQ ID NO 884
<211> LENGTH: 22
<212> TYPE: DNA
<213> ORGANISM: Homo sapiens

<400> SEQUENCE: 884
tggcaatcct gttaaacaac tc                                             22

<210> SEQ ID NO 885
<211> LENGTH: 21
<212> TYPE: DNA
<213> ORGANISM: Homo sapiens

<400> SEQUENCE: 885
aggattagtt tggctcctca g                                              21

<210> SEQ ID NO 886
<211> LENGTH: 22
<212> TYPE: DNA
```

```
<213> ORGANISM: Homo sapiens

<400> SEQUENCE: 886
cccgaacatt gataacagaa ga                                              22

<210> SEQ ID NO 887
<211> LENGTH: 21
<212> TYPE: DNA
<213> ORGANISM: Homo sapiens

<400> SEQUENCE: 887
cctgcactat ttcctcaaag c                                               21

<210> SEQ ID NO 888
<211> LENGTH: 22
<212> TYPE: DNA
<213> ORGANISM: Homo sapiens

<400> SEQUENCE: 888
gcaactcagg aaagactaca tc                                              22

<210> SEQ ID NO 889
<211> LENGTH: 21
<212> TYPE: DNA
<213> ORGANISM: Homo sapiens

<400> SEQUENCE: 889
caatttcctt ctcactgagc c                                               21

<210> SEQ ID NO 890
<211> LENGTH: 22
<212> TYPE: DNA
<213> ORGANISM: Homo sapiens

<400> SEQUENCE: 890
ttaagaaagt acccatcctc cc                                              22

<210> SEQ ID NO 891
<211> LENGTH: 21
<212> TYPE: DNA
<213> ORGANISM: Homo sapiens

<400> SEQUENCE: 891
acgcttccca aatctatctg g                                               21

<210> SEQ ID NO 892
<211> LENGTH: 21
<212> TYPE: DNA
<213> ORGANISM: Homo sapiens

<400> SEQUENCE: 892
gtcatgcctt acaacttagc a                                               21

<210> SEQ ID NO 893
<211> LENGTH: 22
<212> TYPE: DNA
<213> ORGANISM: Homo sapiens

<400> SEQUENCE: 893
cttatttgtg tgcccaatac ca                                              22

<210> SEQ ID NO 894
<211> LENGTH: 21
```

```
<212> TYPE: DNA
<213> ORGANISM: Homo sapiens

<400> SEQUENCE: 894
aatctttgcc aaggtatgag c                                              21

<210> SEQ ID NO 895
<211> LENGTH: 21
<212> TYPE: DNA
<213> ORGANISM: Homo sapiens

<400> SEQUENCE: 895
ttgcagcagg aacaccataa a                                              21

<210> SEQ ID NO 896
<211> LENGTH: 21
<212> TYPE: DNA
<213> ORGANISM: Homo sapiens

<400> SEQUENCE: 896
gccacttata cctccagaca t                                              21

<210> SEQ ID NO 897
<211> LENGTH: 21
<212> TYPE: DNA
<213> ORGANISM: Homo sapiens

<400> SEQUENCE: 897
ctgttcatgt tgctaccaca g                                              21

<210> SEQ ID NO 898
<211> LENGTH: 20
<212> TYPE: DNA
<213> ORGANISM: Homo sapiens

<400> SEQUENCE: 898
ccacaatcct gaatgccatg                                                20

<210> SEQ ID NO 899
<211> LENGTH: 21
<212> TYPE: DNA
<213> ORGANISM: Homo sapiens

<400> SEQUENCE: 899
ctgccttaga ttcactttcg g                                              21

<210> SEQ ID NO 900
<211> LENGTH: 21
<212> TYPE: DNA
<213> ORGANISM: Homo sapiens

<400> SEQUENCE: 900
ctgcaaggta caacacaagt c                                              21

<210> SEQ ID NO 901
<211> LENGTH: 21
<212> TYPE: DNA
<213> ORGANISM: Homo sapiens

<400> SEQUENCE: 901
ccatctgtga ggtcttcttt g                                              21

<210> SEQ ID NO 902
```

```
<211> LENGTH: 21
<212> TYPE: DNA
<213> ORGANISM: Homo sapiens

<400> SEQUENCE: 902
atctctgtgc cagcaagtat t                                              21

<210> SEQ ID NO 903
<211> LENGTH: 21
<212> TYPE: DNA
<213> ORGANISM: Homo sapiens

<400> SEQUENCE: 903
tccttggttg tgtatttagc c                                              21

<210> SEQ ID NO 904
<211> LENGTH: 21
<212> TYPE: DNA
<213> ORGANISM: Homo sapiens

<400> SEQUENCE: 904
attgggaaac tgtcactgat g                                              21

<210> SEQ ID NO 905
<211> LENGTH: 20
<212> TYPE: DNA
<213> ORGANISM: Homo sapiens

<400> SEQUENCE: 905
agactcaact cacattggcc                                                20

<210> SEQ ID NO 906
<211> LENGTH: 21
<212> TYPE: DNA
<213> ORGANISM: Homo sapiens

<400> SEQUENCE: 906
gccctaatag agaagcaaag c                                              21

<210> SEQ ID NO 907
<211> LENGTH: 20
<212> TYPE: DNA
<213> ORGANISM: Homo sapiens

<400> SEQUENCE: 907
ggtctgactc tgtggtttgg                                                20

<210> SEQ ID NO 908
<211> LENGTH: 21
<212> TYPE: DNA
<213> ORGANISM: Homo sapiens

<400> SEQUENCE: 908
gggagccaat cagatagaag t                                              21

<210> SEQ ID NO 909
<211> LENGTH: 21
<212> TYPE: DNA
<213> ORGANISM: Homo sapiens

<400> SEQUENCE: 909
tttcatttca tcctgcccat g                                              21
```

```
<210> SEQ ID NO 910
<211> LENGTH: 22
<212> TYPE: DNA
<213> ORGANISM: Homo sapiens

<400> SEQUENCE: 910
gggaagttgg gctatttaat gc                                              22

<210> SEQ ID NO 911
<211> LENGTH: 21
<212> TYPE: DNA
<213> ORGANISM: Homo sapiens

<400> SEQUENCE: 911
ttctgttatt cgccatcagt c                                               21

<210> SEQ ID NO 912
<211> LENGTH: 21
<212> TYPE: DNA
<213> ORGANISM: Homo sapiens

<400> SEQUENCE: 912
aactgtgtag agcgaccaaa t                                               21

<210> SEQ ID NO 913
<211> LENGTH: 20
<212> TYPE: DNA
<213> ORGANISM: Homo sapiens

<400> SEQUENCE: 913
gaattgggaa cttgggaagc                                                 20

<210> SEQ ID NO 914
<211> LENGTH: 21
<212> TYPE: DNA
<213> ORGANISM: Homo sapiens

<400> SEQUENCE: 914
cagtaaggcc atggtctaga t                                               21

<210> SEQ ID NO 915
<211> LENGTH: 21
<212> TYPE: DNA
<213> ORGANISM: Homo sapiens

<400> SEQUENCE: 915
gaactttgga gaggacagtg t                                               21

<210> SEQ ID NO 916
<211> LENGTH: 21
<212> TYPE: DNA
<213> ORGANISM: Homo sapiens

<400> SEQUENCE: 916
ctcagaacat ttgcaccttc t                                               21

<210> SEQ ID NO 917
<211> LENGTH: 21
<212> TYPE: DNA
<213> ORGANISM: Homo sapiens

<400> SEQUENCE: 917
aactgtcatg tgtgtctgct a                                               21
```

<210> SEQ ID NO 918
<211> LENGTH: 21
<212> TYPE: DNA
<213> ORGANISM: Homo sapiens

<400> SEQUENCE: 918
acctgataca atggagcatg t                                                    21

<210> SEQ ID NO 919
<211> LENGTH: 21
<212> TYPE: DNA
<213> ORGANISM: Homo sapiens

<400> SEQUENCE: 919
tgattccttc cacctaccaa a                                                    21

<210> SEQ ID NO 920
<211> LENGTH: 21
<212> TYPE: DNA
<213> ORGANISM: Homo sapiens

<400> SEQUENCE: 920
gggacctaaa ctcctttgga a                                                    21

<210> SEQ ID NO 921
<211> LENGTH: 21
<212> TYPE: DNA
<213> ORGANISM: Homo sapiens

<400> SEQUENCE: 921
gccaaggtcc attatctcaa g                                                    21

<210> SEQ ID NO 922
<211> LENGTH: 21
<212> TYPE: DNA
<213> ORGANISM: Homo sapiens

<400> SEQUENCE: 922
tctgcagtgg tgttatctag t                                                    21

<210> SEQ ID NO 923
<211> LENGTH: 21
<212> TYPE: DNA
<213> ORGANISM: Homo sapiens

<400> SEQUENCE: 923
gaacctgcat tgtcattctc t                                                    21

<210> SEQ ID NO 924
<211> LENGTH: 20
<212> TYPE: DNA
<213> ORGANISM: Homo sapiens

<400> SEQUENCE: 924
cacttaagtt tccacgccag                                                      20

<210> SEQ ID NO 925
<211> LENGTH: 22
<212> TYPE: DNA
<213> ORGANISM: Homo sapiens

<400> SEQUENCE: 925
aagaacatca acaaactcca gg                                                   22

<210> SEQ ID NO 926
<211> LENGTH: 21
<212> TYPE: DNA
<213> ORGANISM: Homo sapiens

<400> SEQUENCE: 926
gtaatggcga gaggttaaag c                                              21

<210> SEQ ID NO 927
<211> LENGTH: 21
<212> TYPE: DNA
<213> ORGANISM: Homo sapiens

<400> SEQUENCE: 927
tcaattctct ttcacacgtg c                                              21

<210> SEQ ID NO 928
<211> LENGTH: 22
<212> TYPE: DNA
<213> ORGANISM: Homo sapiens

<400> SEQUENCE: 928
tttaggtatc gaagttgggt ca                                             22

<210> SEQ ID NO 929
<211> LENGTH: 21
<212> TYPE: DNA
<213> ORGANISM: Homo sapiens

<400> SEQUENCE: 929
aggtgctgga tcttgaattc a                                              21

<210> SEQ ID NO 930
<211> LENGTH: 22
<212> TYPE: DNA
<213> ORGANISM: Homo sapiens

<400> SEQUENCE: 930
gataagtttg gaagctgcat ca                                             22

<210> SEQ ID NO 931
<211> LENGTH: 21
<212> TYPE: DNA
<213> ORGANISM: Homo sapiens

<400> SEQUENCE: 931
tccctctacc cgaatctctt a                                              21

<210> SEQ ID NO 932
<211> LENGTH: 21
<212> TYPE: DNA
<213> ORGANISM: Homo sapiens

<400> SEQUENCE: 932
aagctctgcc attgactttat c                                             21

<210> SEQ ID NO 933
<211> LENGTH: 21
<212> TYPE: DNA
<213> ORGANISM: Homo sapiens

<400> SEQUENCE: 933
tgggtttaaa ggacactagc a                                              21

<210> SEQ ID NO 934
<211> LENGTH: 20
<212> TYPE: DNA
<213> ORGANISM: Homo sapiens

<400> SEQUENCE: 934
ccctacagaa ccgaggaatc                                                20

<210> SEQ ID NO 935
<211> LENGTH: 21
<212> TYPE: DNA
<213> ORGANISM: Homo sapiens

<400> SEQUENCE: 935
cgaaggtcac acagtttagt c                                              21

<210> SEQ ID NO 936
<211> LENGTH: 21
<212> TYPE: DNA
<213> ORGANISM: Homo sapiens

<400> SEQUENCE: 936
tcaatctttg catacacagc c                                              21

<210> SEQ ID NO 937
<211> LENGTH: 21
<212> TYPE: DNA
<213> ORGANISM: Homo sapiens

<400> SEQUENCE: 937
atgtgccttg ttgattgatg g                                              21

<210> SEQ ID NO 938
<211> LENGTH: 22
<212> TYPE: DNA
<213> ORGANISM: Homo sapiens

<400> SEQUENCE: 938
gtaggtttac atggacagat gc                                             22

<210> SEQ ID NO 939
<211> LENGTH: 21
<212> TYPE: DNA
<213> ORGANISM: Homo sapiens

<400> SEQUENCE: 939
agatggtatg tcacaaagca c                                              21

<210> SEQ ID NO 940
<211> LENGTH: 21
<212> TYPE: DNA
<213> ORGANISM: Homo sapiens

<400> SEQUENCE: 940
tcttctgttt agtgctgtgg t                                              21

<210> SEQ ID NO 941
<211> LENGTH: 21
<212> TYPE: DNA

<213> ORGANISM: Homo sapiens

<400> SEQUENCE: 941
acactttgga gagcttcaga t                                      21

<210> SEQ ID NO 942
<211> LENGTH: 21
<212> TYPE: DNA
<213> ORGANISM: Homo sapiens

<400> SEQUENCE: 942
caagttcatt tcttccctgc a                                      21

<210> SEQ ID NO 943
<211> LENGTH: 22
<212> TYPE: DNA
<213> ORGANISM: Homo sapiens

<400> SEQUENCE: 943
gtgcccagaa ttatttgtgt ct                                     22

<210> SEQ ID NO 944
<211> LENGTH: 21
<212> TYPE: DNA
<213> ORGANISM: Homo sapiens

<400> SEQUENCE: 944
tgcaggaata catggtagac a                                      21

<210> SEQ ID NO 945
<211> LENGTH: 21
<212> TYPE: DNA
<213> ORGANISM: Homo sapiens

<400> SEQUENCE: 945
gctctcttgt ggaaacgatt a                                      21

<210> SEQ ID NO 946
<211> LENGTH: 21
<212> TYPE: DNA
<213> ORGANISM: Homo sapiens

<400> SEQUENCE: 946
cataggcctt catgtctctc a                                      21

<210> SEQ ID NO 947
<211> LENGTH: 21
<212> TYPE: DNA
<213> ORGANISM: Homo sapiens

<400> SEQUENCE: 947
agtttgtttc tctggcctac t                                      21

<210> SEQ ID NO 948
<211> LENGTH: 21
<212> TYPE: DNA
<213> ORGANISM: Homo sapiens

<400> SEQUENCE: 948
tatgagggtg cactaacaga t                                      21

<210> SEQ ID NO 949
<211> LENGTH: 21

```
<212> TYPE: DNA
<213> ORGANISM: Homo sapiens

<400> SEQUENCE: 949
accacctcaa agatttcatg g                                              21

<210> SEQ ID NO 950
<211> LENGTH: 21
<212> TYPE: DNA
<213> ORGANISM: Homo sapiens

<400> SEQUENCE: 950
ggtgctacta ctggtgtatg t                                              21

<210> SEQ ID NO 951
<211> LENGTH: 22
<212> TYPE: DNA
<213> ORGANISM: Homo sapiens

<400> SEQUENCE: 951
gtcttcatct atttcgtgag cc                                             22

<210> SEQ ID NO 952
<211> LENGTH: 21
<212> TYPE: DNA
<213> ORGANISM: Homo sapiens

<400> SEQUENCE: 952
gccatgcaat atcaaatccc a                                              21

<210> SEQ ID NO 953
<211> LENGTH: 21
<212> TYPE: DNA
<213> ORGANISM: Homo sapiens

<400> SEQUENCE: 953
tcatcccaga ttcagaatgc c                                              21

<210> SEQ ID NO 954
<211> LENGTH: 21
<212> TYPE: DNA
<213> ORGANISM: Homo sapiens

<400> SEQUENCE: 954
gaaaccaaag actagtgcag c                                              21

<210> SEQ ID NO 955
<211> LENGTH: 21
<212> TYPE: DNA
<213> ORGANISM: Homo sapiens

<400> SEQUENCE: 955
cgttcaatga agtcccttgt c                                              21

<210> SEQ ID NO 956
<211> LENGTH: 21
<212> TYPE: DNA
<213> ORGANISM: Homo sapiens

<400> SEQUENCE: 956
atgactaaca ctctgccaag t                                              21

<210> SEQ ID NO 957
```

```
<211> LENGTH: 21
<212> TYPE: DNA
<213> ORGANISM: Homo sapiens

<400> SEQUENCE: 957
ttcacaagaa ctctgctgga t                                              21

<210> SEQ ID NO 958
<211> LENGTH: 21
<212> TYPE: DNA
<213> ORGANISM: Homo sapiens

<400> SEQUENCE: 958
aacaaatgca tcccagacag a                                              21

<210> SEQ ID NO 959
<211> LENGTH: 21
<212> TYPE: DNA
<213> ORGANISM: Homo sapiens

<400> SEQUENCE: 959
gaagccttct agtgggacta a                                              21

<210> SEQ ID NO 960
<211> LENGTH: 21
<212> TYPE: DNA
<213> ORGANISM: Homo sapiens

<400> SEQUENCE: 960
gcagagagga gtatgtggta t                                              21

<210> SEQ ID NO 961
<211> LENGTH: 21
<212> TYPE: DNA
<213> ORGANISM: Homo sapiens

<400> SEQUENCE: 961
gttagggtca tgggtcactt t                                              21

<210> SEQ ID NO 962
<211> LENGTH: 21
<212> TYPE: DNA
<213> ORGANISM: Homo sapiens

<400> SEQUENCE: 962
atgggtcatt ctacgaagca a                                              21

<210> SEQ ID NO 963
<211> LENGTH: 21
<212> TYPE: DNA
<213> ORGANISM: Homo sapiens

<400> SEQUENCE: 963
gcctttgtag agtggacttc t                                              21

<210> SEQ ID NO 964
<211> LENGTH: 22
<212> TYPE: DNA
<213> ORGANISM: Homo sapiens

<400> SEQUENCE: 964
tggtgtgtgt ggtgataatt ag                                             22
```

```
<210> SEQ ID NO 965
<211> LENGTH: 21
<212> TYPE: DNA
<213> ORGANISM: Homo sapiens

<400> SEQUENCE: 965
ggcttcttga tactgctttc c                                              21

<210> SEQ ID NO 966
<211> LENGTH: 21
<212> TYPE: DNA
<213> ORGANISM: Homo sapiens

<400> SEQUENCE: 966
agtgaccctc tgaataacct g                                              21

<210> SEQ ID NO 967
<211> LENGTH: 21
<212> TYPE: DNA
<213> ORGANISM: Homo sapiens

<400> SEQUENCE: 967
aggtgtgcaa tactcaagga a                                              21

<210> SEQ ID NO 968
<211> LENGTH: 21
<212> TYPE: DNA
<213> ORGANISM: Homo sapiens

<400> SEQUENCE: 968
tcagcaagta aacctgagac c                                              21

<210> SEQ ID NO 969
<211> LENGTH: 21
<212> TYPE: DNA
<213> ORGANISM: Homo sapiens

<400> SEQUENCE: 969
aaggtcttag gagtgaggac a                                              21

<210> SEQ ID NO 970
<211> LENGTH: 20
<212> TYPE: DNA
<213> ORGANISM: Homo sapiens

<400> SEQUENCE: 970
gtaccttcac cctccagatc                                                20

<210> SEQ ID NO 971
<211> LENGTH: 22
<212> TYPE: DNA
<213> ORGANISM: Homo sapiens

<400> SEQUENCE: 971
tcgtgctatt tcagtcagat ct                                             22

<210> SEQ ID NO 972
<211> LENGTH: 21
<212> TYPE: DNA
<213> ORGANISM: Homo sapiens

<400> SEQUENCE: 972
tcatcaaatt gcccactcct a                                              21
```

```
<210> SEQ ID NO 973
<211> LENGTH: 21
<212> TYPE: DNA
<213> ORGANISM: Homo sapiens

<400> SEQUENCE: 973
tgtccagccg taacatttca t                                              21

<210> SEQ ID NO 974
<211> LENGTH: 21
<212> TYPE: DNA
<213> ORGANISM: Homo sapiens

<400> SEQUENCE: 974
catcagactg tcttgccttt c                                              21

<210> SEQ ID NO 975
<211> LENGTH: 21
<212> TYPE: DNA
<213> ORGANISM: Homo sapiens

<400> SEQUENCE: 975
aatggacatc tttcaggtct g                                              21

<210> SEQ ID NO 976
<211> LENGTH: 21
<212> TYPE: DNA
<213> ORGANISM: Homo sapiens

<400> SEQUENCE: 976
cattcttgct gacatttccc a                                              21

<210> SEQ ID NO 977
<211> LENGTH: 21
<212> TYPE: DNA
<213> ORGANISM: Homo sapiens

<400> SEQUENCE: 977
tcaaattggg atcgcattag g                                              21

<210> SEQ ID NO 978
<211> LENGTH: 22
<212> TYPE: DNA
<213> ORGANISM: Homo sapiens

<400> SEQUENCE: 978
gaagatcagg gtattgctga aa                                             22

<210> SEQ ID NO 979
<211> LENGTH: 22
<212> TYPE: DNA
<213> ORGANISM: Homo sapiens

<400> SEQUENCE: 979
atgcctgggt ttattcatct tg                                             22

<210> SEQ ID NO 980
<211> LENGTH: 21
<212> TYPE: DNA
<213> ORGANISM: Homo sapiens

<400> SEQUENCE: 980
tttgtaggtc attcagcctc c                                              21
```

```
<210> SEQ ID NO 981
<211> LENGTH: 21
<212> TYPE: DNA
<213> ORGANISM: Homo sapiens

<400> SEQUENCE: 981
ggagaagttt gggtttgatc c                                              21

<210> SEQ ID NO 982
<211> LENGTH: 22
<212> TYPE: DNA
<213> ORGANISM: Homo sapiens

<400> SEQUENCE: 982
tggctaggat tcacttagga aa                                             22

<210> SEQ ID NO 983
<211> LENGTH: 21
<212> TYPE: DNA
<213> ORGANISM: Homo sapiens

<400> SEQUENCE: 983
tgataggagc catcagttct t                                              21

<210> SEQ ID NO 984
<211> LENGTH: 21
<212> TYPE: DNA
<213> ORGANISM: Homo sapiens

<400> SEQUENCE: 984
gcaaacaggg tgaattatgc t                                              21

<210> SEQ ID NO 985
<211> LENGTH: 21
<212> TYPE: DNA
<213> ORGANISM: Homo sapiens

<400> SEQUENCE: 985
agcagatgtt gttagctttc c                                              21

<210> SEQ ID NO 986
<211> LENGTH: 21
<212> TYPE: DNA
<213> ORGANISM: Homo sapiens

<400> SEQUENCE: 986
agaagtctgg gaaacgaaga g                                              21

<210> SEQ ID NO 987
<211> LENGTH: 21
<212> TYPE: DNA
<213> ORGANISM: Homo sapiens

<400> SEQUENCE: 987
ttctctgtca cttccatgag g                                              21

<210> SEQ ID NO 988
<211> LENGTH: 21
<212> TYPE: DNA
<213> ORGANISM: Homo sapiens
```

```
<400> SEQUENCE: 988
cagatgctcc attactaggt g                                              21

<210> SEQ ID NO 989
<211> LENGTH: 22
<212> TYPE: DNA
<213> ORGANISM: Homo sapiens

<400> SEQUENCE: 989
ccagtaactt attctgccag ag                                             22

<210> SEQ ID NO 990
<211> LENGTH: 21
<212> TYPE: DNA
<213> ORGANISM: Homo sapiens

<400> SEQUENCE: 990
cacatggaga aaggtgaatc a                                              21

<210> SEQ ID NO 991
<211> LENGTH: 21
<212> TYPE: DNA
<213> ORGANISM: Homo sapiens

<400> SEQUENCE: 991
tgagagacaa gctgcattac a                                              21

<210> SEQ ID NO 992
<211> LENGTH: 20
<212> TYPE: DNA
<213> ORGANISM: Homo sapiens

<400> SEQUENCE: 992
tcccatccaa tactgccttc                                                20

<210> SEQ ID NO 993
<211> LENGTH: 22
<212> TYPE: DNA
<213> ORGANISM: Homo sapiens

<400> SEQUENCE: 993
gcacagaaat tacagttcat gg                                             22

<210> SEQ ID NO 994
<211> LENGTH: 21
<212> TYPE: DNA
<213> ORGANISM: Homo sapiens

<400> SEQUENCE: 994
tctggctcaa aggatcacat g                                              21

<210> SEQ ID NO 995
<211> LENGTH: 21
<212> TYPE: DNA
<213> ORGANISM: Homo sapiens

<400> SEQUENCE: 995
gctctcgtat ctgacagtga a                                              21

<210> SEQ ID NO 996
<211> LENGTH: 21
<212> TYPE: DNA
```

-continued

<213> ORGANISM: Homo sapiens

<400> SEQUENCE: 996
aagatcccat tgaccctgaa t                                              21

<210> SEQ ID NO 997
<211> LENGTH: 21
<212> TYPE: DNA
<213> ORGANISM: Homo sapiens

<400> SEQUENCE: 997
caggcatctt ggtttgtagt g                                              21

<210> SEQ ID NO 998
<211> LENGTH: 21
<212> TYPE: DNA
<213> ORGANISM: Homo sapiens

<400> SEQUENCE: 998
ccacaggctc tctagaacta a                                              21

<210> SEQ ID NO 999
<211> LENGTH: 21
<212> TYPE: DNA
<213> ORGANISM: Homo sapiens

<400> SEQUENCE: 999
cgtgatgaac agtgatgact t                                              21

<210> SEQ ID NO 1000
<211> LENGTH: 21
<212> TYPE: DNA
<213> ORGANISM: Homo sapiens

<400> SEQUENCE: 1000
ttgagagggt ttacaaggtc c                                              21

<210> SEQ ID NO 1001
<211> LENGTH: 21
<212> TYPE: DNA
<213> ORGANISM: Homo sapiens

<400> SEQUENCE: 1001
cgccatttgt tctcctattc a                                              21

<210> SEQ ID NO 1002
<211> LENGTH: 22
<212> TYPE: DNA
<213> ORGANISM: Homo sapiens

<400> SEQUENCE: 1002
cttctcctac tctgcattct ca                                             22

<210> SEQ ID NO 1003
<211> LENGTH: 21
<212> TYPE: DNA
<213> ORGANISM: Homo sapiens

<400> SEQUENCE: 1003
ttcgttagct actgggtact c                                              21

<210> SEQ ID NO 1004
<211> LENGTH: 21

```
<212> TYPE: DNA
<213> ORGANISM: Homo sapiens

<400> SEQUENCE: 1004
gacattagtg gattcaggcc a                                              21

<210> SEQ ID NO 1005
<211> LENGTH: 21
<212> TYPE: DNA
<213> ORGANISM: Homo sapiens

<400> SEQUENCE: 1005
ccacccttta cacctatcca a                                              21

<210> SEQ ID NO 1006
<211> LENGTH: 21
<212> TYPE: DNA
<213> ORGANISM: Homo sapiens

<400> SEQUENCE: 1006
gctgaagtgg aggcaattaa c                                              21

<210> SEQ ID NO 1007
<211> LENGTH: 21
<212> TYPE: DNA
<213> ORGANISM: Homo sapiens

<400> SEQUENCE: 1007
agagtgcaca aaggagaaga c                                              21

<210> SEQ ID NO 1008
<211> LENGTH: 21
<212> TYPE: DNA
<213> ORGANISM: Homo sapiens

<400> SEQUENCE: 1008
tataactgtt gagtctgccc a                                              21

<210> SEQ ID NO 1009
<211> LENGTH: 22
<212> TYPE: DNA
<213> ORGANISM: Homo sapiens

<400> SEQUENCE: 1009
tctactgtgt caaagcagat tg                                             22

<210> SEQ ID NO 1010
<211> LENGTH: 21
<212> TYPE: DNA
<213> ORGANISM: Homo sapiens

<400> SEQUENCE: 1010
actgagctta cattcatgca c                                              21

<210> SEQ ID NO 1011
<211> LENGTH: 21
<212> TYPE: DNA
<213> ORGANISM: Homo sapiens

<400> SEQUENCE: 1011
ttcttcctag ccttcctttc c                                              21

<210> SEQ ID NO 1012
```

```
<211> LENGTH: 21
<212> TYPE: DNA
<213> ORGANISM: Homo sapiens

<400> SEQUENCE: 1012
gccactttct ctgcaaagaa t                                              21

<210> SEQ ID NO 1013
<211> LENGTH: 21
<212> TYPE: DNA
<213> ORGANISM: Homo sapiens

<400> SEQUENCE: 1013
tctctggctg tgcagtaaat t                                              21

<210> SEQ ID NO 1014
<211> LENGTH: 21
<212> TYPE: DNA
<213> ORGANISM: Homo sapiens

<400> SEQUENCE: 1014
acttcctacg gactcaaatc t                                              21

<210> SEQ ID NO 1015
<211> LENGTH: 21
<212> TYPE: DNA
<213> ORGANISM: Homo sapiens

<400> SEQUENCE: 1015
aaactcccag ctttaatccc t                                              21

<210> SEQ ID NO 1016
<211> LENGTH: 21
<212> TYPE: DNA
<213> ORGANISM: Homo sapiens

<400> SEQUENCE: 1016
ggctctcatt acaattggct g                                              21

<210> SEQ ID NO 1017
<211> LENGTH: 21
<212> TYPE: DNA
<213> ORGANISM: Homo sapiens

<400> SEQUENCE: 1017
aagaatgggt gagttgggtt c                                              21

<210> SEQ ID NO 1018
<211> LENGTH: 21
<212> TYPE: DNA
<213> ORGANISM: Homo sapiens

<400> SEQUENCE: 1018
attgctttca gtggtggatt g                                              21

<210> SEQ ID NO 1019
<211> LENGTH: 21
<212> TYPE: DNA
<213> ORGANISM: Homo sapiens

<400> SEQUENCE: 1019
ggaaactgaa ttgccaagtc t                                              21
```

```
<210> SEQ ID NO 1020
<211> LENGTH: 21
<212> TYPE: DNA
<213> ORGANISM: Homo sapiens

<400> SEQUENCE: 1020
ggaatgaaac agaggagtcc c                                              21

<210> SEQ ID NO 1021
<211> LENGTH: 20
<212> TYPE: DNA
<213> ORGANISM: Homo sapiens

<400> SEQUENCE: 1021
ctcccaactt ttatgcagcc                                                20

<210> SEQ ID NO 1022
<211> LENGTH: 21
<212> TYPE: DNA
<213> ORGANISM: Homo sapiens

<400> SEQUENCE: 1022
aagatgctag aaacccacaa g                                              21

<210> SEQ ID NO 1023
<211> LENGTH: 21
<212> TYPE: DNA
<213> ORGANISM: Homo sapiens

<400> SEQUENCE: 1023
gctcagggaa tatcttggga a                                              21

<210> SEQ ID NO 1024
<211> LENGTH: 20
<212> TYPE: DNA
<213> ORGANISM: Homo sapiens

<400> SEQUENCE: 1024
aatgggtggg ttacagagag                                                20

<210> SEQ ID NO 1025
<211> LENGTH: 21
<212> TYPE: DNA
<213> ORGANISM: Homo sapiens

<400> SEQUENCE: 1025
acattcagca agtaggaagg a                                              21

<210> SEQ ID NO 1026
<211> LENGTH: 20
<212> TYPE: DNA
<213> ORGANISM: Homo sapiens

<400> SEQUENCE: 1026
gcatttggac atgaacaagc                                                20

<210> SEQ ID NO 1027
<211> LENGTH: 20
<212> TYPE: DNA
<213> ORGANISM: Homo sapiens

<400> SEQUENCE: 1027
cccagaagag cagtaacaac                                                20
```

```
<210> SEQ ID NO 1028
<211> LENGTH: 20
<212> TYPE: DNA
<213> ORGANISM: Homo sapiens

<400> SEQUENCE: 1028
cattggtggg tggatagctg                                            20

<210> SEQ ID NO 1029
<211> LENGTH: 20
<212> TYPE: DNA
<213> ORGANISM: Homo sapiens

<400> SEQUENCE: 1029
gaaaaagggg gataggcatt                                            20

<210> SEQ ID NO 1030
<211> LENGTH: 20
<212> TYPE: DNA
<213> ORGANISM: Homo sapiens

<400> SEQUENCE: 1030
accaggagga gaaaagcaaa                                            20

<210> SEQ ID NO 1031
<211> LENGTH: 21
<212> TYPE: DNA
<213> ORGANISM: Homo sapiens

<400> SEQUENCE: 1031
cccaacaact gcaataaaag g                                          21

<210> SEQ ID NO 1032
<211> LENGTH: 20
<212> TYPE: DNA
<213> ORGANISM: Homo sapiens

<400> SEQUENCE: 1032
cggaaaacaa accctgaagt                                            20

<210> SEQ ID NO 1033
<211> LENGTH: 20
<212> TYPE: DNA
<213> ORGANISM: Homo sapiens

<400> SEQUENCE: 1033
accgaaattg cttgctctta                                            20

<210> SEQ ID NO 1034
<211> LENGTH: 20
<212> TYPE: DNA
<213> ORGANISM: Homo sapiens

<400> SEQUENCE: 1034
acctgcatat tgagccatac                                            20

<210> SEQ ID NO 1035
<211> LENGTH: 20
<212> TYPE: DNA
<213> ORGANISM: Homo sapiens

<400> SEQUENCE: 1035
ccttagtgtg acaggacagg                                            20
```

<210> SEQ ID NO 1036
<211> LENGTH: 21
<212> TYPE: DNA
<213> ORGANISM: Homo sapiens

<400> SEQUENCE: 1036
tgttctttca cttttagccc c					21

<210> SEQ ID NO 1037
<211> LENGTH: 20
<212> TYPE: DNA
<213> ORGANISM: Homo sapiens

<400> SEQUENCE: 1037
ccaagacaac taggccaatg					20

<210> SEQ ID NO 1038
<211> LENGTH: 21
<212> TYPE: DNA
<213> ORGANISM: Homo sapiens

<400> SEQUENCE: 1038
tttctagaac cctcagcaac t					21

<210> SEQ ID NO 1039
<211> LENGTH: 21
<212> TYPE: DNA
<213> ORGANISM: Homo sapiens

<400> SEQUENCE: 1039
gaagagatga tgcaaaagag c					21

<210> SEQ ID NO 1040
<211> LENGTH: 21
<212> TYPE: DNA
<213> ORGANISM: Homo sapiens

<400> SEQUENCE: 1040
cccccaacag tttttagtgg t					21

<210> SEQ ID NO 1041
<211> LENGTH: 20
<212> TYPE: DNA
<213> ORGANISM: Homo sapiens

<400> SEQUENCE: 1041
tccaagcaag ggatctcttc					20

<210> SEQ ID NO 1042
<211> LENGTH: 20
<212> TYPE: DNA
<213> ORGANISM: Homo sapiens

<400> SEQUENCE: 1042
aaggcaaaac actccctttt					20

<210> SEQ ID NO 1043
<211> LENGTH: 20
<212> TYPE: DNA
<213> ORGANISM: Homo sapiens

<400> SEQUENCE: 1043
gaatggtcag ggaagggttt         20

<210> SEQ ID NO 1044
<211> LENGTH: 22
<212> TYPE: DNA
<213> ORGANISM: Homo sapiens

<400> SEQUENCE: 1044
cagtgattgc ctctagaaaa gg         22

<210> SEQ ID NO 1045
<211> LENGTH: 20
<212> TYPE: DNA
<213> ORGANISM: Homo sapiens

<400> SEQUENCE: 1045
agtcttcagc catcttcctg         20

<210> SEQ ID NO 1046
<211> LENGTH: 20
<212> TYPE: DNA
<213> ORGANISM: Homo sapiens

<400> SEQUENCE: 1046
ctaagcagat tgaagcagct         20

<210> SEQ ID NO 1047
<211> LENGTH: 21
<212> TYPE: DNA
<213> ORGANISM: Homo sapiens

<400> SEQUENCE: 1047
gcatttccag gctttacaag t         21

<210> SEQ ID NO 1048
<211> LENGTH: 20
<212> TYPE: DNA
<213> ORGANISM: Homo sapiens

<400> SEQUENCE: 1048
tgtccccagg cttaagaatc         20

<210> SEQ ID NO 1049
<211> LENGTH: 20
<212> TYPE: DNA
<213> ORGANISM: Homo sapiens

<400> SEQUENCE: 1049
ctctctctcc ctggtcagat         20

<210> SEQ ID NO 1050
<211> LENGTH: 20
<212> TYPE: DNA
<213> ORGANISM: Homo sapiens

<400> SEQUENCE: 1050
agccagaata agcaactgtc         20

<210> SEQ ID NO 1051
<211> LENGTH: 20
<212> TYPE: DNA

<213> ORGANISM: Homo sapiens

<400> SEQUENCE: 1051
cagcaattct caggctcaga                                               20

<210> SEQ ID NO 1052
<211> LENGTH: 20
<212> TYPE: DNA
<213> ORGANISM: Homo sapiens

<400> SEQUENCE: 1052
tttctcctat cccagcttgc                                               20

<210> SEQ ID NO 1053
<211> LENGTH: 21
<212> TYPE: DNA
<213> ORGANISM: Homo sapiens

<400> SEQUENCE: 1053
tctgaaacaa agcctcctta g                                             21

<210> SEQ ID NO 1054
<211> LENGTH: 21
<212> TYPE: DNA
<213> ORGANISM: Homo sapiens

<400> SEQUENCE: 1054
agtacagagg ataacaaggg t                                             21

<210> SEQ ID NO 1055
<211> LENGTH: 21
<212> TYPE: DNA
<213> ORGANISM: Homo sapiens

<400> SEQUENCE: 1055
aggataaggt ttcccatgct c                                             21

<210> SEQ ID NO 1056
<211> LENGTH: 20
<212> TYPE: DNA
<213> ORGANISM: Homo sapiens

<400> SEQUENCE: 1056
ctcccatcag taccctctct                                               20

<210> SEQ ID NO 1057
<211> LENGTH: 21
<212> TYPE: DNA
<213> ORGANISM: Homo sapiens

<400> SEQUENCE: 1057
atgtatctga aggagctctg c                                             21

<210> SEQ ID NO 1058
<211> LENGTH: 21
<212> TYPE: DNA
<213> ORGANISM: Homo sapiens

<400> SEQUENCE: 1058
ggaatgccta aaccatactg t                                             21

<210> SEQ ID NO 1059
<211> LENGTH: 20

```
<212> TYPE: DNA
<213> ORGANISM: Homo sapiens

<400> SEQUENCE: 1059
ggccttcatc acaaacaaca                                              20

<210> SEQ ID NO 1060
<211> LENGTH: 22
<212> TYPE: DNA
<213> ORGANISM: Homo sapiens

<400> SEQUENCE: 1060
agtggtattt caatgctcta cc                                           22

<210> SEQ ID NO 1061
<211> LENGTH: 20
<212> TYPE: DNA
<213> ORGANISM: Homo sapiens

<400> SEQUENCE: 1061
tgtgtcccat ctacaaagcc                                              20

<210> SEQ ID NO 1062
<211> LENGTH: 19
<212> TYPE: DNA
<213> ORGANISM: Homo sapiens

<400> SEQUENCE: 1062
gcagtacatc gtcctggaa                                               19

<210> SEQ ID NO 1063
<211> LENGTH: 20
<212> TYPE: DNA
<213> ORGANISM: Homo sapiens

<400> SEQUENCE: 1063
tccttgaact ctttccaagc                                              20

<210> SEQ ID NO 1064
<211> LENGTH: 21
<212> TYPE: DNA
<213> ORGANISM: Homo sapiens

<400> SEQUENCE: 1064
cctgagcgag aagaaatttg t                                            21

<210> SEQ ID NO 1065
<211> LENGTH: 20
<212> TYPE: DNA
<213> ORGANISM: Homo sapiens

<400> SEQUENCE: 1065
tgttttcctg tccaagtcca                                              20

<210> SEQ ID NO 1066
<211> LENGTH: 21
<212> TYPE: DNA
<213> ORGANISM: Homo sapiens

<400> SEQUENCE: 1066
ggaactgaac aagaagtgga g                                            21

<210> SEQ ID NO 1067
```

```
<211> LENGTH: 19
<212> TYPE: DNA
<213> ORGANISM: Homo sapiens

<400> SEQUENCE: 1067
cagcatccat cgctcgaaa                                                19

<210> SEQ ID NO 1068
<211> LENGTH: 20
<212> TYPE: DNA
<213> ORGANISM: Homo sapiens

<400> SEQUENCE: 1068
acctactctt attccgcact                                               20

<210> SEQ ID NO 1069
<211> LENGTH: 20
<212> TYPE: DNA
<213> ORGANISM: Homo sapiens

<400> SEQUENCE: 1069
ggtattggtg ggggaaatga                                               20

<210> SEQ ID NO 1070
<211> LENGTH: 20
<212> TYPE: DNA
<213> ORGANISM: Homo sapiens

<400> SEQUENCE: 1070
tgacagcctc tctcttcaat                                               20

<210> SEQ ID NO 1071
<211> LENGTH: 24
<212> TYPE: DNA
<213> ORGANISM: Homo sapiens

<400> SEQUENCE: 1071
gcactgctgt aaaagatcta tgag                                          24

<210> SEQ ID NO 1072
<211> LENGTH: 23
<212> TYPE: DNA
<213> ORGANISM: Homo sapiens

<400> SEQUENCE: 1072
tgtcacatac ctctcaactg ttg                                           23

<210> SEQ ID NO 1073
<211> LENGTH: 19
<212> TYPE: DNA
<213> ORGANISM: Homo sapiens

<400> SEQUENCE: 1073
actcaaaggc acatttcgc                                                19

<210> SEQ ID NO 1074
<211> LENGTH: 20
<212> TYPE: DNA
<213> ORGANISM: Homo sapiens

<400> SEQUENCE: 1074
gctgtttttc tgtgtgcttc                                               20
```

-continued

```
<210> SEQ ID NO 1075
<211> LENGTH: 22
<212> TYPE: DNA
<213> ORGANISM: Homo sapiens

<400> SEQUENCE: 1075
attctattcc gatcacagcc tt                                                  22

<210> SEQ ID NO 1076
<211> LENGTH: 20
<212> TYPE: DNA
<213> ORGANISM: Homo sapiens

<400> SEQUENCE: 1076
atgtatttcc tttagcgccc                                                     20

<210> SEQ ID NO 1077
<211> LENGTH: 20
<212> TYPE: DNA
<213> ORGANISM: Homo sapiens

<400> SEQUENCE: 1077
ctacctgaca aatggagctt                                                     20

<210> SEQ ID NO 1078
<211> LENGTH: 20
<212> TYPE: DNA
<213> ORGANISM: Homo sapiens

<400> SEQUENCE: 1078
aattttgcaa gacttccggt                                                     20

<210> SEQ ID NO 1079
<211> LENGTH: 21
<212> TYPE: DNA
<213> ORGANISM: Homo sapiens

<400> SEQUENCE: 1079
gaaatggcca tgtgtactga g                                                   21

<210> SEQ ID NO 1080
<211> LENGTH: 20
<212> TYPE: DNA
<213> ORGANISM: Homo sapiens

<400> SEQUENCE: 1080
tcccagttgt gaacatttgc                                                     20

<210> SEQ ID NO 1081
<211> LENGTH: 20
<212> TYPE: DNA
<213> ORGANISM: Homo sapiens

<400> SEQUENCE: 1081
gaagcctctc aagctacaag                                                     20

<210> SEQ ID NO 1082
<211> LENGTH: 21
<212> TYPE: DNA
<213> ORGANISM: Homo sapiens

<400> SEQUENCE: 1082
atgggttttt gcacagatga c                                                   21
```

<210> SEQ ID NO 1083
<211> LENGTH: 22
<212> TYPE: DNA
<213> ORGANISM: Homo sapiens

<400> SEQUENCE: 1083
gaatgagatt agggagcaaa gt                                              22

<210> SEQ ID NO 1084
<211> LENGTH: 19
<212> TYPE: DNA
<213> ORGANISM: Homo sapiens

<400> SEQUENCE: 1084
gggagtcaga aggaggtca                                                  19

<210> SEQ ID NO 1085
<211> LENGTH: 20
<212> TYPE: DNA
<213> ORGANISM: Homo sapiens

<400> SEQUENCE: 1085
ggaagtaaga agagtgctgc                                                 20

<210> SEQ ID NO 1086
<211> LENGTH: 21
<212> TYPE: DNA
<213> ORGANISM: Homo sapiens

<400> SEQUENCE: 1086
cctctttttg catgaacctg a                                               21

<210> SEQ ID NO 1087
<211> LENGTH: 20
<212> TYPE: DNA
<213> ORGANISM: Homo sapiens

<400> SEQUENCE: 1087
gctcctgatt gaagaagtgt                                                 20

<210> SEQ ID NO 1088
<211> LENGTH: 20
<212> TYPE: DNA
<213> ORGANISM: Homo sapiens

<400> SEQUENCE: 1088
ccttaccctt tccactcaga                                                 20

<210> SEQ ID NO 1089
<211> LENGTH: 19
<212> TYPE: DNA
<213> ORGANISM: Homo sapiens

<400> SEQUENCE: 1089
ctgctccttt gtctcctgt                                                  19

<210> SEQ ID NO 1090
<211> LENGTH: 21
<212> TYPE: DNA
<213> ORGANISM: Homo sapiens

<400> SEQUENCE: 1090
gactggtata atcttgccgt g                                               21

<210> SEQ ID NO 1091
<211> LENGTH: 21
<212> TYPE: DNA
<213> ORGANISM: Homo sapiens

<400> SEQUENCE: 1091
taaggtgaga gtgtgaggaa g        21

<210> SEQ ID NO 1092
<211> LENGTH: 21
<212> TYPE: DNA
<213> ORGANISM: Homo sapiens

<400> SEQUENCE: 1092
tgtctgcatc ttgatctctg g        21

<210> SEQ ID NO 1093
<211> LENGTH: 21
<212> TYPE: DNA
<213> ORGANISM: Homo sapiens

<400> SEQUENCE: 1093 ccagggaac atttactcag a        21

<210> SEQ ID NO 1094
<211> LENGTH: 19
<212> TYPE: DNA
<213> ORGANISM: Homo sapiens

<400> SEQUENCE: 1094
ggttccacag catttgagc        19

<210> SEQ ID NO 1095
<211> LENGTH: 20
<212> TYPE: DNA
<213> ORGANISM: Homo sapiens

<400> SEQUENCE: 1095
agggtacatg taaggcagct        20

<210> SEQ ID NO 1096
<211> LENGTH: 20
<212> TYPE: DNA
<213> ORGANISM: Homo sapiens

<400> SEQUENCE: 1096
aggagccctt aactatggtg        20

<210> SEQ ID NO 1097
<211> LENGTH: 20
<212> TYPE: DNA
<213> ORGANISM: Homo sapiens

<400> SEQUENCE: 1097
ttctgtggca ttgtgtcttg        20

<210> SEQ ID NO 1098
<211> LENGTH: 20
<212> TYPE: DNA
<213> ORGANISM: Homo sapiens

```
<400> SEQUENCE: 1098
tggcttgggt attgcagata                                              20

<210> SEQ ID NO 1099
<211> LENGTH: 20
<212> TYPE: DNA
<213> ORGANISM: Homo sapiens

<400> SEQUENCE: 1099
ccccaaattt accccactct                                              20

<210> SEQ ID NO 1100
<211> LENGTH: 20
<212> TYPE: DNA
<213> ORGANISM: Homo sapiens

<400> SEQUENCE: 1100
ggggacagta gaagatgagt                                              20

<210> SEQ ID NO 1101
<211> LENGTH: 20
<212> TYPE: DNA
<213> ORGANISM: Homo sapiens

<400> SEQUENCE: 1101
atccctagca ctttcaggac                                              20

<210> SEQ ID NO 1102
<211> LENGTH: 20
<212> TYPE: DNA
<213> ORGANISM: Homo sapiens

<400> SEQUENCE: 1102
agttgtttct ggacggactt                                              20

<210> SEQ ID NO 1103
<211> LENGTH: 20
<212> TYPE: DNA
<213> ORGANISM: Homo sapiens

<400> SEQUENCE: 1103
ttaccaatcc atccagcctg                                              20

<210> SEQ ID NO 1104
<211> LENGTH: 21
<212> TYPE: DNA
<213> ORGANISM: Homo sapiens

<400> SEQUENCE: 1104
agaatttccc tgtccatacc a                                            21

<210> SEQ ID NO 1105
<211> LENGTH: 20
<212> TYPE: DNA
<213> ORGANISM: Homo sapiens

<400> SEQUENCE: 1105
agaagctaaa caggttgccc                                              20

<210> SEQ ID NO 1106
<211> LENGTH: 20
<212> TYPE: DNA
```

```
<213> ORGANISM: Homo sapiens

<400> SEQUENCE: 1106
agtgagtgaa cttgccatca                                           20

<210> SEQ ID NO 1107
<211> LENGTH: 20
<212> TYPE: DNA
<213> ORGANISM: Homo sapiens

<400> SEQUENCE: 1107
cataagagca cagccaagat                                           20

<210> SEQ ID NO 1108
<211> LENGTH: 20
<212> TYPE: DNA
<213> ORGANISM: Homo sapiens

<400> SEQUENCE: 1108
ggcttttctc tgcactgatt                                           20

<210> SEQ ID NO 1109
<211> LENGTH: 20
<212> TYPE: DNA
<213> ORGANISM: Homo sapiens

<400> SEQUENCE: 1109
tgtcctgcca cttttacatc                                           20

<210> SEQ ID NO 1110
<211> LENGTH: 21
<212> TYPE: DNA
<213> ORGANISM: Homo sapiens

<400> SEQUENCE: 1110
gcaaaggaaa caggctaact a                                         21

<210> SEQ ID NO 1111
<211> LENGTH: 21
<212> TYPE: DNA
<213> ORGANISM: Homo sapiens

<400> SEQUENCE: 1111
gagctaagca gaacctaagg a                                         21

<210> SEQ ID NO 1112
<211> LENGTH: 21
<212> TYPE: DNA
<213> ORGANISM: Homo sapiens

<400> SEQUENCE: 1112
atggcagctg aatcgatatc t                                         21

<210> SEQ ID NO 1113
<211> LENGTH: 21
<212> TYPE: DNA
<213> ORGANISM: Homo sapiens

<400> SEQUENCE: 1113
ttaagcaaca ggaacctacc c                                         21

<210> SEQ ID NO 1114
<211> LENGTH: 21
```

```
<212> TYPE: DNA
<213> ORGANISM: Homo sapiens

<400> SEQUENCE: 1114
taggtgatgg gcaaattctc a                                              21

<210> SEQ ID NO 1115
<211> LENGTH: 21
<212> TYPE: DNA
<213> ORGANISM: Homo sapiens

<400> SEQUENCE: 1115
gccaagggta atcatagcaa c                                              21

<210> SEQ ID NO 1116
<211> LENGTH: 22
<212> TYPE: DNA
<213> ORGANISM: Homo sapiens

<400> SEQUENCE: 1116
gaaatgcctt cccacttaca at                                             22

<210> SEQ ID NO 1117
<211> LENGTH: 21
<212> TYPE: DNA
<213> ORGANISM: Homo sapiens

<400> SEQUENCE: 1117
tcataatgaa acccttgctg c                                              21

<210> SEQ ID NO 1118
<211> LENGTH: 21
<212> TYPE: DNA
<213> ORGANISM: Homo sapiens

<400> SEQUENCE: 1118
attggcaaat gtacctgaag c                                              21

<210> SEQ ID NO 1119
<211> LENGTH: 21
<212> TYPE: DNA
<213> ORGANISM: Homo sapiens

<400> SEQUENCE: 1119
aatcctagtg catgagactc c                                              21

<210> SEQ ID NO 1120
<211> LENGTH: 21
<212> TYPE: DNA
<213> ORGANISM: Homo sapiens

<400> SEQUENCE: 1120
caatgattgc tcttgtgcca a                                              21

<210> SEQ ID NO 1121
<211> LENGTH: 21
<212> TYPE: DNA
<213> ORGANISM: Homo sapiens

<400> SEQUENCE: 1121
tactgcctgc atcattacca c                                              21

<210> SEQ ID NO 1122
```

-continued

<211> LENGTH: 21
<212> TYPE: DNA
<213> ORGANISM: Homo sapiens

<400> SEQUENCE: 1122
agctgtcctc ctctccatat a                                              21

<210> SEQ ID NO 1123
<211> LENGTH: 21
<212> TYPE: DNA
<213> ORGANISM: Homo sapiens

<400> SEQUENCE: 1123
attaacaatg aggagccagg t                                              21

<210> SEQ ID NO 1124
<211> LENGTH: 21
<212> TYPE: DNA
<213> ORGANISM: Homo sapiens

<400> SEQUENCE: 1124
ggcgttcaag ttactcgatt g                                              21

<210> SEQ ID NO 1125
<211> LENGTH: 21
<212> TYPE: DNA
<213> ORGANISM: Homo sapiens

<400> SEQUENCE: 1125
gagagatggt tgagaaatgc c                                              21

<210> SEQ ID NO 1126
<211> LENGTH: 21
<212> TYPE: DNA
<213> ORGANISM: Homo sapiens

<400> SEQUENCE: 1126
tagtgactag ctttggagag t                                              21

<210> SEQ ID NO 1127
<211> LENGTH: 21
<212> TYPE: DNA
<213> ORGANISM: Homo sapiens

<400> SEQUENCE: 1127
actacaacca ccaattacag c                                              21

<210> SEQ ID NO 1128
<211> LENGTH: 22
<212> TYPE: DNA
<213> ORGANISM: Homo sapiens

<400> SEQUENCE: 1128
agccaatgat cccttatgac tt                                             22

<210> SEQ ID NO 1129
<211> LENGTH: 21
<212> TYPE: DNA
<213> ORGANISM: Homo sapiens

<400> SEQUENCE: 1129
agtgacattt ccaagggctt t                                              21

```
<210> SEQ ID NO 1130
<211> LENGTH: 21
<212> TYPE: DNA
<213> ORGANISM: Homo sapiens

<400> SEQUENCE: 1130
aactaaactg gtaggcaatc g                                        21

<210> SEQ ID NO 1131
<211> LENGTH: 21
<212> TYPE: DNA
<213> ORGANISM: Homo sapiens

<400> SEQUENCE: 1131
ggagatggga agacgattag a                                        21

<210> SEQ ID NO 1132
<211> LENGTH: 21
<212> TYPE: DNA
<213> ORGANISM: Homo sapiens

<400> SEQUENCE: 1132
caatcagacc acaggaagga a                                        21

<210> SEQ ID NO 1133
<211> LENGTH: 22
<212> TYPE: DNA
<213> ORGANISM: Homo sapiens

<400> SEQUENCE: 1133
agtctttcag tcttacatgg gt                                       22

<210> SEQ ID NO 1134
<211> LENGTH: 21
<212> TYPE: DNA
<213> ORGANISM: Homo sapiens

<400> SEQUENCE: 1134
gatgtgttta ttgcctgtgg t                                        21

<210> SEQ ID NO 1135
<211> LENGTH: 21
<212> TYPE: DNA
<213> ORGANISM: Homo sapiens

<400> SEQUENCE: 1135
tagtttctgt gatcctggca g                                        21

<210> SEQ ID NO 1136
<211> LENGTH: 21
<212> TYPE: DNA
<213> ORGANISM: Homo sapiens

<400> SEQUENCE: 1136
gctcctttca tagtttcagg g                                        21

<210> SEQ ID NO 1137
<211> LENGTH: 20
<212> TYPE: DNA
<213> ORGANISM: Homo sapiens

<400> SEQUENCE: 1137
tttctcccag ctgttcctag                                          20
```

```
<210> SEQ ID NO 1138
<211> LENGTH: 22
<212> TYPE: DNA
<213> ORGANISM: Homo sapiens

<400> SEQUENCE: 1138
acacactgca gttctcacta ta                                        22

<210> SEQ ID NO 1139
<211> LENGTH: 21
<212> TYPE: DNA
<213> ORGANISM: Homo sapiens

<400> SEQUENCE: 1139
tacggaactt cgaatcaact c                                         21

<210> SEQ ID NO 1140
<211> LENGTH: 21
<212> TYPE: DNA
<213> ORGANISM: Homo sapiens

<400> SEQUENCE: 1140
tgaatcaagt gacatgacag c                                         21

<210> SEQ ID NO 1141
<211> LENGTH: 21
<212> TYPE: DNA
<213> ORGANISM: Homo sapiens

<400> SEQUENCE: 1141
tcaagtcacc ctcattgtag g                                         21

<210> SEQ ID NO 1142
<211> LENGTH: 21
<212> TYPE: DNA
<213> ORGANISM: Homo sapiens

<400> SEQUENCE: 1142
ttcttacagt cctcagcact t                                         21

<210> SEQ ID NO 1143
<211> LENGTH: 21
<212> TYPE: DNA
<213> ORGANISM: Homo sapiens

<400> SEQUENCE: 1143
tgtaacgtgg atgtgagatt g                                         21

<210> SEQ ID NO 1144
<211> LENGTH: 21
<212> TYPE: DNA
<213> ORGANISM: Homo sapiens

<400> SEQUENCE: 1144
ccactaggct gcactaatgt a                                         21

<210> SEQ ID NO 1145
<211> LENGTH: 21
<212> TYPE: DNA
<213> ORGANISM: Homo sapiens

<400> SEQUENCE: 1145
ttgagctaag tctgcatcac t                                         21
```

<210> SEQ ID NO 1146
<211> LENGTH: 22
<212> TYPE: DNA
<213> ORGANISM: Homo sapiens

<400> SEQUENCE: 1146
cactagcttc tgtaactgtg tg                                              22

<210> SEQ ID NO 1147
<211> LENGTH: 21
<212> TYPE: DNA
<213> ORGANISM: Homo sapiens

<400> SEQUENCE: 1147
ctagagaaag caacgcctaa g                                               21

<210> SEQ ID NO 1148
<211> LENGTH: 21
<212> TYPE: DNA
<213> ORGANISM: Homo sapiens

<400> SEQUENCE: 1148
gtctcacact gctcatttcc a                                               21

<210> SEQ ID NO 1149
<211> LENGTH: 21
<212> TYPE: DNA
<213> ORGANISM: Homo sapiens

<400> SEQUENCE: 1149
agcaccttcc atagcttctt t                                               21

<210> SEQ ID NO 1150
<211> LENGTH: 21
<212> TYPE: DNA
<213> ORGANISM: Homo sapiens

<400> SEQUENCE: 1150
cactagggtt catcagctgt t                                               21

<210> SEQ ID NO 1151
<211> LENGTH: 21
<212> TYPE: DNA
<213> ORGANISM: Homo sapiens

<400> SEQUENCE: 1151
gtgtcttctg atggccaaat g                                               21

<210> SEQ ID NO 1152
<211> LENGTH: 21
<212> TYPE: DNA
<213> ORGANISM: Homo sapiens

<400> SEQUENCE: 1152
caaccaacat tagagtgacc c                                               21

<210> SEQ ID NO 1153
<211> LENGTH: 21
<212> TYPE: DNA
<213> ORGANISM: Homo sapiens

```
<400> SEQUENCE: 1153
aatcaggtga aaggtacctc c                                              21

<210> SEQ ID NO 1154
<211> LENGTH: 21
<212> TYPE: DNA
<213> ORGANISM: Homo sapiens

<400> SEQUENCE: 1154
gctggttgag agagagagag a                                              21

<210> SEQ ID NO 1155
<211> LENGTH: 21
<212> TYPE: DNA
<213> ORGANISM: Homo sapiens

<400> SEQUENCE: 1155
ccttcacaat tcagggaaca a                                              21

<210> SEQ ID NO 1156
<211> LENGTH: 21
<212> TYPE: DNA
<213> ORGANISM: Homo sapiens

<400> SEQUENCE: 1156
acaccagccg aatacagatt t                                              21

<210> SEQ ID NO 1157
<211> LENGTH: 21
<212> TYPE: DNA
<213> ORGANISM: Homo sapiens

<400> SEQUENCE: 1157
tggacccagt tctatgcaat t                                              21

<210> SEQ ID NO 1158
<211> LENGTH: 21
<212> TYPE: DNA
<213> ORGANISM: Homo sapiens

<400> SEQUENCE: 1158
tgcttcatac ctttctgctt c                                              21

<210> SEQ ID NO 1159
<211> LENGTH: 21
<212> TYPE: DNA
<213> ORGANISM: Homo sapiens

<400> SEQUENCE: 1159
aatgaccctt acaactccga a                                              21

<210> SEQ ID NO 1160
<211> LENGTH: 21
<212> TYPE: DNA
<213> ORGANISM: Homo sapiens

<400> SEQUENCE: 1160
atttcccatg cctttcaact c                                              21

<210> SEQ ID NO 1161
<211> LENGTH: 21
<212> TYPE: DNA
```

```
<213> ORGANISM: Homo sapiens

<400> SEQUENCE: 1161
tttgggaagt gattgtgaag g                                              21

<210> SEQ ID NO 1162
<211> LENGTH: 21
<212> TYPE: DNA
<213> ORGANISM: Homo sapiens

<400> SEQUENCE: 1162
tctctcagta ggcgtcttta a                                              21

<210> SEQ ID NO 1163
<211> LENGTH: 21
<212> TYPE: DNA
<213> ORGANISM: Homo sapiens

<400> SEQUENCE: 1163
tcagctgcat agaccttgtt t                                              21

<210> SEQ ID NO 1164
<211> LENGTH: 20
<212> TYPE: DNA
<213> ORGANISM: Homo sapiens

<400> SEQUENCE: 1164
tgactgctac gctagacttg                                                20

<210> SEQ ID NO 1165
<211> LENGTH: 21
<212> TYPE: DNA
<213> ORGANISM: Homo sapiens

<400> SEQUENCE: 1165
tcatttgttc tcattacggg c                                              21

<210> SEQ ID NO 1166
<211> LENGTH: 20
<212> TYPE: DNA
<213> ORGANISM: Homo sapiens

<400> SEQUENCE: 1166
ggatagagga aacccaggtg                                                20

<210> SEQ ID NO 1167
<211> LENGTH: 20
<212> TYPE: DNA
<213> ORGANISM: Homo sapiens

<400> SEQUENCE: 1167
ttctacctgg gttctcttgg                                                20

<210> SEQ ID NO 1168
<211> LENGTH: 21
<212> TYPE: DNA
<213> ORGANISM: Homo sapiens

<400> SEQUENCE: 1168
ggctctttca aagtatccag g                                              21

<210> SEQ ID NO 1169
<211> LENGTH: 21
```

<210> SEQ ID NO 1169
<211> LENGTH: 21
<212> TYPE: DNA
<213> ORGANISM: Homo sapiens

<400> SEQUENCE: 1169
taacttcctg agcacacatc a    21

<210> SEQ ID NO 1170
<211> LENGTH: 22
<212> TYPE: DNA
<213> ORGANISM: Homo sapiens

<400> SEQUENCE: 1170
agactttctt tgttgccttc ag    22

<210> SEQ ID NO 1171
<211> LENGTH: 21
<212> TYPE: DNA
<213> ORGANISM: Homo sapiens

<400> SEQUENCE: 1171
gggtaaattc aggaatgcac a    21

<210> SEQ ID NO 1172
<211> LENGTH: 20
<212> TYPE: DNA
<213> ORGANISM: Homo sapiens

<400> SEQUENCE: 1172
gcctcaacaa ttcagtccac    20

<210> SEQ ID NO 1173
<211> LENGTH: 21
<212> TYPE: DNA
<213> ORGANISM: Homo sapiens

<400> SEQUENCE: 1173
atttcttctg gtgagtttgc g    21

<210> SEQ ID NO 1174
<211> LENGTH: 22
<212> TYPE: DNA
<213> ORGANISM: Homo sapiens

<400> SEQUENCE: 1174
cataagttgc tggaagagaa ca    22

<210> SEQ ID NO 1175
<211> LENGTH: 21
<212> TYPE: DNA
<213> ORGANISM: Homo sapiens

<400> SEQUENCE: 1175
cctcttcctg acatgttgtt g    21

<210> SEQ ID NO 1176
<211> LENGTH: 21
<212> TYPE: DNA
<213> ORGANISM: Homo sapiens

<400> SEQUENCE: 1176
tcgactgctt taagtgaagg a    21

<210> SEQ ID NO 1177

-continued

```
<211> LENGTH: 21
<212> TYPE: DNA
<213> ORGANISM: Homo sapiens

<400> SEQUENCE: 1177
gttggtgcca gattgtaact t                                              21

<210> SEQ ID NO 1178
<211> LENGTH: 22
<212> TYPE: DNA
<213> ORGANISM: Homo sapiens

<400> SEQUENCE: 1178
accagtgatt agtgtttctc ct                                             22

<210> SEQ ID NO 1179
<211> LENGTH: 21
<212> TYPE: DNA
<213> ORGANISM: Homo sapiens

<400> SEQUENCE: 1179
gcctggctca ataatagtcc t                                              21

<210> SEQ ID NO 1180
<211> LENGTH: 21
<212> TYPE: DNA
<213> ORGANISM: Homo sapiens

<400> SEQUENCE: 1180
caagacacac acaaacacac a                                              21

<210> SEQ ID NO 1181
<211> LENGTH: 21
<212> TYPE: DNA
<213> ORGANISM: Homo sapiens

<400> SEQUENCE: 1181
atgttgcctt ctctacgttt g                                              21

<210> SEQ ID NO 1182
<211> LENGTH: 21
<212> TYPE: DNA
<213> ORGANISM: Homo sapiens

<400> SEQUENCE: 1182
ggtaagagtt gccctaatgt c                                              21

<210> SEQ ID NO 1183
<211> LENGTH: 20
<212> TYPE: DNA
<213> ORGANISM: Homo sapiens

<400> SEQUENCE: 1183
gagtggagcg ctacctttat                                                20

<210> SEQ ID NO 1184
<211> LENGTH: 20
<212> TYPE: DNA
<213> ORGANISM: Homo sapiens

<400> SEQUENCE: 1184
gcttggcttc tcacaaatgt                                                20
```

-continued

```
<210> SEQ ID NO 1185
<211> LENGTH: 20
<212> TYPE: DNA
<213> ORGANISM: Homo sapiens

<400> SEQUENCE: 1185
agaatgggaa atgggaagga                                              20

<210> SEQ ID NO 1186
<211> LENGTH: 20
<212> TYPE: DNA
<213> ORGANISM: Homo sapiens

<400> SEQUENCE: 1186
gtttgccagt agaaatggga                                              20

<210> SEQ ID NO 1187
<211> LENGTH: 20
<212> TYPE: DNA
<213> ORGANISM: Homo sapiens

<400> SEQUENCE: 1187
cacaatacat gggctgcttt                                              20

<210> SEQ ID NO 1188
<211> LENGTH: 20
<212> TYPE: DNA
<213> ORGANISM: Homo sapiens

<400> SEQUENCE: 1188
gtaaagtgtt cagaggacgg                                              20

<210> SEQ ID NO 1189
<211> LENGTH: 21
<212> TYPE: DNA
<213> ORGANISM: Homo sapiens

<400> SEQUENCE: 1189
ccactccaac tctgctttta c                                            21

<210> SEQ ID NO 1190
<211> LENGTH: 21
<212> TYPE: DNA
<213> ORGANISM: Homo sapiens

<400> SEQUENCE: 1190
actagggaga agaattggca g                                            21

<210> SEQ ID NO 1191
<211> LENGTH: 21
<212> TYPE: DNA
<213> ORGANISM: Homo sapiens

<400> SEQUENCE: 1191
gatgtggatt gtctttgttg c                                            21

<210> SEQ ID NO 1192
<211> LENGTH: 20
<212> TYPE: DNA
<213> ORGANISM: Homo sapiens

<400> SEQUENCE: 1192
ccagttcatt ccagcttcca                                              20
```

<210> SEQ ID NO 1193
<211> LENGTH: 22
<212> TYPE: DNA
<213> ORGANISM: Homo sapiens

<400> SEQUENCE: 1193
agcctttcat tgcacatttc ag                                                22

<210> SEQ ID NO 1194
<211> LENGTH: 22
<212> TYPE: DNA
<213> ORGANISM: Homo sapiens

<400> SEQUENCE: 1194
gatcgccaac ctgttttata ag                                                22

<210> SEQ ID NO 1195
<211> LENGTH: 20
<212> TYPE: DNA
<213> ORGANISM: Homo sapiens

<400> SEQUENCE: 1195
tcccaccaca agaccaattt                                                   20

<210> SEQ ID NO 1196
<211> LENGTH: 21
<212> TYPE: DNA
<213> ORGANISM: Homo sapiens

<400> SEQUENCE: 1196
gctgtcaaag tggagataac c                                                 21

<210> SEQ ID NO 1197
<211> LENGTH: 21
<212> TYPE: DNA
<213> ORGANISM: Homo sapiens

<400> SEQUENCE: 1197
gaagataggt ggtggagttc a                                                 21

<210> SEQ ID NO 1198
<211> LENGTH: 21
<212> TYPE: DNA
<213> ORGANISM: Homo sapiens

<400> SEQUENCE: 1198
aacgcttcca tccacctaat t                                                 21

<210> SEQ ID NO 1199
<211> LENGTH: 21
<212> TYPE: DNA
<213> ORGANISM: Homo sapiens

<400> SEQUENCE: 1199
ctgtttgaat gaagttggct g                                                 21

<210> SEQ ID NO 1200
<211> LENGTH: 21
<212> TYPE: DNA
<213> ORGANISM: Homo sapiens

<400> SEQUENCE: 1200
acctgcctgt cttaccatta a                                                 21

<210> SEQ ID NO 1201
<211> LENGTH: 21
<212> TYPE: DNA
<213> ORGANISM: Homo sapiens

<400> SEQUENCE: 1201
tatacatggg tgggatttgt c                                    21

<210> SEQ ID NO 1202
<211> LENGTH: 23
<212> TYPE: DNA
<213> ORGANISM: Homo sapiens

<400> SEQUENCE: 1202
gatactttcc tttctccaga tct                                  23

<210> SEQ ID NO 1203
<211> LENGTH: 21
<212> TYPE: DNA
<213> ORGANISM: Homo sapiens

<400> SEQUENCE: 1203
tttgtgatgg accatctaac c                                    21

<210> SEQ ID NO 1204
<211> LENGTH: 20
<212> TYPE: DNA
<213> ORGANISM: Homo sapiens

<400> SEQUENCE: 1204
ggccgcagtt tttgatttag                                      20

<210> SEQ ID NO 1205
<211> LENGTH: 20
<212> TYPE: DNA
<213> ORGANISM: Homo sapiens

<400> SEQUENCE: 1205
gaagatctgg tgtcccacta                                      20

<210> SEQ ID NO 1206
<211> LENGTH: 19
<212> TYPE: DNA
<213> ORGANISM: Homo sapiens

<400> SEQUENCE: 1206
tgggaaggac ggtttgtta                                       19

<210> SEQ ID NO 1207
<211> LENGTH: 20
<212> TYPE: DNA
<213> ORGANISM: Homo sapiens

<400> SEQUENCE: 1207
atctgaagat ctccgtggta                                      20

<210> SEQ ID NO 1208
<211> LENGTH: 20
<212> TYPE: DNA
<213> ORGANISM: Homo sapiens

```
<400> SEQUENCE: 1208
tgaatcatgc tgtggagaac                                                  20

<210> SEQ ID NO 1209
<211> LENGTH: 21
<212> TYPE: DNA
<213> ORGANISM: Homo sapiens

<400> SEQUENCE: 1209
atgtatgaac catttcctgc t                                                21

<210> SEQ ID NO 1210
<211> LENGTH: 20
<212> TYPE: DNA
<213> ORGANISM: Homo sapiens

<400> SEQUENCE: 1210
atagaagagg tacccagcaa                                                  20

<210> SEQ ID NO 1211
<211> LENGTH: 22
<212> TYPE: DNA
<213> ORGANISM: Homo sapiens

<400> SEQUENCE: 1211
agcacagaat tgaatgaagg aa                                               22

<210> SEQ ID NO 1212
<211> LENGTH: 20
<212> TYPE: DNA
<213> ORGANISM: Homo sapiens

<400> SEQUENCE: 1212
ccctgactat gctaagttgc                                                  20

<210> SEQ ID NO 1213
<211> LENGTH: 20
<212> TYPE: DNA
<213> ORGANISM: Homo sapiens

<400> SEQUENCE: 1213
gcatgagtaa ggctgaagtg                                                  20

<210> SEQ ID NO 1214
<211> LENGTH: 20
<212> TYPE: DNA
<213> ORGANISM: Homo sapiens

<400> SEQUENCE: 1214
tgcaagcaaa atgaaaccag                                                  20

<210> SEQ ID NO 1215
<211> LENGTH: 25
<212> TYPE: DNA
<213> ORGANISM: Homo sapiens

<400> SEQUENCE: 1215
aaaggcttat attgcttttg aatca                                            25

<210> SEQ ID NO 1216
<211> LENGTH: 22
<212> TYPE: DNA
```

```
<213> ORGANISM: Homo sapiens

<400> SEQUENCE: 1216
aacttaaagt ttgatgggca ct                                              22

<210> SEQ ID NO 1217
<211> LENGTH: 20
<212> TYPE: DNA
<213> ORGANISM: Homo sapiens

<400> SEQUENCE: 1217
ttgctgttgt tgggatcaag                                                 20

<210> SEQ ID NO 1218
<211> LENGTH: 19
<212> TYPE: DNA
<213> ORGANISM: Homo sapiens

<400> SEQUENCE: 1218
cagctgctcc ttctttagc                                                  19

<210> SEQ ID NO 1219
<211> LENGTH: 20
<212> TYPE: DNA
<213> ORGANISM: Homo sapiens

<400> SEQUENCE: 1219
gcttctgcat ccacctatct                                                 20

<210> SEQ ID NO 1220
<211> LENGTH: 20
<212> TYPE: DNA
<213> ORGANISM: Homo sapiens

<400> SEQUENCE: 1220
tatactgcca aaggtgacct                                                 20

<210> SEQ ID NO 1221
<211> LENGTH: 20
<212> TYPE: DNA
<213> ORGANISM: Homo sapiens

<400> SEQUENCE: 1221
aaaagctgcc taaaatgcca                                                 20

<210> SEQ ID NO 1222
<211> LENGTH: 21
<212> TYPE: DNA
<213> ORGANISM: Homo sapiens

<400> SEQUENCE: 1222
gaagcataat gagaacctcc a                                               21

<210> SEQ ID NO 1223
<211> LENGTH: 20
<212> TYPE: DNA
<213> ORGANISM: Homo sapiens

<400> SEQUENCE: 1223
agtcagcaag ttagcagaaa                                                 20

<210> SEQ ID NO 1224
<211> LENGTH: 20
```

```
<212> TYPE: DNA
<213> ORGANISM: Homo sapiens

<400> SEQUENCE: 1224
aacccaactt gcagacaatc                                          20

<210> SEQ ID NO 1225
<211> LENGTH: 20
<212> TYPE: DNA
<213> ORGANISM: Homo sapiens

<400> SEQUENCE: 1225
cccacattta tcccttgtcc                                          20

<210> SEQ ID NO 1226
<211> LENGTH: 20
<212> TYPE: DNA
<213> ORGANISM: Homo sapiens

<400> SEQUENCE: 1226
atctgtttgc tgtgtcagaa                                          20

<210> SEQ ID NO 1227
<211> LENGTH: 20
<212> TYPE: DNA
<213> ORGANISM: Homo sapiens

<400> SEQUENCE: 1227
tgtctgattc catctttccc                                          20

<210> SEQ ID NO 1228
<211> LENGTH: 23
<212> TYPE: DNA
<213> ORGANISM: Homo sapiens

<400> SEQUENCE: 1228
tccagatata ttcaaaaggg aga                                      23

<210> SEQ ID NO 1229
<211> LENGTH: 19
<212> TYPE: DNA
<213> ORGANISM: Homo sapiens

<400> SEQUENCE: 1229
cagccaccaa aacacaatg                                           19

<210> SEQ ID NO 1230
<211> LENGTH: 20
<212> TYPE: DNA
<213> ORGANISM: Homo sapiens

<400> SEQUENCE: 1230
aggtttttat caaagcccca                                          20

<210> SEQ ID NO 1231
<211> LENGTH: 20
<212> TYPE: DNA
<213> ORGANISM: Homo sapiens

<400> SEQUENCE: 1231
aaggcctgtt ttgtgtgtag                                          20

<210> SEQ ID NO 1232
```

-continued

<210> SEQ ID NO 1232
<211> LENGTH: 21
<212> TYPE: DNA
<213> ORGANISM: Homo sapiens

<400> SEQUENCE: 1232
gggacttgat gttctaagca a                                       21

<210> SEQ ID NO 1233
<211> LENGTH: 21
<212> TYPE: DNA
<213> ORGANISM: Homo sapiens

<400> SEQUENCE: 1233
acagctcaca gatctttaag c                                       21

<210> SEQ ID NO 1234
<211> LENGTH: 20
<212> TYPE: DNA
<213> ORGANISM: Homo sapiens

<400> SEQUENCE: 1234
cctacatgat acgcacagtc                                         20

<210> SEQ ID NO 1235
<211> LENGTH: 23
<212> TYPE: DNA
<213> ORGANISM: Homo sapiens

<400> SEQUENCE: 1235
ggcattataa agagatagct cca                                     23

<210> SEQ ID NO 1236
<211> LENGTH: 20
<212> TYPE: DNA
<213> ORGANISM: Homo sapiens

<400> SEQUENCE: 1236
actgaagctt gccaaatcca                                         20

<210> SEQ ID NO 1237
<211> LENGTH: 20
<212> TYPE: DNA
<213> ORGANISM: Homo sapiens

<400> SEQUENCE: 1237 tgttttcct tgccctgtaa                                          20

<210> SEQ ID NO 1238
<211> LENGTH: 20
<212> TYPE: DNA
<213> ORGANISM: Homo sapiens

<400> SEQUENCE: 1238 gttttctct acccagcaca                                          20

<210> SEQ ID NO 1239
<211> LENGTH: 20
<212> TYPE: DNA
<213> ORGANISM: Homo sapiens

<400> SEQUENCE: 1239
taaccagatg aatgagggca                                         20

```
<210> SEQ ID NO 1240
<211> LENGTH: 21
<212> TYPE: DNA
<213> ORGANISM: Homo sapiens

<400> SEQUENCE: 1240
ctctaatttg ccaccctctt t                                      21

<210> SEQ ID NO 1241
<211> LENGTH: 20
<212> TYPE: DNA
<213> ORGANISM: Homo sapiens

<400> SEQUENCE: 1241
caacaagcca aaaccacatc                                        20

<210> SEQ ID NO 1242
<211> LENGTH: 20
<212> TYPE: DNA
<213> ORGANISM: Homo sapiens

<400> SEQUENCE: 1242
gaacgctaaa gcttttccca                                        20

<210> SEQ ID NO 1243
<211> LENGTH: 20
<212> TYPE: DNA
<213> ORGANISM: Homo sapiens

<400> SEQUENCE: 1243
gttggttctt gaagacctga                                        20

<210> SEQ ID NO 1244
<211> LENGTH: 20
<212> TYPE: DNA
<213> ORGANISM: Homo sapiens

<400> SEQUENCE: 1244
tctttctcct gccaagtaga                                        20

<210> SEQ ID NO 1245
<211> LENGTH: 22
<212> TYPE: DNA
<213> ORGANISM: Homo sapiens

<400> SEQUENCE: 1245
tgtggtaagt agtctctaaa ga                                     22

<210> SEQ ID NO 1246
<211> LENGTH: 20
<212> TYPE: DNA
<213> ORGANISM: Homo sapiens

<400> SEQUENCE: 1246
ataacactgt ccttctgggc                                        20

<210> SEQ ID NO 1247
<211> LENGTH: 20
<212> TYPE: DNA
<213> ORGANISM: Homo sapiens

<400> SEQUENCE: 1247
accaaatttc cagatcacgg                                        20
```

<210> SEQ ID NO 1248
<211> LENGTH: 20
<212> TYPE: DNA
<213> ORGANISM: Homo sapiens

<400> SEQUENCE: 1248
gagcctactc tctgatacga                                        20

<210> SEQ ID NO 1249
<211> LENGTH: 20
<212> TYPE: DNA
<213> ORGANISM: Homo sapiens

<400> SEQUENCE: 1249
aatgaatggt catggctcac                                        20

<210> SEQ ID NO 1250
<211> LENGTH: 21
<212> TYPE: DNA
<213> ORGANISM: Homo sapiens

<400> SEQUENCE: 1250
ccagttgttc acttctctga t                                      21

<210> SEQ ID NO 1251
<211> LENGTH: 20
<212> TYPE: DNA
<213> ORGANISM: Homo sapiens

<400> SEQUENCE: 1251
gccctgaagc acattaaagt                                        20

<210> SEQ ID NO 1252
<211> LENGTH: 20
<212> TYPE: DNA
<213> ORGANISM: Homo sapiens

<400> SEQUENCE: 1252
gccttaaaac caaactgtgt                                        20

<210> SEQ ID NO 1253
<211> LENGTH: 20
<212> TYPE: DNA
<213> ORGANISM: Homo sapiens

<400> SEQUENCE: 1253
gcctccaggt ttatgacaac                                        20

<210> SEQ ID NO 1254
<211> LENGTH: 20
<212> TYPE: DNA
<213> ORGANISM: Homo sapiens

<400> SEQUENCE: 1254
ctggacttca atcacccaag                                        20

<210> SEQ ID NO 1255
<211> LENGTH: 20
<212> TYPE: DNA
<213> ORGANISM: Homo sapiens

<400> SEQUENCE: 1255
cagctctatt ccccttctga                                        20

<210> SEQ ID NO 1256
<211> LENGTH: 20
<212> TYPE: DNA
<213> ORGANISM: Homo sapiens

<400> SEQUENCE: 1256
tgaacaaatt gctgtgctga                                              20

<210> SEQ ID NO 1257
<211> LENGTH: 20
<212> TYPE: DNA
<213> ORGANISM: Homo sapiens

<400> SEQUENCE: 1257
ccttggaagg gaaagttgat                                              20

<210> SEQ ID NO 1258
<211> LENGTH: 20
<212> TYPE: DNA
<213> ORGANISM: Homo sapiens

<400> SEQUENCE: 1258 cccectaaat gaaagtggtc                                              20

<210> SEQ ID NO 1259
<211> LENGTH: 18
<212> TYPE: DNA
<213> ORGANISM: Homo sapiens

<400> SEQUENCE: 1259
gtcccaccct gctcttag                                                18

<210> SEQ ID NO 1260
<211> LENGTH: 22
<212> TYPE: DNA
<213> ORGANISM: Homo sapiens

<400> SEQUENCE: 1260
cagagaagat gctggaatcc ac                                           22

<210> SEQ ID NO 1261
<211> LENGTH: 20
<212> TYPE: DNA
<213> ORGANISM: Homo sapiens

<400> SEQUENCE: 1261
cagagtaaga cagtgggaca                                              20

<210> SEQ ID NO 1262
<211> LENGTH: 20
<212> TYPE: DNA
<213> ORGANISM: Homo sapiens

<400> SEQUENCE: 1262
tgagtgcttg gaattttgca                                              20

<210> SEQ ID NO 1263
<211> LENGTH: 20
<212> TYPE: DNA
<213> ORGANISM: Homo sapiens

<400> SEQUENCE: 1263
aagtgtggtg cataaaggat                                           20

<210> SEQ ID NO 1264
<211> LENGTH: 20
<212> TYPE: DNA
<213> ORGANISM: Homo sapiens

<400> SEQUENCE: 1264
ggttggctac ttcatggtac                                           20

<210> SEQ ID NO 1265
<211> LENGTH: 20
<212> TYPE: DNA
<213> ORGANISM: Homo sapiens

<400> SEQUENCE: 1265
ctgtaagaag gagggtttgg                                           20

<210> SEQ ID NO 1266
<211> LENGTH: 20
<212> TYPE: DNA
<213> ORGANISM: Homo sapiens

<400> SEQUENCE: 1266
tcactgcatt cctagaacct                                           20

<210> SEQ ID NO 1267
<211> LENGTH: 20
<212> TYPE: DNA
<213> ORGANISM: Homo sapiens

<400> SEQUENCE: 1267
gaggttgatg agaggtaggg                                           20

<210> SEQ ID NO 1268
<211> LENGTH: 20
<212> TYPE: DNA
<213> ORGANISM: Homo sapiens

<400> SEQUENCE: 1268
ataactcagg caaaatgggg                                           20

<210> SEQ ID NO 1269
<211> LENGTH: 20
<212> TYPE: DNA
<213> ORGANISM: Homo sapiens

<400> SEQUENCE: 1269
agccagggat attgttgaag                                           20

<210> SEQ ID NO 1270
<211> LENGTH: 20
<212> TYPE: DNA
<213> ORGANISM: Homo sapiens

<400> SEQUENCE: 1270
ccttctgctc tcactttacg                                           20

<210> SEQ ID NO 1271
<211> LENGTH: 20
<212> TYPE: DNA

```
<213> ORGANISM: Homo sapiens

<400> SEQUENCE: 1271
caggtaagtg tgtgttccag                                               20

<210> SEQ ID NO 1272
<211> LENGTH: 20
<212> TYPE: DNA
<213> ORGANISM: Homo sapiens

<400> SEQUENCE: 1272
ggatactagc agaggtggag                                               20

<210> SEQ ID NO 1273
<211> LENGTH: 20
<212> TYPE: DNA
<213> ORGANISM: Homo sapiens

<400> SEQUENCE: 1273
ttgatttcca tgcagaaggg                                               20

<210> SEQ ID NO 1274
<211> LENGTH: 21
<212> TYPE: DNA
<213> ORGANISM: Homo sapiens

<400> SEQUENCE: 1274
tgtacacaat atgccaggaa c                                             21

<210> SEQ ID NO 1275
<211> LENGTH: 20
<212> TYPE: DNA
<213> ORGANISM: Homo sapiens

<400> SEQUENCE: 1275
taatttggcc ttaggggttg                                               20

<210> SEQ ID NO 1276
<211> LENGTH: 20
<212> TYPE: DNA
<213> ORGANISM: Homo sapiens

<400> SEQUENCE: 1276
gcacttgagt tatgggactt                                               20

<210> SEQ ID NO 1277
<211> LENGTH: 21
<212> TYPE: DNA
<213> ORGANISM: Homo sapiens

<400> SEQUENCE: 1277
tccataaaag gtgcttaaag c                                             21

<210> SEQ ID NO 1278
<211> LENGTH: 23
<212> TYPE: DNA
<213> ORGANISM: Homo sapiens

<400> SEQUENCE: 1278
tgtgatatgt agtgtgtatc agt                                           23

<210> SEQ ID NO 1279
<211> LENGTH: 20
```

```
<212> TYPE: DNA
<213> ORGANISM: Homo sapiens

<400> SEQUENCE: 1279
ttgtatcaca ccatcgtgga                                              20

<210> SEQ ID NO 1280
<211> LENGTH: 20
<212> TYPE: DNA
<213> ORGANISM: Homo sapiens

<400> SEQUENCE: 1280
gaatgtgttc aaaggagggt                                              20

<210> SEQ ID NO 1281
<211> LENGTH: 20
<212> TYPE: DNA
<213> ORGANISM: Homo sapiens

<400> SEQUENCE: 1281
actgctgaga acaatcatgc                                              20

<210> SEQ ID NO 1282
<211> LENGTH: 20
<212> TYPE: DNA
<213> ORGANISM: Homo sapiens

<400> SEQUENCE: 1282
gatgaagggg attacgggaa                                              20

<210> SEQ ID NO 1283
<211> LENGTH: 20
<212> TYPE: DNA
<213> ORGANISM: Homo sapiens

<400> SEQUENCE: 1283
ggtgtggaga atttgtttgc                                              20

<210> SEQ ID NO 1284
<211> LENGTH: 20
<212> TYPE: DNA
<213> ORGANISM: Homo sapiens

<400> SEQUENCE: 1284
tttaggaagc agcacaagaa                                              20

<210> SEQ ID NO 1285
<211> LENGTH: 20
<212> TYPE: DNA
<213> ORGANISM: Homo sapiens

<400> SEQUENCE: 1285
tgatattagg cggtggctta                                              20

<210> SEQ ID NO 1286
<211> LENGTH: 18
<212> TYPE: DNA
<213> ORGANISM: Homo sapiens

<400> SEQUENCE: 1286
gagggtgctg gggttatc                                                18

<210> SEQ ID NO 1287
```

```
<211> LENGTH: 20
<212> TYPE: DNA
<213> ORGANISM: Homo sapiens

<400> SEQUENCE: 1287
tctcacctaa aatctggggc                                               20

<210> SEQ ID NO 1288
<211> LENGTH: 20
<212> TYPE: DNA
<213> ORGANISM: Homo sapiens

<400> SEQUENCE: 1288
cccgaaagca cttaccttt                                                20

<210> SEQ ID NO 1289
<211> LENGTH: 22
<212> TYPE: DNA
<213> ORGANISM: Homo sapiens

<400> SEQUENCE: 1289
aggactgtga cactttatct tt                                            22

<210> SEQ ID NO 1290
<211> LENGTH: 20
<212> TYPE: DNA
<213> ORGANISM: Homo sapiens

<400> SEQUENCE: 1290
ttcatgagct gcaatgtgtt                                               20

<210> SEQ ID NO 1291
<211> LENGTH: 21
<212> TYPE: DNA
<213> ORGANISM: Homo sapiens

<400> SEQUENCE: 1291
atgcgaggta gaaaatgaga g                                             21

<210> SEQ ID NO 1292
<211> LENGTH: 20
<212> TYPE: DNA
<213> ORGANISM: Homo sapiens

<400> SEQUENCE: 1292
tgctatgaaa agagggacca                                               20

<210> SEQ ID NO 1293
<211> LENGTH: 21
<212> TYPE: DNA
<213> ORGANISM: Homo sapiens

<400> SEQUENCE: 1293
tgtggcttta aggttctgaa g                                             21

<210> SEQ ID NO 1294
<211> LENGTH: 20
<212> TYPE: DNA
<213> ORGANISM: Homo sapiens

<400> SEQUENCE: 1294
gtcctggatc tacacgtgaa                                               20
```

```
<210> SEQ ID NO 1295
<211> LENGTH: 20
<212> TYPE: DNA
<213> ORGANISM: Homo sapiens

<400> SEQUENCE: 1295
tcgttgctat tctgctttga                                               20

<210> SEQ ID NO 1296
<211> LENGTH: 20
<212> TYPE: DNA
<213> ORGANISM: Homo sapiens

<400> SEQUENCE: 1296
gtaaatctgt gtgccagcaa                                               20

<210> SEQ ID NO 1297
<211> LENGTH: 20
<212> TYPE: DNA
<213> ORGANISM: Homo sapiens

<400> SEQUENCE: 1297 tccctttgt ggtttcttgg                                                20

<210> SEQ ID NO 1298
<211> LENGTH: 20
<212> TYPE: DNA
<213> ORGANISM: Homo sapiens

<400> SEQUENCE: 1298
taaaagaggc gtgtggaaaa                                               20

<210> SEQ ID NO 1299
<211> LENGTH: 20
<212> TYPE: DNA
<213> ORGANISM: Homo sapiens

<400> SEQUENCE: 1299
ttgccgcact cttcattaat                                               20

<210> SEQ ID NO 1300
<211> LENGTH: 20
<212> TYPE: DNA
<213> ORGANISM: Homo sapiens

<400> SEQUENCE: 1300
ccagtagctt gtgatgtgta                                               20

<210> SEQ ID NO 1301
<211> LENGTH: 20
<212> TYPE: DNA
<213> ORGANISM: Homo sapiens

<400> SEQUENCE: 1301
actggcttct cctcattagt                                               20

<210> SEQ ID NO 1302
<211> LENGTH: 20
<212> TYPE: DNA
<213> ORGANISM: Homo sapiens

<400> SEQUENCE: 1302
tacaggcctc tgaaagatga                                               20
```

<210> SEQ ID NO 1303
<211> LENGTH: 20
<212> TYPE: DNA
<213> ORGANISM: Homo sapiens

<400> SEQUENCE: 1303
actgatttgc catgtagagc                                              20

<210> SEQ ID NO 1304
<211> LENGTH: 20
<212> TYPE: DNA
<213> ORGANISM: Homo sapiens

<400> SEQUENCE: 1304
agagcatgct agacgtcttt                                              20

<210> SEQ ID NO 1305
<211> LENGTH: 20
<212> TYPE: DNA
<213> ORGANISM: Homo sapiens

<400> SEQUENCE: 1305
gaatgtcata ttgcctgcca                                              20

<210> SEQ ID NO 1306
<211> LENGTH: 20
<212> TYPE: DNA
<213> ORGANISM: Homo sapiens

<400> SEQUENCE: 1306
ctgggctgta attaaggctc                                              20

<210> SEQ ID NO 1307
<211> LENGTH: 20
<212> TYPE: DNA
<213> ORGANISM: Homo sapiens

<400> SEQUENCE: 1307
tcactcgctt agaatgttgc                                              20

<210> SEQ ID NO 1308
<211> LENGTH: 20
<212> TYPE: DNA
<213> ORGANISM: Homo sapiens

<400> SEQUENCE: 1308
aacacctgca cactttgaaa                                              20

<210> SEQ ID NO 1309
<211> LENGTH: 21
<212> TYPE: DNA
<213> ORGANISM: Homo sapiens

<400> SEQUENCE: 1309
accattaact tcctgcaaac t                                            21

<210> SEQ ID NO 1310
<211> LENGTH: 20
<212> TYPE: DNA
<213> ORGANISM: Homo sapiens

<400> SEQUENCE: 1310
aatgaacttt gtgggctgaa                                              20

```
<210> SEQ ID NO 1311
<211> LENGTH: 20
<212> TYPE: DNA
<213> ORGANISM: Homo sapiens

<400> SEQUENCE: 1311
taaagcccca taccaggatt                                                   20

<210> SEQ ID NO 1312
<211> LENGTH: 20
<212> TYPE: DNA
<213> ORGANISM: Homo sapiens

<400> SEQUENCE: 1312
ccacactctc actggttcta                                                   20

<210> SEQ ID NO 1313
<211> LENGTH: 20
<212> TYPE: DNA
<213> ORGANISM: Homo sapiens

<400> SEQUENCE: 1313
ccaaaaatca cccatatgcg                                                   20

<210> SEQ ID NO 1314
<211> LENGTH: 20
<212> TYPE: DNA
<213> ORGANISM: Homo sapiens

<400> SEQUENCE: 1314
cacagtggat acctcaggaa                                                   20

<210> SEQ ID NO 1315
<211> LENGTH: 20
<212> TYPE: DNA
<213> ORGANISM: Homo sapiens

<400> SEQUENCE: 1315
ataacccagg tgcttcaaag                                                   20

<210> SEQ ID NO 1316
<211> LENGTH: 20
<212> TYPE: DNA
<213> ORGANISM: Homo sapiens

<400> SEQUENCE: 1316
ccaacacagg aggaactttt                                                   20

<210> SEQ ID NO 1317
<211> LENGTH: 19
<212> TYPE: DNA
<213> ORGANISM: Homo sapiens

<400> SEQUENCE: 1317
tccacagcag aagtaacga                                                    19

<210> SEQ ID NO 1318
<211> LENGTH: 22
<212> TYPE: DNA
<213> ORGANISM: Homo sapiens
```

```
<400> SEQUENCE: 1318
gagaaaagcc aacaaaaatg tg                                              22

<210> SEQ ID NO 1319
<211> LENGTH: 21
<212> TYPE: DNA
<213> ORGANISM: Homo sapiens

<400> SEQUENCE: 1319
aggaaagcta tgaagaaagg g                                               21

<210> SEQ ID NO 1320
<211> LENGTH: 22
<212> TYPE: DNA
<213> ORGANISM: Homo sapiens

<400> SEQUENCE: 1320
tgtcattact agaagcacct tt                                              22

<210> SEQ ID NO 1321
<211> LENGTH: 20
<212> TYPE: DNA
<213> ORGANISM: Homo sapiens

<400> SEQUENCE: 1321
agctccagag tgtcagtatt                                                 20

<210> SEQ ID NO 1322
<211> LENGTH: 23
<212> TYPE: DNA
<213> ORGANISM: Homo sapiens

<400> SEQUENCE: 1322
tggtgtgagt tcaggagggt tta                                             23

<210> SEQ ID NO 1323
<211> LENGTH: 22
<212> TYPE: DNA
<213> ORGANISM: Homo sapiens

<400> SEQUENCE: 1323
ttgatttcca gcactgaact tt                                              22

<210> SEQ ID NO 1324
<211> LENGTH: 20
<212> TYPE: DNA
<213> ORGANISM: Homo sapiens

<400> SEQUENCE: 1324
accatttctg acagaacaga                                                 20

<210> SEQ ID NO 1325
<211> LENGTH: 20
<212> TYPE: DNA
<213> ORGANISM: Homo sapiens

<400> SEQUENCE: 1325
tgtttgattt ttcaggctga                                                 20

<210> SEQ ID NO 1326
<211> LENGTH: 20
<212> TYPE: DNA
```

```
<213> ORGANISM: Homo sapiens

<400> SEQUENCE: 1326
tgatgcttaa acacatgcct                                               20

<210> SEQ ID NO 1327
<211> LENGTH: 20
<212> TYPE: DNA
<213> ORGANISM: Homo sapiens

<400> SEQUENCE: 1327
ctggtcattc ctgagtgtct                                               20

<210> SEQ ID NO 1328
<211> LENGTH: 20
<212> TYPE: DNA
<213> ORGANISM: Homo sapiens

<400> SEQUENCE: 1328
aagggatatg cagcttgttc                                               20

<210> SEQ ID NO 1329
<211> LENGTH: 25
<212> TYPE: DNA
<213> ORGANISM: Homo sapiens

<400> SEQUENCE: 1329
tcctgtttta cacttttcta acttt                                         25

<210> SEQ ID NO 1330
<211> LENGTH: 23
<212> TYPE: DNA
<213> ORGANISM: Homo sapiens

<400> SEQUENCE: 1330
gctttaaact atggaactgc tga                                           23

<210> SEQ ID NO 1331
<211> LENGTH: 20
<212> TYPE: DNA
<213> ORGANISM: Homo sapiens

<400> SEQUENCE: 1331
acctcaacct gttttagcac                                               20

<210> SEQ ID NO 1332
<211> LENGTH: 22
<212> TYPE: DNA
<213> ORGANISM: Homo sapiens

<400> SEQUENCE: 1332
gttgtcattc aaatgtcacc ac                                            22

<210> SEQ ID NO 1333
<211> LENGTH: 20
<212> TYPE: DNA
<213> ORGANISM: Homo sapiens

<400> SEQUENCE: 1333
cagtgtgtgt catgccaaat                                               20

<210> SEQ ID NO 1334
<211> LENGTH: 19
```

```
<212> TYPE: DNA
<213> ORGANISM: Homo sapiens

<400> SEQUENCE: 1334
ctcagattcc agagccctc                                            19

<210> SEQ ID NO 1335
<211> LENGTH: 21
<212> TYPE: DNA
<213> ORGANISM: Homo sapiens

<400> SEQUENCE: 1335
ggtctatgtt aatcttgggc c                                         21

<210> SEQ ID NO 1336
<211> LENGTH: 20
<212> TYPE: DNA
<213> ORGANISM: Homo sapiens

<400> SEQUENCE: 1336
acattgctag cagcttttgt                                           20

<210> SEQ ID NO 1337
<211> LENGTH: 21
<212> TYPE: DNA
<213> ORGANISM: Homo sapiens

<400> SEQUENCE: 1337
agccagtctg tatctaaagg t                                         21

<210> SEQ ID NO 1338
<211> LENGTH: 21
<212> TYPE: DNA
<213> ORGANISM: Homo sapiens

<400> SEQUENCE: 1338
acttgccaag aacagtatct g                                         21

<210> SEQ ID NO 1339
<211> LENGTH: 20
<212> TYPE: DNA
<213> ORGANISM: Homo sapiens

<400> SEQUENCE: 1339
actcttgggg tttcttcagt                                           20

<210> SEQ ID NO 1340
<211> LENGTH: 20
<212> TYPE: DNA
<213> ORGANISM: Homo sapiens

<400> SEQUENCE: 1340
ttccttcttc caggtgaaca                                           20

<210> SEQ ID NO 1341
<211> LENGTH: 21
<212> TYPE: DNA
<213> ORGANISM: Homo sapiens

<400> SEQUENCE: 1341
cgaaccaaaa gcaaaatcct t                                         21

<210> SEQ ID NO 1342
```

```
<211> LENGTH: 20
<212> TYPE: DNA
<213> ORGANISM: Homo sapiens

<400> SEQUENCE: 1342
tgtttctcct tcatctggtc                                              20

<210> SEQ ID NO 1343
<211> LENGTH: 20
<212> TYPE: DNA
<213> ORGANISM: Homo sapiens

<400> SEQUENCE: 1343
aatctatgga ggtcactggg                                              20

<210> SEQ ID NO 1344
<211> LENGTH: 20
<212> TYPE: DNA
<213> ORGANISM: Homo sapiens

<400> SEQUENCE: 1344
tgtcaccttg cagatacagg                                              20

<210> SEQ ID NO 1345
<211> LENGTH: 20
<212> TYPE: DNA
<213> ORGANISM: Homo sapiens

<400> SEQUENCE: 1345
aggtccttgt agtttgcttg                                              20

<210> SEQ ID NO 1346
<211> LENGTH: 20
<212> TYPE: DNA
<213> ORGANISM: Homo sapiens

<400> SEQUENCE: 1346
attgttcaca gggtcaagtc                                              20

<210> SEQ ID NO 1347
<211> LENGTH: 20
<212> TYPE: DNA
<213> ORGANISM: Homo sapiens

<400> SEQUENCE: 1347
gtgagagcca atagagtgtg                                              20

<210> SEQ ID NO 1348
<211> LENGTH: 20
<212> TYPE: DNA
<213> ORGANISM: Homo sapiens

<400> SEQUENCE: 1348
atgagccagg agaatcatca                                              20

<210> SEQ ID NO 1349
<211> LENGTH: 20
<212> TYPE: DNA
<213> ORGANISM: Homo sapiens

<400> SEQUENCE: 1349
gcatggtgtg tgaaagtgat                                              20
```

```
<210> SEQ ID NO 1350
<211> LENGTH: 20
<212> TYPE: DNA
<213> ORGANISM: Homo sapiens

<400> SEQUENCE: 1350
catcatttca aagggctca                                                    20

<210> SEQ ID NO 1351
<211> LENGTH: 20
<212> TYPE: DNA
<213> ORGANISM: Homo sapiens

<400> SEQUENCE: 1351
atgctgcttt tgactgatgt                                                   20

<210> SEQ ID NO 1352
<211> LENGTH: 20
<212> TYPE: DNA
<213> ORGANISM: Homo sapiens

<400> SEQUENCE: 1352
tcttctctaa cacccactcc                                                   20

<210> SEQ ID NO 1353
<211> LENGTH: 20
<212> TYPE: DNA
<213> ORGANISM: Homo sapiens

<400> SEQUENCE: 1353
cgaagctgta ttcctgtctc                                                   20

<210> SEQ ID NO 1354
<211> LENGTH: 20
<212> TYPE: DNA
<213> ORGANISM: Homo sapiens

<400> SEQUENCE: 1354
acccttacca aagtagcatc                                                   20

<210> SEQ ID NO 1355
<211> LENGTH: 19
<212> TYPE: DNA
<213> ORGANISM: Homo sapiens

<400> SEQUENCE: 1355
atggactaac tggagagcg                                                    19

<210> SEQ ID NO 1356
<211> LENGTH: 20
<212> TYPE: DNA
<213> ORGANISM: Homo sapiens

<400> SEQUENCE: 1356
atcacgacgc cttgtttatt                                                   20

<210> SEQ ID NO 1357
<211> LENGTH: 20
<212> TYPE: DNA
<213> ORGANISM: Homo sapiens

<400> SEQUENCE: 1357
atgtcctgcc agtaaacaca                                                   20
```

```
<210> SEQ ID NO 1358
<211> LENGTH: 20
<212> TYPE: DNA
<213> ORGANISM: Homo sapiens

<400> SEQUENCE: 1358
actttcctgc caacaatctc                                          20

<210> SEQ ID NO 1359
<211> LENGTH: 20
<212> TYPE: DNA
<213> ORGANISM: Homo sapiens

<400> SEQUENCE: 1359
tgccactaaa cacctaagga                                          20

<210> SEQ ID NO 1360
<211> LENGTH: 20
<212> TYPE: DNA
<213> ORGANISM: Homo sapiens

<400> SEQUENCE: 1360
ttgatagttg catctgggga                                          20

<210> SEQ ID NO 1361
<211> LENGTH: 20
<212> TYPE: DNA
<213> ORGANISM: Homo sapiens

<400> SEQUENCE: 1361
ttggaaattt tggggtcagg                                          20

<210> SEQ ID NO 1362
<211> LENGTH: 22
<212> TYPE: DNA
<213> ORGANISM: Homo sapiens

<400> SEQUENCE: 1362
tttgttaact aacgtgattc ca                                       22

<210> SEQ ID NO 1363
<211> LENGTH: 20
<212> TYPE: DNA
<213> ORGANISM: Homo sapiens

<400> SEQUENCE: 1363
ttctgacctc ccttactgag                                          20

<210> SEQ ID NO 1364
<211> LENGTH: 20
<212> TYPE: DNA
<213> ORGANISM: Homo sapiens

<400> SEQUENCE: 1364
cccactctcc atgtgttctt                                          20

<210> SEQ ID NO 1365
<211> LENGTH: 19
<212> TYPE: DNA
<213> ORGANISM: Homo sapiens

<400> SEQUENCE: 1365
tatgtgcttg cgatgtgtt                                           19
```

-continued

<210> SEQ ID NO 1366
<211> LENGTH: 20
<212> TYPE: DNA
<213> ORGANISM: Homo sapiens

<400> SEQUENCE: 1366
tcctgcttca actcaatacg                                                  20

<210> SEQ ID NO 1367
<211> LENGTH: 20
<212> TYPE: DNA
<213> ORGANISM: Homo sapiens

<400> SEQUENCE: 1367
gaaccttagg gccagtctat                                                  20

<210> SEQ ID NO 1368
<211> LENGTH: 20
<212> TYPE: DNA
<213> ORGANISM: Homo sapiens

<400> SEQUENCE: 1368
acccctcatt ttcgtatgtc                                                  20

<210> SEQ ID NO 1369
<211> LENGTH: 21
<212> TYPE: DNA
<213> ORGANISM: Homo sapiens

<400> SEQUENCE: 1369
agaacctgat gtgttttcct c                                                21

<210> SEQ ID NO 1370
<211> LENGTH: 20
<212> TYPE: DNA
<213> ORGANISM: Homo sapiens

<400> SEQUENCE: 1370
acagttatgg aggaattgcg                                                  20

<210> SEQ ID NO 1371
<211> LENGTH: 20
<212> TYPE: DNA
<213> ORGANISM: Homo sapiens

<400> SEQUENCE: 1371
atgtgagaga agcaaaaccc                                                  20

<210> SEQ ID NO 1372
<211> LENGTH: 22
<212> TYPE: DNA
<213> ORGANISM: Homo sapiens

<400> SEQUENCE: 1372
tcaaacctct tttatctgtc cc                                               22

<210> SEQ ID NO 1373
<211> LENGTH: 20
<212> TYPE: DNA
<213> ORGANISM: Homo sapiens

```
<400> SEQUENCE: 1373
gtagttgtct tgagggcttt                                            20

<210> SEQ ID NO 1374
<211> LENGTH: 20
<212> TYPE: DNA
<213> ORGANISM: Homo sapiens

<400> SEQUENCE: 1374
atttcacgta acactctggt                                            20

<210> SEQ ID NO 1375
<211> LENGTH: 20
<212> TYPE: DNA
<213> ORGANISM: Homo sapiens

<400> SEQUENCE: 1375
cctggtcaac aacatatggg                                            20

<210> SEQ ID NO 1376
<211> LENGTH: 21
<212> TYPE: DNA
<213> ORGANISM: Homo sapiens

<400> SEQUENCE: 1376
ctctggcaaa actttctgga t                                          21

<210> SEQ ID NO 1377
<211> LENGTH: 21
<212> TYPE: DNA
<213> ORGANISM: Homo sapiens

<400> SEQUENCE: 1377
agaatattgc atttggccag a                                          21

<210> SEQ ID NO 1378
<211> LENGTH: 19
<212> TYPE: DNA
<213> ORGANISM: Homo sapiens

<400> SEQUENCE: 1378
gcttctcatg ctcacactg                                             19

<210> SEQ ID NO 1379
<211> LENGTH: 21
<212> TYPE: DNA
<213> ORGANISM: Homo sapiens

<400> SEQUENCE: 1379
aaagctatgc aaatagtggc a                                          21

<210> SEQ ID NO 1380
<211> LENGTH: 21
<212> TYPE: DNA
<213> ORGANISM: Homo sapiens

<400> SEQUENCE: 1380
aatatgactt gccctttga a                                           21

<210> SEQ ID NO 1381
<211> LENGTH: 20
<212> TYPE: DNA
```

```
<213> ORGANISM: Homo sapiens

<400> SEQUENCE: 1381
agttcccaac agaggctaat                                               20

<210> SEQ ID NO 1382
<211> LENGTH: 19
<212> TYPE: DNA
<213> ORGANISM: Homo sapiens

<400> SEQUENCE: 1382
tcacagccag ttacacaga                                                19

<210> SEQ ID NO 1383
<211> LENGTH: 20
<212> TYPE: DNA
<213> ORGANISM: Homo sapiens

<400> SEQUENCE: 1383
agttataggt gaggaagggc                                               20

<210> SEQ ID NO 1384
<211> LENGTH: 20
<212> TYPE: DNA
<213> ORGANISM: Homo sapiens

<400> SEQUENCE: 1384
ctacagtgca gaagagtccc                                               20

<210> SEQ ID NO 1385
<211> LENGTH: 20
<212> TYPE: DNA
<213> ORGANISM: Homo sapiens

<400> SEQUENCE: 1385
cactgcaaaa gaaggaggtt                                               20

<210> SEQ ID NO 1386
<211> LENGTH: 20
<212> TYPE: DNA
<213> ORGANISM: Homo sapiens

<400> SEQUENCE: 1386
ttggtttcat gtggctttga                                               20

<210> SEQ ID NO 1387
<211> LENGTH: 21
<212> TYPE: DNA
<213> ORGANISM: Homo sapiens

<400> SEQUENCE: 1387
tctcaacatc gctgatctag t                                             21

<210> SEQ ID NO 1388
<211> LENGTH: 20
<212> TYPE: DNA
<213> ORGANISM: Homo sapiens

<400> SEQUENCE: 1388
tccttctccc caactttctt                                               20

<210> SEQ ID NO 1389
<211> LENGTH: 20
```

<212> TYPE: DNA
<213> ORGANISM: Homo sapiens

<400> SEQUENCE: 1389
aggtagctgg aaaaggagaa                    20

<210> SEQ ID NO 1390
<211> LENGTH: 21
<212> TYPE: DNA
<213> ORGANISM: Homo sapiens

<400> SEQUENCE: 1390
ctttagattc cagggctctt g                   21

<210> SEQ ID NO 1391
<211> LENGTH: 21
<212> TYPE: DNA
<213> ORGANISM: Homo sapiens

<400> SEQUENCE: 1391
tgaaattgcc cagaattgag t                   21

<210> SEQ ID NO 1392
<211> LENGTH: 20
<212> TYPE: DNA
<213> ORGANISM: Homo sapiens

<400> SEQUENCE: 1392
tgaaagcgtg aaaatcagct                    20

<210> SEQ ID NO 1393
<211> LENGTH: 20
<212> TYPE: DNA
<213> ORGANISM: Homo sapiens

<400> SEQUENCE: 1393
attttcctgg acttctgaca                    20

<210> SEQ ID NO 1394
<211> LENGTH: 20
<212> TYPE: DNA
<213> ORGANISM: Homo sapiens

<400> SEQUENCE: 1394
actcgatccc taggtaatgt                    20

<210> SEQ ID NO 1395
<211> LENGTH: 21
<212> TYPE: DNA
<213> ORGANISM: Homo sapiens

<400> SEQUENCE: 1395
tgttattcct cttcctgtcc a                   21

<210> SEQ ID NO 1396
<211> LENGTH: 20
<212> TYPE: DNA
<213> ORGANISM: Homo sapiens

<400> SEQUENCE: 1396
acaagtgggt agggatgttc                    20

<210> SEQ ID NO 1397

```
<211> LENGTH: 20
<212> TYPE: DNA
<213> ORGANISM: Homo sapiens

<400> SEQUENCE: 1397
taaccacaca actacagctt                                          20

<210> SEQ ID NO 1398
<211> LENGTH: 20
<212> TYPE: DNA
<213> ORGANISM: Homo sapiens

<400> SEQUENCE: 1398
gcacaagttt tcagggaatg                                          20

<210> SEQ ID NO 1399
<211> LENGTH: 20
<212> TYPE: DNA
<213> ORGANISM: Homo sapiens

<400> SEQUENCE: 1399
attcaaaatg gggacgagag                                          20

<210> SEQ ID NO 1400
<211> LENGTH: 20
<212> TYPE: DNA
<213> ORGANISM: Homo sapiens

<400> SEQUENCE: 1400
gtggaaagtc tcgtcagaat                                          20

<210> SEQ ID NO 1401
<211> LENGTH: 19
<212> TYPE: DNA
<213> ORGANISM: Homo sapiens

<400> SEQUENCE: 1401
tcccagtttg ctactctgg                                           19

<210> SEQ ID NO 1402
<211> LENGTH: 20
<212> TYPE: DNA
<213> ORGANISM: Homo sapiens

<400> SEQUENCE: 1402
tccacctctg agcataacat                                          20

<210> SEQ ID NO 1403
<211> LENGTH: 24
<212> TYPE: DNA
<213> ORGANISM: Homo sapiens

<400> SEQUENCE: 1403
tctcattatg tgaagattgc tttc                                     24

<210> SEQ ID NO 1404
<211> LENGTH: 23
<212> TYPE: DNA
<213> ORGANISM: Homo sapiens

<400> SEQUENCE: 1404
ttgatcttca tcctccactg tct                                      23
```

```
<210> SEQ ID NO 1405
<211> LENGTH: 23
<212> TYPE: DNA
<213> ORGANISM: Homo sapiens

<400> SEQUENCE: 1405
ttaagattaa gcagtcttct tgg                                              23

<210> SEQ ID NO 1406
<211> LENGTH: 21
<212> TYPE: DNA
<213> ORGANISM: Homo sapiens

<400> SEQUENCE: 1406
ccaaactgac cgacttacac c                                                21

<210> SEQ ID NO 1407
<211> LENGTH: 20
<212> TYPE: DNA
<213> ORGANISM: Homo sapiens

<400> SEQUENCE: 1407
caacagatct gattctgccc                                                  20

<210> SEQ ID NO 1408
<211> LENGTH: 20
<212> TYPE: DNA
<213> ORGANISM: Homo sapiens

<400> SEQUENCE: 1408
ccatcccact tctccagata                                                  20

<210> SEQ ID NO 1409
<211> LENGTH: 20
<212> TYPE: DNA
<213> ORGANISM: Homo sapiens

<400> SEQUENCE: 1409
catgtgtttc aaagttggct                                                  20

<210> SEQ ID NO 1410
<211> LENGTH: 20
<212> TYPE: DNA
<213> ORGANISM: Homo sapiens

<400> SEQUENCE: 1410
ccaccttcct gcttaaagaa                                                  20

<210> SEQ ID NO 1411
<211> LENGTH: 21
<212> TYPE: DNA
<213> ORGANISM: Homo sapiens

<400> SEQUENCE: 1411
actatagcat tagggtgagg g                                                21

<210> SEQ ID NO 1412
<211> LENGTH: 20
<212> TYPE: DNA
<213> ORGANISM: Homo sapiens

<400> SEQUENCE: 1412
ctccttactt gcactgagtt                                                  20
```

```
<210> SEQ ID NO 1413
<211> LENGTH: 20
<212> TYPE: DNA
<213> ORGANISM: Homo sapiens

<400> SEQUENCE: 1413
gagatttgga catgctttca                                              20

<210> SEQ ID NO 1414
<211> LENGTH: 20
<212> TYPE: DNA
<213> ORGANISM: Homo sapiens

<400> SEQUENCE: 1414
gggaaaactt acgggaactt                                              20

<210> SEQ ID NO 1415
<211> LENGTH: 19
<212> TYPE: DNA
<213> ORGANISM: Homo sapiens

<400> SEQUENCE: 1415
cccaccacca gttgtcatc                                               19

<210> SEQ ID NO 1416
<211> LENGTH: 22
<212> TYPE: DNA
<213> ORGANISM: Homo sapiens

<400> SEQUENCE: 1416
tagaaatgtt tagggtgcat ga                                           22

<210> SEQ ID NO 1417
<211> LENGTH: 21
<212> TYPE: DNA
<213> ORGANISM: Homo sapiens

<400> SEQUENCE: 1417
gccactcact tcctagataa t                                            21

<210> SEQ ID NO 1418
<211> LENGTH: 20
<212> TYPE: DNA
<213> ORGANISM: Homo sapiens

<400> SEQUENCE: 1418
tacccctctt ttccatctgc                                              20

<210> SEQ ID NO 1419
<211> LENGTH: 20
<212> TYPE: DNA
<213> ORGANISM: Homo sapiens

<400> SEQUENCE: 1419
acagtatctc agggccttat                                              20

<210> SEQ ID NO 1420
<211> LENGTH: 20
<212> TYPE: DNA
<213> ORGANISM: Homo sapiens

<400> SEQUENCE: 1420
gcattttgac aggaaagtgg                                              20
```

```
<210> SEQ ID NO 1421
<211> LENGTH: 21
<212> TYPE: DNA
<213> ORGANISM: Homo sapiens

<400> SEQUENCE: 1421
tcagtagttc ctcagatgct a                                              21

<210> SEQ ID NO 1422
<211> LENGTH: 20
<212> TYPE: DNA
<213> ORGANISM: Homo sapiens

<400> SEQUENCE: 1422
tagggccaca gtttctcaat                                                20

<210> SEQ ID NO 1423
<211> LENGTH: 20
<212> TYPE: DNA
<213> ORGANISM: Homo sapiens

<400> SEQUENCE: 1423
aatgcatgaa agtccaggaa                                                20

<210> SEQ ID NO 1424
<211> LENGTH: 20
<212> TYPE: DNA
<213> ORGANISM: Homo sapiens

<400> SEQUENCE: 1424
gaatgagaaa tctggcagga                                                20

<210> SEQ ID NO 1425
<211> LENGTH: 21
<212> TYPE: DNA
<213> ORGANISM: Homo sapiens

<400> SEQUENCE: 1425
acatgcactc ttgtcttatg c                                              21

<210> SEQ ID NO 1426
<211> LENGTH: 20
<212> TYPE: DNA
<213> ORGANISM: Homo sapiens

<400> SEQUENCE: 1426
tcagatgcct gatgaccata                                                20

<210> SEQ ID NO 1427
<211> LENGTH: 22
<212> TYPE: DNA
<213> ORGANISM: Homo sapiens

<400> SEQUENCE: 1427
cacatatact ggctttctgg tc                                             22

<210> SEQ ID NO 1428
<211> LENGTH: 20
<212> TYPE: DNA
<213> ORGANISM: Homo sapiens
```

```
<400> SEQUENCE: 1428
aatatgcagt gggtaggagc                                               20

<210> SEQ ID NO 1429
<211> LENGTH: 19
<212> TYPE: DNA
<213> ORGANISM: Homo sapiens

<400> SEQUENCE: 1429
gcacatgtca ttagcaggg                                                19

<210> SEQ ID NO 1430
<211> LENGTH: 20
<212> TYPE: DNA
<213> ORGANISM: Homo sapiens

<400> SEQUENCE: 1430
gacaacagct gacttccatt                                               20

<210> SEQ ID NO 1431
<211> LENGTH: 20
<212> TYPE: DNA
<213> ORGANISM: Homo sapiens

<400> SEQUENCE: 1431
acatgctcaa ttatggagcc                                               20

<210> SEQ ID NO 1432
<211> LENGTH: 20
<212> TYPE: DNA
<213> ORGANISM: Homo sapiens

<400> SEQUENCE: 1432
cactctctgg aacaaacaca                                               20

<210> SEQ ID NO 1433
<211> LENGTH: 20
<212> TYPE: DNA
<213> ORGANISM: Homo sapiens

<400> SEQUENCE: 1433
acaaagacag gaatagggct                                               20

<210> SEQ ID NO 1434
<211> LENGTH: 20
<212> TYPE: DNA
<213> ORGANISM: Homo sapiens

<400> SEQUENCE: 1434
gttttgaggc ggtttcatga                                               20

<210> SEQ ID NO 1435
<211> LENGTH: 25
<212> TYPE: DNA
<213> ORGANISM: Homo sapiens

<400> SEQUENCE: 1435
caatctgctg acttgcttct tttca                                         25

<210> SEQ ID NO 1436
<211> LENGTH: 22
<212> TYPE: DNA
```

```
<213> ORGANISM: Homo sapiens

<400> SEQUENCE: 1436
ggcactgagg aaattctgag ac                                          22

<210> SEQ ID NO 1437
<211> LENGTH: 21
<212> TYPE: DNA
<213> ORGANISM: Homo sapiens

<400> SEQUENCE: 1437
ctttggctca gaatcttcca a                                           21

<210> SEQ ID NO 1438
<211> LENGTH: 20
<212> TYPE: DNA
<213> ORGANISM: Homo sapiens

<400> SEQUENCE: 1438
gaacacctca aagttgctca                                             20

<210> SEQ ID NO 1439
<211> LENGTH: 21
<212> TYPE: DNA
<213> ORGANISM: Homo sapiens

<400> SEQUENCE: 1439
tgtatgagga ccagcagtaa a                                           21

<210> SEQ ID NO 1440
<211> LENGTH: 20
<212> TYPE: DNA
<213> ORGANISM: Homo sapiens

<400> SEQUENCE: 1440
aagaagcaag gacaaggatg                                             20

<210> SEQ ID NO 1441
<211> LENGTH: 20
<212> TYPE: DNA
<213> ORGANISM: Homo sapiens

<400> SEQUENCE: 1441
tcttttcccc ttgtgcatag                                             20

<210> SEQ ID NO 1442
<211> LENGTH: 20
<212> TYPE: DNA
<213> ORGANISM: Homo sapiens

<400> SEQUENCE: 1442
gaaacaacca ccacaacaaa                                             20

<210> SEQ ID NO 1443
<211> LENGTH: 20
<212> TYPE: DNA
<213> ORGANISM: Homo sapiens

<400> SEQUENCE: 1443
gcttagtgtg tgtgatccgt                                             20

<210> SEQ ID NO 1444
<211> LENGTH: 20
```

-continued

```
<212> TYPE: DNA
<213> ORGANISM: Homo sapiens

<400> SEQUENCE: 1444
ccaccatgtt tacaccgttt                                               20

<210> SEQ ID NO 1445
<211> LENGTH: 20
<212> TYPE: DNA
<213> ORGANISM: Homo sapiens

<400> SEQUENCE: 1445 actcacctttt cccaagaaga                                              20

<210> SEQ ID NO 1446
<211> LENGTH: 20
<212> TYPE: DNA
<213> ORGANISM: Homo sapiens

<400> SEQUENCE: 1446
tttacccatg aattgctgca                                               20

<210> SEQ ID NO 1447
<211> LENGTH: 20
<212> TYPE: DNA
<213> ORGANISM: Homo sapiens

<400> SEQUENCE: 1447
tggtagtggg aagaggttga                                               20

<210> SEQ ID NO 1448
<211> LENGTH: 20
<212> TYPE: DNA
<213> ORGANISM: Homo sapiens

<400> SEQUENCE: 1448
agtttgcatt tgttcaggga                                               20

<210> SEQ ID NO 1449
<211> LENGTH: 20
<212> TYPE: DNA
<213> ORGANISM: Homo sapiens

<400> SEQUENCE: 1449
gcatggagaa caaaagctga                                               20

<210> SEQ ID NO 1450
<211> LENGTH: 20
<212> TYPE: DNA
<213> ORGANISM: Homo sapiens

<400> SEQUENCE: 1450
ttcggatggc tttgattgtc                                               20

<210> SEQ ID NO 1451
<211> LENGTH: 20
<212> TYPE: DNA
<213> ORGANISM: Homo sapiens

<400> SEQUENCE: 1451
tgtgagcaag aaactgaagg                                               20

<210> SEQ ID NO 1452
```

```
<211> LENGTH: 21
<212> TYPE: DNA
<213> ORGANISM: Homo sapiens

<400> SEQUENCE: 1452
cattgtaaat taaacggcct c                                              21

<210> SEQ ID NO 1453
<211> LENGTH: 20
<212> TYPE: DNA
<213> ORGANISM: Homo sapiens

<400> SEQUENCE: 1453
agtatcactt gtccagctca                                                20

<210> SEQ ID NO 1454
<211> LENGTH: 20
<212> TYPE: DNA
<213> ORGANISM: Homo sapiens

<400> SEQUENCE: 1454
ctaatgcaag ctgcttctct                                                20

<210> SEQ ID NO 1455
<211> LENGTH: 20
<212> TYPE: DNA
<213> ORGANISM: Homo sapiens

<400> SEQUENCE: 1455
cacaggacta ggtaggcttt                                                20

<210> SEQ ID NO 1456
<211> LENGTH: 20
<212> TYPE: DNA
<213> ORGANISM: Homo sapiens

<400> SEQUENCE: 1456
tgtctagtgg taatctgggg                                                20

<210> SEQ ID NO 1457
<211> LENGTH: 21
<212> TYPE: DNA
<213> ORGANISM: Homo sapiens

<400> SEQUENCE: 1457
gtgttaacag ctttcccttc a                                              21

<210> SEQ ID NO 1458
<211> LENGTH: 20
<212> TYPE: DNA
<213> ORGANISM: Homo sapiens

<400> SEQUENCE: 1458
tctggacagt ggagttgaaa                                                20

<210> SEQ ID NO 1459
<211> LENGTH: 23
<212> TYPE: DNA
<213> ORGANISM: Homo sapiens

<400> SEQUENCE: 1459
tcatgtacag aaagaattag cct                                            23
```

```
<210> SEQ ID NO 1460
<211> LENGTH: 20
<212> TYPE: DNA
<213> ORGANISM: Homo sapiens

<400> SEQUENCE: 1460
accaccacaa acatagctga                                               20

<210> SEQ ID NO 1461
<211> LENGTH: 20
<212> TYPE: DNA
<213> ORGANISM: Homo sapiens

<400> SEQUENCE: 1461
agaggccaag tgaccaaata                                               20

<210> SEQ ID NO 1462
<211> LENGTH: 20
<212> TYPE: DNA
<213> ORGANISM: Homo sapiens

<400> SEQUENCE: 1462
aggagagaca taactggtct                                               20

<210> SEQ ID NO 1463
<211> LENGTH: 21
<212> TYPE: DNA
<213> ORGANISM: Homo sapiens

<400> SEQUENCE: 1463
aagccagtaa ttcatcttcc c                                             21

<210> SEQ ID NO 1464
<211> LENGTH: 20
<212> TYPE: DNA
<213> ORGANISM: Homo sapiens

<400> SEQUENCE: 1464
attgcaatgt ctgtggatgt                                               20

<210> SEQ ID NO 1465
<211> LENGTH: 21
<212> TYPE: DNA
<213> ORGANISM: Homo sapiens

<400> SEQUENCE: 1465
ccatgacata acacatcacc a                                             21

<210> SEQ ID NO 1466
<211> LENGTH: 19
<212> TYPE: DNA
<213> ORGANISM: Homo sapiens

<400> SEQUENCE: 1466
aagaagttga ggtagcacg                                                19

<210> SEQ ID NO 1467
<211> LENGTH: 20
<212> TYPE: DNA
<213> ORGANISM: Homo sapiens

<400> SEQUENCE: 1467
atagatttcc tcctgggctg                                               20
```

<210> SEQ ID NO 1468
<211> LENGTH: 20
<212> TYPE: DNA
<213> ORGANISM: Homo sapiens

<400> SEQUENCE: 1468
agtgtccttt cctccagttc                                          20

<210> SEQ ID NO 1469
<211> LENGTH: 20
<212> TYPE: DNA
<213> ORGANISM: Homo sapiens

<400> SEQUENCE: 1469
ccacctctgt acccactatc                                          20

<210> SEQ ID NO 1470
<211> LENGTH: 21
<212> TYPE: DNA
<213> ORGANISM: Homo sapiens

<400> SEQUENCE: 1470
ttgaacctga aaggaactgt g                                        21

<210> SEQ ID NO 1471
<211> LENGTH: 20
<212> TYPE: DNA
<213> ORGANISM: Homo sapiens

<400> SEQUENCE: 1471
ttccctggaa gatagccaat                                          20

<210> SEQ ID NO 1472
<211> LENGTH: 20
<212> TYPE: DNA
<213> ORGANISM: Homo sapiens

<400> SEQUENCE: 1472
gctcaatcac ctgttccctt                                          20

<210> SEQ ID NO 1473
<211> LENGTH: 20
<212> TYPE: DNA
<213> ORGANISM: Homo sapiens

<400> SEQUENCE: 1473
tggacacgta aaagaaggtg                                          20

<210> SEQ ID NO 1474
<211> LENGTH: 21
<212> TYPE: DNA
<213> ORGANISM: Homo sapiens

<400> SEQUENCE: 1474
cattgaagct cactctaagg g                                        21

<210> SEQ ID NO 1475
<211> LENGTH: 20
<212> TYPE: DNA
<213> ORGANISM: Homo sapiens

<400> SEQUENCE: 1475
ctgagaacct tgtccaactg                                          20

<210> SEQ ID NO 1476
<211> LENGTH: 20
<212> TYPE: DNA
<213> ORGANISM: Homo sapiens

<400> SEQUENCE: 1476
ctaaagtttg ggttaggggt                                       20

<210> SEQ ID NO 1477
<211> LENGTH: 20
<212> TYPE: DNA
<213> ORGANISM: Homo sapiens

<400> SEQUENCE: 1477
tttcgctagt ctttgcactt                                       20

<210> SEQ ID NO 1478
<211> LENGTH: 20
<212> TYPE: DNA
<213> ORGANISM: Homo sapiens

<400> SEQUENCE: 1478
tgccttacat tttctgtggg                                       20

<210> SEQ ID NO 1479
<211> LENGTH: 20
<212> TYPE: DNA
<213> ORGANISM: Homo sapiens

<400> SEQUENCE: 1479
gcggcaataa ttgtcacaaa                                       20

<210> SEQ ID NO 1480
<211> LENGTH: 20
<212> TYPE: DNA
<213> ORGANISM: Homo sapiens

<400> SEQUENCE: 1480
gccataagat ttccccactc                                       20

<210> SEQ ID NO 1481
<211> LENGTH: 20
<212> TYPE: DNA
<213> ORGANISM: Homo sapiens

<400> SEQUENCE: 1481
cagaaatgtg tcaggctaca                                       20

<210> SEQ ID NO 1482
<211> LENGTH: 21
<212> TYPE: DNA
<213> ORGANISM: Homo sapiens

<400> SEQUENCE: 1482
acaaagcaag aggatgaaac a                                     21

<210> SEQ ID NO 1483
<211> LENGTH: 20
<212> TYPE: DNA
<213> ORGANISM: Homo sapiens

```
<400> SEQUENCE: 1483
aactcttcat tttgacgggg                                                20

<210> SEQ ID NO 1484
<211> LENGTH: 20
<212> TYPE: DNA
<213> ORGANISM: Homo sapiens

<400> SEQUENCE: 1484
caaagcacca tcaacactta                                                20

<210> SEQ ID NO 1485
<211> LENGTH: 20
<212> TYPE: DNA
<213> ORGANISM: Homo sapiens

<400> SEQUENCE: 1485
tgggttgtgc tgttgtttag                                                20

<210> SEQ ID NO 1486
<211> LENGTH: 20
<212> TYPE: DNA
<213> ORGANISM: Homo sapiens

<400> SEQUENCE: 1486
cactgcaact cctagaatga                                                20

<210> SEQ ID NO 1487
<211> LENGTH: 19
<212> TYPE: DNA
<213> ORGANISM: Homo sapiens

<400> SEQUENCE: 1487
gctcagctcc tttcatctg                                                 19

<210> SEQ ID NO 1488
<211> LENGTH: 20
<212> TYPE: DNA
<213> ORGANISM: Homo sapiens

<400> SEQUENCE: 1488
tgtggggaaa ttgctgttta                                                20

<210> SEQ ID NO 1489
<211> LENGTH: 20
<212> TYPE: DNA
<213> ORGANISM: Homo sapiens

<400> SEQUENCE: 1489
aggacattca gcctatttgc                                                20

<210> SEQ ID NO 1490
<211> LENGTH: 20
<212> TYPE: DNA
<213> ORGANISM: Homo sapiens

<400> SEQUENCE: 1490
gtatgggcag ctgtaacttg                                                20

<210> SEQ ID NO 1491
<211> LENGTH: 20
<212> TYPE: DNA
```

```
<213> ORGANISM: Homo sapiens

<400> SEQUENCE: 1491
acacagtatc aaggtcaaca                                          20

<210> SEQ ID NO 1492
<211> LENGTH: 20
<212> TYPE: DNA
<213> ORGANISM: Homo sapiens

<400> SEQUENCE: 1492
tcacaagcca ctgaaaatgt                                          20

<210> SEQ ID NO 1493
<211> LENGTH: 20
<212> TYPE: DNA
<213> ORGANISM: Homo sapiens

<400> SEQUENCE: 1493
gcagaaccac agtctatgag                                          20

<210> SEQ ID NO 1494
<211> LENGTH: 21
<212> TYPE: DNA
<213> ORGANISM: Homo sapiens

<400> SEQUENCE: 1494
tgtatgttaa gctagccaac a                                        21

<210> SEQ ID NO 1495
<211> LENGTH: 21
<212> TYPE: DNA
<213> ORGANISM: Homo sapiens

<400> SEQUENCE: 1495
aatgctccaa gttattccag a                                        21

<210> SEQ ID NO 1496
<211> LENGTH: 20
<212> TYPE: DNA
<213> ORGANISM: Homo sapiens

<400> SEQUENCE: 1496
tgtgttattg aactttgcca                                          20

<210> SEQ ID NO 1497
<211> LENGTH: 20
<212> TYPE: DNA
<213> ORGANISM: Homo sapiens

<400> SEQUENCE: 1497
aagagagaag cgacaaaacc                                          20

<210> SEQ ID NO 1498
<211> LENGTH: 20
<212> TYPE: DNA
<213> ORGANISM: Homo sapiens

<400> SEQUENCE: 1498
ttcatcccta cctcatcacc                                          20

<210> SEQ ID NO 1499
<211> LENGTH: 20
```

```
<212> TYPE: DNA
<213> ORGANISM: Homo sapiens

<400> SEQUENCE: 1499
aatgagaagg aattgggtgc                                        20

<210> SEQ ID NO 1500
<211> LENGTH: 21
<212> TYPE: DNA
<213> ORGANISM: Homo sapiens

<400> SEQUENCE: 1500
agatcacttt tggctgtaac c                                      21

<210> SEQ ID NO 1501
<211> LENGTH: 20
<212> TYPE: DNA
<213> ORGANISM: Homo sapiens

<400> SEQUENCE: 1501
aatgaagtgt tagggccatc                                        20

<210> SEQ ID NO 1502
<211> LENGTH: 20
<212> TYPE: DNA
<213> ORGANISM: Homo sapiens

<400> SEQUENCE: 1502
caagtgacaa tctcagccaa                                        20

<210> SEQ ID NO 1503
<211> LENGTH: 21
<212> TYPE: DNA
<213> ORGANISM: Homo sapiens

<400> SEQUENCE: 1503
gctcatcaca gtttaaggag t                                      21

<210> SEQ ID NO 1504
<211> LENGTH: 20
<212> TYPE: DNA
<213> ORGANISM: Homo sapiens

<400> SEQUENCE: 1504
gcattttcag atggttccct                                        20

<210> SEQ ID NO 1505
<211> LENGTH: 20
<212> TYPE: DNA
<213> ORGANISM: Homo sapiens

<400> SEQUENCE: 1505
atgtggaagc aagagaaagg                                        20

<210> SEQ ID NO 1506
<211> LENGTH: 20
<212> TYPE: DNA
<213> ORGANISM: Homo sapiens

<400> SEQUENCE: 1506
atggagagtt tgagtggagt                                        20

<210> SEQ ID NO 1507
```

-continued

```
<211> LENGTH: 20
<212> TYPE: DNA
<213> ORGANISM: Homo sapiens

<400> SEQUENCE: 1507
tgaaaggtga agtggctttt                                                    20

<210> SEQ ID NO 1508
<211> LENGTH: 22
<212> TYPE: DNA
<213> ORGANISM: Homo sapiens

<400> SEQUENCE: 1508
ctgccactgg gtttatagaa aa                                                 22

<210> SEQ ID NO 1509
<211> LENGTH: 20
<212> TYPE: DNA
<213> ORGANISM: Homo sapiens

<400> SEQUENCE: 1509
gtaagtaagg ggtcctagct                                                    20

<210> SEQ ID NO 1510
<211> LENGTH: 20
<212> TYPE: DNA
<213> ORGANISM: Homo sapiens

<400> SEQUENCE: 1510
acacctttac tcctgtggat                                                    20

<210> SEQ ID NO 1511
<211> LENGTH: 20
<212> TYPE: DNA
<213> ORGANISM: Homo sapiens

<400> SEQUENCE: 1511
tgtgacttcc atgaaactgg                                                    20

<210> SEQ ID NO 1512
<211> LENGTH: 20
<212> TYPE: DNA
<213> ORGANISM: Homo sapiens

<400> SEQUENCE: 1512
gatgtagggc cttatccaca                                                    20

<210> SEQ ID NO 1513
<211> LENGTH: 20
<212> TYPE: DNA
<213> ORGANISM: Homo sapiens

<400> SEQUENCE: 1513
gctgacaaac taaccttcca                                                    20

<210> SEQ ID NO 1514
<211> LENGTH: 20
<212> TYPE: DNA
<213> ORGANISM: Homo sapiens

<400> SEQUENCE: 1514
agcttggtga tcttcaaaca                                                    20
```

```
<210> SEQ ID NO 1515
<211> LENGTH: 20
<212> TYPE: DNA
<213> ORGANISM: Homo sapiens

<400> SEQUENCE: 1515
aaaacctccc aaaacagact                                               20

<210> SEQ ID NO 1516
<211> LENGTH: 20
<212> TYPE: DNA
<213> ORGANISM: Homo sapiens

<400> SEQUENCE: 1516
tgaaatggtg ggtaatgctc                                               20

<210> SEQ ID NO 1517
<211> LENGTH: 20
<212> TYPE: DNA
<213> ORGANISM: Homo sapiens

<400> SEQUENCE: 1517
agtttagtgg ccacgtgaaa                                               20

<210> SEQ ID NO 1518
<211> LENGTH: 20
<212> TYPE: DNA
<213> ORGANISM: Homo sapiens

<400> SEQUENCE: 1518
catgcaagtt cacgaggtta                                               20

<210> SEQ ID NO 1519
<211> LENGTH: 20
<212> TYPE: DNA
<213> ORGANISM: Homo sapiens

<400> SEQUENCE: 1519
ggcagaagtt tcaattccct                                               20

<210> SEQ ID NO 1520
<211> LENGTH: 20
<212> TYPE: DNA
<213> ORGANISM: Homo sapiens

<400> SEQUENCE: 1520
agtctgagga agaagcaact                                               20

<210> SEQ ID NO 1521
<211> LENGTH: 20
<212> TYPE: DNA
<213> ORGANISM: Homo sapiens

<400> SEQUENCE: 1521
aaagcctctg tttgcacttt                                               20

<210> SEQ ID NO 1522
<211> LENGTH: 20
<212> TYPE: DNA
<213> ORGANISM: Homo sapiens

<400> SEQUENCE: 1522
gagtccaatc ttttcccaca                                               20
```

```
<210> SEQ ID NO 1523
<211> LENGTH: 20
<212> TYPE: DNA
<213> ORGANISM: Homo sapiens

<400> SEQUENCE: 1523
tcagtcagct tcttgagtca                                              20

<210> SEQ ID NO 1524
<211> LENGTH: 20
<212> TYPE: DNA
<213> ORGANISM: Homo sapiens

<400> SEQUENCE: 1524
tccactgcgt tcttatcctt                                              20

<210> SEQ ID NO 1525
<211> LENGTH: 20
<212> TYPE: DNA
<213> ORGANISM: Homo sapiens

<400> SEQUENCE: 1525
tgtttcattt gggtcatgga                                              20

<210> SEQ ID NO 1526
<211> LENGTH: 20
<212> TYPE: DNA
<213> ORGANISM: Homo sapiens

<400> SEQUENCE: 1526
ggacagaaca gctacaaagg                                              20

<210> SEQ ID NO 1527
<211> LENGTH: 21
<212> TYPE: DNA
<213> ORGANISM: Homo sapiens

<400> SEQUENCE: 1527
tacagcacta ggatcactct g                                            21

<210> SEQ ID NO 1528
<211> LENGTH: 20
<212> TYPE: DNA
<213> ORGANISM: Homo sapiens

<400> SEQUENCE: 1528
ctggcttgtg aattagaggg                                              20

<210> SEQ ID NO 1529
<211> LENGTH: 20
<212> TYPE: DNA
<213> ORGANISM: Homo sapiens

<400> SEQUENCE: 1529
atgcatgttt cttgcaaagg                                              20

<210> SEQ ID NO 1530
<211> LENGTH: 19
<212> TYPE: DNA
<213> ORGANISM: Homo sapiens

<400> SEQUENCE: 1530
gtaagatggt gggcaggat                                               19
```

```
<210> SEQ ID NO 1531
<211> LENGTH: 20
<212> TYPE: DNA
<213> ORGANISM: Homo sapiens

<400> SEQUENCE: 1531
gtaggattca gggcatttca                                              20

<210> SEQ ID NO 1532
<211> LENGTH: 20
<212> TYPE: DNA
<213> ORGANISM: Homo sapiens

<400> SEQUENCE: 1532
agaagggctc aaaacacatc                                              20

<210> SEQ ID NO 1533
<211> LENGTH: 19
<212> TYPE: DNA
<213> ORGANISM: Homo sapiens

<400> SEQUENCE: 1533
aactggaact gagcgtgag                                               19

<210> SEQ ID NO 1534
<211> LENGTH: 21
<212> TYPE: DNA
<213> ORGANISM: Homo sapiens

<400> SEQUENCE: 1534
tcatgtaggc tttctgattt t                                            21

<210> SEQ ID NO 1535
<211> LENGTH: 20
<212> TYPE: DNA
<213> ORGANISM: Homo sapiens

<400> SEQUENCE: 1535
tgtatgcagt tacctccaga                                              20

<210> SEQ ID NO 1536
<211> LENGTH: 20
<212> TYPE: DNA
<213> ORGANISM: Homo sapiens

<400> SEQUENCE: 1536
tgtagctctt gacctagcaa                                              20

<210> SEQ ID NO 1537
<211> LENGTH: 20
<212> TYPE: DNA
<213> ORGANISM: Homo sapiens

<400> SEQUENCE: 1537
ggatgtatac cagacccctt                                              20

<210> SEQ ID NO 1538
<211> LENGTH: 21
<212> TYPE: DNA
<213> ORGANISM: Homo sapiens
```

```
<400> SEQUENCE: 1538
taagttcacg gtgaagtcaa c                                              21

<210> SEQ ID NO 1539
<211> LENGTH: 20
<212> TYPE: DNA
<213> ORGANISM: Homo sapiens

<400> SEQUENCE: 1539
cgaaagatgt tagcacctca                                                20

<210> SEQ ID NO 1540
<211> LENGTH: 20
<212> TYPE: DNA
<213> ORGANISM: Homo sapiens

<400> SEQUENCE: 1540
gtggcttcaa ctaactggac                                                20

<210> SEQ ID NO 1541
<211> LENGTH: 20
<212> TYPE: DNA
<213> ORGANISM: Homo sapiens

<400> SEQUENCE: 1541
aattggcttt gcagtgtttc                                                20

<210> SEQ ID NO 1542
<211> LENGTH: 20
<212> TYPE: DNA
<213> ORGANISM: Homo sapiens

<400> SEQUENCE: 1542
acccgtaagt gtttgagtga                                                20

<210> SEQ ID NO 1543
<211> LENGTH: 20
<212> TYPE: DNA
<213> ORGANISM: Homo sapiens

<400> SEQUENCE: 1543
gcttgctggt aggaggtata                                                20

<210> SEQ ID NO 1544
<211> LENGTH: 20
<212> TYPE: DNA
<213> ORGANISM: Homo sapiens

<400> SEQUENCE: 1544
tgtagaagta gggtttgcgt                                                20

<210> SEQ ID NO 1545
<211> LENGTH: 20
<212> TYPE: DNA
<213> ORGANISM: Homo sapiens

<400> SEQUENCE: 1545
ctggaaacgg aaggaagttg                                                20

<210> SEQ ID NO 1546
<211> LENGTH: 20
<212> TYPE: DNA
```

<213> ORGANISM: Homo sapiens

<400> SEQUENCE: 1546 cagggggacat ttgaagatgg                                          20

<210> SEQ ID NO 1547
<211> LENGTH: 20
<212> TYPE: DNA
<213> ORGANISM: Homo sapiens

<400> SEQUENCE: 1547
ctgtgttcag taagtggctg                                           20

<210> SEQ ID NO 1548
<211> LENGTH: 20
<212> TYPE: DNA
<213> ORGANISM: Homo sapiens

<400> SEQUENCE: 1548
gaaattgtgc agtgaaagca                                           20

<210> SEQ ID NO 1549
<211> LENGTH: 20
<212> TYPE: DNA
<213> ORGANISM: Homo sapiens

<400> SEQUENCE: 1549
gacagtgaag tgtgatcgtt                                           20

<210> SEQ ID NO 1550
<211> LENGTH: 21
<212> TYPE: DNA
<213> ORGANISM: Homo sapiens

<400> SEQUENCE: 1550
atgtaagaag tgcgttgctt a                                         21

<210> SEQ ID NO 1551
<211> LENGTH: 20
<212> TYPE: DNA
<213> ORGANISM: Homo sapiens

<400> SEQUENCE: 1551
tggtgatgct gttttggaaa                                           20

<210> SEQ ID NO 1552
<211> LENGTH: 21
<212> TYPE: DNA
<213> ORGANISM: Homo sapiens

<400> SEQUENCE: 1552
agatctggaa tctgagactc c                                         21

<210> SEQ ID NO 1553
<211> LENGTH: 22
<212> TYPE: DNA
<213> ORGANISM: Homo sapiens

<400> SEQUENCE: 1553
ttctttcagg cagaagaaat ga                                        22

<210> SEQ ID NO 1554
<211> LENGTH: 22

```
<212> TYPE: DNA
<213> ORGANISM: Homo sapiens

<400> SEQUENCE: 1554
tataggataa ggtcaagcag gt                                         22

<210> SEQ ID NO 1555
<211> LENGTH: 25
<212> TYPE: DNA
<213> ORGANISM: Homo sapiens

<400> SEQUENCE: 1555
aagttccatt actgtattga aaatt                                      25

<210> SEQ ID NO 1556
<211> LENGTH: 21
<212> TYPE: DNA
<213> ORGANISM: Homo sapiens

<400> SEQUENCE: 1556
tccaaaacaa ttctaggccc c                                          21

<210> SEQ ID NO 1557
<211> LENGTH: 20
<212> TYPE: DNA
<213> ORGANISM: Homo sapiens

<400> SEQUENCE: 1557
ggacgtacgt gcttatttca                                            20

<210> SEQ ID NO 1558
<211> LENGTH: 21
<212> TYPE: DNA
<213> ORGANISM: Homo sapiens

<400> SEQUENCE: 1558
tcagtgaatg aggaatcatg c                                          21

<210> SEQ ID NO 1559
<211> LENGTH: 21
<212> TYPE: DNA
<213> ORGANISM: Homo sapiens

<400> SEQUENCE: 1559
cagcctgata ttcccattga g                                          21

<210> SEQ ID NO 1560
<211> LENGTH: 20
<212> TYPE: DNA
<213> ORGANISM: Homo sapiens

<400> SEQUENCE: 1560
ttctcaggag taccacaagc                                            20

<210> SEQ ID NO 1561
<211> LENGTH: 20
<212> TYPE: DNA
<213> ORGANISM: Homo sapiens

<400> SEQUENCE: 1561
tcatgaggct gagtgagtat                                            20

<210> SEQ ID NO 1562
```

```
<211> LENGTH: 20
<212> TYPE: DNA
<213> ORGANISM: Homo sapiens

<400> SEQUENCE: 1562
ggatgaaaca cagaaccatg                                               20

<210> SEQ ID NO 1563
<211> LENGTH: 20
<212> TYPE: DNA
<213> ORGANISM: Homo sapiens

<400> SEQUENCE: 1563
aaagctctcc tatctccagt                                               20

<210> SEQ ID NO 1564
<211> LENGTH: 20
<212> TYPE: DNA
<213> ORGANISM: Homo sapiens

<400> SEQUENCE: 1564 cagatcccctt tcattttgca                                              20

<210> SEQ ID NO 1565
<211> LENGTH: 21
<212> TYPE: DNA
<213> ORGANISM: Homo sapiens

<400> SEQUENCE: 1565
acaaagagtc tggactatcc t                                             21

<210> SEQ ID NO 1566
<211> LENGTH: 20
<212> TYPE: DNA
<213> ORGANISM: Homo sapiens

<400> SEQUENCE: 1566
ggaaaagtgc tcaattaggc                                               20

<210> SEQ ID NO 1567
<211> LENGTH: 21
<212> TYPE: DNA
<213> ORGANISM: Homo sapiens

<400> SEQUENCE: 1567
tgcctaaaaa tacccaaagc t                                             21

<210> SEQ ID NO 1568
<211> LENGTH: 20
<212> TYPE: DNA
<213> ORGANISM: Homo sapiens

<400> SEQUENCE: 1568
ctggcagtta tagtcaccaa                                               20

<210> SEQ ID NO 1569
<211> LENGTH: 20
<212> TYPE: DNA
<213> ORGANISM: Homo sapiens

<400> SEQUENCE: 1569
ccaagacact cactccaaag                                               20
```

```
<210> SEQ ID NO 1570
<211> LENGTH: 20
<212> TYPE: DNA
<213> ORGANISM: Homo sapiens

<400> SEQUENCE: 1570
aggaagtcct tatgatgcca                                              20

<210> SEQ ID NO 1571
<211> LENGTH: 20
<212> TYPE: DNA
<213> ORGANISM: Homo sapiens

<400> SEQUENCE: 1571
ccaggaaaag gagcagtttt                                              20

<210> SEQ ID NO 1572
<211> LENGTH: 20
<212> TYPE: DNA
<213> ORGANISM: Homo sapiens

<400> SEQUENCE: 1572
gctggtgaag ttggagtttt                                              20

<210> SEQ ID NO 1573
<211> LENGTH: 20
<212> TYPE: DNA
<213> ORGANISM: Homo sapiens

<400> SEQUENCE: 1573
gttcaactct ttctgcgaac                                              20

<210> SEQ ID NO 1574
<211> LENGTH: 20
<212> TYPE: DNA
<213> ORGANISM: Homo sapiens

<400> SEQUENCE: 1574
gctgggttta agccacatat                                              20

<210> SEQ ID NO 1575
<211> LENGTH: 20
<212> TYPE: DNA
<213> ORGANISM: Homo sapiens

<400> SEQUENCE: 1575
ccacttcttc tgtttccaac                                              20

<210> SEQ ID NO 1576
<211> LENGTH: 20
<212> TYPE: DNA
<213> ORGANISM: Homo sapiens

<400> SEQUENCE: 1576
tgtagcctaa atagcagcct                                              20

<210> SEQ ID NO 1577
<211> LENGTH: 19
<212> TYPE: DNA
<213> ORGANISM: Homo sapiens

<400> SEQUENCE: 1577
gggaagggca tgctaatca                                               19
```

<210> SEQ ID NO 1578
<211> LENGTH: 23
<212> TYPE: DNA
<213> ORGANISM: Homo sapiens

<400> SEQUENCE: 1578
aggaattgct tttattttaa cca                                                 23

<210> SEQ ID NO 1579
<211> LENGTH: 20
<212> TYPE: DNA
<213> ORGANISM: Homo sapiens

<400> SEQUENCE: 1579
tgttcaatca cctctccatc                                                     20

<210> SEQ ID NO 1580
<211> LENGTH: 20
<212> TYPE: DNA
<213> ORGANISM: Homo sapiens

<400> SEQUENCE: 1580
gctgctttca ggttttgtg                                                      20

<210> SEQ ID NO 1581
<211> LENGTH: 20
<212> TYPE: DNA
<213> ORGANISM: Homo sapiens

<400> SEQUENCE: 1581
agaggagagg ctaagctttg                                                     20

<210> SEQ ID NO 1582
<211> LENGTH: 20
<212> TYPE: DNA
<213> ORGANISM: Homo sapiens

<400> SEQUENCE: 1582
atggtgcaga aaagagcaat                                                     20

<210> SEQ ID NO 1583
<211> LENGTH: 20
<212> TYPE: DNA
<213> ORGANISM: Homo sapiens

<400> SEQUENCE: 1583
acaagagagg aagctgtcag                                                     20

<210> SEQ ID NO 1584
<211> LENGTH: 20
<212> TYPE: DNA
<213> ORGANISM: Homo sapiens

<400> SEQUENCE: 1584
gtgtggtgcc attttctttc                                                     20

<210> SEQ ID NO 1585
<211> LENGTH: 20
<212> TYPE: DNA
<213> ORGANISM: Homo sapiens

<400> SEQUENCE: 1585 agccccttc tccttattct                                                      20

<210> SEQ ID NO 1586
<211> LENGTH: 20
<212> TYPE: DNA
<213> ORGANISM: Homo sapiens

<400> SEQUENCE: 1586
gaacaatact ttctccccgg                                              20

<210> SEQ ID NO 1587
<211> LENGTH: 20
<212> TYPE: DNA
<213> ORGANISM: Homo sapiens

<400> SEQUENCE: 1587
agggaagcag gattttaacg                                              20

<210> SEQ ID NO 1588
<211> LENGTH: 20
<212> TYPE: DNA
<213> ORGANISM: Homo sapiens

<400> SEQUENCE: 1588
gaaatggcca tgctaggaat                                              20

<210> SEQ ID NO 1589
<211> LENGTH: 20
<212> TYPE: DNA
<213> ORGANISM: Homo sapiens

<400> SEQUENCE: 1589
aagtttcaca atacccaggt                                              20

<210> SEQ ID NO 1590
<211> LENGTH: 20
<212> TYPE: DNA
<213> ORGANISM: Homo sapiens

<400> SEQUENCE: 1590
acttccagta acatggatgc                                              20

<210> SEQ ID NO 1591
<211> LENGTH: 20
<212> TYPE: DNA
<213> ORGANISM: Homo sapiens

<400> SEQUENCE: 1591
tcgcagaatg gacaagtact                                              20

<210> SEQ ID NO 1592
<211> LENGTH: 20
<212> TYPE: DNA
<213> ORGANISM: Homo sapiens

<400> SEQUENCE: 1592
gaaacaccca gacttgtagc                                              20

<210> SEQ ID NO 1593
<211> LENGTH: 20
<212> TYPE: DNA
<213> ORGANISM: Homo sapiens

```
<400> SEQUENCE: 1593
ggctcccaga ttttgatcat                                           20

<210> SEQ ID NO 1594
<211> LENGTH: 20
<212> TYPE: DNA
<213> ORGANISM: Homo sapiens

<400> SEQUENCE: 1594
ttaaatcttt gtgtgcgtgt                                           20

<210> SEQ ID NO 1595
<211> LENGTH: 20
<212> TYPE: DNA
<213> ORGANISM: Homo sapiens

<400> SEQUENCE: 1595
cctagaactg caaaacacct                                           20

<210> SEQ ID NO 1596
<211> LENGTH: 20
<212> TYPE: DNA
<213> ORGANISM: Homo sapiens

<400> SEQUENCE: 1596
cctccaggaa ctttgttcag                                           20

<210> SEQ ID NO 1597
<211> LENGTH: 21
<212> TYPE: DNA
<213> ORGANISM: Homo sapiens

<400> SEQUENCE: 1597
ttccattatt ttctcaccgg c                                         21

<210> SEQ ID NO 1598
<211> LENGTH: 20
<212> TYPE: DNA
<213> ORGANISM: Homo sapiens

<400> SEQUENCE: 1598
aaaaaccttc acaaacccca                                           20

<210> SEQ ID NO 1599
<211> LENGTH: 20
<212> TYPE: DNA
<213> ORGANISM: Homo sapiens

<400> SEQUENCE: 1599
cagtccaaca aagaggtcac                                           20

<210> SEQ ID NO 1600
<211> LENGTH: 20
<212> TYPE: DNA
<213> ORGANISM: Homo sapiens

<400> SEQUENCE: 1600
gagtggatat tgtctcgctg                                           20

<210> SEQ ID NO 1601
<211> LENGTH: 20
<212> TYPE: DNA
```

```
<213> ORGANISM: Homo sapiens

<400> SEQUENCE: 1601
ttgtgtgtgt tgaagcctag                                               20

<210> SEQ ID NO 1602
<211> LENGTH: 20
<212> TYPE: DNA
<213> ORGANISM: Homo sapiens

<400> SEQUENCE: 1602
actagcccac taatgttgct                                               20

<210> SEQ ID NO 1603
<211> LENGTH: 20
<212> TYPE: DNA
<213> ORGANISM: Homo sapiens

<400> SEQUENCE: 1603
agtgggggta ggaagaaaaa                                               20

<210> SEQ ID NO 1604
<211> LENGTH: 22
<212> TYPE: DNA
<213> ORGANISM: Homo sapiens

<400> SEQUENCE: 1604
cgattatcag aacagatgag gt                                            22

<210> SEQ ID NO 1605
<211> LENGTH: 20
<212> TYPE: DNA
<213> ORGANISM: Homo sapiens

<400> SEQUENCE: 1605
gttccaacaa tgtaaggcac                                               20

<210> SEQ ID NO 1606
<211> LENGTH: 20
<212> TYPE: DNA
<213> ORGANISM: Homo sapiens

<400> SEQUENCE: 1606
attgcacagc tgaaaatcct                                               20

<210> SEQ ID NO 1607
<211> LENGTH: 20
<212> TYPE: DNA
<213> ORGANISM: Homo sapiens

<400> SEQUENCE: 1607
ggaaccctct atggtcaaag                                               20

<210> SEQ ID NO 1608
<211> LENGTH: 20
<212> TYPE: DNA
<213> ORGANISM: Homo sapiens

<400> SEQUENCE: 1608
ggcacactga ccgtatttat                                               20

<210> SEQ ID NO 1609
<211> LENGTH: 20
```

```
<212> TYPE: DNA
<213> ORGANISM: Homo sapiens

<400> SEQUENCE: 1609
attgctgtgt agttccttga                                               20

<210> SEQ ID NO 1610
<211> LENGTH: 20
<212> TYPE: DNA
<213> ORGANISM: Homo sapiens

<400> SEQUENCE: 1610
tggtagtggg tcaggaattt                                               20

<210> SEQ ID NO 1611
<211> LENGTH: 20
<212> TYPE: DNA
<213> ORGANISM: Homo sapiens

<400> SEQUENCE: 1611
tttcttgcca ccattctgac                                               20

<210> SEQ ID NO 1612
<211> LENGTH: 20
<212> TYPE: DNA
<213> ORGANISM: Homo sapiens

<400> SEQUENCE: 1612
tctcttgaaa agaaaggcgg                                               20

<210> SEQ ID NO 1613
<211> LENGTH: 20
<212> TYPE: DNA
<213> ORGANISM: Homo sapiens

<400> SEQUENCE: 1613
cacacgttct aaccaagtgc                                               20

<210> SEQ ID NO 1614
<211> LENGTH: 20
<212> TYPE: DNA
<213> ORGANISM: Homo sapiens

<400> SEQUENCE: 1614
tgaattacac agcaaagccc                                               20

<210> SEQ ID NO 1615
<211> LENGTH: 21
<212> TYPE: DNA
<213> ORGANISM: Homo sapiens

<400> SEQUENCE: 1615
tagccacatc ttaacagacc t                                             21

<210> SEQ ID NO 1616
<211> LENGTH: 20
<212> TYPE: DNA
<213> ORGANISM: Homo sapiens

<400> SEQUENCE: 1616
ctgccaatgg gatcgaattt                                               20

<210> SEQ ID NO 1617
```

```
<211> LENGTH: 20
<212> TYPE: DNA
<213> ORGANISM: Homo sapiens

<400> SEQUENCE: 1617
attcctgagg gtgacatgaa                                               20

<210> SEQ ID NO 1618
<211> LENGTH: 20
<212> TYPE: DNA
<213> ORGANISM: Homo sapiens

<400> SEQUENCE: 1618
gagtgacgct gttcattctt                                               20

<210> SEQ ID NO 1619
<211> LENGTH: 20
<212> TYPE: DNA
<213> ORGANISM: Homo sapiens

<400> SEQUENCE: 1619
cctgccccat caacttaaaa                                               20

<210> SEQ ID NO 1620
<211> LENGTH: 20
<212> TYPE: DNA
<213> ORGANISM: Homo sapiens

<400> SEQUENCE: 1620
gatagtaacc gggtgtagca                                               20

<210> SEQ ID NO 1621
<211> LENGTH: 18
<212> TYPE: DNA
<213> ORGANISM: Homo sapiens

<400> SEQUENCE: 1621
ctgggtgcag aggatctc                                                 18

<210> SEQ ID NO 1622
<211> LENGTH: 23
<212> TYPE: DNA
<213> ORGANISM: Homo sapiens

<400> SEQUENCE: 1622
tccaaaagca aaggatcac tga                                            23

<210> SEQ ID NO 1623
<211> LENGTH: 22
<212> TYPE: DNA
<213> ORGANISM: Homo sapiens

<400> SEQUENCE: 1623
ttgagttgaa ctttgcttta ga                                            22

<210> SEQ ID NO 1624
<211> LENGTH: 23
<212> TYPE: DNA
<213> ORGANISM: Homo sapiens

<400> SEQUENCE: 1624
tctaataagg gattgatgga gtt                                           23
```

```
<210> SEQ ID NO 1625
<211> LENGTH: 20
<212> TYPE: DNA
<213> ORGANISM: Homo sapiens

<400> SEQUENCE: 1625
gaactaggag acactgggtt                                                  20

<210> SEQ ID NO 1626
<211> LENGTH: 20
<212> TYPE: DNA
<213> ORGANISM: Homo sapiens

<400> SEQUENCE: 1626
gggagatttc ctgcttgtag                                                  20

<210> SEQ ID NO 1627
<211> LENGTH: 21
<212> TYPE: DNA
<213> ORGANISM: Homo sapiens

<400> SEQUENCE: 1627
caagaatagc taactggtgc t                                                21

<210> SEQ ID NO 1628
<211> LENGTH: 20
<212> TYPE: DNA
<213> ORGANISM: Homo sapiens

<400> SEQUENCE: 1628
aatccatgca gcttctctct                                                  20

<210> SEQ ID NO 1629
<211> LENGTH: 21
<212> TYPE: DNA
<213> ORGANISM: Homo sapiens

<400> SEQUENCE: 1629
agttacacac tgaatcatgg g                                                21

<210> SEQ ID NO 1630
<211> LENGTH: 20
<212> TYPE: DNA
<213> ORGANISM: Homo sapiens

<400> SEQUENCE: 1630
tgcattgtct ctggtttgaa                                                  20

<210> SEQ ID NO 1631
<211> LENGTH: 20
<212> TYPE: DNA
<213> ORGANISM: Homo sapiens

<400> SEQUENCE: 1631
cccatgtggc ttcactaata                                                  20

<210> SEQ ID NO 1632
<211> LENGTH: 20
<212> TYPE: DNA
<213> ORGANISM: Homo sapiens

<400> SEQUENCE: 1632
tcctgaatgc atccttaacc                                                  20
```

<210> SEQ ID NO 1633
<211> LENGTH: 20
<212> TYPE: DNA
<213> ORGANISM: Homo sapiens

<400> SEQUENCE: 1633
gattgtggtc acgtggagag                                              20

<210> SEQ ID NO 1634
<211> LENGTH: 20
<212> TYPE: DNA
<213> ORGANISM: Homo sapiens

<400> SEQUENCE: 1634
tgggaaaggt gagaaggatt                                              20

<210> SEQ ID NO 1635
<211> LENGTH: 20
<212> TYPE: DNA
<213> ORGANISM: Homo sapiens

<400> SEQUENCE: 1635
cagatccagg tattcggaga                                              20

<210> SEQ ID NO 1636
<211> LENGTH: 20
<212> TYPE: DNA
<213> ORGANISM: Homo sapiens

<400> SEQUENCE: 1636
ttcgggaccc atacctaaaa                                              20

<210> SEQ ID NO 1637
<211> LENGTH: 20
<212> TYPE: DNA
<213> ORGANISM: Homo sapiens

<400> SEQUENCE: 1637
acaacaacaa ccattaccca                                              20

<210> SEQ ID NO 1638
<211> LENGTH: 20
<212> TYPE: DNA
<213> ORGANISM: Homo sapiens

<400> SEQUENCE: 1638
tcttttctgg acccacatga                                              20

<210> SEQ ID NO 1639
<211> LENGTH: 20
<212> TYPE: DNA
<213> ORGANISM: Homo sapiens

<400> SEQUENCE: 1639
tggccatagt actgcttgta                                              20

<210> SEQ ID NO 1640
<211> LENGTH: 22
<212> TYPE: DNA
<213> ORGANISM: Homo sapiens

<400> SEQUENCE: 1640
gacctctaca tctgtatctt cc                                           22

<210> SEQ ID NO 1641
<211> LENGTH: 20
<212> TYPE: DNA
<213> ORGANISM: Homo sapiens

<400> SEQUENCE: 1641
tgtctcactg ttgggaactt                                               20

<210> SEQ ID NO 1642
<211> LENGTH: 20
<212> TYPE: DNA
<213> ORGANISM: Homo sapiens

<400> SEQUENCE: 1642
cccttcattt tctgtcccat                                               20

<210> SEQ ID NO 1643
<211> LENGTH: 20
<212> TYPE: DNA
<213> ORGANISM: Homo sapiens

<400> SEQUENCE: 1643
tttgtctgta tcctatgccc                                               20

<210> SEQ ID NO 1644
<211> LENGTH: 21
<212> TYPE: DNA
<213> ORGANISM: Homo sapiens

<400> SEQUENCE: 1644
tcagccttga gtattagcct a                                             21

<210> SEQ ID NO 1645
<211> LENGTH: 20
<212> TYPE: DNA
<213> ORGANISM: Homo sapiens

<400> SEQUENCE: 1645
gctgacaaaa ttggatccca                                               20

<210> SEQ ID NO 1646
<211> LENGTH: 20
<212> TYPE: DNA
<213> ORGANISM: Homo sapiens

<400> SEQUENCE: 1646
aagtttgcca tgaaggtcat                                               20

<210> SEQ ID NO 1647
<211> LENGTH: 20
<212> TYPE: DNA
<213> ORGANISM: Homo sapiens

<400> SEQUENCE: 1647
aaaatcctcc tgagtcctct                                               20

<210> SEQ ID NO 1648
<211> LENGTH: 20
<212> TYPE: DNA
<213> ORGANISM: Homo sapiens

```
<400> SEQUENCE: 1648
gacttctggt tgtttcctca                                              20

<210> SEQ ID NO 1649
<211> LENGTH: 20
<212> TYPE: DNA
<213> ORGANISM: Homo sapiens

<400> SEQUENCE: 1649
ttcactgggc tcttcagcta                                              20

<210> SEQ ID NO 1650
<211> LENGTH: 20
<212> TYPE: DNA
<213> ORGANISM: Homo sapiens

<400> SEQUENCE: 1650
atgtgtctat tgccctacct                                              20

<210> SEQ ID NO 1651
<211> LENGTH: 20
<212> TYPE: DNA
<213> ORGANISM: Homo sapiens

<400> SEQUENCE: 1651
aaagggcagg agttaggtaa                                              20

<210> SEQ ID NO 1652
<211> LENGTH: 19
<212> TYPE: DNA
<213> ORGANISM: Homo sapiens

<400> SEQUENCE: 1652
tgcgggaagt tcacatgaa                                               19

<210> SEQ ID NO 1653
<211> LENGTH: 20
<212> TYPE: DNA
<213> ORGANISM: Homo sapiens

<400> SEQUENCE: 1653
aggcataaga aaccaggttg                                              20

<210> SEQ ID NO 1654
<211> LENGTH: 19
<212> TYPE: DNA
<213> ORGANISM: Homo sapiens

<400> SEQUENCE: 1654
gtgaacttca ggctgctta                                               19

<210> SEQ ID NO 1655
<211> LENGTH: 20
<212> TYPE: DNA
<213> ORGANISM: Homo sapiens

<400> SEQUENCE: 1655
gtagttcggt ccaatgtcag                                              20

<210> SEQ ID NO 1656
<211> LENGTH: 20
<212> TYPE: DNA
```

-continued

<213> ORGANISM: Homo sapiens

<400> SEQUENCE: 1656
tggtttcgtc ccgtaaatag                                            20

<210> SEQ ID NO 1657
<211> LENGTH: 20
<212> TYPE: DNA
<213> ORGANISM: Homo sapiens

<400> SEQUENCE: 1657
gatggtcaca attgcaggtt                                            20

<210> SEQ ID NO 1658
<211> LENGTH: 20
<212> TYPE: DNA
<213> ORGANISM: Homo sapiens

<400> SEQUENCE: 1658
aattcctttc aatgctggct                                            20

<210> SEQ ID NO 1659
<211> LENGTH: 20
<212> TYPE: DNA
<213> ORGANISM: Homo sapiens

<400> SEQUENCE: 1659
gccaaagatc tcaattgcca                                            20

<210> SEQ ID NO 1660
<211> LENGTH: 21
<212> TYPE: DNA
<213> ORGANISM: Homo sapiens

<400> SEQUENCE: 1660
agaaagacac atatgccatg g                                          21

<210> SEQ ID NO 1661
<211> LENGTH: 20
<212> TYPE: DNA
<213> ORGANISM: Homo sapiens

<400> SEQUENCE: 1661
gaccaagact gtctctcctt                                            20

<210> SEQ ID NO 1662
<211> LENGTH: 20
<212> TYPE: DNA
<213> ORGANISM: Homo sapiens

<400> SEQUENCE: 1662
ttgttggtgt cagttctgaa                                            20

<210> SEQ ID NO 1663
<211> LENGTH: 22
<212> TYPE: DNA
<213> ORGANISM: Homo sapiens

<400> SEQUENCE: 1663
taatggtcaa atccctctca aa                                         22

<210> SEQ ID NO 1664
<211> LENGTH: 20

```
<212> TYPE: DNA
<213> ORGANISM: Homo sapiens

<400> SEQUENCE: 1664
tgtaggaaca gattagggca                                              20

<210> SEQ ID NO 1665
<211> LENGTH: 20
<212> TYPE: DNA
<213> ORGANISM: Homo sapiens

<400> SEQUENCE: 1665
catgtaggct gaagactcct                                              20

<210> SEQ ID NO 1666
<211> LENGTH: 20
<212> TYPE: DNA
<213> ORGANISM: Homo sapiens

<400> SEQUENCE: 1666
ctccaagctg atatgccatc                                              20

<210> SEQ ID NO 1667
<211> LENGTH: 20
<212> TYPE: DNA
<213> ORGANISM: Homo sapiens

<400> SEQUENCE: 1667
tttctctcca aactggttgc                                              20

<210> SEQ ID NO 1668
<211> LENGTH: 20
<212> TYPE: DNA
<213> ORGANISM: Homo sapiens

<400> SEQUENCE: 1668
ccacccctca tttcttcctt                                              20

<210> SEQ ID NO 1669
<211> LENGTH: 21
<212> TYPE: DNA
<213> ORGANISM: Homo sapiens

<400> SEQUENCE: 1669
tacaggcaag aaatagtgtc t                                            21

<210> SEQ ID NO 1670
<211> LENGTH: 20
<212> TYPE: DNA
<213> ORGANISM: Homo sapiens

<400> SEQUENCE: 1670
gggtccttcg ttttctgttt                                              20

<210> SEQ ID NO 1671
<211> LENGTH: 20
<212> TYPE: DNA
<213> ORGANISM: Homo sapiens

<400> SEQUENCE: 1671
ttcagcaaga atggggattc                                              20

<210> SEQ ID NO 1672
```

```
<211> LENGTH: 21
<212> TYPE: DNA
<213> ORGANISM: Homo sapiens

<400> SEQUENCE: 1672
taggaaacag gctaaaaggg a                                              21

<210> SEQ ID NO 1673
<211> LENGTH: 20
<212> TYPE: DNA
<213> ORGANISM: Homo sapiens

<400> SEQUENCE: 1673
caaagagaga gccatcacag                                                20

<210> SEQ ID NO 1674
<211> LENGTH: 20
<212> TYPE: DNA
<213> ORGANISM: Homo sapiens

<400> SEQUENCE: 1674
tactgtgtag aaggcagtgt                                                20

<210> SEQ ID NO 1675
<211> LENGTH: 21
<212> TYPE: DNA
<213> ORGANISM: Homo sapiens

<400> SEQUENCE: 1675
tgagaacact gctatttctg c                                              21

<210> SEQ ID NO 1676
<211> LENGTH: 20
<212> TYPE: DNA
<213> ORGANISM: Homo sapiens

<400> SEQUENCE: 1676
gctaaggaca aagaaccact                                                20

<210> SEQ ID NO 1677
<211> LENGTH: 18
<212> TYPE: DNA
<213> ORGANISM: Homo sapiens

<400> SEQUENCE: 1677
gcatggtcag gacattgg                                                  18

<210> SEQ ID NO 1678
<211> LENGTH: 22
<212> TYPE: DNA
<213> ORGANISM: Homo sapiens

<400> SEQUENCE: 1678
aaagacaagg gaaaaggtga ca                                             22

<210> SEQ ID NO 1679
<211> LENGTH: 20
<212> TYPE: DNA
<213> ORGANISM: Homo sapiens

<400> SEQUENCE: 1679
gattgaatca ggagggaagc                                                20
```

```
<210> SEQ ID NO 1680
<211> LENGTH: 20
<212> TYPE: DNA
<213> ORGANISM: Homo sapiens

<400> SEQUENCE: 1680
tggctaagac caggattgtt                                               20

<210> SEQ ID NO 1681
<211> LENGTH: 23
<212> TYPE: DNA
<213> ORGANISM: Homo sapiens

<400> SEQUENCE: 1681
agcttaaatg atgaagtgct ttc                                           23

<210> SEQ ID NO 1682
<211> LENGTH: 25
<212> TYPE: DNA
<213> ORGANISM: Homo sapiens

<400> SEQUENCE: 1682
tcttatgttt ggtgatttgg acttt                                         25

<210> SEQ ID NO 1683
<211> LENGTH: 20
<212> TYPE: DNA
<213> ORGANISM: Homo sapiens

<400> SEQUENCE: 1683
ttctcctacg tatcttggca                                               20

<210> SEQ ID NO 1684
<211> LENGTH: 20
<212> TYPE: DNA
<213> ORGANISM: Homo sapiens

<400> SEQUENCE: 1684
tgataggcag atcattcccc                                               20

<210> SEQ ID NO 1685
<211> LENGTH: 20
<212> TYPE: DNA
<213> ORGANISM: Homo sapiens

<400> SEQUENCE: 1685
acctgggaca taaccttgat                                               20

<210> SEQ ID NO 1686
<211> LENGTH: 20
<212> TYPE: DNA
<213> ORGANISM: Homo sapiens

<400> SEQUENCE: 1686
gcaaatggca aagggaaaac                                               20

<210> SEQ ID NO 1687
<211> LENGTH: 20
<212> TYPE: DNA
<213> ORGANISM: Homo sapiens

<400> SEQUENCE: 1687
ccattttcct actgcgtgtc                                               20
```

<210> SEQ ID NO 1688
<211> LENGTH: 19
<212> TYPE: DNA
<213> ORGANISM: Homo sapiens

<400> SEQUENCE: 1688
cacggctagt gctcatttt                                           19

<210> SEQ ID NO 1689
<211> LENGTH: 20
<212> TYPE: DNA
<213> ORGANISM: Homo sapiens

<400> SEQUENCE: 1689
gaacatacca aacccactgg                                          20

<210> SEQ ID NO 1690
<211> LENGTH: 21
<212> TYPE: DNA
<213> ORGANISM: Homo sapiens

<400> SEQUENCE: 1690
ccgtaatacc caagtcatct g                                        21

<210> SEQ ID NO 1691
<211> LENGTH: 20
<212> TYPE: DNA
<213> ORGANISM: Homo sapiens

<400> SEQUENCE: 1691
acccaatgat gtacagttcc                                          20

<210> SEQ ID NO 1692
<211> LENGTH: 22
<212> TYPE: DNA
<213> ORGANISM: Homo sapiens

<400> SEQUENCE: 1692
agcaaactaa aacagcaact tc                                       22

<210> SEQ ID NO 1693
<211> LENGTH: 22
<212> TYPE: DNA
<213> ORGANISM: Homo sapiens

<400> SEQUENCE: 1693
acctattcga cttgaaactc ag                                       22

<210> SEQ ID NO 1694
<211> LENGTH: 19
<212> TYPE: DNA
<213> ORGANISM: Homo sapiens

<400> SEQUENCE: 1694
agcctgctat cttcactgg                                           19

<210> SEQ ID NO 1695
<211> LENGTH: 20
<212> TYPE: DNA
<213> ORGANISM: Homo sapiens

<400> SEQUENCE: 1695
atttctgcac aactgttcca                                          20

<210> SEQ ID NO 1696
<211> LENGTH: 24
<212> TYPE: DNA
<213> ORGANISM: Homo sapiens

<400> SEQUENCE: 1696
accacatata tagagacttt gaag                                         24

<210> SEQ ID NO 1697
<211> LENGTH: 20
<212> TYPE: DNA
<213> ORGANISM: Homo sapiens

<400> SEQUENCE: 1697
gctgtaatgt gactaaccct                                              20

<210> SEQ ID NO 1698
<211> LENGTH: 19
<212> TYPE: DNA
<213> ORGANISM: Homo sapiens

<400> SEQUENCE: 1698
ctccagactc tgcaaggat                                               19

<210> SEQ ID NO 1699
<211> LENGTH: 20
<212> TYPE: DNA
<213> ORGANISM: Homo sapiens

<400> SEQUENCE: 1699
tttcccgagg ttcacagata                                              20

<210> SEQ ID NO 1700
<211> LENGTH: 20
<212> TYPE: DNA
<213> ORGANISM: Homo sapiens

<400> SEQUENCE: 1700
tttcctgttg ctcttgatca                                              20

<210> SEQ ID NO 1701
<211> LENGTH: 20
<212> TYPE: DNA
<213> ORGANISM: Homo sapiens

<400> SEQUENCE: 1701
gaacttgtgt gacccaaaac                                              20

<210> SEQ ID NO 1702
<211> LENGTH: 20
<212> TYPE: DNA
<213> ORGANISM: Homo sapiens

<400> SEQUENCE: 1702
ccacaaagat gaaggccaag                                              20

<210> SEQ ID NO 1703
<211> LENGTH: 20
<212> TYPE: DNA
<213> ORGANISM: Homo sapiens

```
<400> SEQUENCE: 1703
cattgcactg tgatgtcatg                                               20

<210> SEQ ID NO 1704
<211> LENGTH: 21
<212> TYPE: DNA
<213> ORGANISM: Homo sapiens

<400> SEQUENCE: 1704 ccataccttta gttctcaggg t                                            21

<210> SEQ ID NO 1705
<211> LENGTH: 20
<212> TYPE: DNA
<213> ORGANISM: Homo sapiens

<400> SEQUENCE: 1705
gcactggaaa ttgacatcac                                               20

<210> SEQ ID NO 1706
<211> LENGTH: 20
<212> TYPE: DNA
<213> ORGANISM: Homo sapiens

<400> SEQUENCE: 1706
gtaagagaga gctgggacaa                                               20

<210> SEQ ID NO 1707
<211> LENGTH: 20
<212> TYPE: DNA
<213> ORGANISM: Homo sapiens

<400> SEQUENCE: 1707
gggagaggct gaaagaagaa                                               20

<210> SEQ ID NO 1708
<211> LENGTH: 20
<212> TYPE: DNA
<213> ORGANISM: Homo sapiens

<400> SEQUENCE: 1708
tgtgaccatc ctatccacaa                                               20

<210> SEQ ID NO 1709
<211> LENGTH: 20
<212> TYPE: DNA
<213> ORGANISM: Homo sapiens

<400> SEQUENCE: 1709
tgtatcactt cctcatgcca                                               20

<210> SEQ ID NO 1710
<211> LENGTH: 20
<212> TYPE: DNA
<213> ORGANISM: Homo sapiens

<400> SEQUENCE: 1710
agaaccagtt gtacgagttc                                               20

<210> SEQ ID NO 1711
<211> LENGTH: 20
<212> TYPE: DNA
```

-continued

```
<213> ORGANISM: Homo sapiens

<400> SEQUENCE: 1711
ccaagagttt cctgtttcca                                              20

<210> SEQ ID NO 1712
<211> LENGTH: 20
<212> TYPE: DNA
<213> ORGANISM: Homo sapiens

<400> SEQUENCE: 1712
agtcttctcc cttccttgtc                                              20

<210> SEQ ID NO 1713
<211> LENGTH: 22
<212> TYPE: DNA
<213> ORGANISM: Homo sapiens

<400> SEQUENCE: 1713
atgacacata catccattta ca                                           22

<210> SEQ ID NO 1714
<211> LENGTH: 20
<212> TYPE: DNA
<213> ORGANISM: Homo sapiens

<400> SEQUENCE: 1714
gcccttttct ctctttgacc                                              20

<210> SEQ ID NO 1715
<211> LENGTH: 20
<212> TYPE: DNA
<213> ORGANISM: Homo sapiens

<400> SEQUENCE: 1715
ctcaaactgc ccagtgattt                                              20

<210> SEQ ID NO 1716
<211> LENGTH: 21
<212> TYPE: DNA
<213> ORGANISM: Homo sapiens

<400> SEQUENCE: 1716
tcttgttcca agtattcctg g                                            21

<210> SEQ ID NO 1717
<211> LENGTH: 20
<212> TYPE: DNA
<213> ORGANISM: Homo sapiens

<400> SEQUENCE: 1717
tcctagcttg ccaaagaaat                                              20

<210> SEQ ID NO 1718
<211> LENGTH: 20
<212> TYPE: DNA
<213> ORGANISM: Homo sapiens

<400> SEQUENCE: 1718
accactttag cccatctctt                                              20

<210> SEQ ID NO 1719
<211> LENGTH: 20
```

```
<212> TYPE: DNA
<213> ORGANISM: Homo sapiens

<400> SEQUENCE: 1719
cctcctctcc aggcatttta                                        20

<210> SEQ ID NO 1720
<211> LENGTH: 20
<212> TYPE: DNA
<213> ORGANISM: Homo sapiens

<400> SEQUENCE: 1720
gtggtggatt attgagctgg                                        20

<210> SEQ ID NO 1721
<211> LENGTH: 20
<212> TYPE: DNA
<213> ORGANISM: Homo sapiens

<400> SEQUENCE: 1721
aacagagtag cacagagagt                                        20

<210> SEQ ID NO 1722
<211> LENGTH: 21
<212> TYPE: DNA
<213> ORGANISM: Homo sapiens

<400> SEQUENCE: 1722
tgcttaatgg gatcattgac c                                      21

<210> SEQ ID NO 1723
<211> LENGTH: 20
<212> TYPE: DNA
<213> ORGANISM: Homo sapiens

<400> SEQUENCE: 1723
ttcagagaga cagacagcat                                        20

<210> SEQ ID NO 1724
<211> LENGTH: 20
<212> TYPE: DNA
<213> ORGANISM: Homo sapiens

<400> SEQUENCE: 1724
cccacatagt gcaaaagaca                                        20

<210> SEQ ID NO 1725
<211> LENGTH: 20
<212> TYPE: DNA
<213> ORGANISM: Homo sapiens

<400> SEQUENCE: 1725
agaggaaaat cacaagcagt                                        20

<210> SEQ ID NO 1726
<211> LENGTH: 20
<212> TYPE: DNA
<213> ORGANISM: Homo sapiens

<400> SEQUENCE: 1726
gtatgtgtga agtagccgag                                        20

<210> SEQ ID NO 1727
```

```
<211> LENGTH: 20
<212> TYPE: DNA
<213> ORGANISM: Homo sapiens

<400> SEQUENCE: 1727
tttgaaaacc caacagacct                                              20

<210> SEQ ID NO 1728
<211> LENGTH: 20
<212> TYPE: DNA
<213> ORGANISM: Homo sapiens

<400> SEQUENCE: 1728
tggtcctaac tcagaccttt                                              20

<210> SEQ ID NO 1729
<211> LENGTH: 20
<212> TYPE: DNA
<213> ORGANISM: Homo sapiens

<400> SEQUENCE: 1729
aatccacaca ccaacagagg                                              20

<210> SEQ ID NO 1730
<211> LENGTH: 20
<212> TYPE: DNA
<213> ORGANISM: Homo sapiens

<400> SEQUENCE: 1730
aacatgaagg gaaggttgtg                                              20

<210> SEQ ID NO 1731
<211> LENGTH: 21
<212> TYPE: DNA
<213> ORGANISM: Homo sapiens

<400> SEQUENCE: 1731
tgttcacatc tgttggtttg c                                            21

<210> SEQ ID NO 1732
<211> LENGTH: 21
<212> TYPE: DNA
<213> ORGANISM: Homo sapiens

<400> SEQUENCE: 1732
tatacttcaa cttgcaggca g                                            21

<210> SEQ ID NO 1733
<211> LENGTH: 21
<212> TYPE: DNA
<213> ORGANISM: Homo sapiens

<400> SEQUENCE: 1733
gttactcggt gggtgatatt t                                            21

<210> SEQ ID NO 1734
<211> LENGTH: 21
<212> TYPE: DNA
<213> ORGANISM: Homo sapiens

<400> SEQUENCE: 1734
gccaaagaca atgagagagt c                                            21
```

```
<210> SEQ ID NO 1735
<211> LENGTH: 21
<212> TYPE: DNA
<213> ORGANISM: Homo sapiens

<400> SEQUENCE: 1735
aagaaacacc agcatcagtt c                                             21

<210> SEQ ID NO 1736
<211> LENGTH: 21
<212> TYPE: DNA
<213> ORGANISM: Homo sapiens

<400> SEQUENCE: 1736
atttagcagc catgaccagt a                                             21

<210> SEQ ID NO 1737
<211> LENGTH: 21
<212> TYPE: DNA
<213> ORGANISM: Homo sapiens

<400> SEQUENCE: 1737
aggtttagag gtgagtgaac a                                             21

<210> SEQ ID NO 1738
<211> LENGTH: 21
<212> TYPE: DNA
<213> ORGANISM: Homo sapiens

<400> SEQUENCE: 1738
tgggccaatt cctaatccat t                                             21

<210> SEQ ID NO 1739
<211> LENGTH: 22
<212> TYPE: DNA
<213> ORGANISM: Homo sapiens

<400> SEQUENCE: 1739
agaaacttca ctgtcttcca ct                                            22

<210> SEQ ID NO 1740
<211> LENGTH: 23
<212> TYPE: DNA
<213> ORGANISM: Homo sapiens

<400> SEQUENCE: 1740
cgatctcatg aataagtctg acc                                           23

<210> SEQ ID NO 1741
<211> LENGTH: 21
<212> TYPE: DNA
<213> ORGANISM: Homo sapiens

<400> SEQUENCE: 1741
tgtgatggac attggtacct g                                             21

<210> SEQ ID NO 1742
<211> LENGTH: 21
<212> TYPE: DNA
<213> ORGANISM: Homo sapiens

<400> SEQUENCE: 1742
tggaaagcag actaacagtg a                                             21
```

<210> SEQ ID NO 1743
<211> LENGTH: 21
<212> TYPE: DNA
<213> ORGANISM: Homo sapiens

<400> SEQUENCE: 1743
atatcatctg cctgtcccaa c                                              21

<210> SEQ ID NO 1744
<211> LENGTH: 21
<212> TYPE: DNA
<213> ORGANISM: Homo sapiens

<400> SEQUENCE: 1744
gggaccctat gtagagattg t                                              21

<210> SEQ ID NO 1745
<211> LENGTH: 21
<212> TYPE: DNA
<213> ORGANISM: Homo sapiens

<400> SEQUENCE: 1745
gagtgctctg tgtttgtttc a                                              21

<210> SEQ ID NO 1746
<211> LENGTH: 21
<212> TYPE: DNA
<213> ORGANISM: Homo sapiens

<400> SEQUENCE: 1746
ggagcccaag gatgtattag a                                              21

<210> SEQ ID NO 1747
<211> LENGTH: 22
<212> TYPE: DNA
<213> ORGANISM: Homo sapiens

<400> SEQUENCE: 1747
tcagtggtga gctcttgaat at                                             22

<210> SEQ ID NO 1748
<211> LENGTH: 21
<212> TYPE: DNA
<213> ORGANISM: Homo sapiens

<400> SEQUENCE: 1748
ctaatagctg gttctgcaca c                                              21

<210> SEQ ID NO 1749
<211> LENGTH: 21
<212> TYPE: DNA
<213> ORGANISM: Homo sapiens

<400> SEQUENCE: 1749
actctctctt cacacatgca a                                              21

<210> SEQ ID NO 1750
<211> LENGTH: 22
<212> TYPE: DNA
<213> ORGANISM: Homo sapiens

<400> SEQUENCE: 1750
gatgaaatga atgctgactc tc                                             22

<210> SEQ ID NO 1751
<211> LENGTH: 21
<212> TYPE: DNA
<213> ORGANISM: Homo sapiens

<400> SEQUENCE: 1751
gtgttgaagt cagtaaagcc t                                              21

<210> SEQ ID NO 1752
<211> LENGTH: 21
<212> TYPE: DNA
<213> ORGANISM: Homo sapiens

<400> SEQUENCE: 1752
aaactgaagc ttcgagaacc c                                              21

<210> SEQ ID NO 1753
<211> LENGTH: 21
<212> TYPE: DNA
<213> ORGANISM: Homo sapiens

<400> SEQUENCE: 1753
tgctttcaca tggcactaga t                                              21

<210> SEQ ID NO 1754
<211> LENGTH: 21
<212> TYPE: DNA
<213> ORGANISM: Homo sapiens

<400> SEQUENCE: 1754
tgccgacaac tactttaggt a                                              21

<210> SEQ ID NO 1755
<211> LENGTH: 21
<212> TYPE: DNA
<213> ORGANISM: Homo sapiens

<400> SEQUENCE: 1755
ggagagagaa atcccaactg a                                              21

<210> SEQ ID NO 1756
<211> LENGTH: 21
<212> TYPE: DNA
<213> ORGANISM: Homo sapiens

<400> SEQUENCE: 1756
tgtatccaat cacctgtcag a                                              21

<210> SEQ ID NO 1757
<211> LENGTH: 21
<212> TYPE: DNA
<213> ORGANISM: Homo sapiens

<400> SEQUENCE: 1757
gggagatgtc aacactaggt c                                              21

<210> SEQ ID NO 1758
<211> LENGTH: 21
<212> TYPE: DNA
<213> ORGANISM: Homo sapiens

```
<400> SEQUENCE: 1758
cagcacctta agcagaaatc a                                              21

<210> SEQ ID NO 1759
<211> LENGTH: 20
<212> TYPE: DNA
<213> ORGANISM: Homo sapiens

<400> SEQUENCE: 1759
atatgacatg gtggctctcc                                                20

<210> SEQ ID NO 1760
<211> LENGTH: 21
<212> TYPE: DNA
<213> ORGANISM: Homo sapiens

<400> SEQUENCE: 1760
aagcccttca tccatttctc t                                              21

<210> SEQ ID NO 1761
<211> LENGTH: 21
<212> TYPE: DNA
<213> ORGANISM: Homo sapiens

<400> SEQUENCE: 1761
aacatagagc catgggaggt a                                              21

<210> SEQ ID NO 1762
<211> LENGTH: 21
<212> TYPE: DNA
<213> ORGANISM: Homo sapiens

<400> SEQUENCE: 1762
atcttggtgc catcttaagg t                                              21

<210> SEQ ID NO 1763
<211> LENGTH: 21
<212> TYPE: DNA
<213> ORGANISM: Homo sapiens

<400> SEQUENCE: 1763
gatagccttc aaatcatgcc t                                              21

<210> SEQ ID NO 1764
<211> LENGTH: 21
<212> TYPE: DNA
<213> ORGANISM: Homo sapiens

<400> SEQUENCE: 1764
agcaaaccaa tcgcaaacta g                                              21

<210> SEQ ID NO 1765
<211> LENGTH: 21
<212> TYPE: DNA
<213> ORGANISM: Homo sapiens

<400> SEQUENCE: 1765
gaaagcgggt gaacaacaat a                                              21

<210> SEQ ID NO 1766
<211> LENGTH: 22
<212> TYPE: DNA
```

<213> ORGANISM: Homo sapiens

<400> SEQUENCE: 1766
aatcatcatc ttcatcagct cg                                    22

<210> SEQ ID NO 1767
<211> LENGTH: 21
<212> TYPE: DNA
<213> ORGANISM: Homo sapiens

<400> SEQUENCE: 1767
gatagagagc acaaagagca t                                     21

<210> SEQ ID NO 1768
<211> LENGTH: 21
<212> TYPE: DNA
<213> ORGANISM: Homo sapiens

<400> SEQUENCE: 1768
cctttcgcct tgcttatatg g                                     21

<210> SEQ ID NO 1769
<211> LENGTH: 21
<212> TYPE: DNA
<213> ORGANISM: Homo sapiens

<400> SEQUENCE: 1769
aacaagagga ataggagcca g                                     21

<210> SEQ ID NO 1770
<211> LENGTH: 21
<212> TYPE: DNA
<213> ORGANISM: Homo sapiens

<400> SEQUENCE: 1770
actactcaac agcctaccaa a                                     21

<210> SEQ ID NO 1771
<211> LENGTH: 21
<212> TYPE: DNA
<213> ORGANISM: Homo sapiens

<400> SEQUENCE: 1771
tgggtgctga tagtaacaaa g                                     21

<210> SEQ ID NO 1772
<211> LENGTH: 21
<212> TYPE: DNA
<213> ORGANISM: Homo sapiens

<400> SEQUENCE: 1772
tggagctggg aactttaatg t                                     21

<210> SEQ ID NO 1773
<211> LENGTH: 21
<212> TYPE: DNA
<213> ORGANISM: Homo sapiens

<400> SEQUENCE: 1773
actattgaac tgttggcttc g                                     21

<210> SEQ ID NO 1774
<211> LENGTH: 21

-continued

```
<212> TYPE: DNA
<213> ORGANISM: Homo sapiens

<400> SEQUENCE: 1774
gaagagagag agaatgcgtg t                                         21

<210> SEQ ID NO 1775
<211> LENGTH: 21
<212> TYPE: DNA
<213> ORGANISM: Homo sapiens

<400> SEQUENCE: 1775
tccactaaag agcaaccaaa c                                         21

<210> SEQ ID NO 1776
<211> LENGTH: 21
<212> TYPE: DNA
<213> ORGANISM: Homo sapiens

<400> SEQUENCE: 1776
gacatggata ttctggtgcc a                                         21

<210> SEQ ID NO 1777
<211> LENGTH: 21
<212> TYPE: DNA
<213> ORGANISM: Homo sapiens

<400> SEQUENCE: 1777
tgaagtggtc agtaacaatg g                                         21

<210> SEQ ID NO 1778
<211> LENGTH: 21
<212> TYPE: DNA
<213> ORGANISM: Homo sapiens

<400> SEQUENCE: 1778
ctgttgcaag atgacccaaa t                                         21

<210> SEQ ID NO 1779
<211> LENGTH: 21
<212> TYPE: DNA
<213> ORGANISM: Homo sapiens

<400> SEQUENCE: 1779
atttcagagc tcctttgtcc t                                         21

<210> SEQ ID NO 1780
<211> LENGTH: 22
<212> TYPE: DNA
<213> ORGANISM: Homo sapiens

<400> SEQUENCE: 1780
agatacacac acgttcacaa ac                                        22

<210> SEQ ID NO 1781
<211> LENGTH: 21
<212> TYPE: DNA
<213> ORGANISM: Homo sapiens

<400> SEQUENCE: 1781
ggcaaagaaa tctggtgttc a                                         21

<210> SEQ ID NO 1782
```

-continued

<210> SEQ ID NO 1782
<211> LENGTH: 21
<212> TYPE: DNA
<213> ORGANISM: Homo sapiens

<400> SEQUENCE: 1782
gatggcaatg cttgataacg a          21

<210> SEQ ID NO 1783
<211> LENGTH: 21
<212> TYPE: DNA
<213> ORGANISM: Homo sapiens

<400> SEQUENCE: 1783
ttgctggttg ataggcattt g          21

<210> SEQ ID NO 1784
<211> LENGTH: 22
<212> TYPE: DNA
<213> ORGANISM: Homo sapiens

<400> SEQUENCE: 1784
ttccatgaag ttcctcaaga ct         22

<210> SEQ ID NO 1785
<211> LENGTH: 21
<212> TYPE: DNA
<213> ORGANISM: Homo sapiens

<400> SEQUENCE: 1785
attcccgcaa ttgtgagatt c          21

<210> SEQ ID NO 1786
<211> LENGTH: 21
<212> TYPE: DNA
<213> ORGANISM: Homo sapiens

<400> SEQUENCE: 1786
ccacccacat accctgaaat t          21

<210> SEQ ID NO 1787
<211> LENGTH: 22
<212> TYPE: DNA
<213> ORGANISM: Homo sapiens

<400> SEQUENCE: 1787
aaagaggtac agaactcaga cc         22

<210> SEQ ID NO 1788
<211> LENGTH: 20
<212> TYPE: DNA
<213> ORGANISM: Homo sapiens

<400> SEQUENCE: 1788
gtaacacacg gatgctgaag           20

<210> SEQ ID NO 1789
<211> LENGTH: 21
<212> TYPE: DNA
<213> ORGANISM: Homo sapiens

<400> SEQUENCE: 1789
gtcttcatga acgttgccaa t          21

```
<210> SEQ ID NO 1790
<211> LENGTH: 21
<212> TYPE: DNA
<213> ORGANISM: Homo sapiens

<400> SEQUENCE: 1790
tggacacgag gctatttgta g                                              21

<210> SEQ ID NO 1791
<211> LENGTH: 21
<212> TYPE: DNA
<213> ORGANISM: Homo sapiens

<400> SEQUENCE: 1791
cttctcaggg ctctttgtgt a                                              21

<210> SEQ ID NO 1792
<211> LENGTH: 21
<212> TYPE: DNA
<213> ORGANISM: Homo sapiens

<400> SEQUENCE: 1792
ggcttaagaa ggagagtggt t                                              21

<210> SEQ ID NO 1793
<211> LENGTH: 21
<212> TYPE: DNA
<213> ORGANISM: Homo sapiens

<400> SEQUENCE: 1793
gcaacagaaa ccaagattcc t                                              21

<210> SEQ ID NO 1794
<211> LENGTH: 21
<212> TYPE: DNA
<213> ORGANISM: Homo sapiens

<400> SEQUENCE: 1794
tagtttcctt tggccttctc c                                              21

<210> SEQ ID NO 1795
<211> LENGTH: 22
<212> TYPE: DNA
<213> ORGANISM: Homo sapiens

<400> SEQUENCE: 1795
tcattgtcta cctcaaagag ca                                             22

<210> SEQ ID NO 1796
<211> LENGTH: 21
<212> TYPE: DNA
<213> ORGANISM: Homo sapiens

<400> SEQUENCE: 1796
ctagggttcc cagttcacaa a                                              21

<210> SEQ ID NO 1797
<211> LENGTH: 21
<212> TYPE: DNA
<213> ORGANISM: Homo sapiens

<400> SEQUENCE: 1797
ctctgaagga acaaaggatg g                                              21
```

<210> SEQ ID NO 1798
<211> LENGTH: 21
<212> TYPE: DNA
<213> ORGANISM: Homo sapiens

<400> SEQUENCE: 1798
gaaacaacat tgagggcatt g         21

<210> SEQ ID NO 1799
<211> LENGTH: 21
<212> TYPE: DNA
<213> ORGANISM: Homo sapiens

<400> SEQUENCE: 1799
cattagaatg cggtggtttc a         21

<210> SEQ ID NO 1800
<211> LENGTH: 21
<212> TYPE: DNA
<213> ORGANISM: Homo sapiens

<400> SEQUENCE: 1800
gagctctttg aagtagaagc a         21

<210> SEQ ID NO 1801
<211> LENGTH: 21
<212> TYPE: DNA
<213> ORGANISM: Homo sapiens

<400> SEQUENCE: 1801
gatgtctggg ctgaggttta a         21

<210> SEQ ID NO 1802
<211> LENGTH: 20
<212> TYPE: DNA
<213> ORGANISM: Homo sapiens

<400> SEQUENCE: 1802
ccattccaac aaagcttccg           20

<210> SEQ ID NO 1803
<211> LENGTH: 21
<212> TYPE: DNA
<213> ORGANISM: Homo sapiens

<400> SEQUENCE: 1803
ttcctcttga agatgcactg g         21

<210> SEQ ID NO 1804
<211> LENGTH: 21
<212> TYPE: DNA
<213> ORGANISM: Homo sapiens

<400> SEQUENCE: 1804
ctacttgccc tattgtgtcg a         21

<210> SEQ ID NO 1805
<211> LENGTH: 21
<212> TYPE: DNA
<213> ORGANISM: Homo sapiens

<400> SEQUENCE: 1805
ccagcatgtg aggaattgaa c         21

```
<210> SEQ ID NO 1806
<211> LENGTH: 21
<212> TYPE: DNA
<213> ORGANISM: Homo sapiens

<400> SEQUENCE: 1806
ccagggtgtt tgaaggtaga a                                              21

<210> SEQ ID NO 1807
<211> LENGTH: 21
<212> TYPE: DNA
<213> ORGANISM: Homo sapiens

<400> SEQUENCE: 1807
cccacttagt catccacaca t                                              21

<210> SEQ ID NO 1808
<211> LENGTH: 21
<212> TYPE: DNA
<213> ORGANISM: Homo sapiens

<400> SEQUENCE: 1808
ctggaggtaa gaaggaatgc a                                              21

<210> SEQ ID NO 1809
<211> LENGTH: 21
<212> TYPE: DNA
<213> ORGANISM: Homo sapiens

<400> SEQUENCE: 1809
gtttcacaca ccagaagaga g                                              21

<210> SEQ ID NO 1810
<211> LENGTH: 20
<212> TYPE: DNA
<213> ORGANISM: Homo sapiens

<400> SEQUENCE: 1810
atgtgggact ctttgctctc                                                20

<210> SEQ ID NO 1811
<211> LENGTH: 21
<212> TYPE: DNA
<213> ORGANISM: Homo sapiens

<400> SEQUENCE: 1811
ccatacacct gctctgacat t                                              21

<210> SEQ ID NO 1812
<211> LENGTH: 21
<212> TYPE: DNA
<213> ORGANISM: Homo sapiens

<400> SEQUENCE: 1812
atgaatacag ctttgcatgg c                                              21

<210> SEQ ID NO 1813
<211> LENGTH: 21
<212> TYPE: DNA
<213> ORGANISM: Homo sapiens
```

```
<400> SEQUENCE: 1813
atcagtaaca gtcccattgc t                                              21

<210> SEQ ID NO 1814
<211> LENGTH: 21
<212> TYPE: DNA
<213> ORGANISM: Homo sapiens

<400> SEQUENCE: 1814
gttaaagcat tcacagccct c                                              21

<210> SEQ ID NO 1815
<211> LENGTH: 21
<212> TYPE: DNA
<213> ORGANISM: Homo sapiens

<400> SEQUENCE: 1815
catgaggcat ttgatccatg g                                              21

<210> SEQ ID NO 1816
<211> LENGTH: 21
<212> TYPE: DNA
<213> ORGANISM: Homo sapiens

<400> SEQUENCE: 1816
ctgggacttg tctatcctcc t                                              21

<210> SEQ ID NO 1817
<211> LENGTH: 21
<212> TYPE: DNA
<213> ORGANISM: Homo sapiens

<400> SEQUENCE: 1817
accctgtttc actgaacaac t                                              21

<210> SEQ ID NO 1818
<211> LENGTH: 21
<212> TYPE: DNA
<213> ORGANISM: Homo sapiens

<400> SEQUENCE: 1818
atgtctgtcc aagtgaacag t                                              21

<210> SEQ ID NO 1819
<211> LENGTH: 21
<212> TYPE: DNA
<213> ORGANISM: Homo sapiens

<400> SEQUENCE: 1819
ccctgtaatg agagcgttat t                                              21

<210> SEQ ID NO 1820
<211> LENGTH: 21
<212> TYPE: DNA
<213> ORGANISM: Homo sapiens

<400> SEQUENCE: 1820
aaagtatcca gacccagaac c                                              21

<210> SEQ ID NO 1821
<211> LENGTH: 22
<212> TYPE: DNA
```

```
<213> ORGANISM: Homo sapiens

<400> SEQUENCE: 1821
gagagaatgg gttaaatctg cc                                        22

<210> SEQ ID NO 1822
<211> LENGTH: 21
<212> TYPE: DNA
<213> ORGANISM: Homo sapiens

<400> SEQUENCE: 1822
ataggccagc actccaaata a                                         21

<210> SEQ ID NO 1823
<211> LENGTH: 21
<212> TYPE: DNA
<213> ORGANISM: Homo sapiens

<400> SEQUENCE: 1823
ctgcctgact tagccttaaa t                                         21

<210> SEQ ID NO 1824
<211> LENGTH: 21
<212> TYPE: DNA
<213> ORGANISM: Homo sapiens

<400> SEQUENCE: 1824
caaatcaagt cccatggtag g                                         21

<210> SEQ ID NO 1825
<211> LENGTH: 21
<212> TYPE: DNA
<213> ORGANISM: Homo sapiens

<400> SEQUENCE: 1825
aaccagaatg ttactagccc a                                         21

<210> SEQ ID NO 1826
<211> LENGTH: 21
<212> TYPE: DNA
<213> ORGANISM: Homo sapiens

<400> SEQUENCE: 1826
ctttccgtct ttataggcag c                                         21

<210> SEQ ID NO 1827
<211> LENGTH: 21
<212> TYPE: DNA
<213> ORGANISM: Homo sapiens

<400> SEQUENCE: 1827
caatcctgtg tgtttagtgg a                                         21

<210> SEQ ID NO 1828
<211> LENGTH: 21
<212> TYPE: DNA
<213> ORGANISM: Homo sapiens

<400> SEQUENCE: 1828
agaaatcgtg ttcacagcct a                                         21

<210> SEQ ID NO 1829
<211> LENGTH: 20
```

```
<212> TYPE: DNA
<213> ORGANISM: Homo sapiens

<400> SEQUENCE: 1829
tgtgggaagc attgactctt                                              20

<210> SEQ ID NO 1830
<211> LENGTH: 21
<212> TYPE: DNA
<213> ORGANISM: Homo sapiens

<400> SEQUENCE: 1830
ccgtaaatga agtggcttga a                                            21

<210> SEQ ID NO 1831
<211> LENGTH: 21
<212> TYPE: DNA
<213> ORGANISM: Homo sapiens

<400> SEQUENCE: 1831
tcctgtgaga aatggagctt t                                            21

<210> SEQ ID NO 1832
<211> LENGTH: 21
<212> TYPE: DNA
<213> ORGANISM: Homo sapiens

<400> SEQUENCE: 1832
cctttcttgc aaccttgaga t                                            21

<210> SEQ ID NO 1833
<211> LENGTH: 22
<212> TYPE: DNA
<213> ORGANISM: Homo sapiens

<400> SEQUENCE: 1833
gttgccaagc ttaaatacct gt                                           22

<210> SEQ ID NO 1834
<211> LENGTH: 21
<212> TYPE: DNA
<213> ORGANISM: Homo sapiens

<400> SEQUENCE: 1834
ctctagatgc tcaacctcag g                                            21

<210> SEQ ID NO 1835
<211> LENGTH: 21
<212> TYPE: DNA
<213> ORGANISM: Homo sapiens

<400> SEQUENCE: 1835
ccacaacaac ataaacactg c                                            21

<210> SEQ ID NO 1836
<211> LENGTH: 21
<212> TYPE: DNA
<213> ORGANISM: Homo sapiens

<400> SEQUENCE: 1836
aataacagtc caccagaacc a                                            21

<210> SEQ ID NO 1837
```

-continued

```
<211> LENGTH: 21
<212> TYPE: DNA
<213> ORGANISM: Homo sapiens

<400> SEQUENCE: 1837
tcttccaggc atattcattg c                                              21

<210> SEQ ID NO 1838
<211> LENGTH: 21
<212> TYPE: DNA
<213> ORGANISM: Homo sapiens

<400> SEQUENCE: 1838
tccaaggacc tgcaaatgtt a                                              21

<210> SEQ ID NO 1839
<211> LENGTH: 21
<212> TYPE: DNA
<213> ORGANISM: Homo sapiens

<400> SEQUENCE: 1839
atccattctc tctacttggg a                                              21

<210> SEQ ID NO 1840
<211> LENGTH: 21
<212> TYPE: DNA
<213> ORGANISM: Homo sapiens

<400> SEQUENCE: 1840
aggttacatc attcacccac a                                              21

<210> SEQ ID NO 1841
<211> LENGTH: 22
<212> TYPE: DNA
<213> ORGANISM: Homo sapiens

<400> SEQUENCE: 1841
ggctagaggg tgattataag ct                                             22

<210> SEQ ID NO 1842
<211> LENGTH: 21
<212> TYPE: DNA
<213> ORGANISM: Homo sapiens

<400> SEQUENCE: 1842
atgaagacaa tgacatctgc g                                              21

<210> SEQ ID NO 1843
<211> LENGTH: 21
<212> TYPE: DNA
<213> ORGANISM: Homo sapiens

<400> SEQUENCE: 1843
tactcatccc gatttcttcc c                                              21

<210> SEQ ID NO 1844
<211> LENGTH: 21
<212> TYPE: DNA
<213> ORGANISM: Homo sapiens

<400> SEQUENCE: 1844
cacttgtcat ggtttaggga c                                              21
```

-continued

<210> SEQ ID NO 1845
<211> LENGTH: 21
<212> TYPE: DNA
<213> ORGANISM: Homo sapiens

<400> SEQUENCE: 1845
ttctctttct cttctgggca g                                              21

<210> SEQ ID NO 1846
<211> LENGTH: 21
<212> TYPE: DNA
<213> ORGANISM: Homo sapiens

<400> SEQUENCE: 1846
acctccacct tattgcttca a                                              21

<210> SEQ ID NO 1847
<211> LENGTH: 21
<212> TYPE: DNA
<213> ORGANISM: Homo sapiens

<400> SEQUENCE: 1847
ttgtgagact caaggccatt t                                              21

<210> SEQ ID NO 1848
<211> LENGTH: 21
<212> TYPE: DNA
<213> ORGANISM: Homo sapiens

<400> SEQUENCE: 1848
gaattgcaaa ggatgggtag g                                              21

<210> SEQ ID NO 1849
<211> LENGTH: 21
<212> TYPE: DNA
<213> ORGANISM: Homo sapiens

<400> SEQUENCE: 1849
ttggtagaga gaggccattt g                                              21

<210> SEQ ID NO 1850
<211> LENGTH: 21
<212> TYPE: DNA
<213> ORGANISM: Homo sapiens

<400> SEQUENCE: 1850
ctgcattgtg agtccatgta a                                              21

<210> SEQ ID NO 1851
<211> LENGTH: 21
<212> TYPE: DNA
<213> ORGANISM: Homo sapiens

<400> SEQUENCE: 1851
ggaggaagct cttgaagaca t                                              21

<210> SEQ ID NO 1852
<211> LENGTH: 21
<212> TYPE: DNA
<213> ORGANISM: Homo sapiens

<400> SEQUENCE: 1852
tcctatcttc atccctcttc c                                              21

```
<210> SEQ ID NO 1853
<211> LENGTH: 21
<212> TYPE: DNA
<213> ORGANISM: Homo sapiens

<400> SEQUENCE: 1853
agcatcttcc gtttaactcc a                                              21

<210> SEQ ID NO 1854
<211> LENGTH: 21
<212> TYPE: DNA
<213> ORGANISM: Homo sapiens

<400> SEQUENCE: 1854
ttccatttag cctcccatct g                                              21

<210> SEQ ID NO 1855
<211> LENGTH: 20
<212> TYPE: DNA
<213> ORGANISM: Homo sapiens

<400> SEQUENCE: 1855
ctgcctgcca agtatgttct                                                20

<210> SEQ ID NO 1856
<211> LENGTH: 21
<212> TYPE: DNA
<213> ORGANISM: Homo sapiens

<400> SEQUENCE: 1856
tagctttatg ggccttgttc t                                              21

<210> SEQ ID NO 1857
<211> LENGTH: 21
<212> TYPE: DNA
<213> ORGANISM: Homo sapiens

<400> SEQUENCE: 1857
ctactccttg tgtcattggc t                                              21

<210> SEQ ID NO 1858
<211> LENGTH: 21
<212> TYPE: DNA
<213> ORGANISM: Homo sapiens

<400> SEQUENCE: 1858
ccacctctca aacccagatt t                                              21

<210> SEQ ID NO 1859
<211> LENGTH: 21
<212> TYPE: DNA
<213> ORGANISM: Homo sapiens

<400> SEQUENCE: 1859
tgattctgag acacgtgctt a                                              21

<210> SEQ ID NO 1860
<211> LENGTH: 22
<212> TYPE: DNA
<213> ORGANISM: Homo sapiens

<400> SEQUENCE: 1860
gtcagcgtat ttgggattga at                                             22
```

<210> SEQ ID NO 1861
<211> LENGTH: 21
<212> TYPE: DNA
<213> ORGANISM: Homo sapiens

<400> SEQUENCE: 1861
cttgaggacc tttcatgctt g                                             21

<210> SEQ ID NO 1862
<211> LENGTH: 21
<212> TYPE: DNA
<213> ORGANISM: Homo sapiens

<400> SEQUENCE: 1862
aaatctgcca cccatttctt c                                             21

<210> SEQ ID NO 1863
<211> LENGTH: 21
<212> TYPE: DNA
<213> ORGANISM: Homo sapiens

<400> SEQUENCE: 1863
ttgtgatttc aggtaggagg g                                             21

<210> SEQ ID NO 1864
<211> LENGTH: 21
<212> TYPE: DNA
<213> ORGANISM: Homo sapiens

<400> SEQUENCE: 1864
tattctgagt tctacccagg t                                             21

<210> SEQ ID NO 1865
<211> LENGTH: 21
<212> TYPE: DNA
<213> ORGANISM: Homo sapiens

<400> SEQUENCE: 1865
ttccctcaga gacagtatcc t                                             21

<210> SEQ ID NO 1866
<211> LENGTH: 21
<212> TYPE: DNA
<213> ORGANISM: Homo sapiens

<400> SEQUENCE: 1866
tacatgagac ccagaaacag a                                             21

<210> SEQ ID NO 1867
<211> LENGTH: 20
<212> TYPE: DNA
<213> ORGANISM: Homo sapiens

<400> SEQUENCE: 1867
aaaggaggtc tggctttgaa                                               20

<210> SEQ ID NO 1868
<211> LENGTH: 21
<212> TYPE: DNA
<213> ORGANISM: Homo sapiens

<400> SEQUENCE: 1868
cttcttggca gactatcagg a                                         21

<210> SEQ ID NO 1869
<211> LENGTH: 21
<212> TYPE: DNA
<213> ORGANISM: Homo sapiens

<400> SEQUENCE: 1869
gcataaacct ggactgtgaa a                                         21

<210> SEQ ID NO 1870
<211> LENGTH: 21
<212> TYPE: DNA
<213> ORGANISM: Homo sapiens

<400> SEQUENCE: 1870
aagctgctaa atctgtaggg a                                         21

<210> SEQ ID NO 1871
<211> LENGTH: 20
<212> TYPE: DNA
<213> ORGANISM: Homo sapiens

<400> SEQUENCE: 1871
cactcagcga ttctcctcac                                           20

<210> SEQ ID NO 1872
<211> LENGTH: 21
<212> TYPE: DNA
<213> ORGANISM: Homo sapiens

<400> SEQUENCE: 1872
ctgaccagac ctgttgacta a                                         21

<210> SEQ ID NO 1873
<211> LENGTH: 21
<212> TYPE: DNA
<213> ORGANISM: Homo sapiens

<400> SEQUENCE: 1873
aaagccagac acagactagt t                                         21

<210> SEQ ID NO 1874
<211> LENGTH: 22
<212> TYPE: DNA
<213> ORGANISM: Homo sapiens

<400> SEQUENCE: 1874
tgatatgttc agtttgccta cc                                        22

<210> SEQ ID NO 1875
<211> LENGTH: 20
<212> TYPE: DNA
<213> ORGANISM: Homo sapiens

<400> SEQUENCE: 1875
attcctggga ccacaagcat                                           20

<210> SEQ ID NO 1876
<211> LENGTH: 20
<212> TYPE: DNA

```
<213> ORGANISM: Homo sapiens

<400> SEQUENCE: 1876
agcttgagtt tcttgctggg                                              20

<210> SEQ ID NO 1877
<211> LENGTH: 20
<212> TYPE: DNA
<213> ORGANISM: Homo sapiens

<400> SEQUENCE: 1877
tattgcctca tgtggttgtg                                              20

<210> SEQ ID NO 1878
<211> LENGTH: 21
<212> TYPE: DNA
<213> ORGANISM: Homo sapiens

<400> SEQUENCE: 1878
ttcccgcaaa gtagaagcta t                                            21

<210> SEQ ID NO 1879
<211> LENGTH: 22
<212> TYPE: DNA
<213> ORGANISM: Homo sapiens

<400> SEQUENCE: 1879
gtgttgactt gaaaggaatc ac                                           22

<210> SEQ ID NO 1880
<211> LENGTH: 21
<212> TYPE: DNA
<213> ORGANISM: Homo sapiens

<400> SEQUENCE: 1880
aaacgcatac aaacaggaga c                                            21

<210> SEQ ID NO 1881
<211> LENGTH: 21
<212> TYPE: DNA
<213> ORGANISM: Homo sapiens

<400> SEQUENCE: 1881
caggttagga atgacagtgg g                                            21

<210> SEQ ID NO 1882
<211> LENGTH: 21
<212> TYPE: DNA
<213> ORGANISM: Homo sapiens

<400> SEQUENCE: 1882
cttctaaacc catcacctgc t                                            21

<210> SEQ ID NO 1883
<211> LENGTH: 21
<212> TYPE: DNA
<213> ORGANISM: Homo sapiens

<400> SEQUENCE: 1883
ttaggttacc cagggacgtt a                                            21

<210> SEQ ID NO 1884
<211> LENGTH: 21
```

```
<212> TYPE: DNA
<213> ORGANISM: Homo sapiens

<400> SEQUENCE: 1884
cacccaaact cacaggtaca a                                              21

<210> SEQ ID NO 1885
<211> LENGTH: 21
<212> TYPE: DNA
<213> ORGANISM: Homo sapiens

<400> SEQUENCE: 1885
cggtttgctt tctgaacaac a                                              21

<210> SEQ ID NO 1886
<211> LENGTH: 21
<212> TYPE: DNA
<213> ORGANISM: Homo sapiens

<400> SEQUENCE: 1886
tgaattctga gatcgagagc c                                              21

<210> SEQ ID NO 1887
<211> LENGTH: 21
<212> TYPE: DNA
<213> ORGANISM: Homo sapiens

<400> SEQUENCE: 1887
catttgggac cctttgaaac t                                              21

<210> SEQ ID NO 1888
<211> LENGTH: 21
<212> TYPE: DNA
<213> ORGANISM: Homo sapiens

<400> SEQUENCE: 1888
agattaactg ttgcctcact g                                              21

<210> SEQ ID NO 1889
<211> LENGTH: 21
<212> TYPE: DNA
<213> ORGANISM: Homo sapiens

<400> SEQUENCE: 1889
ggttatctct gggcaaagtt c                                              21

<210> SEQ ID NO 1890
<211> LENGTH: 20
<212> TYPE: DNA
<213> ORGANISM: Homo sapiens

<400> SEQUENCE: 1890
caagacagtg cattccatgg                                                20

<210> SEQ ID NO 1891
<211> LENGTH: 21
<212> TYPE: DNA
<213> ORGANISM: Homo sapiens

<400> SEQUENCE: 1891
tagagagcag agaacaaacc c                                              21

<210> SEQ ID NO 1892
```

```
<211> LENGTH: 21
<212> TYPE: DNA
<213> ORGANISM: Homo sapiens

<400> SEQUENCE: 1892
ccaaggaaag agttgagaag g                                              21

<210> SEQ ID NO 1893
<211> LENGTH: 21
<212> TYPE: DNA
<213> ORGANISM: Homo sapiens

<400> SEQUENCE: 1893
ataagggcat ttggagggaa a                                              21

<210> SEQ ID NO 1894
<211> LENGTH: 21
<212> TYPE: DNA
<213> ORGANISM: Homo sapiens

<400> SEQUENCE: 1894
tgagtgcagt cgataaggaa g                                              21

<210> SEQ ID NO 1895
<211> LENGTH: 21
<212> TYPE: DNA
<213> ORGANISM: Homo sapiens

<400> SEQUENCE: 1895
aatgcacact tagacaccac a                                              21

<210> SEQ ID NO 1896
<211> LENGTH: 21
<212> TYPE: DNA
<213> ORGANISM: Homo sapiens

<400> SEQUENCE: 1896
aacaccgaga aagagagaga g                                              21

<210> SEQ ID NO 1897
<211> LENGTH: 21
<212> TYPE: DNA
<213> ORGANISM: Homo sapiens

<400> SEQUENCE: 1897
ggattgctac ccaggagata a                                              21

<210> SEQ ID NO 1898
<211> LENGTH: 21
<212> TYPE: DNA
<213> ORGANISM: Homo sapiens

<400> SEQUENCE: 1898
tgtactgctt tcgtcttatg c                                              21

<210> SEQ ID NO 1899
<211> LENGTH: 21
<212> TYPE: DNA
<213> ORGANISM: Homo sapiens

<400> SEQUENCE: 1899
agaggttctg tgtatgagtg t                                              21
```

```
<210> SEQ ID NO 1900
<211> LENGTH: 21
<212> TYPE: DNA
<213> ORGANISM: Homo sapiens

<400> SEQUENCE: 1900
catattcgca ctgtatagcc g                                              21

<210> SEQ ID NO 1901
<211> LENGTH: 21
<212> TYPE: DNA
<213> ORGANISM: Homo sapiens

<400> SEQUENCE: 1901
tagagaattg tacgctggac a                                              21

<210> SEQ ID NO 1902
<211> LENGTH: 21
<212> TYPE: DNA
<213> ORGANISM: Homo sapiens

<400> SEQUENCE: 1902
ctgatggatt ctctggtgtg a                                              21

<210> SEQ ID NO 1903
<211> LENGTH: 21
<212> TYPE: DNA
<213> ORGANISM: Homo sapiens

<400> SEQUENCE: 1903
tctggagaaa tgcacaagag a                                              21

<210> SEQ ID NO 1904
<211> LENGTH: 21
<212> TYPE: DNA
<213> ORGANISM: Homo sapiens

<400> SEQUENCE: 1904
tcaaggagaa gagagagggt a                                              21

<210> SEQ ID NO 1905
<211> LENGTH: 21
<212> TYPE: DNA
<213> ORGANISM: Homo sapiens

<400> SEQUENCE: 1905
tgggttagaa catggtgctt a                                              21

<210> SEQ ID NO 1906
<211> LENGTH: 21
<212> TYPE: DNA
<213> ORGANISM: Homo sapiens

<400> SEQUENCE: 1906
tctcccaaag cagacaaaga c                                              21

<210> SEQ ID NO 1907
<211> LENGTH: 21
<212> TYPE: DNA
<213> ORGANISM: Homo sapiens

<400> SEQUENCE: 1907
atcgcatcac acccttacta t                                              21
```

```
<210> SEQ ID NO 1908
<211> LENGTH: 21
<212> TYPE: DNA
<213> ORGANISM: Homo sapiens

<400> SEQUENCE: 1908
agtcagttgt tacgtgcaaa g                                              21

<210> SEQ ID NO 1909
<211> LENGTH: 21
<212> TYPE: DNA
<213> ORGANISM: Homo sapiens

<400> SEQUENCE: 1909
ggaaatttag cttgacatgg c                                              21

<210> SEQ ID NO 1910
<211> LENGTH: 21
<212> TYPE: DNA
<213> ORGANISM: Homo sapiens

<400> SEQUENCE: 1910
aaaggtttgt tcatcctccc t                                              21

<210> SEQ ID NO 1911
<211> LENGTH: 22
<212> TYPE: DNA
<213> ORGANISM: Homo sapiens

<400> SEQUENCE: 1911
tttgtaaatc cacagtgcct ac                                             22

<210> SEQ ID NO 1912
<211> LENGTH: 21
<212> TYPE: DNA
<213> ORGANISM: Homo sapiens

<400> SEQUENCE: 1912
acagagcacg caatatagga a                                              21

<210> SEQ ID NO 1913
<211> LENGTH: 21
<212> TYPE: DNA
<213> ORGANISM: Homo sapiens

<400> SEQUENCE: 1913
ggtactggag agcatagaag a                                              21

<210> SEQ ID NO 1914
<211> LENGTH: 21
<212> TYPE: DNA
<213> ORGANISM: Homo sapiens

<400> SEQUENCE: 1914
ctgcattcac ccatgtactt t                                              21

<210> SEQ ID NO 1915
<211> LENGTH: 21
<212> TYPE: DNA
<213> ORGANISM: Homo sapiens

<400> SEQUENCE: 1915
aaacaagcta tcttcaggca g                                              21
```

<210> SEQ ID NO 1916
<211> LENGTH: 21
<212> TYPE: DNA
<213> ORGANISM: Homo sapiens

<400> SEQUENCE: 1916
tccagccata ccatgtctat c                                              21

<210> SEQ ID NO 1917
<211> LENGTH: 21
<212> TYPE: DNA
<213> ORGANISM: Homo sapiens

<400> SEQUENCE: 1917
cgaacaatca gagactcgac t                                              21

<210> SEQ ID NO 1918
<211> LENGTH: 21
<212> TYPE: DNA
<213> ORGANISM: Homo sapiens

<400> SEQUENCE: 1918
ctcactaggg aagaacagca g                                              21

<210> SEQ ID NO 1919
<211> LENGTH: 21
<212> TYPE: DNA
<213> ORGANISM: Homo sapiens

<400> SEQUENCE: 1919
ctggttgaca atctgcaagt t                                              21

<210> SEQ ID NO 1920
<211> LENGTH: 22
<212> TYPE: DNA
<213> ORGANISM: Homo sapiens

<400> SEQUENCE: 1920
tgctgggtct gagtgttata aa                                             22

<210> SEQ ID NO 1921
<211> LENGTH: 21
<212> TYPE: DNA
<213> ORGANISM: Homo sapiens

<400> SEQUENCE: 1921
accatccaag tcgtcttcat a                                              21

<210> SEQ ID NO 1922
<211> LENGTH: 21
<212> TYPE: DNA
<213> ORGANISM: Homo sapiens

<400> SEQUENCE: 1922
gttgtgtgaa tggtgctgtt a                                              21

<210> SEQ ID NO 1923
<211> LENGTH: 21
<212> TYPE: DNA
<213> ORGANISM: Homo sapiens

```
<400> SEQUENCE: 1923
atagctacgc atacoctgta g                                              21

<210> SEQ ID NO 1924
<211> LENGTH: 21
<212> TYPE: DNA
<213> ORGANISM: Homo sapiens

<400> SEQUENCE: 1924
ggcccagaag actcttgtaa t                                              21

<210> SEQ ID NO 1925
<211> LENGTH: 21
<212> TYPE: DNA
<213> ORGANISM: Homo sapiens

<400> SEQUENCE: 1925
agcagaagaa acagtaaggc a                                              21

<210> SEQ ID NO 1926
<211> LENGTH: 21
<212> TYPE: DNA
<213> ORGANISM: Homo sapiens

<400> SEQUENCE: 1926
cgacctacat cagctaatgg t                                              21

<210> SEQ ID NO 1927
<211> LENGTH: 20
<212> TYPE: DNA
<213> ORGANISM: Homo sapiens

<400> SEQUENCE: 1927
acccagggac ctatttgttc                                                20

<210> SEQ ID NO 1928
<211> LENGTH: 22
<212> TYPE: DNA
<213> ORGANISM: Homo sapiens

<400> SEQUENCE: 1928
aagggaagaa taacaatggt gc                                             22

<210> SEQ ID NO 1929
<211> LENGTH: 21
<212> TYPE: DNA
<213> ORGANISM: Homo sapiens

<400> SEQUENCE: 1929
caagggctca ggtcttcatt a                                              21

<210> SEQ ID NO 1930
<211> LENGTH: 21
<212> TYPE: DNA
<213> ORGANISM: Homo sapiens

<400> SEQUENCE: 1930
atgggagtat gggagtagga a                                              21

<210> SEQ ID NO 1931
<211> LENGTH: 21
<212> TYPE: DNA
```

```
<213> ORGANISM: Homo sapiens

<400> SEQUENCE: 1931
tcactgtgac ttggagacta a                                              21

<210> SEQ ID NO 1932
<211> LENGTH: 20
<212> TYPE: DNA
<213> ORGANISM: Homo sapiens

<400> SEQUENCE: 1932
ttggtggctt gcagagattt                                                20

<210> SEQ ID NO 1933
<211> LENGTH: 21
<212> TYPE: DNA
<213> ORGANISM: Homo sapiens

<400> SEQUENCE: 1933
tgctctgctt cactgtgatt a                                              21

<210> SEQ ID NO 1934
<211> LENGTH: 22
<212> TYPE: DNA
<213> ORGANISM: Homo sapiens

<400> SEQUENCE: 1934
tcacacgatc atcatactca ca                                             22

<210> SEQ ID NO 1935
<211> LENGTH: 22
<212> TYPE: DNA
<213> ORGANISM: Homo sapiens

<400> SEQUENCE: 1935
gatgaatgac taatagccca cg                                             22

<210> SEQ ID NO 1936
<211> LENGTH: 21
<212> TYPE: DNA
<213> ORGANISM: Homo sapiens

<400> SEQUENCE: 1936
ggtagcagat gactagacga t                                              21

<210> SEQ ID NO 1937
<211> LENGTH: 21
<212> TYPE: DNA
<213> ORGANISM: Homo sapiens

<400> SEQUENCE: 1937
ccatgtttag tttggtgctg t                                              21

<210> SEQ ID NO 1938
<211> LENGTH: 21
<212> TYPE: DNA
<213> ORGANISM: Homo sapiens

<400> SEQUENCE: 1938
acgcctctgt catttcctaa c                                              21

<210> SEQ ID NO 1939
<211> LENGTH: 20
```

```
<212> TYPE: DNA
<213> ORGANISM: Homo sapiens

<400> SEQUENCE: 1939
agccaagtga ggtgctaaat                                              20

<210> SEQ ID NO 1940
<211> LENGTH: 21
<212> TYPE: DNA
<213> ORGANISM: Homo sapiens

<400> SEQUENCE: 1940
cagttgactc aatggtgcaa t                                            21

<210> SEQ ID NO 1941
<211> LENGTH: 21
<212> TYPE: DNA
<213> ORGANISM: Homo sapiens

<400> SEQUENCE: 1941
tcagggagaa atgatgtcac c                                            21

<210> SEQ ID NO 1942
<211> LENGTH: 21
<212> TYPE: DNA
<213> ORGANISM: Homo sapiens

<400> SEQUENCE: 1942
ataggttaca gattgccacg t                                            21

<210> SEQ ID NO 1943
<211> LENGTH: 21
<212> TYPE: DNA
<213> ORGANISM: Homo sapiens

<400> SEQUENCE: 1943
cagtagctgg caagaatcat c                                            21

<210> SEQ ID NO 1944
<211> LENGTH: 21
<212> TYPE: DNA
<213> ORGANISM: Homo sapiens

<400> SEQUENCE: 1944
gatgctgcta tcaaaggaac a                                            21

<210> SEQ ID NO 1945
<211> LENGTH: 21
<212> TYPE: DNA
<213> ORGANISM: Homo sapiens

<400> SEQUENCE: 1945
caacactgct agaattccca a                                            21

<210> SEQ ID NO 1946
<211> LENGTH: 21
<212> TYPE: DNA
<213> ORGANISM: Homo sapiens

<400> SEQUENCE: 1946
aagacaaaga gatggaaggc a                                            21

<210> SEQ ID NO 1947
```

```
<211> LENGTH: 21
<212> TYPE: DNA
<213> ORGANISM: Homo sapiens

<400> SEQUENCE: 1947
cctgagaagc acctgattgt a                                              21

<210> SEQ ID NO 1948
<211> LENGTH: 21
<212> TYPE: DNA
<213> ORGANISM: Homo sapiens

<400> SEQUENCE: 1948
aataccctct tcccttcctc a                                              21

<210> SEQ ID NO 1949
<211> LENGTH: 21
<212> TYPE: DNA
<213> ORGANISM: Homo sapiens

<400> SEQUENCE: 1949
tgttgtcaga aatcccagga a                                              21

<210> SEQ ID NO 1950
<211> LENGTH: 22
<212> TYPE: DNA
<213> ORGANISM: Homo sapiens

<400> SEQUENCE: 1950
ccaccgtcaa tatttatcag ct                                             22

<210> SEQ ID NO 1951
<211> LENGTH: 21
<212> TYPE: DNA
<213> ORGANISM: Homo sapiens

<400> SEQUENCE: 1951
aactggagcc atataacgat g                                              21

<210> SEQ ID NO 1952
<211> LENGTH: 21
<212> TYPE: DNA
<213> ORGANISM: Homo sapiens

<400> SEQUENCE: 1952
gcctcagtcc aaatcttaga t                                              21

<210> SEQ ID NO 1953
<211> LENGTH: 21
<212> TYPE: DNA
<213> ORGANISM: Homo sapiens

<400> SEQUENCE: 1953
gaaatggtgc cctattgttg a                                              21

<210> SEQ ID NO 1954
<211> LENGTH: 22
<212> TYPE: DNA
<213> ORGANISM: Homo sapiens

<400> SEQUENCE: 1954
ccttaggatt ctcaaagagt gt                                             22
```

```
<210> SEQ ID NO 1955
<211> LENGTH: 22
<212> TYPE: DNA
<213> ORGANISM: Homo sapiens

<400> SEQUENCE: 1955
tcttacatgc agtcatactc ct                                          22

<210> SEQ ID NO 1956
<211> LENGTH: 22
<212> TYPE: DNA
<213> ORGANISM: Homo sapiens

<400> SEQUENCE: 1956
gcagtacaga ttcttgaaca gt                                          22

<210> SEQ ID NO 1957
<211> LENGTH: 22
<212> TYPE: DNA
<213> ORGANISM: Homo sapiens

<400> SEQUENCE: 1957
gtccctcagt aacaccatct ta                                          22

<210> SEQ ID NO 1958
<211> LENGTH: 22
<212> TYPE: DNA
<213> ORGANISM: Homo sapiens

<400> SEQUENCE: 1958
agaggattag atgtcttgct gt                                          22

<210> SEQ ID NO 1959
<211> LENGTH: 21
<212> TYPE: DNA
<213> ORGANISM: Homo sapiens

<400> SEQUENCE: 1959
gaagcaagag gatcaggcaa t                                           21

<210> SEQ ID NO 1960
<211> LENGTH: 21
<212> TYPE: DNA
<213> ORGANISM: Homo sapiens

<400> SEQUENCE: 1960
tactgcaggc aattcaggta a                                           21

<210> SEQ ID NO 1961
<211> LENGTH: 21
<212> TYPE: DNA
<213> ORGANISM: Homo sapiens

<400> SEQUENCE: 1961
agtgtttcag aggcttgaaa g                                           21

<210> SEQ ID NO 1962
<211> LENGTH: 21
<212> TYPE: DNA
<213> ORGANISM: Homo sapiens

<400> SEQUENCE: 1962
gaagaggtcc agtaagtgag g                                           21
```

<210> SEQ ID NO 1963
<211> LENGTH: 21
<212> TYPE: DNA
<213> ORGANISM: Homo sapiens

<400> SEQUENCE: 1963
atccggcatc ctttaaactc t                                              21

<210> SEQ ID NO 1964
<211> LENGTH: 21
<212> TYPE: DNA
<213> ORGANISM: Homo sapiens

<400> SEQUENCE: 1964
ttgtgagtcc ttgtctcctt g                                              21

<210> SEQ ID NO 1965
<211> LENGTH: 21
<212> TYPE: DNA
<213> ORGANISM: Homo sapiens

<400> SEQUENCE: 1965
aggctaggaa gaaatgggaa a                                              21

<210> SEQ ID NO 1966
<211> LENGTH: 21
<212> TYPE: DNA
<213> ORGANISM: Homo sapiens

<400> SEQUENCE: 1966
gacgactaag acattgcatc a                                              21

<210> SEQ ID NO 1967
<211> LENGTH: 21
<212> TYPE: DNA
<213> ORGANISM: Homo sapiens

<400> SEQUENCE: 1967
acacatatgc tctgtctctc a                                              21

<210> SEQ ID NO 1968
<211> LENGTH: 21
<212> TYPE: DNA
<213> ORGANISM: Homo sapiens

<400> SEQUENCE: 1968
agaagtctct ctccgttgtt t                                              21

<210> SEQ ID NO 1969
<211> LENGTH: 21
<212> TYPE: DNA
<213> ORGANISM: Homo sapiens

<400> SEQUENCE: 1969
agttagttat cacctcgtcc c                                              21

<210> SEQ ID NO 1970
<211> LENGTH: 21
<212> TYPE: DNA
<213> ORGANISM: Homo sapiens

<400> SEQUENCE: 1970
cttatgtgca tcaactgtgc t                                              21

<210> SEQ ID NO 1971
<211> LENGTH: 22
<212> TYPE: DNA
<213> ORGANISM: Homo sapiens

<400> SEQUENCE: 1971
tgtgtatttc cctctagttg ca 22

<210> SEQ ID NO 1972
<211> LENGTH: 21
<212> TYPE: DNA
<213> ORGANISM: Homo sapiens

<400> SEQUENCE: 1972
agtgtctctc agaatcagga c 21

<210> SEQ ID NO 1973
<211> LENGTH: 21
<212> TYPE: DNA
<213> ORGANISM: Homo sapiens

<400> SEQUENCE: 1973
agcctctttc tacatcgttc g 21

<210> SEQ ID NO 1974
<211> LENGTH: 21
<212> TYPE: DNA
<213> ORGANISM: Homo sapiens

<400> SEQUENCE: 1974
tttatttccc tacgcaaagc c 21

<210> SEQ ID NO 1975
<211> LENGTH: 21
<212> TYPE: DNA
<213> ORGANISM: Homo sapiens

<400> SEQUENCE: 1975
ttacctgtgc agaagagtga c 21

<210> SEQ ID NO 1976
<211> LENGTH: 21
<212> TYPE: DNA
<213> ORGANISM: Homo sapiens

<400> SEQUENCE: 1976
agcctttgat gactgagttg a 21

<210> SEQ ID NO 1977
<211> LENGTH: 21
<212> TYPE: DNA
<213> ORGANISM: Homo sapiens

<400> SEQUENCE: 1977
tcttgtgttc tagcgtgttt g 21

<210> SEQ ID NO 1978
<211> LENGTH: 21
<212> TYPE: DNA
<213> ORGANISM: Homo sapiens

```
<400> SEQUENCE: 1978
ttggtttcta ttctgcactg c                                              21

<210> SEQ ID NO 1979
<211> LENGTH: 21
<212> TYPE: DNA
<213> ORGANISM: Homo sapiens

<400> SEQUENCE: 1979
tgtggttagt cagaaatgtg g                                              21

<210> SEQ ID NO 1980
<211> LENGTH: 21
<212> TYPE: DNA
<213> ORGANISM: Homo sapiens

<400> SEQUENCE: 1980
ttagagcttg ctagtatcgg g                                              21

<210> SEQ ID NO 1981
<211> LENGTH: 21
<212> TYPE: DNA
<213> ORGANISM: Homo sapiens

<400> SEQUENCE: 1981
gggtcctgat gagtctttgt c                                              21

<210> SEQ ID NO 1982
<211> LENGTH: 21
<212> TYPE: DNA
<213> ORGANISM: Homo sapiens

<400> SEQUENCE: 1982
gaaatcccaa actgcctgaa a                                              21

<210> SEQ ID NO 1983
<211> LENGTH: 21
<212> TYPE: DNA
<213> ORGANISM: Homo sapiens

<400> SEQUENCE: 1983
tggtgccttt gtttattcag c                                              21

<210> SEQ ID NO 1984
<211> LENGTH: 21
<212> TYPE: DNA
<213> ORGANISM: Homo sapiens

<400> SEQUENCE: 1984
atccttcttg tgaaccttcc t                                              21

<210> SEQ ID NO 1985
<211> LENGTH: 21
<212> TYPE: DNA
<213> ORGANISM: Homo sapiens

<400> SEQUENCE: 1985
tgttatgtgc cagggtttaa c                                              21

<210> SEQ ID NO 1986
<211> LENGTH: 22
<212> TYPE: DNA
```

```
<213> ORGANISM: Homo sapiens

<400> SEQUENCE: 1986
accagatgca tgtgattaaa gg                                              22

<210> SEQ ID NO 1987
<211> LENGTH: 21
<212> TYPE: DNA
<213> ORGANISM: Homo sapiens

<400> SEQUENCE: 1987
attggttcca gatacagtcg a                                               21

<210> SEQ ID NO 1988
<211> LENGTH: 21
<212> TYPE: DNA
<213> ORGANISM: Homo sapiens

<400> SEQUENCE: 1988
gtgtactcta ggctactgtc a                                               21

<210> SEQ ID NO 1989
<211> LENGTH: 21
<212> TYPE: DNA
<213> ORGANISM: Homo sapiens

<400> SEQUENCE: 1989
ggaaggaagt acagcatgga t                                               21

<210> SEQ ID NO 1990
<211> LENGTH: 21
<212> TYPE: DNA
<213> ORGANISM: Homo sapiens

<400> SEQUENCE: 1990
gtcagcagca agtaaaggtt c                                               21

<210> SEQ ID NO 1991
<211> LENGTH: 21
<212> TYPE: DNA
<213> ORGANISM: Homo sapiens

<400> SEQUENCE: 1991
ccttattgaa gctgaccatg c                                               21

<210> SEQ ID NO 1992
<211> LENGTH: 21
<212> TYPE: DNA
<213> ORGANISM: Homo sapiens

<400> SEQUENCE: 1992
catctagtca agggttccac a                                               21

<210> SEQ ID NO 1993
<211> LENGTH: 21
<212> TYPE: DNA
<213> ORGANISM: Homo sapiens

<400> SEQUENCE: 1993
cagtgggaaa tgtgcttaca t                                               21

<210> SEQ ID NO 1994
<211> LENGTH: 21
```

```
<212> TYPE: DNA
<213> ORGANISM: Homo sapiens

<400> SEQUENCE: 1994
caagtcatgc tccaaactgt t                                              21

<210> SEQ ID NO 1995
<211> LENGTH: 21
<212> TYPE: DNA
<213> ORGANISM: Homo sapiens

<400> SEQUENCE: 1995
aaagggccta tattcaccag a                                              21

<210> SEQ ID NO 1996
<211> LENGTH: 21
<212> TYPE: DNA
<213> ORGANISM: Homo sapiens

<400> SEQUENCE: 1996
aggacttagg acaacagaga a                                              21

<210> SEQ ID NO 1997
<211> LENGTH: 22
<212> TYPE: DNA
<213> ORGANISM: Homo sapiens

<400> SEQUENCE: 1997
agagccattt aagactctct gt                                             22

<210> SEQ ID NO 1998
<211> LENGTH: 21
<212> TYPE: DNA
<213> ORGANISM: Homo sapiens

<400> SEQUENCE: 1998
tgcccaacac catctctaat a                                              21

<210> SEQ ID NO 1999
<211> LENGTH: 21
<212> TYPE: DNA
<213> ORGANISM: Homo sapiens

<400> SEQUENCE: 1999
taccttgttc tctgcctcaa t                                              21

<210> SEQ ID NO 2000
<211> LENGTH: 21
<212> TYPE: DNA
<213> ORGANISM: Homo sapiens

<400> SEQUENCE: 2000
gccttcatca ctcagaactt c                                              21

<210> SEQ ID NO 2001
<211> LENGTH: 21
<212> TYPE: DNA
<213> ORGANISM: Homo sapiens

<400> SEQUENCE: 2001
tttagaagga tgtggacagg g                                              21

<210> SEQ ID NO 2002
```

```
<211> LENGTH: 21
<212> TYPE: DNA
<213> ORGANISM: Homo sapiens

<400> SEQUENCE: 2002
agggtatcta ttctccggac a                                              21

<210> SEQ ID NO 2003
<211> LENGTH: 20
<212> TYPE: DNA
<213> ORGANISM: Homo sapiens

<400> SEQUENCE: 2003
agcaggacat ggacttcaaa                                                20

<210> SEQ ID NO 2004
<211> LENGTH: 21
<212> TYPE: DNA
<213> ORGANISM: Homo sapiens

<400> SEQUENCE: 2004
atttgcccaa gtaagttcca c                                              21

<210> SEQ ID NO 2005
<211> LENGTH: 21
<212> TYPE: DNA
<213> ORGANISM: Homo sapiens

<400> SEQUENCE: 2005
gcggctcttg tttctgaaat c                                              21

<210> SEQ ID NO 2006
<211> LENGTH: 21
<212> TYPE: DNA
<213> ORGANISM: Homo sapiens

<400> SEQUENCE: 2006
tggaagtaca tgggatgcat t                                              21

<210> SEQ ID NO 2007
<211> LENGTH: 21
<212> TYPE: DNA
<213> ORGANISM: Homo sapiens

<400> SEQUENCE: 2007
acaggtagga gttcagagac a                                              21

<210> SEQ ID NO 2008
<211> LENGTH: 21
<212> TYPE: DNA
<213> ORGANISM: Homo sapiens

<400> SEQUENCE: 2008
cttgaagagt tccaatgcca a                                              21

<210> SEQ ID NO 2009
<211> LENGTH: 22
<212> TYPE: DNA
<213> ORGANISM: Homo sapiens

<400> SEQUENCE: 2009
tttcctattc tgctcttctg ct                                             22
```

```
<210> SEQ ID NO 2010
<211> LENGTH: 21
<212> TYPE: DNA
<213> ORGANISM: Homo sapiens

<400> SEQUENCE: 2010
cgctgctgtt taaatcgatc a                                              21

<210> SEQ ID NO 2011
<211> LENGTH: 21
<212> TYPE: DNA
<213> ORGANISM: Homo sapiens

<400> SEQUENCE: 2011
aaatgctgct cagggttaga g                                              21

<210> SEQ ID NO 2012
<211> LENGTH: 21
<212> TYPE: DNA
<213> ORGANISM: Homo sapiens

<400> SEQUENCE: 2012
gctctgcttt gctcaaattc t                                              21

<210> SEQ ID NO 2013
<211> LENGTH: 21
<212> TYPE: DNA
<213> ORGANISM: Homo sapiens

<400> SEQUENCE: 2013
caactttact ctgcacagct c                                              21

<210> SEQ ID NO 2014
<211> LENGTH: 22
<212> TYPE: DNA
<213> ORGANISM: Homo sapiens

<400> SEQUENCE: 2014
tgagctccag aattagatgt gt                                             22

<210> SEQ ID NO 2015
<211> LENGTH: 22
<212> TYPE: DNA
<213> ORGANISM: Homo sapiens

<400> SEQUENCE: 2015
cagtgccact acaagaaat ca                                              22

<210> SEQ ID NO 2016
<211> LENGTH: 22
<212> TYPE: DNA
<213> ORGANISM: Homo sapiens

<400> SEQUENCE: 2016
aacacctcct ttctcactac ag                                             22

<210> SEQ ID NO 2017
<211> LENGTH: 21
<212> TYPE: DNA
<213> ORGANISM: Homo sapiens

<400> SEQUENCE: 2017
agaagcagag gttggatatg g                                              21
```

```
<210> SEQ ID NO 2018
<211> LENGTH: 20
<212> TYPE: DNA
<213> ORGANISM: Homo sapiens

<400> SEQUENCE: 2018
acaaacttca ttcaccgcag                                                   20

<210> SEQ ID NO 2019
<211> LENGTH: 21
<212> TYPE: DNA
<213> ORGANISM: Homo sapiens

<400> SEQUENCE: 2019
ccacaatccc atagtcacca t                                                 21

<210> SEQ ID NO 2020
<211> LENGTH: 20
<212> TYPE: DNA
<213> ORGANISM: Homo sapiens

<400> SEQUENCE: 2020
aactacgcca cccaactaaa                                                   20

<210> SEQ ID NO 2021
<211> LENGTH: 21
<212> TYPE: DNA
<213> ORGANISM: Homo sapiens

<400> SEQUENCE: 2021
gctggttctt gttgctgata a                                                 21

<210> SEQ ID NO 2022
<211> LENGTH: 21
<212> TYPE: DNA
<213> ORGANISM: Homo sapiens

<400> SEQUENCE: 2022
gcttcagtgt aaccatgact c                                                 21

<210> SEQ ID NO 2023
<211> LENGTH: 21
<212> TYPE: DNA
<213> ORGANISM: Homo sapiens

<400> SEQUENCE: 2023
tccctcacga cttatgtttg a                                                 21

<210> SEQ ID NO 2024
<211> LENGTH: 22
<212> TYPE: DNA
<213> ORGANISM: Homo sapiens

<400> SEQUENCE: 2024
tgcacaatta agctacttct cc                                                22

<210> SEQ ID NO 2025
<211> LENGTH: 21
<212> TYPE: DNA
<213> ORGANISM: Homo sapiens

<400> SEQUENCE: 2025
ctaccttctc cagtgcacta t                                                 21
```

<210> SEQ ID NO 2026
<211> LENGTH: 21
<212> TYPE: DNA
<213> ORGANISM: Homo sapiens

<400> SEQUENCE: 2026
caacaccaaa cttgcctgaa t                                             21

<210> SEQ ID NO 2027
<211> LENGTH: 21
<212> TYPE: DNA
<213> ORGANISM: Homo sapiens

<400> SEQUENCE: 2027
ggacctctct ttgaaatgga c                                             21

<210> SEQ ID NO 2028
<211> LENGTH: 21
<212> TYPE: DNA
<213> ORGANISM: Homo sapiens

<400> SEQUENCE: 2028
tccacaattt ctacagcaac c                                             21

<210> SEQ ID NO 2029
<211> LENGTH: 21
<212> TYPE: DNA
<213> ORGANISM: Homo sapiens

<400> SEQUENCE: 2029
tgggttgtgt ttctctgact t                                             21

<210> SEQ ID NO 2030
<211> LENGTH: 21
<212> TYPE: DNA
<213> ORGANISM: Homo sapiens

<400> SEQUENCE: 2030
gtgtcatttg attggtgctc t                                             21

<210> SEQ ID NO 2031
<211> LENGTH: 21
<212> TYPE: DNA
<213> ORGANISM: Homo sapiens

<400> SEQUENCE: 2031
tacaagcctc ctttaaccct t                                             21

<210> SEQ ID NO 2032
<211> LENGTH: 22
<212> TYPE: DNA
<213> ORGANISM: Homo sapiens

<400> SEQUENCE: 2032
gggtgtttca gtaggttagg at                                            22

<210> SEQ ID NO 2033
<211> LENGTH: 21
<212> TYPE: DNA
<213> ORGANISM: Homo sapiens

<400> SEQUENCE: 2033
aaagggtttg atacagttgg g                                              21

<210> SEQ ID NO 2034
<211> LENGTH: 21
<212> TYPE: DNA
<213> ORGANISM: Homo sapiens

<400> SEQUENCE: 2034
tgggattcta atgtctggtg c                                              21

<210> SEQ ID NO 2035
<211> LENGTH: 22
<212> TYPE: DNA
<213> ORGANISM: Homo sapiens

<400> SEQUENCE: 2035
aggtattgga gagcaagaaa ga                                             22

<210> SEQ ID NO 2036
<211> LENGTH: 18
<212> TYPE: DNA
<213> ORGANISM: Homo sapiens

<400> SEQUENCE: 2036
agaggtggtt ggttggtt                                                  18

<210> SEQ ID NO 2037
<211> LENGTH: 21
<212> TYPE: DNA
<213> ORGANISM: Homo sapiens

<400> SEQUENCE: 2037
gcaaactgga gctaaagtca t                                              21

<210> SEQ ID NO 2038
<211> LENGTH: 21
<212> TYPE: DNA
<213> ORGANISM: Homo sapiens

<400> SEQUENCE: 2038
gggcatcctg tctgaaatat g                                              21

<210> SEQ ID NO 2039
<211> LENGTH: 21
<212> TYPE: DNA
<213> ORGANISM: Homo sapiens

<400> SEQUENCE: 2039
ttggttgcta gctctcaaat g                                              21

<210> SEQ ID NO 2040
<211> LENGTH: 21
<212> TYPE: DNA
<213> ORGANISM: Homo sapiens

<400> SEQUENCE: 2040
aagaagcgca gatacagtac a                                              21

<210> SEQ ID NO 2041
<211> LENGTH: 21
<212> TYPE: DNA

<213> ORGANISM: Homo sapiens

<400> SEQUENCE: 2041
ttcaatgccc ttacttctcc t                                      21

<210> SEQ ID NO 2042
<211> LENGTH: 21
<212> TYPE: DNA
<213> ORGANISM: Homo sapiens

<400> SEQUENCE: 2042
cacagcaagt ttgaacctag t                                      21

<210> SEQ ID NO 2043
<211> LENGTH: 20
<212> TYPE: DNA
<213> ORGANISM: Homo sapiens

<400> SEQUENCE: 2043
gcttgaggcg catatgattg                                        20

<210> SEQ ID NO 2044
<211> LENGTH: 21
<212> TYPE: DNA
<213> ORGANISM: Homo sapiens

<400> SEQUENCE: 2044
agtgcaaatg atgacctgtt g                                      21

<210> SEQ ID NO 2045
<211> LENGTH: 20
<212> TYPE: DNA
<213> ORGANISM: Homo sapiens

<400> SEQUENCE: 2045
catatggtgc ttgttctggg                                        20

<210> SEQ ID NO 2046
<211> LENGTH: 21
<212> TYPE: DNA
<213> ORGANISM: Homo sapiens

<400> SEQUENCE: 2046
gaactgttgc atgagaggta c                                      21

<210> SEQ ID NO 2047
<211> LENGTH: 21
<212> TYPE: DNA
<213> ORGANISM: Homo sapiens

<400> SEQUENCE: 2047
caaactcacc acccttcatt c                                      21

<210> SEQ ID NO 2048
<211> LENGTH: 21
<212> TYPE: DNA
<213> ORGANISM: Homo sapiens

<400> SEQUENCE: 2048
ctttgtcctt ctctgttgtg t                                      21

<210> SEQ ID NO 2049
<211> LENGTH: 21

```
<212> TYPE: DNA
<213> ORGANISM: Homo sapiens

<400> SEQUENCE: 2049
ccttagccct gcaaataaca c                                              21

<210> SEQ ID NO 2050
<211> LENGTH: 22
<212> TYPE: DNA
<213> ORGANISM: Homo sapiens

<400> SEQUENCE: 2050
tttcttctag agtccagagg tg                                             22

<210> SEQ ID NO 2051
<211> LENGTH: 20
<212> TYPE: DNA
<213> ORGANISM: Homo sapiens

<400> SEQUENCE: 2051
tcacagatac ggacaagctc                                                20

<210> SEQ ID NO 2052
<211> LENGTH: 21
<212> TYPE: DNA
<213> ORGANISM: Homo sapiens

<400> SEQUENCE: 2052
attctcttct ctcttccagc c                                              21

<210> SEQ ID NO 2053
<211> LENGTH: 21
<212> TYPE: DNA
<213> ORGANISM: Homo sapiens

<400> SEQUENCE: 2053
gccacaggta tcaatcactt c                                              21

<210> SEQ ID NO 2054
<211> LENGTH: 21
<212> TYPE: DNA
<213> ORGANISM: Homo sapiens

<400> SEQUENCE: 2054
tatggctttg ctaccttgtc a                                              21

<210> SEQ ID NO 2055
<211> LENGTH: 21
<212> TYPE: DNA
<213> ORGANISM: Homo sapiens

<400> SEQUENCE: 2055
gcttctgtgg cactaatcaa g                                              21

<210> SEQ ID NO 2056
<211> LENGTH: 21
<212> TYPE: DNA
<213> ORGANISM: Homo sapiens

<400> SEQUENCE: 2056
ctatttctct ggctcttgac c                                              21

<210> SEQ ID NO 2057
```

```
<211> LENGTH: 22
<212> TYPE: DNA
<213> ORGANISM: Homo sapiens

<400> SEQUENCE: 2057
gccttattga cttactggac tg                                              22

<210> SEQ ID NO 2058
<211> LENGTH: 21
<212> TYPE: DNA
<213> ORGANISM: Homo sapiens

<400> SEQUENCE: 2058
ttcttaaacc tctgtgtggc t                                               21

<210> SEQ ID NO 2059
<211> LENGTH: 21
<212> TYPE: DNA
<213> ORGANISM: Homo sapiens

<400> SEQUENCE: 2059
gtcagggatt agaggcagaa c                                               21

<210> SEQ ID NO 2060
<211> LENGTH: 21
<212> TYPE: DNA
<213> ORGANISM: Homo sapiens

<400> SEQUENCE: 2060
tggacaaaca agaactgggt a                                               21

<210> SEQ ID NO 2061
<211> LENGTH: 22
<212> TYPE: DNA
<213> ORGANISM: Homo sapiens

<400> SEQUENCE: 2061
caatcacttg gtcagatagt gt                                              22

<210> SEQ ID NO 2062
<211> LENGTH: 21
<212> TYPE: DNA
<213> ORGANISM: Homo sapiens

<400> SEQUENCE: 2062
ccatgatcac tgaaaccaac a                                               21

<210> SEQ ID NO 2063
<211> LENGTH: 22
<212> TYPE: DNA
<213> ORGANISM: Homo sapiens

<400> SEQUENCE: 2063
agtggagagg ttgagtatag tg                                              22

<210> SEQ ID NO 2064
<211> LENGTH: 21
<212> TYPE: DNA
<213> ORGANISM: Homo sapiens

<400> SEQUENCE: 2064
ccatatgccc tgctctttaa g                                               21
```

```
<210> SEQ ID NO 2065
<211> LENGTH: 21
<212> TYPE: DNA
<213> ORGANISM: Homo sapiens

<400> SEQUENCE: 2065
tgagaaggga ggaagaatgt g                                              21

<210> SEQ ID NO 2066
<211> LENGTH: 21
<212> TYPE: DNA
<213> ORGANISM: Homo sapiens

<400> SEQUENCE: 2066
gggtggacaa agcaattcaa a                                              21

<210> SEQ ID NO 2067
<211> LENGTH: 21
<212> TYPE: DNA
<213> ORGANISM: Homo sapiens

<400> SEQUENCE: 2067
aaggtcaaac tctccattcc a                                              21

<210> SEQ ID NO 2068
<211> LENGTH: 22
<212> TYPE: DNA
<213> ORGANISM: Homo sapiens

<400> SEQUENCE: 2068
cagcattcaa ttcatccttg tg                                             22

<210> SEQ ID NO 2069
<211> LENGTH: 21
<212> TYPE: DNA
<213> ORGANISM: Homo sapiens

<400> SEQUENCE: 2069
ggagatgtct ttgccctgat t                                              21

<210> SEQ ID NO 2070
<211> LENGTH: 21
<212> TYPE: DNA
<213> ORGANISM: Homo sapiens

<400> SEQUENCE: 2070
aagtagaagc aagccctgaa t                                              21

<210> SEQ ID NO 2071
<211> LENGTH: 21
<212> TYPE: DNA
<213> ORGANISM: Homo sapiens

<400> SEQUENCE: 2071
ggtcctcgtt tgtccttaag a                                              21

<210> SEQ ID NO 2072
<211> LENGTH: 22
<212> TYPE: DNA
<213> ORGANISM: Homo sapiens

<400> SEQUENCE: 2072
gtgtggtagg gatgagaatt at                                             22
```

-continued

<210> SEQ ID NO 2073
<211> LENGTH: 21
<212> TYPE: DNA
<213> ORGANISM: Homo sapiens

<400> SEQUENCE: 2073
agtattgctt tgagggctct a							21

<210> SEQ ID NO 2074
<211> LENGTH: 20
<212> TYPE: DNA
<213> ORGANISM: Homo sapiens

<400> SEQUENCE: 2074
tcaggtaagc ttccctccac							20

<210> SEQ ID NO 2075
<211> LENGTH: 22
<212> TYPE: DNA
<213> ORGANISM: Homo sapiens

<400> SEQUENCE: 2075
agctatcatg taagtcactc cc						22

<210> SEQ ID NO 2076
<211> LENGTH: 21
<212> TYPE: DNA
<213> ORGANISM: Homo sapiens

<400> SEQUENCE: 2076
actggttgta gaaaggacct c							21

<210> SEQ ID NO 2077
<211> LENGTH: 21
<212> TYPE: DNA
<213> ORGANISM: Homo sapiens

<400> SEQUENCE: 2077
aggaaattca gtacctcagc t							21

<210> SEQ ID NO 2078
<211> LENGTH: 21
<212> TYPE: DNA
<213> ORGANISM: Homo sapiens

<400> SEQUENCE: 2078
agtaagaggc cagaagtcag a							21

<210> SEQ ID NO 2079
<211> LENGTH: 22
<212> TYPE: DNA
<213> ORGANISM: Homo sapiens

<400> SEQUENCE: 2079
caaccttctc attgttgaag ct						22

<210> SEQ ID NO 2080
<211> LENGTH: 21
<212> TYPE: DNA
<213> ORGANISM: Homo sapiens

<400> SEQUENCE: 2080
gcagtgcagg cctatatata g							21

```
<210> SEQ ID NO 2081
<211> LENGTH: 20
<212> TYPE: DNA
<213> ORGANISM: Homo sapiens

<400> SEQUENCE: 2081
ggtgactttg ctttcccaag                                                   20

<210> SEQ ID NO 2082
<211> LENGTH: 21
<212> TYPE: DNA
<213> ORGANISM: Homo sapiens

<400> SEQUENCE: 2082
aaatctctga gtcggccata a                                                 21

<210> SEQ ID NO 2083
<211> LENGTH: 20
<212> TYPE: DNA
<213> ORGANISM: Homo sapiens

<400> SEQUENCE: 2083
gctgacaaac ggagggagag                                                   20

<210> SEQ ID NO 2084
<211> LENGTH: 20
<212> TYPE: DNA
<213> ORGANISM: Homo sapiens

<400> SEQUENCE: 2084
aggcatggca aacttacttg                                                   20

<210> SEQ ID NO 2085
<211> LENGTH: 21
<212> TYPE: DNA
<213> ORGANISM: Homo sapiens

<400> SEQUENCE: 2085
tgttcttcat caggcacaat g                                                 21

<210> SEQ ID NO 2086
<211> LENGTH: 21
<212> TYPE: DNA
<213> ORGANISM: Homo sapiens

<400> SEQUENCE: 2086
catttcactt tcgaggatgg t                                                 21

<210> SEQ ID NO 2087
<211> LENGTH: 21
<212> TYPE: DNA
<213> ORGANISM: Homo sapiens

<400> SEQUENCE: 2087
accatttgtg tgatccagaa c                                                 21

<210> SEQ ID NO 2088
<211> LENGTH: 21
<212> TYPE: DNA
<213> ORGANISM: Homo sapiens
```

```
<400> SEQUENCE: 2088
gtcagactaa agtgaggacc a                                              21

<210> SEQ ID NO 2089
<211> LENGTH: 20
<212> TYPE: DNA
<213> ORGANISM: Homo sapiens

<400> SEQUENCE: 2089
cttgtcttga gtgcggtaca                                                20

<210> SEQ ID NO 2090
<211> LENGTH: 21
<212> TYPE: DNA
<213> ORGANISM: Homo sapiens

<400> SEQUENCE: 2090
ccagccctac ctaaagtgaa t                                              21

<210> SEQ ID NO 2091
<211> LENGTH: 22
<212> TYPE: DNA
<213> ORGANISM: Homo sapiens

<400> SEQUENCE: 2091
gcctctcagt ttcctcttat ag                                             22

<210> SEQ ID NO 2092
<211> LENGTH: 21
<212> TYPE: DNA
<213> ORGANISM: Homo sapiens

<400> SEQUENCE: 2092 cccttcaca agactcttct c                                               21

<210> SEQ ID NO 2093
<211> LENGTH: 25
<212> TYPE: DNA
<213> ORGANISM: Homo sapiens

<400> SEQUENCE: 2093
cctagatcag tgcagagaat ttagt                                          25

<210> SEQ ID NO 2094
<211> LENGTH: 24
<212> TYPE: DNA
<213> ORGANISM: Homo sapiens

<400> SEQUENCE: 2094
tgctgtataa acaccttctg aaga                                           24

<210> SEQ ID NO 2095
<211> LENGTH: 22
<212> TYPE: DNA
<213> ORGANISM: Homo sapiens

<400> SEQUENCE: 2095
ctttagtttg gaggcctcat tc                                             22

<210> SEQ ID NO 2096
<211> LENGTH: 22
<212> TYPE: DNA
```

```
<213> ORGANISM: Homo sapiens

<400> SEQUENCE: 2096
ccaaatgtag aacaggatca gc                                              22

<210> SEQ ID NO 2097
<211> LENGTH: 21
<212> TYPE: DNA
<213> ORGANISM: Homo sapiens

<400> SEQUENCE: 2097
ctgacatcga tggaattctg g                                               21

<210> SEQ ID NO 2098
<211> LENGTH: 20
<212> TYPE: DNA
<213> ORGANISM: Homo sapiens

<400> SEQUENCE: 2098
tagcagtagg tgtggctttc                                                 20

<210> SEQ ID NO 2099
<211> LENGTH: 21
<212> TYPE: DNA
<213> ORGANISM: Homo sapiens

<400> SEQUENCE: 2099
acactgcacg aatggaagat c                                               21

<210> SEQ ID NO 2100
<211> LENGTH: 21
<212> TYPE: DNA
<213> ORGANISM: Homo sapiens

<400> SEQUENCE: 2100
ttggattctc ttggttgtga g                                               21

<210> SEQ ID NO 2101
<211> LENGTH: 21
<212> TYPE: DNA
<213> ORGANISM: Homo sapiens

<400> SEQUENCE: 2101
ataaacttgg tgctcagtgg t                                               21

<210> SEQ ID NO 2102
<211> LENGTH: 22
<212> TYPE: DNA
<213> ORGANISM: Homo sapiens

<400> SEQUENCE: 2102
caacgctttg gtatagtttg tg                                              22

<210> SEQ ID NO 2103
<211> LENGTH: 21
<212> TYPE: DNA
<213> ORGANISM: Homo sapiens

<400> SEQUENCE: 2103
acaagcatta cagaattcgg c                                               21

<210> SEQ ID NO 2104
<211> LENGTH: 21
```

```
<212> TYPE: DNA
<213> ORGANISM: Homo sapiens

<400> SEQUENCE: 2104
ccaggtgcca tcgttaaaga a                                   21

<210> SEQ ID NO 2105
<211> LENGTH: 25
<212> TYPE: DNA
<213> ORGANISM: Homo sapiens

<400> SEQUENCE: 2105
actgacagat tctcacctat atcag                               25

<210> SEQ ID NO 2106
<211> LENGTH: 23
<212> TYPE: DNA
<213> ORGANISM: Homo sapiens

<400> SEQUENCE: 2106
acaatccaaa ctcttcatgc agt                                 23

<210> SEQ ID NO 2107
<211> LENGTH: 21
<212> TYPE: DNA
<213> ORGANISM: Homo sapiens

<400> SEQUENCE: 2107
ggatcaaagc cactctagac t                                   21

<210> SEQ ID NO 2108
<211> LENGTH: 22
<212> TYPE: DNA
<213> ORGANISM: Homo sapiens

<400> SEQUENCE: 2108
ggataagtca actaccatgg tt                                  22

<210> SEQ ID NO 2109
<211> LENGTH: 22
<212> TYPE: DNA
<213> ORGANISM: Homo sapiens

<400> SEQUENCE: 2109
ttgagatggc atcaagttca ag                                  22

<210> SEQ ID NO 2110
<211> LENGTH: 21
<212> TYPE: DNA
<213> ORGANISM: Homo sapiens

<400> SEQUENCE: 2110
aatggaatta ctcagctgtg g                                   21

<210> SEQ ID NO 2111
<211> LENGTH: 22
<212> TYPE: DNA
<213> ORGANISM: Homo sapiens

<400> SEQUENCE: 2111
actggattca tgcgttatca ag                                  22

<210> SEQ ID NO 2112
```

```
<211> LENGTH: 21
<212> TYPE: DNA
<213> ORGANISM: Homo sapiens

<400> SEQUENCE: 2112
ggcagaaact gatagagact g                                         21

<210> SEQ ID NO 2113
<211> LENGTH: 21
<212> TYPE: DNA
<213> ORGANISM: Homo sapiens

<400> SEQUENCE: 2113
tattcttgtg tggaccctgt g                                         21

<210> SEQ ID NO 2114
<211> LENGTH: 21
<212> TYPE: DNA
<213> ORGANISM: Homo sapiens

<400> SEQUENCE: 2114
accatgttct gagtacctct t                                         21

<210> SEQ ID NO 2115
<211> LENGTH: 22
<212> TYPE: DNA
<213> ORGANISM: Homo sapiens

<400> SEQUENCE: 2115
tgatattgca tgaaagtccc tg                                        22

<210> SEQ ID NO 2116
<211> LENGTH: 23
<212> TYPE: DNA
<213> ORGANISM: Homo sapiens

<400> SEQUENCE: 2116
agtcctgaat caatgtctaa cac                                       23

<210> SEQ ID NO 2117
<211> LENGTH: 20
<212> TYPE: DNA
<213> ORGANISM: Homo sapiens

<400> SEQUENCE: 2117
tcacacatga ggagtagaca                                           20

<210> SEQ ID NO 2118
<211> LENGTH: 20
<212> TYPE: DNA
<213> ORGANISM: Homo sapiens

<400> SEQUENCE: 2118
tggtccctgt gctttgatat                                           20

<210> SEQ ID NO 2119
<211> LENGTH: 20
<212> TYPE: DNA
<213> ORGANISM: Homo sapiens

<400> SEQUENCE: 2119
cacagcagga gacatgagaa                                           20
```

```
<210> SEQ ID NO 2120
<211> LENGTH: 20
<212> TYPE: DNA
<213> ORGANISM: Homo sapiens

<400> SEQUENCE: 2120
tggcttttct ttcctcggta                                          20

<210> SEQ ID NO 2121
<211> LENGTH: 20
<212> TYPE: DNA
<213> ORGANISM: Homo sapiens

<400> SEQUENCE: 2121
tttcctcctg gcttgatcac                                          20

<210> SEQ ID NO 2122
<211> LENGTH: 20
<212> TYPE: DNA
<213> ORGANISM: Homo sapiens

<400> SEQUENCE: 2122
ccaaggctgc tttaattcca                                          20

<210> SEQ ID NO 2123
<211> LENGTH: 20
<212> TYPE: DNA
<213> ORGANISM: Homo sapiens

<400> SEQUENCE: 2123
caaaggagag aagtgaccca                                          20

<210> SEQ ID NO 2124
<211> LENGTH: 20
<212> TYPE: DNA
<213> ORGANISM: Homo sapiens

<400> SEQUENCE: 2124
caaactatcg ctgaggacct                                          20

<210> SEQ ID NO 2125
<211> LENGTH: 20
<212> TYPE: DNA
<213> ORGANISM: Homo sapiens

<400> SEQUENCE: 2125
ctacgagtga aacagagtgc                                          20

<210> SEQ ID NO 2126
<211> LENGTH: 20
<212> TYPE: DNA
<213> ORGANISM: Homo sapiens

<400> SEQUENCE: 2126
gtctgctgcc attgagttat                                          20

<210> SEQ ID NO 2127
<211> LENGTH: 20
<212> TYPE: DNA
<213> ORGANISM: Homo sapiens

<400> SEQUENCE: 2127
agactaaaag cctccaagcc                                          20
```

-continued

```
<210> SEQ ID NO 2128
<211> LENGTH: 20
<212> TYPE: DNA
<213> ORGANISM: Homo sapiens

<400> SEQUENCE: 2128
gctcaccctc tcttctctct                                                 20

<210> SEQ ID NO 2129
<211> LENGTH: 20
<212> TYPE: DNA
<213> ORGANISM: Homo sapiens

<400> SEQUENCE: 2129
tagaatatgt cacccagccc                                                 20

<210> SEQ ID NO 2130
<211> LENGTH: 20
<212> TYPE: DNA
<213> ORGANISM: Homo sapiens

<400> SEQUENCE: 2130
acctgtttct cccagttaca                                                 20

<210> SEQ ID NO 2131
<211> LENGTH: 20
<212> TYPE: DNA
<213> ORGANISM: Homo sapiens

<400> SEQUENCE: 2131
acagaatcat cccatagcca                                                 20

<210> SEQ ID NO 2132
<211> LENGTH: 20
<212> TYPE: DNA
<213> ORGANISM: Homo sapiens

<400> SEQUENCE: 2132
gcccatgaaa gagaaaccag                                                 20

<210> SEQ ID NO 2133
<211> LENGTH: 21
<212> TYPE: DNA
<213> ORGANISM: Homo sapiens

<400> SEQUENCE: 2133
cgccattctg tgcttaattt g                                               21

<210> SEQ ID NO 2134
<211> LENGTH: 20
<212> TYPE: DNA
<213> ORGANISM: Homo sapiens

<400> SEQUENCE: 2134
ctccatcagt gcagaagtcc                                                 20

<210> SEQ ID NO 2135
<211> LENGTH: 21
<212> TYPE: DNA
<213> ORGANISM: Homo sapiens

<400> SEQUENCE: 2135
gtgaagcaag agaaagcaag a                                               21
```

```
<210> SEQ ID NO 2136
<211> LENGTH: 20
<212> TYPE: DNA
<213> ORGANISM: Homo sapiens

<400> SEQUENCE: 2136
acagtcagca gccctaaaat                                              20

<210> SEQ ID NO 2137
<211> LENGTH: 20
<212> TYPE: DNA
<213> ORGANISM: Homo sapiens

<400> SEQUENCE: 2137
tgattcggct gcaggttatt                                              20

<210> SEQ ID NO 2138
<211> LENGTH: 20
<212> TYPE: DNA
<213> ORGANISM: Homo sapiens

<400> SEQUENCE: 2138
gcctccttca cataatgcag                                              20

<210> SEQ ID NO 2139
<211> LENGTH: 20
<212> TYPE: DNA
<213> ORGANISM: Homo sapiens

<400> SEQUENCE: 2139
ctggcttcaa atgcatctga                                              20

<210> SEQ ID NO 2140
<211> LENGTH: 20
<212> TYPE: DNA
<213> ORGANISM: Homo sapiens

<400> SEQUENCE: 2140
ttgtcaacag agagtcagct                                              20

<210> SEQ ID NO 2141
<211> LENGTH: 20
<212> TYPE: DNA
<213> ORGANISM: Homo sapiens

<400> SEQUENCE: 2141
actgggaaat tggaattcgc                                              20

<210> SEQ ID NO 2142
<211> LENGTH: 20
<212> TYPE: DNA
<213> ORGANISM: Homo sapiens

<400> SEQUENCE: 2142
ctgaaatggt ctgggagtct                                              20

<210> SEQ ID NO 2143
<211> LENGTH: 20
<212> TYPE: DNA
<213> ORGANISM: Homo sapiens
```

```
<400> SEQUENCE: 2143
ggtaaaactg cctggaaact                                               20

<210> SEQ ID NO 2144
<211> LENGTH: 20
<212> TYPE: DNA
<213> ORGANISM: Homo sapiens

<400> SEQUENCE: 2144
tcaaagacag agtgagtgga                                               20

<210> SEQ ID NO 2145
<211> LENGTH: 20
<212> TYPE: DNA
<213> ORGANISM: Homo sapiens

<400> SEQUENCE: 2145
agaccacggg ctctatctat                                               20

<210> SEQ ID NO 2146
<211> LENGTH: 21
<212> TYPE: DNA
<213> ORGANISM: Homo sapiens

<400> SEQUENCE: 2146
tttgggggtt acacttcata g                                             21

<210> SEQ ID NO 2147
<211> LENGTH: 22
<212> TYPE: DNA
<213> ORGANISM: Homo sapiens

<400> SEQUENCE: 2147
catcttgctt attggcttac ga                                            22

<210> SEQ ID NO 2148
<211> LENGTH: 21
<212> TYPE: DNA
<213> ORGANISM: Homo sapiens

<400> SEQUENCE: 2148
agccagcaga ataataccag g                                             21

<210> SEQ ID NO 2149
<211> LENGTH: 20
<212> TYPE: DNA
<213> ORGANISM: Homo sapiens

<400> SEQUENCE: 2149
gaggtagagg cagtgtcttg                                               20

<210> SEQ ID NO 2150
<211> LENGTH: 20
<212> TYPE: DNA
<213> ORGANISM: Homo sapiens

<400> SEQUENCE: 2150
acctcatctt ttgtcagcct                                               20

<210> SEQ ID NO 2151
<211> LENGTH: 20
<212> TYPE: DNA
```

```
<213> ORGANISM: Homo sapiens

<400> SEQUENCE: 2151
tagtccttga actccctggt                                              20

<210> SEQ ID NO 2152
<211> LENGTH: 20
<212> TYPE: DNA
<213> ORGANISM: Homo sapiens

<400> SEQUENCE: 2152
acagttccat aggcaggttt                                              20

<210> SEQ ID NO 2153
<211> LENGTH: 20
<212> TYPE: DNA
<213> ORGANISM: Homo sapiens

<400> SEQUENCE: 2153
ccagcttagc gtctgttttt                                              20

<210> SEQ ID NO 2154
<211> LENGTH: 21
<212> TYPE: DNA
<213> ORGANISM: Homo sapiens

<400> SEQUENCE: 2154
gcagttccag atccaatatg c                                            21

<210> SEQ ID NO 2155
<211> LENGTH: 21
<212> TYPE: DNA
<213> ORGANISM: Homo sapiens

<400> SEQUENCE: 2155
gaccacaact atcaagagca c                                            21

<210> SEQ ID NO 2156
<211> LENGTH: 20
<212> TYPE: DNA
<213> ORGANISM: Homo sapiens

<400> SEQUENCE: 2156
tttgggaaag atgggagagc                                              20

<210> SEQ ID NO 2157
<211> LENGTH: 20
<212> TYPE: DNA
<213> ORGANISM: Homo sapiens

<400> SEQUENCE: 2157
ccaaagaaag gttgaagccc                                              20

<210> SEQ ID NO 2158
<211> LENGTH: 21
<212> TYPE: DNA
<213> ORGANISM: Homo sapiens

<400> SEQUENCE: 2158
ttgcaggtaa ggtacagaag a                                            21

<210> SEQ ID NO 2159
<211> LENGTH: 21
```

<212> TYPE: DNA
<213> ORGANISM: Homo sapiens

<400> SEQUENCE: 2159
aataatgtgc actgtgatgg c                                              21

<210> SEQ ID NO 2160
<211> LENGTH: 19
<212> TYPE: DNA
<213> ORGANISM: Homo sapiens

<400> SEQUENCE: 2160
cttcagctgc atcttgagc                                                 19

<210> SEQ ID NO 2161
<211> LENGTH: 20
<212> TYPE: DNA
<213> ORGANISM: Homo sapiens

<400> SEQUENCE: 2161
tttaagggtc tgatggttgc                                                20

<210> SEQ ID NO 2162
<211> LENGTH: 20
<212> TYPE: DNA
<213> ORGANISM: Homo sapiens

<400> SEQUENCE: 2162
ggcacttcaa aaacaaaccc                                                20

<210> SEQ ID NO 2163
<211> LENGTH: 20
<212> TYPE: DNA
<213> ORGANISM: Homo sapiens

<400> SEQUENCE: 2163
gaaaatgccc atcgtctcaa                                                20

<210> SEQ ID NO 2164
<211> LENGTH: 20
<212> TYPE: DNA
<213> ORGANISM: Homo sapiens

<400> SEQUENCE: 2164
agggttttat ggtctcctgg                                                20

<210> SEQ ID NO 2165
<211> LENGTH: 20
<212> TYPE: DNA
<213> ORGANISM: Homo sapiens

<400> SEQUENCE: 2165
attccttgtc tttcccctc                                                 20

<210> SEQ ID NO 2166
<211> LENGTH: 21
<212> TYPE: DNA
<213> ORGANISM: Homo sapiens

<400> SEQUENCE: 2166
tcaacacgga gaactgaaaa c                                              21

<210> SEQ ID NO 2167

```
<211> LENGTH: 22
<212> TYPE: DNA
<213> ORGANISM: Homo sapiens

<400> SEQUENCE: 2167
tcatttctct agcccaaaga tg                                              22

<210> SEQ ID NO 2168
<211> LENGTH: 22
<212> TYPE: DNA
<213> ORGANISM: Homo sapiens

<400> SEQUENCE: 2168
tccgtgtaaa tgaacaaagc ac                                              22

<210> SEQ ID NO 2169
<211> LENGTH: 20
<212> TYPE: DNA
<213> ORGANISM: Homo sapiens

<400> SEQUENCE: 2169
ttggtttgtt gacttcagcc                                                 20

<210> SEQ ID NO 2170
<211> LENGTH: 20
<212> TYPE: DNA
<213> ORGANISM: Homo sapiens

<400> SEQUENCE: 2170
ttcagggaat ggtttgcatt                                                 20

<210> SEQ ID NO 2171
<211> LENGTH: 20
<212> TYPE: DNA
<213> ORGANISM: Homo sapiens

<400> SEQUENCE: 2171
gctcagtgac agttgggatt                                                 20

<210> SEQ ID NO 2172
<211> LENGTH: 20
<212> TYPE: DNA
<213> ORGANISM: Homo sapiens

<400> SEQUENCE: 2172
gagatgccat tcccaaaagg                                                 20

<210> SEQ ID NO 2173
<211> LENGTH: 22
<212> TYPE: DNA
<213> ORGANISM: Homo sapiens

<400> SEQUENCE: 2173
gtcttgtctc tcttcttcca ct                                              22

<210> SEQ ID NO 2174
<211> LENGTH: 20
<212> TYPE: DNA
<213> ORGANISM: Homo sapiens

<400> SEQUENCE: 2174
ccctaccata gtgccagatg                                                 20
```

```
<210> SEQ ID NO 2175
<211> LENGTH: 20
<212> TYPE: DNA
<213> ORGANISM: Homo sapiens

<400> SEQUENCE: 2175
tttagagcag gtggaaacga                                            20

<210> SEQ ID NO 2176
<211> LENGTH: 20
<212> TYPE: DNA
<213> ORGANISM: Homo sapiens

<400> SEQUENCE: 2176
cagctttcag tgacagagga                                            20

<210> SEQ ID NO 2177
<211> LENGTH: 21
<212> TYPE: DNA
<213> ORGANISM: Homo sapiens

<400> SEQUENCE: 2177
cttgggtttt tatcggttgc t                                          21

<210> SEQ ID NO 2178
<211> LENGTH: 20
<212> TYPE: DNA
<213> ORGANISM: Homo sapiens

<400> SEQUENCE: 2178
ccaaaggcag atgagtgttt                                            20

<210> SEQ ID NO 2179
<211> LENGTH: 20
<212> TYPE: DNA
<213> ORGANISM: Homo sapiens

<400> SEQUENCE: 2179
gttgcctgga ttgctctaaa                                            20

<210> SEQ ID NO 2180
<211> LENGTH: 20
<212> TYPE: DNA
<213> ORGANISM: Homo sapiens

<400> SEQUENCE: 2180
gcctgggata gaaatgggaa                                            20

<210> SEQ ID NO 2181
<211> LENGTH: 20
<212> TYPE: DNA
<213> ORGANISM: Homo sapiens

<400> SEQUENCE: 2181
aaatcacgac gtaggaaacc                                            20

<210> SEQ ID NO 2182
<211> LENGTH: 20
<212> TYPE: DNA
<213> ORGANISM: Homo sapiens

<400> SEQUENCE: 2182
ggaaaggaaa ggaagctgtg                                            20
```

```
<210> SEQ ID NO 2183
<211> LENGTH: 20
<212> TYPE: DNA
<213> ORGANISM: Homo sapiens

<400> SEQUENCE: 2183
tcaccttgga gcaggtcata                                               20

<210> SEQ ID NO 2184
<211> LENGTH: 20
<212> TYPE: DNA
<213> ORGANISM: Homo sapiens

<400> SEQUENCE: 2184
tcagagaggt cttgctgaag                                               20

<210> SEQ ID NO 2185
<211> LENGTH: 20
<212> TYPE: DNA
<213> ORGANISM: Homo sapiens

<400> SEQUENCE: 2185
cgaagaaggt ctgggagatg                                               20

<210> SEQ ID NO 2186
<211> LENGTH: 21
<212> TYPE: DNA
<213> ORGANISM: Homo sapiens

<400> SEQUENCE: 2186
tctctctgtt gcttgtttcc t                                             21

<210> SEQ ID NO 2187
<211> LENGTH: 21
<212> TYPE: DNA
<213> ORGANISM: Homo sapiens

<400> SEQUENCE: 2187
caccattgtt tcatcaggac t                                             21

<210> SEQ ID NO 2188
<211> LENGTH: 20
<212> TYPE: DNA
<213> ORGANISM: Homo sapiens

<400> SEQUENCE: 2188
cgcatgtggt agatcatcag                                               20

<210> SEQ ID NO 2189
<211> LENGTH: 21
<212> TYPE: DNA
<213> ORGANISM: Homo sapiens

<400> SEQUENCE: 2189
ttgcatcatc agctcacata c                                             21

<210> SEQ ID NO 2190
<211> LENGTH: 20
<212> TYPE: DNA
<213> ORGANISM: Homo sapiens

<400> SEQUENCE: 2190
tataacaccc tcacctccca                                               20
```

```
<210> SEQ ID NO 2191
<211> LENGTH: 20
<212> TYPE: DNA
<213> ORGANISM: Homo sapiens

<400> SEQUENCE: 2191
agacctggaa aatgatgggt                                               20

<210> SEQ ID NO 2192
<211> LENGTH: 21
<212> TYPE: DNA
<213> ORGANISM: Homo sapiens

<400> SEQUENCE: 2192
cacccaaatc accttgctat g                                             21

<210> SEQ ID NO 2193
<211> LENGTH: 20
<212> TYPE: DNA
<213> ORGANISM: Homo sapiens

<400> SEQUENCE: 2193
cctggaagtg tgtaacaagc                                               20

<210> SEQ ID NO 2194
<211> LENGTH: 20
<212> TYPE: DNA
<213> ORGANISM: Homo sapiens

<400> SEQUENCE: 2194
caactaccgt ggattccgtt                                               20

<210> SEQ ID NO 2195
<211> LENGTH: 21
<212> TYPE: DNA
<213> ORGANISM: Homo sapiens

<400> SEQUENCE: 2195
ctccctagca aaaacttctc a                                             21

<210> SEQ ID NO 2196
<211> LENGTH: 20
<212> TYPE: DNA
<213> ORGANISM: Homo sapiens

<400> SEQUENCE: 2196
tctatcatga gtcgcttcca                                               20

<210> SEQ ID NO 2197
<211> LENGTH: 20
<212> TYPE: DNA
<213> ORGANISM: Homo sapiens

<400> SEQUENCE: 2197
tgccttattc actgtgcaac                                               20

<210> SEQ ID NO 2198
<211> LENGTH: 20
<212> TYPE: DNA
<213> ORGANISM: Homo sapiens
```

```
<400> SEQUENCE: 2198
tttctgtcac tttctgggct                                                20

<210> SEQ ID NO 2199
<211> LENGTH: 20
<212> TYPE: DNA
<213> ORGANISM: Homo sapiens

<400> SEQUENCE: 2199
tgatggccta gtgagtttcc                                                20

<210> SEQ ID NO 2200
<211> LENGTH: 21
<212> TYPE: DNA
<213> ORGANISM: Homo sapiens

<400> SEQUENCE: 2200
cgtgtgtttc tagtgcattg t                                              21

<210> SEQ ID NO 2201
<211> LENGTH: 20
<212> TYPE: DNA
<213> ORGANISM: Homo sapiens

<400> SEQUENCE: 2201
tgcaatgtaa caaaagcgtg                                                20

<210> SEQ ID NO 2202
<211> LENGTH: 20
<212> TYPE: DNA
<213> ORGANISM: Homo sapiens

<400> SEQUENCE: 2202
gggctcagag ggaatatcag                                                20

<210> SEQ ID NO 2203
<211> LENGTH: 20
<212> TYPE: DNA
<213> ORGANISM: Homo sapiens

<400> SEQUENCE: 2203
gccacatttg ctttcacaca                                                20

<210> SEQ ID NO 2204
<211> LENGTH: 20
<212> TYPE: DNA
<213> ORGANISM: Homo sapiens

<400> SEQUENCE: 2204
ccgacgaatg gatgaaagac                                                20

<210> SEQ ID NO 2205
<211> LENGTH: 19
<212> TYPE: DNA
<213> ORGANISM: Homo sapiens

<400> SEQUENCE: 2205
acgtcattgg gttcatggc                                                 19

<210> SEQ ID NO 2206
<211> LENGTH: 20
<212> TYPE: DNA
```

```
<213> ORGANISM: Homo sapiens

<400> SEQUENCE: 2206
acccaaattc catgcctact                                              20

<210> SEQ ID NO 2207
<211> LENGTH: 20
<212> TYPE: DNA
<213> ORGANISM: Homo sapiens

<400> SEQUENCE: 2207
attttacccc cttaggcacc                                              20

<210> SEQ ID NO 2208
<211> LENGTH: 20
<212> TYPE: DNA
<213> ORGANISM: Homo sapiens

<400> SEQUENCE: 2208
tgtacagcag tctccagaaa                                              20

<210> SEQ ID NO 2209
<211> LENGTH: 20
<212> TYPE: DNA
<213> ORGANISM: Homo sapiens

<400> SEQUENCE: 2209
tcttctacac agcccttcag                                              20

<210> SEQ ID NO 2210
<211> LENGTH: 20
<212> TYPE: DNA
<213> ORGANISM: Homo sapiens

<400> SEQUENCE: 2210
gccctcttac cctttctcat                                              20

<210> SEQ ID NO 2211
<211> LENGTH: 20
<212> TYPE: DNA
<213> ORGANISM: Homo sapiens

<400> SEQUENCE: 2211
attgggatcg tcagcatcaa                                              20

<210> SEQ ID NO 2212
<211> LENGTH: 21
<212> TYPE: DNA
<213> ORGANISM: Homo sapiens

<400> SEQUENCE: 2212
cattcaaaga tccagaccag g                                            21

<210> SEQ ID NO 2213
<211> LENGTH: 20
<212> TYPE: DNA
<213> ORGANISM: Homo sapiens

<400> SEQUENCE: 2213
tgattgtctt gtccactggt                                              20

<210> SEQ ID NO 2214
<211> LENGTH: 19
```

```
<212> TYPE: DNA
<213> ORGANISM: Homo sapiens

<400> SEQUENCE: 2214
atctgtgatt gctgccctc                                               19

<210> SEQ ID NO 2215
<211> LENGTH: 20
<212> TYPE: DNA
<213> ORGANISM: Homo sapiens

<400> SEQUENCE: 2215
acatcacact tcatgccctt                                              20

<210> SEQ ID NO 2216
<211> LENGTH: 20
<212> TYPE: DNA
<213> ORGANISM: Homo sapiens

<400> SEQUENCE: 2216
ctagaaactc ccaggacaga                                              20

<210> SEQ ID NO 2217
<211> LENGTH: 20
<212> TYPE: DNA
<213> ORGANISM: Homo sapiens

<400> SEQUENCE: 2217
atgaaggcat taggagggag                                              20

<210> SEQ ID NO 2218
<211> LENGTH: 20
<212> TYPE: DNA
<213> ORGANISM: Homo sapiens

<400> SEQUENCE: 2218
catgtgtgga aaggattggt                                              20

<210> SEQ ID NO 2219
<211> LENGTH: 20
<212> TYPE: DNA
<213> ORGANISM: Homo sapiens

<400> SEQUENCE: 2219
aaagtggaga agtggcagat                                              20

<210> SEQ ID NO 2220
<211> LENGTH: 20
<212> TYPE: DNA
<213> ORGANISM: Homo sapiens

<400> SEQUENCE: 2220
tatgaatgaa ccgtggctca                                              20

<210> SEQ ID NO 2221
<211> LENGTH: 22
<212> TYPE: DNA
<213> ORGANISM: Homo sapiens

<400> SEQUENCE: 2221
ccttaggatt ctgagaggtg ag                                           22

<210> SEQ ID NO 2222
```

-continued

```
<211> LENGTH: 20
<212> TYPE: DNA
<213> ORGANISM: Homo sapiens

<400> SEQUENCE: 2222
aagttgagtc gtttgtccca                                          20

<210> SEQ ID NO 2223
<211> LENGTH: 20
<212> TYPE: DNA
<213> ORGANISM: Homo sapiens

<400> SEQUENCE: 2223
agggcttctg attgatttgc                                          20

<210> SEQ ID NO 2224
<211> LENGTH: 20
<212> TYPE: DNA
<213> ORGANISM: Homo sapiens

<400> SEQUENCE: 2224
tagtgtttca ggagcgtgtt                                          20

<210> SEQ ID NO 2225
<211> LENGTH: 20
<212> TYPE: DNA
<213> ORGANISM: Homo sapiens

<400> SEQUENCE: 2225
cagggtagtc gggatttctc                                          20

<210> SEQ ID NO 2226
<211> LENGTH: 20
<212> TYPE: DNA
<213> ORGANISM: Homo sapiens

<400> SEQUENCE: 2226
ccaggacaag cagacatttt                                          20

<210> SEQ ID NO 2227
<211> LENGTH: 20
<212> TYPE: DNA
<213> ORGANISM: Homo sapiens

<400> SEQUENCE: 2227
cccggtaatg atctacagca                                          20

<210> SEQ ID NO 2228
<211> LENGTH: 21
<212> TYPE: DNA
<213> ORGANISM: Homo sapiens

<400> SEQUENCE: 2228
gctgctggtg atttttgaag a                                        21

<210> SEQ ID NO 2229
<211> LENGTH: 19
<212> TYPE: DNA
<213> ORGANISM: Homo sapiens

<400> SEQUENCE: 2229
aacggcactt ggttcacta                                           19
```

```
<210> SEQ ID NO 2230
<211> LENGTH: 20
<212> TYPE: DNA
<213> ORGANISM: Homo sapiens

<400> SEQUENCE: 2230
ctctgggcaa acaagaaacc                                               20

<210> SEQ ID NO 2231
<211> LENGTH: 20
<212> TYPE: DNA
<213> ORGANISM: Homo sapiens

<400> SEQUENCE: 2231
actctgaact cctcctcctg                                               20

<210> SEQ ID NO 2232
<211> LENGTH: 20
<212> TYPE: DNA
<213> ORGANISM: Homo sapiens

<400> SEQUENCE: 2232
gtgtgtgttt gtggaagtgt                                               20

<210> SEQ ID NO 2233
<211> LENGTH: 20
<212> TYPE: DNA
<213> ORGANISM: Homo sapiens

<400> SEQUENCE: 2233
tttgctcaca cacaagacac                                               20

<210> SEQ ID NO 2234
<211> LENGTH: 21
<212> TYPE: DNA
<213> ORGANISM: Homo sapiens

<400> SEQUENCE: 2234
aaagcccaat ctctctggtt a                                             21

<210> SEQ ID NO 2235
<211> LENGTH: 20
<212> TYPE: DNA
<213> ORGANISM: Homo sapiens

<400> SEQUENCE: 2235
acgactgcat cctttcatg                                                20

<210> SEQ ID NO 2236
<211> LENGTH: 20
<212> TYPE: DNA
<213> ORGANISM: Homo sapiens

<400> SEQUENCE: 2236
taggcgggct tattgtgttt                                               20

<210> SEQ ID NO 2237
<211> LENGTH: 22
<212> TYPE: DNA
<213> ORGANISM: Homo sapiens

<400> SEQUENCE: 2237
ccatcatagc ctacaaatac cc                                            22
```

```
<210> SEQ ID NO 2238
<211> LENGTH: 20
<212> TYPE: DNA
<213> ORGANISM: Homo sapiens

<400> SEQUENCE: 2238
tcaatgtaaa ctgcccggag                                          20

<210> SEQ ID NO 2239
<211> LENGTH: 22
<212> TYPE: DNA
<213> ORGANISM: Homo sapiens

<400> SEQUENCE: 2239
agagagttga aaatatcccc ca                                       22

<210> SEQ ID NO 2240
<211> LENGTH: 21
<212> TYPE: DNA
<213> ORGANISM: Homo sapiens

<400> SEQUENCE: 2240
atgggagtcg aatggtgtaa a                                        21

<210> SEQ ID NO 2241
<211> LENGTH: 20
<212> TYPE: DNA
<213> ORGANISM: Homo sapiens

<400> SEQUENCE: 2241
actttcttga acaccccagt                                          20

<210> SEQ ID NO 2242
<211> LENGTH: 20
<212> TYPE: DNA
<213> ORGANISM: Homo sapiens

<400> SEQUENCE: 2242
taacatttga gggcatggga                                          20

<210> SEQ ID NO 2243
<211> LENGTH: 20
<212> TYPE: DNA
<213> ORGANISM: Homo sapiens

<400> SEQUENCE: 2243
tgcctgtgtc ctacttttcc                                          20

<210> SEQ ID NO 2244
<211> LENGTH: 20
<212> TYPE: DNA
<213> ORGANISM: Homo sapiens

<400> SEQUENCE: 2244
cagaataccc tcactgtgct                                          20

<210> SEQ ID NO 2245
<211> LENGTH: 20
<212> TYPE: DNA
<213> ORGANISM: Homo sapiens

<400> SEQUENCE: 2245
tgactgccca agaatgtaca                                          20
```

<210> SEQ ID NO 2246
<211> LENGTH: 20
<212> TYPE: DNA
<213> ORGANISM: Homo sapiens

<400> SEQUENCE: 2246
ggagataaca gcagaggtcc                                               20

<210> SEQ ID NO 2247
<211> LENGTH: 20
<212> TYPE: DNA
<213> ORGANISM: Homo sapiens

<400> SEQUENCE: 2247
ccgaacacgc tgtatgtatt                                               20

<210> SEQ ID NO 2248
<211> LENGTH: 20
<212> TYPE: DNA
<213> ORGANISM: Homo sapiens

<400> SEQUENCE: 2248
tgtgggtgat atctgtgtct                                               20

<210> SEQ ID NO 2249
<211> LENGTH: 20
<212> TYPE: DNA
<213> ORGANISM: Homo sapiens

<400> SEQUENCE: 2249
ggaagggaat tgaagcacag                                               20

<210> SEQ ID NO 2250
<211> LENGTH: 20
<212> TYPE: DNA
<213> ORGANISM: Homo sapiens

<400> SEQUENCE: 2250
gccatcctgt aactgaatgc                                               20

<210> SEQ ID NO 2251
<211> LENGTH: 20
<212> TYPE: DNA
<213> ORGANISM: Homo sapiens

<400> SEQUENCE: 2251
tcatcctatc caccaacctg                                               20

<210> SEQ ID NO 2252
<211> LENGTH: 20
<212> TYPE: DNA
<213> ORGANISM: Homo sapiens

<400> SEQUENCE: 2252
gtattttccc tttgccgcag                                               20

<210> SEQ ID NO 2253
<211> LENGTH: 20
<212> TYPE: DNA
<213> ORGANISM: Homo sapiens -continued

<400> SEQUENCE: 2253
aatgaactgg ccctgactta                                               20

<210> SEQ ID NO 2254
<211> LENGTH: 20
<212> TYPE: DNA
<213> ORGANISM: Homo sapiens

<400> SEQUENCE: 2254
attacagcaa agaacgtggc                                               20

<210> SEQ ID NO 2255
<211> LENGTH: 20
<212> TYPE: DNA
<213> ORGANISM: Homo sapiens

<400> SEQUENCE: 2255
taagatacca taccgcagct                                               20

<210> SEQ ID NO 2256
<211> LENGTH: 20
<212> TYPE: DNA
<213> ORGANISM: Homo sapiens

<400> SEQUENCE: 2256
tctgtgtgtt ttgcattggt                                               20

<210> SEQ ID NO 2257
<211> LENGTH: 21
<212> TYPE: DNA
<213> ORGANISM: Homo sapiens

<400> SEQUENCE: 2257
tcagcgttca tggtaccaat a                                             21

<210> SEQ ID NO 2258
<211> LENGTH: 20
<212> TYPE: DNA
<213> ORGANISM: Homo sapiens

<400> SEQUENCE: 2258
gtgacagttt tccaaggcat                                               20

<210> SEQ ID NO 2259
<211> LENGTH: 21
<212> TYPE: DNA
<213> ORGANISM: Homo sapiens

<400> SEQUENCE: 2259
gtttcccaac caacaaacaa g                                             21

<210> SEQ ID NO 2260
<211> LENGTH: 20
<212> TYPE: DNA
<213> ORGANISM: Homo sapiens

<400> SEQUENCE: 2260
gcattacttt ttcgcacact                                               20

<210> SEQ ID NO 2261
<211> LENGTH: 20
<212> TYPE: DNA

<213> ORGANISM: Homo sapiens

<400> SEQUENCE: 2261
tctatcggga tggagagtga                                      20

<210> SEQ ID NO 2262
<211> LENGTH: 20
<212> TYPE: DNA
<213> ORGANISM: Homo sapiens

<400> SEQUENCE: 2262
ggggattgtt ttaagcaggc                                      20

<210> SEQ ID NO 2263
<211> LENGTH: 20
<212> TYPE: DNA
<213> ORGANISM: Homo sapiens

<400> SEQUENCE: 2263
gttcagacag gtggactagg                                      20

<210> SEQ ID NO 2264
<211> LENGTH: 20
<212> TYPE: DNA
<213> ORGANISM: Homo sapiens

<400> SEQUENCE: 2264
ccattgttct caccaactct                                      20

<210> SEQ ID NO 2265
<211> LENGTH: 20
<212> TYPE: DNA
<213> ORGANISM: Homo sapiens

<400> SEQUENCE: 2265
aagcaacctg ggaaattgtg                                      20

<210> SEQ ID NO 2266
<211> LENGTH: 19
<212> TYPE: DNA
<213> ORGANISM: Homo sapiens

<400> SEQUENCE: 2266
cctgaaacac aagcagcag                                       19

<210> SEQ ID NO 2267
<211> LENGTH: 20
<212> TYPE: DNA
<213> ORGANISM: Homo sapiens

<400> SEQUENCE: 2267
gggttaaggt tgctgggtta                                      20

<210> SEQ ID NO 2268
<211> LENGTH: 20
<212> TYPE: DNA
<213> ORGANISM: Homo sapiens

<400> SEQUENCE: 2268
agctgcctat ttgattggtg                                      20

<210> SEQ ID NO 2269
<211> LENGTH: 21

<212> TYPE: DNA
<213> ORGANISM: Homo sapiens

<400> SEQUENCE: 2269
gtgaaatgtg gttgtagtgc a                                               21

<210> SEQ ID NO 2270
<211> LENGTH: 20
<212> TYPE: DNA
<213> ORGANISM: Homo sapiens

<400> SEQUENCE: 2270
cagtacagtc agccttcctt                                                 20

<210> SEQ ID NO 2271
<211> LENGTH: 20
<212> TYPE: DNA
<213> ORGANISM: Homo sapiens

<400> SEQUENCE: 2271
gtgactgcct tgcttcattt                                                 20

<210> SEQ ID NO 2272
<211> LENGTH: 20
<212> TYPE: DNA
<213> ORGANISM: Homo sapiens

<400> SEQUENCE: 2272
tgcattcaaa ctaccccaag                                                 20

<210> SEQ ID NO 2273
<211> LENGTH: 20
<212> TYPE: DNA
<213> ORGANISM: Homo sapiens

<400> SEQUENCE: 2273
cagttctgga gccttctact                                                 20

<210> SEQ ID NO 2274
<211> LENGTH: 20
<212> TYPE: DNA
<213> ORGANISM: Homo sapiens

<400> SEQUENCE: 2274
ccgaaaagag gcaagcaatt                                                 20

<210> SEQ ID NO 2275
<211> LENGTH: 20
<212> TYPE: DNA
<213> ORGANISM: Homo sapiens

<400> SEQUENCE: 2275
ttagggcagg atgtacagaa                                                 20

<210> SEQ ID NO 2276
<211> LENGTH: 20
<212> TYPE: DNA
<213> ORGANISM: Homo sapiens

<400> SEQUENCE: 2276
gtcacctcaa cctaactcca                                                 20

<210> SEQ ID NO 2277

```
<211> LENGTH: 20
<212> TYPE: DNA
<213> ORGANISM: Homo sapiens

<400> SEQUENCE: 2277
gctggtgacc ttcattcaag                                               20

<210> SEQ ID NO 2278
<211> LENGTH: 20
<212> TYPE: DNA
<213> ORGANISM: Homo sapiens

<400> SEQUENCE: 2278
gcaacagtct acccgtctag                                               20

<210> SEQ ID NO 2279
<211> LENGTH: 19
<212> TYPE: DNA
<213> ORGANISM: Homo sapiens

<400> SEQUENCE: 2279
taaaaccatg ttcggggca                                                19

<210> SEQ ID NO 2280
<211> LENGTH: 20
<212> TYPE: DNA
<213> ORGANISM: Homo sapiens

<400> SEQUENCE: 2280
atcaatgctc tgacctcctg                                               20

<210> SEQ ID NO 2281
<211> LENGTH: 21
<212> TYPE: DNA
<213> ORGANISM: Homo sapiens

<400> SEQUENCE: 2281
ctacctgtcc gtttcccttac                                              21

<210> SEQ ID NO 2282
<211> LENGTH: 21
<212> TYPE: DNA
<213> ORGANISM: Homo sapiens

<400> SEQUENCE: 2282
atacatcagg cctccagaat t                                             21

<210> SEQ ID NO 2283
<211> LENGTH: 21
<212> TYPE: DNA
<213> ORGANISM: Homo sapiens

<400> SEQUENCE: 2283
gacaaagatg actggaggtg a                                             21

<210> SEQ ID NO 2284
<211> LENGTH: 22
<212> TYPE: DNA
<213> ORGANISM: Homo sapiens

<400> SEQUENCE: 2284
cacatcttta gagctcaggt ga                                            22
```

```
<210> SEQ ID NO 2285
<211> LENGTH: 21
<212> TYPE: DNA
<213> ORGANISM: Homo sapiens

<400> SEQUENCE: 2285
gggtggatgg tgagatatgt g                                              21

<210> SEQ ID NO 2286
<211> LENGTH: 21
<212> TYPE: DNA
<213> ORGANISM: Homo sapiens

<400> SEQUENCE: 2286
ccatcacttc acaatccaca c                                              21

<210> SEQ ID NO 2287
<211> LENGTH: 21
<212> TYPE: DNA
<213> ORGANISM: Homo sapiens

<400> SEQUENCE: 2287
cttcaaacct gatccatgtg c                                              21

<210> SEQ ID NO 2288
<211> LENGTH: 20
<212> TYPE: DNA
<213> ORGANISM: Homo sapiens

<400> SEQUENCE: 2288
aatcctgcag tcatcttccc                                                20

<210> SEQ ID NO 2289
<211> LENGTH: 21
<212> TYPE: DNA
<213> ORGANISM: Homo sapiens

<400> SEQUENCE: 2289
gcagaaacag catgaatctc c                                              21

<210> SEQ ID NO 2290
<211> LENGTH: 21
<212> TYPE: DNA
<213> ORGANISM: Homo sapiens

<400> SEQUENCE: 2290
caagtctggt ttgtgagaag c                                              21

<210> SEQ ID NO 2291
<211> LENGTH: 21
<212> TYPE: DNA
<213> ORGANISM: Homo sapiens

<400> SEQUENCE: 2291
tgacttcaaa catcccatcc a                                              21

<210> SEQ ID NO 2292
<211> LENGTH: 21
<212> TYPE: DNA
<213> ORGANISM: Homo sapiens

<400> SEQUENCE: 2292
gggagcttct gtagtctttg a                                              21
```

```
<210> SEQ ID NO 2293
<211> LENGTH: 21
<212> TYPE: DNA
<213> ORGANISM: Homo sapiens

<400> SEQUENCE: 2293
gtgggatgag ttctagagga a                                              21

<210> SEQ ID NO 2294
<211> LENGTH: 21
<212> TYPE: DNA
<213> ORGANISM: Homo sapiens

<400> SEQUENCE: 2294
taaggagagc aggacttaca g                                              21

<210> SEQ ID NO 2295
<211> LENGTH: 21
<212> TYPE: DNA
<213> ORGANISM: Homo sapiens

<400> SEQUENCE: 2295
agtcacacac atacacacag t                                              21

<210> SEQ ID NO 2296
<211> LENGTH: 21
<212> TYPE: DNA
<213> ORGANISM: Homo sapiens

<400> SEQUENCE: 2296
ccaacggttc atttgtcgta t                                              21

<210> SEQ ID NO 2297
<211> LENGTH: 21
<212> TYPE: DNA
<213> ORGANISM: Homo sapiens

<400> SEQUENCE: 2297
acgacttccc tgtgtaactt a                                              21

<210> SEQ ID NO 2298
<211> LENGTH: 21
<212> TYPE: DNA
<213> ORGANISM: Homo sapiens

<400> SEQUENCE: 2298
ccttgctctg ttaatgggtt t                                              21

<210> SEQ ID NO 2299
<211> LENGTH: 21
<212> TYPE: DNA
<213> ORGANISM: Homo sapiens

<400> SEQUENCE: 2299
ccttctcttg tctctagtgc c                                              21

<210> SEQ ID NO 2300
<211> LENGTH: 21
<212> TYPE: DNA
<213> ORGANISM: Homo sapiens

<400> SEQUENCE: 2300
aacaatgctt aacgggaatc c                                              21
```

<210> SEQ ID NO 2301
<211> LENGTH: 21
<212> TYPE: DNA
<213> ORGANISM: Homo sapiens

<400> SEQUENCE: 2301
ctggaaatac acacacacct g                                              21

<210> SEQ ID NO 2302
<211> LENGTH: 21
<212> TYPE: DNA
<213> ORGANISM: Homo sapiens

<400> SEQUENCE: 2302
gcagagttca tagaagggtc a                                              21

<210> SEQ ID NO 2303
<211> LENGTH: 21
<212> TYPE: DNA
<213> ORGANISM: Homo sapiens

<400> SEQUENCE: 2303
atttgtaaac cacccacttc g                                              21

<210> SEQ ID NO 2304
<211> LENGTH: 21
<212> TYPE: DNA
<213> ORGANISM: Homo sapiens

<400> SEQUENCE: 2304
aaaccgagac gaccacctaa t                                              21

<210> SEQ ID NO 2305
<211> LENGTH: 21
<212> TYPE: DNA
<213> ORGANISM: Homo sapiens

<400> SEQUENCE: 2305
tcactgtgct gacaaatcct a                                              21

<210> SEQ ID NO 2306
<211> LENGTH: 21
<212> TYPE: DNA
<213> ORGANISM: Homo sapiens

<400> SEQUENCE: 2306
gagtgatgat gagccatgat g                                              21

<210> SEQ ID NO 2307
<211> LENGTH: 21
<212> TYPE: DNA
<213> ORGANISM: Homo sapiens

<400> SEQUENCE: 2307
cccatcatca tcccttcaga c                                              21

<210> SEQ ID NO 2308
<211> LENGTH: 21
<212> TYPE: DNA
<213> ORGANISM: Homo sapiens

```
<400> SEQUENCE: 2308
ggatattgga gatagcaggc a                                              21

<210> SEQ ID NO 2309
<211> LENGTH: 21
<212> TYPE: DNA
<213> ORGANISM: Homo sapiens

<400> SEQUENCE: 2309
tcatcacttt atcctcccag t                                              21

<210> SEQ ID NO 2310
<211> LENGTH: 21
<212> TYPE: DNA
<213> ORGANISM: Homo sapiens

<400> SEQUENCE: 2310
gtttggcact gcaactagat a                                              21

<210> SEQ ID NO 2311
<211> LENGTH: 21
<212> TYPE: DNA
<213> ORGANISM: Homo sapiens

<400> SEQUENCE: 2311
atgggcacag gtaaagagtt t                                              21

<210> SEQ ID NO 2312
<211> LENGTH: 21
<212> TYPE: DNA
<213> ORGANISM: Homo sapiens

<400> SEQUENCE: 2312
tgaaataagg gaagccacac a                                              21

<210> SEQ ID NO 2313
<211> LENGTH: 21
<212> TYPE: DNA
<213> ORGANISM: Homo sapiens

<400> SEQUENCE: 2313
tttgtaagct gagtgtgagg t                                              21

<210> SEQ ID NO 2314
<211> LENGTH: 21
<212> TYPE: DNA
<213> ORGANISM: Homo sapiens

<400> SEQUENCE: 2314
tccttagtgt gccaattagc c                                              21

<210> SEQ ID NO 2315
<211> LENGTH: 21
<212> TYPE: DNA
<213> ORGANISM: Homo sapiens

<400> SEQUENCE: 2315
ttactgtttg aatgccagct c                                              21

<210> SEQ ID NO 2316
<211> LENGTH: 20
<212> TYPE: DNA
```

-continued

<213> ORGANISM: Homo sapiens

<400> SEQUENCE: 2316
ttaatgtgga gagacaggcc                                                  20

<210> SEQ ID NO 2317
<211> LENGTH: 21
<212> TYPE: DNA
<213> ORGANISM: Homo sapiens

<400> SEQUENCE: 2317
tcccttctcc catcacaatt c                                                21

<210> SEQ ID NO 2318
<211> LENGTH: 21
<212> TYPE: DNA
<213> ORGANISM: Homo sapiens

<400> SEQUENCE: 2318
caatgcatct tactcaccct t                                                21

<210> SEQ ID NO 2319
<211> LENGTH: 21
<212> TYPE: DNA
<213> ORGANISM: Homo sapiens

<400> SEQUENCE: 2319
gaagactgca tgtgtgtcct a                                                21

<210> SEQ ID NO 2320
<211> LENGTH: 21
<212> TYPE: DNA
<213> ORGANISM: Homo sapiens

<400> SEQUENCE: 2320
agtatggaag tgggaattgg a                                                21

<210> SEQ ID NO 2321
<211> LENGTH: 21
<212> TYPE: DNA
<213> ORGANISM: Homo sapiens

<400> SEQUENCE: 2321
ttctcactct caactgaacc a                                                21

<210> SEQ ID NO 2322
<211> LENGTH: 21
<212> TYPE: DNA
<213> ORGANISM: Homo sapiens

<400> SEQUENCE: 2322
ttgcttccac agaaactctt c                                                21

<210> SEQ ID NO 2323
<211> LENGTH: 22
<212> TYPE: DNA
<213> ORGANISM: Homo sapiens

<400> SEQUENCE: 2323
tcagggagct tctaattaag ga                                               22

<210> SEQ ID NO 2324
<211> LENGTH: 21

```
<212> TYPE: DNA
<213> ORGANISM: Homo sapiens

<400> SEQUENCE: 2324
aaccgaccta ttccaaagtc t                                              21

<210> SEQ ID NO 2325
<211> LENGTH: 21
<212> TYPE: DNA
<213> ORGANISM: Homo sapiens

<400> SEQUENCE: 2325
aagatgatcc caggcttaag g                                              21

<210> SEQ ID NO 2326
<211> LENGTH: 21
<212> TYPE: DNA
<213> ORGANISM: Homo sapiens

<400> SEQUENCE: 2326
tgtgaagcga atacagctca a                                              21

<210> SEQ ID NO 2327
<211> LENGTH: 21
<212> TYPE: DNA
<213> ORGANISM: Homo sapiens

<400> SEQUENCE: 2327
gttgaggttt gctgatcttg g                                              21

<210> SEQ ID NO 2328
<211> LENGTH: 21
<212> TYPE: DNA
<213> ORGANISM: Homo sapiens

<400> SEQUENCE: 2328
gttctaacta caccaggctc t                                              21

<210> SEQ ID NO 2329
<211> LENGTH: 21
<212> TYPE: DNA
<213> ORGANISM: Homo sapiens

<400> SEQUENCE: 2329
caaagataga ttcgcacacc a                                              21

<210> SEQ ID NO 2330
<211> LENGTH: 21
<212> TYPE: DNA
<213> ORGANISM: Homo sapiens

<400> SEQUENCE: 2330
gtatgagtgt aggtgtggag g                                              21

<210> SEQ ID NO 2331
<211> LENGTH: 21
<212> TYPE: DNA
<213> ORGANISM: Homo sapiens

<400> SEQUENCE: 2331
gagctggaca aattaaatgg c                                              21

<210> SEQ ID NO 2332
```

```
<211> LENGTH: 21
<212> TYPE: DNA
<213> ORGANISM: Homo sapiens

<400> SEQUENCE: 2332
aatctggatc tagcgaagga c                                              21

<210> SEQ ID NO 2333
<211> LENGTH: 20
<212> TYPE: DNA
<213> ORGANISM: Homo sapiens

<400> SEQUENCE: 2333
ccagtgcatt tggtttgaca                                                20

<210> SEQ ID NO 2334
<211> LENGTH: 21
<212> TYPE: DNA
<213> ORGANISM: Homo sapiens

<400> SEQUENCE: 2334
taatgagaag gcaggatgag g                                              21

<210> SEQ ID NO 2335
<211> LENGTH: 21
<212> TYPE: DNA
<213> ORGANISM: Homo sapiens

<400> SEQUENCE: 2335
tatgtgaatc ctctgtgtgg c                                              21

<210> SEQ ID NO 2336
<211> LENGTH: 21
<212> TYPE: DNA
<213> ORGANISM: Homo sapiens

<400> SEQUENCE: 2336
aagacaactc tctaggcctc a                                              21

<210> SEQ ID NO 2337
<211> LENGTH: 21
<212> TYPE: DNA
<213> ORGANISM: Homo sapiens

<400> SEQUENCE: 2337
agcttctctc tcattctgct t                                              21

<210> SEQ ID NO 2338
<211> LENGTH: 21
<212> TYPE: DNA
<213> ORGANISM: Homo sapiens

<400> SEQUENCE: 2338
gtttatggtt gtccctggag a                                              21

<210> SEQ ID NO 2339
<211> LENGTH: 21
<212> TYPE: DNA
<213> ORGANISM: Homo sapiens

<400> SEQUENCE: 2339
gactcccgat ttcatttgct g                                              21
```

```
<210> SEQ ID NO 2340
<211> LENGTH: 21
<212> TYPE: DNA
<213> ORGANISM: Homo sapiens

<400> SEQUENCE: 2340
tccaccttct gatcacacaa t                                             21

<210> SEQ ID NO 2341
<211> LENGTH: 22
<212> TYPE: DNA
<213> ORGANISM: Homo sapiens

<400> SEQUENCE: 2341
tcccaatcgt tgtgaaacat ac                                            22

<210> SEQ ID NO 2342
<211> LENGTH: 21
<212> TYPE: DNA
<213> ORGANISM: Homo sapiens

<400> SEQUENCE: 2342
aagatcaggt accaaggcat t                                             21

<210> SEQ ID NO 2343
<211> LENGTH: 21
<212> TYPE: DNA
<213> ORGANISM: Homo sapiens

<400> SEQUENCE: 2343
tctttacagg aagttgggac c                                             21

<210> SEQ ID NO 2344
<211> LENGTH: 21
<212> TYPE: DNA
<213> ORGANISM: Homo sapiens

<400> SEQUENCE: 2344
atgatgtgaa gtccatggtg a                                             21

<210> SEQ ID NO 2345
<211> LENGTH: 21
<212> TYPE: DNA
<213> ORGANISM: Homo sapiens

<400> SEQUENCE: 2345
taagttcaga tcagggagca g                                             21

<210> SEQ ID NO 2346
<211> LENGTH: 21
<212> TYPE: DNA
<213> ORGANISM: Homo sapiens

<400> SEQUENCE: 2346
tccaaattga cttccatgag c                                             21

<210> SEQ ID NO 2347
<211> LENGTH: 22
<212> TYPE: DNA
<213> ORGANISM: Homo sapiens

<400> SEQUENCE: 2347
gttgaaagtc ttacagaacg ct                                            22
```

-continued

<210> SEQ ID NO 2348
<211> LENGTH: 21
<212> TYPE: DNA
<213> ORGANISM: Homo sapiens

<400> SEQUENCE: 2348
gtggtttcag gaatttggag g                                        21

<210> SEQ ID NO 2349
<211> LENGTH: 21
<212> TYPE: DNA
<213> ORGANISM: Homo sapiens

<400> SEQUENCE: 2349
caacataggc acattgtcct c                                        21

<210> SEQ ID NO 2350
<211> LENGTH: 22
<212> TYPE: DNA
<213> ORGANISM: Homo sapiens

<400> SEQUENCE: 2350
tatttgctgc ttcattcttc cc                                       22

<210> SEQ ID NO 2351
<211> LENGTH: 21
<212> TYPE: DNA
<213> ORGANISM: Homo sapiens

<400> SEQUENCE: 2351
gtcaggcctc ataactctct t                                        21

<210> SEQ ID NO 2352
<211> LENGTH: 21
<212> TYPE: DNA
<213> ORGANISM: Homo sapiens

<400> SEQUENCE: 2352
aagtcattac gtcccacact g                                        21

<210> SEQ ID NO 2353
<211> LENGTH: 21
<212> TYPE: DNA
<213> ORGANISM: Homo sapiens

<400> SEQUENCE: 2353
gttgtgtggc tttccttatc a                                        21

<210> SEQ ID NO 2354
<211> LENGTH: 21
<212> TYPE: DNA
<213> ORGANISM: Homo sapiens

<400> SEQUENCE: 2354
aaagtcatca gaagggtagc a                                        21

<210> SEQ ID NO 2355
<211> LENGTH: 21
<212> TYPE: DNA
<213> ORGANISM: Homo sapiens

<400> SEQUENCE: 2355
cctgcagctc tgtgtaaatt t                                        21

<210> SEQ ID NO 2356
<211> LENGTH: 21
<212> TYPE: DNA
<213> ORGANISM: Homo sapiens

<400> SEQUENCE: 2356
aatgatgccg aacagtgagt a                                              21

<210> SEQ ID NO 2357
<211> LENGTH: 21
<212> TYPE: DNA
<213> ORGANISM: Homo sapiens

<400> SEQUENCE: 2357
ctttggccag ttctttctct c                                              21

<210> SEQ ID NO 2358
<211> LENGTH: 21
<212> TYPE: DNA
<213> ORGANISM: Homo sapiens

<400> SEQUENCE: 2358
aatgtaagac agggacagag a                                              21

<210> SEQ ID NO 2359
<211> LENGTH: 20
<212> TYPE: DNA
<213> ORGANISM: Homo sapiens

<400> SEQUENCE: 2359
gtggcccagc attatttgtt                                                20

<210> SEQ ID NO 2360
<211> LENGTH: 21
<212> TYPE: DNA
<213> ORGANISM: Homo sapiens

<400> SEQUENCE: 2360
tgaattccac agtccagtca a                                              21

<210> SEQ ID NO 2361
<211> LENGTH: 21
<212> TYPE: DNA
<213> ORGANISM: Homo sapiens

<400> SEQUENCE: 2361
tcttggtgtg acttgctaac a                                              21

<210> SEQ ID NO 2362
<211> LENGTH: 21
<212> TYPE: DNA
<213> ORGANISM: Homo sapiens

<400> SEQUENCE: 2362
aatgccttca aagacagtga c                                              21

<210> SEQ ID NO 2363
<211> LENGTH: 21
<212> TYPE: DNA
<213> ORGANISM: Homo sapiens

```
<400> SEQUENCE: 2363
tttctggctg agataagacc c                                              21

<210> SEQ ID NO 2364
<211> LENGTH: 21
<212> TYPE: DNA
<213> ORGANISM: Homo sapiens

<400> SEQUENCE: 2364
cacacctgca attgagatga a                                              21

<210> SEQ ID NO 2365
<211> LENGTH: 21
<212> TYPE: DNA
<213> ORGANISM: Homo sapiens

<400> SEQUENCE: 2365
acaattccgt ggtatacagc t                                              21

<210> SEQ ID NO 2366
<211> LENGTH: 21
<212> TYPE: DNA
<213> ORGANISM: Homo sapiens

<400> SEQUENCE: 2366
gtcatgatga tgcaacagct a                                              21

<210> SEQ ID NO 2367
<211> LENGTH: 21
<212> TYPE: DNA
<213> ORGANISM: Homo sapiens

<400> SEQUENCE: 2367
tgattgtgcc ctaaccaaac t                                              21

<210> SEQ ID NO 2368
<211> LENGTH: 21
<212> TYPE: DNA
<213> ORGANISM: Homo sapiens

<400> SEQUENCE: 2368
tttcacggta agaggagcaa a                                              21

<210> SEQ ID NO 2369
<211> LENGTH: 21
<212> TYPE: DNA
<213> ORGANISM: Homo sapiens

<400> SEQUENCE: 2369
tgtcgtatcc tgctgtttag a                                              21

<210> SEQ ID NO 2370
<211> LENGTH: 21
<212> TYPE: DNA
<213> ORGANISM: Homo sapiens

<400> SEQUENCE: 2370
ttctctctag gcaggtgaac t                                              21

<210> SEQ ID NO 2371
<211> LENGTH: 21
<212> TYPE: DNA
```

```
<213> ORGANISM: Homo sapiens

<400> SEQUENCE: 2371
tcaggagtaa agtcaggacc t                                              21

<210> SEQ ID NO 2372
<211> LENGTH: 21
<212> TYPE: DNA
<213> ORGANISM: Homo sapiens

<400> SEQUENCE: 2372
accctttgaa agaaccagga a                                              21

<210> SEQ ID NO 2373
<211> LENGTH: 21
<212> TYPE: DNA
<213> ORGANISM: Homo sapiens

<400> SEQUENCE: 2373
tgagctgatt tactgtgaca c                                              21

<210> SEQ ID NO 2374
<211> LENGTH: 21
<212> TYPE: DNA
<213> ORGANISM: Homo sapiens

<400> SEQUENCE: 2374
aatgagccac tgttctctag g                                              21

<210> SEQ ID NO 2375
<211> LENGTH: 21
<212> TYPE: DNA
<213> ORGANISM: Homo sapiens

<400> SEQUENCE: 2375
tagcaccttg acttcaggat t                                              21

<210> SEQ ID NO 2376
<211> LENGTH: 21
<212> TYPE: DNA
<213> ORGANISM: Homo sapiens

<400> SEQUENCE: 2376
atttgcacat tagggcctca a                                              21

<210> SEQ ID NO 2377
<211> LENGTH: 21
<212> TYPE: DNA
<213> ORGANISM: Homo sapiens

<400> SEQUENCE: 2377
tgaggttgga aagggtcaat t                                              21

<210> SEQ ID NO 2378
<211> LENGTH: 20
<212> TYPE: DNA
<213> ORGANISM: Homo sapiens

<400> SEQUENCE: 2378
gaacttccct gcttccttct                                                20

<210> SEQ ID NO 2379
<211> LENGTH: 21
```

```
<212> TYPE: DNA
<213> ORGANISM: Homo sapiens

<400> SEQUENCE: 2379
cagctttcct tcctcttctc t                                        21

<210> SEQ ID NO 2380
<211> LENGTH: 21
<212> TYPE: DNA
<213> ORGANISM: Homo sapiens

<400> SEQUENCE: 2380
aaatacttgg ctgtgaccat g                                        21

<210> SEQ ID NO 2381
<211> LENGTH: 21
<212> TYPE: DNA
<213> ORGANISM: Homo sapiens

<400> SEQUENCE: 2381
acagtgagag gaaagaacag c                                        21

<210> SEQ ID NO 2382
<211> LENGTH: 21
<212> TYPE: DNA
<213> ORGANISM: Homo sapiens

<400> SEQUENCE: 2382
aagacccttg agaacttcca a                                        21

<210> SEQ ID NO 2383
<211> LENGTH: 21
<212> TYPE: DNA
<213> ORGANISM: Homo sapiens

<400> SEQUENCE: 2383
ggaaataaat tgtgagctgg c                                        21

<210> SEQ ID NO 2384
<211> LENGTH: 21
<212> TYPE: DNA
<213> ORGANISM: Homo sapiens

<400> SEQUENCE: 2384
atgtgtaaag acgtcctgga a                                        21

<210> SEQ ID NO 2385
<211> LENGTH: 21
<212> TYPE: DNA
<213> ORGANISM: Homo sapiens

<400> SEQUENCE: 2385
agacagccct tcaatccata c                                        21

<210> SEQ ID NO 2386
<211> LENGTH: 21
<212> TYPE: DNA
<213> ORGANISM: Homo sapiens

<400> SEQUENCE: 2386
tctatgtgga gggatttgac a                                        21

<210> SEQ ID NO 2387
```

-continued

```
<211> LENGTH: 21
<212> TYPE: DNA
<213> ORGANISM: Homo sapiens

<400> SEQUENCE: 2387
cctacatccc ttcctccttt c                                              21

<210> SEQ ID NO 2388
<211> LENGTH: 22
<212> TYPE: DNA
<213> ORGANISM: Homo sapiens

<400> SEQUENCE: 2388
ttcctgaagt ttatggtgca ac                                             22

<210> SEQ ID NO 2389
<211> LENGTH: 21
<212> TYPE: DNA
<213> ORGANISM: Homo sapiens

<400> SEQUENCE: 2389
tcacccatct tccaattagc t                                              21

<210> SEQ ID NO 2390
<211> LENGTH: 21
<212> TYPE: DNA
<213> ORGANISM: Homo sapiens

<400> SEQUENCE: 2390
aaggttgaat gaggatcaag c                                              21

<210> SEQ ID NO 2391
<211> LENGTH: 22
<212> TYPE: DNA
<213> ORGANISM: Homo sapiens

<400> SEQUENCE: 2391
tttctaagca caaactgaca cc                                             22

<210> SEQ ID NO 2392
<211> LENGTH: 21
<212> TYPE: DNA
<213> ORGANISM: Homo sapiens

<400> SEQUENCE: 2392
gagggaagaa cacaacacat g                                              21

<210> SEQ ID NO 2393
<211> LENGTH: 21
<212> TYPE: DNA
<213> ORGANISM: Homo sapiens

<400> SEQUENCE: 2393
gatgtttgca ctggagggat a                                              21

<210> SEQ ID NO 2394
<211> LENGTH: 21
<212> TYPE: DNA
<213> ORGANISM: Homo sapiens

<400> SEQUENCE: 2394
cagactagcc tacaatcctc c                                              21
```

<210> SEQ ID NO 2395
<211> LENGTH: 21
<212> TYPE: DNA
<213> ORGANISM: Homo sapiens

<400> SEQUENCE: 2395
gaagactaaa tgttggccga a                                    21

<210> SEQ ID NO 2396
<211> LENGTH: 21
<212> TYPE: DNA
<213> ORGANISM: Homo sapiens

<400> SEQUENCE: 2396
cattcaggtt cttaagggct g                                    21

<210> SEQ ID NO 2397
<211> LENGTH: 21
<212> TYPE: DNA
<213> ORGANISM: Homo sapiens

<400> SEQUENCE: 2397
gtagagagag ggaggatcac a                                    21

<210> SEQ ID NO 2398
<211> LENGTH: 21
<212> TYPE: DNA
<213> ORGANISM: Homo sapiens

<400> SEQUENCE: 2398
gaaaggcaga cgatgaaaga g                                    21

<210> SEQ ID NO 2399
<211> LENGTH: 21
<212> TYPE: DNA
<213> ORGANISM: Homo sapiens

<400> SEQUENCE: 2399
cttgccatga agtttgacca g                                    21

<210> SEQ ID NO 2400
<211> LENGTH: 21
<212> TYPE: DNA
<213> ORGANISM: Homo sapiens

<400> SEQUENCE: 2400
atctccatca gcacaggaat t                                    21

<210> SEQ ID NO 2401
<211> LENGTH: 21
<212> TYPE: DNA
<213> ORGANISM: Homo sapiens

<400> SEQUENCE: 2401
aggatgagca tttgtaacct g                                    21

<210> SEQ ID NO 2402
<211> LENGTH: 21
<212> TYPE: DNA
<213> ORGANISM: Homo sapiens

<400> SEQUENCE: 2402
gcagtgtgac atctgtgaat g                                    21

<210> SEQ ID NO 2403
<211> LENGTH: 21
<212> TYPE: DNA
<213> ORGANISM: Homo sapiens

<400> SEQUENCE: 2403
tgtcgctttc aaattaccca c                                              21

<210> SEQ ID NO 2404
<211> LENGTH: 21
<212> TYPE: DNA
<213> ORGANISM: Homo sapiens

<400> SEQUENCE: 2404
agactttcct gttcctcttc a                                              21

<210> SEQ ID NO 2405
<211> LENGTH: 21
<212> TYPE: DNA
<213> ORGANISM: Homo sapiens

<400> SEQUENCE: 2405
catacaagtg ctctgttagg c                                              21

<210> SEQ ID NO 2406
<211> LENGTH: 21
<212> TYPE: DNA
<213> ORGANISM: Homo sapiens

<400> SEQUENCE: 2406
tttacaatga actagccagg c                                              21

<210> SEQ ID NO 2407
<211> LENGTH: 21
<212> TYPE: DNA
<213> ORGANISM: Homo sapiens

<400> SEQUENCE: 2407
aggacttgga accagaaaga c                                              21

<210> SEQ ID NO 2408
<211> LENGTH: 21
<212> TYPE: DNA
<213> ORGANISM: Homo sapiens

<400> SEQUENCE: 2408
taacatctgc ctgaaagctt c                                              21

<210> SEQ ID NO 2409
<211> LENGTH: 21
<212> TYPE: DNA
<213> ORGANISM: Homo sapiens

<400> SEQUENCE: 2409
aaagagggct gatatcgtct g                                              21

<210> SEQ ID NO 2410
<211> LENGTH: 21
<212> TYPE: DNA
<213> ORGANISM: Homo sapiens

<400> SEQUENCE: 2410
ctcgtgtgtg caatttggaa t                                              21

<210> SEQ ID NO 2411
<211> LENGTH: 21
<212> TYPE: DNA
<213> ORGANISM: Homo sapiens

<400> SEQUENCE: 2411
ctcactgcaa actatggaac c                                           21

<210> SEQ ID NO 2412
<211> LENGTH: 21
<212> TYPE: DNA
<213> ORGANISM: Homo sapiens

<400> SEQUENCE: 2412
ggagagatgg agaagacctt t                                           21

<210> SEQ ID NO 2413
<211> LENGTH: 21
<212> TYPE: DNA
<213> ORGANISM: Homo sapiens

<400> SEQUENCE: 2413
tattctgccc atcttcttcc t                                           21

<210> SEQ ID NO 2414
<211> LENGTH: 21
<212> TYPE: DNA
<213> ORGANISM: Homo sapiens

<400> SEQUENCE: 2414
aatgtattac tgtgctcccg t                                           21

<210> SEQ ID NO 2415
<211> LENGTH: 20
<212> TYPE: DNA
<213> ORGANISM: Homo sapiens

<400> SEQUENCE: 2415
ggagacagcc caaacataga                                             20

<210> SEQ ID NO 2416
<211> LENGTH: 21
<212> TYPE: DNA
<213> ORGANISM: Homo sapiens

<400> SEQUENCE: 2416
accacctgcc actgtataaa t                                           21

<210> SEQ ID NO 2417
<211> LENGTH: 21
<212> TYPE: DNA
<213> ORGANISM: Homo sapiens

<400> SEQUENCE: 2417
agcaatggtg aagttctgga t                                           21

<210> SEQ ID NO 2418
<211> LENGTH: 21
<212> TYPE: DNA
<213> ORGANISM: Homo sapiens

<400> SEQUENCE: 2418
aattcttctt ctggtgcaag g                                              21

<210> SEQ ID NO 2419
<211> LENGTH: 21
<212> TYPE: DNA
<213> ORGANISM: Homo sapiens

<400> SEQUENCE: 2419
ctggtcagtg agagaaggga a                                              21

<210> SEQ ID NO 2420
<211> LENGTH: 21
<212> TYPE: DNA
<213> ORGANISM: Homo sapiens

<400> SEQUENCE: 2420
ttgccctttg aactgttgat c                                              21

<210> SEQ ID NO 2421
<211> LENGTH: 20
<212> TYPE: DNA
<213> ORGANISM: Homo sapiens

<400> SEQUENCE: 2421
tttctccact ggcatgaact                                                20

<210> SEQ ID NO 2422
<211> LENGTH: 21
<212> TYPE: DNA
<213> ORGANISM: Homo sapiens

<400> SEQUENCE: 2422
aagcacacta aggcctgata a                                              21

<210> SEQ ID NO 2423
<211> LENGTH: 21
<212> TYPE: DNA
<213> ORGANISM: Homo sapiens

<400> SEQUENCE: 2423
catgatcaca attccaagcc a                                              21

<210> SEQ ID NO 2424
<211> LENGTH: 21
<212> TYPE: DNA
<213> ORGANISM: Homo sapiens

<400> SEQUENCE: 2424
tcagtatcca ttcagcatcc a                                              21

<210> SEQ ID NO 2425
<211> LENGTH: 21
<212> TYPE: DNA
<213> ORGANISM: Homo sapiens

<400> SEQUENCE: 2425
acccagtcaa gttacagtct t                                              21

<210> SEQ ID NO 2426
<211> LENGTH: 20
<212> TYPE: DNA

-continued

<213> ORGANISM: Homo sapiens

<400> SEQUENCE: 2426
taaccgaagc ccatactctg         20

<210> SEQ ID NO 2427
<211> LENGTH: 22
<212> TYPE: DNA
<213> ORGANISM: Homo sapiens

<400> SEQUENCE: 2427
tgtaaagcat atcaagggaa cg       22

<210> SEQ ID NO 2428
<211> LENGTH: 21
<212> TYPE: DNA
<213> ORGANISM: Homo sapiens

<400> SEQUENCE: 2428
tccttactcc agatacccga t        21

<210> SEQ ID NO 2429
<211> LENGTH: 21
<212> TYPE: DNA
<213> ORGANISM: Homo sapiens

<400> SEQUENCE: 2429
tgcagagata tgttcccgta t        21

<210> SEQ ID NO 2430
<211> LENGTH: 21
<212> TYPE: DNA
<213> ORGANISM: Homo sapiens

<400> SEQUENCE: 2430
tctggcttct ttcttggaga g        21

<210> SEQ ID NO 2431
<211> LENGTH: 21
<212> TYPE: DNA
<213> ORGANISM: Homo sapiens

<400> SEQUENCE: 2431
agaagacagt acaaggaagg c        21

<210> SEQ ID NO 2432
<211> LENGTH: 21
<212> TYPE: DNA
<213> ORGANISM: Homo sapiens

<400> SEQUENCE: 2432
gcaacattca tttcatcctg c        21

<210> SEQ ID NO 2433
<211> LENGTH: 21
<212> TYPE: DNA
<213> ORGANISM: Homo sapiens

<400> SEQUENCE: 2433
tgtttgccat ttgttctcct c        21

<210> SEQ ID NO 2434
<211> LENGTH: 21

```
<212> TYPE: DNA
<213> ORGANISM: Homo sapiens

<400> SEQUENCE: 2434
catcacgaca tccatttcca c                                              21

<210> SEQ ID NO 2435
<211> LENGTH: 21
<212> TYPE: DNA
<213> ORGANISM: Homo sapiens

<400> SEQUENCE: 2435
ttgaaggcaa gagaagtttg g                                              21

<210> SEQ ID NO 2436
<211> LENGTH: 21
<212> TYPE: DNA
<213> ORGANISM: Homo sapiens

<400> SEQUENCE: 2436
gtggttatta tcggtgggtg a                                              21

<210> SEQ ID NO 2437
<211> LENGTH: 21
<212> TYPE: DNA
<213> ORGANISM: Homo sapiens

<400> SEQUENCE: 2437
gccaaggaaa tgtagggaaa g                                              21

<210> SEQ ID NO 2438
<211> LENGTH: 20
<212> TYPE: DNA
<213> ORGANISM: Homo sapiens

<400> SEQUENCE: 2438
ctgccattcc ttgtttccaa                                                20

<210> SEQ ID NO 2439
<211> LENGTH: 21
<212> TYPE: DNA
<213> ORGANISM: Homo sapiens

<400> SEQUENCE: 2439
aaccttcaca cctagagaca g                                              21

<210> SEQ ID NO 2440
<211> LENGTH: 20
<212> TYPE: DNA
<213> ORGANISM: Homo sapiens

<400> SEQUENCE: 2440
atttggactt gaagcagcct                                                20

<210> SEQ ID NO 2441
<211> LENGTH: 21
<212> TYPE: DNA
<213> ORGANISM: Homo sapiens

<400> SEQUENCE: 2441
gcataacagg gaaagtcacc t                                              21

<210> SEQ ID NO 2442
```

```
<211> LENGTH: 21
<212> TYPE: DNA
<213> ORGANISM: Homo sapiens

<400> SEQUENCE: 2442
ctgtattctt tgtccaccac c                                    21

<210> SEQ ID NO 2443
<211> LENGTH: 21
<212> TYPE: DNA
<213> ORGANISM: Homo sapiens

<400> SEQUENCE: 2443
aggatgttag tggtttgggt a                                    21

<210> SEQ ID NO 2444
<211> LENGTH: 21
<212> TYPE: DNA
<213> ORGANISM: Homo sapiens

<400> SEQUENCE: 2444
gacaggacac cttggattga t                                    21

<210> SEQ ID NO 2445
<211> LENGTH: 20
<212> TYPE: DNA
<213> ORGANISM: Homo sapiens

<400> SEQUENCE: 2445
tctgacactg accttcaact                                      20

<210> SEQ ID NO 2446
<211> LENGTH: 20
<212> TYPE: DNA
<213> ORGANISM: Homo sapiens

<400> SEQUENCE: 2446
gagtaattcc cccgatgcag                                      20

<210> SEQ ID NO 2447
<211> LENGTH: 20
<212> TYPE: DNA
<213> ORGANISM: Homo sapiens

<400> SEQUENCE: 2447
gaaacattgc tttccctcca                                      20

<210> SEQ ID NO 2448
<211> LENGTH: 21
<212> TYPE: DNA
<213> ORGANISM: Homo sapiens

<400> SEQUENCE: 2448
tgagaatcat tgagccaaac c                                    21

<210> SEQ ID NO 2449
<211> LENGTH: 20
<212> TYPE: DNA
<213> ORGANISM: Homo sapiens

<400> SEQUENCE: 2449
ttccacacat ctcttctccg                                      20
```

-continued

<210> SEQ ID NO 2450
<211> LENGTH: 20
<212> TYPE: DNA
<213> ORGANISM: Homo sapiens

<400> SEQUENCE: 2450
aattgtgagc gttagagtgc                                         20

<210> SEQ ID NO 2451
<211> LENGTH: 20
<212> TYPE: DNA
<213> ORGANISM: Homo sapiens

<400> SEQUENCE: 2451
gggagccttg aaaacctgaa                                         20

<210> SEQ ID NO 2452
<211> LENGTH: 21
<212> TYPE: DNA
<213> ORGANISM: Homo sapiens

<400> SEQUENCE: 2452
ccagtgggtc ttaacattga g                                       21

<210> SEQ ID NO 2453
<211> LENGTH: 19
<212> TYPE: DNA
<213> ORGANISM: Homo sapiens

<400> SEQUENCE: 2453
attggtagcg ttgtcagca                                          19

<210> SEQ ID NO 2454
<211> LENGTH: 20
<212> TYPE: DNA
<213> ORGANISM: Homo sapiens

<400> SEQUENCE: 2454
aaaaggctag tagagggtgc                                         20

<210> SEQ ID NO 2455
<211> LENGTH: 20
<212> TYPE: DNA
<213> ORGANISM: Homo sapiens

<400> SEQUENCE: 2455
ttcctgcatc ttgtagaccc                                         20

<210> SEQ ID NO 2456
<211> LENGTH: 20
<212> TYPE: DNA
<213> ORGANISM: Homo sapiens

<400> SEQUENCE: 2456
tcgctgaaga actgagacac                                         20

<210> SEQ ID NO 2457
<211> LENGTH: 20
<212> TYPE: DNA
<213> ORGANISM: Homo sapiens

<400> SEQUENCE: 2457
gggctaatgt tttgcttcca                                         20

<210> SEQ ID NO 2458
<211> LENGTH: 20
<212> TYPE: DNA
<213> ORGANISM: Homo sapiens

<400> SEQUENCE: 2458
gggaagtgat tggagagagg                                              20

<210> SEQ ID NO 2459
<211> LENGTH: 20
<212> TYPE: DNA
<213> ORGANISM: Homo sapiens

<400> SEQUENCE: 2459
tgttgattag agcttccccc                                              20

<210> SEQ ID NO 2460
<211> LENGTH: 20
<212> TYPE: DNA
<213> ORGANISM: Homo sapiens

<400> SEQUENCE: 2460
ccgcttggta tagagtgctg                                              20

<210> SEQ ID NO 2461
<211> LENGTH: 19
<212> TYPE: DNA
<213> ORGANISM: Homo sapiens

<400> SEQUENCE: 2461
agaggttttc ttccccgtg                                               19

<210> SEQ ID NO 2462
<211> LENGTH: 20
<212> TYPE: DNA
<213> ORGANISM: Homo sapiens

<400> SEQUENCE: 2462
ttgaggttgt caggaaagct                                              20

<210> SEQ ID NO 2463
<211> LENGTH: 20
<212> TYPE: DNA
<213> ORGANISM: Homo sapiens

<400> SEQUENCE: 2463
tagtgccctc tattgtgcct                                              20

<210> SEQ ID NO 2464
<211> LENGTH: 20
<212> TYPE: DNA
<213> ORGANISM: Homo sapiens

<400> SEQUENCE: 2464
tcttgggaaa gggtcattct                                              20

<210> SEQ ID NO 2465
<211> LENGTH: 20
<212> TYPE: DNA
<213> ORGANISM: Homo sapiens

<400> SEQUENCE: 2465
actgctggac tttgaaatgc                                              20

-continued

<210> SEQ ID NO 2466
<211> LENGTH: 19
<212> TYPE: DNA
<213> ORGANISM: Homo sapiens

<400> SEQUENCE: 2466
tctcttccat gcactccac                                                    19

<210> SEQ ID NO 2467
<211> LENGTH: 20
<212> TYPE: DNA
<213> ORGANISM: Homo sapiens

<400> SEQUENCE: 2467
caaacagtga gatgtggctg                                                   20

<210> SEQ ID NO 2468
<211> LENGTH: 19
<212> TYPE: DNA
<213> ORGANISM: Homo sapiens

<400> SEQUENCE: 2468
gatctgaccc tctgctcac                                                    19

<210> SEQ ID NO 2469
<211> LENGTH: 21
<212> TYPE: DNA
<213> ORGANISM: Homo sapiens

<400> SEQUENCE: 2469
ttgcttcctg aaaactggtt c                                                 21

<210> SEQ ID NO 2470
<211> LENGTH: 20
<212> TYPE: DNA
<213> ORGANISM: Homo sapiens

<400> SEQUENCE: 2470
cctgaaagat gcatggttgg                                                   20

<210> SEQ ID NO 2471
<211> LENGTH: 20
<212> TYPE: DNA
<213> ORGANISM: Homo sapiens

<400> SEQUENCE: 2471
attccaatca cgtctctgca                                                   20

<210> SEQ ID NO 2472
<211> LENGTH: 20
<212> TYPE: DNA
<213> ORGANISM: Homo sapiens

<400> SEQUENCE: 2472
gccacagaac aaccagattc                                                   20

<210> SEQ ID NO 2473
<211> LENGTH: 20
<212> TYPE: DNA
<213> ORGANISM: Homo sapiens

```
<400> SEQUENCE: 2473
acaatctcac agcctggaaa                                               20

<210> SEQ ID NO 2474
<211> LENGTH: 20
<212> TYPE: DNA
<213> ORGANISM: Homo sapiens

<400> SEQUENCE: 2474
tggggttaag agctcaagag                                               20

<210> SEQ ID NO 2475
<211> LENGTH: 20
<212> TYPE: DNA
<213> ORGANISM: Homo sapiens

<400> SEQUENCE: 2475
tcagatgggt gaggttcttg                                               20

<210> SEQ ID NO 2476
<211> LENGTH: 20
<212> TYPE: DNA
<213> ORGANISM: Homo sapiens

<400> SEQUENCE: 2476
agtgtggatg acttctgcaa                                               20

<210> SEQ ID NO 2477
<211> LENGTH: 20
<212> TYPE: DNA
<213> ORGANISM: Homo sapiens

<400> SEQUENCE: 2477
ctgctccttc cctccaatta                                               20

<210> SEQ ID NO 2478
<211> LENGTH: 20
<212> TYPE: DNA
<213> ORGANISM: Homo sapiens

<400> SEQUENCE: 2478
gccccattat cctcctttgt                                               20

<210> SEQ ID NO 2479
<211> LENGTH: 20
<212> TYPE: DNA
<213> ORGANISM: Homo sapiens

<400> SEQUENCE: 2479
aaatgccagt cctgtaaagg                                               20

<210> SEQ ID NO 2480
<211> LENGTH: 21
<212> TYPE: DNA
<213> ORGANISM: Homo sapiens

<400> SEQUENCE: 2480
caaatcagac ccactaagca c                                             21

<210> SEQ ID NO 2481
<211> LENGTH: 20
<212> TYPE: DNA
```

```
<213> ORGANISM: Homo sapiens

<400> SEQUENCE: 2481
tgtcccattg cttaggaagt                                              20

<210> SEQ ID NO 2482
<211> LENGTH: 20
<212> TYPE: DNA
<213> ORGANISM: Homo sapiens

<400> SEQUENCE: 2482
tgttttggac tgcttcactc                                              20

<210> SEQ ID NO 2483
<211> LENGTH: 20
<212> TYPE: DNA
<213> ORGANISM: Homo sapiens

<400> SEQUENCE: 2483
tgtgtgatcc agagaccta                                               20

<210> SEQ ID NO 2484
<211> LENGTH: 21
<212> TYPE: DNA
<213> ORGANISM: Homo sapiens

<400> SEQUENCE: 2484
attatcatgc tcactcctcc a                                            21

<210> SEQ ID NO 2485
<211> LENGTH: 20
<212> TYPE: DNA
<213> ORGANISM: Homo sapiens

<400> SEQUENCE: 2485
accaatgtag acttagcggg                                              20

<210> SEQ ID NO 2486
<211> LENGTH: 20
<212> TYPE: DNA
<213> ORGANISM: Homo sapiens

<400> SEQUENCE: 2486
gacatagcac gggaggagta                                              20

<210> SEQ ID NO 2487
<211> LENGTH: 20
<212> TYPE: DNA
<213> ORGANISM: Homo sapiens

<400> SEQUENCE: 2487
actctcatat tgccccactt                                              20

<210> SEQ ID NO 2488
<211> LENGTH: 20
<212> TYPE: DNA
<213> ORGANISM: Homo sapiens

<400> SEQUENCE: 2488
gctagtggcg ttttaggaaa                                              20

<210> SEQ ID NO 2489
<211> LENGTH: 20
```

-continued

```
<212> TYPE: DNA
<213> ORGANISM: Homo sapiens

<400> SEQUENCE: 2489
ccagggattg atgtactggt                                               20

<210> SEQ ID NO 2490
<211> LENGTH: 19
<212> TYPE: DNA
<213> ORGANISM: Homo sapiens

<400> SEQUENCE: 2490
tcgcttggaa gtcatagcc                                                19

<210> SEQ ID NO 2491
<211> LENGTH: 20
<212> TYPE: DNA
<213> ORGANISM: Homo sapiens

<400> SEQUENCE: 2491
aattctggtc tatctggcgt                                               20

<210> SEQ ID NO 2492
<211> LENGTH: 23
<212> TYPE: DNA
<213> ORGANISM: Homo sapiens

<400> SEQUENCE: 2492
cagagctgct ttgaagataa tcc                                           23

<210> SEQ ID NO 2493
<211> LENGTH: 20
<212> TYPE: DNA
<213> ORGANISM: Homo sapiens

<400> SEQUENCE: 2493
gccagccctt ttcacatatt                                               20

<210> SEQ ID NO 2494
<211> LENGTH: 20
<212> TYPE: DNA
<213> ORGANISM: Homo sapiens

<400> SEQUENCE: 2494
gaagcctgat agatgtgcct                                               20

<210> SEQ ID NO 2495
<211> LENGTH: 20
<212> TYPE: DNA
<213> ORGANISM: Homo sapiens

<400> SEQUENCE: 2495
aactacacca tccctgttt                                                20

<210> SEQ ID NO 2496
<211> LENGTH: 20
<212> TYPE: DNA
<213> ORGANISM: Homo sapiens

<400> SEQUENCE: 2496
tacctctgcc tccaattgtc                                               20

<210> SEQ ID NO 2497
```

```
<211> LENGTH: 20
<212> TYPE: DNA
<213> ORGANISM: Homo sapiens

<400> SEQUENCE: 2497
ccatttcaaa catgctggtc                                               20

<210> SEQ ID NO 2498
<211> LENGTH: 20
<212> TYPE: DNA
<213> ORGANISM: Homo sapiens

<400> SEQUENCE: 2498
cccatgtaga caaagtgctt                                               20

<210> SEQ ID NO 2499
<211> LENGTH: 22
<212> TYPE: DNA
<213> ORGANISM: Homo sapiens

<400> SEQUENCE: 2499
agattataag aaggcaggga ac                                            22

<210> SEQ ID NO 2500
<211> LENGTH: 20
<212> TYPE: DNA
<213> ORGANISM: Homo sapiens

<400> SEQUENCE: 2500
ggcaggtttg tcttacagtt                                               20

<210> SEQ ID NO 2501
<211> LENGTH: 22
<212> TYPE: DNA
<213> ORGANISM: Homo sapiens

<400> SEQUENCE: 2501
gtagagggct taaaacatgt cc                                            22

<210> SEQ ID NO 2502
<211> LENGTH: 20
<212> TYPE: DNA
<213> ORGANISM: Homo sapiens

<400> SEQUENCE: 2502
tgtgagattg cattcccctt                                               20

<210> SEQ ID NO 2503
<211> LENGTH: 21
<212> TYPE: DNA
<213> ORGANISM: Homo sapiens

<400> SEQUENCE: 2503
acaagaacac agtcgttaag c                                             21

<210> SEQ ID NO 2504
<211> LENGTH: 20
<212> TYPE: DNA
<213> ORGANISM: Homo sapiens

<400> SEQUENCE: 2504
cgggtcagag aaagatcagg                                               20
```

```
<210> SEQ ID NO 2505
<211> LENGTH: 20
<212> TYPE: DNA
<213> ORGANISM: Homo sapiens

<400> SEQUENCE: 2505
tctctccttc actcccttca                                              20

<210> SEQ ID NO 2506
<211> LENGTH: 22
<212> TYPE: DNA
<213> ORGANISM: Homo sapiens

<400> SEQUENCE: 2506
aaacatttgt aaccactccc tg                                           22

<210> SEQ ID NO 2507
<211> LENGTH: 20
<212> TYPE: DNA
<213> ORGANISM: Homo sapiens

<400> SEQUENCE: 2507
tgtccacccc tctttgattg                                              20

<210> SEQ ID NO 2508
<211> LENGTH: 21
<212> TYPE: DNA
<213> ORGANISM: Homo sapiens

<400> SEQUENCE: 2508
cctgtaatat gggactcctg g                                            21

<210> SEQ ID NO 2509
<211> LENGTH: 20
<212> TYPE: DNA
<213> ORGANISM: Homo sapiens

<400> SEQUENCE: 2509
tttagcttct cctgcctttg                                              20

<210> SEQ ID NO 2510
<211> LENGTH: 20
<212> TYPE: DNA
<213> ORGANISM: Homo sapiens

<400> SEQUENCE: 2510
ccaaaccaca cacacaaact                                              20

<210> SEQ ID NO 2511
<211> LENGTH: 20
<212> TYPE: DNA
<213> ORGANISM: Homo sapiens

<400> SEQUENCE: 2511
agaagcaatt caccaggtca                                              20

<210> SEQ ID NO 2512
<211> LENGTH: 21
<212> TYPE: DNA
<213> ORGANISM: Homo sapiens

<400> SEQUENCE: 2512
aggagaagga catttcacag g                                            21
```

<210> SEQ ID NO 2513
<211> LENGTH: 20
<212> TYPE: DNA
<213> ORGANISM: Homo sapiens

<400> SEQUENCE: 2513
tggagtcaga agtgtgtgtt                                              20

<210> SEQ ID NO 2514
<211> LENGTH: 20
<212> TYPE: DNA
<213> ORGANISM: Homo sapiens

<400> SEQUENCE: 2514
aggccgataa gacaaggttc                                              20

<210> SEQ ID NO 2515
<211> LENGTH: 20
<212> TYPE: DNA
<213> ORGANISM: Homo sapiens

<400> SEQUENCE: 2515
tctggtgtca aagcttaggg                                              20

<210> SEQ ID NO 2516
<211> LENGTH: 19
<212> TYPE: DNA
<213> ORGANISM: Homo sapiens

<400> SEQUENCE: 2516
gtttcccata gagccctgg                                               19

<210> SEQ ID NO 2517
<211> LENGTH: 20
<212> TYPE: DNA
<213> ORGANISM: Homo sapiens

<400> SEQUENCE: 2517
tgccgatgat gtgtgttttg                                              20

<210> SEQ ID NO 2518
<211> LENGTH: 20
<212> TYPE: DNA
<213> ORGANISM: Homo sapiens

<400> SEQUENCE: 2518
ctccactctc tccaaccaac                                              20

<210> SEQ ID NO 2519
<211> LENGTH: 20
<212> TYPE: DNA
<213> ORGANISM: Homo sapiens

<400> SEQUENCE: 2519
tgtcccttcc taatcccaaa                                              20

<210> SEQ ID NO 2520
<211> LENGTH: 20
<212> TYPE: DNA
<213> ORGANISM: Homo sapiens

<400> SEQUENCE: 2520
aaactgtgaa aggacgagga                                              20

<210> SEQ ID NO 2521
<211> LENGTH: 20
<212> TYPE: DNA
<213> ORGANISM: Homo sapiens

<400> SEQUENCE: 2521
aggatgttta agttgcagca                                              20

<210> SEQ ID NO 2522
<211> LENGTH: 20
<212> TYPE: DNA
<213> ORGANISM: Homo sapiens

<400> SEQUENCE: 2522
tcccttgctt ttgtaccagg                                              20

<210> SEQ ID NO 2523
<211> LENGTH: 20
<212> TYPE: DNA
<213> ORGANISM: Homo sapiens

<400> SEQUENCE: 2523
tatgcagttt taccccctcc                                              20

<210> SEQ ID NO 2524
<211> LENGTH: 20
<212> TYPE: DNA
<213> ORGANISM: Homo sapiens

<400> SEQUENCE: 2524
catgtgtgta ctgtgcctca                                              20

<210> SEQ ID NO 2525
<211> LENGTH: 20
<212> TYPE: DNA
<213> ORGANISM: Homo sapiens

<400> SEQUENCE: 2525
ttctgtgtgg tctcctcttg                                              20

<210> SEQ ID NO 2526
<211> LENGTH: 21
<212> TYPE: DNA
<213> ORGANISM: Homo sapiens

<400> SEQUENCE: 2526
tctttcactg tcactatggg g                                            21

<210> SEQ ID NO 2527
<211> LENGTH: 20
<212> TYPE: DNA
<213> ORGANISM: Homo sapiens

<400> SEQUENCE: 2527
atggagggac aagtgagaca                                              20

<210> SEQ ID NO 2528
<211> LENGTH: 20
<212> TYPE: DNA
<213> ORGANISM: Homo sapiens

```
<400> SEQUENCE: 2528
aaatgcagct tcccaacatc                                              20

<210> SEQ ID NO 2529
<211> LENGTH: 20
<212> TYPE: DNA
<213> ORGANISM: Homo sapiens

<400> SEQUENCE: 2529
ggggaacatg gagctgtaaa                                              20

<210> SEQ ID NO 2530
<211> LENGTH: 20
<212> TYPE: DNA
<213> ORGANISM: Homo sapiens

<400> SEQUENCE: 2530
gagactttct ggaggacgaa                                              20

<210> SEQ ID NO 2531
<211> LENGTH: 20
<212> TYPE: DNA
<213> ORGANISM: Homo sapiens

<400> SEQUENCE: 2531
ggacccccta ccacatttac                                              20

<210> SEQ ID NO 2532
<211> LENGTH: 22
<212> TYPE: DNA
<213> ORGANISM: Homo sapiens

<400> SEQUENCE: 2532
gaaacgtaat ttagtgactg gc                                           22

<210> SEQ ID NO 2533
<211> LENGTH: 21
<212> TYPE: DNA
<213> ORGANISM: Homo sapiens

<400> SEQUENCE: 2533
agatggagaa atgtgcagag a                                            21

<210> SEQ ID NO 2534
<211> LENGTH: 22
<212> TYPE: DNA
<213> ORGANISM: Homo sapiens

<400> SEQUENCE: 2534
atgtgtctat tgctacctgt ga                                           22

<210> SEQ ID NO 2535
<211> LENGTH: 19
<212> TYPE: DNA
<213> ORGANISM: Homo sapiens

<400> SEQUENCE: 2535
atgactgcat ccaagagca                                               19

<210> SEQ ID NO 2536
<211> LENGTH: 20
<212> TYPE: DNA
```

```
<213> ORGANISM: Homo sapiens

<400> SEQUENCE: 2536
ctccttcatt ttgctggtgg                                               20

<210> SEQ ID NO 2537
<211> LENGTH: 20
<212> TYPE: DNA
<213> ORGANISM: Homo sapiens

<400> SEQUENCE: 2537
cagaatttcc aggcagttgt                                               20

<210> SEQ ID NO 2538
<211> LENGTH: 20
<212> TYPE: DNA
<213> ORGANISM: Homo sapiens

<400> SEQUENCE: 2538
ggtgatcatt tgtctgcaca                                               20

<210> SEQ ID NO 2539
<211> LENGTH: 21
<212> TYPE: DNA
<213> ORGANISM: Homo sapiens

<400> SEQUENCE: 2539
gaatccagaa gctcagtcct t                                             21

<210> SEQ ID NO 2540
<211> LENGTH: 20
<212> TYPE: DNA
<213> ORGANISM: Homo sapiens

<400> SEQUENCE: 2540
tgaagggatg aaggcagaag                                               20

<210> SEQ ID NO 2541
<211> LENGTH: 20
<212> TYPE: DNA
<213> ORGANISM: Homo sapiens

<400> SEQUENCE: 2541
agccctggaa tcttgacatt                                               20

<210> SEQ ID NO 2542
<211> LENGTH: 20
<212> TYPE: DNA
<213> ORGANISM: Homo sapiens

<400> SEQUENCE: 2542
attgtgttgt ccttccgttt                                               20

<210> SEQ ID NO 2543
<211> LENGTH: 19
<212> TYPE: DNA
<213> ORGANISM: Homo sapiens

<400> SEQUENCE: 2543
gtgcattata cggatggcc                                                19

<210> SEQ ID NO 2544
<211> LENGTH: 20
```

<212> TYPE: DNA
<213> ORGANISM: Homo sapiens

<400> SEQUENCE: 2544
ctgaagcatc actggcattg                                                    20

<210> SEQ ID NO 2545
<211> LENGTH: 20
<212> TYPE: DNA
<213> ORGANISM: Homo sapiens

<400> SEQUENCE: 2545
ggtagagggt cctgtgattc                                                    20

<210> SEQ ID NO 2546
<211> LENGTH: 20
<212> TYPE: DNA
<213> ORGANISM: Homo sapiens

<400> SEQUENCE: 2546
aagcttgtag tctgggtagc                                                    20

<210> SEQ ID NO 2547
<211> LENGTH: 20
<212> TYPE: DNA
<213> ORGANISM: Homo sapiens

<400> SEQUENCE: 2547
gtaactgcta gccactgagt                                                    20

<210> SEQ ID NO 2548
<211> LENGTH: 22
<212> TYPE: DNA
<213> ORGANISM: Homo sapiens

<400> SEQUENCE: 2548
tccctctgta ctatgtagca tg                                                 22

<210> SEQ ID NO 2549
<211> LENGTH: 20
<212> TYPE: DNA
<213> ORGANISM: Homo sapiens

<400> SEQUENCE: 2549
gccttttTgg gaatcctagt                                                    20

<210> SEQ ID NO 2550
<211> LENGTH: 20
<212> TYPE: DNA
<213> ORGANISM: Homo sapiens

<400> SEQUENCE: 2550
ttcatttccc tttgttgccc                                                    20

<210> SEQ ID NO 2551
<211> LENGTH: 33
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(5)
<223> OTHER INFORMATION: Residues linked by the phosphothioate bond
<220> FEATURE:

```
<221> NAME/KEY: modified_base
<222> LOCATION: (29)..(33)
<223> OTHER INFORMATION: Residues linked by the phosphothioate bond

<400> SEQUENCE: 2551
acactctttc cctacacgac gctcttccga tct                              33

<210> SEQ ID NO 2552
<211> LENGTH: 34
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(5)
<223> OTHER INFORMATION: Residues linked by the phosphorothioate bond
<220> FEATURE:
<221> NAME/KEY: modified_base
<222> LOCATION: (30)..(34)
<223> OTHER INFORMATION: Residues linked by the phosphorothioate bond

<400> SEQUENCE: 2552
gtgactggag ttcagacgtg tgctcttccg atct                             34

<210> SEQ ID NO 2553
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(5)
<223> OTHER INFORMATION: Residues linked by the phosphorothioate bond
<220> FEATURE:
<221> NAME/KEY: modified_base
<222> LOCATION: (9)..(13)
<223> OTHER INFORMATION: Residues linked by the phosphorothioate bond

<400> SEQUENCE: 2553
agatcggaag agc                                                    13
```